(12) United States Patent
Reeves et al.

(10) Patent No.: US 7,332,576 B2
(45) Date of Patent: Feb. 19, 2008

(54) BIOSYNTHETIC GENE CLUSTER FOR AMBRUTICINS AND THE ENCODED PROTEINS

(75) Inventors: Christopher D. Reeves, Orinda, CA (US); Bryan Julien, Oakland, CA (US); Ralph C. Reid, San Rafael, CA (US)

(73) Assignee: Kosan Biosciences Inc., Hayward, CA (US)

( * ) Notice: Subject to any disclaimer, the term of this patent is extended or adjusted under 35 U.S.C. 154(b) by 119 days.

(21) Appl. No.: 11/075,185

(22) Filed: Mar. 7, 2005

(65) Prior Publication Data

US 2005/0266434 A1   Dec. 1, 2005

Related U.S. Application Data

(60) Provisional application No. 60/551,103, filed on Mar. 8, 2004, provisional application No. 60/568,290, filed on May 4, 2004.

(51) Int. Cl.
*C07K 1/00* (2006.01)
(52) U.S. Cl. .................... 530/350; 530/300; 435/7.1; 435/69.1
(58) Field of Classification Search ............... None
See application file for complete search history.

(56) References Cited

OTHER PUBLICATIONS

Wells, Biochemistry, vol. 29, pp. 8509-8517, 1990.*

* cited by examiner

*Primary Examiner*—Hope Robinson
(74) *Attorney, Agent, or Firm*—Gary W. Ashley

(57) ABSTRACT

Domains of ambruticin polyketide synthase and modification enzymes and polynucleotides encoding them are provided. Methods to prepare ambruticin in pharmaceutically useful quantities are described, as are methods to prepare ambruticin analogs and other polyketides using the polynucleotides encoding ambruticin synth R = OH         ambruticin S
R = NMe$_3^+$  ambruticin VS-1
R = NHMe$_2^+$ ambruticin VS-3
R = NOMe$_2$   ambruticin VS-3 N-oxide
R = NH$_2$Me$^+$ ambruticin VS-4
R = NH$_3^+$   ambruticin VS-5

FIGURE 3. SEQ ID NO: 1

```
LOCUS       AMB_PATENT  78869 BP DS-DNA            SYN        01-MAR-2004
DEFINITION  -
ACCESSION   -
KEYWORDS    -
SOURCE      -
FEATURES                Location/Qualifiers
     source             1..78869
                        /note="Sorangium cellulosum strain So ce10; and derived
                        strains containing transposon inserts"
     variation          60178..63179
                        /note="old vs new breakpoint"
     source             <1..720
                        /note="pKOS344-135B; 15Kb NheI/EcoRI subclone of cosmid
                        1-16 from Sorangium strain K433-47.1 (Tn1A11 insertion
                        strain)"
     source             1..42241
                        /note="pKOS344-112E; ""cosmid 10B3""; from Sorangium
                        cellulosum strain So ce10"
     source             43983..78869
                        /note="pKOS344-190; cosmid insert containing transposon
                        insertion site 16B11, from Sorangium strain K375-93"
     source             40665..51778
                        /note="pKOS375-77Bg; BglI fragment with transposon
                        insertion site 2B8, from Sorangium strain K433-47.2"
     source             44025..60178
                        /note="pKOS344-135F (partial); fragment of cosmid insert
                        containing transposon insertion site 5F7, from Sorangium
                        strain K433-48"
     variation          48689..48689
                        /note="C vs G; pKOS375-77Bg vs pKOS344-135F"
     insertion_seq      15790..15791
                        /note="transposon insertion site 1A11 (Sorangium strain
                        K433-47.1)"
     insertion_seq      25345..25346
                        /note="transposon insertion site 7B2 (Sorangium strain
                        K433-55)"
     insertion_seq      41477..41478
                        /note="transposon insertion site 2B8 (Sorangium strain
                        K433-47.2)"
     insertion_seq      41834..41835
                        /note="transposon insertion site 10B1 (Sorangium strain
                        K433-71.4)"
     insertion_seq      45982..45983
                        /note="transposon insertion site 10G1 (Sorangium strain
                        K433-71.5)"
     insertion_seq      47815..47816
                        /note="transposon insertion site 5F7 (Sorangium strain
                        K433-48)"
     insertion_seq      57483..57484
                        /note="transposon insertion site 16B11 (Sorangium strain
                        K375-93)"
     CDS                765..4145
                        /note="AmbA"
                        /note="PKS"
                        /note="(module 0)"
```

/translation="MGFPCIRRVSGSAASPATCVKVRRTFRSRPFRAARSTKSAQVEAR

LSRIFSMPDTSSSSPVLAMGLRDSDARFVEDTPPASDRPRPFAGIAVVGMGCRLPGGVD

SPESLWAALSEGRDLISEVPPDRWDVNAHYDADASVPGKIATRHGGFLAGVAAFDAPFF

DLSPREAKHMDPQQRLGLETAWEALEDAGLDARSLRGSRAGVFVGSMWAEYDVLASRHP

ESISPHGATGSDPGMIAARIAYTFGLRGPALSVNTASSSSLVAVHLALQSLQSGECELA

LAGGANLILTPYNTIKMTKLGTMSPDGRCKAFDHRANGYVRAEGVGFVVLKRLSRATAD

GDRIYAVVRGSAVNNDGLTEGLTAPSVEAQEAVLREAYARAGVSPAEVDYVEAHGTGTP

LGDRVEATALGRVLGAGRAADRALRVGSVKTNLGHAEAAAGVAGLMKTALSLRHGSLPA

SLHVERPNPEIPLEALGLRLQTELGAWPEVDRPRRAGVSSFGFGGTNCHVVLEEWRGGV

EQSAAETGSEPGAAVSPPALPLVLSARDHGALRAQAGRWAAWLTEHREARWADVIHTAA

ARRTHLGARATVVAAGVAEAVDALRALADGRAHGAVTVGEARERGKVVFVFPGQGSQWP

AMGRALLSASRVFAEAVEACDAALRPLTGWSVLSLLRGDAGEAAPSLDRVDAVQPALFA

MAVGLSAVFRAWGLDPSAVVGHSQGEVPAAYVAGALSLDDAARVVAVRSALVRRLSGAG

AMAAVELPAGEVERRLAPFGGALSVAVVNTSSSTAVSGDAEAVDRLVAQLEAEGIFCRK

VNVDYASHSAHVDVVLPELLERLAPIRPGATRIPFYSTVTGGVLEGTALDGAYWCRNLR

QPVRLDRALARLLDDGHGVFVEVSAHPVLASPLTAACAEREGVVVGSLHRDDGGLARLL

GALGALHVQGQPVDWRAVLAPFGGGLVNLPTYAFQRQRYWFDTDESVALAAASSIAEES

WSEKLAGLSPARREERLLEWVRAEIAAVLGLEAPAVPPDVPLRDLGLKSPIAVELGSRL

GRRTRRKLPVSFVYNHPTPRAIARALLEGMFSSSKDSPPSTADDRRPPGVPAGVAPPQA
                              LETSEMSDDELFQSIDALV*"
    misc_structure    1026..2300
                           /note="KS0s"
    misc_structure    2628..3674
                           /note="AT0_1; [GHSQ; YASH]"
    misc_structure    3744..3998
                           /note="ACP0"
    CDS               4202..15271
                           /note="AmbB"
                           /note="PKS"
                           /note="(modules 1-2)"

/translation="MDRSDKLRAYLEKTTASLVEAKSRIRELEARSREPIAIVAMACRF

PGGVDSPEKLWALLDEERDVITEVPPSRWDLERFYDPDPDAAGKTYSRWGGFVGDLDRF

DAAFFGISPREARSIDPQERWLLETTWEALERAGVRADTLEGTLGGVYIGLSGSEYQAE

AFHDAERIDAYSLTGASPSTTVGRLAYWLGLRGPAVAVDTACSSSLVAVHLACQALRNG

ECDFALAGGVNALLAPESYVAFCRLRALSPTGRCRTFSANADGYVRAEGCGVLLLKRLS

DAQRDGDRVLAVIRGNAINQDGRSQGLTAPNGLAQEDVIRRALSQAAVEPTTVDVVECH

GTGTALGDPIEVQALGAVYGHGRPGDRPLVIGSVKTNLGHTEAAAGMAGLIKAVLSLQH

AQVPRSLHFAAPSDYIPWDTLPVRVAAQRVAWERREHPRRAGVSSFGISGTNAHVILEE

APASEAPATAPVAAPVAAPLPATLPLLVSGRDEAALRAQAGQWAAWLAAHPEAPWADVV

HTAAARRTHLEARAAVAAGSAADAAAALEALAAGHPHRAVSLGEARARGEVVFVYPGQG
SQWPAMGRALLAESEVFAAAVAACDAALRPLTGWSVLSVLRGEQGEAVPPADRVDVVQP
ALFAMAVGLSAVWRAWGIEPSAVVGHSQGEVAAAYVAGALTLEDAARVVALRSQLVRRI
AGGGAMAVIERPVGEVEQRLSRFGGQLSVAAVNTPGSTVVSGDAAAVDRLLAELEAERV
FARRIKVDYASHSAHVDAILPELEATLASVEPRACTIPLYSTVTGEVLAGPELGGGYWC
RNLREPVRLDRALSRLLADGHGVFVEVSAHPVLAMPLSAASAERGGVVVGSLQRDDGGL
GRLASMLGALHVQGHAVNWQRVLAPYGGALVDLPTYAFQRQRHWLEAPRYAAEDTDGAA
RRDPLYRVTWIEAALEEAPWAAERHVVLGADGALASGLGALALAGLPELLEALENGAAA
PERLVLDLTEGRPGAVAESVHATTRSALALVQAWLAAPRLSGTELVVVTREAVAAGPDE
GVAALGPAAVWGLLRTVRVEHPERAVRSVDLGREPPDVAVLRRALGTAAEPELALRAGG
ARAPRLRAVNAGADARAPAAALDPQGTVWITGGTGELGRQVARHLVAAHGVRHLLLTSR
RGAAAPDAEALVEQLRADGAETVEVVACDVTDGAALSAAVQVAAAKRPLTAVVHTAGVL
ADGVLTALTAEQLTRALAPKVDGACHVYAAAQDQPLAAFVLFSSIVGTLGNAGQANYGA
ANAFLDAFAAQLRARGVPATSLAWGFWEQAGLGMTAHLGAADLARLGRQGLVPLSVAQG
LRLLDRALAHPEATLVPAALDLSALQRAASDAGRVPPLLRGLVRASPGRPTATATPEAG
PAAASALRARLSALPEAERAGALLELVRAEVAVVLRLAGPAQVPADKPLKELGLDSLTA
VELKNRLGARAETVLPTTLAFDHPTPRAIADLLLQRAFSELAGATRAQAPRARGAHDEP
IAIVSMACRLPGGVDTPAALWDLLSEGRDAIGPFPEGRGWDVAGLYDPDPDAPGKSITT
QGGFLYDADRFDPTFFGISPREAERMDPQQRLLLECAWEALERAGLAPHALEASATGVF
FGLAHGDYGGRLLQQLESFDGHVLTGNFLSVGSGRIAYTLGLRGPAVTVDTACSSSLVA
VHLACMSLRAGECDLALAGGATVMATPMIFVEFSRQRGTALDGRCKAFGAGADGAGWSE
GCGILALKRLSDARRDGDRVLAVIRSSAVNQDGRSQGLTAPNGPAQQDVIRQALAAAGL
TPADIDAVEAHGTGTRLGDPIEAQALLATYGTAHTAERPLWLGSLKSNLGHTQVAAGVS
GLMKLVLAMQHAELPRTLHADPPSPHVDWSQGHVKLLNEPAPWPRTDRPRRAAVSSFGI
SGTNAHVIVEEAPEPAPAADAKAVEALPILPLLVSGADEAALRAQVRRLVEHLRSHPDQ
RLLDVAASLATTRTHLATRLALPVSAGAPRDAWMDELEAFARGGAAPTQASQTPVESST
GKVAVLFTGQGSQRAGMGRALYATHPVFRAALDAACAELDRHLDRPLMSVLFADAGSEA
AALLDQTAWAQPALFALEVALYRQWDAWGLRPELLLGHSIGELAAAHIAGVLDLADASA
LVAARGRLMQALPLGGAMASVEATEDELRPLLDQHTGRLSLAALNTPRQSVVSGDEPAV
DQVCAHFTALGRRAKRLVVSHAFHSAHMEPMLDAFARVARGLTFHPPRLPIVSSVTGAR
ASADELTSPDYWVRQVREPVRFVDGMRALHAAGAATFVECGPHGVLSAAGAECLAPDGA

RDAGFVPSLRNERDEALALVHAACAVHVRGHALDWLRFFDATGARRVELPTYAFQRQRY

WLQAPRPRPSLEGVGLTAANHPWLGAAVRLADRDGYVLSGRLSTSDHPWVLDHVVLGTA

LLPGTGFVELAWAAAEAVGLSGVSELAIEAPLALPARGAVALQVAIEAPDPAGRRGIAI

YSRPDGAADAPWTAHARGVLGAAASDRDAAWAQGAWPPPGAVPVDVTQWLEIVDAWVGP

AFRGVVALWRVGRTIYADVALPDGVAGTAQDFGLHPALLDVALRAFLRAELSADPSPRE

GTVVPFAWSDVALEARGTAALRVRAEVEAGGDGDAITASIQLADGQGRPVARVGALQMR

WTTAERVRAAAAAGAAERDLYRVAWTDVALDDTAFVPEEHVVVGGDGALAAALGARAVA

GLPELLASLPDGAAAPRRLVVDLTADAAGAVVDAVHAAARDALSLVQGWLAAPQLAATE

LVVVTRGAVAVAPDEGVAALGPAAVWGLLRATRVEHADRTVRMLDLGPGAPDMALLRRA

LTAAEEPELALRAGGARAPRLDAAGETDGELAPPDGARSLRLSIRTKGSFDALHLADAP

DALRPLGPGQVRLAVRATGLNFRDVLNVLGTYRGEAGPLGLEGAGVVLDVGEGVTALRP

GDRVMGILHAGMATHAVVDARLLTHIPRGLSFVEAATIPAAFLTALYGLRDLGALKAGQ

RVLVHAAAGGVGMAAVQLARLWGAEVFATASEGKWPALRGMGIDQAHIASSRTLHFRKA

FLDATRGQGVDVVLDALAGEFVDASLDLLPRGGRFVEMGKSDVRDPERVAKDHPGVRYT

AFDLLDAGPDHIQAMLRELVPLFEEGVLAPLPFAVHDLRRAPHAFRSMANARHVGKLVL

VPPAALDPDGTALITGGTGELGRQIARHLVAAHGVRHLVLTSRRGMDAPDAAALVGSLR

AAGAATVEVAACDVTDRDALAAVVQAIPAARPLTAIVHTAAVLDDGIVAGLSAEQLARV

LRPKVDGAWRLYEATRDAPLAAFMLFSSVAGTLGSSGQANYAAANAFLDGLAAELRTRG

VPAMSLAWGFWEQGGIGMTAHLGAADLARLKRQGIAPMTVAHGLRLLDRALERPDAALV

PASLDVAVIQRAASDHRQVPPMLRGLVRVAPRQAAGAANGRSHEASTLRQQLAALPEPE

RQRALLDLVRTEAAAVLVLRGPDAVPADKPLRELGLDSLTAVELRNRLRTRAQTDLPST

LAFDYPTPKAVAVYLAQELDVHDVMTEMRGPSLRSDDEIKSAIASIRISTLRQAGLLDS
LLRLAASEAVSTSSDTTPETDELTLQHVGDDELARLVFDLAGGAQ*"
```
          misc_structure  4301..5575
                          /note="KS1"
          misc_structure  5900..6952
                          /note="AT1_1; [GHSQ; YASH]"
          misc_structure  7553..8404
                          /note="KR1_1; [DD->AD]"
          misc_structure  8438..8695
                          /note="ACP1"
          misc_structure  8756..10033
                          /note="KS2"
          misc_structure  10358..11425
                          /note="AT2_0; [GHSI; HAFH]"
          misc_structure  11459..12034
                          /note="DH2"
          misc_structure  13019..13894
                          /note="ER2"
          misc_structure  13910..14707
                          /note="KR2_1; [DD]"
          misc_structure  14756..15013
```

```
                              /note="ACP2"
         CDS       15268..26235
                              /note="AmbC"
                              /note=" (module 3-4)"
```

/translation="MKEDISARQALEKSFIELRRIKRELDQLKAKSSEPIAIVSMACRL

PGGVDTPAALWQLLSEGRDAIGPFPEGRGWDVAGLYDPDPDAPGKSITAQGGFLYDADR

FDPAFFAISPREAERMDPQQRLLLECAWEALERAGLAPHSLEASATGVFVGLSVTDYGG

RLLHEPEALDGYIATGTLPSVGSGRIAYTLGLRGPAVTVDTACSSSLVSLHLACMSLRA

GECDLALAGGATVMATPMAFIEFSRQRGTALDGRCKAFGAGADGAGWSEGCGILTLKRL

SDARRDGDRVLAVIRGSAVNQDGRSQGLTAPNGPAQQDVIRQALAAAGLTPADVDAVEA

HGTGTRLGDPIEAQALLATYGTAHTAERPLWLGSLKSNLGHTQAAAGVSGLMKLVLAMQ

HAELPRTLHADPPSPHVDWSRGHVKLLNEPVPWPRTDRPRRAAVSSFGFSGTNAHVIVE

EAPAASTEATTRGEKTPAAAPPSTLPLLVSGADEAALRAHAGRWAAWLAAHPEAGWADV

VYTAAARRTHLGARAALTAADAAGAVAALTALSQGQPHAALAVGEARARGKVVFVFPGQ

GSQWPAMGRALLSQSEVFAAAVAACDAALRPFTGWSVLSVLRGDTGAEVPPLERVDVVQ

PALFAMAVGLAAVWRAWGLEPSAVVGHSQGEVPAAYVAGALSLEDAARIVALRSRLVRR

LSGTGAMAVIELPVGEVEQRLSRFGGALSVAAVNTPRSTVVSGDAEAVDRLLTEFEGEQ

VFARKVNVDYASHSRHIDGLLPELEDGLGAVRPRASTIPFYSTVTGTVLTGAELDAAYW

CRNLREPVRLDRALSRLLDDGHGLFVEVSAHPVLTLPLTGASATSGGVVVGSLQRDDGG

LGRLLGVLAALHVHGHDVDWRAVLAPWGGGVADLPTYAFQRQRYWLEAPRGRAGLESGG

LLAVKHPWLSAAVRLADRDGYVLSGRLSTVEHAWVLDHVVLGTVILPGTAFVELALAAA

DAVGLPSVSELTIEAPLALPARGAVTLQVTVEALDATGRRGFAVHSRPDGAHDAPWTAH

ARGVLGAAPAAATTAWAAGAWPPAGAEPVDVTRWVEALDAWVGPAFRGVTAAWRVGRSI

YADLALPEGVSERAQDFGLHPALLDAALQALLRAELGAGSSPREGIPMPFAWSDVALEA

RGAAALRARVEVEDASDGDQLAASIELADAQGQPVARAGTFRARWATAEHVRKAAAGAS

ERDLYRVTWTDVALEEAAWAPEEHIVLGGDGALAAALGARTAALPELIAALPEGAAAPR

RLVIDAAAGDPGDGLVAAAHAATQRVLSLVQGWLSEARLADSELVVVTRGAVAAGPDDG

VAALSHAPLWGLVRTARQENPGRAVRLVDLGPEPLDGALVRRAVAAAEEPELALRGGAA

RAPRLREVRAGAADAARPTRLDPGGTVLITGGTGELGRQVARHLVAAHGVRHLVLTSRR

GMDAPDAAALVDELRAAGAATVDVAACDVADGAALGAVIAAIPAAHPLTAVVHMAGVLD

DVIVTKLSAEQLARVLRPKIDGGWHLAAATRGHRLAAFVLFSSAAGTLGSAGQANYAAA

NAFLDALAAQLRARGVPAMSLAWGFWEQAGLGMTAHLGAADLARLRRQGIAPIALAQGM

QLLDRALARPEAALVPAALDLSALQRAASDAGQVPALLRGLVRPAAGRRAASPAAAATG

```
AAALRARLSALPEAERAGALLELVRAEAAAVLQLAGPAQVPADKPLKELGLTSLTAVEL
RNRLGARAETALPATLAFDHPTPRAIADLLLQRAFSELAAAGATRAQAPRARGAHDEPI
AIVSMACRLPGGVDTPAALWQLLSEGRDAIGPFPEGRGWDVAGLYDPDPDAPGKSVTNL
GGFLYDADRFDPTFFGISPREAERMDPQQRLLLECAWEALERAGLAPHSLEASATGVFV
GLVYSDYGGRLLEHLEVFDGYVATGSFPSVGSGRIAYTLGLRGPAVTVDTACSSSLVSL
HLACMSLRAGECDLALAGGATVMATPMAFIEFSRQRGMAPDARCKAFGAAANGIGPAEG
CGLLVLKRLSDARRDGDRVLAVLRGSAVNQDGRSQGLTAPNGPAQQDVIRQALAAAGLT
PADIDAVEAHGTGTRLGDPIEAQALLATYGTAHTAERPLWLGSIKSNLGHTQAAAGVVG
LMKLVLAMQHAELPRTLYAEPRSPHIDWSQGHINLLNEPVPWPRTDRPRRAAVSSFGIS
GTNAHVIVEEAPAAAQTAAEAAAAVPSTLPLLLSGRDEPALRAQAGRLAEHLRAHPDQR
LLDVAASLATTRTHLATRLALPLAPDAATEELGARLAEFASGGPAPSGAAVTAPGQPPG
KVAVLFTGQGSQRAGMGRALYATHPVFRAALDAACAELDRHLDRPLMSVLFADAGSEAA
ALLDQTAWAQPALFALEVALYRQWDAWGLRPELLLGHSIGELAAAHIAGVLDLADASAL
VAARGRLMQALPLGGAMASVEATEDELRPLLDQHTGRLSLAALNTPRQSVVSGDEPAVD
QVCAHFTALGRRAKRLVVSHAFHSAHMEPMLDAFARVARGLTFHPPRLPIVSSVTGARA
SADELTSPDYWVRQVREPVRFADGMRALHAAGAATFVECGPHGVLSAAGAECLAPDGAR
DAGFVPSLRKDRDEALALVHAACAVHVRGHALDWLRLFDPSGARRVELPTYAFQRQRYW
LQAPRPRPSLEGVGLTAANHPWLGAAVRLADRDGYVLSGRLSTLDHPWVLDHVVAGTVI
LPGTAFVDLAWAAAEVVGAAAVSEVTFTTPLVLPPRSVVELQVRIGEPDASGRRTFAAY
SRPDAASEAEWTQHATGVLSAQAAAGADVADLSVWPPPGAEVVALDGGYAWLAAQGYGY
GPAFQALREVWRAGTTLYARVALPDAVADTAQSFGIHPALLDAVLHSLLARSPQEEASD
DDKVLLAFAFSDVVIEARGAAEVRVRLNKQAGDDGEGLTASIHLADAQGRPVARVGAFQ
ARATTTERVRALAGASERDLHRVTWTDVTLDEAPWAHEDSVVVGGDGALAAALGVRAVA
GLPELFAGGAAAPRRLVIDATAGDPGDGLVAATHAATQRGLALLQGWLAEARLASTELV
LVTRGATAAEPDEGVAALSHAPLWGLVRAAREEHPARALRLVDLGREAPDGAVLRRAIA
ADDEPELVVRRGALRAARLSLAHAAPDAAGRATRLAPGGTVLITGGTGELGRQVARHLV
TAHGVRHLVLTSRRGMDAPDAAALVEALRAAGAATVEIAACDVADRDALAAVLRAIPAA
HPLTAVVHTAGVLEDGVVTGLSAEQLARVLRPKVDGAWQLYEATRDAPLAAFMLFSSAA
GTLGSAGQANYAAANAFLDALAAELRTRGVPAMSLAWGFWEQGGIGMTAHLGAADLARM
KRQGIVPMAVTHGLRLLDRALERPEATLVPLSLDVAALQRAAGDAGRVPALLRGLVRPA
AARHTAVPAAAATGATGLRARLLPLSEAERQDVLLDLVRTEIADILALSGPAAVPPDQP
IRELGLDSLTAVDVRSRLVQRSEIDLPVTLAYDYPTARAIAGHLSEQMGLEGAPEDRES
```

```
              ALDEAQIRALLMQIPISTLRQSGLLGDLVRLASPQAPPREEGESETLSFDHLGNEEFLS
                              LASKLIAEEGS*"
        misc_structure   15367..16644
                         /note="KS3"
        misc_structure   16969..18021
                         /note="AT3_1; [GHSQ; YASH]"
        misc_structure   18055..18606
                         /note="DH3"
        misc_structure   19534..20358
                         /note="KR3_1; [DD]"
        misc_structure   20380..20637
                         /note="ACP3"
        misc_structure   20704..21981
                         /note="KS4"
        misc_structure   22306..23373
                         /note="AT4_0; [GHSI; HAFH]"
        misc_structure   23407..23967
                         /note="DH4"
        misc_structure   24886..25710
                         /note="KR4_1; [DD->ED]"
        misc_structure   25732..25989
                         /note="ACP4"
        CDS              26232..31910
                         /note="AmbD"
                         /note="(module 5)"
```

/translation="MNQETVLRQTLEKSLHKIQHLNRELERLKAKSSEPIAIVSMACRF

PGGVDTPAALWDLLSEGRDAIGPFPEGRGWDVAGLYDPDPDAPGKSITTQGGFLYDADR

FDPTFFGISPREAERMDPQQRLLLECAWEALERAGLAPHSLEASATGVFVGLVYSDYGG

RLLEHLEVFDGYVATGSFPSVGSGRIAYTLGLRGPAVTVDTACSSSLVSLHLACMSLRA

GECDLALAGGATVMATPMAFIEFSRQRGMAPDARCKAFGAAANGIGPAEGCGLLVLKRL

SDARRDGDRVLAVIRSSAVNQDGRSQGLTAPNGPAQQDVIRQALAAAGLTPADVDAVEA

HGTGTPLGDPIEAQALLATYGKAHTAERPLWLGSIKSNFGHTQAAAGVAGIIKLVLAMQ

HAELPRTLHADPPSPRVDWSQGHVKLLNEPVPWPRTDRPRRAAVSSFGVSGTNAHVIIE

EAPAEAPTAAQTAAAAATEPAAAVVPSTLPLLLSGRDEPALRAQAGRLAEHLRAHPDLR

LLDVAAGLATTRTHLATRLALPLAPDAATEELGARLAEFAAGGPAPSGAAVTAPGQPPG

KVAVLFTGQGSQRAGMGRALYATHPVFRAALDAACAELDRHLDRPLVSVLFADAGSEAA

ALLDQTAWAQPALFALEVALYRQWEAWGLRAHALLGHSLGEIVAAHIAGVLDLHDASAL

VAARGRLMQALPHGGAMASIEATEHELRPLLDQHTGRVSLAALNAPRQSVVSGDQPVVD

QVCAHFKALGRRAKRLDVSHAFHSARMEPMLDAFAHVARGLTYRAPRLPVVSNVTGRMA

TADELTSPDYWVRHVREPVRFVAGVRALHATGVTTYLECGPDPVLGGMAADCLTPDETR

DVGLIPSLRKDRDEALALAQAACALYVRGHALDWLRLFDATRARRVELPTYAFQRQRYW

IDAPRRAAGLDSVGLTAADHPWLGAAVRLADRDVHVLSGRLSTVDHPWILDHVVAGTPL

MPGTGFVELAWATAQAVDAAAIAELTLTTPLVLPARGAVQLQVTVDEADANGRRAFAIH

SRPHGPGDLAWTQHATGVLSAEEPAGADEAAGLSEWPPPGAEAVALDGGYEQLSEHGYG

HGPAFQGLRGLWRADRTLYAHVALPDAVAGTEQGFGLHPALFDAALQSLARLSREEAAA

GDPVLVPFAWTDVALYATGATELRARIALEQAEGGAPAVASLLLADAHGRTVATTGRVR

GASAAQTRSAASRAEPMYRVAWTDVALEAATWAPEEHVVLGGDGALAAALGVRAAAGLP

ELLEALADGAAAPRRLVVDLTAGDAGAVVAAVHAAVRGALALVQGWLAAPQLAATELLV

VTRCAVATGPDEGVDALGPAAVWGLLRATRAEYPDRAVRVLDVGREPLDGALLRRALAA

GTEPELSVRSGEARAPRLREVRGSEPAAAPATRLDPDGTALITGGTGELGRHVAKHLVT

AHGVRHLVLTSRRGMDAPDAAALVDELRAAGAATVDVAACDAADAAALAAVVEAIPAAR

PLTAVVHTAGVLDDSVVTKLSAEQLARVLRPKVDGAFHLHELTKHAPLAAFVLFSSAAG

TLGSPGQANYAAANTFLDALASHLRARGVPAMSLAWGFWAQTGLGMTAHLGAADIARMK

RHGVVSMPVAQGLRLLDRALAQAEATLVPLALDLSSLQRAGSNAGPVPPLLRGLVRAPA

GRRTAASAAGANGNGTGAAALRARLSPLPGAERQKVLLDLVRTEIAEVFQLPGPAHIPA

DRPLKELGLDSLMSVELRNRLGPRVEAALPATLVFDYPTPGAIASYLGTLLNLSGEDAH

PGQTGRDPDEEHEIRAAIARIPITTLREAGLLQSLLRLAPNQTASDDVTPRTDELMVEH
                     LGDEELLKLAFASTGGAK*"
        misc_structure    26331..27608
                          /note="KS5"
        misc_structure    27960..29027
                          /note="AT5_0; [GHSL; HAFH]"
        misc_structure    29061..29657
                          /note="DH5"
        misc_structure    30528..31361
                          /note="KR5_1; [DD]"
        misc_structure    31395..31652
                          /note="ACP5"
        CDS               31907..42430
                          /note="AmbE [possible alternate N-terminus 12 bp
                          downstream (bp 31919)]"
                          /note="PKS"
                          /note="(modules 6-7a)"

/translation="MKDEVLSFRRALEKTVVEIRRLNTEIDGLRAKSVEPIAIVSMACR

YPGGVDSPAALWQLLSEGRDAIGPFPEGRGWDVAGLYDPDPDAPGKSITTQGGFLYDAD

HFDPMFFGISPREAERIDPQQRLLLECAWEALESAGIAPHTLGASATGVFIGLMYTEYG

LRLMNQPEALDGYIGIGSAGSTASGRISYTLGLRGPAVTVDTACSSSLVSLHLACTALR

RGECDLALAGGAAVVSTPAPFIEFSRQRALAVDGRCKSFGAGADGVSWSEGCGLLVLKR

LSDAQRDGDRVLAVLRGSAVNQDGRSQGLTAPNGPAQQDVIRQALAAAGLTPADIDAVE

GHGTGTPLGDPIEAQALLATYGKAHTAERPLWLGSIKSNFGHTQAAAGVAGVMKLVLAM

QHAELPRTLRANPPSPHVDWSQGHIALLNEPASWPRTDRPRRAAVSSFGVSGTNAHVII

EEAPAPAAEVTSPGAEPPAVALPLLVSGRDDAALRAQAERWAAWLAAHPEARWADVVHT

AAVRRTHLEARAAVTAASAADAAAALTALSQGEPHPAVTAGEARARGKVVFVAPGQGSQ

```
WPAMGRALLAESEVFAAAVAACDAALRPFTGWSVLSVLRGEQGEAVPPADRVDVVQPAL

FAMAVGLSAVWRAWGIEPSAVVGHSQGEVAAAYVAGALTLEDAARVVALRSQLVRRIAG

GGAMAVIERPVGEVEQRLSRFGGQLSVAAVNTPGSTVVSGDAAAVDRLLAELEHEEVFA

RRVNVDYASHSAHVDAILPELEACLASVEPRACAIPLYSTVTGEVLAGPELGAAYWCRN

LREPVRLDRALSRLLADGHGVFVEVSAHPVLAIPLTAASAERGGVVVGSLQRDDGGLGR

LVSALGALHVQGHSVEWARVLAPYGGNLVDLPTYAFQRQRYWLEASRSRIDASDLGLAA

TGRPLLGAATRVAGTDSYILAGRLSTAEHPWLSGQVVFERTLFPATGFLELALEAADAM

GVAGVTELVVPAPLILPARGAVHVQVAVQGPDEAGRRPFSVYSRAETAGLDAEWTLHAT

GLLGGARASAAADTGLEAWPPEGAAPVDVSDAYARLEDAGVRYAPSLRALVEAWQAERR

IYARAVLPGGATQGHGLHPALWDAALHALALVVLGQDAEHAGVLLPRAWSDVTLAAQGA

TELRVRVELADADAEHVSASLTMADADGQPVATVGSVEVRRATAAQVRAMSTATQHLYG

VEWKAVALAEPPRSAGEQVVLGPDGELATRLGARRAGNLDELFADGEAARPAPRRLVVD

ARTRRDGDVPAAVHQATRQALELVQRWLADARLTDTELVVLTREAVSTGPDVGVEDLGH

AALWGFLRAVRSEHPDRGVRLIDLGPDASAAELLDRALETVAEPELALRQGIALAPRLG

VPRDRAGAPAPMRLDPDGTALITGGTGELGRHVAKHLVTAHGVRHLVLTSRRGMDAPDA

AALVDELRAAGAATVDVAACDAADAAALAAVVEAIPAARPLTAVVHTAGVLDDSVVTKL

SAEQMARVLRPKVDGAFHLHELTKHAPLAAFVLFSSAAGTLGSPGQANYAAANTFLDAL

ASHLRARGVPAMSLAWGFWAQAGLGMTAHLGAADIARMKRLGVVTMSPQEGLELLDASL

QRPDPLLVPAPLDLAALERAAREGAPASPMLRELVRGAPARRAAAGDGASGKASALRAL

LARRPQSERFAAVLELVRAEAARVLRLPGAAAVPPDRPLKELGLDSLTAVELRNRLAAR

TEAKQPATLVFDHPTPSAISRFLLKQAGADLAPSEAAASLAPSSRRAPLDEPIAIVAMA

CRCPGGVDSPEALWRLLSEGRDAIGPLPEERGWSVEQILGRDPGASSKPFSGRGGFLYG

ADQFDAEFFGITPREARFLDPQHALLLECTWEALERASIVPQSLEGSSTGVFVGMVGGM

AAGHGSVSSEGYALTGTALSTASGRISYALGLQGAAVTVDTACSSSAVAIHLACTSLRT

GECDLALAGGVTVMGRPEIFSEFGRLDILASDGRCKAFGATADGVGWGEGCGVLLLKRL

SDAQRDGDRVLAVIRGSAVNQDGRSQGLTAPNGPSQEAVIQRALASAGLTAADVDAVEA

HGTGTRLGDPIEAQALLSTYGQAHAAGQPLWLGSIKSNLGHTQAAAGVAGVIKMVLAMQ

HGQLPRTLYADTPSPDIDWSQGHVRLLVDAVPWPQSARRRAGVSSFGISGTNAHILVE

EAPEPPRAGAAPEAPVTLPFLPLLVSGRDLAALRSQAARLAAHLRERPDQRLVDVTASL

ATTRTHLAARLALPVAATAGRDEICGALDAFAARGLALNGAWVTPAQHRAGKVAVLFAG

QGAQRPAMGRGLYEALPVFREALDEVCARLDAHLGAPLKDVLFSAEGSPEASTLHQTGW
```

AQPALFALEVALYRQWEAWGLRPDALMGHSLGEIVAAHVAGVFDLADACALIAARGRLM

QALPTGGAMASIEASEDDVRPLLDAQQGRASLAALNGPRQTVVSGDEDAVEAVCDHFKA

QGRRVKRLTVSHAFHSARMEPMLEAFRAVAATLTFRAPQIPIVSNVTGERAPVEALTSP

DYWVRQVREAVRWTDGVRALEADGITTYVECGPDGATCAMASQCVTRAAKAPAFVSSLN

RKGDEVQALVSAACAVHVRGDSLDWSAFFAGSGARRVELPTYAFQRRRYGVDEPSPRPA

EVRAPDTTRTRVHVSADDPTVRGHVVGSQTLYPAASYIDLALRVAASAGQACVRAANMA

WFAPAIVPPEGLSLDVQLRRTKAGLECEVSSGDSDQRTIHFQGTLLGGDPGPWPAVDLR

RIIGECSLRLDRAHLYGIFANYGFGYDRAFQSVAWLVSNANDVVGRVELPASESATAEH

HLQPNLLDGAFQTIIGLDAVSALSGPTPDAGFNFVPSAIQDVQIFGRLRRAAYVHATRR

GKAHGSPSCDFQLLGENGEPIALVTGLTFRKLRSRAELDAPSAPAQRPSNGEAARPRNV

PAPANVPAPANVPAPGGDHADASPRAPSAEVLFFSPAWVPEKPVMAASVTGDIVVFGDD

DAQITHLRGLLPLARLIHVRSGPGFQRTGPAAYAVRPDSQEDLSALFTEFDDARSKSLR

ALYLWEPSRRAAEGSAPPGDGDVAAAIRSLFCLFKAHMAERRKGMQLLYLTSSATSAVP

VNEAVLAFFRTIRTENPTYVGKVIAVADPGHIGRACATELGLPTGSDVVQHVDGARHVR

KLFSREPAPRERLRDALPLAPGGTFVLTGGAGKIGLLLTDMLVREYQVNVALIGRSQLD

EPRRQAIDSIRSGPARALYYSADVGVLSDTERAIGEIRETLGPIRGAIHAAAIIRDSFF

IKKTLAEVDSVLRPKVNGAIYLDFLLRDDPLEVFVLCSGLASLLGNQGQSDYAAANGFL

DGFAIQREALRQAGRRQGRTISINWPLWGGDGGMGVPDYIETELLKRGLVPLDISDGVT

```
                         AFRQAIAMKEPQVAVVAGQRAAARRLLRPWLSEGRTEDHQ*"
           misc_structure 32009..33286
                          /note="KS6"
           misc_structure 33599..34651
                          /note="AT6; [GHSQ; YASH]"
           misc_structure 34685..35236
                          /note="DH6"
           misc_structure 36143..36955
                          /note="KR6_1; [DD]"
           misc_structure 36998..37255
                          /note="ACP6"
           misc_structure 37325..38593
                          /note="KS7"
           misc_structure 38921..39985
                          /note="AT7_0; [GHSL; HAFH]"
           misc_structure 40055..40531
                          /note="DH7"
           misc_structure 41660..42379
                          /note="KR7_1; [DD->RD]"
           CDS            42427..49020
                          /note="AmbF"
                          /note="(modules 7b-8 & TEII & X)"
```

/translation="MTSWLLAKTEEFLGDLVSEVSEIRRDTISPDADFQEFGLDSRFVI

AMNSRLEQYFSGLPRTLFFEYPSIRAVASYLVEEFQDQLHELFPDGEPAEASRPAQSVP

VARPSGAIPSGASPSGASPSGAIPSGASPSGAIPSGASPSGAIPSGASPQTSTSSAADL

```
SDLASLIQQIPLPEAVLSSVERPRVDPRPAAPAPSVVRASSGDQSGDDIAVIGVAGRYP
KARNIEEFWRNLREGRDCIEPLPKERWSPDPSDPLRWGGYLDGVTDFDSLFFGISPREG
EGMDPQERLFLEVAWETIESAGYDPLRLGRSGEPASVGVFVGVMYGEYQVFGAELTLLG
QPTLVSSSYATIPNRVSYFLNFSGPSLALDTMCSSSLTALHLACASLRSGDCKMALVGG
TNVTIHPNKYRLLEAGKYLASDGRCRSYGADGDGYVPAEGVGAVLIKPLADARRDGDTI
WGVIKSTSINHGARARGYTTPNPNAQSASLSLALERAKIEPHTLGYIEGHGTGTSLGDP
IEIRGIQKAVGRVSEKIPIGSVKSNIGHAESAAGVAGLTKVLLQLRARELVPSIHCEPP
NPNIDFDRAPIQVQRHAAPWNRRTITSGGVTREVPRRAVVSAFGAGGSNAHVVVEEADA
PALQRTVSAQPRLFVLSARSVERLRAHAQSFLDFFSRMPTLREAEARELFYDMCATLYF
GRAPFEARLAIVAESLRTLQQKLAAFVYGASRDPDILVSDGRSLAATDGGQRQLSGLAD
LGRRWVAGEAVDASELFPHPWKKLALPTYPFERRRLWAPSGEKLYDLRSAAAPAPAAPP
GNGASPREVPANVPRAARTDTAETAVVSGPQHARIAPAERRLAVAEQVIEVAERPSPPD
RGPSTSETRGSESDPHVTSTLNGHTSALNGHTSALNGHAARATGPERPAAAVQAADQGA
AVEIVQEMVRDLVAQILFVDRSTILPDAALFDYGLESVSSVELAERLNAMLGTDITPTS
FYEFNTLAHFSRHLVERYNLADRLSGLSAGLAGGSSAPAGPSGRGDSPPRAAAGAEGPV
VGAAAAEGAAAPAAGGPTVEELWASAMHAEGLAALPSPEPRRSASKAPRPAPPVQPSDQ
ATPVEIVQEIVRDLVAQILFVDRSTILPTTALFDYGLESVSSVELAERLNAMLGTDITP
TSFYEFNTLAHFSRHLVERYNLADRLSGLSAGLAGGSSAPARASAPRAQGPAALSSSEP
RRSDAGIELHVIPGVDGHAVEFATLGSGVPLFVLGGLLATHDALTLNPDILSLGQTYRV
IMVHPPGAGRSELPRGELTMDFIVRQVEGVRQSLGLSSVVLVGYSFGGLVAQAYVAQFP
ERASKLVLACTTSDPASVVNGMHLVAAEAQRHPDGLRALQFADVSKFPLYSQLSTRLRP
ETLAYPAIPTLIVAGAEDRYVPTIHAERLARANPNATLHIVEGAGHFLGLSHGGVLVHL
VNGFVLGDRTAPARSPAVSASRRGGLRKMSQESVGALKSYLEEGEIASGVEASPVAGQV
GYLLNRLLSGQEAPSSPYHCFFMPSGLEAVDAALRFGRRAKLSRGLGDAKTLVLDPEG
ALRRHFEFLPQERLFPDLIFVGESRELLRLLQSAEDVGAAYVTTACDDATLETVAAECA
RRGIVSVLGELHADTGELVSARLRSKPDVVVLDEAIAGFELPFGVCAIRRFHESGVWTR
QPEEFAVRVPGSMAGPALTVVRENILRRFRAVVTNDTTANLRAIAVDQRRTKEAHRSYV
NPVLLESLDAFGLAGRQRHADRRGYEIERDDGSSARVINLYLVTSASFRGHTGSEIAQS
VLGTHDITRDYWADLERRIPRETDFGRVFPAAGPATAVETAVKLGLLAARKGSALLVLK
GSPIFTRLGALVSHAEPGSPLEALVESCPWSKVIAVDPFGEGAAAELEAKLTSDDVGFV
WLETLQSDWGGLRSVPDAVLEVIDRHRERSGYLVGVDETYTSLGCGRMFHWQGKLARPD
```

```
VVAVCVGWTDCQLLAGYVLTTEEVAARARQRNEAVVSALQEQLRCQLTAHATLRLLDVL

KEDRILAQIAETERRFSGALNDFAAECGMVKRVWGEGLFWAVQFDLDGWPRFVRDWFSS

FLWSECLRDPVAPVAVSMQPLTPACIRVEPRYDIPAAELDAAMGTLKRVLGKGVEGIVA
                       SVADDVERRGDARRAELFRRILRGFKTT*"
     misc_structure   42427..42666
                       /note="ACP7"
     misc_structure   43054..44322
                       /note="KS8"
     misc_structure   45193..45447
                       /note="ACP8a"
     misc_structure   45766..45972
                       /note="ACP8b"
     misc_structure   46102..46785
                       /note="TEa; homolog of terminal ""hydrolase"" domain of
                       leinamycin PKS subunit LmnJ"
     misc_structure   47053..48753
                       /note="X; distant homolog of aminotransferases"
     CDS              49017..50336
                       /note="AmbI"
                       /note="putative FAD-dependent monooxygenase"
                       /note="close homolog of PedG"

/translation="MSAQPEYCIVGGGPIGIGIGKCFAQEGLKFTIVEADEDFGGTWAL

SQRSGLVYKSTHLISSKKNTQFLDFPMPEDYPHYPSHAQMLSYLRSLATHYGLYDRALF

GTRVEHVEPNGAGCRVRLSNGETRTFSAVVVANGRMRTPLIPRYPGVFSGETMHSAAYK

SHEVFRGKRVLVIGGGNSGCDIAVDAALAAEQTFHSTRRGYHYMPKFIHGKPTQEWLMD

MGSKFRSQDDYWSFVQREFKAAGYDPVDYGLPRPDHAIHEAHPILNSLVLYYIGHGDIH

PKPDVRRFEGRTVEFVDGTRAEVDLILYATGYEMDFPFLAEDLRPSDGALELFLSMFHR

KADSLVFVGYFNAASGLGNLLNCGGALVTDYLVAREKNTDAFRVLRRLIQGPEPDIGRG
                       RFLNSPRHRVETDLWKAMKVMNFFRSVLNPARAAGDVVRA*"
     CDS              50524..52734
                       /note="AmbG"
                       /note="AL"
                       /note="CoA ligase-containing didomain"
                       /note="NRPS/PKS load module homolog"

/translation="MSREGTSSMNIGSPLPPIENALDLFKHYATSAPEARIAVFIEEEG

QEQGLTYRELERAATNLSLELASVAAPGDRVLVAYDSGPMYLVGVWAALYAGMIAVPVD

PLGPDRPAANLTRLLNVTADSGATVCIASRSMLDAVKSHPGARQLTEQLRWVVPSLPDL

LGRAPGSPPAALRTEKDVAMLQYASGSTGAPKGTIVTHASLLMLARALLISTSAESPFG

RPDVEVTWLPLTHSTAGYGLIMKCLTGATMSAWYIAPSAFARSPAIWLRTISRHKGKQV

YSVAPNFALDWCVSSTTEAERKQLDLSCWTHVMSMGEKVRPETWKAFSDAFRESGFHPK

LFIAGYGMSETGYVSGSVNGGKTVRFDRAAMDEGSLVEAPEGGILLLSSSGFTLPGVRV

AIVDPETREVLPEGKIGEIWVSTPTAMTGYWNRPEETEQQFRARAADGSGPFFRSGDMG

AFYGGNLFVTGRRKSIVVIRGRKHYAEDIESTLERALDWLGANSSIAFADDVNGVEELF

IAVDPRGARDGVGFEERTDAIRSVVAREFGVRVHEVLFLAAGQLPRTSMGKVSRVSCKD
```

LFRSGELEIAARSGSIARGGADLPAVDLRAILDEPDAELRVARMTEYIRSLLSASLSVP

ADALSLTKSFDELGVDSMTGVRFRGELVRALGLELPESIVYNYPTIAQLASFVCEKLTG
TAGSNDAERADRGPAALAALDVESMSEEAAAAALRAHLDGRK*"
```
     misc_structure    50524..52248
                       /note="AL; CoA ligase homolog"
     misc_structure    52354..52599
                       /note="ACP"
     CDS               52776..58076
                       /note="AmbH"
                       /note="(module 10 & TE)"
```

/translation="MSESGELSLTKRALLALQKAELEIGRLRDARPEPIAIIGVGCRIP

GGATSPSRFWKLLEEGFDALAEIPAARRKLFELQGARSPTSGGFLDEIDKFDPSFFSIS

PREAISMDPAQRLLLEVSVEALEDGGVPMAQIRGTRTGTFMGFSGYSGYGSLTGAQVEQ

LYAVTGLSINVAAGRISYVLDLQGPCVSVDTACCSSLVAVHLASQSLRSRECDLALAGG

VNVIAAMAGNEAMAATGALSSSGGRCRTFDAAADGYIRSEGCGVVLLKRLTDAMEAGDR

ILGVVAGSAVKHDGHSNGLTAPNGRAQQQLVREALAAARVRPEEIDYIETHGTGTPLGD

PIEVDALAEVFGSSHGPDRRIMLGSVKTNVGHPEGAAGIVGLIKVLGMFRRGMVPRHLH

FNTPNPRVPWDSVPFLVPRDTLPWPATDKVRVAGVSAFGFSGTISHAIVMEPPKAPERS

VDVGPATAGRPLLLPISARTPEALRAYAASYLDHLSAEATPEETDRDVAYTASLRRDHH

AHRLAVVGSDRAAWREKLQSYVSGEGCRGLVEGVVPEARPRLAFVFCGQGPQWWGMGRE

LLDKEPVFRGALEACHERIREAGGPSLLDELRREADTSRLNQTEVAQPALFALQVALAA

LWRSWGVQADAVVGHSIGEVAAAHVAGALSLEDAARLVVHRGRIMQRATGLGKMLSVAL

PLSAAQRIVSDYGQRISIGASNSPTSTVLSGEAAALDEVVEQLQGRQVEAKWLPVEYAF

HSAQMEGFGEELSKELRGLAPGANGPLLMSTVTGTEQRGTSFDADYWGQQIRKPVLFAQ

CVEELARKGCSLFLEIGPHPVLSASMTETLLAQEKSGRVVASLRRREEEVPTLLEALGQ

LHCAGYPVDWSKQHPVRGRTVSLPTYPWQRESYWLEAPKSQTPRQHGAEHHYETEWRLA

ERERPAEPRRGGWLILDDQAERAAALQDYLEARGQTCVRVVAADTYARRGARDYQIDPR

EPEHFARLLGEQEVVDALADASPSDRCGVVHLWSAHSSPAPTLESIQQAQALGSISALH

LVQALARAGWRQPPRLWLVTQEVQAIKNPTVSVAQAPVWGFGATVALEMPELQCTLLDL

DATPNIDALGQELLSASDEDRIALRGAERHVARLVPHVPEQRPAPEPLSFKADATYLLT

GGLGGIGLVVLEWMAARGARHFALLGRSGPSASAQPVLDRMREDGAQVRTFSVDVADRE

RLRTVLAQIQTSMPPLAGIIHAAGVGDQKMIPDLDGPSLQAIGRPKVDGSWNLHELTSE

LPLDFFVLFSSVSSLFGSHGQSSYAAGNAFLDALSHHRRALGLPALSLNWTAWTDVGMA

TPIIAHTSRYLATQGMGALSSREGVAALEQLFRASSAQIGVVPLSIPSLPRKPFYSVVA

PPTAPTPTAQTVRASERIAARPPGERQEAIEGTLRELFARALRMPPDKLKLTEALQNLG

```
VDSLIALELRRRIDEELGVKLQAAEIARVANVRELAQLVTAKFDALHGSAGVAQQARLE

VRGPLTVLKPSRQRPRLRLVCFPASGGSAGDFAEWAKVMPDDCELVAVEYPGSGARQLE

SCEHPLAALTLQAAGALMAMPRVPLVLFGHSLGGLIAHATAVELERHAMGPSCVVLSNP

ANVITVQRDLPRDGFRDQKFLTWLARSTGISIEPEATDSDATRQFLKTFGEQLAWTFDF

DLGWRVSCPVIISCGRDDTTLHAESLEFWRRSGGDLEEWTFAGAHDYIRQEFAEIVSKI
                       MNRAAGKDRT*"
        misc_structure  52872..54125
                        /note="KS10"
        misc_structure  54447..55496
                        /note="AT10_0; [GHSI; YAFH]"
        misc_structure  56253..56942
                        /note="KR10_2; [DD->DQ]"
        misc_structure  57033..57299
                        /note="ACP10"
        misc_structure  57300..58073
                        /note="TEb; thioesterase domain"
        CDS             58073..59494
                        /note="AmbJ"
                        /note="putative epoxidase"
                        /note="homolog of NanO and MonCI"

/translation="MSRAIVIGGSIAGMCSARVLCDFFDEVVILDRDQFPTEIAPRPGV

PQSRHTHVLLPRGEQELEELFPGFSASMMAAGALKFDVGTGMAVRRVFGWQTVGPTGRE

LLWASRDLFEGTIRSLMRQQTKVRIREGSQVLALRSTAGERPRIRGVLLRDDAAEQELE

ADLVVDASGRHTRAEQWLTELGLPAPKTQCVDSRAGYASRFYKVPPPERRPSDWWWKGL

WVEAEPDRPRGAVVFPIEGDRWLVTASGFSGSYPPTDEQGFLEHLASLSSPIVARAVAL

AEPISPIYGNRSMANVSRAYDRWEIQLPGFVAVGDAACAFNPVYGQGMSTSTVSAVILR

DVLRRRGPGAGFEPGFFQQQAKFLRSVWDFATRSDFRWPGTVGERPHTPAIIGAYAKLA

IESAHHDSAIRRHLFPAFDLTGSATLLFEPLFVGKVLLSAGQRRLRQRLLGTPPIPESP
                        PVPAGVPRWAAGAAM*"
        CDS             complement(60013..61083)
                        /note="AmbP"
                        /note="predicted FeS protein"
                        /note="dioxygenase homolog"
                        /note="78% identity vs ORF8_jer and 32% vs ORF10_jer"

/translation="MAELDHWHPVLLSHELRRKPRSVRLAGREIVVFRTSSGGLGAFTD

RCPHRSMRLSEGWVEGDRLVCAYHGWRWAADGRGDIPATPAARPCARRDDVFDAVERYG

AIWVKRAGAQATFPRFDAEGYVPAGVLRHRAAVPFELALDNFIEVEHTPFVHFMLGYSL

DQMPQVEAQVTLSDDAVQVVNTGPKRPIPRIVEKMFRIPHDAKFVVEWTARFSPVHAIY

DHSFINPRTREVVTYPLRSAVFFNPVGPESSEIYTFLFASLGRWSEFGLGSLIWPPLRV

AMDLELRLDMRLLSRLADKRGILKGNVLGRFDKALVASRDRIDRIYRGQAAEATPEAGD
                        GHEATRAARRLPLAAS*"
        CDS             complement(61086..62216)
                        /note="AmbO"
                        /note="FMO"
                        /note="78% identity vs ORF9_jer"
```

/note="putative flavin monooxygenase"

/translation="MVIEESHVIIIGAGPSGLAVGACLRERGIPFVLLEQSDAVGASWR
RHYQRLHLHTVKQFSSLPGLAWPRYAPPYPSRAQMVDYLQRYAERFRLEPRFGAEVVRA
YRDGSRWVTQTRAGEFTSRALVVATGYSRLPNVPTWPGQERFRGPILHSSTYGSGAAFR
GQRVLVVGSGNSGGEIAMDLWEHAAETTVSARSGIHVIPRDPLRLPAQFSALALYGALP
PAVGDRLATAFLSRTVGDLSRWGIHRPEIGPGTRAVKEGRIPLIDMGTLALIQQGKIAV
VPGPRAFTETGVIFTDGRELPFDAVVLATGYRAGLGDFLEDAARFTDERGYPRWHGAPT
PTPGLFFIGFRNPITGQLRDIAAEAPRVARHLRGVN*"
```
        CDS             complement(62288..63916)
                        /note="AmbN"
                        /note="aldehyde dehydrogenase homolog"
```

/translation="MRDAHCEPRGASGKLPPRFRANEEPLMAQAFPASPTTTPSTRTLV
VQSPIDGSRLGEVPLMGDAEVHAAVERARLAQRAWAQLPIETRAGRVARVIDAFVERLD
DLVDAVVLETGKPRNDALAEWITVVDACHYFTRHAGRILADTSITLHHMKWRGSYVTYV
PMGVVAVISPWNLPLAIPMGSVIEALIAGNAVVVKPSEVTPLTLLKAKEVVDAIGIPTD
LFQVVTGDARTGAALIDAGVQKVVFTGGVSSGRRVGAACAERLIPCVLELGGKAPLIAC
DDCEIERTARSIVAGGFINSGQLCISVERVLATEAVHDRLVDRVVALTRELRQGDPRAD
DVDVGAIIFAKQMDIAEAHIKDAVARGALVATGGRRRPGPGMFFEPTVLTRCTPEMTVM
REEIFGPVVPIMKVRDEDEAVRIANDSPLGLHAYVFSRDKTRARAVAERIEAGTVMIND
VLVSYCAPEAPFGGIKNSGYGRVHSDDSLRAMCYARHVNHERFAMPLNSPLLFPYTTAK
YRGMRAAIRATFKRTPLLGRLADLL*"
```
        CDS             63946..65550
                        /note="AmbQ"
                        /note="desaturase homolog"
```

/translation="MVWQHGRQSLHECHDGGREPCSETSEIRGAPPGLDRMTVPGLSTR
HVFHLCYKPQLGGLARLRRSATSSWDARRPRQRQLEPRADNATLNARLPQAPLADTMEP
KAHGTIPEEMMQSTATIAPLAVLFVLMAIEAVVARHRRGDTTYRLPDTVASVGVGVGYF
ALVAFFSFISIVVYDIVYERWAITHHARSAVTIVFTIFAADFLYYLFHRASHRINVLWA
IHVVHHQSREQNLAVNLRMPWLQPAYQWFFYLPLAFLGIPPAVFLLARGVSISYNVFTH
TRAVGKLGPLEYVLNTPSHHRVHHGMDEQYLDCNYGGIFIVWDRLLGTFVPEGKEPTYG
TRRRVVSWNPIWLNVEPFIHLAKLSRAARSPWDRVKVWFMPPEWQPAGVLEASAPPEPR
DVESRGSTASSIAQMALSVGVTVVIGAMVIMYTGTSSTMPRLALLVLLLASLGAHARSL
ESPGFAWRFELARAALLLAVAGWLDASGARPLASVALMAGGLSAASGVLFRLGRRPRGS
RAGGAEDAAPSMSLPGS*"
```
        CDS             65637..66977
                        /note="AmbR"
                        /note="glutamamate semialdehyde aminotransferase homolog"
```

/translation="MASSEDGTRSWSNTKSLALHERAAKVMPGGQANFRGGLLSTPLFF

```
SHARGARLWDVDGNEYVDLINAGGPGILGHNDPEYIDALKRQLDTVYSLGSGICQTEQD

IELAEKIASHVPCAERVRFCVTGSEAVHLALRLARAYTKRPYFIRFQTHYHGWFDSVLG

GVVDEHPEGRPLPLESEQSFFHTEGRVPDAFKYSFLLPWNDIDVLEETLKKYGHEVAMI

HMEPILVNGGGCPPRPGYLERVRELCDQHGIVLGFDEVITGFRVGLGGAQAALGVTPDL

ATFGKALGGGMPMAAVAGKAEIMDQLRTGKVTGAGTFNGYPLGVAASLATLKILERDDG

AVYRRIDMMQARLKEGLLDICKRRGIPALVQGPRGVFFLLFTDKPVIYSFQELMEAALP
                  RQFKFYSTMPEEGTLLMYGGRWYISAALTEADVDCALESADRTLARI*"
     CDS          67076..68155
                  /note="AmbS"
                  /note="putative N-methyltransferase"

/translation="MPPTEDLKQILEQLGSARLSHEVELSQLMAPLSPEEVLFCFLFIK

SGSAEGFGEEPVRFKDLPSAPDRFWKAMALHVGALSGQFKPLPPSYLKDAWLRFVKERP

GDEPLSLLEYYSLAAQLLSDTDRVFINHGYAFLNPAEAPSLAAWEEPSRLSIHLYHKLL

GGQDFTGLDVVDMACGRGGGSLYLKQRKEARLVAGIDAVRTHVLLAREAHPSVDGVYFL

HGRAEEIPLPTGAFDALIAVDAVFHFPLREFLHEAHRVVKPGGRCFLNSWGPPTWYMDL

EGAVESCGWKLEHAEDITTGVLLAREQWRTHDMFTWVRSRPRKCRPEIYIEFDRMVMLP
                  VEGRRYYNFHLTRLDQKAS*"
     CDS          complement(68191..69378)
                  /note="AmbM"
                  /note="putative C-methyltransferase"
                  /note="95% identity vs ORF11_jer.JerN"

/translation="MICFVPALRRMGATPARICMRQRLDVTDLYNDAYTAYIEAFRRQT

ELVASEILLEHLVDQSGAVQVLDDRPESAPSVTAYQFRRKLLDYFSDKGDLIQDPSGRL

VPSEAVRKRVAEREAMELADRAILGEMVEFLQRYRGLAGPVLAGKDALATMDLQYGMQA

SLKFWEYSMISLPAKKPCNVMLARALMAKLAEGPGISVFEGGAGLGVVLRQALSDPRFL

PLSRNLVRYDYTDISALLMETGKQWLRTHAPADLFQRIHFQRLDLDALPSAGNTFARAA

SVDLIVLEHVLYDVRDLHATLQAFHTMLKPGGQLAFTMSFRDRPGLFFPNEFFQSMLHT
                  YSKAKLDPPRRQHVGYLTLQEWELSLRAAGFSEWEVYPAPEDHAKWPFGGIVAYR*"
     CDS          complement(70491..76754)
                  /note="ORF9"
                  /note="multidomain 2-component sensor/regulator"
                  /note="the C-terminal portion has 93%  identity vs
                  ORF15cter_jer"

/translation="MAPPWRGSNMEQRTSGKIASPRSRTASSKDGAAKGTNGKDGKHPR

NGKNAAAKRAEGAARTSQATALQQRSQPVHLEDLPRPRRRAAQDDVMRRPARQALEMGQ

MLAVLVALKKGDFSVRLPIDLEGLDGKIADTFNDVVEMNEKFAFELERLSRAVGKEGKI

GQRVSMGEVSGAWADEVASVNALIGDLVQPTREMARVIGAVAKGDLSQTMALEVGGRPL

EGEFLQTAQTVNTVVYQLGSFASEVTRVAREVGTEGKLGQAEVKGVAGTWKDLTDSVN

SMAGNLTAQVRNIAAVTTAVANGDLTQKITVDVRGEILELKDTFNTMVDQLRSFASEVT
```

```
RVAREVGTEGKLGGQASVPGVAGTWKDLTDSVNSMASNLTAQVRNIAAVTTAVANGDLT

QKITVDVKGEILELKDTFNTMVDQLRSFASEVTRVAREVGTEGKLGGQAEVKGVAGTWK

DLTDSVNSMASNLTAQVRNIAAVTTAVARGDLTQKITVDVRGEILELKDTFNTMVDQLR

SFASEVTRVAREVGTEGKLGGQAEVKGVAGTWKDLTDSVNSMASNLTVQLRDVSKVATA

IANGDLTQKITVDVRGEILQIKDVINTTVDQLSSFAAEVTRVARDVGTEGKLGGQAEVK

GVAGTWKDLTDSVNSMASNLTAQVRNIAAVTTAVARGDLTQKITVDVRGEILELKNTFN

TMVDQLRSFAAQVTRVAREVGTEGKLGGQAEVTGVAGTWKDLTDSVNSMASNLTAQVRN

IADVTTAVANGDLSKKITVDVRGEILELKDTFNTMVDQLRSFASEVTRVAREVGTEGKL

GGQASVPGVAGTWKDLTDSVNSMASNLTAQVRNIADVTTAVARGDLSKKITVDVKGEIL

ELKNTFNTMVDQLSSFAAEVTRVAREVGTEGKLGGQAEVTGVAGTWKDLTDSVNSMASN

LTAQVRNIAAVTTAVANGDLSKKITVDVRGEILELKNTINNTMVDQLNAFASEVTRVAR

EVGTEGKLGGQASVPGVAGTWKDLTDNVNFMAGNLTNQVRGIAKVVTAVANGDLKRKLA

FDAKGEIAALADTINGVIETLATFADQVTTVAREVGVEGKLGGQASVPGAAGTWKDLTD

NVNQLAANLTTQVRAIAEVATAVTKGDLTRTIRVEAQGEVASLKDTINEMIRNLKDTTL

KNSEQDWLKTNLAKFSRLLQGQKDLLTVGRLILSELAPVVGAQQGVFFTMDVAKEEPIL

KLLASYAYKVRKHVDNHFKLGEGLVGQCALEKEKILLVNAPPDYIRITSGLGEAPPVNI

IVIPVLFEGQVKAVIELASFERFSPTHQAFLDQLTESIGIVLNTIEANMRTEDLLKQSQ

SLARELQSQQEELQQTNAELGEKARLLAQQNVEVERKNREVEQARQALEEKARQLAITS

KYKSEFLANMSHELRTPLNSLLILSDQLSKNNDRNLTGRQVEFAKTIHSSGNDLLALIN

DILDLSKIESGTVIVDVGELSFSDLQDYVERTFRHVAESKKLEFELNFAQNLPQVIYTD

AKRVQQVLKNLLSNSFKFTERGSVALDVDLVTSGWAPENEGLSRAGAAIAMSVRDTGIG

IPHDKQQIIFEAFQQADGSTSRKYGGTGLGLAISREIAWMLGGEIKLSSKPGSGSSFTL

YLPLTYTPARPRRKEQTVEVPSAPPAVVSGDVPPRSAAEPPPHLLNQSVDDSAGLKPSD

SVVLIVENDASFAHFVMDVAHDHGFKAILAYRGGAALSIVRERRVNAITLDINLPDMDG

WRVLDRVKRDLETRHIPVQVITTDEERERALRMGAKGVLCKPLKTRDALDETFRRLSQF

MVSSRRKIVLAGPDDAERQELVELLGGDDVTIRSVASGEEALDALVTERPDVLILRLDL

PDVRCFDLIGQLAQGSGSTDLPVLVYAPEEISPADEAQLSRFSQLMVLKHVRSKERLFD

DVSLFLHRPVAALSERQLQIVEELHQSNKVLVGKKVLVVDDDVRNIFAMTTILDAQHMK

TVYVETGRAAIEMLQRTPDIEMVLMDIMMPEMDGYDTIRAIRARPEHHALPIIAVTAKA
                    MKGDREKCFEAGANDYISKPVDPEHLLAMLRLWLHR*"
     CDS         complement(76992..77699)
                 /note="ORF10"
                 /note="probable transcriptional regulator of MarR type"
```

```
/translation="MGTLPSPARQRVIGAITRRFGSDRGPSLKGLNSRSAAVVTIDAPC

KEDVTSEREAASVKEASWTRATSCQGTSFLVVKGSSCPGRGMKHSCQHLCDGFQAAMDV

LAKPWNGLIIATLDEGPLRFGEIGERLDAISDRMLSSRLKELEALGLVVRRVLPGPPVR

VEYELTDSGRGFQAVAQAISRWGEMLAESAPRAGTGASSSSGARGRVKAKAGRAAPRTR
                    SRNAARVRGEGTA*"
     CDS             77581..78699
                     /note="ORF11"
                     /note="predicted NADH:flavin oxidoreductase of OYE type"

/translation="MTTAADLLFSPFKLGPLSLPNRLVMAPMTRCRAGEGNVPTELNAV

YYEQRASAGLIITEATQVSQQGVGYLRTPGIHTDAQVEGWRRVTDAVHRAGGHIFAQLW

HVGRASHVSFQPGRQAPVSSSALPIRTGHAHTPEGAQPYSTPRALETREIPGVVAQFED

GARRARAAGFDGIELHAANGYIIDQFLRDGVNQRTDQYGGSVENRARFLLEIVDAVTGV

FDPDRVGARVSPLGGYNDMSDSNPKAIFGHVAAELSARKLAYLHVVEPVDGQAEDAAGR

VMPLLRERFRGVLMANGGYTLETAEAALRTGAADLVSFGAPFLANPDLPERLSRRAPLN
                    PPDVSTFYSEGPRGYTDYPRLAEAQAAAQPSA*"
BASE COUNT    10766 A    27557 C   28922 G   11624 T        0 OTHER
ORIGIN
        1 GATCTGGTCC ACGACGCCCA GCCCCCGTGC GAGCTCGCGG GCGCCGCCCG CTCGAGGTGC
       61 CCGAAGATCA CCGGCAGCCC GCCGTCCGAG CGGCCGAGGG CACGGGTGGG GCCTGGACCT
      121 GCAAGACCAG CGCGCCAAGC GGGGGTCCGA GCTCGTGCGG GGCGGCCGAC ACGAGCCTCG
      181 CGGATCTGGC TTGCCCCCCG CTCCGTACCT GCTCGACAGG GGACCACCCA GCGCACGCTG
      241 TCATTCGGTC GAGCACCCGC CTTCTGTTCG CAGGGAGCGC CTTGAAGAGC GGACAGGGA
      301 GCCTTCCGGA AAGCCAGTTG CCTGGTATCC ACCATGTTTC CGGTGTGCTT CGGCTCAGGC
      361 AACGGGCCAC ATCCGCCCGG GCGACTCGAT CGGATGCAAC GTGATCGAGT CCGCATGGTC
      421 GGCAGCGGTC CCCGCCCCCT CCTGCCTCTG ACAACAGCGG ATCGCAGCCC CGCCTGTGAT
      481 GCCGGCAGCG GCACATCTAC ACAGATGAAT GTTCACCCGG CGGGCAATGT TCCGGGCTGA
      541 AAAGAATAAT CCAGTCTCAG TTCAATGAGG TGCCATGGCG GCGCCAAACT CACCACATCG
      601 CACTCGGCGC AATCAGTCGA CCATAGAATT GAAATGTAAG ACAAATTACA TGCGAAAATG
      661 CTTGAAATAT CATAAAAAAG AATGGATTGA TTGGTTGCGT AGATCACCGT TGATGCTAGC
      721 CTCGACTCGG ACACTCTTTG TGCCTTGCGG CCGCCCTTGT TTTCATGGGC TTCCCGTGCA
      781 TCCGCAGGGT TTCGGGGTCC GCAGCGTCTC CGGCCACCTG TGTCAAGGTG CGCCGGACCT
      841 TCAGATCCAG GCCGTTCCGC GCCGCCCGGT CTACGAAAAG TGCCCAAGTC GAGGCTCGCT
      901 TGTCACGCAT CTTCTCTATG CCCGACACGT CGTCGTCTAG CCCCGTACTA GCGATGGGGC
      961 TACGGGATTC AGATGCCCGG TTCGTGGAGG ATACGCCGCC TGCCTCGGAC CGCCCTCGTC
     1021 CATTCGCGGG CATTGCGGTG GTGGGAATGG GATGTCGCTT GCCCGGCGGC GTCGATTCGC
     1081 CCGAATCCTT GTGGGCGGCC CTATCCGAAG GGCGCGACCT TATCAGCGAG GTCCCGCCGG
     1141 ACAGGTGGGA TGTCAATGCC CACTACGACG CCGACGCGAG TGTCCCGGG AAGATCGCGA
     1201 CCCGTCATGG CGGCTTCCTC GCCGGGGTCG CGGCGTTCGA CGCGCCCTTC TTCGACCTCT
     1261 CGCCGCGCGA GGCGAAGCAT ATGGATCCGC AGCAGCGCCT CGGCCTCGAG ACGGCGTGGG
     1321 AGGCGCTGGA GGACGCAGGC CTGGACGCGA GGAGCTTGCG GGGCAGCCGG CAGGGGTGT
     1381 TCGTCGGCTC GATGTGGGCG GAGTACGACG TGCTCGCGTC GCGACACCCC GAATCCATCT
     1441 CGCCGCACGG GGCCACGGGG AGCGACCCGG GGATGATCGC GGCGCGCATC GCCTACACCT
     1501 TCGGCCTTCG TGGGCCGGCC TTGTCGGTGA ATACGGCGTC GTCGTCCTCC CTCGTGGCGG
     1561 TGCACCTCGC ATTGCAAAGC TTGCAGAGCG GAGAGTGCGA GCTCGCGCTG GCCGGTGGCG
     1621 CGAACCTCAT CCTGACCCCG TACAACACGA TCAAGATGAC GAAGCTCGGG ACGATGTCGC
     1681 CCGACGGCCG GTGCAAGGCG TTCGACCACC GCGCCAACGG CTACGTGCGC GCCGAGGGCG
     1741 TCGGGTTCGT GGTCCTGAAG CGGCTGTCGC GCGCGACCGC GGACGGGGAT CGCATCTATG
     1801 CGGTCGTGCG TGGCTCGGCC GTGAACAACG ACGGGCTCAC CGAGGGGCTG ACCGCGCCGA
     1861 GCGTGGAGGC GCAGGAGGCC GTGCTGCGAG AGGCGTACGC GCGCGCCGGG GTGTCTCCCG
     1921 CCGAGGTGGA CTACGTCGAG GCGCATGGGA CGGGGACGCC GCTCGGCGAT CGCGTGGAGG
     1981 CGACGGCGCT GGGACGGGTG CTCGGCGCAG GACGCGCGGC GGATCGCGCG CTGCGGGTCG
     2041 GTTCGGTCAA GACCAACCTC GGTCACGCGG AAGCAGCCGC CGGGGTCGCC GGTCTGATGA
     2101 AGACGGCGCT GTCGCTGCGC CACGGATCGC TTCCGGCGAG CCTGCACGTC GAGCGCCCGA
     2161 ACCCCGAGAT ACCCCTCGAA GCGCTGGGCC TCCGGCTCCA GACGGAGCTC GGCGCATGGC
```

```
2221 CGGAGGTCGA TCGGCCCCGG CGAGCAGGCG TGAGCTCCTT CGGCTTCGGC GGCACGAACT
2281 GCCATGTGGT GCTCGAGGAG TGGCGCGGAG GCGTCGAGCA GAGCGCCGCC GAGACGGGCA
2341 GCGAACCCGG CGCCGCCGTA TCGCCGCCTG CCCTTCCCCT GGTGCTGTCG GCGAGGGACC
2401 ACGGGGCGCT GCGGGCGCAG GCGGGCCGGT GGGCGGCGTG GCTCACGGAG CACCGCGAGG
2461 CGCGCTGGGC GGACGTCATC CACACGGCGG CAGCGCGGCG GACGCACCTG GGCGCTCGGG
2521 CCACGGTGGT GGCGGCGGGC GTGGCCGAAG CCGTCGATGC GCTGAGGGCC CTGGCCGACG
2581 GGCGCGCCCA CGGGGCCGTG ACGGTCGGCG AGGCGCGCGA GCGGGGCAAG GTGGTCTTCG
2641 TGTTTCCGGG CCAGGGCAGC CAGTGGCCGG CGATGGGGCG AGCGCTCCTG TCCGCGTCGA
2701 GGGTGTTCGC CGAGGCCGTC GAGGCGTGCG ATGCGGCGCT GAGGCCGCTG ACGGGCTGGT
2761 CGGTGCTCTC GTTGCTGCGC GGCGACGCCG GGGAGGCAGC GCCGTCGCTC GACCGCGTCG
2821 ACGCGGTGCA GCCGGCCCTG TTCGCGATGG CCGTCGGCCT GTCCGCGGTC TTTCGCGCGT
2881 GGGGCCTCGA TCCTTCGGCC GTGGTGGGCC ACAGCCAAGG CGAGGTCCCG GCGGCGTACG
2941 TCGCGGGGGC GCTCTCGCTC GACGACGCGG CGCGGGTCGT GGCGGTCCGA AGCGCGCTCG
3001 TGCGGCGGCT CTCGGGCGCA GGGGCGATGG CGGCGGTGGA GCTGCCGGCC GGCGAGGTGG
3061 AGCGCCGCCT GGCGCCGTTC GGGGGGGCTC TGTCCGTTGC GGTGGTCAAC ACGTCGAGCT
3121 CGACGGCCGT TTCGGGAGAC GCCGAGGCGG TGGACAGGCT GGTCGCGCAG CTCGAGGCCG
3181 AAGGCATCTT CTGCCGAAAG GTGAACGTCG ATTACGCATC CCACAGCGCG CACGTGGACG
3241 TCGTGCTGCC AGAGCTCCTG GAGCGCCTGG CGCCGATCCG ACCAGGGGCC ACGAGGATCC
3301 CCTTCTATTC GACCGTGACC GGCGGTGTGC TGGAGGGGAC GGCGCTCGAC GGGGCGTACT
3361 GGTGCCGCAA CCTGCGCCAG CCGGTACGGC TGGACCGCGC GCTCGCCCGG CTGCTGGACG
3421 ACGGCCATGG CGTCTTCGTG GAGGTCAGTG CGCACCCGGT GCTGGCGTCG CCGCTGACCG
3481 CGGCGTGCGC CGAGCGCGAG GGCGTCGTGG TCGGCAGCCT GCACCGCGAC GACGGCGGGC
3541 TTGCGCGGCT GCTGGGCGCG CTGGGCGCGC TGCATGTGCA GGGCCAGCCG GTCGATTGGC
3601 GCGCGGTGCT GGCGCCGTTC GGCGGCGGCC TGGTGAACCT GCCGACGTAC GCATTCCAGC
3661 GCCAGCGCTA CTGGTTCGAT ACCGACGAGA GCGTTGCGCT CGCAGCGGCG TCCAGCATTG
3721 CGGAAGAGTC GTGGTCAGAG AAGCTGGCCG GGCTGTCTCC CGCGCGACGG GAAGAACGGC
3781 TGCTCGAATG GGTGCGCGCA GAAATCGCGG CGGTGCTCGG GCTGGAGGCG CCGGCGGTGC
3841 CGCCGGACGT CCCGCTGCGG GATCTCGGGT TGAAATCGCC GATCGCCGTG GAGCTGGGGA
3901 GCCGCCTGGG ACGCAGGACA CGCCGGAAGC TGCCCGTGTC CTTCGTTTAC AACCACCCGA
3961 CGCCACGAGC GATCGCTCGC GCCCTCCTGG AGGGAATGTT TTCTTCGAGC AAGGACTCTC
4021 CTCCGAGCAC CGCTGACGAC CGCCGGCCGC CGGGGGTGCC CGCCGGCGTT GCGCCCCCAC
4081 AGGCGCTGGA GACGTCCGAG ATGTCCGACG ACGAGCTGTT CCAGTCCATC GATGCGCTCG
4141 TCTAGGAAGA CCGAGCTCTC GTCGAAAAAG ACCGTTCAAC GCTGCGAGGC GAGGATTGCT
4201 CGTGGATCGA AGCGATAAAC TGCGTGCGTA TCTGGAGAAG ACCACGGCAT CGCTGGTCGA
4261 GGCGAAAAGC CGGATCCGGG AGCTGGAGGC GCGTTCGCGC GAGCCGATCG CGATCGTGGC
4321 GATGGCGTGC CGGTTTCCGG GCGGCGTCGA CAGCCCCGAG AAGCTCTGGG CCCTGCTCGA
4381 CGAGGAGAGG GACGTCATCA CCGAGGTGCC GCCCTGACTC TGGGACCTCG AGCGCTTCTA
4441 TGACCCCGAT CCGGACGCCG CAGGCAAGAC CTACAGCCGC TGGGGCGGCT TCGTGGGCGA
4501 TCTGGATCGT TTCGACGCGG CGTTCTTCGG GATCAGCCCT CGCGAGGCCC GGAGCATCGA
4561 CCCGCAAGAG CGCTGGCTGC TGGAGACCAC GTGGGAGGCC CTCGAGCGGG CCGGCGTGCG
4621 CGCGGACACG CTGGAAGGGA CCCTGGGGGG CGTTTACATC GGCCTGTCCG GCTCGGAGTA
4681 CCAGGCGGAG GCATTTCACG ATGCGGAGCG CATCGATGCC TATTCGCTGA CCGGCGCTTC
4741 GCCGAGCACA ACCGTGGGGC GCCTCGCCTA CTGGCTCGGG CTACGAGGTC CCGCGGTCGC
4801 CGTGGACACG GCGTGCAGCT CCTCGCTCGT CGCGGTGCAC CTGGCCTGCC AGGCGCTGCG
4861 GAACGGGGAG TGCGATTTTG CGCTGGCAGG CGGCGTCAAC GCGCTCCTGG CCCCCGAGAG
4921 CTATGTTGCC TTCTGCCGCC TCAGGGCGCT GTCCCCCACC GGGCGCTGCC GGACCTTTTC
4981 CGCGAACGCC GATGGCTACG TGCGCGCGGA AGGGTGCGGG GTGCTGCTGC TCAAGCGCCT
5041 GTCGGACGCG CAGCGGGATG GAGACCGTGT GCTCGCGGTC ATCCGGGGCA ATGCCATCAA
5101 CCAGGACGGT CGCAGCCAGG GGTTGACGGC GCCCAATGGG CTCGCCCAGG AGGACGTCAT
5161 CCGCAGGGCG CTGTCGCAAG CCGCGGTGGA GCCGACGACG GTCGATGTGG TCGAATGCCA
5221 CGGGACCGGC ACGGCGCTTG GCGATCCGAT CGAGGTCCAG GCGCTCGGGG CGGTTTACGG
5281 CCATGGGCGC CCCGGAGACA GGCCGCTCGT GATCGGCTCC GTCAAGACGA ACCTCGGTCA
5341 CACCGAGGCG GCCGCAGGCA TGGCCGGCCT CATCAAGGCC GTCCTTTCGC TGCAGCACGC
5401 CCAGGTGCCT CGATCGCTGC ACTTCGCTGC GCCGAGCGAT TACATTCCCT GGGATACCCT
5461 CCCCGTCCGG GTGGCCGCGC AGCGCGTCGC ATGGGAGCGA CGCGAGCACC CGCGGCGCGC
5521 CGGGGTCTCG TCGTTCGGGA TCAGCGGCAC CAACGCGCAC GTGATCCTCG AGGAGGCGCC
5581 GGCGTCGGAA GCGCCGGCAA CGGCGCCGGT GGCGGCGCCG GTGGCGGCGC CGTTGCCGGC
5641 GACGCTGCCG CTGCTCGTGT CGGGGCGGGA CGAGGCGGCG CTCAGGGCGC AAGCCGGGCA
5701 GTGGGCGGCG TGGCTCGCGG CGCACCCGGA GGCTCCCTGG GCGGACGTGG TGCACACGGC
5761 CGCCGCGCGG CGCACGCACC TGGAGGCGCG GCGGCGGGTG GCGGCGGGGA GCGCCGCCGA
5821 CGCGGCCGCG GCGCTAGAGG CGCTGGCCGC CGGACACCCG CACAGGGCGG TGTCGCTGGG
5881 CGAGGCGCGC GCGCGCGGCG AGGTCGTGTT CGTGTATCCG GGCAGGGCA GCCAGTGGCC
5941 GGCGATGGGG CGCGCGCTGC TGGCCGAGTC CGAGGTGTTC GCCGCCGCGG TCGCGGCCTG
```

```
6001 CGACGCGGCG CTGCGGCCGC TGACGGGCTG GTCGGTGCTC TCGGTGCTGC GCGGCGAGCA
6061 GGGAGAGGCG GTGCCGCCCG CGGACCGCGT GGACGTGGTG CAGCCGGCGC TGTTCGCGAT
6121 GGCCGTGGGG CTCTCGGCGG TCTGGCGGGC GTGGGGCATC GAGCCTTCGG CGGTCGTCGG
6181 CCACAGCCAG GGCGAGGTCG CGGCGGCGTA CGTCGCCGGG GCGCTGACGC TCGAGGACGC
6241 GGCGCGGGTC GTGGCGCTGC GCAGCCAGCT CGTGCGGCGC ATCGCCGGCG GCGGCGCGAT
6301 GGCCGTGATC GAGCGCCCGG TCGGCGAGGT GGAGCAGCGG CTCTCTCGCT TCGGAGGGCA
6361 GCTGTCCGTG GCGGCGGTGA ACACGCCGGG CTCGACGGTG GTGTCCGGGG ACGCCGCAGC
6421 GGTCGATCGC TTGCTGGCCG AGCTGGAGGC CGAGCGGGTC TTCGCGCGGC GGATCAAGGT
6481 CGATTACGCG TCGCACAGCG CGCACGTGGA CGCGATCCTG CCGGAGCTCG AGGCCACGCT
6541 GGCCTCGGTC GAGCCCCGTG CCTGCACCAT CCCGCTGTAC TCGACGGTGA CGGGAGAAGT
6601 GCTCGCCGGC CCGGAGCTCG GCGGCGGCTA CTGGTGCCGC AACCTGCGCG AGCCGGTGCG
6661 GCTCGACCGG GCGCTCTCGC GGCTGCTGGC GGACGGGCAC GGGGTGTTCG TCGAGGTCAG
6721 CGCGCATCCG GTGCTGGCCA TGCCGCTGTC GGCCGCGAGC GCCGAGCGCG GCGGCGTTGT
6781 GGTCGGCAGC CTGCAGCGCG ACGACGGCGG TCTGGGGCGG CTGGCGTCGA TGCTGGGCGC
6841 GCTGCACGTC CAGGGCCACG CCGTGAACTG GCAGCGGGTG CTGGCGCCGT ACGGCGGGGC
6901 GCTCGTGGAT CTGCCGACGT ACGCGTTCCA GCGCCAGCGC CACTGGCTCG AGGCGCCGCG
6961 GTACGCGGCG GAGGACACGG ACGGCGCGGC GCGGCGCGAC CCGCTGTACC GGGTCACGTG
7021 GATCGAGGCG GCGCTGGAGG AGGCGCCCTG GCGGCCGAG CGCCACGTCG TGCTCGGCGC
7081 GGACGGCGCG CTGGCGTCGG GGCTGGGGC GCTCGCGCTG GCGGGCTGC GGAGCTGCT
7141 CGAGGCGCTG GAGAACGGGG CGGCGGCGCC CGAGCGGCTG GTGCTGGACC TGACGGAGGG
7201 CCGCCCAGGC GCGGTGGCGG AGTCCGTGCA CGCCACGACG CGCAGCGCGC TCGCGCTGGT
7261 GCAGGCATGG CTCGCGGCGC CGCGGCTTTC GGGCACCGAG CTGGTCGTGG TGACGCGGGA
7321 GGCGGTGGCG GCCGGTCCGG ACGAGGGCGT GGCGGCGCTG GGCCCGCGG CGGTCTGGGG
7381 GCTGCTGCGC ACGGTCCGCG TCGAGCACCC CGAGCGCGCG GTGCGCTCGG TGGATCTGGG
7441 GCGCGAGCCG CCGGATGTCG CGGTCTTGCG GCGGGCGCTG GGGACGGCGG CCGAGCCGGA
7501 GCTCGCGCTG CGCGCGGGCG GGGCGCGGGC GCCGCGCCTG CGCGCGGTCA ACGCCGGCGC
7561 GGACGCCAGG GCGCCAGCGG CGGCGCTGGA CCCGCAGGGC ACGGTGTGGA TCACGGGCGG
7621 CACCGGGGAG CTCGGGCGGC AGGTCGCGCG GCACCTGGTC GCGGCGCACG GCGTGCGGCA
7681 CCTCCTGCTG ACGTCGCGGG GAGGCGCGGC CGCGCCGGAC GCCGAGGCGC TGGTCGAACA
7741 GCTGCGGGCC GACGGCGCCG AGACGGTCGA GGTCGTGGCG TGCGACGTGA CGGACGGCGC
7801 GGCGCTTTCG GCAGCAGTCC AGGTCGCCGC GGCGAAGCGC CCGCTGACGG CCGTGGTGCA
7861 CACCGCCGGG GTGCTGGCGG ACGGGGTGCT CACGGCGCTG ACGGCGGAGC AGCTCACGCG
7921 GGCCCTGGCG CCGAAGGTCG ACGGGGCGTG CCACGTGTAC GCCGCCGCGC AGGACCAGCC
7981 GCTCGCGGCC TTCGTGCTGT CTCCTCGAT CGTCGGTACG CTGGGCAACG CGGGCCAGGC
8041 GAACTACGGG GCTGCCAATG CGTTCCTGGA CGCGTTCGCG GCGCAGCTCC GCGCGCGCGG
8101 CGTGCCGGCG ACGAGCCTCG CCTGGGGCTT CTGGGAGCAG GCCGGGCTCG GCATGACGGC
8161 GCACCTCGGC GCCGCCGACC TGGCACGCCT CGGACGGCAG GGCCTTGTGC CGCTGTCGGT
8221 CGCGCAGGGC CTGCGCCTCC TCGACCGGGC GCTCGCGCAC CCGGAGGCGA CGCTGGTGCC
8281 GGCGGCGCTC GACCTGTCGG CGCTCCAGCG TGCGGCGAGC GACGCCGGAC GGGTGCCGCC
8341 GCTGCTGCGC GGGCTGGTGC GCGCGAGCCC CGGCCGCCCC ACGGCGACCG CGACCCCCGA
8401 AGCCGGACCA GCGGCCGCGT CGGCGCTGCG CGCACGGCTC TCGGCGTTGC CGAGGCCGA
8461 GCGGGCGGGC GCGCTGCTCG AGCTGGTGCG CGCGGAGGTG GCGGTCGTGC TGCGGCTGGC
8521 AGGTCCGGCG CAGGTGCCCG CGGACAAGCC GCTGAAGGAG CTGGGGCTCG ATTCGCTCAC
8581 GGCCGTCGAG CTGAAGAACC GCCTCGGCGC GCGCGCCGAG ACGGTGCTGC CGACGACCCT
8641 CGCGTTCGAC CATCCGACGC CGCGCGCGAT CGCGGATCTG CTGCTTCAGC GTGCGTTCTC
8701 GGAGCTCGCG GGGCGACGC GCGCACAGGC CCCGCGCGCG CGGGGAGCGC ACGACGAGCC
8761 GATCGCGATC GTGTCGATGG CGTGCCGGCT CCCGGGCGGC GTCGATACCC CCGCGGCGCT
8821 GTGGGACCTG CTCTCGGAGG GCCGGGACGC GATCGGGCCG TTCCCCGAGG GGCGCGGCTG
8881 GGATGTGGCG GGGCTGTACG ACCCCGACCC GGACGCCCCG GCAAGTCGA TCACCACGCA
8941 GGGCGGCTTC CTCTACGACG CCGATCGCTT CGATCCGACC TTCTTCGGCA TCAGCCCGCG
9001 CGAAGCGGAG CGCATGGACC CGCAGCAGCG GCTGCTGCTC GAGTGCGCCT GGGAGGCGCT
9061 CGAGCGCGCG GGCCTGCCGC CCCACGCGCT CGAGGCGAGC GCCACCGGCG TCTTCTTCGG
9121 GCTCGCTCAC GGGGACTACG GCGGGCGGCT CTTGCAGCAG CTCGAGTCCT TCGACGGCCA
9181 CGTCCTCACC GGCAACTTCC TCAGCGTCGG CTCGGGCGC ATCGCCTACA CGCTGGGCT
9241 CCGCGGCCCC GCGGTCACCG TCGACACGGC GTGCTCGTCG TCGCTCGTGG CGGTCCACCT
9301 CGCGTGCATG TCGCTCCGCG CCGGCGAGTG CGACCTGGCC CTCGCCGGCG GCGCCACCGT
9361 GATGGCCACG CCGATGATCT TCGTCGAGTT CAGCCGCCAG CGCGGCACGG CGCTGGACGG
9421 TCGTTGCAAG GCCTTCGGCG CCGGGGCCGA TGGCGCCGGC TGGTCGGAGG GCTGCGGGAT
9481 CCTGGCGCTG AAGCGGCTGT CGGACGCGCG GCGCGACGGC GACCGCGTGC TGGCGGTCAT
9541 CCGCAGCTCC GCCGTCAACC AGGACGGCCG CAGCCAGGGG CTCACCGCCC CAACGGCCC
9601 GGCCCAGCAG GACGTCATCC GCCAGGCCCT GGCCGCGGCG GGCTGACCC CGGCGGACAT
9661 CGACGCCGTC GAGGCGCACG GCACCGGAAC GCGCCTCGGT GACCCCATCG AGGCGCAGGC
9721 GCTGCTGGCG ACCTACGGCA CCGCGCACAC CGCCGAGCGG CCGCTCTGGC TCGGCTCGCT
```

```
 9781 CAAGTCCAAC CTCGGGCACA CGCAGGTCGC CGCGGGCGTG TCGGGGCTGA TGAAGCTGGT
 9841 GCTGGCGATG CAGCACGCAG AGCTGCCGAG GACGCTGCAC GCCGACCCGC CCTCGCCGCA
 9901 CGTCGACTGG TCGCAGGGGC ACGTCAAGCT CCTGAACGAG CCCGCGCCGT GGCCGCGCAC
 9961 GGACCGGCCG CGGCGCGCGG CGGTCTCGTC CTTCGGCATC AGCGGCACCA ACGCGCACGT
10021 CATCGTCGAG GAGGCGCCGG AGCCGGCGCC CGCGGCGGAC GCGAAGGCGG TGGAGGCGCT
10081 TCCGATCCTG CCGCTGCTGG TCTCGGGCGG GGACGAGGCG GCGCTGCGCG CGCAGGTGCG
10141 GCGGTTGGTG GAGCACTTGC GGTCGCACCC GGACCAGCGG CTGCTGGACG TGGCAGCGAG
10201 CCTTGCGACC ACGCGCACGC ATCTCGCCAC GCGGCTCGCG CTGCCCGTCT CGGCGGGGGC
10261 GCCCCGGGAT GCGTGGATGG ATGAGCTGGA GGCGTTTGCC AGGGGAGGAG CGGCTCCGAC
10321 GCAGGCATCG CAGACCCCCG TCGAGAGCAG CACGGGCAAG GTCGCGGTGC TGTTCACCGG
10381 CCAGGGCAGC CAGCGCGCCG GCATGGGCCG CGCCCTGTAT GCCACCCACC CCGTCTTCCG
10441 CGCCGCGCTC GACGCCGCCT GCGCCGAGCT CGACCGCCAC CTCGACCGGC CCCTCATGAG
10501 CGTCCTCTTC GCCGACGCCG GCTCCGAGGC CGCGGCGCTG CTCGACCAGA CAGCCTGGGC
10561 TCAGCCCGCC CTGTTCGCTC TCGAGGTGGC CCTCTACCGC CAGTGGGATG CCTGGGGCCT
10621 GCGCCCCGAG CTGCTGCTCG GCCACAGCAT CGGCGAGCTC GCCGCCGCCC ACATCGCCGG
10681 CGTGCTCGAC CTCGCCGACG CCTCCGCCCT GGTCGCCGCC CGCGGGCGGC TCATGCAGGC
10741 CCTCCCCCTC GGCGGCGCCA TGGCCTCCGT CGAGGCCACC GAGGACGAGC TACGCCCCTT
10801 GCTCGACCAG CACACAGGAC GCCTCTCGCT CGCCGCCCTC AACACCCCAC GCCAGTCGGT
10861 CGTCAGCGGC GACGAGCCCG CCGTCGACCA AGTCTGCGCC CACTTCACCG CCCTCGGCCG
10921 ACGCGCCAAG CGGCTCGTCG TCAGCCACGC CTTCCACTCG GCGCACATGG AGCCCATGCT
10981 CGACGCCTTC GCCCGCGTCG CTCGCGGCCT GACCTTCCAC CCGCCCCGGC TGCCCATCGT
11041 CAGCAGCGTC ACCGGCGCAC GCGCCTCCGC CGACGAGCTC ACCTCGCCCG ACTACTGGGT
11101 CCGCCAGGTG CGCGAGCCCG TCCGCTTCGT CGACGGCATG CGCGCACTGC ACGCCGCCGG
11161 CGCGGCCACC TTCGTCGAGT GCGGGCCGCA CGGCGTGCTC AGCGCCGCCG GCGCAGAGTG
11221 CCTCGCTCCC GACGGCGCTC GCGACGCCGG CTTCGTCCCC AGCCTCCGCA ACGAACGCGA
11281 CGAGGCCCTC GCCCTGGTCC ACGCCGCCTG CGCCGTCCAT GTACGCGGAC ACGCCCTCGA
11341 CTGGCTCCGC TTCTTCGACG CCACCGGCGC GCGCCGCGTC GAGCTGCCCA CCTACGCCTT
11401 CCAGCGACAG CGCTACTGGC TCCAGGCGCC GAGGCCTCGC CCCAGCCTCG AGGGCGTTGG
11461 CCTCACCGCC GCAAACCACC CATGGCTCGG CGCAGCCGTC CGCCTCGCCG ACCGCGATGG
11521 CTACGTCCTC AGCGGCCGCC TCTCCACCAG CGACCACCCG TGGGTCCTGG ACCACGTGGT
11581 GCTGGGCACG GCGCTGCTCC CGGGCACGGG CTTCGTCGAG CTGGCGTGGG CGGCGGCCGA
11641 GGCGGTCGGG CTGTCCGGGG TATCGGAGCT GGCGATCGAG GCGCCGCTGG CGCTCCCGGC
11701 GCGCGGGGCG GTGGCGCTGC AGGTCGCGAT CGAGGCCCCG GACCCGGCGG GGCGGCGCGG
11761 CATCGCGATC TACAGCCGCC CCGACGGCGC AGCCGACGCG CCCTGGACAG CGCACGCGCG
11821 CGGCGTGCTG GGCGCCGCGG CGTCCGACAG GGACGCGGCC TGGGCGCAGG GCGCGTGGCC
11881 GCCGCCGGGG GCCGTACCGG TCGACGTGAC GCAGTGGCTC GAGATCGTGG ACGCGTGGGT
11941 CGGCCCGGCG TTCCGGGGCG TCGTGGCGCT GTGGCGCGTC GGGCGGACGA TCTACGCGGA
12001 CGTGGCGCTG CCGGACGGTG TGGCGGGCAC GGCGCAGGAT TTCGGGCTGC ATCCGGCCTT
12061 GCTCGATGTG GCGCTACGCG CGTTCCTGAG AGCGGAGCTC AGCGCCGATC CGTCGCCACG
12121 AGAGGGCACG GTGGTGCCGT TCGCGTGGTC GGACGTGGCG CTCGAGGCGC GTGGGACGGC
12181 GGCGCTGCGG GTGCGCGCCG AGGTGGAGGC CGGTGGGGAT GGCGACGCGA TCACCGCGTC
12241 GATCCAGCTG GCCGACGGGC AGGGCCGCCC GGTCGCGCGG GTGGGCGCGC TCCAGATGCG
12301 GTGGACGACG GCCGAGCGGG TGCGCGCGGC CGCCGCCGCG GGCGCGGCGG AGCGCGATCT
12361 GTACCGCGTC GCGTGGACGG ACGTGGCGCT GGACGACACG GCGTTTGTGC CGGAGGAGCA
12421 CGTCGTGGTC GGCGGCGACG GCGCGCTGGC GGCGGCGCTC GGTGCACGCG CGGTGGCGGG
12481 GCTGCCCGAG CTGCTCCGCGT CGCTGCCGGA CGGCGCGGCG GCGCCACGCC GCCTGGTGGT
12541 GGACCTCACG GCGGACGCCG CGGGCGCGCT CGTCGACGCC GTGCACGCCG CGGCGCGCGA
12601 CGCGCTGTCC CTGGTGCAGG GGTGGCGTGG CGGCGCCGCAG CTGGCGGCGA CGGAGCTCGT
12661 CGTCGTGACG CGCGGCGCGG TGGCGGTCGC GCCGGACGAG GGCGTGGCGG CGCTGGGTCC
12721 CGCTGCGGTC TGGGGGCTGC TCCGCGCGAC GCGCGTCGAG CACGCGGATC GCACGGTTCG
12781 CATGCTCGAT CTGGGCCCCG GGCGCCGGA CATGGCGCTC TTGCGCCGGG CGCTCACGGC
12841 GGCCGAGGAG CCAGAGCTCG CGCTGCGCGC GGGCGGGGCG CGGGCGCCGC GCCTCGACGC
12901 GGCCGGCGAG ACCGACGGAG AGCTGGCGCC GCCCGACGGG GCGCGCTCTC TTCGCCTGTC
12961 CATCCGGACG AAAGGCTCGT TCGACGCGCT CCACCTCGCG GACGCTCCCG ATGCGCTGCG
13021 CCCGCTCGGG CCGGGGCAGG TCCGGCTCGC GGTCCGCGCT ACGGGCTCA ACTTCCGCGA
13081 TGTCTTGAAC GTCCTGGGGA CGTACCGCGG CGAAGCGGGG CCTCTCGGTC TGGAGGGGGC
13141 CGGGGTGGTG CTGGACGTGG GCGAGGGAGT CACTGCCCTT CGACCCGGCG ACCGGGTGAT
13201 GGGCATCCTG CACGCGGGCA TGGCGACCCA TGCGGTCGTC GACGCCCGGC TGCTGACGCA
13261 CATCCCGCGG GGGCTTTCCT TCGTGGAAGC GGCGACGATC CCAGCGGCCT TCCTCACCGC
13321 TCTGTACGGG CTGCGCGACC TGGGCGCGCT GAAGGCGGGG CAGCGCGTGC TGGTGCACGC
13381 CGCGGCCGGC GGGGTCGGCA TGGCGGCGGT CCAGCTGGCG CGCCTCTGGG AGCCGAGGT
13441 GTTCGCGACG GCGAGCGAGG GCAAGTGGCC GGCGCTGCGC GGGATGGGGA TCGACCAGGC
13501 CCATATCGCC TCGTCGCGAA CCCTCCACTT CAGGAAAGCC TTCCTCGACG CGACGCGGGG
```

```
13561 ACAGGGCGTC GACGTGGTGC TCGACGCGCT CGCGGGCGAG TTCGTCGACG CTTCGCTCGA
13621 CCTGCTCCCG CGCGGGGGCC GGTTCGTGGA GATGGGCAAG AGCGATGTGC GCGACCCCGA
13681 GCGCGTCGCC AAGGACCACC CCGGCGTTCG CTACACGGCC TTCGATCTGC TCGACGCGGG
13741 GCCCGACCAC ATCCAGGCGA TGCTGCGGGA GCTCGTCCCG CTGTTCGAGG AGGGCGTCCT
13801 CGCTCCCCTC CCCTTCGCGG TCCACGACCT GCGTCGCGCC CCGCACGCCT TCCGATCCAT
13861 GGCCAACGCG CGCCACGTGG GCAAGCTCGT GCTGGTGCCG CCTGCGGCGC TCGACCCTGA
13921 CGGCACGGCC TTGATCACGG GCGGGACGGG GGAGCTCGGG CGGCAGATCG CGCGGCACCT
13981 GGTGGCGGCG CACGGCGTGC GCCACCTGGT GCTCACGTCC CGGCGCGGGA TGGACGCGCC
14041 CGACGCCGCG GCGCTGGTGG GATCGCTGCG CGCGGCGGGC GCCGCGACGG TGGAGGTCGC
14101 GGCGTGCGAT GTGACAGACC GTGACGCGCT CGCGGCCGTC GTGCAGGCGA TCCCCGCGGC
14161 GCGCCCGCTG ACCGCCATCG TGCACACGGC CGCCGTGCTG GACGACGGCA TCGTGGCGGG
14221 GCTCTCGGCC GAGCAGCTCG CGCGCGTGCT GCGGCCGAAG GTCGACGGCG CCTGGCGGCT
14281 CTACGAGGCG ACGCGGGACG CGCCGCTCGC GGCGTTCATG CTCTTCTCGT CGGTCGCCGG
14341 CACGCTGGGC AGCTCGGGGC AGGCGAACTA CGCCGCCGCG AACGCGTTCC TCGACGGGCT
14401 GGCGGCAGAG CTCCGCACGC GCGGCGTGCC GGCGATGAGC CTCGCGTGGG GCTTCTGGGA
14461 GCAGGGCGGG ATCGGGATGA CGGCGCACCT CGGCGCCGCC GACCTGGCGC GGCTGAAGCG
14521 GCAGGGCATC GCGCCGATGA CGGTCGCGCA CGGCCTGCGG CTGCTCGACC GCGCCCTCGA
14581 GCGCCCGGAC GCGGCGCTGG TGCCGGCCTC CCTGGACGTG GCGGTGATCC AGCGGGCGGC
14641 GAGCGACCAC CGTCAGGTGC CGCCCATGCT GCGCGGGCTC GTCCGCGTCG CGCCGCGGCA
14701 GGCGGCAGGG GCAGCCAACG GCAGGAGCCA TGAAGCCTCG ACCCTGCGGC AGCAGCTCGC
14761 CGCCCTGCCC GAACCGGAGC GGCAGCGAGC GTTGCTCGAT CTGGTCCGGA CCGAGGCGGC
14821 CGCCGTCCTG GTGCTGCGCG GGCCGGACGC CGTCCCCGCC GACAAGCCGC TCAGGGAGCT
14881 CGGGCTCGAC TCGCTCACGG CAGTGGAGCT CAGGAATCGG CTCAGGACCC GTGCGCAGAC
14941 CGATCTCCCA TCGACCCTCG CCTTCGACTA CCCGACGCCG AAGGCGGTCG CCGTGTATCT
15001 AGCCCAGGAG CTCGACGTTC ACGACGTCAT GACGGAGATG CGCGGACCGA GCTTGCGCTC
15061 TGACGACGAG ATCAAGTCGG CCATCGCGAG CATCCGGATC TCGACGCTAC GCCAGGCGGG
15121 GCTGCTCGAC AGCCTGCTTC GGCTCGCCGC CAGCGAAGCC GTCTCCACAT CCAGCGACAC
15181 GACACCTGAA ACCGACGAGC TGACGCTGCA GCATGTTGGA GACGATGAGC TGGCACGGCT
15241 TGTCTTCGAC CTCGCCGGAG GAGCGCAATG AAAGAAGATA TCTCCGCCCG TCAAGCTCTC
15301 GAGAAGAGCT TCATTGAACT TCGCCGTATC AAGCGGGAGC TCGATCAGCT CAAGGCGAAG
15361 TCGAGCGAGC CGATCGCGAT CGTGTCGATG GCGTGCCGGC TCCCGGGCGG CGTCGATACC
15421 CCCGCGGCGC TGTGGCAGCT GCTCTCGGAG GGCCGGGACG CGATCGGGCC GTTCCCCGAG
15481 GGGCGCGGCT GGGATGTGGC GGGGCTGTAC GACCCCGACC CGGACGCGCC GGGCAAGTCG
15541 ATCACCGCGC AGGGCGGCTT CCTCTACGAC GCCGACCGCT TCGATCCGGC GTTCTTCGCC
15601 ATCAGCCCGC GCGAAGCGGA GCGCATGGAC CCGCAGCAGC GGCTGCTGCT CGAGTGCGCC
15661 TGGGAGGCGC TCGAGCGCGC GGGCCTGGCG CCTCACTCGC TCGAGGCGAG CGCCACCGGC
15721 GTCTTCGTCG GGCTGTCGGT CACGGACTAC GGCGGGCGGC TGCTGCACGA GCCCGAGGCC
15781 CTCGACGGCT ACATCGCCAC CGGCACCCTG CCCAGCGTCG GCTCGGGGCG CATCGCCTAC
15841 ACGCTGGGGC TCCGCGGCCC CGCGGTCACC GTGGACACGG CGTGCTCGTC GTCGCTCGTG
15901 TCCCTCCACC TCGCGTGCAT GTCGCTCCGC GCCGGCGAGT GCGACCTGGC CCTCGCCGGC
15961 GGCGCCACCG TGATGGCCAC GCCCATGGCC TTCATCGAGT CAGCCGACA GCGGCACG
16021 GCGCTGGACG GTCGTTGCAA GGCGTTCGGC GCCGGGGCCG ATGGCGCCGG CTGGTCGGAG
16081 GGCTGCGGGA TCCTGACGCT GAAGCGGCTG TCGGACGCGC GGCGCGACGG CGACCGCGTG
16141 CTGGCTGTCA TCCGCGGCTC CGCCGTCAAC CAGGACGGGC GCAGCCAGGG GCTCACCGCC
16201 CCCAACGGCC CGGCCCAGCA GGACGTCATC CGCCAGGCCC TGGCCGCGGC GGGGCTCACG
16261 CCCGCCGACG TCGACGCCGT CGAGGCGCAC GGCACCGGCA CGCGCCTCGG CGACCCCATC
16321 GAGGCGCAGG CGCTGCTGGC GACCTACGGC ACCGCGCACA CCGCGGAGCG GCCGCTCTGG
16381 CTCGGCTCGC TCAAGTCCAA CCTCGGGCAC ACGCAGGCCG CCGCGGGCGT GTCGGGGCTG
16441 ATGAAGCTGG TGCTGGCGAT GCAGCACGCA GAGCTGCCGA GGACGCTGCA CGCCGACCCG
16501 CCCTCGCCGC ACGTCGACTG GTCGCGTGGG CACGTCAAGC TCCTGAACGA GCCCGTGCCG
16561 TGGCCGCGCA CGGACCGGCC GCGGCGCGCG GCGGTCTCGT CCTTCGGCTT CAGCGGCACC
16621 AACGCGCACG TCATCGTCGA GGAGGCGCCG GCGGCCTCCA CCGAGGCGAC GACCCGCGGG
16681 GAGAAGACGC CCGCGGCCGC GCCGCCGTCG ACCCTGCCGC TGCTGGTCTC GGGGGCGGAC
16741 GAGGCGGCGC TACGAGCGCA TGCGGGGCGG TGGGCGGCGT GGCTCGCGGC GCACCCGGAG
16801 GCGGGCTGGG CGGACGTGGT GTACACCGCG GCAGCGCGTC GGACGCACCT GGGGGCGCGC
16861 GCGGCGCTGA CGGCGGCGGA CGCGGCCGGC GCGGTCGCAG CGCTGACGGC GCTCTCGCAG
16921 GGGCAGCCGC ACGCCGCGCT CGCCGTGGGC GAGGCGCGCG CTCGGGGAA GGTCGTCTTC
16981 GTGTTTCCGG GCCAGGGCAG CCAGTGGCCG GCGATGGGGC GGGCGCTGCT CTCGCAGTCG
17041 GAGGTGTTCG CCGCGGCGGT CGCGGCGTGC GACGCGGCGC TGCGGCCGTT CACCGGCTGG
17101 TCGGTGCTCT CGGTGCTGCG CGGCGACACG GCGCGGAGG TGCCGCCGCT GGAGCGCGTC
17161 GACGTCGTGC AGCCGGCGCT GTTCGCGATG GCGGTGGGGC TCGCCGCGGT GTGGCGCGCG
17221 TGGGGCCTCG AGCCGTCGGC GGTGGTGGGC CACAGCCAGG GGGAGGTCCC GGCGGCGTAC
17281 GTCGCGGGGG CGCTGTCGCT CGAGGACGCG GCGCGGATCG TGGCGCTGCG CAGCCGGCTC
```

```
17341 GTGCGGCGCC TGTCCGGAAC TGGCGCGATG GCCGTGATCG AGCTCCCGGT GGGCGAGGTC
17401 GAGCAACGGC TCTCGCGGTT CGGCGGCGCG CTGTCGGTGG CGGCGGTCAA CACGCCGCGC
17461 TCGACGGTGG TGTCGGGCGA TGCCGAGGCG GTCGATCGAC TGCTGACGGA GTTCGAGGGC
17521 GAGCAAGTCT TCGCGCGGAA GGTCAACGTC GACTACGCGT CGCACAGCCG ACACATCGAC
17581 GGGCTGCTGC CAGAGCTGGA GGACGGCCTG GGCGCGGTGC GGCCGCGCGC GAGCACGATC
17641 CCGTTCTACT CGACGGTGAC CGGGACGGTG CTGACGGGCG CGGAGCTGGA CGCGGCGTAC
17701 TGGTGTCGCA ACCTGCGCGA GCCGGTGCGG CTCGACCGGG CGCTCTCGCG GCTCCTGGAC
17761 GACGGGCACG GCCTGTTCGT CGAGGTCAGC GCGCACCCGG TGCTGACGCT GCCGCTCACA
17821 GGAGCGAGCG CGACGAGCGG CGGTGTGGTG GTCGGCAGCC TGCAGCGCGA CGACGGCGGG
17881 CTGGGACGGC TCCTGGGGGT GCTGGCCGCG CTGCACGTGC ACGGCCACGA CGTCGACTGG
17941 CGCGCGGTGC TGGCGCCGTG GGGCGGAGGC GTGGCGGACT TGCCGACCTA CGCGTTCCAG
18001 CGGCAGCGCT ACTGGCTCGA GGCGCCGCGC GGCCGGGCAG GGCTGGAGAG CGGAGGGCTC
18061 CTGGCGGTGA AGCACCCGTG GCTCAGCGCG GCGGTGCGGC TGGCCGACCG CGACGGCTAC
18121 GTGCTGAGCG GACGGCTGTC GACGGTCGAG CACGCGTGGG TCCTGGACCA CGTGGTGCTG
18181 GGCACGGTGA TCCTCCCGGG CACGGCGTTC GTCGAGCTGG CGCTCGCGGC GGCCGATGCC
18241 GTCGGACTGC CCTCGGTGTC AGAGCTCACG ATCGAGGCGC CGCTGGCGCT GCCGGCGCGC
18301 GGGGCGGTGA CGCTGCAGGT GACGGTGGAG GCGTTGGACG CGACGGGGCG GCGGGGCTTC
18361 GCGGTCCACA GCCGGCCCGA CGGCGCGCAC GACGCGCCGT GGACGGCGCA CGCGCGCGGC
18421 GTGCTGGGCG CAGCGCCCGC GGCGGCCACG ACGGCGTGGG CGGCGGGCGC GTGGCCGCCG
18481 GCGGGGGCCG AGCCGGTCGA CGTCACGCGG TGGGTCGAGG CGCTCGACGC GTGGGTCGGC
18541 CCGGCGTTCC GGGGCGTGAC GGCGGCGTGG CGCGTGGGGC GGTCGATCTA CGCCGACCTG
18601 GCGTTGCCCG AGGGGGTCTC GGAGCGGGCG CAGGACTTCG GCTTGCATCC GGCCTTGCTC
18661 GATGCGGCGC TCCAGGCCCT CCTGCGGGCG GAGCTCGGCG CAGGCTCGTC GCCGCGGGAG
18721 GGCATCCCGA TGCCCTTCGC GTGGTCGGAC GTGGCGCTCG AGGCGCGGGG GGCAGCGGCG
18781 CTGCGGGCGC GCGTGGAGGT CGAGGACGCC AGCGATGGGG ACCAGCTCGC GGCGTCGATC
18841 GAGCTGGCCG ACGCGCAGGG GCAGCCGGTC GCGCGCGCAG GGACGTTCCG GGCGCGGTGG
18901 GCGACGGCGG AGCACGTGCG CAAAGCTGCG GCGGGTGCGA GCGAGCGTGA CCTGTACCGG
18961 GTCACGTGGA CGGACGTGGC GCTGGAAGAA GCGGCGTGGG CGCCGGAGGA GCACATCGTG
19021 CTCGGCGGCG ACGGGCGCT CGCGGCGGCG CTGGGCGCGC GCACGGCGGC GCTGCCGGAG
19081 CTCATCGCGG CGCTGCCGGA GGGCGCGGCC GCGCCGCGCC GGCTGGTGAT CGACGCGGCC
19141 GCGGGCGACC CCGGCGACGG CCTGGTCGCG GCGGCGCACG CGGCGACGCA GCGGGTCCTG
19201 TCGCTGGTGC AGGGGTGGCT CTCGGAGGCG CGGCTCGCGG ACAGCGAGCT GGTGGTGGTG
19261 ACGCGCGGCG CTGTGGCCGC CGGGCCCGAC GACGGCGTCG CGGCGTTGAG CCACGCGCCG
19321 CTGTGGGGGC TCGTGCGCAC GGCGCGCCAG GAGAACCCCG GCCGGGCGGT GCGCCTCGTC
19381 GACCTGGGGC CCGAGCCGCT GGACGGAGCG CTCGTGCGCC GGGCGGTGGC GGCGGCCGAG
19441 GAGCCGGAGC TCGCGCTGCG CGGGGGCGCG GCGCGCGCGC CACGCCTGCG CGAGGTGCGC
19501 GCGGGCGCGG CCGACGCGGC GCGACCGACG CGGCTGGATC CCGGCGGGAC GGTGCTGATC
19561 ACGGGCGGCA CCGGGGAGCT CGGGCGGCAG GTCGCGCGGC ACCTGGTCGC GGCGCACGGC
19621 GTGCGGCACC TCGTGCTCAC GTCGCGGCGC GGGATGGATG CGCCGGACGC CGCGGCGCTG
19681 GTGGACGAGC TGCGCGCCGC GGGCGCCGCG ACGGTCGACG TCGCGGCGTG CGACGTCGCC
19741 GACGGCGCGG CGCTGGGGGC GGTCATCGCG GCGATCCCGG CTGCACACCC CCTCACGGCG
19801 GTCGTGCACA TGGCGGGCGT GCTGGACGAC GTCATCGTGA CGAAGCTCTC GGCCGAGCAG
19861 CTCGCGCGCG TGCTGCGGCC GAAGATCGAC GGCGGCTGGC ACCTGGCCGC GGCGACGCGA
19921 GGCCATCGGC TCGCGGCCTT CGTGCTGTTC TCGTCGGCGG CCGGCACGCT GGGCAGCGCG
19981 GGGCAGGCGA ACTACGCCGC GGCCAACGCG TTCCTGGACG CGCTCGCGGC GCAGCTCCGC
20041 GCGCGCGGCG TGCCGGCGAT GAGCCTCGCC TGGGGCTTCT GGGAGCAGGC CGGGCTCGGC
20101 ATGACGGCGC ACCTCGGCGC CGCCGACCTG GCACGCCTCA GACGGCAGGG CATCGCGCCG
20161 ATCGCGCTCG CGCAGGGCAT GCAGCTGCTG GACCGGGCGC TCGCGCGCCC GGAGGCGGCG
20221 CTGGTGCCGG CGGCGCTCGA CCTGTCGGCG CTCCAGCGTG CGGCGAGCGA CGCCGGGCAG
20281 GTGCCGGCGC TGCTGCGCGG GCTCGTGCGC CCGGCGGCCG GCGGCGCGCG GCGTCGCCT
20341 GCGGCCGCCG CGACCGGAGC GGCGGCGCTG CGCGCGCGGC TCTCGGCGCT GCCCGAGGCC
20401 GAGCGGGCGG GCGCGCTGCT CGAGCTGGTG CGCGCGGAGG CGGCGGCCGT GCTGCAGCTG
20461 GCAGGTCCGG CGCAGGTCCC CGCGGACAAG CCGCTGAAGG AGCTGGGGCT CACCTCGCTC
20521 ACGGCCGTCG AGCTGAGGAA CCGGCTCGCC GCGCGCGCCG AGACGGCGTT GCCGGCGACC
20581 CTCGCGTTCG ACCATCCGAC GCCGCGGCGG ATCGCGGATC TGCTGCTTCA GCGTGCGTTC
20641 TCGGAGCTCG CGGCCGCGGG GGCGACGCGC GCACAGGCCC CGCGCGTGCG GGGAGCGCAC
20701 GACGAGCCGA TCGCGATCGT GTCGATGGCG TGCCGGCTCC CGGGCGGCGT CGATACCCCC
20761 GCGGCGCTGT GGCAGCTGCT CTCGGAGGGC CGGGACGCCA TCGGGCCGTT CCCCGAGGGG
20821 CGCGGCTGGG ATGTGGCGGG GCTGTACGAC CCCGACCCGG ACGCCCGGG CAAGTCGGTC
20881 ACCAACCTGG GCGGCTTCCT CTACGACGCT GACCGCTTCG ATCCGACCTT CTTCGGCATC
20941 AGCCCGCGCG AAGCGGAGCG CATGGACCCG CAGCAGCGGC TGCTGCTCGA GTGCGCCTGG
21001 GAGGCGCTCG AGCGCGCGGG CCTCGCGCCC CATTCGCTCG AGGCGAGCGC CACCGGCGTC
21061 TTCGTCGGGC TGGTGTACAG CGACTACGGC GGGCGGCTGC TCGAGCACCT CGAGGTCTTC
```

```
21121 GACGGCTACG TCGCCACCGG CAGCTTTCCC AGCGTCGGCT CGGGGCGCAT CGCCTACACG
21181 CTGGGGCTCC GCGGCCCCGC GGTCACCGTC GACACGGCGT GCTCGTCGTC GCTCGTGTCC
21241 CTCCACCTCG CGTGCATGTC GCTCCGCGCC GGCGAGTGCG ACCTGGCCCT CGCCGGCGGC
21301 GCCACCGTGA TGGCCACGCC CATGGCCTTC ATCGAGTTCA GCCGACAGCG CGGCATGGCC
21361 CCGGACGCAC GGTGCAAGGC CTTCGGGGCG GCGGCGAACG GCATCGGCCC CGCGGAGGGC
21421 TGCGGGCTCC TGGTGCTCAA GCGGCTGTCG GACGCGCGGC GCGACGGCGA CCGCGTGCTG
21481 GCCGTCCTCC GCGGCTCCGC CGTCAACCAG GACGGCCGCA GCCAGGGGCT CACCGCCCCC
21541 AACGGCCCGG CCCAGCAGGA CGTCATCCGC CAGGCCCTGG CCGCGGCGGG GCTGACCCCG
21601 GCGGACATCG ACGCCGTCGA GGCGCACGGC ACTGGCACGC GCCTCGGCGA TCCCATCGAG
21661 GCGCAGGCGC TGCTGGCGAC CTACGGCACC GCGCACACCG CCGAGCGGCC GCTCTGGCTC
21721 GGCTCGATCA AGTCCAACCT CGGGCACACG CAGGCCGCCG CGGGCGTCGT GGGGCTGATG
21781 AAGCTGGTGC TGGCGATGCA GCACGCAGAG CTGCCAAGGA CGCTGTATGC CGAGCCCCGA
21841 TCGCCGCACA TCGACTGGTC GCAGGGGCAC ATCAACCTCC TGAACGAGCC CGTGCCGTGG
21901 CCGCGCACGG ACCGGCCGCG GCGCGCGGCG GTCTCGTCCT TCGGCATCAG CGGCACCAAC
21961 GCGCACGTCA TCGTCGAGGA GGCGCCGGCG GCCGCGCAGA CGGCGGCGGA GGCGGCGGCG
22021 GCGGTGCCGT CGACGCTGCC GCTGCTCCTG TCGGGTCGCG ACGAGCCGGC GCTGCGCGCC
22081 CAGGCCGGGC GGCTCGCCGA GCACCTGCGC GCCCACCCGG ACCAGCGGCT GCTCGACGTC
22141 GCCGCGAGCC TGGCCACGAC GCGCACGCAC CTCGCCACGC GGCTCGCGCT GCCGCTCGCG
22201 CCGGACGCAG CCACGGAGGA GCTGGGCGCC CGCCTTGCCG AGTTCGCCTC AGGCGGCCCG
22261 GCGCCCAGCG GCGCCGCCGT GACCGCGCCG GGGCAGCCGC CCGGCAAGGT CGCGGTGCTC
22321 TTCACCGGCC AGGGCAGCCA GCGCGCCGGC ATGGGGCGCG CCCTGTACGC CACCCACCCC
22381 GTCTTCCGCG CCGCGCTCGA CGCCGCCTGC GCCGAGCTCG ACCGCCACCT CGACCGGCCC
22441 CTCATGAGCG TCCTCTTCGC CGACGCCGGC TCCGAGGCCG CGGCGCTGCT CGACCAGACA
22501 GCCTGGGCTC AGCCCGCCCT CTTCGCTCTC GAGGTGGCCC TCTACCGCCA GTGGGATGCC
22561 TGGGGCCTGC GCCCCGAGCT GCTGCTCGGC CACAGCATCG GCGAGCTCGC CGCCGCCCAC
22621 ATCGCCGGCG TGCTCGACCT CGCCGACGCC TCCGCCCTGG TCGCCGCCCG CGGGCGGCTC
22681 ATGCAGGCCC TCCCCCTCGG CGGCGCCATG GCCTCCGTCG AGGCCACCGA GGACGAGCTA
22741 CGCCCCTTGC TCGACCAGCA CACAGGACGC CTCTCGCTCG CCGCCCTCAA CACCCACGC
22801 CAGTCGGTCG TCAGCGGCGA CGAGCCCGCC GTCGACCAGG TCTGCGCCCA CTTCACCGCC
22861 CTCGGCCGAC GCGCCAAGCG GCTCGTGGTC AGCCACGCCT TCCACTCGGC GCACATGGAG
22921 CCCATGCTCG ACGCCTTCGC CCGCGTCGCT CGCGGCCTGA CCTTCCACCC GCCCCGGCTG
22981 CCCATCGTCA GCAGCGTCAC CGGCGCACGC GCCTCCGCCG ACGAGCTCAC CTCGCCCGAC
23041 TACTGGGTCC GCCAGGTGCG CGAGCCCGTC CGCTTCGCCG ACGGCATGCG CGCACTGCAC
23101 GCCGCGGGCG CGGCCACCTT CGTCGAGTGC GGGCCGCACG GCGTGCTCAG CGCCGCCGGC
23161 GCAGAGTGCC TCGCTCCCGA CGGCGCTCGC GACGCCGGCT TCGTCCCCAG CCTCCGCAAG
23221 GACCGCGACG AGGCCCTCGC CCTGGTCCAC GCCGCCTGCG CCGTCCATGT CCGCGGGCAC
23281 GCCCTCGACT GGCTCCGCCT CTTCGACCCC TCCGGCGCGC GCCGCGTCGA GCTGCCCACC
23341 TACGCCTTCC AGCGACAGCG CTACTGGCTC CAGGCGCCGA GGCCTCGCCC CAGCCTCGAG
23401 GGCGTTGGCC TCACCGCCGC AAACCACCCA TGGCTCGGCG CAGCCGTCCG CCTCGCCGAC
23461 CGCGATGGCT ACGTCCTCAG CGGCCGCCTC TCCACACTCG ACCACCCGTG GGTCCTGGAC
23521 CACGTGGTGG CAGGCACGGT GATCTTGCCA GGAACGGCGT TCGTCGACCT GGCGTGGGCG
23581 GCGGCCGAGG TGGTGGGCGC CGCCGCTGTG TCCGAGGTGA CCTTCACGAC GCCGCTCGTG
23641 CTTCCGCCGC GCAGCGTGGT GGAGCTGCAG GTGAGGATCG GCGAGCCGGA CGCGTCCGGG
23701 CGGCGGACGT TCGCCGCGTA CAGCCGCCCG GACGCGGCGA GCGAGGCGGA GTGGACGCAA
23761 CACGCGACCG GCGTGCTGAG CGCGCAGGCG GCGGCCGGGG CCGACGTGGC GGACCTTTCG
23821 GTGTGGCCGC CGCCGGGCGC CGAGGTGGTG GCGCTCGACG GCGGCTACGC GTGGCTGGCG
23881 GCGCAGGGCT ACGGCTACGG CCCGGCGTTC CAGGCGCTGC GCGAGGTGTG GCGCGCGGGC
23941 ACGACGCTGT ACGCGCGGGT CGCGCTGCCG GACGCGGGTG CGGACACGGC GCAGAGCTTC
24001 GGGATCCATC CGGCGCTGCT CGACGCGGTG CTGCACTCGT TGCTGGCGCG GTCGCCGCAG
24061 GAGGAGGCGT CCGACGACGA CAAGGTGCTG CTGGCGTTCG CGTTCTCGGA CGTCGTGATC
24121 GAGGCGCGCG GGGCAGCGGA GGTGCGCGTC CGCCTGAACA AGCAGGCCGG AGACGACGGG
24181 GAGGGGCTCA CGGCGTCGAT CCACCTCGCC GACGCGCAGG GCGGCCGGT CGCGCGCGTG
24241 GGGGCGTTCC AGGCGCGGGC GACGACCACG GAGCGGGTGC GCGCGCTCGC GGGCGCGAGC
24301 GAGCGCGATC TGCATCGGGT CACGTGGACG GACGTGACGC TGGACGAGGC GCCGTGGGCG
24361 CACGAGGACA GCGTCGTGGT CGGCGGCGAC GGCGCGCTGG CGGCGGCGCT GGGCGTGCGC
24421 GCGGTGGCCG GGTTGCCCGA GCTGTTCGCG GGCGGCGCGG CGGCGCCGCG TCGTCTGGTG
24481 ATCGACGCGA CCGCGGGCGA CCCCGGCGAC GGCCTTGTCG CGGCGACGCA CGCGGCGACG
24541 CAGCGGGGCC TCGCGCTCTT GCAGGGATGG CTCGCGGAGG CGCGGCTCGC GTCGACGGAG
24601 CTGGTGCTCG TGACGCGCGG CGCGACGGCG GCCGAGCCGG ACGAGGGTGT GGCGGCGCTG
24661 AGCCACGCGC CGCTCTGGGG GCTCGTGCGC GCGGCGCGCG AAGAGCACCC GGCGCGCGCG
24721 CTGCGCCTGG TCGATCTGGG GCGCGAGGCG CCGGACGGGG CGGTCCTGCG CCGGGCGATC
24781 GCGGCGGACG ACGAGCCGGA GCTCGTGGTC CGGCGCGGGG CGCTGCGGGC GGCGCGCCTG
24841 AGCCTCGCCC ACGCCGCCCC GGACGCCGCG GGGCGAGCGA CGCGGCTGGC CCCCGGCGGG
```

```
24901 ACGGTGCTGA TCACGGGCGG CACGGGGGAG CTCGGGCGGC AGGTCGCGCG GCACCTGGTG
24961 ACGGCGCACG GCGTGCGCCA TCTGGTGCTC ACGTCCCGGC GCGGGATGGA CGCGCCCGAC
25021 GCCGCGGCGC TTGTGGAAGC GTTGCGCGCG GCGGGCGCCG CGACGGTGGA GATCGCGGCG
25081 TGCGACGTGG CGGACCGCGA CGCGCTGGCG GCGGTGCTCC GGGCCATCCC GGCGGCGCAC
25141 CCGCTGACCG CGGTCGTGCA CACGGCGGGC GTGCTCGAAG ACGGCGTCGT GACGGGGCTC
25201 TCGGCCGAGC AGCTCGCGCG CGTGCTGCGG CCGAAGGTCG ACGGCGCCTG GCAGCTCTAC
25261 GAGGCGACGA GGGACGCGCC GCTCGCGGCG TTCATGCTCT TCTCGTCGGC GGCGGGCACG
25321 CTGGGCAGCG CGGGGCAGGC GAACTACGCC GCTGCGAACG CGTTCCTCGA TGCGCTGGCG
25381 GCAGAGCTCC GCACGCGCGG CGTGCCGGCG ATGAGCCTGG CCTGGGGCTT CTGGGAGCAA
25441 GGTGGGATCG GGATGACGGC GCACCTCGGC GCCGCCGACC TGGCGCGGAT GAAGCGGCAG
25501 GGCATCGTAC CGATGGCGGT CACGCACGGC CTGCGGCTGC TGGATCGCGC GCTGGAGCGG
25561 CCCGAGGCGA CGCTGGTGCC CCTATCGCTC GACGTGGCGG CGCTCCAGCG CGCGGCGGGC
25621 GACGCCGGAC GGGTGCCGGC GCTGCTGCGT GGCCTGGTGC GCCCGGCGGC CGCCCGGCAC
25681 ACGGCGGTGC CGGCGGCCGC GGCGACGGGG GCGACAGGGC TCCGCGCGCG GCTCTTGCCG
25741 TTGTCCGAGG CCGAGCGCCA GGACGTGTTG CTCGATCTGG TGCGCACGGA GATCGCGGAC
25801 ATCCTCGCGC TGTCCGGGCC AGCGGCGGTG CCTCCCGATC AACCCATCAG GGAGCTGGGG
25861 CTCGATTCGC TCACGGCGGT GGACGTTCGG AGCCGGCTTG TGCAGAGGAG CGAGATCGAC
25921 CTCCCCGTGA CCCTCGCGTA CGATTATCCG ACCGCGCGAG CGATCGCTGG ACATCTGAGC
25981 GAGCAGATGG GCCTCGAAGG AGCGCCGGAA GATCGGGAGT CGGCGCTCGA CGAGGCCCAG
26041 ATCCGCGCCC TGCTCATGCA GATTCCTATT TCCACGTTGC GCCAGTCGGG GCTGCTCGGA
26101 GACCTGGTTC GCCTGGCCTC CCCGCAAGCG CCCCCGCGCG AAGAAGGCGA GAGCGAGACG
26161 TTGAGCTTCG ATCACCTTGG AAATGAAGAG TTCCTCAGCC TCGCGTCGAA GCTCATTGCA
26221 GAAGAGGGAT CATGAACCAA GAGACTGTTC TTCGGCAGAC ACTCGAGAAG AGTCTCCACA
26281 AGATCCAGCA CCTCAATCGG GAGCTCGAGC GTCTCAAGGC GAAGTCGAGC GAGCCGATCG
26341 CGATCGTGTC GATGGCGTGC CGGTTTCCGG GCGGCGTCGA TACCCCCGCG GCGCTGTGGG
26401 ACCTGCTCTC GGAGGGCCGG GACGCGATCG GGCCGTTCCC CGAGGGGCGC GGCTGGGATG
26461 TGGCGGGGCT GTACGACCCC GACCCGGACG CCCCGGGCAA GTCGATCACC ACGCAGGGCG
26521 GCTTCCTCTA CGACGCTGAC CGCTTCGATC CGACGTTCTT CGGCATCAGC CCGCGCGAAG
26581 CGGAGCGCAT GGACCCGCAG CAGCGGCTGC TGCTCGAGTG CGCCTGGGAG GCGCTCGAGC
26641 GCGCGGGCCT CGCGCCCCAT TCGCTCGAGG CGAGCGCCAC CGGCGTCTTC GTCGGGCTGG
26701 TGTACAGCGA CTACGGCGGG CGGCTGCTCG AGCACCTCGA GGTCTTCGAC GGCTACGTCG
26761 CCACCGGCAG CTTTCCCAGC GTCGGCTCGG GGCGCATCGC CTACACGCTG GGGCTCCGCG
26821 GCCCCGCGGT CACCGTCGAC ACGGCGTGCT CGTCGTCGCT CGTGTCCCTC CACCTCGCGT
26881 GCATGTCGCT CCGCGCCGGC GAGTGCGACC TGGCCCTCGC CGGCGGCGCC ACCGTGATGG
26941 CCACGCCCAT GGCCTTCATC GAGTTCAGCC GACAGCGCGG CATGGCCCCG GACGCACGGT
27001 GCAAGGCCTT CGGGGCGGCG GCGAACGGCA TCGGCCCCGC GGAGGGCTGC GGGCTCCTGG
27061 TGCTCAAGCG GCTGTCGGAC GCGCGGCGCG ACGGCGACCG CGTGCTGGCG GTCATCCGCA
27121 GCTCCGCCGT CAACCAGGAC GGCCGCAGCC AGGGGCTCAC CGCGCCCAAC GGTCCGGCCC
27181 AGCAGGACGT CATCCGCCAG GCCCTGGCGG CAGCGGGGCT CACGCCCGCC GACGTCGACG
27241 CCGTCGAGGC GCACGGCACC GGCACGCCCC TCGGCGATCC CATCGAGGCG CAGGCGCTGC
27301 TGGCGACCTA CGGCAAGGCG CACACAGCGG AGCGGCCGCT CTGGCTCGGC TCGATCAAGT
27361 CCAACTTCGG CCACACGCAG GCCGCCGCAG GGGTCGCGGG CATCATCAAG CTGGTGCTGG
27421 CGATGCAGCA CGCAGAGCTG CCGAGGACGC TGCACGCCGA CCCCCCGTCG CCGCGCGTCG
27481 ACTGGTCGCA GGGGCACGTC AAGCTCCTGA ACGAGCCCGT GCCGTGGCCG CGCACGGACC
27541 GGCCGCGGCG CGCGGCGGTC TCGTCCTTCG GCGTCAGCGG CACCAACGCG CACGTCATCA
27601 TCGAGGAGGC GCCGGCCGAA GCGCCGACGG CCGCGCAGAC GGCGGCAGCG GCGGCGACAG
27661 AGCCGGCGGC GGCGGTGGTG CCGTCGACGC TGCCGTCGT CCTGTCGGGT CGCGACGAGC
27721 CGGCGCTGCG CGCCCAGGCC GGGCGGCTCG CCGAGCACCT GCGCGCCCAC CCGGACCTGC
27781 GGTTGCTCGA CGTCGCCGCG GGCCTGGCCA CGACGCGCAC GCACCTCGCC ACGCGGCTCG
27841 CGCTGCCGCT CGCGCCGGAC GCAGCCACGG AGGAGCTGGG CGCCCGCCTT GCCGAGTTCG
27901 CCGCCGGCGG CCCGGCGCCC AGCGGCGCCG CCGTGACCGC GCCGGGGCAG CCGCCCGGCA
27961 AGGTCGCGGT GCTCTTCACC GGCCAGGGCA GCCAGCGCGC CGGCATGGGG CGCGCCCTGT
28021 ATGCCACCCA CCCCGTCTTC CGCGCCGCGC TCGACGCCGC CTGCGCCGAG CTCGACCGCC
28081 ACCTCGACCG GCCCCTCGTG AGCGTCCTCT TCGCCGACGC CGGCTCCGAG GCCGCGGCGC
28141 TGCTCGACCA GACAGCCTGG GCTCAGCCCG CCCTGTTCGC TCTCGAGGTC GCGCTCTACC
28201 GACAGTGGGA AGCCTGGGGC CTGCGCGCCC ACGCGCTGCT CGGCCACAGC CTCGGCGAGA
28261 TCGTCGCCGC CCACATCGCC GGCGTGCTCG ACCTCCACGA CGCCTCCGCC CTGGTCGCCG
28321 CCCGCGGGCG GCTCATGCAG GCCCTCCCCC ACGGCGGCGC CATGGCCTCC ATCGAGGCCA
28381 CCGAGCACGA GCTCCGACCC CTGCTCGACC AGCACACAGG ACGCGTCTCG CTCGCCGCCC
28441 TCAACGCTCC ACGCCAGTCG GTCGTGAGCG GCGACCAGCC CGTCGTCGAC CAGGTCTGCG
28501 CCCACTTCAA GGCCCTCGGC CGACGCGCCA AGCGGCTCGA CGTCAGCCAC GCCTTCCACT
28561 CGGCCCGCAT GGAACCCATG CTCGACGCCT TCGCCCACGT CGCCCGCGGC CTGACCTACC
28621 GCGCCCCGCG CCTGCCCGTC GTGAGCAATG TCACCGGGCG CATGGCCACC GCCGACGAGC
```

```
28681 TCACCTCGCC CGACTACTGG GTGCGCCACG TGCGCGAGCC CGTGCGCTTC GTCGCCGGCG
28741 TGCGCGCGCT GCACGCCACC GGCGTCACCA CCTACCTCGA GTGCGGGCCC GACCCGGTGC
28801 TCGGCGGCAT GGCCGCAGAC TGCCTCACCC CGGACGAGAC CCGCGACGTC GGCCTGATCC
28861 CGAGCCTGCG CAAGGACCGC GACGAGGCCC TGGCCCTCGC CCAGGCCGCC TGCGCCCTGT
28921 ACGTCCGCGG ACACGCCCTC GACTGGCTCC GCCTCTTCGA CGCCACCCGC GCGCGCCGCG
28981 TCGAGCTGCC CACCTACGCC TTTCAACGCC AGCGCTACTG GATCGATGCG CCGCGGCGCG
29041 CGGCGGGGCT CGACAGCGTC GGGCTCACGG CCGCAGATCA CCCCTGGCTG GGCGCGGCGG
29101 TGCGGCTCGC CGACCGGGAC GTCCACGTGC TGAGCGGGCG GCTGTCGACG GTCGACCACC
29161 CGTGGATCCT GGACCACGTG GTGGCGGGCA CGCCGCTGAT GCCAGGAACG GGCTTCGTCG
29221 AGCTGGCGTG GGCGACGGCC CAGGCGGTGG ACGCCGCCGC GATCGCGGAG CTCACCCTGA
29281 CGACGCCGCT CGTGTTGCCG GCGCGCGGCG CGGTGCAGCT CCAGGTGACG GTCGACGAGG
29341 CCGACGCGAA TGGCCGGCGG GCATTCGCCA TCCACAGCCG GCCGCATGGC CCCGGCGACC
29401 TCGCGTGGAC GCAACACGCG ACCGGCGTGC TGAGCGCGGA GGAGCCGGCG GGAGCCGACG
29461 AGGCGGCGGG GCTCTCGGAG TGGCCGCCGC CGGGCGCGGA GGCGGTGGCG CTCGACGGCG
29521 GGTACGAGCA GCTGTCCGAG CACGGCTACG CCACGGCCC GGCGTTCCAG GGGCTCCGCG
29581 GGCTCTGGCG CGCGGACCGT ACGCTGTACG CGCACGTCGC GCTGCCGGAC GCTGTCGCGG
29641 GCACCGAGCA GGGCTTCGGG CTCCATCCGG CGCTCTTCGA TGCGGCGCTG CAGTCGCTGG
29701 CGCGGCTGTC GCGCGAGGAA GCGGCCGCTG GCGACCCGGT GCTGGTGCCG TTCGCGTGGA
29761 CGGACGTGGC GCTGTACGCG ACCGGCGCGA CCGAGCTGCG GGCGCGCATC GCGCTGGAGC
29821 AGGCGGAGGG CGGCGCGCCG GCGGTGGCGT CGCTGCTGCT GGCCGACGCG CACGGACGAA
29881 CCGTGGCGAC GACCGGGCGG GTGCGCGGGG CGAGCGCGGC GCAGACGCGG TCCGCCGCGA
29941 GCCGCGCGGA GCCGATGTAC CGGGTCGCGT GGACGGACGT GGCGCTGGAG CGGCGACGT
30001 GGGCGCCCGA GGAGCACGTC GTGCTCGGCG GTGACGGTGC GCTCGCGGCG GCGCTGGGCG
30061 TGCGCGCGGC GGCCGGGCTG CCGGAGCTGC TCGAGGCGCT GGCGGACGGC GCGGCCGCGC
30121 CGCGGCGGCT GGTCGTGGAC CTGACGGCGG GCGATGCAGG CGCGGTCGTC GCGGCCGTGC
30181 ACGCCGCGGT GCGCGGCGCG CTGGCCCTGG TGCAGGGGTG GCTCGCCGCG CCGCAGCTGG
30241 CGGCGACGGA GCTCCTGGTG GTGACGCGCT GCGCGGTGGC GACCGGGCCG GACGAGGGCG
30301 TGGACGCGCT GGGGCCGGCG GCCGTCTGGG GCCTGCTGCG GGCCACGCGC GCCGAGTACC
30361 CCGACCGCGC GGTCCGGGTG CTGGACGTGG GGCGCGAGCC GCTGGACGGG GCGCTCTTGC
30421 GTCGGGCGCT GGCCGCGGGG ACGGAGCCGG AGCTTTCGGT GCGCAGCGGC GAGGCGCGCG
30481 CGCCGCGCCT GCGCGAGGTG CGCGGGAGCG AGCCGGCCGC GGCGCCGGCG ACGCGGCTGG
30541 ATCCCGACGG AACAGCGCTG ATCACGGGCG GCACCGGGGA GCTCGGGCGG CATGTCGCGA
30601 AGCACCTGGT GACGGCGCAC GGCGTGCGGC ACCTCGTGCT GACGTCGCGG CGCGGGATGG
30661 ACGCGCCCGA CGCCGCGGCG CTGGTGGACG AGCTGCGCGC CGCGGGCGCG GCGACGGTCG
30721 ACGTCGCCGC GTGCGACGCG GCGGACGCAG CGGCGCTGGC GGCGGTGGTG GAGGCGATCC
30781 CGGCGGCGCG TCCCCTGACG GCCGTCGTGC ACACCGCAGG TGTGCTGGAC GACAGCGTCG
30841 TGACCAAGCT CTCCGGCCGA GCAGCTGGCGC GCGTGCTGCG GCCGAAGGTC GACGGCGCCT
30901 TTCATCTCCA CGAGCTCACG AAGCACGCGC CGCTCGCGGC CTTCGTGCTG TTCTCGTCCG
30961 CGGCGGGCAC GCTGGGCAGC CCGGGGCAGG CGAACTACGC CGCGGCCAAC ACGTTCCTGG
31021 ACGCGCTCGC GTCGCACCTG CGCGCGCGCG CGTGCCCGC GATGAGCCTC GCATGGGGCT
31081 TCTGGGCGCA GACTGGGCTC GGCATGACGG CGCACCTCGG CGCCGCCGAC ATCGCCCGGA
31141 TGAAGCGGCA CGGCGTCGTA TCGATGCCCG TCGCGCAGGG GTTGCGGCTG CTCGATCGCG
31201 CGCTCGCGCA GGCCGAGGCG ACGCTGGTGC CGCTCGCGCT CGACCTCTCG TCGCTGCAAC
31261 GCGCGGGGAG CAACGCCGGG CCGGTGCCGC CGCTGCTGCG CGGGCTCGTG CGCGCACCGG
31321 CCGGCCGGCG CACGGCGGCG TCCGCTGCTG GGGCGAACGG GAACGGGACG GGAGCAGCGG
31381 CGCTGCGCGC GCGGCTCTCG CCCTTGCCCG GGGCCGAGCG CCAGAAGGTG CTGCTCGATC
31441 TGGTGCGCAC GGAAATCGCG GAGGTGTTTC AGTTGCCGGG CCCTGCCCAC ATCCCTGCGG
31501 ACAGGCCGCT GAAGGAGCTG GGGCTCGACT CGCTCATGTC GGTGGAGCTG CGCAATCGCC
31561 TGGGCCGCGC CGTCGAGGCG GCGCTGCCCG CGACGCTCGT GTTCGACTAC CCCACGCCCG
31621 GGGCCATTGC ATCCTATCTG GGCACGTTGC TCAACCTCTC CGGCGAGGAC GCACACCCGG
31681 GCCAAACGGG GCGCGACCCG GACGAAGAAC ACGAGATCCG GGCCGCGATA GCGCGCATCC
31741 CGATAACAAC CTTGCGCGAG GCAGGGCTCC TCCAGAGCTT GCTCCGACTC GCCCCCAACC
31801 AGACGGCGTC CGATGACGTC ACGCCGAGGA CTGATGAGCT GATGGTCGAA CACCTCGGAG
31861 ATGAAGAGCT GCTGAAGCTT GCTTTCGCGT CCACCGGAGG AGCCAAGTGA AGGACGAGGT
31921 GCTTTCGTTC CGCCGCGCTT TGGAGAAGAC GGTCGTCGAG ATCCGCCGCC TCAACACGGA
31981 GATCGACGGC CTGCGCGCGA AGTCGGTCGA GCCGATCGCG ATCGTGTCGA TGGCGTGCCG
32041 CTACCCGGGC GGCGTGGACA GCCCCGCGGC GCTCTGGCAG CTTCTCTCCG AGGGGCGAGA
32101 CGCGATCGGG CCGTTCCCCG AGGGGCGCGG CTGGGACGTG GCGGGCTGT ACGACCCCGA
32161 CCCGGACGCG CCGGGCAAGT CGATCACCAC GCAGGGCGGC TTCCTCTACG ACGCCGACCA
32221 CTTCGATCCG ATGTTCTTCG GCATCAGCCC GCGCGAGGCC GAGCGCATCG ACCCGCAGCA
32281 GCGGCTGCTG CTCGAGTGCG CCTGGGAGGC GCTCGAGAGC GCGGGCATCG CGCCCACAC
32341 GCTCGGCGCG AGCGCCACGG GCGTCTTCAT CGGACTGATG TACACGGAGT ATGGCCTGCG
32401 GCTGATGAAC CAGCCCGAGG CCCTCGACGG CTACATCGGC ATCGGCAGCG CCGGGAGCAC
```

```
32461  GGCCTCCGGG CGCATCTCCT ACACGCTGGG GCTCCGCGGC CCCGCGGTCA CCGTCGACAC
32521  GGCGTGCTCG TCGTCGCTCG TGTCGCTCCA CCTGGCGTGC ACGGCGCTCC GCCGTGGAGA
32581  GTGCGACCTG GCGCTGGCGG GCGGCGCCGC CGTGGTGTCG ACGCCGGCCC CGTTCATCGA
32641  GTTCAGCCGG CAGCGGGCCC TCGCGGTCGA CGGTCGATGC AAGTCGTTCG GCGCCGGGGC
32701  CGACGGCGTG AGCTGGTCAG AGGGTTGCGG GCTGCTCGTC CTCAAGCGGC TGTCGGACGC
32761  GCAGCGCGAC GGCGACCGCG TGCTGGCCGT CCTCCGCGGC TCCGCCGTCA ACCAGGACGG
32821  CCGCAGCCAG GGGCTCACCG CGCCCAACGG CCCGGCCCAG CAGGACGTCA TCCGCCAGGC
32881  CCTGGCTGCG GCGGGGCTCA CCCCGGCGGA CATCGACGCG GTGGAGGGGC ACGGCACCGG
32941  CACGCCCCTC GGCGACCCCA TCGAGGCGCA GGCGCTGCTG GCGACCTACG GCAAGGCGCA
33001  CACAGCAGAG CGGCCGCTCT GGCTCGGCTC GATCAAGTCC AACTTCGGCC ACACGCAGGC
33061  CGCCGCAGGG GTCGCGGGCG TGATGAAGCT CGTGCTGGCG ATGCAGCACG CAGAGCTGCC
33121  GAGGACGCTG CGCGCCAACC CGCCCTCGCC GCACGTCGAC TGGTCGCAGG GGCACATCGC
33181  GCTCTTGAAT GAGCCAGCGT CGTGGCCGCG CACGGACCGA CCGCGGCGCG CGGCGGTCTC
33241  GTCCTTCGGC GTCAGCGGCA CCAACGCGCA CGTCATCATC GAGGAGGCGC CGGCGCCCGC
33301  CGCGGAGGTG ACGAGCCCTG GAGCAGAGCC GCCCGCTGTC GCGCTGCCGC TGCTGGTGTC
33361  GGGGCGGGAT GACGCGGCGC TCAGGCGCA GGCGGAGCGC TGGGCGGCGT GGCTCGCGGC
33421  GCACCCGGAG GCGCGCTGGG CGGACGTGGT GCACACGGCC GCCGTGCGGC GCACGCACCT
33481  GGAGGCGCGC GCGGCGGTGA CGGCGGCGAG CGCCGCCGAC GCGGCCGCGG CCCTGACGGC
33541  GCTCTCGCAA GGGGAGCCGC ACCCCGCGGT GACCGCGGGC GAGGCGCGCG CGCGCGGCAA
33601  GGTCGTGTTC GTGGCTCCGG GCCAGGGGAG CCAGTGGCCG GCGATGGGGC GGGCGCTGCT
33661  GGCCGAGTCC GAGGTGTTTG CCGCCGCGGT CGCGGCCTGC GACGCGGCGC TGCGGCCGTT
33721  CACCGGCTGG TCGGTGCTCT CGGTCCTGCG CGGCGAGCAG GGAGAGGCGG TGCCGCCCGC
33781  GGACCGCGTG GACGTGGTGC AGCCGGCGCT GTTCGCGATG GCCGTGGGGC TCTCGGCGGT
33841  CTGGCGGGCG TGGGGCATCG AGCCTTCGGC GGTCGTCGGC ACAGCCAGG GCGAGGTCGC
33901  GGCGGCGTAC GTCGCCGGGG CGCTGACGCT CGAGGACGCG GCGCGGGTCG TGGCGCTGCG
33961  CAGCCAGCTC GTGCGGCGCA TCGCCGGCGG CGGCGCGATG GCCGTGATCG AGCGCCCGGT
34021  CGGCGAGGTG GAGCAGCGGC TCTCTCGCTT CGGAGGGCAG CTGTCCGTGG CGGCGGTGAA
34081  CACGCCGGGC TCGACGGTGG TGTCCGGGGA CGCCGCAGCG GTCGATCGCT TGCTGGCCGA
34141  GCTGGAGCAC GAGGAGGTCT TCGCGCGGCG GGTCAACGTC GATTACGCGT CGCACAGCGC
34201  GCACGTGGAC GCGATCCTGC CGGAGCTCGA GGCCTGCCTG GCCTCGGTCG AGCCCGTGC
34261  CTGCGCCATC CCGCTGTACT CGACGGTGAC GGGAGAAGTG CTCGCCGGCC CGGAGCTCGG
34321  CGCGGCATAC TGGTGCCGCA ACCTGCGCGA GCCGGTGCGG CTCGACCGGG CGCTCTCGCG
34381  GCTGCTGGCG GACGGGCACG GGGTGTTCGT CGAGGTCAGC GCGCATCCGG TGCTGGCCAT
34441  CCCGCTGACG GCCGCGAGCG CCGAGCGCGG CGGCGTTGTG GTGGGCAGCT TGCAGCGCGA
34501  CGACGGCGGC CTGGGGCGTC TTGTTTCAGC GCTGGGCGCG CTGCACGTCC AGGGGCATTC
34561  GGTGGAGTGG GCCAGGGTGC TCGCGCCGTA CGGCGGCAAC CTGGTGGACT TGCCGACGTA
34621  CGCGTTCCAG CGGCAGCGCT ACTGGCTCGA GGCGTCGAGG AGCCGGATCG ACGCGAGCGA
34681  CCTCGGGCTC GCGGCGACGG GCCGCCCGCT GCTGGGCGCC GCAACGCGGG TCGCCGGCAC
34741  GGACAGCTAC ATCCTGGCGG GTCGGCTGTC GACAGCGGAG CACCCGTGGC TGTCGGGACA
34801  GGTCGTCTTC GAGCGGACGC TGTTCCCGGC GACGGGGTTT CTGGAGCTGG CGCTCGAAGC
34861  CGCTGACGCG ATGGGGGTGG CGGGGGTGAC CGAGCTGGTC GTGCCCGCTC CGCTGATCTT
34921  GCCGGCGCGG GGTGCGGTGC ACGTCCAGGT TGCGGTCCAG GGACCAGACG AGGCGGGACG
34981  CCGGCCGTTT TCCGTGTACA GCCGCGCGGA AACCGCGGGG CTGGACGCGG AATGGACGCT
35041  GCATGCCACG GGGCTGCTCG GGGGAGCGCG CGCCAGTGCG GCGGCGGACA CGGGCCTCGA
35101  GGCGTGGCCG CCGGAGGGAG CCGCGCCGGT GGACGTCAGC GACGCCTATG CGCGGCTGGA
35161  GGACGCCGGC GTGCGTTATG CGCCGAGCTT GCGAGCGCTC GTGGAGGCCT GGCAGGCGGA
35221  GCGGCGCATC TATGCGCGCG CGGTGCTGCC GGGCGGCGCG ACGCAGGGCC ACGGGCTCCA
35281  CCCGGCGCTG TGGGACGCGG CGCTGCACGC GCTGGCGCTG GTGGTCCTCG GCAGGACGC
35341  GGAGCACGCG GGCGTGCTGT TGCCCCGGGC CTGGTCGGAC GTGACGCTCG CGGCGCAGGG
35401  GGCGACCGAG CTGCGGGTGC GCGTCGAGCT CGCGGACGCG GACGCGGAGC ACGTGTCGGC
35461  GTCGCTGACG ATGGCCGACG CGGACGGTCA ACCCGTGGCG ACGGTGGGGT CGGTGGAGGT
35521  GCGTCGCGCG ACCGCGGCCC AGGTGCGCGC CATGAGCACC GCGACCCAGC ACCTTTACGG
35581  GGTCGAGTGG AAGGCGGTGG CGCTGGCGGA GCCGCCGCGG TCTGCGGGGG AGCAGGTCGT
35641  GCTCGGACCG GACGCGGAGC TCGCGACAAG GCTGGCGCGG CGACGCGCCG GCAACCTCGA
35701  TGAGCTGTTT GCCGACGGCG AGGCGGCGCG CCCCGCGCCC AGGCGGCTCG TGGTCGACGC
35761  GCGGACGCGC CGCGACGGCG ACGTGCCTGC GGCTGTGCAC CAGGCGACGC GCCAGGCCCT
35821  CGAGCTCGTG CAGCGATGGC TGGCGGACGC GCGACTGACG GACACCGAGC TCGTGGTGCT
35881  GACGCGCGAG GCGGTGTCGA CCGGCCCGGA CGTGGGGGTC GAAGACCTGG GCCACGCGGC
35941  GCTCTGGGGA TTCTTACGCG CAGTGCGGAG TGAGCACCCG GACCGCGGGG TGCGCCTCAT
36001  CGACCTCGGA CCTGACGCCT CTGCGGCGGA GCTGCTCGAC AGGGCCCTCG AGACCGTGGC
36061  GGAGCCCGAG CTGGCGCTCC GGCAGGGGAT CGCGCTGGCG CCCCGGCTCG GTGTGCCTCG
36121  TGATCGCGCC GGCGCCCCGG CGCCGATGCG GCTGGACCCG GACGGGACGG CGCTGATCAC
36181  CGGCGGCACC GGGGAGCTCG GCGGCATGT CGCGAAGCAC CTGGTGACGG CGCACGGCGT
```

```
36241 GCGGCACCTC GTGCTGACGT CGCGGCGCGG GATGGACGCG CCCGACGCCG CGGCGCTGGT
36301 GGACGAGCTG CGCGCCGCGG GCGCGGCGAC GGTCGACGTC GCCGCGTGCG ACGCGGCGGA
36361 CGCAGCGGCG CTGGCGGCGG TGGTGGAGGC GATCCCGGCG GCGCGTCCCC TGACGGCCGT
36421 CGTGCACACC GCAGGTGTGC TGGACGACAG CGTCGTGACC AAGCTCTCGG CCGAGCAGAT
36481 GGCGCGCGTG CTGCCGGCCGA AGGTCGACGG CGCCTTTCAT CTCCACGAGC TCACGAAGCA
36541 CGCGCCGCTC GCGGCCTTCG TGCTGTTCTC GTCCGCGGCG GGCACGCTGG GCAGCCCGGG
36601 GCAGGCGAAC TACGCCGCGG CCAACACGTT CCTGGACGCG CTCGCGTCGC ACCTGCGCGC
36661 GCGCGGCGTG CCCGCGATGA GCCTCGCATG GGGCTTCTGG GCGCAGGCTG GGCTCGGCAT
36721 GACGGCGCAC CTCGGCGCGG CCGACATCGC CCGGATGAAG CGCCTGGGTG TCGTGACGAT
36781 GTCGCCGCAA GAAGGGCTCG AGCTGCTGGA CGCGTCGCTC CAGCGGCCGG ACCCGCTGCT
36841 GGTGCCGGCG CCGCTCGATC TCGCCGCGCT CGAGCGAGCC GCGCGCGAGG GCGCGCCCGC
36901 TTCGCCGATG CTGCGCGAGC TGGTGCGCGG CGCGCCCGCG CGGCGCGCCG CCGCGGGCGA
36961 CGGCGCGAGC GGCAAGGCCT CGGCGCTGCG CGCGCTCCTG GCGCGACGGC CCCAGAGCGA
37021 ACGATTCGCG GCGGTCCTCG AGCTCGTCAG GGCGGAGGCG GCGCGCGTGC TCCGGCTGCC
37081 GGGGGCCGCG GCAGTGCCGC CAGATCGGCC GCTCAAGGAG CTGGGCTCG ACTCCCTCAC
37141 CGCGGTCGAG CTGCGGAACC GGCTGGCGGC GCGGACGGAA GCCAAGCAGC CGGCGACGCT
37201 CGTCTTCGAC CATCCGACGC CCAGCGCCAT CAGCCGATTC CTGCTCAAGC AAGCCGGCGC
37261 TGATCTCGCT CCGAGCGAGG CCGCGGCGAG CCTCGCACCG AGCAGCCGAC GTGCTCCCCT
37321 GGATGAGCCG ATCGCGATCG TCGCCATGGC GTGTCGGTGC CCCGGCGGAG TCGATAGCCC
37381 CGAGGCGCTG TGGAGGCTGC TCTCCGAGGG ACGCGACGCG ATCGGCCCGC TCCCGGAGGA
37441 GCGAGGCTGG AGCGTGGAGC AGATCCTCGG CCGTGATCCG GGCGCCTCGA GCAAACCGTT
37501 CAGCGGCCGG GGTGGCTTCC TCTACGGCGC CGACCAGTTC GACGCCGAGT TCTTCGGGAT
37561 CACCCCGCGC GAGGCCAGGT TCCTCGACCC GCAGCACGCC TTGCTCCTCG AGTGCACCTG
37621 GGAGGCGCTC GAGCGCGCAA GCATCGTCCC GCAGTCGCTG GAAGGGAGCT CCACGGGTGT
37681 GTTCGTGGGC ATGGTGGGCG GCATGGCCGC TGGTCACGGC TCGGTATCGA GCGAGGGCTA
37741 TGCGCTCACC GGGACCGCGT TGAGCACCGC CTCGGGGCGT ATTTCCTACG CGCTCGGCCT
37801 GCAGGGCGCG GCGGTGACGG TCGACACGGC GTGCAGCTCG TCGGCCGTGG CGATTCACCT
37861 CGCGTGCACG TCGTTGCGGA CCGGAGAGTG CGATCTGGCG CTGGCGGGGG GCGTGACCGT
37921 CATGGGCAGG CCCGAGATCT TCTCGGAGTT CGGCCGGCTC GACATCCTCG CCTCGGACGG
37981 CCGATGCAAG GCGTTCGGGG CCACGGCCGA CGGCGTCGGC TGGGGCGAAG GCTGCGGGGT
38041 CTTGCTGCTG AAGCGGCTGT CGGACGCGCA GCGCGACGGC GACCGGGTGC TCGCGGTGAT
38101 CCGCGGCTCG GCCGTCAACC AGGACGGCCG CAGCCAGGGG CTCACCGCGC CCAACGGCCC
38161 GAGCCAGGAG GCGGTCATCC AGAGAGCGCT GGCGTCAGGCC GGCCTGACGG CGGCGGATGT
38221 CGACGCCGTC GAGGCGCACG GCACCGGCAC GCGCCTCGGC GACCCGATCG AGGCGCAGGC
38281 GCTGCTCTCG ACCTACGGCC AGGCCCACGC CGCGGGGCAG CCGCTGTGGC TCGGCTCGAT
38341 CAAGTCCAAC CTCGGGCACA CGCAGGCCGC CGCGGGGGTC GCGGGCGTGA TCAAGATGGT
38401 GCTGGCGATG CAGCACGGGC AGCTCCCGAG GACGCTGTAC GCCGACACGC CCTCGCCGGA
38461 CATCGATTGG TCGCAGGGGC ACGTCAGGCT CCTGGTCGAC GCCGTGCCGT GGCCGCAGAG
38521 CGCGCGGCGG AGGCGCGCGG GCGTCTCGTC GTTCGGCATC AGCGGCACCA ACGCGCACAT
38581 CCTCGTCGAG GAGGCCCCGG AACCGCCGCG GCGGGGGCC GCGCCGGAAG CGCCGGTGAC
38641 GCTGCCCTTT CTGCCGCTGC TGGTCTCCGG CCGCGACCTC GCGGCGTTGC GGTCGCAGGC
38701 AGCGCGCCTC GCCGCGCACC TGCGTGAGCG CCCCGACCAG CGGCTGGTCG ACGTGACGGC
38761 GAGCCTTGCC ACGACGCGCA CGCACCTCGC CGCGCGGCTG GCGCTGCCGG TCGCCGCGAC
38821 CGCTGGACGC GACGAGATAT GCGGCGCGCT CGACGCGTTC GCGGCGCGGG GCTGGCCTT
38881 GAACGGCGCG TGGGTCACAC CGGCGCAACA CCGCGCCGGC AAGGTCGCCG TGCTGTTCGC
38941 GGGGCAGGGT GCCCAGCGGC CCGCGATGGG GCGTGGCCTC TACGAGGCGC TGCCGGTGTT
39001 CCGCGAGGCG CTGGACGAGG TGTGCGCGCG CCTCGACGCT CACCTCGGCG CGCCCCTGAA
39061 GGACGTCCTC TTCTCCGCCG AGGGCTCCCC GGAAGCGAGC ACGCTGCACC AGACCGGATG
39121 GGCGCAGCCG GCGCTGTTCG CGCTGGAGGT GGCGCTGTAC CGGCAGTGGG AGGCCTGGGG
39181 GCTGCGGCCC GACGCCTTGA TGGGCCACAG CCTCGGCGAG ATCGTGGCGG CGCACGTGGC
39241 TGGGGTGTTC GACCTCGCGG ACGCGTGCGC GCTGATCGCG GCGCGCGGGC GGCTGATGCA
39301 GGCGCTGCCG ACGGGCGGCG CGATGGCCTC CATCGAGGCC TCCGAGGACG ACGTGCGGCC
39361 GCTGCTCGAT GCCCAGCAGG GACGGGCGTC GCTGGCGGCG CTCAATGGCC CGAGGCAGAC
39421 CGTCGTCAGC GGCGACGAGG ACGCGGTCGA GGCGGTCTGC GACCACTTCA AGGCGCAGGG
39481 GCGCCGCGTC AAACGGCTGA CGGTCAGCCA CGCGTTCCAC TCGGCGCGCA TGGAGCCGAT
39541 GCTCGAAGCG TTCCGCGCGG TCGCGGCGAC GTTGACCTTC CGGGCGCCGC AGATCCCGAT
39601 CGTGAGCAAC GTCACGGGCG AGCGGGCGCC GGTCGAGGCG CTGACGTCGC CCGACTACTG
39661 GGTCCGGCAG GTGCGCGAGG CCGTTCGCTG GACGGACGGC GTGCGCGCGC TCGAGGCGGA
39721 CGGCATCACC ACCTACGTGG AGTGCGGCCC GGATGGGGCG ACGTGCGCGA TGGCATCGCA
39781 GTGCGTGACG CGCGCTGCGA AGGCCCCGC GTTCGTCTCC AGCCTGAACC GGAAGGGCGA
39841 CGAGGTTCAG GCGCTCGTCA GCGCCGCCTG CGCCGTTCAT GTTCGCGGCG ACTCCCTCGA
39901 CTGGAGCGCA TTCTTCGCGG GCTCGGGCGC TCGGCGGGTG GAGCTGCCGA CCTACGCGTT
39961 TCAGCGACGG CGATACGGGG TGGACGAGCC GAGCCCTCGC CCCGCGGAGG TCCGGGCCCC
```

```
40021 GGATACCACG CGGACGCGCG TGCACGTGAG CGCGGACGAT CCGACGGTCC GCGGGCACGT
40081 CGTCGGCTCG CAGACCCTCT ACCCTGCCGC CAGCTACATC GACCTCGCGC TCCGTGTCGC
40141 CGCGAGCGCC GGGCAGGCCT GTGTGCGCGC CGCGAACATG GCCTGGTTCG CCCCCGCCAT
40201 CGTGCCGCCC GAGGGCCTGT CGCTCGACGT CCAGCTACGA CGCACGAAGG CTGGCCTCGA
40261 ATGCGAGGTC TCCAGTGGAG ACTCCGACCA GCGGACCATC CATTTCCAGG GCACCCTGCT
40321 CGGCGGCGAT CCCGGACCGT GGCCGGCGGT CGACCTCCGA CGGATCATCG GAGAGTGCTC
40381 TCTTCGTCTC GACAGGGCCC ACCTCTACGG CATCTTCGCA AACTACGGAT TCGGCTACGA
40441 CCGGGCTTTC CAGTCCGTCG CGTGGCTCGT CAGCAACGCG AACGACGTGG TGGGGCGCGT
40501 GGAGCTGCCG GCGTCCGAGT CCGCGACCGC CGAGCACCAC CTCCAGCCGA ACCTGCTCGA
40561 CGGCGCCTTC CAGACCATCA TCGGGCTCGA CGCGGTGAGC GCGCTGAGCG GGCCCACGCC
40621 CGACGCGGGC TTCAACTTCG TGCCGTCCGC CATCCAGGAT GTGCAGATCT TCGGGCGCCT
40681 TCGCCGCGCT GCGTACGTTC ACGCGACCCG ACGCGGCAAG GCGCACGGCT CGCCCTCGTG
40741 CGACTTCCAG CTCCTCGGCG AGAACGGCGA GCCGATCGCG CTCGTCACGG GCCTGACGTT
40801 CCGCAAGCTC CGGTCCCGAG CTGAGCTCGA CGCGCCCTCC GCGCCCGCGC AGAGACCGAG
40861 CAACGGAGAG GCCGCTCGCC CCAGGAACGT GCCAGCTCCT GCCAATGTGC CAGCTCCTGC
40921 CAACGTGCCA GCTCCTGGCG GTGACCACGC CGACGCGTCT CCTCGCGCGC CGTCGGCGGA
40981 GGTGCTGTTC TTCTCGCCCG CATGGGTCCC GGAGAAGCCC GTCATGGCCG CCTCCGTGAC
41041 GGGAGACATC GTCGTGTTCG GGACGACGA CGCGCAGATC ACCCATCTCC GGGGGCTCCT
41101 GCCGCTGGCT CGGCTGATTC ACGTCCGCTC CGGACCGGGC TTTCAGCGCA CCGGTCCCGC
41161 CGCCTACGCG GTCCGACCCG ACAGCCAGGA GGATCTCTCC GCGCTCTTTA CCGAGTTCGA
41221 CGACGCTCGG TCGAAGTCGC TTCGGGCCCT TTATCTCTGG GAGCCGTCCC GCCGCGCGGC
41281 CGAGGGCTCG GCGCCCCCGG GCGACGGCGA CGTCGCGGCG GCGATCCGAT CGTTGTTCTG
41341 CCTCTTCAAG GCTCACATGG CCGAGCGGCG AAAAGGGATG CAGCTCCTCT ATCTCACGTC
41401 GTCGGCGACG AGCGCAGTGC CGGTGAACGA AGCCGTGCTG GCGTTCTTCC GGACCATCCG
41461 CACGGAGAAC CCGACGTATG TGGGCAAGGT GATCGCCGTG GCCGATCCGG GTCACATCGG
41521 CCGCGCCTGC GCCACGGAGC TCGGCCTCCC GACCGGCAGC GACGTGGTCC AGCATGTCGA
41581 CGGCGCGCGC CACGTCCGGA AGCTCTTCTC GCGAGAGCCG GCCCCTCGGG AGCGCCTGCG
41641 AGACGCGCTC CCGCTGGCGC CGGGCGGCAC GTTCGTCCTG ACCGGCGGCG CAGGCAAGAT
41701 CGGCCTGCTC CTGACGGACA TGCTGGTGCG GGAGTACCAG GTGAACGTCG CCCTCATCGG
41761 TCGCTCGCAG CTCGACGAGC CCCGGCGACA GGCCATCGAC AGCATCCGGT CAGGTCCTGC
41821 CCGGGCGCTC TACTACTCGG CGGACGTCGG GGTGCTCAGC GACACCGAGC GGGCCATCGG
41881 AGAGATCCGC GAGACGCTCG GCCCCATCCG CGGGGCGATC CATGCGGCGG CGATCATCCG
41941 CGACAGCTTC TTCATCAAGA AGACCCTGGC GGAGGTCGAC AGCGTGCTGC GACCGAAGGT
42001 CAACGGCGCC ATCTACCTGG ACTTCCTCCT GCGCGACGAT CCGCTCGAGG TGTTCGTCTT
42061 GTGCTCGGGC CTGGCCTCTC TCCTGGGCAA TCAGGGCAA TCGGACTACG CGGCCGCGAA
42121 CGGGTTCCTC GATGGATTCG CGATCCAGCG CGAAGCGCTC CGGCAAGCAG GCCGACGTCA
42181 GGGGCGAACA ATCTCCATCA ACTGGCCGTT GTGGGGGGGC GACGGAGGCA TGGGCGTGCC
42241 AGATTACATC GAGACCGAGC TCCTGAAGCG GGGACTCGTG CCGCTCGACA TCAGCGACGG
42301 CGTGACGGCG TTTCGGCAAG CGATCGCCAT GAAGGAGCCG CAGGTGGCGG TCGTCGCCGG
42361 ACAGAGGGCC GCAGCACGGC GGCTCCTGCG CCCGTGGCTT TCAGAGGGGC GAACGGAGGA
42421 TCATCAATGA CAAGCTGGTT GCTGGCGAAG ACGGAGGAAT TTCTCGGGGA CCTGGTCTCC
42481 GAGGTCAGTG AGATCCGCCG GGACACGATC TCTCCCGACG CTGACTTCCA GGAGTTTGGT
42541 CTCGACTCTC GCTTCGTCAT CGCGATGAAC TCGAGGCTGG AGCAGTATTT TTCCGGCCTG
42601 CCTCGCACGC TGTTCTTCGA GTACCCGTCC ATCCGCGCCG TCGCCAGCTA CCTGGTCGAA
42661 GAGTTTCAAG ACCAGCTCCA CGAGCTCTTT CCCGACGGCG AGCCAGCCGA GGCGTCGCGA
42721 CCTGCGCAGA GCGTGCCGGT CGCCCGACCC AGCGGCGCCA TTCCTAGCGG CGCTTCGCCC
42781 AGCGGCGCTT CGCCCAGCGG CGCCATCCCC AGCGGCGCTT CGCCCAGCGG CGCCATCCCC
42841 AGCGGCGCTT CGCCCAGCGG CGCCATCCCC AGCGGCGCTT CGCCACAGAC CTCCACGAGC
42901 TCCGCGGCCG ATCTCTCCGA TCTCGCTTCC CTGATCCAGC AGATCCCGCT CCCGGAAGCG
42961 GTCCTGTCGA GCGTCGAGCG TCCCCGGGTC GACCCTCGGC CGGCGGCACC CGCTCCCTCT
43021 GTGGTCAGAG CGTCATCCGG CGACCAGAGC GGCGATGACA TCGCCGTGAT CGGGGTGGCG
43081 GGCAGATACC CGAAGGCAAG AAACATCGAG GAGTTCTGGC GCAATCTGCG CGAGGGCCGC
43141 GACTGCATCG AACCGTTGCC GAAGGAGAGA TGGAGCCCGG ATCCGTCGGA CCCGCTCCGC
43201 TGGGCGGGT ATCTCGACGG CGTCACCGAT TTCGATTCGC TCTTCTTCGG CATCTCGCCG
43261 CGTGAAGGAG AAGGGATGGA CCCCCAGGAG CGGCTCTTCC TGGAGGTCGC CTGGGAGACC
43321 ATCGAGAGCG CCGGCTACGA CCCCCTCAGG CTGGGTCGCA GCGGAGAGCC AGCGTCCGTC
43381 GGCGTCTTCG TGGGTGTCAT GTACGGCGAA TATCAGGTCT TTGGCGCAGA GCTGACGCTC
43441 CTCGGCCAGC CGACCCTGGT CAGCTCCTCG TACGCGACGA TTCCGAACCG CGTCTCGTAC
43501 TTCCTGAACT TCAGCGGCCC GAGCCTGGCC CTGGACACGA TGTGCTCGTC GTCCCTGACG
43561 GCGCTTCACC TCGCGTGCGC GAGCCTGCGC TCAGGAGACT GCAAGATGGC CCTGGTCGGA
43621 GGGACCAACG TCACGATCCA TCCAAACAAG TACCGGCTGC TGGAAGCTGG GAAGTACCTG
43681 GCGAGCGACG GCCGGTGCCG GAGCTACGGC GCGGATGGCG ACGGGTATGT CCCCGCCGAG
43741 GGCGTCGGCG CAGTGCTCAT CAAGCCCTTG GCCGACGCTC GCCGAGACGG CGACACGATC
```

```
43801  TGGGGCGTCA TCAAGAGCAC GAGCATCAAC CATGGCGCGC GCGCGCGCGG CTACACGACC
43861  CCCAATCCCA ACGCGCAATC GGCCTCCCTG TCCCTCGCGC TGGAGCGCGC GAAGATCGAG
43921  CCGCACACGC TCGGATACAT CGAGGGTCAC GGGACTGGCA CGTCGCTGGG TGATCCGATC
43981  GAGATCCGCG GCATCCAGAA GGCCGTGGGC CGTGTTTCGG AGAAGATCCC GATCGGCTCG
44041  GTCAAGTCGA ACATCGGGCA CGCGGAGTCT GCCGCGGGCG TCGCGGGCCT CACGAAGGTG
44101  CTCTTGCAGC TTCGGGCGCG GGAGCTCGTT CCCTCGATCC ACTGCGAGCC CCCGAACCCG
44161  AACATCGACT TCGACAGGGC GCCCATCCAG GTGCAGCGGC ACGCCGCTCC CTGGAACCGC
44221  AGGACCATCA CGTCGGGTGG GGTCACTCGA GAGGTCCCCC GGCGGGCCGT CGTCTCCGCC
44281  TTCGGTGCGG GAGGCAGCAA CGCGCACGTC GTCGTCGAGG AGGCCGACGC GCCGGCGCTG
44341  CAACGCACCG TGTCCGCACA GCCTCGGTTG TTCGTCCTGT CGGCTCGTTC CGTCGAGCGG
44401  CTCCGCGCCC ACGCGCAGAG CTTTCTCGAC TTCTTCTCGA GGATGCCGAC CCTCAGGGAG
44461  GCCGAGGCGA GGGAGCTCTT CTACGATATG TGCGCGACGC TGTACTTCGG CCGCGCTCCG
44521  TTCGAGGCGC GGCTTGCCAT CGTGGCCGAG AGTCTGCGGA CGTTGCAGCA AAAGCTCGCC
44581  GCGTTCGTTT ACGGCGCCTC GCGAGACCCG GACATCCTCG TGAGCGATGG GCGATCGCTC
44641  GCGGCCACGG ACGGCGGGCA GCGTCAGCTC TCTGGCCTCG CCGATCTGGG GCGGCGCTGG
44701  GTCGCCGGAG AGGCGGTCGA CGCGAGCGAG CTGTTTCCGC ATCCCTGGAA GAAGCTGGCA
44761  CTGCCTACCT ATCCGTTCGA ACGGCGGCGG CTGTGGGCGC CTTCCGGAGA GAAGCTGTAC
44821  GATCTCAGAT CCGCCGCGGC GCCGGCTCCG GCGGCTCCAC CAGGGAACGG GGCTTCACCG
44881  AGGGAGGTCC CAGCGAACGT GCCACGGGCG GCTCGTACGG ACACCGCAGA GACAGCCGTC
44941  GTGAGCGGTC CGCAGCACGC ACGGATCGCG CCGGCCGAGC GGAGGCTCGC CGTGGCCGAG
45001  CAGGTGATCG AGGTGGCCGA GCGCCCCTCA CCCCCTGACC GGGGCCCGTC GACGAGCGAG
45061  ACGCGGGGGA GCGAGAGCGA TCCGCACGTC ACGAGCACGT TGAACGGCCA CACGAGCGCG
45121  TTGAACGGCC ACACGAGCGC ATTGAACGGC CACGCCGCGC GAGCGACAGG TCCCGAACGC
45181  CCGGCGGCGG CCGTTCAGGC AGCAGATCAG GGGGCGGCCG TCGAGATCGT CCAGGAGATG
45241  GTCCGCGATC TCGTGGCGCA GATCCTCTTC GTCGACCGCT CCACCATCCT GCCCGACGCG
45301  GCGCTGTTCG ATTATGGCCT CGAGTCCGTC AGCTCTGTCG AGCTCGCGGA GCGCCTCAAC
45361  GCGATGCTCG GCACGGACAT CACGCCGACG AGCTTCTACG AGTTCAACAC GCTCGCACAT
45421  TTCAGCCGTC ACCTGGTCGA GCGCTACAAC CTCGCGGACC GGCTCTCCGG TCTGAGCGCC
45481  GGTCTCGCCG GGGGAGCTC CGCTCCCGCG GCCCCTCCG GTCGTGGTGA TTCGCCGCCA
45541  CGAGCGGCCG CCGGAGCCGA GGGCCCCGTG GTCGGCGCAG CGGCCGCCGA GGGCGCTGCC
45601  GCGCCTGCGG CAGGCGGACC CACCGTCGAG GAGCTCTGGG CCAGCGCGAT GCACGCCGAA
45661  GGGCTCGCGG CGCTCCCGAG CCCCGAGCCC CGGCGCTCGG CCTCCAAGGC TCCACGCCCG
45721  GCGCCGCCCG TTCAGCCGTC GGATCAGGCC ACGCCCGTCG AGATCGTCCA GGAGATCGTC
45781  CGCGATCTCG TGGCGCAGAT TCTCTTCGTC GACCGCTCCA CCATCCTGCC CACCACGGCG
45841  CTGTTCGATT ACGGCCTCGA GTCCGTCAGC TCTGTCGAGC TCGCGGAGCG CCTCAACGCG
45901  ATGCTCGGCA CGGACATCAC GCCGACGAGC TTCTACGAGT TCAACACGCT CGCACATTTC
45961  AGCCGTCACC TGGTCGAGCG CTACAACCTT GCGGACCGGC TCTCCGGCCT GAGCGCCGGT
46021  CTCGCCGGGG GGAGCTCCGC TCCCGCGCGG CCAGCGCGC CTCGCGCCCA AGGGCCCGCG
46081  GCGCTCTCGA GCTCCGAGCC CCGACGCTCG GACGCCGGGA TCGAGCTGCA CGTGATCCCT
46141  GGCGTCGACG GACACGCCGT GGAGTTCGCC ACGCTCGGCT CGGGCGTACC GCTCTTCGTG
46201  CTCGGTGGCC TGCTGGCGAC CCATGATGCG CTGACCTTGA ACCGGATAT CCTGTCGCTC
46261  GGGCAGACCT ACCGGGTGAT CATGGTGCAT CCGCCTGGCG CAGGCCGGAG CGAGCTGCCG
46321  CGCGGCGAGC TCACGATGGA TTTCATCGTG CGGCAGGTCG AAGGCGTGCG GCAGTCCCTC
46381  GGCCTCTCGT CTGTCGTGCT GGTCGGCTAC TCGTTCGGTG GCCTCGTCGC GCAGGCCTAC
46441  GTCGCGCAGT TTCCCGAGCG GGCGTCGAAG CTCGTCCTGG CGTGCACGAC GTCGGACCCG
46501  GCGAGCGTCG TGAACGGCAT GCACCTCGTC GCGGCCGAAG CGCAGCGCCA CCCGGACGGC
46561  CTCCGGGCGC TGCAGTTCGC CGACGTGAGC AAGTTCCCGC TCTACTCCCA GCTCAGCACG
46621  CGGCTCCGGC CGGAGACGCT CGCTTACCCC GCCATTCCGA CCCTGATCGT GGCGGGAGCC
46681  GAGGATCGGT ACGTGCCGAC CATCCACGCC GAACGGCTCG CGCGCGCCAA TCCCAACGCG
46741  ACGCTCCACA TCGTCGAGGG CGCGGGCAC TTCCTCGGCC TGTCTCACGG TGGCGTGCTG
46801  GTCCACCTCG TGAATGGCTT CGTGCTCGGG GACAGGACCG CTCCGGCGAG GTCTCCTGCG
46861  GTCAGCGCCT CGCGCGCGG TGGGTTGCGC AAGATGAGCC AGGAGTCCGT CGGCGCGCTG
46921  AAGAGCTACC TGGAAGAGGG AGAGATCGCT TCGGGGGTGG AGGCCTCGCC CGTCGCGGGT
46981  CAGGTCGGCT ATTTGCTCAA CCGGCTCCTG AGCGGACAGG AAGCGCCGAG CAGCCCCTAC
47041  CACTGCTTCT TCATGCCGTC CGGCCTCGAG GCGGTCGACG CAGCGCTGCG GTTCGGACGC
47101  CGTCGGGCAA AGCTCTCCAG GGGCCTCGGC GACGCGAAGA CGCTCGTCCT CGATCCCGAG
47161  GGAGCTCTCC GCCGGCATTT CGAGTTCCTC CCGCAGGAGC GGCTCTTCCC CGATCTGATC
47221  TTCGTGGGCG AATCGCGCGA GCTGCTCCGG CTGCTGCAGA GCGCCGAGGA CGTCGGCGCC
47281  GCGTACGTCA CCACGGCATG CGATGACGCC ACCCTCGAGA CGGTCGCGGC GGAGTGCGCC
47341  CGGCGCGGGA TCGTGTCGGT GCTCGGAGAG CTGCACGCGG ACACCGGCGA GCTCGTCTCG
47401  GCGAGGCTGC GCTCGAAGCC TGACGTCGTG GTGCTCGACG AGGCCATCGC TGGTTTCGAG
47461  CTGCCGTTCG GCGTGTGCGC GATACGGCGC TTCCATGAGA GCGGCGTGTG GACGCGCCAG
47521  CCCGAGGAGT CGCGGGTGCG AGTCCCGGGG TCGATGGCGG GGCCCGCGCT GACCGTCGTG
```

```
47581 AGGGAGAACA TCCTGCGGCG ATTCCGCGCC GTCGTGACGA ACGACACCAC CGCGAACCTG
47641 CGCGCGATCG CCGTGGATCA ACGGCGCACG AAGGAGGCTC ACCGGAGCTA TGTGAACCCC
47701 GTGCTCCTGG AGTCGCTCGA CGCGTTCGGA CTGGCGGGCC GGCAAAGGCA CGCGGACCGA
47761 CGCGGCTATG AGATCGAGCG AGATGACGGA AGCTCGGCCC GGGTCATCAA CCTGTACCTC
47821 GTGACGAGCG CGTCGTTTCG AGGGCACACC GGCTCCGAGA TCGCGCAGTC GGTCCTGGGC
47881 ACCCACGACA TCACGAGGGA CTACTGGGCG GATCTCGAGC GGCGCATACC GCGCGAGACG
47941 GACTTCGGGC GGGTCTTTCC CGCGGCGGGC CCCGCGACGG CGGTCGAGAC GGCGGTGAAG
48001 CTCGGGCTGC TCGCCGCGAG GAAGGGCTCG GCGCTGCTCG TCCTCAAGGG GAGCCCCATC
48061 TTCACGCGGC TCGGGGCGTT GGTCTCGCAC GCGGAGCCCG GCTCGCCGCT GGAGGCCCTC
48121 GTGGAGAGCT GCCCTTGGTC CAAGGTGATC GCCGTCGATC CGTTCGGCGA AGGCGCGGCC
48181 GCCGAGCTCG AAGCGAAGCT GACGTCGGAC GACGTCGGAT TCGTCTGGCT CGAGACGCTG
48241 CAGTCGGACT GGGGTGGTCT ACGGAGCGTT CCGGATGCCG TGCTCGAGGT GATCGACAGG
48301 CATCGGGAGC GGTCGGGATA CCTGGTGGGC GTCGACGAGA CCTACACGAG CCTGGGTTGT
48361 GGCCGGATGT TCACTGGCA AGGCAAGCTC GCCCGCCCCG ATGTCGTCGC GGTGTGCGTG
48421 GGCTGGACGG ACTGCCAGCT CCTGGCGGGC TACGTCCTCA CCACCGAAGA GGTCGCGGCG
48481 CGCGCGCGGC AGCGCAACGA GGCGGTGGTC TCCGCGCTGC AGGAGCAACT TCGCTGCCAG
48541 CTCACGGCTC ACGCGACGCT GCGCCTCCTC GACGTCCTGA AGGAGGACCG GATCCTGGCG
48601 CAAATCGCCG AGACCGAGCG ACGATTCTCC GGCGCATTGA ACGACTTCGC GGCGGAATGC
48661 GGCATGGTCA AGCGCGTCTG GGGGGAACGG CTCTTCTGGG CGGTGCAGTT CGACCTCGAT
48721 GGGTGGCCCC GCTTCGTCCG TGACTGGTTC TCGTCATTCC TCTGGAGTGA GTGCTTGCGA
48781 GATCCGGTGG CGCCCGTCGC GGTGTCGATG CAACCGCTGA CGCCAGCGTG CATCCGCGTC
48841 GAGCCGCGCT ACGACATCCC GGCTGCGGAG CTCGACGCCG CGATGGGCAC GCTGAAGCGC
48901 GTGCTCGGCA AGGGTGTGGA GGGGATCGTC GCGAGCGTCG CCGACGACGT CGAGCGACGG
48961 GGAGACGCCC GCCGCGCAGA GCTGTTTCGG AGGATTCTTC GAGGGTTCAA GACGACATGA
49021 GCGCTCAACC TGAGTACTGC ATCGTTGGCG GCGGGCCCAT CGGCATCGGC ATCGGGAAGT
49081 GCTTCGCCCA GGAGGGGCTG AAATTCACGA TCGTCGAGGC CGATGAAGAC TTCGGTGGCA
49141 CATGGGCGCT GTCCCAGCGT TCGGGCCTCG TCTACAAATC GACCCACCTG ATCTCATCGA
49201 AGAAGAACAC GCAGTTCCTC GACTTCCCGA TGCCGGAGGA TTACCCGCAT TATCCCAGCC
49261 ATGCGCAGAT GCTGTCCTAT CTGCGCAGCC TGGCCACGCA TTATGGCCTT TACGACAGAG
49321 CATTGTTCGG CACACGCGTC GAGCACGTGG AGCCGAATGG CGCGGGCTGC CGCGTTCGCC
49381 TCTCGAACGG AGAAACGCGG ACGTTCTCGG CCGTCGTCGT GGCCAACGGG CGCATGCGCA
49441 CGCCCCTGAT CCCGCGTTAT CCGGGGGTCT TCAGCGGGGA GACGATGCAC TCGGCCGCCT
49501 ACAAGTCACA CGAGGTCTTC CGCGGGAAGC GCGTGCTCGT CATCGGCGGC GGGAACTCGG
49561 GCTGCGACAT CGCCGTGGAC GCAGCGCTGG CGGCCGAGCA GACGTTCCAC AGCACGCGGC
49621 GTGGGTACCA TTACATGCCC AAGTTCATTC ACGGCAAGCC CACCCAGGAA TGGCTCATGG
49681 ACATGGGGTC GAAGTTCCGC TCCCAGGACG ATTACTGGTC GTTCGTCCAG CGGGAGTTCA
49741 AGGCGGCCGG CTACGACCCC GTCGATTACG GTCTGCCGCG CCCCGACCAC GCCATTCATG
49801 AGGCGCATCC GATCTTGAAC TCCCTCGTCC TCTATTACAT CGGTCACGGG GACATTCATC
49861 CCAAGCCGGA TGTCCGGCGC TTCGAGGGAC GGACGGTAGA GTTCGTGGAT GGCACGCGCG
49921 CAGAGGTCGA TCTCATCCTT TATGCGACAG GCTACGAGAT GGATTTCCCG TTCCTGGCGG
49981 AGGATCTGAG GCCGAGCGAC GGCGCGCTGG AGCTGTTCCT GTCGATGTTC CACCGGAAGG
50041 CCGACAGCCT CGTGTTCGTC GGATATTTCA ACGCGGCGTC GGGGCTCGGC AACCTGCTCA
50101 ACTGCGGCGG AGCTCTGGTC ACAGACTATT TGGTCGCCCG CGAGAAGAAC ACAGATGCAT
50161 TTCGAGTGCT GCGCAGGCTC ATCCAAGGGC CCGAGCCCGA TATCGGCAGA GGTCGCTTCC
50221 TGAACTCCCC ACGGCACCGG GTCGAGACGG ATCTATGGAA GGCGATGAAG GTCATGAATT
50281 TCTTCCGGTC AGTGCTCAAT CCGGCACGGG CAGCCGGGGA CGTGGTGCGC GCCTGACGGA
50341 GGCCAAGCGC GCTTCGCAGC CGCGGTCGAG TCGACCCAGG CGGGGCGACG TGAGAGCCTC
50401 ATGCCCACGG CGCTACCTCC GCGGGCGGCA CACGCTCGAC TCGCCCCGAG ACTGCGCTGA
50461 ATCGCTTGAC GTCAGAGCCG CTTCATCGTA ATCGTGACTG AATAAGGCTG CACCTTGCAG
50521 TGCATGAGCA GGGAAGGAAC AAGCTCGATG AACATTGGGA GTCCGTTGCC GCCCATTGAA
50581 AATGCTCTGG ACCTGTTCAA GCATTACGCC ACGAGCGCTC CCGAAGCGAG AATCGCCGTA
50641 TTCATCGAGG AGGAGGGGCA GGAGCAGGGC CTCACCTACA GGGAGCTTGA GCGCGCGGCC
50701 ACGAACCTCA GCCTCGAGCT CGCGTCGGTC GCCGCGCCGG GTGACAGGGT CCTCGTCGCT
50761 TACGATTCCG GTCCCATGTA TCTGGTGGGG GTATGGGCGG CTCTTTATGC CGGCATGATC
50821 GCCGTCCCCG TAGATCCGCT CGGCCCTGAT CGCCCCGCGG CGAACCTCAC GCGATTGTTG
50881 AACGTCACCG CCGACTCGGG CGCCACGGTT TGCATCGCGT CGCGCAGCAT GCTCGATGCG
50941 GTGAAGAGCC ACCCAGGCGC GCGGCAGCTC ACGGAGCAGC TCCGATGGGT CGTCCCCTCG
51001 CTCCCCGATC TCCTGGGGCG AGCGCCCGGC TCCCCGCCGG CTGCCCTGCG GACCGAGAAG
51061 GACGTCGCGA TGCTCCAGTA CGCGTCGGGC TCGACCGGCG CGCCGAAGGG CACGATCGTG
51121 ACGCACGCCA GCTGCTGAT GCTCGCGCGC GCGCTGCTCA TCTCGACCTC GGCCGAAAGC
51181 CCGTTCGGCC GCCCCGACGT CGAGGTCACG TGGCTCCCCC TGACCCACTC GACGGCTGGA
51241 TACGGCTTGA TCATGAAGTG CCTGACGGGA GCGACGATGT CCGCGTGGTA CATCGCGCCC
51301 AGCGCGTTCG CCCGGTCGCC CGCGATATGG CTGCGGACGA TCTCTCGCCA CAAGGGAAAG
```

```
51361 CAGGTGTATT CCGTCGCTCC GAACTTCGCG CTTGACTGGT GTGTCTCGTC GACGACGGAG
51421 GCCGAGCGCA AGCAGCTCGA TCTGAGCTGC TGGACGCACG TCATGAGCAT GGGGGAGAAG
51481 GTGCGCCCCG AGACGTGGAA GGCGTTCTCG GACGCGTTTC GCGAGAGCGG CTTCCACCCC
51541 AAGCTGTTCA TCGCCGGGTA CGGCATGTCG GAGACGGGAT ATGTCTCCGG CTCGGTGAAC
51601 GGCGGCAAGA CGGTTCGCTT CGATCGTGCG GCGATGGACG AAGGCAGCTT GGTAGAGGCG
51661 CCGGAGGGCG GGATCCTTCT GCTGTCGTCG TCCGGGTTCA CCCTTCCCGG CGTGCGCGTG
51721 GCGATCGTGG ACCCGGAGAC CAGAGAGGTC CTCCCGGAGG GCAAGATCGG CGAGATCTGG
51781 GTGTCGACGC CCACGGCCAT GACGGGCTAC TGGAACCGGC CAGAGGAGAC CGAGCAGCAG
51841 TTTCGCGCGC GGGCGGCCGA TGGAAGCGGC CCCTTCTTCC GCAGCGGGGA CATGGGCGCC
51901 TTCTATGGGG GCAATCTATT CGTGACGGGC CGGCGAAAGA GCATCGTCGT CATACGCGGG
51961 CGCAAGCACT ATGCGGAAGA CATCGAGTCG ACGCTCGAGC GTGCGCTCGA CTGGCTTGGC
52021 GCGAACTCGT CCATCGCCTT CGCGGACGAC GTGAACGGCG TCGAGGAGCT GTTCATCGCG
52081 GTCGACCCGA GGGGCGCGCG CGACGGCGTC GGCTTCGAGG AACGCACGGA CGCCATACGC
52141 AGCGTCGTCG CGCGTGAGTT CGGCGTCCGC GTTCACGAGG TCCTGTTCCT GGCCGCGGGG
52201 CAGCTTCCGC GGACCAGCAT GGGCAAGGTC TCCCGGGTCT CTTGCAAGGA CCTCTTCCGC
52261 AGCGGCGAGC TCGAGATCGC GGCGCGGTCC GGCAGCATCG CGCGTGGCGG CGCCGACCTG
52321 CCGGCCGTGG ACCTTCGCGC GATCCTCGAC GAGCCGGACG GGAGCTGCG CGTCGCGCGA
52381 ATGACCGAGT ACATCAGGAG CCTGCTTTCG GCATCGCTCT CTGTTCCGGC CGACGCGCTG
52441 AGCCTCACGA AGTCGTTCGA CGAGCTTGGA GTCGACTCGA TGACGGGGGT CCGGTTTCGC
52501 GGCGAGCTCG TCCGCGCGCT CGGATTGGAG CTCCCTGAAT CCATCGTCTA CAATTATCCG
52561 ACCATCGCAC AACTCGCGTC CTTCGTGTGC GAGAAGCTGA CCGGCACCGC TGGCAGCAAC
52621 GATGCGGAGC GGGCGGATCG AGGTCCCGCG GCGCTCGCGG CTCTCGACGT CGAGAGCATG
52681 TCCGAGGAGG CCGCCGCGGC CGCGCTGCGC GCCCACCTCG ATGGTCGAAA GTAGGAAACG
52741 GGCTGGCCGA CGCCAGCACC CCGGAGTGAA GTGAGATGAG CGAATCCGGC GAACTGTCTC
52801 TCACGAAGCG CGCGCTCCTC GCCCTGCAGA AGGCGGAGCT CGAGATCGGC CGGCTCCGGG
52861 ACGCTCGGCC GGAGCCGATC GCGATCATCG GCGTCGGATG CCGCATCCCC GGCGGCGCCA
52921 CGTCGCCGAG CCGGTTCTGG AAGCTGCTGG AGGAGGGCTT CGACGCGCTC GCCGAGATAC
52981 CGGCCGCGCG GCGGAAGCTG TTCGAGCTCC AGGGAGCCCG CAGCCCGACG TCGGGAGGGT
53041 TCCTCGATGA GATCGACAAG TTCGATCCAT CCTTCTTCTC GATCTCCCCA CGGGAGGCCA
53101 TCTCCATGGA TCCGGCGCAG CGGCTCCTGC TCGAGGTCTC GGTCGAGGCG CTCGAGGACG
53161 GCGGCGTCCC GATGGCACAG ATCCGGGGCA CCCGGACGGG GACGTTCATG GGGTTCTCCG
53221 GGTACAGCGG CTATGGCTCG CTGACCGGTG CGCAGGTCGA GCAGCTCTAC GCCGTGACCG
53281 GGCTCTCGAT CAACGTGGCC GCCGGCCGGA TCTCGTACGT GCTCGACCTG CAGGGGCCAT
53341 GCGTGTCCGT GGACACCGCC TGTTGCTCGT CGCTGGTCGC GGTCCACCTC GCGTCTCAGA
53401 GCCTCCGCAG CCGCGAATGC GACCTCGCCC TCGCCGGAGG CGTCAACGTG ATCGCGGCGA
53461 TGGCCGGCAA CGAGGCGATG GCGGCCACGG GAGCGCTCTC TTCGTCCGGC GGACGTTGCA
53521 GGACGTTCGA CGCGGCGGCG GACGGCTACA TCCGGTCGGA AGGCTGCGGC GTGGTCCTCC
53581 TGAAGCGGCT GACGGACGCG ATGGAGGCGG GAGATCGGAT CCTCGGTGTC GTCGCCGGCT
53641 CCGCCGTGAA GCATGACGGA CATAGCAACG GGCTCACCGC GCCGAACGGC CGCGCGCAGC
53701 AGCAGCTCGT CCGCGAGGCG CTGGCCGCCG CGCGCGTCCG ACCTGAAGAG ATCGACTACA
53761 TCGAGACGCA CGGGACTGGC ACGCCGCTCG GCGATCCTAT CGAGGTCGAT GCGCTGGCGG
53821 AGGTCTTTGG CAGCTCGCAC GGCCCCGACC GGCGCATCAT GCTGGGCTCG GTGAAGACCA
53881 ACGTCGGGCA TCCGGAGGGG GCGGCCGGCA TCGTCGGTCT CATCAAGGTC CTCGGAATGT
53941 TCCGGCGCGG CATGGTCCCA CGTCATCTTC ACTTCAACAC CCCGAACCCG CGAGTCCCCT
54001 GGGATTCGGT CCCCTTCCTG GTCCCGCGCG ACACGCTCCC CTGGCCTGCC ACCGACAAGG
54061 TGCGGGTGGC CGGCGTCAGC GCTTTCGGGT TCAGCGGCAC CATCTCGCAC GCCATCGTCA
54121 TGGAGCCGCC GAAGGCGCCG GAGCGGAGCG TGGACGTCGG TCCGGCGACG GCGGGGCGCC
54181 CGCTGCTCCT GCCCATCTCC GCCAGGACCC CGGAGGCGCT GAGGGCCTAT GCCGCGTCCT
54241 ATCTCGATCA CTTGAGCGCG GAGGCGACGC CGGAGGAGAC CGATCGGGAT GTGGCCTATA
54301 CCGCCAGTCT GCGGCGGGAT CATCATGCGC ACCGGCTGGC GGTGGTGGGC AGCGATCGCG
54361 CAGCGTGGCG CGAGAAGCTG CAGAGCTACG TGTCCGGCGA GGGCTGCCGT GGTCTGGTCG
54421 AGGGGGTGGT GCCCGAAGCG CGTCCGCGCC TCGCCTTCGT CTTCTGCGGC CAGGGTCCGC
54481 AATGGTGGGG GATGGGCGGG GAGCTGCTGG ACAAGGAGCC GGTGTTTCGC GGCGCGCTGG
54541 AAGCGTGCCA CGAGCGCATA CGGGAGGCGG GAGGCCCATC GCTGCTGGAC GAGCTGCGGC
54601 GCGAGGCCGA CACGTCGAGG TTGAACCAGA CCGAGGTGGC CCAGCCGGCG CTGTTCGCGC
54661 TGCAGGTGGC GCTGGCGGCC CTCTGGCGTT CCTGGGAGT ACAGGCGGAC GCCGTGGTGG
54721 GTCACAGCAT CGGTGAGGTG GCCGCCGCCC ACGTCGCCGG CGCGCTGAGC TTGGAGGACG
54781 CCGCGCGGCT GGTGGTCCAC CGCGGTCGGA TCATGCAGCG AGCGACCGGC CTCGGAAAGA
54841 TGCTGTCTGT GGCGCTACCG CTCTCGGCGG CGCAGCGGAT CGTGAGTGAT TACGGCCAGC
54901 GCATCTCCAT CGGCGCGAGC AACAGCCCCA CATCGACCGT GCTGTCGGGA GAGGCAGCGG
54961 CCCTCGATGA GGTCGTCGAG CAGCTTCAGG GCGGCAGGT CGAGGCCAAG TGGCTGCCGG
55021 TCGAGTATGC CTTTCACAGC GCCCAGATGG AGGGCTTTGG GGAGGAGCTG AGCAAGGAGC
55081 TGCGCGGGCT CGCCCCGGGG GCGAACGGTC CGCTGCTGAT GTCGACGGTC ACCGGCACAG
```

```
55141  AGCAGCGCGG GACCTCGTTC GACGCGGACT ACTGGGGGCA GCAGATCCGC AAGCCGGTCC
55201  TCTTCGCGCA GTGCGTGGAG GAGCTGGCGC GCAAAGGGTG CAGCCTCTTC CTGGAGATCG
55261  GGCCCCACCC AGTCCTCTCG GCGTCCATGA CCGAGACGTT GCTCGCCCAG GAGAAGAGCG
55321  GCCGCGTGGT GGCCTCGCTG AGGCGCCGCG AAGAGGAGGT ACCCACGCTC CTCGAGGCGC
55381  TGGGGCAGCT CCACTGCGCC GGCTACCCGG TGGACTGGTC GAAGCAGCAC CCGGTGCGCG
55441  GCCGTACCGT TTCGCTGCCC ACGTATCCGT GGCAGCGGGA GAGCTACTGG CTCGAAGCCC
55501  CGAAATCGCA GACGCCGCGC CAGCACGGCG CGGAGCACCA CTATGAGACG GAATGGCGCC
55561  TGGCCGAGCG CGAGCGGCCC GCCGAGCCTC GGCGGGGCGG ATGGCTGATC CTGGACGACC
55621  AGGCGGAGCG CGCTGCTGCG CTGCAGGACT ACCTCGAGGC GCGCGGCCAG ACGTGTGTTC
55681  GTGTGGTTGC TGCCGACACC TACGCGCGG  GCGGCGCGCG CGACTACCAG ATCGACCCAC
55741  GGGAGCCCGA GCACTTTGCC CGGCTCCTGG GTGAACAGGA GGTGGTGGAC GCCCTGGCCG
55801  ACGCCTCTCC TTCAGATCGG TGCGGCGTGG TGCACCTGTG GAGCGCGCAC AGCTCGCCCG
55861  CGCCCACCCT CGAATCGATC CAGCAGGCGC AGGCGCTGGG TTCGATCAGC GCCCTTCACC
55921  TCGTCCAGGC CCTGGCGCGC GCGGGATGGC GACAGCCGCC GCGCCTCTGG CTCGTGACGC
55981  AGGAGGTCCA GGCCATCAAG AACCCGACCG TCTCGGTGGC GCAGGCGCCC GTGTGGGGAT
56041  TTGGCGCGAC CGTAGCGCTC GAGATGCCGG AGCTCCAGTG CACCCTGCTC GACCTGGACG
56101  CCACGCCGAA CATCGATGCT CTGGGACAGG AACTCCTCTC CGCCAGCGAC GAGGATCGGA
56161  TCGCGCTGCG CGGAGCCGAG CGTCACGTCG CGAGGCTGGT CCCGCATGTA CCGGAGCAGC
56221  GCCCGGCCCC GGAGCCGTTG TCGTTCAAGG CCGACGCGAC CTACCTCCTG ACCGGAGGCC
56281  TGGGGGGCAT TGGACTGGTG GTCCTGGAGT GGATGGCGGC GCGAGGCGCC AGGCACTTCG
56341  CGCTGCTGGG GCGGAGCGGC CCATCCGCCT CGGCGCAACC CGTGCTGGAC CGGATGCGCG
56401  AGGACGGCGC GCAAGTCCGG ACTTTCTCCG TCGATGTCGC CGACCGGGAG CGGCTCCGCA
56461  CCGTCCTGGC GCAGATCCAG ACGTCGATGC CACCGCTGGC CGGGATCATT CACGCGGCCG
56521  GGGTGGGAGA TCAGAAAATG ATCCCCGACC TGGACGGGCC CTCTCTGCAG GCGATCGGCC
56581  GGCCGAAGGT CGACGGGAGC TGGAATCTGC ACGAGTTGAC GAGCGAGCTG CCGCTCGACT
56641  TCTTCGTCCT GTTCTCCTCC GTCTCGTCGC TCTTCGGCTC GCACGGGCAG TCGAGCTACG
56701  CCGCCGGCAA CGCCTTCCTC GACGCGCTGT CGCACCACCG GCGGGCGCTC GGCCTCCCGG
56761  CGCTCAGCCT GAACTGGACG GCGTGGACCG ACGTCGGGAT GGCGACGCCG ATCATCGCCC
56821  ACACGTCGCG GTACCTCGCC ACGCAAGGCA TGGGCGCCCT CTCCTCCAGG GAGGGCGTCG
56881  CCGCGCTGGA GCAGCTCTTT CGCGCCTCCT CGGCCCAGAT CGGCGTCGTG CCGCTGTCGA
56941  TCCCCTCGCT GCCGAGGAAG CCGTTCTATT CCGTGGTGGC TCCGCCCACC GCCCCGACGC
57001  CGACGGCGCA GACGGTCCGG GCGTCCGAGC GCATCGCTGC GCGGCCACCC GGGGAGCGGC
57061  AGGAGGCGAT CGAGGGCACG CTGCGGGAGC TGTTCGCCAG AGCGCTGCGG ATGCCGCCTG
57121  ACAAGCTGAA GCTGACCGAG GCGCTCCAGA ACCTGGGTGT CGACTCCTTG ATCGCCCTCG
57181  AGCTCCGCCG CCGCATCGAC GAAGAGCTCG GCGTGAAGCT GCAGGCCGCC GAGATCGCCA
57241  GGGTCGCCAA CGTGCGTGAG CTGGCCCAGC TCGTGACCGC CAAGTTCGAC GCGCTCCACG
57301  GCAGCGCGGG CGTGGCCCAG CAAGCGCGGC TCGAGGTCCG CGGCCCATTG ACCGTCCTCA
57361  AGCCCAGCCG GCAGAGGCCG CGCTTGCGGC TGGTCTGCTT CCCCGCTTCG GGCGGCAGCG
57421  CCGGCGACTT CGCCGAGTGG GCGAAGGTGA TGCCGGACGA CTGCGAGCTC GTCGCCGTGG
57481  AATACCCGGG GAGCGGCGCG CGGCAGCTAG AGTCGTGCGA GCATCCGCTG GCCGCGCTCA
57541  CGCTGCAAGC GGCCGGCGCC CTCATGGCGA TGCCCAGGGT GCCGCTCGTG CTCTTCGGGC
57601  ACAGCCTGGG GGGCCTCATC GCGCACGCGA CGGCCGTGGA GCTGGAACGG CACGCCATGG
57661  GACCGTCGTG CGTGGTCCTG TCCAATCCAG CCAATGTGAT CACCGTCCAG CGGGACCTCC
57721  CCCGAGACGG ATTCCGTGAC CAGAAGTTCC TGACATGGCT GGCCAGGTCG ACCGGGGATT T
57781  CCATCGAGCC CGAAGCGACC GACAGCGATG CCACGCGTCA GTTCTTGAAG ACGTTCGGCG
57841  AGCAGCTCGC GTGGACGTTC GACTTCGACC TGGGGTGGCG GGTCTCCTGC CCGGTCATTA
57901  TTTCGTGCGG TCGAGACGAC ACGACGCTCC ACGCCGAGAG CCTCGAGTTC TGGAGGCGCA
57961  GCGGAGGCGA TCTGGAGGAG TGGACCTTCG CCGGAGCCCA CGACTACATC CGCCAGGAGT
58021  TCGCCGAGAT CGTGTCCAAA ATCATGAACA GGGCTGCGGG TAAAGACAGA ACATGAGCCG
58081  TGCAATCGTT ATCGGGGGCA GCATCGCAGG GATGTGCAGC GCTCGTGTGC TGTGCGATTT
58141  CTTCGATGAG GTCGTGATCC TGGACCGGGA CCAGTTTCCC ACCGAGATCG CGCCTCGGCC
58201  TGGCGTGCCG CAGAGCCGGC ATACACATGT GCTCCTGCCG CGGGGAGAGC AGGAGCTCGA
58261  GGAGCTCTTT CCCGGCTTTT CCGCCTCGAT GATGGCCGCG GGTGCGCTGA AATTCGACGT
58321  CGGGACGGGC ATGGCGGTGC GACGCGTCTT CGGCTGGCAG ACGGTCGGAC CCACGGGCCG
58381  CGAGCTACTC TGGGCCAGCC GTGACCTGTT CGAGGGCACG ATACGCTCGC TGATGCGACA
58441  GCAGACCAAA GTGCGCATTC GGGAAGGCTC TCAGGTGCTC GCGCTGCGCA GCACAGCGGG
58501  CGAGAGGCCA AGGATCAGGG GCGTACTTCT GCGCGATGAC GCTGCGGAGC AGGAGCTTGA
58561  AGCCGACCTG GTCGTCGATG CCAGCGGCCG GCATACGCGC GCCGAGCAGT GGCTGACCGA
58621  GCTCGGGCTA CCTGCGCCCA AGACGCAGTG CGTCGACTCG CGCGCTGGCT ACGCCTCGCG
58681  GTTCTACAAG GTGCCCCCGC CGAGCGCCG  GCCGTCGGAC TGGTGGTGGA AGGGTCTGTG
58741  GGTCGAGGCG GAGCCCGACC GGCCGCGGGG CGCTGTCGTC TTTCCGATCG AGGGCGATCG
58801  CTGGCTGGTG ACCGCCTCGG GCTTCAGCGG CTCGTATCCG CCCACGGACG AGCAAGGTTT
58861  TCTCGAGCAC CTCGCGAGCC TGAGCTCACC GATCGTGGCT CGGGCCGTGG CGCTGGCCGA
```

```
58921 GCCCATCTCG CCGATCTACG GCAACCGCTC CATGGCCAAC GTATCCCGTG CTTACGACCG
58981 CTGGGAGATC CAGCTCCCTG GCTTCGTCGC TGTTGGCGAC GCGGCTTGCG CCTTCAACCC
59041 CGTCTACGGC CAGGGCATGT CGACCTCGAC CGTCTCTGCC GTCATCCTGC GCGACGTGCT
59101 GCGCCGCCGC GGCCCAGGCG CGGGCTTCGA GCCGGGCTTC TTCCAGCAGC AAGCCAAGTT
59161 CCTGCGCTCG GTCTGGGATT CGCCACGCG CTCCGATTTC CGATGGCCGG GGACGGTAGG
59221 CGAGCGCCCG CACACGCCGG CGATCATCGG CGCGTACGCG AAGCTCGCCA TCGAGTCTGC
59281 TCATCATGAC AGCGCCATAC GGCGCCATCT GTTCCCGGCG TTCGACCTCA CCGGCTCGGC
59341 GACCTTGCTC TTCGAGCCCC TCTTCGTGGG CAAGGTGCTG CTCTCCGCTG GCCAGCGTCG
59401 GCTCCGCCAG CGCCTGCTCG GCACACCTCC GATCCCGAA TCGCCGCCCG TGCCCGCGGG
59461 TGTACCTCGA TGGGCGGCCG GCGCCGCCAT GTGATGGACG CCGGAGCGG GCGCCAGCCG
59521 AGAGCAGGCC TGCTCCGGCG GAGGCGTGGT TGAGTCACAT CCGCTTCCCA TGGTAGGAAA
59581 TGGGCGAACG GACCCTTCCA GAACAAGGAG AATCAACAAT GCGTTACATG ATCTTCGTAG
59641 CGAGCGACGA GTCGTTGTGG GCGAACGCGA CCCCCAAGCA GCGGGAAGAG GTCTACGGCA
59701 AGTACATCCA GTACACCGAG GAGATGCGGA AGGCGGGCGT CCTGCTTGGA GGCGAATCCC
59761 TCCAGCCGAC GAGCAAGGGC GCGCGCGTAT CGATCCGGAA CGGCGAGCGG GTCGTCGTCG
59821 ACGGTCCGTT CGGCGAGCCG ACGGCCATCG GGGCCATGT CCTCATCAAG GTCAACTCGA
59881 AAGAGGAGGC CATCGAATGG GCGGCGAAGA GCCCGGGCGC CGTCTACGGG ACCATGGAGG
59941 TGCGCGAGGT GACCGAGTTC GGCTGACGCC CGCTCGGTGA AACGCTCGCG CAGCGGCGTG
60001 CTGGGACGGT GATCACGAGG CGGCGAGCGG CAGCCTGCGG GCCGCGCGCG TGGCCTCGTG
60061 CCCGTCTCCC GCCTCAGGCG TCGCCTCGGC CGCCTGCCCA CGGTAGATCC GATCGATCCG
60121 GTCGCGCGAC GCGACCAGGG CCTTGTCGAA CCGACCAAGG ACATTGCCCT TCAGGATCCC
60181 GCGCTTGTCC GCCAGACGGG ACAGCAACCT CATGTCAAGG CGCAGCTCGA GATCCATGGC
60241 CACCCGGAGG GGAGGCCAGA TCAATGAGCC GAGCCCGAAC TCGCTCCAGC GCCCCAAGCT
60301 CGCGAAGAGG AACGTGTAGA TCTCCGAAGA CTCCGGGCCC ACCGGATTGA AGAACACGGC
60361 CGACCGAAGC GGGTATGTCA CGACCTCCCG GGTCCTCGGG TTGATGAAGG AGTGGTCGTA
60421 GATCGCGTGC ACCGGCGAGA ACCGCGCCGT CCATTCGACG ACGAATTTCG CGTCGTGCGG
60481 GATGCGGAAC ATTTTCTCCA CGATCCGGGG GATGGGCCGC TTCGGACCCG TATTGACGAC
60541 CTGGACGGCG TCGTCGGACA GGGTTACCTG CGCCTCCACC TGCGGCATCT GGTCGAGCGA
60601 GTAGCCGAGC ATGAAGTGGA CGAACGGCGT GTGCTCGACC TCGATGAAAT TGTCGAGCGC
60661 CAGCTCGAAC GGCACGGCAG CGCGGTGCCG GAGGACACCG GCCGGACGT ACCCCTCGGC
60721 ATCGAAGCGC GGGAACGTGG CCTGCGCCCC TGCGCGCTTC ACCCAGATTG CGCCGTACCG
60781 CTCCACCGCG TCAACACAT CATCGCGCCG CGCGCACGGC CGTGCCGCCG GGTGGCAGG
60841 GATGTCGCCC CGGCCGTCCG CGGCCCAGCG CCAGCCGTGG TAGGCACACA CCAGCGGTC
60901 GCCCTCTACC CATCCCTCGC TCAGGCGCAT GCTGCGGTGC GGGCAGCGAT CCGTGAACGC
60961 CCCGAGTCCG CCGCTCGATG TCCGAACAC CACGATCTCG CGACCCGCGA GCCGCACGCT
61021 GCGGGGCTTG CGGCGGAGCT CGTGGCTGAG GAGTACCGGG TGCCAATGGT CGAGTTCAGC
61081 CATGATCAAT TCACCCCTCG GAGATGCCGC GCGACGCGCG GCGCCTCGGC TGCGATGTCG
61141 CGAAGCTGCC CTGTGATGGG ATTGCGGAAA CCGATGAAGA ACAGCCCCGG CGTCGGCGTC
61201 GGTGCGCCAT GCCAGCGCGG GTAGCCGCGC TCGTCCGTGA AGCGCGCCGC GTCCTCGAGG
61261 AAGTCGCCGA GCCCGGCCCG GTAGCCGGTG GCGAGCACGA CGGCATCGAA GGGCAGCTCG
61321 CGACCGTCCG TGAAGATCAC GCCGGTCTCG GTGAACGCGC GCGGGCCGGG GACCACCGCG
61381 ATCTTTCCCT GCTGGATCAG CGCGAGCGTA CCCATATCGA TGAGCGGAAT ACGACCTTCC
61441 TTCACGGCCC TGGTACCCGG GCCGATCTCG GGCCGATGGA TCCCCAGCG CGACAGGTCC
61501 CCCACCGTGC GGGACAGGAA TGCGGTCGCG AGCCGGTCCC CTACGGCCGG CGGGAGGGCT
61561 CCGTAGAGGG CAAGGGCACT GAACTGGGCG GGGAGCCTGA GCGGATCTCG CGGGATCACG
61621 TGAATACCGC TGCGCGCGGA GACGGTCGTC TCCGCCGCAT GCTCCCAGAG GTCCATCGCG
61681 ATCTCGCCGC CAGAATTGCC GGAGCCCACC ACGAGCACGC GCTGACCGCG GAATGCCGCG
61741 CCCGACCCGT AGGTGGAGCT ATGGAGGATG GGCCCGCGAA AGCGCTCCTG GCCGGGCCAG
61801 GTGGGTACGT TGGGAAGACG GCTGTAGCCC GTGGCCACGA CGAGGGCGCG GCTCGTGAAC
61861 TCTCCCGCGC GCGTCTGGGT CACCCACCGC GACCCGTCGC GGTAAGCGCG CACCACCTCG
61921 GCGCCGAAGC GCGGCTCCAG GCGGAAGCGC TCGGCGTAGC GCTGGAGGTA ATCGACCATC
61981 TGCGCCCGGG AGGGATACGG CGGGGCATAT CTGGGCCAAG CGAGCCCGGG CAGCGAGGAG
62041 AATTGCTTGA CCGTGTGGAG GTGCAGCCGT TGATAGTGGC GCCGCCAGCT GGCGCCGACC
62101 GCATCCGATT GCTCGAGCAG GACGAATGGG ATGCCCCGCT CGCGCAGACA GGCGCCCACC
62161 GCTAGCCCAG ACGGACCGGC GCCGATGATG ATGACATGGC TCTCCTCGAT CACGACCGGA
62221 GTTTAACCGA ATTTCGTCCA GATACCAACC ACATCGACTC GCGGAGCGAG CGACGCGGGC
62281 GGACCGCCTA CAGGAGGTCC GCGAGCCGGC CGAGCAGGGG AGTGCGCTTG AACGTAGCGC
62341 GGATCGCCGC GCGCATCCCG CGGTACTTGG CCGTCGTGTA CGGGAACAGG AGAGGGCTGT
62401 TCAGCGGCAT CGCAAAGCGC TCGTGGTTGA CGTGACGCGC GTAGCACATC GCGCGCAACG
62461 AGTCGTCCGA GTGCACGCGG CCGTAGCCCG AGTTCTTGAT CCCGCCGAAC GGCGCCTCGG
62521 GCGCGCAGTA CGAGACGAGC ACGTCGTTGA TCATCACGGT GCCCGCCTCG ATCCGCTCGG
62581 CGACCGCCCG CGCACGCGTC TTGTCCCGCG AGAAGACGTA CGCGTGCAGC CCGAGCGGCG
62641 AGTCGTTCGC GATCCGGACG GCCTCGTCCT CGTCGCGCAC TTTCATGATG GGGACGACCG
```

```
62701 GGCCGAAGAT CTCTTCGCGC ATCACGGTCA TCTCGGGGGT GCAGCGGGTC AGCACCGTGG
62761 GCTCGAAGAA CATTCCCGGC CCCGGCCTGC GCCGCCCGCC CGTGGCCACG AGCGCGCCGC
62821 GCGCGACGGC ATCCTTGATG TGCGCCTCGG CGATATCCAT CTGCTTTGCG AAGATGATCG
62881 CGCCCACGTC CACGTCGTCC GCGCGCGGGT CGCCCTGGCG AAGCTCACGC GTGAGCGCCA
62941 CCACGCGGTC CACCAGCCGG TCGTGCACCG CCTCGGTGGC CAGCACCCGC TCGACCGAGA
63001 TGCATAGCTG ACCCGAATTG ATGAAGCCGC CGGCGACGAT CGACCGTGCG GTGCGCTCGA
63061 TCTCGCAGTC GTCGCAGGCG ATGAGCGGCG CCTTCCCGCC GAGCTCGAGC ACGCACGGGA
63121 TCAACCGCTC AGCGCACGCG GCCCCGACGC GCCGCCCGGA GCTCACCCCG CCGGTGAAGA
63181 CCACCTTCTG CACGCCGGCG TCGATCAGCG CAGCCCCGGT GCGGGCATCG CCGGTCACCA
63241 CCTGGAATAG ATCGGTTGGA ATCCCGATCG CGTCCACGAC TTCCTTGGCC TTGAGCAGCG
63301 TGAGCGGCGT GACCTCCGAG GGCTTGACCA CCACGGCGTT ACCAGCGATC AGCGCCTCGA
63361 TAACGCTGCC CATCGGGATC GCCAGCGGCA GATTCCACGG CGAGATCACG GCGACGACGC
63421 CCATTGGCAC GTACGTGACG TAGCTCCCAC GCCACTTCAT ATGGTGTAGC GTGATGGACG
63481 TATCGGCGAG GATCCGGCCG GCGTGGCGCG TGAAGTAGTG GCACGCGTCC ACCACCGTGA
63541 TCCACTCGGC GAGCGCGTCG TTGCGCGGCT TGCCGGTCTC GAGCACCACC GCGTCCACCA
63601 GGTCGTCCAG CCGCTCGACG AATGCGTCGA TCACGCGCGC CACGCGCCCG GCGCGGGTCT
63661 CGATCGGGAG CTGCGCCCAG GCGCGCTGGG CGAGGCGCGC GCGCTCCACC GCGGCGTGCA
63721 CCTCGGCATC GCCCATCAGC GGCACCTCGC CCAGGCGCGA GCCGTCGATT GGCGATTGGA
63781 CCACGAGCGT GCGGGTGGAG GGCGTCGTCG TCGGGGATGC GGGAAAGGCT TGGGCCATGA
63841 GCGGCTCCTC GTTTGCTCGA AAGCGGGGCG GCAGCTTACC ACTCGCGCCG CGCGGCTCGC
63901 AATGGGCGTC CCGCACGCCG CGCGCGTCCT CTGCGGCGCT CACGCGTGGT GTGGCAGCAT
63961 GGGCGCCAGT CCTTGCACGA GTGCCATGAC GGCGGACGCG AGCCATGCTC CGAAACGTCC
64021 GAAATACGCG GCGCACCACC TGGGCTTGAC AGGATGACGG TCCCGGGTCT TTCTACGCGA
64081 CATGTCTTTC ATTTGTGCTA CAAGCCACAG CTCGGCGGGC TCGCGCGGCT CCGGAGGAGC
64141 GCAACCAGCT CCTGGGACGC GAGGCGGCCA CGGCAGCGAC AGTTGGAGCC GCGCGCGGAC
64201 AACGCCACCC TGAACGCCCG GCTTCCCCAG GCACCGCTGG CGGACACGAT GGAGCCCAAG
64261 GCGCACGGAA CGATCCCCGA GGAAATGATG CAATCGACGG CCACCATCGC CCCCCTGGCA
64321 GTCCTGTTCG TACTGATGGC CATCGAGGCG GTCGTGGCCC GGCATCGGCG CGGTGACACG
64381 ACGTACCGCC TGCCTGACAC GGTGGCCAGC GTGGGCGTCG GTGTCGGGTA CTTCGCGCTG
64441 GTCGCGTTCT TCAGCTTCAT CTCGATCGTG GTCTACGACA TCGTCTATGA GCGCTGGGCG
64501 ATCACGCACC ATGCTCGCTC GGCGGTGACG ATCGTCTTCA CCATCTTCGC GGCGGACTTT
64561 CTCTACTACC TGTTCCACCG CGCCAGCCAT CGCATCAACG TCCTCTGGGC GATCCACGTC
64621 GTACACCACC AGAGCCGCGA GCAAAACCTG GCGGTCAACC TCCGCATGCC GTGGCTCCAG
64681 CCGGCATACC AGTGGTTCTT CTATCTGCCG CTCGCCTTCC TGGGGATACC TCCGGCCGTC
64741 TTCTTGCTCG CGCGCGGGGT AAGCATCTCT ACAACGTCT TCACTCACAC GCGCGCGGTC
64801 GGGAAGCTCG GCCCGCTCGA GTATGTGCTC AACACGCCCT CCCACCACCG CGTGCATCAT
64861 GGGATGGACG AGCAGTACCT CGACTGCAAC TACGGCGGGA TCTTCATCGT GTGGGATCGC
64921 CTCCTCGGGA CGTTCGTCCC GGAGGGCAAA GAGCCGACCT ACGGAACGCG CAGAAGGGTG
64981 GTCTCGTGGA ATCCGATCTG GCTCAACGTG GAGCCGTTCA TCCACCTCGC GAAGCTATCG
65041 CGCGCAGCCA GATCTCCGTG GGATCGCGTC AAGGTATGGT TCATGCCGCC CGAGTGGCAG
65101 CCCGCCGGCG TCCTGGAGGC CAGCGCTCCG CCCGAGCCGC GCGACGTGGA GAGCCGTGGT
65161 TCTACGGCTT CGTCGATCGC CCAGATGGCG CTCAGCGTCG GCGTCACGGT GGTCATCGGC
65221 GCGATGGTCA TCATGTACAC GGGCACGTCG TCGACGATGC CGAGGCTTGC CCTCCTCGTG
65281 CTGCTGCTCG CGTCGCTCGG CGCGCATGCT CGGTCTCTCG AGAGTCCTGG CTTCGCCTGG
65341 AGGTTTGAGC TCGCGCGCGC AGCCCTGCTC CTCGCCGTCG CGGGCTGGCT CGACGCCAGC
65401 GGAGCGAGGC CGCTGGCCAG CGTGGCCCTG ATGGCCGGCG GCCTCTCGGC CGCGAGCGGT
65461 GTCCTGTTCC GCCTCGGGCG CCGCCCGCGC GGCTCGCGGG CGGGAGGGGC CGAGGACGCC
65521 GCCCCGTCGA TGTCGCTCCC AGGATCGTAG CAGGTCGGCC GAGGCGGGCG CCTCGGCCCT
65581 GACCGCCCGT CGCACGCAGC TAGCCAGGGG ATTCTCTCCT GATCCGGAGG TGAGACATGG
65641 CTTCTTCCGA AGATGGAACG CGCAGCTGGT CGAACACGAA GAGCCTGGCG CTACATGAGC
65701 GCGCGGCGAA GGTGATGCCG GGAGGCCAGG CGAACTTCAG GGGAGGTTTG TTGAGCACTC
65761 CCCTCTTCTT CTCCCACGCG CGAGGCGCGC GACTGTGGGA CGTCGACGGC AACGAGTACG
65821 TCGACCTGAT CAACGCCGGC GGTCCGGGCA TCCTCGGCCA CAACGATCCG GAGTACATCG
65881 ACGCGCTGAA GCGCCAGCTC GACACGGTGT ACTCGCTCGG GTCGGGGATC TGCCAGACCG
65941 AGCAGGATAT CGAGCTGGCC GAGAAGATCG CGAGCCACGT CCCGTGCGCC GAGCGCGTCC
66001 GCTTCTGCGT CACCGGATCG GAGCGGTAC ACCTGGCCCT ACGGCTCGCG CGGGCGTACA
66061 CGAAGCGCCC CTATTTCATT CGCTTCCAGA CTCACTACCA CGGCTGGTTT GACAGCGTGC
66121 TGGGGGGTGT CGTTGACGAG CACCCCGAAG GGCGACCTCT CCCGCTGGAG AGCGAGCAGA
66181 GCTTCTTTCA CACCGAGGGC AGGGTCCCCG ACGCATTCAA GTACTCGTTC CTCTTGCCCT
66241 GGAACGACAT CGATGTCCTC GAGGAGACGC TGAAGAAGTA CGGGCACGAG GTGGCCATGA
66301 TCCACATGGA GCCGATCCTG GTGAACGGCG GAGGCTGCCC CCCCAGGCCC GGCTATCTCG
66361 AGCGTGTGCG CGAGCTCTGC GACCAGCATG GAATCGTGCT CGGCTTCGAC GAGGTCATCA
66421 CCGGCTTCCG CGTGGGCCTC GGCGGCGCGC AGGCGGCGCT CGGCGTCACG CCCGATCTGG
```

```
66481 CGACGTTCGG TAAGGCGCTA GGGGGTGGGA TGCCGATGGC GGCCGTCGCC GGGAAGGCGG
66541 AGATCATGGA TCAGCTCCGG ACCGGCAAGG TGACAGGGGC TGGCACGTTC AACGGTTATC
66601 CTCTCGGCGT GGCCGCGTCC CTCGCGACGC TCAAGATCCT GGAGAGGGAC GATGGCGCGG
66661 TCTACAGGAG GATCGACATG ATGCAGGCTC GGCTCAAGGA GGGCCTGCTC GATATCTGCA
66721 AGCGACGTGG GATCCCCGCC CTGGTGCAGG GGCCGCGCGG CGTCTTCTTC TTACTCTTCA
66781 CGGACAAACC CGTGATCTAT AGCTTCCAAG AGTCATGGA GGCCGCTCTG CCCAGGCAGT
66841 TCAAGTTCTA CTCGACGATG CCCGAGGAGG GGACTCTCCT CATGTACGGC GGCCGCTGGT
66901 ACATCTCCGC GGCGTTGACC GAGGCTGACG TGGACTGCGC GCTGGAGAGC GCCGACAGGA
66961 CCTTGGCTAG AATCTGACGT AGTCTCGCTT CCGCAAACGA CGTTGACTTG AACGGTCGGG
67021 TGCGCTGAAC GCCGGCCCAG AAGAGGAGCG CCAGCCTGGG GCTGGCGTCT GTTCGATGCC
67081 CCCTACAGAA GATTTGAAGC AGATCTTGGA GCAGCTCGGT TCGGCCAGGT TGAGCCATGA
67141 GGTCGAGCTG AGCCAGCTCA TGGCGCCGCT CTCGCCAGAA GAAGTTTTGT TTTGCTTTCT
67201 GTTCATCAAG TCCGGCTCGG CCGAGGGCTT CGGCGAAGAG CCCGTTCGGT TCAAGGACTT
67261 GCCGAGCGCG CCTGACAGAT TCTGGAAGGC GATGGCGCTG CACGTCGGCG CGCTCTCCGG
67321 GCAGTTCAAG CCGCTGCCGC CGTCGTATCT CAAGGATGCG TGGCTCCGTT TCGTGAAGGA
67381 GCGGCCCGGG GACGAGCCGC TGTCGCTCCT CGAGTACTAC AGCCTCGCCG CGCAGCTCCT
67441 CAGCGACACG GACAGGGTCT TCATCAACCA CGGGTACGCG TTCCTGAACC CAGCAGAGGC
67501 GCCCTCTCTC GCTGCCTGGG AGGAGCCGTC GCGCCTCAGC ATCCACCTCT ACCACAAGCT
67561 CCTGGGCGGC CAGGATTTCA CGGGGCTCGA TGTGGTCGAT ATGGCCTGCG GACGGGGGGG
67621 CGGCAGCCTC TACCTGAAGC AGCGGAAGGA GGCCCGGCTC GTCGCCGGCA TCGACGCGGT
67681 GCGCACCCAC GTGCTGCTCG CGCGAGAAGC CCATCCCTCG GTCGACGGCG TCTACTTCCT
67741 CCACGGCCGA GCGGAAGAGA TACCGCTGCC CACCGGTGCC TTCGACGCGC TGATCGCGGT
67801 GGACGCGGTC TTCCACTTCC CGCTCAGGGA GTTCCTCCAC GAAGCCCATC GCGTGGTGAA
67861 GCCGGGGGGG CGCTGTTTCC TCAATAGCTG GGGCCCGCCG ACCTGGTACA TGGATCTCGA
67921 GGGTGCGGTC GAGTCGTGTG GTTGGAAGCT CGAGCACGCC GAGGACATCA CGACGGGCGT
67981 CCTCCTGGCC AGAGAGCAAT GGAGGACTCA CGACATGTTC ACGTGGGTCC GCTCGCGGCC
68041 GCGCAAATGC CGGCCGGAGA TCTACATCGA GTTCGACAGG ATGGTGATGT TGCCCGTCGA
68101 GGGCCGCCGC TATTACAATT TCCACCTCAC CCGGCTCGAC CAGAAGGCAA GCTGAACCGA
68161 GGCGGCCCAC GCTCTCCTCG ACGCGGCTGG CTACCGGTAG GCGACGATGC CACCGAACGG
68221 CCACTTCGCG TGGTCCTCGG GCGCCGGATA GACCTCCCAT TCGGAGAACC CGGCCGCGCG
68281 GAGCGACAGC TCCCACTCTT GCAGCGTCAG ATAACCAACA TGCTGGCGGC GAGGCGGATC
68341 GAGCTTGGCC TTGCTGTAGG TGTGCAGCAT CGACTGAAAA AATTCATTGG GAAAGAACAG
68401 CCCGGGCCGA TCGCGGAACG ACATGGTGAA CGCGAGCTGG CCGCCGGCT TCAGCATCGT
68461 GTGGAACGCC TGGAGCGTGG CGTGAAGATC GCGCACGTCG TAGAGCACGT GCTCAAGGAC
68521 GATCAGATCG ACCGAGGCGG CCCGGGCGAA CGTGTTGCCA GCGGAGGGCA GCGCGTCCAG
68581 GTCCAGGCGC TGGAAATGAA TGCGCTGAAA CAGGTCAGCC GGCGCGTGGG TCCGCAGCCA
68641 CTGCTTCCCC GTCTCCATCA ACAGGGCGCT GATGTCGGTG TAATCGTAAC GGACGAGGTT
68701 CCTGCTCAGC GGGAGGAACC TCGGATCGGA TAACGCCTGC CGCAGCACCA CGCCGAGCCC
68761 CGCGCCCCCC TCGAATACAG AGATCCCCGG CCCCTCTGCG AGCTTGGCCA TCAGCGCCCG
68821 CGCCAGCATC ACGTTGCACG GCTTCTTGGC GGGAAGGCTG ATCATCGAGT ATTCCCAAAA
68881 TTTCAGCGAG GCCTGCATCC CGTACTGGAG ATCCATGGTG CCAGCGCGT CCTTGCCCGC
68941 CAGCACCGGC CCGGCCAGGC CCCGATAGCG CTGCAGGAAC TCGACCATTT CGCCGAGAAT
69001 CGCGCGGTCT GCGAGCTCCA TGGCCTCCCT CTCGGCGACG CGCTTTCGCA CCGCCTCGCT
69061 GGGCACCAGC CGCCCGCTGG GGTCCTGGAT GAGGTCGCCC TTGTCGCTGA AGTAGTCGAG
69121 CAGCTTCCTG CGAAACTGGT AGGCGGTGAC CGACGGAGCC GACTCCGGGC GATCGTCGAG
69181 CACCTGGACC GCGCCGCTCT GGTCGACGAG GTGCTCGAGC AGAATCTCAC TGGCAACAAG
69241 CTCGGTCTGA CGACGGAATG CTTCTATGTA AGCCGTGTAA GCGTCGTTGT AGAGATCGGT
69301 CACGTCCAGT CGTTGTCGCA TGCAGATCCT CGCGGGTGTG GCGCCCATCC TGCGCAGCGC
69361 AGGGACGAAG CAGATCATGG AATGGTCCAG CTCGCCGTGG AACGCAAGGA TGGACCGGCC
69421 GCCGCGGGCG GGCGCCGCGC CTCCGAGCGT CGCGCGCCGG CCAGCTCTG GCCACCTCGA
69481 GGGCCACGCG TCACCTGGAG CTCGGCACCT GCCCGCCGTT CCCGCGGTTC TTGTGCACGA
69541 TGGCGTACAG GATGAGCACG TAGGCGAGGA GCCGGAACAG GTACAGGTAA TGGATGGCGT
69601 CTTCCTCGAC GCGGTTCAGG GCGACGGCGA TGCGGCCCAG CATCATCAGC CAGAACGCCG
69661 CCGAGAACTT CGCGAACAGC CGGTCGCCCG TCTTCTTCCA GAAGCGGAGG AAGAAGAGCG
69721 CGATGGTCGC ATACCCGAGC GTCATCGCAC CGATCAAGAA GTCGTTCAAA GGTACTACCT
69781 CGCCTCTACG TGCGTTTACT CGCGCAGGTC CCAGATGAGG CCATACAGGA GCAGGGTCAG
69841 CCCGATGAGC GCGGTGAGGT GGCGCAGGGA CGATAGATCG ATGCTCCGGA TCACGACGAG
69901 GTCCACGAAG AGCAGGATGT TGTTCGCGGC GAGCCCGGCG AAGCAGAGCC CGCTCCACAA
69961 GAGGAGGCGG ACCTTGCGCT GCGCGTATCC GCGCAGGAGC AGCACGGCGC ACGCGATGCT
70021 GGTCAGGGAG CAGAGCATGT AGACCGCCGC TGCCATGGCT AGCCCTCCTT TCCCTTCTTC
70081 GTGATCCGGA ATGCGTCCGA GAAGCTCTGG ATGTCGCTCG GCGGGGGCGT GGCGTAGATG
70141 TGATTGATCA CGCTCAGCCG GCGCTCCTTG TAAGCCTGCG CCAGGTCGTC GATCGTCCGG
70201 CGGGTGTCAT CGTCCGCCGG GGCGTACCGG TAGACGATGT CCTCCCCGTC CTCCCGGGCC
```

```
70261 ACGAGCAGGC CCCTGCTGGC GAGGCCCCCG AACCGGTCCT GGATCGACAT CTTGCTGGAT
70321 CCTATCTCGC GCGCCATCGC CGCCGCACTC CACTCGCGCT CCGCCGTGCG ACGCATCAGC
70381 AGGAGCACTT CGAGCTCTTC GATCGAGGAG ATGTGCGCGC CAAGGAAGCG CTGGACCCGG
70441 TCGGGGAGCC CGCTAGACAC GAGCTCCTCG CCGGCCGCGC GCCCCTCCGG TCACCGGTGC
70501 AACCATAGCC GGAGCATAGC GAGCAGGTGC TCCGGATCCA CCGGCTTCGA GATGTAATCG
70561 TTCGCGCCCG CCTCGAAGCA CTTCTCCCGG TCGCCCTTCA TCGCCTTGGC CGTGACCGCG
70621 ATGATGGGCA GCGCATGGTG CTCGGGCCTC GCGCGGATGG CACGGATCGT GTCATAGCCG
70681 TCCATCTCTG GCATCATGAT GTCCATGAGC ACCATCTCGA TGTCCGGCGT CCGCTGCAGC
70741 ATCTCGATCG CCGCTCTGCC CGTCTCCACG TAGACCGTCT TCATATGCTG GGCGTCGAGG
70801 ATGGTCGTCA TCGCGAAGAT GTTCCGAACG TCGTCGTCGA CGACCAGCAC CTTCTTGCCC
70861 ACGAGCACCT TGTTCGACTG GTGCAGCTCC TCGACGATCT GCAGCTGTCG CTCGGAGAGC
70921 GCCGCCACCG GGCGGTGCAG GAACAGGGAG ACGTCATCGA AGAGCCGCTC CTTGGAGCGG
70981 ACGTGCTTGA GCACCATCAG CTGGCTGAAG CGGCTCAGCT GCGCCTCGTC TGCGGGCGAG
71041 ATCTCCTCCG GCGCGTAGAC CAAGACGGGC AGGTCCGTGG ACCCGCTGCC CTGCGCGAGC
71101 TGCCCGATCA GATCGAAGCA GCGCACGTCG GCAGGTCGA GGCGCAGGAT GAGGACGTCC
71161 GGCCGCTCGG TGACGAGCGC GTCGAGCGCC TCCTCCCCGG AGGCCACACT CCGGATCGTG
71221 ACGTCGTCGC CGCCGAGGAG CTCGACGAGC TCCTGGCGCT CGGCGTCGTC CGGCCCGGCG
71281 AGCACGATCT TCCGCCGGCT CGACACCATG AACTGCGAGA GGCGCCTGAA CGTCTCGTCG
71341 AGCGCGTCCC GGGTCTTGAG CGGCTTGCAG AGCACACCCT TCGCGCCCAT CCGTAGCGCG
71401 CGCTCGCGCT CCTCGTCCGT CGTGATCACC TGGACGGGGA TGTGCCGCGT CTCGAGATCG
71461 CGCTTCACCC GGTCGAGCAC GCGCCAGCCG TCCATGTCCG GCAGGTTGAT GTCGAGCGTG
71521 ATCGCGTTCA CCCGCCGCTC ACGGACGATG GAGAGCGCCG CCCCGCCGCG GTAGGCGAGG
71581 ATCGCCTTGA CCCGTGGTC GTGCGCGACA TCCATGACGA AGTGCGCGAA GCTCGCGTCG
71641 TTCTCGACGA TGAGCACCAC GGAGTCGCTG GGCTTGAGGC CCGCGCTGTC GTCGACGCTC
71701 TGGTTGAGCA GGTGCGGCGG CGGCTCGGCC GCCGACCGCG GCGGGACGTC GCCGGAGACG
71761 ACGGCCGGCG GCGCTGAGGG CACCTCCACG GTCTGCTCCT TCCTGCGCGG GCGCGCCGGC
71821 GTGTACGTGA GCGGCAGGTA AAGCGTGAAG CTGCTCCCGC TCCCCGGCTT GCTCGAGAGC
71881 TTGATCTCGC CGCCCAGCAT CCACGCGATC TCGCGGCTGA TCGCGAGGCC GAGGCCGGTG
71941 CCGCCGTACT TCCGGCTCGT CGAGCCGTCA GCCTGCTGGA AGGCCTCGAA GATGATCTGC
72001 TGCTTGTCAT GCGGGATGCC GATGCCCGTG TCCCGCACCG ACATGGCGAT CGCCGCGCCG
72061 GCGCGCGAGA GGCCCTCGTT CTCGGGCGCC CACCCCGAGG TGACCAGATC GACGTCGAGC
72121 GCGACGCTGC CGCGCTCCGT GAACTTGAAG GAGTTCGACA GCAGGTTCTT GAGTACCTGC
72181 TGTACGCGCT TCGCGTCCGT GTAGATGACC TGCGGCAGGT TCTGCGCGAA GTTGAGCTCG
72241 AACTCGAGCT TCTTCGACTC GGCGACGTGA CGGAAGGTGC GCTCGACGTA GTCCTGCAGA
72301 TCGCTGAACG ACAGCTCGCC GACGTCGACG ATCACGGTCC CGGACTCGAT CTTGGACAGG
72361 TCCAGGATGT CGTTGATGAG CGCGAGCAGG TCGTTGCCCG ACGAGTGGAT CGTCTTGGCG
72421 AACTCGACCT GCCGCCCCGT GAGGTTGCGG TCGTTGTTCT TCGAGAGCTG ATCGGACAGG
72481 ATGAGCAGGC TGTTCAGGGG CGTCCGGAGC TCGTGCGACA TGTTCGCGAG GAACTCGGAC
72541 TTGTACTTGG AGGTGATGGC GAGCTGCCGC GCCTTCTCTT CGAGCGCCTG CCGCGCCTGC
72601 TCGACCTCGC GGTTCTTCCG CTCGACCTCG ACGTTCTGCT GGGCGAGCAG GCGCGCCTTC
72661 TCCCCGAGCT CCGCGTTCGT CTGCTGCAGC TCCTCCTGCT GGCTCTGGAG CTCGCGCGCG
72721 AGGGACTGGG ACTGCTTGAG CAGGTCCTCT GTGCGCATGT TCGCCTCGAT CGTGTTGAGC
72781 ACGATCCCGA TCGACTCCGT GAGCTGGTCG AGGAAGGCCT GGTGGGTCGG GCTGAAGCGC
72841 TCGAACGACG CGAGCTCGAT GACCGCTTG ACCTGCCCCT CGAAGAGCAC GGGGATGACG
72901 ATGATGTTGA CCGGCGGCGC CTCGCCGAGC CCGCTCGTGA TGCGGATGTA GTCGGGGGGC
72961 GCGTTGACGA GGAGGATCTT CTCCTTCTCG AGCGCGCATT GCCCGACCAG CCCTTCGCCG
73021 AGCTTGAAAT GGTTGTCGAC GTGCTTCCGC ACCTTGTACG CGTAGCTCGC GAGGAGCTTG
73081 AGGATCGGCT CCTCCTTCGC CACGTCCATC GTGAAGAACA CGCCCTGCTG CGCACCGACG
73141 ACCGGGGCCA GCTCGGACAG GATGAGCCGA CCGACCGTGA GCAGATCCTT CTGCCCCTGG
73201 AGCAGGCGCG AGAACTTGGC GAGGTTGGTC TTGAGCCAAT CCTGCTCGCT GTTCTTCAGC
73261 GTCGTGTCCT TGAGGTTCCG GATCATCTCA TTGATGGTGT CCTTGAGCGA CGCGACCTCC
73321 CCCTGCGCCT CGACCCGGAT GGTCCGGGTG AGGTCGCCCT TCGTCACCGC GGTCGCGACC
73381 TCGGCGATGG CGCGCACCTG CGTCGTCAGG TTGGCGGCGA GCTGGTTCAC GTTGTCGGTC
73441 AGGTCCTTCC ACGTGCCGGC CGCGCCGGGG ACGCTGGCCT GCCCGCCGAG CTTGCCCTCG
73501 ACGCCGACCT CGCGCGCCAC CGTGGTCACC TGGTCGGCGA AGGTCGCGAG CGTCTCGATC
73561 ACGCCGTTGA TCGTATCCGC CAGCGCCGCG ATCTCGCCCT TCGCGTCGAA GGCCAGCTTG
73621 CGCTTCAGGT CGCCGTTCGC GACCGCGGTC ACGACCTTGG CGATGCCGCG CACCTGGTTC
73681 GTCAGGTTGC CGGCCATGAA ATTCACGTTG TCGGTCAGGT CCTTCCACGT GCCGGCGACG
73741 CCGGGGACGC TGGCCTGCCC GCCGAGCTTG CCCTCGGTGC CTACCTCGCG CGCCACGCGC
73801 GTCACCTCCG ACGCGAAGGC GTTGAGCTGG TCCACCATCG TGTTGTTGAT GGTGTTCTTG
73861 AGCTCCAGGA TCTCGCCGCG GACATCGACG GTGATCTTCT TCGACAGATC GCCGTTGGCG
73921 ACGGCCGTGG TGACGGCGGC GATGTTGCGC ACCTGCGCGG TCAGGTTCGA CGCCATCGAG
73981 TTGACGGAGT CGGTCAGGTC CTTCCACGTG CCGGCGACGC CGGTCACCTC CGCCTGCCCG
```

```
74041 CCGAGCTTGC CCTCGGTGCC TACCTCGCGC GCCACGCGCG TCACCTCGGC CGCGAAGGAG
74101 CTGAGCTGAT CCACCATCGT GTTGAAGGTG TTCTTCAGCT CCAGGATCTC GCCCTTGACG
74161 TCGACGGTGA TCTTCTTCGA CAGGTCGCCG CGGGCGACGG CCGTGGTGAC GTCGGCGATG
74221 TTGCGCACCT GCGCGGTCAG GTTCGACGCC ATCGAGTTGA CGGAGTCGGT CAGGTCCTTC
74281 CACGTGCCGG CGACGCCGGG GACGCTGGCC TGCCCGCCGA GCTTGCCCTC GGTGCCTACC
74341 TCGCGCGCCA CGCGCGTCAC CTCCGACGCG AACGAGCGGA GCTGATCCAC CATCGTGTTG
74401 AAGGTGTCCT TCAGCTCCAG GATCTCGCCG CGGACATCGA CGGTGATCTT CTTCGACAGG
74461 TCGCCGTTGG CGACCGCGGT GGTCACGTCG GCGATGTTGC GCACCTGCGC GGTCAGGTTC
74521 GACGCCATCG AGTTGACGGA GTCGGTCAGG TCCTTCCACG TGCCGGCGAC GCCGGTCACC
74581 TCCGCCTGCC CGCCGAGCTT GCCCTCGGTG CCTACCTCGC GCGCCACGCG CGTCACCTGG
74641 GCCGCGAAGG AGCGGAGCTG ATCCACCATC GTGTTGAAGG TGTTCTTCAG CTCCAGGATC
74701 TCGCCGCGGA CATCGACGGT GATCTTCTGC GTCAGGTCGC CGCGGGCGAC GGCCGTGGTG
74761 ACGGCGGCGA TGTTGCGGAC CTGCGCGGTC AGGTTCGACG CCATCGAGTT GACGGAGTCG
74821 GTCAGGTCCT TCCACGTGCC GGCGACGCCC TTCACCTCCG CCTGCCCGCC GAGCTTGCCC
74881 TCGGTGCCCA CGTCGCGGGC GACGCGCGTC ACCTCGGCCG CGAAGGAGCT GAGCTGATCG
74941 ACCGTCGTGT TGATGACGTC CTTGATCTGG AGGATCTCGC CGCGGACATC GACGGTGATC
75001 TTCTGCGTCA GATCGCCGTT CGCGATGGCG GTCGCGACCT TCGACACGTC GCGGAGCTGG
75061 ACCGTGAGGT TCGACGCCAT CGAGTTGACG GAGTCGGTCA GGTCCTTCCA CGTGCCGGCG
75121 ACGCCCTTCA CCTCCGCCTG CCCGCCGAGC TTGCCCTCGG TGCCTACCTC GCGCGCCACG
75181 CGCGTCACCT CCGACGCGAA CGAGCGGAGC TGATCCACCA TCGTGTTGAA GGTGTCCTTC
75241 AGCTCCAGGA TCTCGCCGCG GACATCGACG GTGATCTTCT GGGTCAGGTC GCCGCGGGCG
75301 ACGGCCGTGG TGACGGCGGC GATGTTGCGC ACCTGCGCGG TCAGGTTCGA CGCCATCGAG
75361 TTGACGGAGT CGGTCAGGTC CTTCCACGTG CCGGCGACGC CCTTCACCTC CGCCTGCCCG
75421 CCGAGCTTGC CCTCGGTGCC TACCTCGCGC GCCACGCGCG TCACCTCCGA CGCGAACGAG
75481 CGGAGCTGAT CCACCATCGT GTTGAAGGTG TCCTTCAGCT CCAGGATCTC GCCCTTGACG
75541 TCGACGGTGA TCTTCTGGGT CAGGTCGCCG TTGGCGACGG CCGTGGTGAC GGCGGCGATG
75601 TTGCGCACCT GCGCGGTCAG GTTCGACGCC ATCGAGTTGA CGGAGTCGGT CAGGTCCTTC
75661 CACGTGCCGG CGACGCCGGG GACGCTGGCC TGCCCGCCGA GCTTGCCCTC GGTGCCTACC
75721 TCGCGCGCCA CGCGCGTCAC CTCCGACGCG AACGAGCGGA GCTGATCCAC CATCGTGTTG
75781 AAGGTGTCCT TCAGCTCCAG GATCTCGCCG CGGACATCGA CGGTGATCTT CTGCGTCAGA
75841 TCGCCGTTGG CGACGGCCGT GGTGACGGCG GCGATGTTGC GCACCTGGGC GGTGAGGTTG
75901 CCGGCCATCG AGTTGACGGA ATCGGTCAGG TCCTTCCAGG TGCCGGCGAC GCCCTTCACC
75961 TCCGCCTGCC CGCCGAGCTT GCCCTCGGTG CCTACCTCGC GCGCCACGCG CGTCACTTCG
76021 GACGCGAAGG AGCCGAGCTG ATAGACCACG GTGTTCACGG TCTGGGCGGT CTGGAGGAAC
76081 TCGCCCTCCA GCGGCCGCCC GCCCACCTCG AGCGCCATCG TCTGGGAGAG ATCGCCCTTG
76141 GCGACCGCGC CGATGACGCG CGCCATCTCT CTCGTGGGCT GCACGAGATC GCCGATCAGC
76201 GCGTTGACGG AGGCGACCTC GTCGGCCCAG GCGCCGCTCA CCTCGCCCAT CGAGACGCGC
76261 TGGCCGATCT TGCCTTCCTT GCCGACCGCG CGGCTCAGCC GCTCGAGCTC GAACGCGAAC
76321 TTCTCGTTCA TCTCGACGAC ATCGTTGAAG GTGTCGGCGA TCTTCCCGTC CAGCCCCTCG
76381 AGGTCGATCG GCAGGCGTAC CGAGAAGTCC CCCTTCTTGA GCGCCACCAG GACCGCGAGC
76441 ATCTGGCCCA TCTCGAGGGC CTGCCGCGCC GGCCGGCGCA TGACGTCATC CTGCGCAGCG
76501 CGCCGCCGCG GGCGTGGCAG GTCTTCGAGA TGGACGGGCT GCGACCGCTG CTGAAGCGCG
76561 GTGGCTTGCG ACGTCCGGGC CGCGCCCTCT GCGCGCTTGG CCGCCGCGTT CTTCCCGTTC
76621 CTGGGGTGCT TGCCGTCCTT GCCGTTCGTG CCCTTCGCCG CGCCGTCCTT CGAGGACGCC
76681 GTCCGGCTCC GAGGAGACGC TATCTTGCCG CTCGCCGCTT GCTCCATGTT GGACCCTCTC
76741 CAGGGCGGCG CCATGCTAAC GCGCGCGGCG GGAGGTGAGC CACACTAAAG AACTTCCTGT
76801 ATCTACCCTG TGAGAGGCGC CCAACACGGG TCAGGATGAC CCCGATACCG CTGGCGGAGC
76861 TTCTCGCGCC CGTGGCGGAC ACAGCCCTGG GAACATCGAG GAAGTACACG GTTGGTCAGC
76921 GAACGAAAGC CACCTTCGAC AAGCGGGCTC GACCGTCGGT GAGCGGATAC CGCTCTCGCA
76981 GCTCCGTCTG ATTACGCCGT CCCCTCGCCT CTCACCCTTG CTGCATTTCG TGACCGCGTT
77041 CGCGGCGCCG CGCGCCCTGC CTTCGCCTTT ACCGCCCGC GCGCGCCGCT GCTGCTCGAG
77101 GCGCCCGTGC CCGCGCGCGG CGCGCTCTCG GCCAGCATCT CCCCCAGCG CGAGATCGCC
77161 TGCGCGACCG CCTGGAACCC CCGTCCGGAG TCGGTCAGCT CGTACTCCAC CCGGACCGGA
77221 GGCCCCGGCA GCACGCGCCG CACCACGAGG CCGAGCGCCT CGAGCTCCTT CAGCCGGCTG
77281 GAGAGCATCC GGTCGCTGAT CGCGTCGAGC CGCTCGCCGA TCTCGCCGAA GCGCAGCGGG
77341 CCCTCGTCGA GCGTCGCGAT GATGAGGCCG TTCCACGGCT TCGCGAGCAC GTCCATGGCC
77401 GCCTGGAACC CGTCGCAGAG GTGCTGGCAT GAATGCTTCA TTCCGCGTCC TGGACAGGAT
77461 GACCCCTTCA CTACCAAAAA GGAAGTCCCT TGACACGAGG TAGCGCGTGT CCATGATGCT
77521 TCCTTGACGG ATGCTGCTTC TCTTTCGGAA GTAACATCTT CTTTACAAGG AGCATCGATC
77581 GTGACCACTG CCGCCGACCT GCTGTTCAGC CCCTTCAAGC TCGGCCCCT GTCGCTGCCG
77641 AACCGCCTCG TGATGGCGCC GATGACGCGC TGCCGCGCGG GCGAGGGCAA CGTGCCCACC
77701 GAGCTCAACG CGGTGTATTA CGAGCAGCGC GCGTCCGCCG GCCTCATCAT CACCGAGGCC
77761 ACCCAGGTCA GCCAGCAGGG CGTGGGGTAC CTCCGCACGC CGGGCATCCA CACCGACGCG
```

```
77821 CAGGTCGAGG GGTGGCGGCG CGTCACGGAC GCGGTGCACC GGGCAGGGGG GCACATCTTC
77881 GCCCAGCTCT GGCACGTCGG GCGGGCGTCG CACGTCTCGT TCCAGCCGGG CCGGCAGGCG
77941 CCTGTCTCGT CCTCGGCCCT CCCCATCCGC ACCGGCCACG CGCACACGCC CGAGGGCGCG
78001 CAGCCGTACA GCACCCCGCG CGCCCTCGAG ACGCGCGAGA TCCCCGGCGT CGTCGCGCAG
78061 TTCGAGGACG GCGCGCGCCG GGCGAGGGCG GCCGGCTTCG ATGGAATCGA GCTCCACGCG
78121 GCGAACGGCT ACATCATCGA CCAGTTCCTC CGCGACGGCG TGAACCAGCG GACGGACCAG
78181 TATGGCGGCT CGGTCGAGAA CCGGGCGCGG TTCCTGCTCG AGATCGTCGA CGCGGTGACC
78241 GGCGTCTTCG ACCCGGACCG GGTCGGCGCG CGGGTCTCGC CGCTGGGCGG CTACAACGAC
78301 ATGAGCGACT CGAACCCGAA GGCGATCTTC GGCCACGTCG CCGCCGAGCT CTCGGCGCGC
78361 AAGCTCGCCT ACCTGCACGT CGTGGAGCCC GTGGACGGGC AGGCGGAGGA CGCCGCGGGT
78421 CGCGTGATGC CCCTGCTCCG CGAGCGGTTC CGCGGCGTCC TCATGGCGAA CGGCGGCTAC
78481 ACGCTCGAGA CAGCGGAGGC GGCGCTGCGG ACGGGCGCGG CGGACCTCGT CTCGTTCGGC
78541 GCGCCGTTCC TGGCCAACCC CGATCTGCCC GAGCGCCTGT CGCGCCGGGC GCCGCTCAAC
78601 CCGCCCGACG TGTCGACGTT CTACTCCGAG GGGCCGCGCG GCTACACCGA TTATCCGCGC
78661 CTCGCCGAGG CGCAGGCCGC CGCGCAGCCG TCGGCCTGAG CGCGGCATCC GGCGCAGGCG
78721 CGGCGAGGGC TCCCGCGCCG CGGACCATGG TAGGCTCCAG GGCCGATGTC GGCGGCCCTG
78781 GATCTGTTCC CGAGAGCGGT CGTTGTTCTG CGCGCGCGCG TCGATGAGCG CCCGGCGCCC
78841 GGCGCGGCGC GCTCGCCCGC GGAGGCGCC
```

FIGURE 4. SEQ ID NO: 2

```
LOCUS       AMB_PATENT   14172 BP DS-DNA              SYN         01-MAR-2004
DEFINITION  -
ACCESSION   -
KEYWORDS    -
SOURCE      -
FEATURES             Location/Qualifiers
     source          1..>14172
                     /note="Sorangium cellulosum strain So ce10; and derived
                     strains containing transposon inserts"
     source          <1..14172
                     /note="pKOS344-135B; 15Kb NheI/EcoRI subclone of cosmid
                     1-16 from Sorangium strain K433-47.1 (Tn1A11 insertion
                     strain)"
     source          13453..>14172
                     /note="pKOS344-112E; ""cosmid 10B3""; from Sorangium
                     cellulosum strain So ce10"
     CDS             complement(>1..765)
                     /note="ORF1 (nter)"
                     /note="AtoC homolog"
                     /note="RespReg subunit in His/Asp kinase
regulatory pathway
                     /note="37% identity vs ORF5_jer Nter"

/translation="MPKILVIDDQPAVCVALTTLFELHGLEVRVAATPDAAIAAVLDDE

LGAVVQDMNFRQSATSGEEGMELLRRIKSIDPELPVVAMTAFTSIAGAVELIKAGASDY

VPKPWDDQKLVAVVSNLARLRSLEQENARLVAQRGRARHRLAERHDLGGLVYASDAMHE

VVSLAVKVAPADVPVLITGPNGTGKELLAGIVQANSRRRDRPFVKVNAGALPDELVEAE
                     LFGAEAGAFTGAARLRIGRFEEADGGTLFLDEI"
     CDS             complement(2607..3557)
                     /note="ORF2"
                     /note="TrReg(LysR)"
                     /note="94% identity vs ORF2_jer"

/translation="MRLQSVDTHLVVALHALLQEKSVTRAARRVGVTQPSMSHALARLR

AHFEDPLLIQVGRQMTLSERARDLAPRAAEAVERLEHVFRPVERFDPRRSQRTFRLVAT

DNLELLVLPALTALLAVEAPRVNLRCRNIPADFAELLRRGELDGKLGRGGPVPDGCRST

LLAAEEIVCVMRRGHPASRGPLTAARYAACEHLMVSPHGEDHGVIDRALAEQGLRRRVT

LTVSHFLVAPFIVSGSDLLLTVSARVAAALARRLDLVVRPCPFQLEGYTLTLVWPERSE
                     HDEGHRWLRDAIQRAVALDPGSPAPGAGPARCDTA*"
     CDS             3595..4041
                     /note="ORF3"
                     /note="unknown"
                     /note="homolog of ORF3_jer and partial homolog of SAV3316
                     from Streptomyces avermitilis"

/translation="MDRRADCRFDARSVGAYLSSPDGTCRRAARPCPPAEESNPMIIEY

IRYTIPAEQEKEFLAAYRDAAAELRGSEHCLDHEISRCVEDPTSFVVRICWDSLQGHLQ
                     GFRKAAAFPSFFAKVKPFYERIQEMRHYALTDVATRQAGKAATG*"
     CDS             5141..6361
                     /note="ORF4"
                     /note="cytochrome P450 hydroxylase"
```

```
/translation="MAVPSGFDLTSERFFADPFPTLERLRTEAPVYFFEPLQCFLITAP

ADIEGLVKDSSFTARRATALLGGLGMLGEDELSRKTFDSLSRLAFFQDPPRHTQLRQLI

MKGFSPSAVEWMRPRVVGLVQRAIEGARRDGEMDVVSAFSEAVALNTLAEMFVIPEVDR

PQFLRWSTDLLKLAGGGVSSEEQKRAVKQSCCDMLDYMMRLVEERRKAPGEDVASRFIA

AEDGDTELAGEAAMQCFQMVAAGFVTSVNQIANTVLALLNHPAELAKLREAPGLVRGAV

EESLRFEPSVLSLSRMCKKDTEIRGARVSEGQFVFAMIAAANRDPGLFSEPDRFDITRQ

QSRHLTFGSGAHYCPGAPLIRMEVEESLRALLSLPRWELAEETLSYAGSNLQDRGPSSL
                    RVRFPAA*"
     CDS             6503..7282
                     /note="ORF5"
                     /note="Sensor1"
                     /note="putative two-component sensor, HisK subunit"
                     /note="homolog of portions of ORF4_jer"

/translation="MKLARKLTLALVFGVFLVLALSAYAQIRRDAMVFENDVQRDHHTM

GRALAAAVMEVWRSEGAARALRLVEDANEREQQVNIRWVWLDGQADEPHRPRLAPELLV

PVIRGTFTMLKPLADKQGVTIVEEGDTPDRLVHADADQLQQALTNVVVNAIQAMPSGGT

IAVRVQAVRAIPPADQGGAEGDYIALSVRDEGQGMMAGVLEHVFEPFFTTKPVGEGTGL
                    GLSVAYGIIKEHGGWIDVDSRAGSGSQFTMYLPQEKP*"
     CDS             7279..8664
                     /note="ORF6"
                     /note="AtoC homolog"
                     /note="RespReg subunit in His/Asp kinase
regulatory pathway
                     /note="97% identity vs ORF5_jer"

/translation="MSGRVLIVDDERGVCELLDAGLKKRGFQAAWRTSAAEALELLGAE

DFDVVVTDMTMRGMSGLELCERIAQNRPDLPVIVITAFGSLDTATSAIRAGAYDFVTKP

FELDALRLTVERALRHRALREEVRRLRRAVDDSHRYEQILGGSPAMKGVFDLLDRVADS

DTSILITGESGTGKELVARAVHQRSRRGQGAFVAVNCAAVPDALLESELFGHARGAFTD

AKGPRSGLFARAHGGTLFLDEIGELPVGLQPKLLRALQERVVRPVGADEEVPVDVRLIA

ATNRDLETAIEERRFREDLYYRINVVHVDLPPLRSRGADVLLLAQRFLEHFATVKERPI

KGLSAPAAEKLVAYAWPGNVRELQNCVERAVALARYDQITVDDLPEKIRSYRSSHVLVS

SDDPTELVPMEEVERRYILRVLEVVGGNKSQAAQILGFDRATLYRKLERYGLRAGRASD
                    PKP*"
     CDS             complement(9474..11000)
                     /note="ORF7"
                     /note="Sensor2"
                     /note="91% vs ORF6_jer"
                     /note="COG0642"
                     /note="Signal transduction histidine kinase"

/translation="MGRPTPRGLSWLRFPRPVRLSALLGAATLLLTSVAIVVASALMVA

STTMQQATRILGATVESVRLVERLEIDLLLDAQQSGRAVGSDRGELAPSLAAWERGLRS
```

GLAAARGHVSSPEEGEILEHAERRVEDYLARRRAADARELPSAPGARDPALLGVHDPAL

DEAFRALDRLVEINLEQARASEALVAYLTRRTTGAGVAAVVFFLAGASTVLLSARRLIY

RPIVAIQQAIGRYGAGDRAARAPLIGPRELGEIARAFNDMAESLERQREAQFAFLGGVA

HDLRNPLSALRMSVHVLDLDSLPPASSVRRTMALVGRQVDRLERMVGDLLDASQIEACK

LELRVEERDLRDLAQEAVDLYRPVSPEHPIELSLPETPVLVPCDATRIAQVLNNLLSNA

LKYSPAGGQIDVAVRAGGDGAEIAIRDRGLGIEPAELAHLFEPFRRLKSSSGSIPGTGL

```
                   GLTVAKRIVEAHGGRLLVESRPGAGSVFRIDLPRSPSREQADGPRGVSHG*"
     CDS           11030..12463
                   /note="ORF8"
                   /note="conserved hypothetical protein"
                   /note="YehP family"
```

/translation="MQRRLDGEIELQRDRAHRDSERYARRPRGAPRAPAPASPAPRAPV

SSVLWTVIPVSSTLRAMPARTPRKPPPPASPAGPAGAPDDLSDSDRDALLRWRLALGPE

AERVDPRLSLGGLGGAAPALDVDPRRLGDLDKALSFIYDERAGNLGGSRPYVPEWLSAV

REFFSHEVVALVQKDAIERKGLTQLLFEPETLPFLEKNVELVATLMSAKGLIPDAARET

ARQIVREVVEEVRRALESEVRTAVLGALRRNTTSPLRVLRNLDWKRTIRKNLKGWDAER

RRLVPDKLYFWANQTRRHEWDVAILVDQSGSMGESVVYSSIMAAIFASLDVLRTRLLFF

DTEVVDVTPMLVDPVDVLFTAQLGGGTDINRAVAYAQANFIERPEKTLLILITDLFEGG

NAEELVARMRQLADSKVKSICLLALSDGGKPSYDHEMAQKLAALGTPCFGCTPKLLVKV

```
                   VERLMRGQDLGPLLGAEAR*"
BASE COUNT    2031 A    5244 C    4999 G    1898 T       0 OTHER
ORIGIN
        1 GATCTCGTCG AGGAACAGCG TGCCGCCGTC GGCCTCCTCG AACCTGCCGA TCCGGAGGCG
       61 CGCGGCGCCG GTGAAGGCGC CCGCCTCGGC GCCGAACAGC TCCGCCTCGA CGAGCTCGTC
      121 GGGGAGCGCG CCGGCGTTCA CCTTCACGAA CGGCCGGTCC CGCCGGCGCG AGTTGGCCTG
      181 GACGATGCCG GCGAGGAGCT CCTTGCCGGT CCCGTCCGGT CCGGTGATGA GCACCGGCAC
      241 GTCCGCGGGC GCGACCTTCA CCGCGAGGCT CACCACCTCG TGCATCGCGT CGCTCGCGTA
      301 CACGAGCCCG CCGAGGTCGT GGCGCTCGGC GAGCCTGTGC CGCGCGCGCC CGCGCTGGGC
      361 GACGAGGCGC GCGTTCTCCT GCTCGAGCGA CCGCAGCCGG GCGAGGTTGC TCACCACGGC
      421 GACGAGCTTC TGGTCGTCCC ACGGCTTCGG CACGTAGTCG CTCGCCCCGG CCTTGATGAG
      481 CTCGACCGCG CCCGCGATCG ACGTGAACGC CGTCATGGCG ACGACGGGCA GCTCGGGGTC
      541 GATCGACTTG ATGCGGCGGA GCAGCTCCAT GCCCTCCTCG CCCGATGTCG CGCTCTGTCG
      601 GAAGTTCATG TCCTGGACCA CGGCCCCGAG CTCGTCGTCG AGCACCGCCG CGATCGCCGC
      661 GTCCGGCGTC GCCGCGACGC GGACCTCCAG CCCGTGCAGC TCGAAGAGCG TCGTCAGCGC
      721 GACGCAGACC GCGGGCTGAT CGTCGATGAC CAGGATCTTC GGCACCCCGG GAGCGTAGCC
      781 GCTCCCGGCC GCCGGCAGGC TCACTCGTCC TGGCCAGCCC GCGACCAGCC GCCGAGCTTG
      841 ACGCCCGGCG TCTGCGCCAG GAACGCCTGC ACGGCGGGCG GCGGCGACGC CCACGCCGCG
      901 AGGCGCCCCG GCTCCGCGG GATCGGCGCC GTCGCCGAGC GCGAGTAGGA GCTCCACGCG
      961 CCGTCGCCGC AGGCATAGCA GGCCGAGCGC GCGAGCTGCG CGGTGAGCCG GAGCGACCCC
     1021 CGCGCGTCGT AGGCCGGCGC GATCTTCACG AGCTGCGGGG GGTCCTTCTC TCGCCGCGCG
     1081 GCCTCCGGGT CCTCCTCGAG GTCGTCGAGC GTCGCCTCGG CCGCGCGCTG CAGCGACGGG
     1141 ACGCCGGACA CCTCGGCGAG CAGGTCGACC GCCGCGCCGC GCTCGGCGTC CCACACAGTG
     1201 AACGCGGCGC CCTCGGAGCC GTGCGCGCCG CAGAGATCGC TGTACGTGCG CTCCTCGATG
     1261 AACAGGTACG GCCCCACGCT GCCGATCAGC GCCGCGCTGT GCTGGAACTC GTTGCTCTCG
     1321 TCCTGGTCGG CGCCGTGAT CACCGCCTGG CGCTCGCCGT CCCCGCGCAG CACGAGCTCC
     1381 GCGTCGGTCG CCGTGCCCTC GCCCGGCTCG CGCGTGTCCC GTCCCAGAG CTCGCAGGGC
     1441 GTGGTCTCGA CCTCCTTCGC GCGCGCCTCC CAGCGCCACT CCCCGCGCCG GGTCGCCACG
     1501 ACGATCCCGG GCTCCTCGCG GATCACCGCG CCGCCCTCGG CGACGTGCCA CGTCCTCGGC
     1561 GTCCCCTCGC CCGTGCTGCC CCAGATCAGG ACCACCCCGG CCGTCGCGGC GTCCCCGGCC
     1621 GCCTGGGGCT CGGACGGGCG CGGGGCGGGC GCGAGCTGGA TGTCGGTGGA AGCGGCGGGC
```

```
1681 GCAGGCCGGG GTCGGGCGGC ACAGCCGGAG ATCAGCGCCA GCGAGACGAT CAACGCGGCA
1741 GGTCGGGAGC GCAGCATGCG GAGCCGAGAG AGCATGGTGT GTGCCGCGGA CCGCGGCCAG
1801 GAAAGCCGCG CGGCGCGCGC TGGAGGTGTA GCCGCGCGCC CACGCCGCGT GGCACGAGCG
1861 CCCCGTCACC GCCTCGAGAT CCGGCGATGG AGCGCCGGCG CGGGCAGCGG CAGGAACGGC
1921 GCGTCCCCCG TGTCGGCGAT CGCGCCGTCC TCAGGTGCCG GGACCCGAGC GCGCCTGGCG
1981 CAGGAGCTCC CGCTGCGCGG CGTTCAGCCG GATCCCGGGC CTGCGCTGCC GGATCCGGGC
2041 CTCCATCGCG TCGACGTCGG CGGCGAGCTC GCGCTCCAGC AGCAGCGCGG TCGCGAGGGT
2101 CGCCGATCGG CCGCGGCCGG AGGCGCAGTG CAGGTACACG CCGTCCACGC CGCGCAGCCG
2161 CGCGAGGAGC TCCCGGAGCC GCTCCACCTC GGGCCCCGTG CCGTCGAGCG TCGGCACGCA
2221 GACGTAGCCG GGGTGGCGCC GCACCGCGGC GGCCGCCGGA AACTCGGCCG TCATGTCCAC
2281 GACCAGCCGC ACGCCCGCCG GCAGCTCGTG GGCGAGCGGC CGCCGGCCGA CCCAGAGCCC
2341 GGGCGCCACC TCGTTGGCGC AGTCCGCCCG CCCGAGCGCC CGCTCCGCGC GCCATACCGC
2401 CCAGGTCAGG AGGAAATACG GACCGAGCAG GACGAGCGCC CACGCGGCCT GCGTGCCGTC
2461 AGGCTGCTTG CCCAGCAGCG CGGGCCGGCG CGCGAGGTAC GCGGCGCCGA CAAGGCCGAA
2521 GCTCAGCGCC GGCCAGAGCA GCGCGAGCGC AGCCCCGCCG GCGAGGAAGG CGAGCGCGGC
2581 GAGGGAGGCG CTCAGGACGA GGAAGGTCAG GCCGTATCGC ATCGAGCAGG TCCCGCCCCC
2641 GGCGCGGGTG ATCCCGGATC TAGCGCGACG GCCCGCTGGA TGGCGTCGCG GAGCCACCGG
2701 TGGCCCTCGT CGTGCTCGGA GCGCTCCGGC CAGACGAGCG TCAGCGTGTA GCCCTCGAGC
2761 TGGAACGGGC ACGGCCGCAC CACGAGATCG AGCCTCCGCG CCAGGGCCGC GGCGACGCGC
2821 GCGGACACGG TGAGCAGCAG GTCGGAGCCG GAGACGATGA ACGGGGCGAC CAGGAAATGG
2881 GACACGGTCA GCGTCACCCG CCGGCGCAAT CCCTGCTCCG CCAGCGCCCG ATCGATGACG
2941 CCGTGGTCCT CTCCGTGCGG CGAGACCATC AGGTGCTCGC AGGCAGCGTA GCGCGCCGCG
3001 GTGAGCGGCC CCCGTGACGC CGGGTGTCCG CGGCGCATCA CACAGACGAT CTCCTCGGCC
3061 GCCAGCAGCG TCGACCGGCA GCCGTCGGGC ACGGGCCCC CGCGCCCGAG CTTGCCGTCG
3121 AGCTCGCCGC GGCGCAGGAG CTCGGCGAAG TCGGCCGGGA TGTTCCGGCA GCGCAGGTTG
3181 ACGCGCGGCG CCTCGACGGC GAGGAGCGCG GTCAGCGCCG GGAGCACGAG CAGCTCCAGG
3241 TTGTCGGTCG CGACCAGCCG GAACGTGCGC TGCGACCGCC GCGGGTCGAA CCGCTCGACC
3301 GGGCGGAAGA CGTGCTCGAG CCGCTCGACC GCCTCGGCCG CCCGCGGGGC CAGGTCCGC
3361 GCGCGCTCGC TCAGCGTCAT CTGCCGGCCG ACCTGGATGA GCAGCGGGTC CTCGAAATGG
3421 GCGCGCAGCC GCGCGAGCGC GTGGCTCATC GAGGGCTGCG TCACGCCCAC GCGGCGCGCG
3481 GCGCGGGTGA CGCTCTTCTC CTGGAGCAGG GCGTGCAACG CCACGACGAG GTGGGTGTCG
3541 ACCGACTGCA GGCGCATGGT CGATGGATAG CACGGCGACC CATCGACGCT GTCTATGGAT
3601 CGCCGCGCCG ACTGTCGATT CGACGCCCGG AGCGTGGGTG CCTATCTCTC CTCTCCGGAC
3661 GGCACATGCC GCCGCGCGGC GCGCCCCTGC CCCCCAGCCG AGGAGAGCAA CCCCATGATC
3721 ATCGAGTACA TTCGCTACAC GATCCCCGCG GAGCAAGAGA AGGAGTTCCT GGCCGCCTAC
3781 CGCGACGCCG CCGCGGAGCT GCGCGGCTCG GAGCATTGCC TCGATCACGA GATCTCCCGC
3841 TGCGTCGAAG ATCCGACGAG CTTCGTCGTC CGCATCTGCT GGGACTCGCT ACAAGGCCAC
3901 CTCCAGGGCT TCCGCAAGGC GGCGGCGTTC CCGTCGTTCT TCGCCAAGGT GAAGCCGTTC
3961 TACGAGCGTA TCCAGGAGAT GAGGCACTAC GCCTTGACCG ACGTCGCCAC GCGGCAGGCG
4021 GGGAAGGCCG CGACGGGCTG AAGGGTAGAC GGCCCGCCGA GCCGCTCCCC TTTGCAGGTC
4081 GCGCCGGATC GATATCGAGG CTACCCTCGC GCGTCGACCC CTCATCGGCC GCCTCTCGCG
4141 ATCGCCTGGA GCACCCTCAT GCCGCGCGCG CTGGCTCTCG GACTCTCCCT CCCGCTCCTT
4201 CTCTCGCTCT CGCACTGCGC GGGCGCGCGG AGCCCGAGCA CGCCCCCCGC TGACCCGGAT
4261 CGCTCGCCCG CGCCGGCGCC TGGATCGAGC GCCGGGCCGG CGAGCGAGCT CGACCCGGCA
4321 CCGGCGCCCC TACCCGACGG CGCGCCGCAG CCAGCTCCCG GATCCAGCAC GGGCGACGCG
4381 TCGACGTCCG ATCCCGGCCA GGCGCCCGCG ATCGCTCCGG GCCGGACACC TGAGCCCGGT
4441 GAGGCGCCCG CACCGGACAG CGGGCCGCCC GCGGGGCCCT CGCGATGCGC GGCGCCAGCC
4501 CGTCCCGCGC CGGGCTTCAC CGACTGCGCC CGCCAGGAGG TCTTTGCCGG CGGATGCTGC
4561 TATCCGAGCT TCGAGGCCGC CTGCGCCGGC CTCGGCTGCT CCCCGCCCGC TGCCTGCGC
4621 CTCAAATCGA GCCCCTTGCA GGCCCGGTGC GCCCGGTGAG GGGCGGTGTG ACGCCGCGAT
4681 CCGGGAAAGC TGCTGGGCAG ACCGCGCGGC GCCCTCCGGG ACGCGCGCCC GACGCGCCGC
4741 TTCCGCCGCG CGCGGGCAG GTGCAGGATG AGGCCATGAG AATGCCTCCG GCGCTCGACC
4801 GAGACCACCG CCGCGCCGCG CGCGCGCCCG CCGTCGCCCT CATCGCGCTC CTCGCAGCCG
4861 GCCGCGCGCT CGCGGCCTGC TCCAGGAGCA CGGCGGGCC GAAGCACCGC GAGGCGGCGC
4921 CGGAGCGCGA CAGCGCCTGC ACGGATCCAG CGAAGCCCAG GGCGTACTTC TATCCTGCGG
4981 AGAACCGGAC GGACTACGCG CCTGACGATC CCTGGAAGGA CGGCTGCGCC ATGCTGGTGC
5041 CAGATCACCT GTTCTGCTGT CCGGAGAAGG CCTCCATCGG CTCGCCCTGA TCCGCTCCGC
5101 CCCGCGGCGC GCCGCGGGCG CCACAAGGAA AGAAGGACTC ATGGCCGTTC CCTCTGGATT
5161 CGACCTCACG AGCGAGCGCT TCTTCGCCGA TCCCTTCCCG ACCCTCGAGC GGCTCCGGAC
5221 CGAGGCGCCC GTCTACTTCT TCGAGCCGCT ACAGTGCTTC CTCATCACCG CTCCTGCCGA
5281 TATCGAGGGG CTCGTGAAAG ACTCGAGCTT CACCGCGCGG CGGGCGACGG CGCTCCTCGG
5341 CGGCCTCGGC ATGCTCGGCG AGGACGAGCT CTCGAGGAAG ACGTTCGACT CCCTGTCGCG
5401 GCTCGCCTTC TTCCAGGACC CGCCGCGCCA CACGCAGCTT CGACAGCTCA TCATGAAAGG
```

```
5461 GTTCTCGCCC TCGGCCGTGG AGTGGATGCG CCCGCGGGTC GTGGGGCTCG TACAGCGGGC
5521 CATCGAGGGG GCGCGCCGCG ACGGCGAGAT GGATGTCGTC TCGGCGTTCT CCGAGGCGGT
5581 CGCGCTCAAC ACGCTGGCCG AGATGTTCGT GATACCCGAG GTCGATCGCC CGCAGTTCCT
5641 GAGATGGTCG ACCGATCTCT TGAAGCTCGC CGGCGGCGGG GTGAGCTCGG AGGAGCAGAA
5701 GCGGGCGGTG AAGCAGAGCT GCTGCGACAT GCTCGACTAC ATGATGAGGC TCGTCGAGGA
5761 GCGCCGGAAG GCGCCGGGGG AGGACGTCGC GAGCAGGTTC ATCGCGGCGG AGGACGGTGA
5821 CACCGAGCTC GCGGGCGAGG CGGCCATGCA GTGCTTCCAG ATGGTCGCCG CCGGATTCGT
5881 CACCTCCGTG AACCAGATCG CGAACACCGT GCTCGCGCTC CTCAACCACC CCGCAGAGCT
5941 CGCGAAGCTG CGGGAGGCGC CGGGCCTCGT CCGCGGCGCG GTCGAGGAGA GCCTGCGCTT
6001 CGAGCCGTCC GTGCTCTCCC TCAGCCGCAT GTGCAAGAAG GACACCGAGA TCCGGGGCGC
6061 CAGGGTGTCC GAGGGGCAGT TCGTCTTCGC GATGATCGCC GCAGCGAACC GCGATCCCGG
6121 GCTGTTCTCC GAGCCGGATC GATTCGATAT CACCCGGCAG CAGAGCCGGC ACCTGACCTT
6181 CGGGAGCGGC GCTCATTACT GCCCGGGGGC CCCGCTCATC CGGATGGAAG TAGAGGAGTC
6241 GCTGCGCGCC CTGCTCTCGC TGCCGCGCTG GGAGCTCGCC GAAGAGACGT TGAGCTACGC
6301 CGGGTCGAAC CTGCAGGACC GCGGGCCGAG CTCGCTGCGC GTTCGCTTCC CCGCAGCCTG
6361 AAGCCGGGCG AGCGCGGCGC CGCGGCAGGA CGGCCGACGC GGGTGCCGCA CAACGCGGCA
6421 TGTCGCATTT TGCGACGGCG TCGGGCGGGC GGCTGGACGC GCGCACCCGC GCCGCGCGCC
6481 ACCTGCGCTA CGACGCCGGG CAATGAAGCT CGCGCGCAAG CTGACGCTCG CCCTCGTGTT
6541 CGGGGTCTTC CTCGTGCTCG CGCTGAGCGC CTACGCCCAG ATCCGCAGAG ACGCCATGGT
6601 GTTCGAGAAC GACGTCCAGC GCGATCACCA CACGATGGGC CGCGCGCTCG CGGCCGCCGT
6661 CATGGAGGTG TGGCGCTCCG AGGGCGCGGC GCGGCGCTG CGCCTGGTGG AAGACGCCAA
6721 CGAGCGGGAG CAGCAGGTGA ACATCCGCTG GGTCTGGCTC GACGGCCAGG CCGACGAGCC
6781 CCATCGCCCC CGGCTGGCTC CGGAGCTGCT CGTCCCCGTC ATCCGCGGCA CGTTCACGAT
6841 GCTGAAGCCG CTGGCGGACA AGCAGGGTGT CACGATCGTC GAGGAGGGAG ACACGCCGGA
6901 TCGGCTGGTC CACGCCGACG CCGACCAGCT CCAGCAGGCG CTCACGAACG TGGTGGTCAA
6961 CGCGATCCAG GCCATGCCGT CCGGCGGCAC GATCGCGGTG CGTGTCCAGG CCGTCCGCGC
7021 CATCCCACCG GCCGATCAGG GAGGGGCCGA GGGCGACTAC ATCGCGCTGT CGGTGCGCGA
7081 CGAGGGACAG GGCATGATGG CCGGCGTCCT CGAGCACGTC TTCGAGCCGT TCTTCACGAC
7141 CAAGCCCGTC GGCGAGGGCA CCGGGCTCGG CCTGTCGGTC GCCTACGGCA TCATCAAGGA
7201 GCACGGCGGC TGGATCGACG TCGACAGCCG CGCCGGCTCG GGGAGCCAGT TCACGATGTA
7261 CCTGCCGCAG GAGAAGCCAT GAGCGGTCGC GTCCTGATCG TCGACGATGA GCGGGCGTC
7321 TGCGAGCTCC TCGACGCCGG GCTCAAGAAG CGGGGTTTCC AGGCGGCGTG GCGCACGTCG
7381 GCCGCCGAGG CGCTCGAGCT CCTCGGCGCG GAGGACTTCG ACGTCGTCGT CACCGACATG
7441 ACCATGCGCG GCATGAGCGG CCTCGAGCTC TGCGAGCGCA TCGCCCAGAA CCGGCCCGAT
7501 CTGCCGGTCA TCGTCATCAC CGCGTTCGGG AGCCTCGACA CCGCCACGTC GGCGATCCGC
7561 GCCGGCGCCT ACGACTTCGT GACCAAGCCG TTCGAGCTCG ACGCGCTCCG GCTCACCGTC
7621 GAGCGCGCCC TGCGCCACCG CGCCCTCCGC GAGGAGGTGC GCCGGCTGCG GCGCGCCGTG
7681 GACGACTCCC ACCGTTACGA GCAGATCCTC GGCGGCAGCC CGGCGATGAA GGGCGTCTTC
7741 GATCTGCTCG ACCGGGTCGC CGACTCGGAC ACGTCGATCC TCATCACGGG CGAGAGCGGC
7801 ACCGGCAAGG AGCTCGTCGC GCGCGCCGTG CACCAGCGCA GCCGGCGCGG CCAGGGCGCG
7861 TTCGTCGCGG TGAACTGCGC GGCGGTCCCG GACGCCCTGC TCGAGAGCGA GCTGTTCGGC
7921 CACGCGCGGG GCGCCTTCAC CGACGCCAAG GGGCCGAGGA GCGGCCTGTT CGCGCGGGCC
7981 CACGGCGGCA CCCTGTTCCT CGACGAGATC GGCGAGCTGC CGGTCGGGCT CCAGCCGAAG
8041 CTCCTGCGCG CCCTCCAGGA GCGCGTCGTC CGCCCCGTCG GCGCGGACGA GGAGGTCCCC
8101 GTGGACGTGC GGCTCATCGC GGCGACGAAC CGCGACCTGG AGACCGCGAT CGAGGAGCGC
8161 CGCTTCCGCG AGGACCTCTA TTACCGGATC AACGTGGTCC ACGTCGATCT GCCGCCGCTC
8221 CGCTCCCGCG CGCCGACGT GCTCCTGCTC GCGCAGCGCT TCCTCGAGCA CTTCGCGACC
8281 GTCAAGGAGC GGCCGATCAA GGGCCTCTCG GCGCCCGCGG CCGAGAAGCT CGTCGCCTAC
8341 GCGTGGCCAG GCAACGTCCG CGAGCTCCAG AACTGCGTCG AGCGGGCGGT CGCGCTCGCG
8401 CGGTACGATC AGATCACCGT CGACGATCTC CCCGAGAAGA TACGGAGTTA CCGGAGCTCC
8461 CACGTCCTGG TCTCCAGCGA CGACCCGACC GAGCTCGTCC CCATGGAGGA GGTCGAGCGG
8521 CGCTACATCC TGCGCGTCCT GGAGGTGGTC GGCGGAAACA AGAGCCAGGC AGCCCAGATC
8581 CTGGGCTTCG ATCGAGCGAC CCTGTACCGG AAGCTCGAGC GGTACGGCCT GCGCGCGGGG
8641 CGCGCGAGCG ACCCGAAGCC GTGACCCGCC CGGCGTCGCG CCGGAGGTGA TGCCCGGAGA
8701 GCCTCGCGGC GGCGACTCCG CTCGTCCCTC GCTGTTGCAG AACGCGACAC CCGCGCCGCC
8761 GCGCGATCGG CAGCGCCGCT CGCGGGCGCG CGCGGGCGCC CGCGACTCTG CCTCGTGGCA
8821 TGAGAGCTGC CTGAAAGCCG GGCGCGAACA TGAGCCACAC CACGGCGGAG CCTGTCGCTC
8881 CGGGTCGGAG AGTGCCAGTC GACTGGATCG CGCTCGCGAA CGCGTTCGAC AACATCGCTC
8941 GAGGCGTGCG CCATTTCCTT CACCTCGACA CGGGCGCCGT GCTCCGGCTG AACGAGCGGC
9001 TCGTCGATCC CGCCACGCGC GCGCGCATCG AGGAGGATCC GGGGTGCGTG CTCATCGAGG
9061 CCATCGCCGC CCGGGACCAG TATCGATGGC TGCAGGCGTT CATTCCGACG GTCGACGATC
9121 TGGAGTTCCG GCTGGCGCTC CTGCACAGCA TGCAGGGCCC AGGGTCGTTC GGCGGTTCA
9181 AGGCCGCGCT CTCGTCCAGA CCGGAGCAGC TCCGCCGCTG GCGCGCCTTC CGGCAGGAGC
```

```
 9241 AGATCCGGGT CGCCATCGTC CGGTGGTTTC ACGCCCGCGG CCTCACGCCG GTCGCCCTCG
 9301 AGCACGCGCG GCCGGACGCG CGCTCCGAGC CGCCGAGGTC GCGCTCCGCC GACGCGGCCC
 9361 GCCAGCAGCT TTACGCCGCG GCGGACAGCC TCTCTCCCCA GGACCTCCAC GCGCTGACGT
 9421 CGCTCGCCGA GTTCCTGCGC GCGGCGCGCT CCGCGCTGCG GATCCCCGCG GATTCATCCA
 9481 TGGGAGACGC CGCGCGGGCC GTCCGCCTGC TCCCTTGAAG GCGAGCGCGG CAGATCGATC
 9541 CGGAAGACCG AGCCGGCGCC GGGACGGCTC TCGACGAGGA GCCGGCCGCC GTGCGCCTCG
 9601 ACGATGCGCT TCGCCACCGT GAGGCCGAGG CCCGTGCCCG GGATGGATCC AGACGAGGAC
 9661 TTGAGTCGCC GGAACGGCTC GAAGAGGTGC GCCAGCTCCG CGGGCTCGAT CCCGAGCCCT
 9721 CGATCGCGAA TGGCGATCTC GGCCCCGTCG CCGCCGGCGC GGACCGCCAC GTCGATCTGC
 9781 CCCCCGGCGG GAGAATACTT GAGCGCGTTC GACAGCAGGT TGTTCAGCAC CTGCGCGATC
 9841 CGGGTCGCGT CGCAGGGGAC GAGCACCGGT GTCTCGGGGA GCGACAGCTC GATGGGGTGC
 9901 TCCGGCGAGA CAGGGCGATA GAGGTCCACC GCCTCCTGCG CGAGGTCGCG CAGATCGCGC
 9961 TCCTCCACCC GGAGCTCGAG CTTGCAGGCC TCGATCTGGG ACGCGTCGAG GAGGTCCCCG
10021 ACCATGCGCT CGAGCCGGTC GACCTGCCGC CCCACGAGCG CCATGGTGCG GCGCACGCTC
10081 GACGCCGGGG GCAGGCTGTC GAGGTCGAGG ACGTGCACGG ACATCCGGAG CGCCGACAGC
10141 GGGTTCCTGA GGTCGTGGGC CACGCCGCCG AGGAACGCGA ACTGCGCCTC GCGCTGGCGC
10201 TCCAGCGACT CCGCCATGTC GTTGAAGGCG CGCGCGATCT CCCCGAGCTC GCGCGGCCCG
10261 ATCAGCGGCG CGCGCGCGGC GCGGTCGCCC GCGCCGTAGC GCCCGATCGC CTGCTGGATC
10321 GCGACGATGG GGCGGTAGAT GAGCCGCCGC GCGCTGAGGA GGACCGTGGA AGCGCCCGCG
10381 AGGAAGAACA CGACCGCCGC CACGCCGGCG CCGGTCGTGC GCCGGGTCAG GTACGCGACG
10441 AGCGCCTCCG ACGCGCGGGC CTGCTCGAGG TTGATCTCGA CCAGGCGATC GAGCGCCCTG
10501 AACGCCTCGT CGAGGGCGGG ATCGTGCACG CCGAGCAGGG CGGGATCGCG CGCGCCAGGC
10561 GCCGACGGGA GCTCGCGGGC GTCGGCGGCG CGGCGCCGGG CGAGGTAGTC CTCCACGCGC
10621 CGCTCCGCGT GCTCGAGGAT CTCGCCCTCC TCCGGGCTGC TCACGTGGCC GCGCGCCGCC
10681 GCGAGGCCGC TCCTCAGGCC GCGCTCCCAC GCCGCCAGGG AGGGGCCAG CTCCCCGCGG
10741 TCGAGCCGA CCGCGCGGCC GCTCTGCTGC GCGTCGAGCA GGAGGTCGAT CTCCAGCCGC
10801 TCCACGAGCC GGACGCTCTC GACCGTGGCG CCGAGGATCC TGGTGGCCTG TTGCATGGTC
10861 GTCGACGCGA CCATCAGCGC GCTGGCGACC ACGATGGCCA CGCTCGTGAG AAGAAGCGTG
10921 GCGGCCCCGA GGAGCGCGCT CAGGCGCACG GGCCGCGGAA AACGGAGCCA GCTCAGGCCC
10981 CGCGGAGTTG GCCGTCCCAT CCTCCTGCGT TGGTTCGGAT CCGCGCCGGA TGCAACGTCG
11041 CCTCGATGGA GAGATCGAAC TGCAGAGGGA CAGAGCACAT CGAGACAGCG AGCGATACGC
11101 GCGGCGCCCC CGCGGCGCTC CCCGCGCCCC CGCGCCGGCC TCACCGGCGC CTCGCGCCCC
11161 GGTCAGCTCG GTCCTCTGGA CGGTGATCCC CGTTTCATCG ACACTACGCG CGATGCCCGC
11221 GCGCACCCCC CGCAAGCCCC CGCCGCCCGC CTCGCCCGCT GGTCCGCCG GCGCGCCGGA
11281 CGACCTCAGC GACAGCGATC GCGACGCGCT CTTGCGCTGG CGGCTCGCGC TCGGGCCCGA
11341 GGCCGAGCGG GTCGACCCGC GCCTCTCCCT GGGCGGGCTC GGCGGCGCGG CGCCCGCGCT
11401 CGACGTCGAC CCGCGGCGGC TGGGCGACCT CGACAAGGCG CTGTCGTTCA TCTACGACGA
11461 GCGCGCCGGC AACCTCGGCG GCTCGCGGCC GTACGTGCCC GAGTGGCTCT CCGCCGTGCG
11521 CGAGTTCTTC AGCCACGAGG TCGTCGCCCT CGTCCAGAAG GACGCCATCG AGCGAAAGGG
11581 GCTGACGCAG CTGCTCTTCG AGCCCGAGAC GCTGCCGTTC CTCGAGAAGA ACGTCGAGCT
11641 CGTCGCCACG CTCATGAGCG CCAAGGGCCT CATCCCCGAC GCCGCGCGGG AGACCGCCCG
11701 GCAGATCGTG CGCGAGGTCG TCGAGGAGGT GCGGCGCGCG CTCGAGTCCG AGGTCCGCAC
11761 CGCCGTCCTC GGCGCGCTGC GCCGGAACAC GACGAGCCCG CTGCGCGTCC TCAGGAACCT
11821 CGACTGGAAG CGCACCATCC GCAAGAACCT GAAGGGGTGG GACGCGGAGC GGCGCCGCCT
11881 CGTCCCGGAC AAGCTCTATT TCTGGGCGAA CCAGACGCGA AGGCACGAGT GGGACGTGGC
11941 CATCCTCGTC GACCAGTCGG GCTCGATGGG CGAGAGCGTC GTCTACAGCT CCATCATGGC
12001 GGCGATCTTC GCGTCGCTCG ACGTCCTCCG CACCCGGCTC CTCTTCTTCG ACACCGAGGT
12061 CGTCGACGTG ACTCCGATGC TCGTCGATCC GGTCGACGTG CTGTTCACGG CGCAGCTCGG
12121 CGGCGGCACC GACATCAACC GCGCCGTGGC CTACGCCCAG GCGAACTTCA TCGAGCGACC
12181 CGAGAAGACG CTGCTCATCC TGATCACCGA CCTGTTCGAG GGCGGCAACG CCGAGGAGCT
12241 CGTCGCGCGC ATGCGCCAGC TCGCCGACAG CAAGGTGAAG TCGATCTGCC TGCTCGCGCT
12301 GTCGGACGGC GGAAAGCCCT CGTACGACCA CGAGATGGCG CAGAAGCTCG CCGCCCTCGG
12361 GACCCCGTGC TTCGGCTGCA CGCCAAAGCT GCTCGTCAAG GTGGTGGAGC GGCTCATGCG
12421 AGGTCAGGAC CTCGGCCCGC TGCTCGGCGC CGAGGCGCGG TAAAGCCACG GAGGCACAGA
12481 GGACACAGAG GTTCTTGCCT CTCCTCTGCG TCGTCTGTGC CTCCGTGGCC GCCCGTCAGG
12541 GGCCCCGAGA CCGACCGGCG CGGCTTGCGA ACGTCGTCGA CGTCAGCGAA GGCGCGCCCG
12601 GGACATCCGC GGCCGCGCAG GCCGCGTCAC GGCGCGCGAC GGATCGCCTT GGCGGCGCGC
12661 TCGTCCGCCC GCCGGGCGGC GGCGCGCTTT CGCGACGTGG CGCCGTGGGC AGCGCTCGCG
12721 GAGACGCGAC GGCGGGTGCC GGCCGCGCGA ACCACCGCTT CGAGCGAGGG TGACTGGCCC
12781 ATGAGAGGAC CAGTGCTGAT CGAGGGGCCG ACTAGGCTGA TAGAAAGTTT CACTTGACTA
12841 CCGATGTGGT GGCGGACCGA TCACGTCGCT CAGCGGAGGG CTCGTCGACC TATAAACTGT
12901 TTTGATCTTT TACGCAGCGT CACGGTGCGG AGATCACGAA CCCTGAGCGC CGTCCGGAC
12961 GTGAACTTGT CCACCCGGGA GGTCCACTCG CCTTCCGCCT CTCACGACGG ACGCATGCAC
```

```
13021  GCACACACCA CGGAGGCACG AAGGCACGGG TCTGGGTTCG CTCCGTGCCT TCGTGTCTCC
13081  GCGGTGCTCG GCGAGGGACT GCCCCGGAGG TTGCACCGGG CGCTCTGTTA TGATTCCAAG
13141  AAGCACGATG CAGGCCAACG ATGGCCCGAT GCCGGCCTCG CCCGTTTTCC GGGGATGGCC
13201  GTGGGCCGCC TTTCATGGTT GAAACCATCG GTTGCAACCA TGGCGCAACG GAGCGGCGTC
13261  CCTGTCCGCG GGGCGCCAGG CGACCCTGGG AGCATGCCTC TCGGCCGGCA GGACCGGTCA
13321  GCGAGGATCC AGGGCGCTGG CCCAGCGGCC CCGACGATCC AGCCGCGCGG GGCAGAAGCG
13381  TCAGCGCCGC CTGGGACCTC GCCCCAGGCC CGGCGCGCGC TCGACCTGGA TGCTCCCGCC
13441  GTGGGCCCCG AGGATCTGGT CCACGACGCC CAGCCCCCGT GCGAGCTCGC GGGCGCCGCC
13501  CGCTCGAGGT GCCCGAAGAT CACCGGCAGC CCGCCGTCCG AGCGGCCGAG GCACGGGTG
13561  GGGCCTGGAC CTGCAAGACC AGCGCGCCAA GCGGGGTCC GAGCTCGTGC GGGGCGGCCG
13621  ACACGAGCCT CGCGGATCTG GCTTGCCCCC CGCTCCGTAC CTGCTCGACA GGGGACCACC
13681  CAGCGCACGC TGTCATTCGG TCGAGCACCC GCCTTCTGTT CGCAGGGAGC GCCTTGAAGA
13741  GCCGGACAGG GAGCCTTCCG GAAAGCCAGT TGCCTGGTAT CCACCATGTT TCCGGTGTGC
13801  TTCGGCTCAG GCAACGGGCC ACATCCGCCC GGGCGACTCG ATCGGATGCA ACGTGATCGA
13861  GTCCGCATGG TCGGCAGCGG TCCCCGCCCC CTCCTGCCTC TGACAACAGC GGATCGCAGC
13921  CCCGCCTGTG ATGCCGGCAG CGGCACATCT ACACAGATGA ATGTTCACCC GGCGGGCAAT
13981  GTTCCGGGCT GAAAAGAATA ATCCAGTCTC AGTTCAATGA GGTGCCATGG CGGCGCCAAA
14041  CTCACCACAT CGCACTCGGC GCAATCAGTC GACCATAGAA TTGAAATGTA AGACAAATTA
14101  CATGCGAAAA TGCTTGAAAT ATCATAAAAA AGAATGGATT GATTGGTTGC GTAGATCACC
14161  GTTGATGCTA GC
```

FIGURE 5.

```
           10         20         30         40         50         60         70         80         90
AATAATGAGTCAGGCAACTATGGATGAACGAAATAGACAGATCGCTGAGATAGGTGCCTCACTGATTAAGCATTGGTAACTGTCAGACCA 100        110        120        130        140        150        160        170        180
AGTTTACTCATATATACTTTAGATTGATTTAAAACTTCATTTTTAATTTAAAAGGATCTAGGTGAAGATCCTTTTTGATAATCTCATGAC 190        200        210        220        230        240        250        260        270
CAAAATCCCTTAACGTGAGTTTTCGTTCCACTGAGCGTCAGACCCCTTAATAAGATGATCTTCTTGAGATCGTTTTGGTCTGCGCGTAAT 280        290        300        310        320        330        340        350        360
CTCTTGCTCTGAAAACGAAAAAACCGCCTTGCAGGGCGGTTTTTCGAGCTTCGTGGATCCAGATCTGAAGCTCTTGTTGGCTAGTGCGTA 370        380        390        400        410        420        430        440        450
GTCGTTGGCAGTTCAACCTGTTGATAGTACGTACTAAGCTCTCATGTTTCACGTACTAAGCTCTCATGTTTAACGTACTAAGCTCTCATG
         <_____R6K ORI_____

460        470        480        490        500        510        520        530        540
TTTAACGAACTAAACCCTCATGGCTAACGTACTAAGCTCTCATGGCTAACGTACTAAGCTCTCATGTTTCACGTACTAAGCTCTCATGTT
<_____R6K ORI_____

550        560        570        580        590        600        610        620        630
TGAACAATAAAATTAATATAAATCAGCAACTTAAATAGCCTCTAAGGTTTTAAGTTTTATAAGAAAAAAAAGAATATATAAGGCTTTTAA
<_____R6K ORI_____

640        650        660        670        680        690        700        710        720
AGCTCTAGCGCTGAGGTCTGCCTCGTGAAGAAGGTGTTGCTGACTCATACCAGGCCTGAATCGCCCCATCATCCAGCCAGAAAGTGAGGG
<_____

730        740        750        760        770        780        790        800        810
AGCCACGGTTGATGAGAGCTTTGTTGTAGGTGGACCAGTTGGTGATTTTGAACTTTTGCTTTGCCACGGAACGGTCTGCGTTGTCGGGAA 820        830        840        850        860        870        880        890        900
GATGCGTGATCTGATCCTTCAACTCAGCAAAAGTTCGATTTATTCAACAAAGCCACGTTGTGTCTCAAAATCTCTGATGTTACATTGCAC 910        920        930        940        950        960        970        980        990
AAGATAAAAATATATCATCATGAACAATAAAACTGTCTGCTTACATAAACAGTAATACAAGGGGTGTTATGAGCCATATTCAACGGGAAA 1000       1010       1020       1030       1040       1050       1060       1070       1080
CGTCTTGCTCGATTAATCAGATAAAATCTAGAATTCCCGGGCATAGATCCGCTTGCCCTCATCTGTTACGCCGGCGGTAGCCGGCCAGCC
                                                      <_____ORIT_____

1090       1100       1110       1120       1130       1140       1150       1160       1170
TCGCAGAGCAGGATTCCCGTTGAGCACCGCCAGGTGCGAATAAGGGACAGTGAAGAAGGAACACCCGCTCGCGGGTGGGCCTACTTCACC
<_____ORIT_____

1180       1190       1200       1210       1220       1230       1240       1250       1260
TATCCTGCCCGGCTGACGCCGTTGGATACACCAAGGAAAGTCTACACGAACCCTTTGGCAAAATCCTGTATATCGTGCGAAAAAGGATGG
<_____ORIT_____

1270       1280       1290       1300       1310       1320       1330       1340       1350
ATATACCGAAAAAATCGCTATAATGACCCCGAAGCAGGGTTATGCAGCGGAAAAGCGCTGCTTCCCTGCTGTTTTGTGGAATATCTACCG
<_____ORIT_____

1360       1370       1380       1390       1400       1410       1420       1430       1440
ACTGGAAACAGGCAAATGCAGGAAATTACTGAACTGAGGGGACAGGCGAGAGACGGGGCCTAGAGCGGCCAATTCCTGCAGCCCAGCTTC
<_____ORIT_____
                                                                                          _____>
```

```
      1450      1460      1470      1480      1490      1500      1510      1520      1530
ACGCTGCCGCAAGCACTCAGGGCGCAAGGGCTGCTAAAGGAAGCGGAACACGTAGAAAGCCAGTCCGCAGAAACGGTGCTGACCCCGGAT
                        TN5 KANAMYCIN RESISTANCE PROMOTER                                >

1540      1550      1560      1570      1580      1590      1600      1610      1620
GAATGTCAGCTACTGGGCTATCTGGACAAGGGAAAACGCAAGCGCAAAGAGAAAGCAGGTAGCTTGCAGTGGGCTTACATGGCGATAGCT
                        TN5 KANAMYCIN RESISTANCE PROMOTER                                >

1630      1640      1650      1660      1670      1680      1690      1700      1710
AGACTGGGCGGTTTTATGGACAGCAAGCGAACCGGAATTGCCAGCTGGGGCGCCCTCTGGTAAGGTTGGGAAGCCCTGCAAAGTAAACTG
                        TN5 KANAMYCIN RESISTANCE PROMOTER                                >

1720      1730      1740      1750      1760      1770      1780      1790      1800
GATGGCTTTCTTGCCGCCAAGGATCTGATGGCGCAGGGGATCAAGATCAATTCATTAAAGAGGAGAAATTAACCATGGCCGACCAAGCGA
   TN5 KANAMYCIN RESISTANCE PROMOTER         >
                                                                              BLEO RESI  >

1810      1820      1830      1840      1850      1860      1870      1880      1890
·CGCCCAACCTGCCATCACGAGATTTCGATTCCACCGCCGCCTTCTATGAAAGGTTGGGCTTCGGAATCGTTTTCCGGGACGCCGGCTGGA
                          BLEO RESISTANCE GENE                                           >

1900      1910      1920      1930      1940      1950      1960      1970      1980
TGATCCTCCAGCGCGGGGATCTCATGCTGGAGTTCTTCGCCCACCCCGGGCTCGATCCCCTCGCGAGTTGGTTCAGCTGCTGCCTGAGGC
                         BLEO RESISTANCE GENE                                           .>

1990      2000      2010      2020      2030      2040      2050      2060      2070
TGGACGACCTCGCGGAGTTCTACCGGCAGTGCAAATCCGTCGGCATCCAGGAAACCAGCAGCGGCTATCCGCGCATCCATGCCCCCGAAC
                          BLEO RESISTANCE GENE                                           >

2080      2090      2100      2110      2120      2130      2140      2150      2160
TGCAGGAGTGGGGAGGCACGATGGCCGCTTTGGTCGACCCGGACGGGACGCTCCTGCGCCTGATACAGAACGAATTGCTTGCAGGCATCT
                           BLEO RESISTANCE GENE                                          >

2170      2180      2190      2200      2210      2220      2230      2240      2250
CATGAAGCTTATGTCCGGTACCGTCGACTGATAACTTCGTATAATGTATGCTATACGAAGTTATGCGGCCATCGATCGCGCGCAGATCTG
      >
                                <               LOXP               >

2260      2270      2280      2290      2300      2310      2320      2330      2340
TCATGATGATATTGCAATTGGATCCATATATAGGGCCCGGGTTATAATTACCTCAGGTCGACGTCCCATGTCGAGAAAATTTATCAAAAA
                                                                           T7A1 PROMOTER>

2350      2360      2370      2380      2390      2400      2410      2420      2430
GAGTGTTGACTTGTGAGCGGATAACAATGATACTTAGATTCAATTGTGAGCGGATAACAATTTCACACAGAATTCATTAAAGAGGAGAAA
               T7A1 PROMOTER              >

2440      2450      2460      2470      2480      2490      2500      2510      2520
TTAACCATGGCGCTCAGGGGTGCGTCGGACGCCACTACCAACCCCTCTCGACTTGTGCAGTCCGTCGCCGCCGGCCCGCGTGCGACTCCG
                              MX9 INT                                                    >

2530      2540      2550      2560      2570      2580      2590      2600      2610
TGGGGTGTCAGTGCGTCGTGGTACCTGCTAGGGCGTACAGCAACGGGGGAGTACATCGTGAGTAGCGACGCGGCGAAGAAGGGCCATCCA
                        MX9 INT                                                          >

2620      2630      2640      2650      2660      2670      2680      2690      2700
ATGGCAACTGCGGCGGAGCGGTTGCCGACGTCACCAATCGACGTCAACGCTCTGGCGCTGGAGGTGGCCCGGCTTGTGGCCCTCCAGCAG
                         MX9 INT                                                         >

2710      2720      2730      2740      2750      2760      2770      2780      2790
CAAAGTGCGACGCCGCCATCGTCCGGCCGCACTTTCGGCGCGGTGGCGGATGACTGGCTCATCACTGAGGCCAAGCGCCTCGTGTGCCCC
                          MX9 INT                                                        >

2800      2810      2820      2830      2840      2850      2860      2870      2880
```

```
GACAATGAGCGCCGCCATCTTCGCCATATGGAGGCGCTCTGGGGCATGACGGATGTGGAGCTCACGCCGCGCGTCGTGAAGGCGCACCTG
                                  MX9 INT                                                   >
      2890      2900      2910      2920      2930      2940      2950      2960      2970
GCGGGACTTCTCAAGCCAGAGGGGCCGCTGAGCGCAGCCACCGTCAATAAGGTGCGCTCAGCCGGCAAGCGCATCATCAAGGCGGCGCAA
                                  MX9 INT                                                   >
      2980      2990      3000      3010      3020      3030      3040      3050      3060
ATCAACGGCGAGTGGGGCCCGGTGAATCCTTTCGGCGTGCTCGACCGCGAAAAAGAGGCGAAGGCCGAGCGCCTCACGCTGACGGCAGCG
                                  MX9 INT                                                   >
      3070      3080      3090      3100      3110      3120      3130      3140      3150
GAGTGCCGGGCGGTGCTCCCGCACTTCCGCGCGGACCGGCGCCGCGAGTTTCTCTTCCAGGTCTTTCTGGGGCCACGCCCCGGCGAAGAG
                                  MX9 INT                                                   >
      3160      3170      3180      3190      3200      3210      3220      3230      3240
AAGGCGCTCCTCAAGGAAGATGTGGACGTCGAGGCGCGCACCGTCATTTTCCGGCGCAGCAATGGACGAGACACGACAAAGACGGGACGC
                                  MX9 INT                                                   >
      3250      3260      3270      3280      3290      3300      3310      3320      3330
GAGCGTCGCGTGCCGGTGCCGGATGAGTTGTGGCCCGTGCTCCTCGATGCGATGCAGGCCAGTCCGTCTGACCTCGTTTTCCCGAACGCG
                                  MX9 INT                                                   >
      3340      3350      3360      3370      3380      3390      3400      3410      3420
AAGGGTGAGAGGCAGCGCGCAGACACGAAGATGACGCGCGTGCTGCGCACTGCGCTATCCGCGGCTGGTGTCGTGGTGGGCTGGGATTAC
                                  MX9 INT                                                   >
      3430      3440      3450      3460      3470      3480      3490      3500      3510
ATCTGCCGCACGCAGGGCTGCGGCTACCGAGATGTGCAGTCTGGTGGCGCGCGCCAGGAGCGTCGGTGCCCCGCCTGCGACAAGCGCATG
                                  MX9 INT                                                   >
      3520      3530      3540      3550      3560      3570      3580      3590      3600
TGGGCCAGTGGTCGCCCCAAACCCGCCGTCTGGTACGGGCTCCGTCACACCGCGGCGACACTGCACAGGAAGGCGGGCTGCGACCCGCTC
                                  MX9 INT                                                   >
      3610      3620      3630      3640      3650      3660      3670      3680      3690
GTCATCAAGCTCGTGCTGGGGCATGCGGCTGTCGACACCACGGACGACGTGTACACGCACCTCGACGAGGACTACTGCCGCGCCGAACTT
                                  MX9 INT                                                   >
      3700      3710      3720      3730      3740      3750      3760      3770      3780
AACAAGTTGTCGCTGAAGGCCCCGCCGCCACCACCTACTCACCAGGGAGGAAGTGACGGCGGCCCTGACTCAGGACGCAACACCTACGGT
                                  MX9 INT                                                   >
      3790      3800      3810      3820      3830      3840      3850      3860      3870
GAAGGAGGCACCATGCACGGATTGGGAGATTTGCAGCATCACCGGGCGAGAGCTTGGGAAGCTCGTGCTCTACCAACTGAGCTACCACCG
                                  MX9 INT                                                   >
                                                            MX9 ATTP                    >
      3880      3890      3900      3910      3920      3930      3940      3950      3960
CGGAACTTGGCCGGGGGTATACCGGCGCCGCTGCTGAGCGTCAAGGACGTTGCGGCTTCACTCTCAGTGAGCACGGCGAAGGTGTACCAG
                                  MX9 INT                                                   >
      3970      3980      3990      4000      4010      4020      4030      4040      4050
CTCCTCGCCGCCGGCGTCCTGCCTACCGTGTGGGTGGGCCAGTCGCGCCGCGTCAAGCGTGAGGACCTGGACGCCTACATCGCCCGCGCG
                                  MX9 INT                                                   >
      4060      4070      4080      4090      4100      4110      4120      4130      4140
ACGGCCACCGGCGGGAAGCGGGGTGGCAAATGAGCCGCTGCCCTGAGCCAATTGGGATCCTGCAGGAATTGCCAAGCTGTCACCATCCTG
               MX9 INT            >
      4150      4160      4170      4180      4190      4200      4210      4220      4230
TCGGCTGTGGCACAGGCTGAACGCCGGAGGATCCTAGAGCGCACGAATGAGGGCCGACAGGAAGCAAAGCTGAAAGGAATCAAATTTGGC
```

```
       4240      4250      4260      4270      4280      4290      4300      4310      4320
CGCAGGCGTACCGTGGACAGGAACGTCGTGCTGACGCTTCATCAGAAGGGCACTGGTGCAACGGAAATTGCTCATCAGCTCAGTATTGCC 4330      4340      4350      4360      4370      4380      4390      4400      4410
CGCTCCACGGTTTATAAAATTCTTGAAGACGAAAGGGCCTCGTGATACGCCTATTTTTATAGGTTAATGTCATGATAATAATGGTTTCTT 4420      4430      4440      4450      4460      4470      4480      4490      4500
AGACGTCAGGTGGCACTTTTCGGGGAAATGTGCGCGGAACCCCTATTTGTTTATTTTTCTAAATACATTCAAATATGTATCCGCTCATGA 4510      4520
GACAATAACCCTGATAAATGCTTC
```

BIOSYNTHETIC GENE CLUSTER FOR AMBRUTICINS AND THE ENCODED PROTEINS

CROSS-REFERENCE TO RELATED APPLICATIONS

This application claims benefit under 35 U.S.C. § 119 to U.S. provisional application Ser. Nos. 60/551,103, filed Mar. 8, 2004, and 60/568,290, filed May 4, 2004, the entire contents of which are incorporated herein by reference.

BACKGROUND OF THE INVENTION

1. Field of the Invention

This invention relates to nucleic acid encoding polypeptides capable of synthesizing compounds having anti-fungal activity, methods for their preparation, and methods for their use.

2. Description of Related Art

Polyketides are complex natural products that are produced by microorganisms such as fungi and mycelial bacteria. There are about 10,000 known polyketides, from which numerous pharmaceutical products in many therapeutic areas have been derived, including: adriamycin, epothilone, erythromycin, mevacor, rapamycin, tacrolimus, tetracycline, rapamycin, and many others. However, polyketides are made in very small amounts in microorganisms and are difficult to make or modify chemically. For this and other reasons, biosynthetic methods are preferred for production of therapeutically active polyketides. See PCT publication Nos. WO 93/13663; WO 95/08548; WO 96/40968; WO 97/02358; and WO 98/27203; U.S. Pat. Nos. 4,874,748; 5,063,155; 5,098,837; 5,149,639; 5,672,491; 5,712,146 and 6,410,301; Fu et al. (1994), *Biochemistry* 33:9321-26; McDaniel et al. (1993) *Science* 262: 1546-1550; Kao et al. (1994) *Science*, 265:509-12, and Rohr (1995) *Angew. Chem. Int. Ed. Engl.* 34: 881-88, each of which is incorporated herein by reference.

Biosynthesis of polyketides may be accomplished by heterologous expression of Type I or modular polyketide synthase enzymes (PKSs). Type I PKSs are large multifunctional protein complexes, the protein components of which are encoded by multiple open reading frames (ORF) of PKS gene clusters. Each ORF of a Type I PKS gene cluster can encode one, two, or more modules of ketosynthase activity. Each module activates and incorporates a two-carbon (ketide) unit into the polyketide backbone. Each module also contains multiple ketide-modifying enzymatic activities, or domains. In classical Type I PKSs, the number and order of modules, and the types of ketide-modifying domains within each module, determine the structure of the resulting product. Recently, variants of Type I PKSs have been found in which single modules may be used in an iterative fashion to add more than one two-carbon unit to the growing polyketide chain (see, for example, Müller (2004) *Chem. Biol.* 11(1):4-6). Polyketide synthesis may also involve the activity of nonribosomal peptide synthetases (NRPSs) to catalyze incorporation of an amino acid-derived building block into the polyketide, as well as post-synthesis modification, or tailoring enzymes. The modification enzymes modify the polyketide by oxidation or reduction, addition of carbohydrate groups or methyl groups, or other modifications.

In PKS polypeptides, the regions that encode enzymatic activities (domains) are separated by linker regions. These regions collectively can be considered to define boundaries of the various domains. Generally, this organization permits PKS domains of different or identical substrate specificities to be substituted (usually at the level of encoding DNA) from other PKSs by various available methodologies. Using this method, new polyketide synthases (which produce novel polyketides) can be produced. It will be recognized from the foregoing that genetic manipulation of PKS genes and heterologous expression of PKSs can be used for the efficient production of known polyketides, and for production of novel polyketides structurally related to, but distinct from, known polyketides (see references above, and Hutchinson (1998) *Curr. Opin. Microbiol.* 1:319-29; Carreras and Santi (1998) *Curr. Opin. Biotech.* 9:403-11; and U.S. Pat. Nos. 5,712,146 and 5,672,491, each of which is incorporated herein by reference).

One valuable class of polyketides includes the ambruticins and their analogs (FIG. 1), produced by the myxobacterium *Polyangium cellulosum* (also known as *Sorangium cellulosum*) var. *fulvum*, deposited as ATCC 25532. Ambruticin S (also known as "Acid S" or "W7783") was described in U.S. Pat. Nos. 3,651,216 and 3,804,948. Ambruticins VS1, VS3, and VS5 and a fermentative process for producing them using *Sorangium cellulosum* So ce10, deposited as DSM 5386, are disclosed in PCT publication WO91/00860. The ambruticins are anti-fungal agents. It is believed that the ambruticins kill fungi through interference with osmoregulation (Knauth and Reichenbach (2000) *J. Antibiotics* 53:1182-1190).

Given the promise of ambruticins in the treatment of fungal infections, there exists an unmet need for a production system that can provide large quantities of ambruticins. The present invention meets this need by providing the biosynthetic genes responsible for the production of ambruticins and providing for their expression in heterologous hosts.

BRIEF SUMMARY OF THE INVENTION

The present invention provides recombinant nucleic acids encoding polyketide synthases and polyketide modification enzymes. The recombinant nucleic acids of the invention are useful in the production of polyketides, including but not limited to ambruticins and ambruticin analogs and derivatives in recombinant host cells. The biosynthesis of ambruticin is performed by a modular PKS together with polyketide modification enzymes. The ambruticin synthase is made up of several proteins, each having one or more modules. Each module has one or more domains with specific synthetic functions.

The present invention also provides domains and modules of the ambruticin PKS and corresponding nucleic acid sequences encoding them and/or parts thereof. Such compounds are useful in the production of hybrid PKS enzymes and the recombinant genes that encode them.

The present invention also provides modifying genes of the ambruticin biosynthetic gene cluster, including but not limited to isolated and recombinant forms and forms incorporated into a vector or the chromosomal DNA of a host cell.

The present invention also provides recombinant host cells that contain the nucleic acids of the invention. In one embodiment, the host cell provided by the invention is a *Streptomyces* host cell that produces an ambruticin modification enzyme and/or a domain, module, or protein of the ambruticin PKS. Methods for the genetic manipulation of *Streptomyces* are described in Kieser et al, "Practical *Streptomyces* Genetics," The John Innes Foundation, Norwich (2000), which is incorporated herein by reference in its entirety. In other embodiments, the host cells provided by the invention are eubacterial cells such as *E. coli*, yeast cells such as *Saccharomyces cerevisiae*, or myxobacterial cells such as *Myxococcus xanthus*.

Accordingly, there is provided a recombinant PKS wherein at least 10, 15, 20, or more consecutive amino acids in one or more domains of one or more modules thereof are derived from one or more domains of one or more modules of the ambruticin polyketide synthase. Preferably at least an entire domain of a module of the ambruticin synthase is included. Representative ambruticin PKS domains useful in this aspect of the invention include, for example, β-ketoreductase (KR), dehydratase (DH), enoylreductase (ER), acyltransferase (AT), acyl carrier protein (ACP) and β-ketoacylsynthase (KS) domains. In one embodiment of the invention, the PKS is assembled from polypeptides encoded by DNA molecules that comprise coding sequences for PKS domains, wherein at least one encoded domain corresponds to a domain of ambruticin PKS. In such DNA molecules, the coding sequences are operably linked to control sequences so that expression therefrom in host cells is effective. In this manner, ambruticin PKS coding sequences or modules and/or domains can be made to encode PKS to biosynthesize compounds having antibiotic or other useful bioactivity other than ambruticin.

These and other aspects of the present invention are described in more detail in the Detailed Description of the Invention, below.

BRIEF DESCRIPTION OF THE DRAWINGS

FIG. 3 shows the nucleotide sequence of the ambruticin biosynthetic gene cluster (SEQ ID NO:1), and the sequence of the deduced translated proteins of the ambA, ambB, ambC, ambD, ambE, ambF, ambG, ambH, ambI, ambJ, ambM, ambN, ambO, ambP, ambQ, ambR, and ambS genes (SEQ ID NOS:3-19, respectively). Also shown is the sequence of the deduced translated proteins of ORFs 9-11 (SEQ ID NOS:28-30, respectively).

FIG. 4 shows the nucleotide sequence of the region upstream of the ambruticin biosynthetic gene cluster (SEQ ID NO:2), and the sequence of the deduced translated proteins of ORFs 1-8 (SEQ ID NOS:20-27, respectively).

FIG. 5 shows the nucleotide sequence of plasmid pKOS375-151.1 (SEQ ID NO:61). Example 3 describes the construction of plasmid pKOS375-151.1.

DETAILED DESCRIPTION OF THE INVENTION

Figure 1:
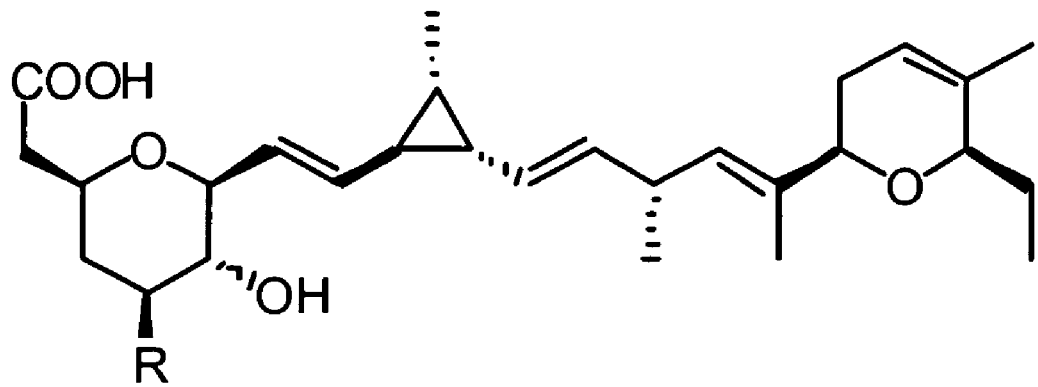
FIG. 1 shows various members of the ambruticin family of natural polyketides.

The present invention provides recombinant materials for the production of polyketides. In one aspect, the invention provides recombinant nucleic acids encoding at least one domain of a polyketide synthase required for ambruticin biosynthesis. Methods and host cells for using these genes to produce a polyketide in recombinant host cells are also provided.

The nucleotide sequences encoding ambruticin PKS domains, modules and polypeptides of the present invention were isolated from *Sorangium cellulosum* So ce10(hereafter "So ce10") as described in Example 1. Given the valuable properties of ambruticin and its derivatives and analogs, means to produce useful quantities of these molecules in a highly pure form are of great potential value. The compounds produced may be used as antitumor agents or for other therapeutic uses, and/or intermediates for further enzymatic or chemical modification. The nucleotide sequences of the ambruticin biosynthetic gene cluster encoding domains, modules and polypeptides of ambruticin synthase, and modifying enzymes, and other polypeptides can be used, for example, to make both known and novel polyketides.

The present invention provides isolated or recombinant nucleic acid comprising a nucleotide sequence that encodes at least one polypeptide involved in or required for the biosynthesis of ambruticin. Preferably, the complement of the nucleotide sequence hybridizes, under highly stringent conditions, to a nucleic acid encoding at least one domain or module as disclosed in Table 1. In one aspect, the nucleic acid encodes an amino acid sequence selected from the group consisting of SEQ ID NOS:3-19, or comprises a nucleotide sequence selected from the group consisting of SEQ ID NOS:33-49. Preferably, the nucleic acid comprises the nucleotide sequence of SEQ ID NOS:33-49 or SEQ ID NO:1.

The invention also provides for a vector comprising the purified or recombinant nucleic acid, wherein said polypeptide is operatively linked to a promoter. The invention further provides for a host cell comprising the vector, wherein said polypeptide is capable of expression in said host cell. Preferably, the host cell is a *Streptomyces* spp., *E. coli*, yeast, or myxobacteria.

The invention also provides for a method of producing an ambruticin or ambruticin analog, said method comprising culturing a cell comprising the vector under conditions under which said cell produces said ambruticin or ambruticin analog, wherein said polypeptide is capable of expression in said cell.

The invention further provides for a purified or recombinant polypeptide involved in or required for the biosynthesis of ambruticin comprising a domain as listed in Table 1. Preferably, the purified or recombinant polypeptide comprises a module as listed in Table 1. In one aspect, the purified or recombinant polypeptide comprises the amino acid sequence of one selected from SEQ ID NOs:3-19.

In one aspect of the invention, purified and isolated DNA molecules are provided that comprise one or more coding sequences for one or more domains or modules of ambruticin synthase. Examples of such encoded domains include ambruticin synthase KR, DH, ER, AT, ACP, and KS domains. Domains will herein be referred to according to the module in which they are found as "domain(module)"; for example, the module 1 AT domain will be referred to as "AT(1)." In one aspect, the invention provides DNA molecules in which sequences encoding one or more polypeptides of ambruticin synthase are operably linked to expression control sequences that are effective in suitable host cells to express said polypeptides and produce ambruticin, its analogs or derivatives, or novel polyketides.

Figures 2A, 2B:
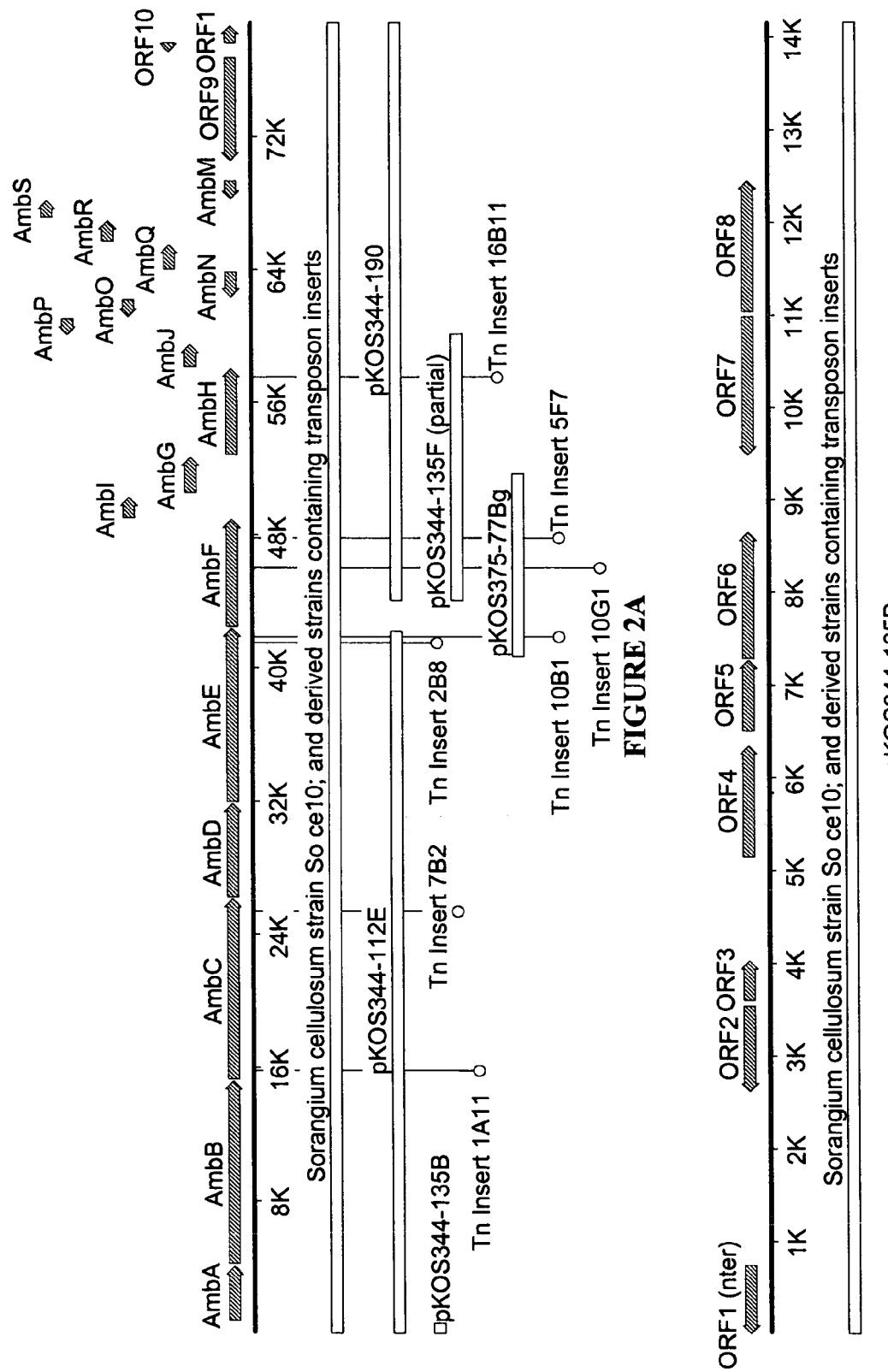
FIG. 2A shows the organization of the portion of the ambruticin biosynthetic cluster as deduced from SEQ ID NO:1.
FIG. 2B shows the organization of the portion of the upstream region of the ambruticin biosynthetic cluster as deduced from SEQ ID NO:2. The open bars indicate the cosmid inserts, the hatched arrows indicate ORFs, and the open circles indicate transposon integration sites that result in disruption of ambruticin biosynthesis or export.

The sequence of the ambruticin gene cluster were assembled from sequences deduced from cosmids 10K10B3 (pKOS344-112E) and 10T5F7 (pKOS344-135F), and plasmid pKOS375-77Bg, and is shown as SEQ ID NO:1 in FIG. 3. The organization of the ambruticin gene cluster is shown in FIG. 2A. This gene cluster is found to comprise at least seventeen open reading frames (ORFs), named ambA, ambB, ambC, ambD, ambE, ambF, ambG, ambH, ambI, ambJ, ambM, ambN, ambO, ambP, ambQ, ambR, and ambS. The ambA gene encodes the loading module of the ambruticin PKS, also referred to herein as "module 0," and comprises KS and AT domains. The KS(0) domain is apparently inactive as a ketosynthase, having the active site cysteine residue replaced with a serine, and is thought to act as a decarboxylase to prime the PKS with a propionate group derived from methylmalonate. The AT(0) domain comprises the signature amino acid sequences (GHSQ and YASH (SEQ ID NOs:31 and 32, respectively)) of a methylmalonyl-specific AT domain. The ambB gene encodes modules 1 and 2 of the ambruticin PKS, the ambC gene encodes modules 3 and 4, the ambD gene encodes module 5, and the ambE gene encodes modules 6 and 7, the ambF gene encodes an ACP domain and module 8, together with a thioesterase domain and an aminotransferase domain. Unlike in canonical modular PKS, the ACP domain of the ambF gene is located on a different polypeptide from the remainder of the domains of module 7. Further, KS(8) is followed by a pair of ACP domains, labeled ACP(8a) and ACP(8b), and there is no clear AT domain in module 8. The ambH gene encodes module 9 and a terminal thioesterase (TE) domain. The ambG gene encodes a didomain protein having a CoA-ligase and an ACP domain, while the ambJ gene encodes a sequence with strong homology to a family including known and putative FAD-dependent monooxygenases, and is likely to be involved in oxidation of the polyketide. The ambJ gene encodes a sequence with strong homology to those of MonCI and NanO, predicted to be responsible for the formation of epoxide functionalities during the biosynthesis of monensin and nanchangmycin respectively, and may play a similar role in the biosynthesis of ambruticin. The ambP gene encodes a dioxygenase. The ambO gene encodes a flavin monooxygenase. The ambN gene encodes an aldehyde dehydrogenase. The ambQ gene encodes a desaturase. The ambR gene encodes a glutamate semialdehyde aminotransferase. The ambS gene encodes a N-methyltransferase. The ambM gene encodes a C-methyltransferase. The function of each of the amb genes in ambruticin biosynthesis is shown in FIG. 6. The downstream region of the ambruticin gene cluster resides ORF9-11. ORF9 (amb7) encodes a histidine kinase response regulator containing multiple domains. ORF10 (amb8) encodes a transcription regulator. ORF11 (amb9) encodes a NADH:flavin oxidoreductase.

Table 1 provides a description of the genes, modules, and domains/activities of the ambruticin proteins.

TABLE 1

Genes, modules, and domains/activities of the ambruticin PKS determined from the nucleotide sequence given in SEQ ID NO: 1.

| Gene | Module | Domain/Activity | boundaries |
|---|---|---|---|
| ambA | | | 765-4145 |
| | module 0 | | 765-4145 |
| | | KS(0) | 1026-2300 |
| | | AT(0) | 2628-3674 |
| | | ACP(0) | 3744-3998 |
| ambB | | | 4202-15271 |
| | module 1 | | 4301-8695 |
| | | KS(1) | 4301-5575 |
| | | AT(1) | 5900-6952 |
| | | KR(1) | 7553-8404 |
| | | ACP(1) | 8438-8695 |
| | module 2 | | 8756-15013 |
| | | KS(2) | 8756-10033 |
| | | AT(2) | 10358-11425 |

TABLE 1-continued

Genes, modules, and domains/activities of the ambruticin PKS determined from the nucleotide sequence given in SEQ ID NO: 1.

| Gene | Module | Domain/Activity | boundaries |
|---|---|---|---|
| | | DH(2) | 11459-12034 |
| | | ER(2) | 13019-13894 |
| | | KR(2) | 13910-14707 |
| | | ACP(2) | 14756-15013 |
| ambC | | | 15268-26235 |
| | module 3 | | 15367-20637 |
| | | KS(3) | 15367-16644 |
| | | AT(3) | 16969-18021 |
| | | DH(3) | 18055-18606 |
| | | KR(3) | 19534-20358 |
| | | ACP(3) | 20380-20637 |
| | module 4 | | 20704-25989 |
| | | KS(4) | 20704-21981 |
| | | AT(4) | 22306-23373 |
| | | DH(4) | 23407-23967 |
| | | KR(4) | 24886-25710 |
| | | ACP(4) | 25732-25989 |
| ambD | | | 26232-31910 |
| | module 5 | | 26331-31652 |
| | | KS(5) | 26331-27608 |
| | | AT(5) | 27960-29027 |
| | | DH(5) | 29061-29657 |
| | | KR(5) | 30528-31361 |
| | | ACP(5) | 31395-31652 |
| ambE | | | 31907-42430 |
| | module 6 | | 32009-37255 |
| | | KS(6) | 32009-33286 |
| | | AT(6) | 33599-34651 |
| | | DH(6) | 34685-35236 |
| | | KR(6) | 36143-36955 |
| | | ACP(6) | 36998-37255 |
| | module 7a | | 37325-42379 |
| | | KS(7) | 37325-38593 |
| | | AT(7) | 38921-39985 |
| | | DH(7) | 40055-40531 |
| | | KR(7) | 41660-42379 |
| ambF | | | 42427-49020 |
| | | ACP | 42427-42666 |
| | module 8 | | 43054-45972 |
| | | KS(8) | 43054-44322 |
| | | ACP(8a) | 45193-45447 |
| | | ACP(8b) | 45766-45972 |
| | TE(a) | | 46102-46785 |
| | AmTr | | 47053-48753 |
| ambG | | | 50524-52734 |
| | | CoA ligase | 50524-52248 |
| | | ACP | 52354-52599 |
| ambH | | | 52776-58076 |
| | module 9 | | 52872-57299 |
| | | KS(9) | 52872-54125 |
| | | AT(9) | 54447-55496 |
| | | KR(9) | 56253-56942 |
| | | ACP(9) | 57033-57299 |
| | TE(b) | | 57300-58073 |
| ambI | | FAD oxygenase | 49017-50336 |
| ambJ | | Epoxidase | 58073-59494 |
| ambP | | Dioxygenase | 60013-61083 |
| ambO | | Flavin monooxygenase | 61086-62216 |
| ambN | | aldehyde dehydrogenase | 62288-63916 |
| ambQ | | Desaturase | 63946-65550 |
| ambR | | glutamate semialdehyde aminotransferase | 65637-66977 |
| ambS | | N-methyltransferase | 67076-68155 |
| ambM | | C-methyltransferase | 68191-69378 |
| ORF9 | | multidomain 2-component sensor/regulator | 70491-76754 |
| ORF10 | | transcriptional regulator | 76992-77699 |
| ORF11 | | NADH: flavin oxidoreductase | 77581-78699 |

The sequence of the upstream region of the ambruticin gene cluster was assembled from sequences deduced from cosmids 10K10B3 (pKOS344-112E) and 1-16 (pKOS344-135B), and is shown as SEQ ID NO:2 in FIG. 4. The organization of the upstream region of the ambruticin gene cluster is shown in FIG. 2B. This gene cluster is found to comprise at least eight ORFs. ORF1 encodes a homolog of *E. coli* AtoC homolog (43% identity), and is a response regulator subunit of a His/Asp kinase regulatory pathway (Grebe and Stock (1999) *Adv. Microb. Physiol.* 41:139-227). ORF2 (amb1) encodes a homolog of the LysR family of transcription regulators (Henikoff et al. (1988) *Proc. Natl. Acad. Sci. USA* 85(18):6602-6606). ORF3 encodes a homolog to ORF3 of the jerangolid gene cluster and is a partial homolog of SAV3316 from *Streptomyces avermitilis*. ORF4 (amb2) encodes a cytochrome P540 hydroxylase. ORF5 (amb3) encodes a two-component sensor, HisK subunit. ORF 6 (amb4) encodes a response regulator subunit in a His/Asp kinase regulatory pathway. ORF5 is transcriptionally coupled to ORF6. ORF7 (amb5) encodes a signal transduction histidine kinase subunit. ORF8 (amb6) encodes a conserved hypothetical protein of the YehP family.

Table 2 provides a description of the genes of the upstream region of the ambruticin proteins.

TABLE 2

Genes in the region upstream of the ambruticin PKS determined from the nucleotide sequence given in SEQ ID NO: 2.

| Gene | Domain/Activity | boundaries |
| --- | --- | --- |
| ORF1 | response regulator subunit in His/Asp kinase | 1-765 |
| ORF2 (amb1) | transcriptional regulator | 2607-3557 |
| ORF3 | homolog of ORF3 of jerangolid gene cluster | 3595-4041 |
| ORF4 (amb2) | cytochrome P540 hydroxylase | 5141-6361 |
| ORF5 (amb3) | two-component sensor, HisK subunit | 6503-7282 |
| ORF6 (amb4) | response regulator subunit in His/Asp kinase | 7279-8664 |
| ORF7 (amb5) | signal transduction histidine kinase | 9474-11000 |
| ORF8 (amb6) | YehP family | 11030-12463 |

The invention provides for nucleic acids comprising the ORFs and the polypeptides encoded by the ORFs downstream and upstream of the ambruticin gene cluster (ORF1-11).

The involvement of the genes and proteins of the invention in the biosynthesis of ambruticins is clear based upon the results of transposon mutagenesis. Transposon inserted in each of the transposon integration sites indicated in FIG. 2A results in disruption of ambruticin biosynthesis or export.

In one aspect, the invention provides an isolated or recombinant DNA molecule comprising a nucleotide sequence that encodes at least one domain, alternatively at least one module, alternatively at least one polypeptide, involved in the biosynthesis of an ambruticin.

In one aspect, the invention provides an isolated or recombinant DNA molecule comprising a sequence identical or substantially similar to SEQ ID NOS:33-49 or its complement. Hereinafter, each reference to a nucleic acid sequence is also intended to refer to and include the complementary sequence, unless otherwise stated or apparent from context. In an embodiment the subsequence comprises a sequence encoding a complete ambruticin PKS domain, module or polypeptide.

In one aspect, the present invention provides an isolated or recombinant DNA molecule comprising a nucleotide sequence that encodes an ORF, module or domain having an amino acid sequence identical or substantially similar to an ORF, module or domain encoded by SEQ ID NOS:33-49. Generally, a polypeptide, module or domain having a sequence substantially similar to a reference sequence has substantially the same activity as the reference protein, module or domain (e.g., when integrated into an appropriate PKS framework using methods known in the art). In certain embodiments, one or more activities of a substantially similar polypeptide, module or domain are modified or inactivated as described below.

In one aspect, the invention provides an isolated or recombinant DNA molecule comprising a nucleotide sequence that encodes at least one polypeptide, module or domain encoded by SEQ ID NOS:33-49, e.g., a polypeptide, module or domain involved in the biosynthesis of an ambruticin, wherein said nucleotide sequence comprises at least 10, 20, 25, 30, 35, 40, 45, or 50 contiguous base pairs identical to a sequence of SEQ ID NOS:33-49. In one aspect, the invention provides an isolated or recombinant DNA molecule comprising a nucleotide sequence that encodes at least one polypeptide, module or domain encoded by SEQ ID NOS:33-49, e.g., a polypeptide, module or domain involved in the biosynthesis of a ambruticin, wherein said polypeptide, module or domain comprises at least 10, 15, 20, 30, or 40 contiguous residues of a corresponding polypeptide, module or domain comprising a sequence of SEQ ID NOS:33-49.

It will be understood that SEQ ID NO:1 was determined using the inserts of cosmids 10K10B3 (pKOS344-112E), 10T5F7 (pKOS344-135F), and plasmid pKOS375-77Bg. Accordingly, the invention provides an isolated or recombinant DNA molecule comprising a sequence identical or substantially similar to an ORF encoding sequence of the inserts of cosmids 10K10B3 (pKOS344-112E), 10T5F7 (pKOS344-135F), and plasmid pKOS375-77Bg.

It will be understood that SEQ ID NO:2 was determined using the insert of plasmid pKOS344-135B. Accordingly, the invention provides an isolated or recombinant DNA molecule comprising a sequence identical or substantially similar to an ORF encoding sequence of the insert of plasmid pKOS344-135B.

In another aspect, the invention provides the proteins encoded by the genes of SEQ ID NOS:1 and 2 in both purified and recombinant form, as well as proteins having amino acid sequences substantial identity to the proteins encoded by the genes of SEQ ID NOS:1 and 2. The amino acid sequences of these genes are provided in FIGS. 3 and 4, respectively.

Those of skill will recognize that, due to the degeneracy of the genetic code, a large number of DNA sequences encode the amino acid sequences of the domains, modules, and proteins of the ambruticin PKS, the enzymes involved in ambruticin modification and other polypeptides encoded by the genes of the ambruticin biosynthetic gene cluster. The present invention contemplates all such DNAs. For example, it may be advantageous to optimize sequence to account for the codon preference of a host organism. The invention also contemplates naturally occurring genes encoding the ambruticin PKS that are polymorphic or other variants.

As used herein, the terms "substantial identity," "substantial sequence identity," or "substantial similarity" in the context of nucleic acids, refers to a measure of sequence similarity between two polynucleotides. Substantial sequence identity can be determined by hybridization under stringent conditions, by direct comparison, or other means. For example, two polynucleotides can be identified as having substantial sequence identity if they are capable of specifically hybridizing to each other under stringent hybridization conditions. Other degrees of sequence identity (e.g., less than "substantial") can be characterized by hybridization under different conditions of stringency. "Stringent hybridization conditions" refers to conditions in a range from about 5° C. to about 20° C. or 25° C. below the melting temperature (Tm) of the target sequence and a probe with exact or nearly exact complimentarily to the target. As used herein, the melting temperature is the temperature at which a population of double-stranded nucleic acid molecules becomes half-dissociated into single strands. Methods for calculating the Tm of nucleic acids are well known in the art (see, e.g., Berger and Kimmel, 1987, *Methods In Enzymology*, Vol. 152: Guide To Molecular Cloning Techniques, San Diego: Academic Press, Inc. and Sambrook et al., 1989, Molecular Cloning: A Laboratory Manual, 2nd Ed., Vols. 1-3, Cold Spring Harbor Laboratory). Typically, stringent hybridization conditions for probes greater than 50 nucleotides are salt concentrations less than about 1.0 M sodium ion, typically about 0.01 to 1.0 M sodium ion at pH 7.0 to 8.3, and temperatures at least about 50° C., preferably at least about 60° C. As noted, stringent conditions may also be achieved with the addition of destabilizing agents such as formamide, in which case lower temperatures may be employed. Exemplary conditions include hybridization at 65° C. for 36 hours and washing 3 times at high stringency with 0.1×SSC and 0.5% SDS for 20 minuets at 65° C., or at 7% sodium dodecyl sulfate (SDS), 0.5 M NaPO$_4$ pH 7.0, 1 mM EDTA at 65° C.; wash with 2×SSC, 1% SDS, at 50° C.

Alternatively, substantial sequence identity can be described as a percentage identity between two nucleotide or amino acid sequences. Two nucleic acid sequences are considered substantially identical when they are at least about 70% identical, or at least about 80% identical, or at least about 90% identical, or at least about 95% or 98% identical. Two amino acid sequences are considered substantially identical when they are at least about 60%, more often at least about 70%, at least about 80%, or at least about 90% sequence identity to the reference sequence. Percentage sequence (nucleotide or amino acid) identity is typically calculated using art known means to determine the optimal alignment between two sequences and comparing the two sequences. Optimal alignment of sequences may be conducted using the local homology algorithm of Smith and Waterman (1981) *Adv. Appi. Math*. 2: 482, by the homology alignment algorithm of Needleman and Wunsch (1970) *J. Mol. Biol*. 48: 443, by the search for similarity method of Pearson and Lipman (1988) *Proc. Nati. Acad. Sci*. U.S.A. 85: 2444, by the BLAST™ (Basic Local Alignment Search Tool, National Library of Medicine) algorithm of Altschul (1990) *J. Mol. Biol*. 215: 403-410; and Shpaer (1996) *Genomics* 38: 179-191, or by the algorithm of Needleham et al. (1970) *J. Mol. Biol*. 48: 443-453; and Sankoff et al.m 1983, *Time Warps, String Edits, and Macromolecules, The Theory and Practice of Sequence Comparison*, Chapter One, Addison-Wesley, Reading, MA; generally by computerized implementations of these algorithms (GAP, BESTFIT, FASTA, and TFASTA in the Wisconsin Genetics Software Package, Genetics Computer Group, 575 Science Dr., Madison, Wis.; BLAST™ from the National Center for Biotechnology Information (www.ncbi.nlm.nih.gov/). In each case default parameters are used (for example the BLAST™ program uses as defaults a wordlength (W) of 11, the BLOSUM62 scoring matrix (see Henikoff (1992) *Proc. Nati. Acad. Sci*. USA 89: 10915-10919) alignments (B) of 50, expectation (E) of 10, M=5, N=−4, and a comparison of both strands).

The invention methods may be directed to the preparation of an individual polyketide. The polyketide may or may not be novel, but the method of preparation permits a more convenient or alternative method of preparing it. The resulting polyketides may be further modified to convert them to other useful compounds. Examples of chemical structures of that can be made using the materials and methods of the present invention include known analogs, such as those described in Kalesse and Christmann, 2002, "The Chemistry and Biology of the Ambruticin Family" *Synthesis* (8):981-1003 and the references cited therein, and novel molecules produced by modified or chimeric PKSs comprising a portion of the ambruticin PKS sequence, molecules produced by the action of polyketide modifying enzymes from the ambruticin PKS cluster on products of other PKSs, molecules produced by the action on products of the ambruticin PKS of polyketide modifying enzymes from other PKSs, and the like.

In one aspect, the cell is native to the ambruticin biosynthetic gene cluster. Alternatively, the cell is a host cell that is either native or heterologous to the ambruticin gene cluster, wherein the ambruticin biosynthetic genes are present, either on a vector or integrated into the chromosome of the cell. A cell native to the ambruticin biosynthetic gene cluster is a cell of the genus *Sorangium*. Preferably, the cell is a *Sorangium cellulosum*. More preferably, the cell is the So ce10, NCIMB12601 or So ce307 strain of *Sorangium cellulosum*. A host cell heterologous to the ambruticin gene cluster includes, but is not limited to, eubacterial cells such as *E. coli*, yeast cells such as *Saccharomyces cerevisiae*, or myxobacterial cells such as *Myxococcus xanthus*.

In one embodiment, one or more, or all the necessary, ambruticin biosynthetic genes are integrated into the chromosome of a myxobacteria, such as *Myxococcus xanthus*, and the myxobacteria, when cultured, expresses the ambruticin PKS and produces ambruticin. The ambruticins produced include, but are not limited to, ambruticin VS3, ambruticin VS4, and ambruticin VS5. In another aspect, the ambruticin biosynthetic genes are integrated into the chromosome of a myxobacteria, such as *Myxococcus xanthus*, using the necessary helper plasmids.

As noted, in one aspect the invention provides recombinant PKS wherein at least 10, 15, 20, or more consecutive amino acids in one or more domains of one or more modules thereof are derived from one or more domains of one or more modules of the ambruticin polyketide synthase. A polyketide synthase "derived from" a naturally occurring PKS contains the scaffolding encoded by all the portion employed of the naturally occurring synthase gene, contains at least two modules that are functional, and contains mutations, deletions, or replacements of one or more of the activities of these functional modules so that the nature of the resulting polyketide is altered. This definition applies both at the protein and genetic levels. Particular embodiments include those wherein a KS, AT, KR, DH, or ER has been deleted or replaced by a version of the activity from a different PKS or from another location within the same PKS, and derivatives where at least one noncondensation cycle enzymatic activity (KR, DH, or ER) has been deleted or wherein any of these activities has been added or mutated so as to change the ultimate polyketide synthesized. There are at least five degrees of freedom for constructing a polyketide synthase in terms of the polyketide that will be produced. See, U.S. Pat. No. 6,509,455 for a discussion.

As can be appreciated by those skilled in the art, polyketide biosynthesis can be manipulated to make a product other than the product of a naturally occurring PKS biosynthetic cluster. For example, AT domains can be altered or replaced to change specificity. The variable domains within a module can be deleted and or inactivated or replaced with other variable domains found in other modules of the same PKS or from another PKS. See e.g., Katz and McDaniel, *Med. Res. Rev.* 19: 543-558 (1999) and WO 98/49315. Similarly, entire modules can be deleted and/or replaced with other modules from the same PKS or another PKS. See e.g., Gokhale et al., *Science* 284: 482 (1999) and WO 00/47724 each of which are incorporated herein by reference. Protein subunits of different PKSs also can be mixed and matched to make compounds having the desired backbone and modifications. For example, subunits of 1 and 2 (encoding modules 1-4) of the pikromycin PKS were combined with the DEBS3 subunit to make a hybrid PKS product (see Tang et al., *Science*. 287: 640 (2001), WO 00/26349 and WO 99/6159).

Mutations can be introduced into PKS genes such that polypeptides with altered activity are encoded. Polypeptides with "altered activity" include those in which one or more domains are inactivated or deleted, or in which a mutation changes the substrate specificity of a domain, as well as other alterations in activity. Mutations include deletions to the entire or substantially the entire gene. Example 4 teaches the construction of a recombinant vector and a recombinant cell deleted for the ambS gene. It is well within the art for one to design similar deletions of one or mote other ambruticin biosynthetic genes. Mutations can be made to the native sequences using conventional techniques. The substrates for mutation can be an entire cluster of genes or only one or two of them; the substrate for mutation may also be portions of one or more of these genes. Techniques for mutation include preparing synthetic oligonucleotides including the mutations and inserting the mutated sequence into the gene encoding a PKS subunit using restriction endonuclease digestion. (See, e.g., Kunkel, T. A. *Proc. Natl. Acad. Sci.* USA (1985) 82:448; Geisselsoder et al. *BioTechniques* (1987) 5:786.) Alternatively, the mutations can be effected using a mismatched primer (generally 10-20 nucleotides in length) that hybridizes to the native nucleotide sequence (generally cDNA corresponding to the RNA sequence), at a temperature below the melting temperature of the mismatched duplex. The primer can be made specific by keeping primer length and base composition within relatively narrow limits and by keeping the mutant base centrally located. (See Zoller and Smith, *Methods in Enzymology* (1983) 100:468). Primer extension is effected using DNA polymerase. The product of the extension reaction is cloned, and those clones containing the mutated DNA are selected. Selection can be accomplished using the mutant primer as a hybridization probe. The technique is also applicable for generating multiple point mutations. (See, e.g., Dalbie-McFarland et al. *Proc. Natl. Acad. Sci.* USA (1982) 79:6409). PCR mutagenesis can also be used for effecting the desired mutations. Random mutagenesis of selected portions of the nucleotide sequences encoding enzymatic activities can be accomplished by several different techniques known in the art, e.g., by inserting an oligonucleotide linker randomly into a plasmid, by chemical mutagenesis, or by irradiation. In addition to providing mutated forms of regions encoding enzymatic activity, regions encoding corresponding activities from different PKS synthases or from different locations in the same PKS synthase can be recovered, for example, using PCR techniques with appropriate primers. By "corresponding" activity encoding regions is meant those regions encoding the same general type of activity—e.g., a ketoreductase activity in one location of a gene cluster would "correspond" to a ketoreductase-encoding activity in another location in the gene cluster or in a different gene cluster; similarly, a complete reductase cycle could be considered corresponding—e.g., KR/DH/ER could correspond to KR alone.

If replacement of a particular target region in a host polyketide synthase is to be made, this replacement can be conducted in vitro using suitable restriction enzymes or can be effected in vivo using recombinant techniques involving homologous sequences framing the replacement gene. One such system involving plasmids of differing temperature sensitivities is described in PCT application WO 96/40968. Another useful method for modifying a PKS gene (e.g., making domain substitutions or "swaps") is a RED/ET cloning procedure developed for constructing domain swaps or modifications in an expression plasmid without first introducing restriction sites. The method is related to ET cloning methods (see, Datansko and Wanner, 2000, *Proc. Natl. Acad. Sci.* USA 97, 6640-45; Muyrers et al., 2000, *Genetic Engineering* 22:77-98). The RED/ET cloning procedure is used to introduce a unique restriction site in the recipient plasmid at the location of the targeted domain. This restriction site is used to subsequently linearize the recipient plasmid in a subsequent ET cloning step to introduce the modification. This linearization step is necessary in the absence of a selectable marker, which cannot be used for domain substitutions. An advantage of using this method for PKS engineering is that restriction sites do not have to be introduced in the recipient plasmid in order to construct the swap, which makes it faster and more powerful because boundary junctions can be altered more easily.

In a further aspect, the invention provides methods for expressing chimeric or hybrid PKSs and products of such PKSs. For example, the invention provides (1) encoding DNA for a chimeric PKS that is substantially patterned on a non-ambruticin producing enzyme, but which includes one or more functional domains, modules or polypeptides of ambruticin PKS; and (2) encoding DNA for a chimeric PKS that is substantially patterned on the ambruticin PKS, but which includes one or more functional domains, modules, or polypeptides of another PKS or NRPS.

With respect to item (1) above, in one embodiment, the invention provides chimeric PKS enzymes in which the genes for a non-ambruticin PKS function as accepting genes, and one or more of the above-identified coding sequences for ambruticin domains or modules are inserted as replacements for one or more domains or modules of comparable function. Construction of chimeric molecules is most effectively achieved by construction of appropriate encoding polynucleotides. In making a chimeric molecule, it is not necessary to replace an entire domain or module accepting of the PKS with an entire domain or module of ambruticin PKS: subsequences of a PKS domain or module that correspond to a peptide subsequence in an accepting domain or module, or which otherwise provide useful function, may be used as replacements. Accordingly, appropriate encoding DNAs for construction of such chimeric PKS include those that encode at least 10, 15, 20 or more amino acids of a selected ambruticin domain or module.

Recombinant methods for manipulating modular PKS genes to make chimeric PKS enzymes are described in U.S. Pat. Nos. 5,672,491; 5,843,718; 5,830,750; and 5,712,146; and in PCT publication Nos. 98/49315 and 97/02358. A number of genetic engineering strategies have been used with DEBS to demonstrate that the structures of polyketides can be manipulated to produce novel natural products, primarily analogs of the erythromycins (see the patent publications referenced supra and Hutchinson, 1998*, Curr. Opin. Microbiol*. 1:319-329, and Baltz, 1998*, Trends Micro-* biol. 6:76-83). In one embodiment, the components of the chimeric PKS are arranged onto polypeptides having interpolypeptide linkers that direct the assembly of the polypeptides into the functional PKS protein, such that it is not required that the PKS have the same arrangement of modules in the polypeptides as observed in natural PKSs. Suitable interpolypeptide linkers to join polypeptides and intrapolypeptide linkers to join modules within a polypeptide are described in PCT publication WO 00/47724.

A partial list of sources of PKS sequences for use in making chimeric molecules, for illustration and not limitation, includes Avermectin (U.S. Pat. No. 5,252,474; MacNeil et al., 1993, Industrial Microorganisms: Basic and Applied Molecular Genetics, Baltz, Hegeman, & Skatrud, eds. (ASM), pp. 245-256; MacNeil et al., 1992, Gene 115: 119-25); Candicidin (FR0008) (Hu et al., *Mol. Microbiol.* 14: 163-72); Epothilone (U.S. Pat. No. 6,303,342); Erythromycin (WO 93/13663; U.S. Pat. No. 5,824,513; Donadio et al., 1991, *Science* 252:675-79; Cortes et al.,1990, *Nature* 348:176-8); FK-506 (Motamedi et al., 1998, *Eur. J. Biochem.* 256:528-34; Motamedi et al., 1997, *Eur. J. Biochem.* 244:74-80); FK-520 (U.S. Pat. No. 6,503,737; see also Nielsen et al., 1991, *Biochem.* 30:5789-96); Lovastatin (U.S. Pat. No. 5,744,350); Nemadectin (MacNeil et al., 1993, supra); Niddamycin (Kakavas et al., 1997, *J. Bacteriol.* 179:7515-22); Oleandomycin (Swan et al., 1994, *Mol. Gen. Genet.* 242:358-62; U.S. Pat. No. 6,388,099; Olano et al., 1998, *Mol. Gen. Genet.* 259:299-308); Platenolide (EP Pat. App. 791,656); Rapamycin (Schwecke et al., 1995, *Proc. Natl. Acad. Sci.* USA 92:7839-43); Aparicio et al., 1996, *Gene* 169:9-16); Rifamycin (August et al., 1998, *Chemistry & Biology*, 5: 69-79); Soraphen (U.S. Pat. No. 5,716,849; Schupp et al., 1995, *J. Bacteriology* 177: 3673-79); Spiramycin (U.S. Pat. No. 5,098,837); Tylosin (EP 0 791,655; Kuhstoss et al., 1996, Gene 183:231-36; U.S. Pat. No. 5,876,991). Additional suitable PKS coding sequences remain to be discovered and characterized, but will be available to those of skill (e.g., by reference to GenBank™ (Genetic Sequence Data Bank, U.S. Department of Health and Human Services).

The ambruticin PKS-encoding polynucleotides of the invention may also be used in the production of libraries of PKSs (i.e., modified and chimeric PKSs comprising at least a portion of the ambruticin PKS sequence. The invention provides libraries of polyketides by generating modifications in, or using a portion of, the ambruticin PKS so that the protein complexes produced by the cluster have altered activities in one or more respects, and thus produce polyketides other than the natural ambruticin product of the PKS. Novel polyketides may thus be prepared, or polyketides in general prepared more readily, using this method. By providing a large number of different genes or gene clusters derived from a naturally occurring PKS gene cluster, each of which has been modified in a different way from the native PKS cluster, an effectively combinatorial library of polyketides can be produced as a result of the multiple variations in these activities. Expression vectors containing nucleotide sequences encoding a variety of PKS systems for the production of different polyketides can be transformed into the appropriate host cells to construct a polyketide library. In one approach, a mixture of such vectors is transformed into the selected host cells and the resulting cells plated into individual colonies and selected for successful transformants. Each individual colony has the ability to produce a particular PKS synthase and ultimately a particular polyketide. A variety of strategies can be devised to obtain a multiplicity of colonies each containing a PKS gene cluster derived from the naturally occurring host gene cluster so that each colony in the library produces a different PKS and ultimately a different polyketide. The number of different polyketides that are produced by the library is typically at least four, more typically at least ten, and preferably at least 20, more preferably at least 50, reflecting similar numbers of different altered PKS gene-clusters and PKS gene products. The number of members in the library is arbitrarily chosen; however, the degrees of freedom outlined above with respect to the variation of starter, extender units, stereochemistry, oxidation state, and chain length is quite large. The polyketide producing colonies can be identified and isolated using known techniques and the produced polyketides further characterized. The polyketides produced by these colonies can be used collectively in a panel to represent a library or may be assessed individually for activity.

Colonies in the library are induced to produce the relevant synthases and thus to produce the relevant polyketides to obtain a library of candidate polyketides. The polyketides secreted into the media can be screened for binding to desired targets, such as receptors, signaling proteins, and the like. The supernatants per se can be used for screening, or partial or complete purification of the polyketides can first be effected. Typically, such screening methods involve detecting the binding of each member of the library to receptor or other target ligand. Binding can be detected either directly or through a competition assay. Means to screen such libraries for binding are well known in the art. Alternatively, individual polyketide members of the library can be tested against a desired target. In this event, screens wherein the biological response of the target is measured can be included.

As noted above, the DNA compounds of the invention can be expressed in host cells for production of proteins and of known and novel compounds. Preferred hosts include fungal systems such as yeast and procaryotic hosts, but single cell cultures of, for example, mammalian cells could also be used. A variety of methods for heterologous expression of PKS genes and host cells suitable for expression of these genes and production of polyketides are described, for example, in U.S. Pat. Nos. 5,843,718; 5,830,750 and 6,262,340; WO 01/31035, WO 01/27306, and WO 02/068613; and U.S. Patent Application Pub. Nos. 20020192767 and 20020045220.

Appropriate host cells for the expression of the hybrid PKS genes include those organisms capable of producing the needed precursors, such as malonyl-CoA, methylmalonyl-CoA, ethylmalonyl-CoA, and methoxymalonyl-ACP, and having phosphopantotheinylation systems capable of activating the ACP domains of modular PKSs. See, for example, U.S. Pat. No. 6,579,695. However, as disclosed in U.S. Pat. No. 6,033,883, a wide variety of hosts can be used, even though some hosts natively do not contain the appropriate post-translational mechanisms to activate the acyl carrier proteins of the synthases. Also see WO 97/13845 and WO 98/27203. The host cell may natively produce none, some, or all of the required polyketide precursors, and may be genetically engineered so as to produce the required polyketide precursors. Such hosts can be modified with the appropriate recombinant enzymes to effect these modifications. Suitable host cells can be heterologous to the nucleotide sequences encoding ambruticin PKS domains, modules or polypeptides, heterologous to the promoter operatively linked to the nucleotide sequences, or both. Suitable host cells include *Streptomyces, E. coli*, yeast, and other procaryotic hosts that use control sequences compatible with *Strep-*

*tomyces* spp. Examples of suitable hosts that either natively produce modular polyketides or have been engineered so as to produce modular polyketides include but are not limited to actinomyctes such as *Streptomyces lividans, Streptomyces coelicolor, Streptomyces venezuelae, Streptomyces fradiae, Streptomyces ambofaciens*, and *Saccharopolyspora erythraea*, eubacteria such as *E. coli*, myxobacteria such as *Myxococcus xanthus, Stigmatella, Cystobacter, Archangium*, and *Angiococcus*, and yeasts such as *Saccharomyces cerevisiae*.

In one embodiment, any native modular PKS genes in the host cell have been deleted to produce a "clean host," as described in U.S. Pat. No. 5,672,491, incorporated herein by reference.

In some embodiments, the host cell expresses, or is engineered to express, a polyketide "tailoring" or "modifying" enzyme. Once a PKS product is released, it is subject to post-PKS tailoring reactions. These reactions are important for biological activity and for the diversity seen among polyketides. Tailoring enzymes normally associated with polyketide biosynthesis include oxygenases, glycosyl- and methyl-transferases, acyltransferases, halogenases, cyclases, aminotransferases, and hydroxylases. In addition to biosynthetic accessory activities, secondary metabolite clusters often code for activities such as transport.

Tailoring enzymes for modification of a product of the ambruticin PKS, a non-ambruticin PKS, or a chimeric PKS, can be those normally associated with ambruticin biosynthesis or "heterologous" tailoring enzymes. Tailoring enzymes can be expressed in the organism in which they are naturally produced, or as recombinant proteins in heterologous hosts. In some cases, the structure produced by the heterologous or hybrid PKS may be modified with different efficiencies by post-PKS tailoring enzymes from different sources. In such cases, post-PKS tailoring enzymes can be recruited from other pathways to obtain the desired compound. For example, the tailoring enzymes of the ambruticin PKS gene cluster can be expressed heterologously to modify polyketides produced by non-ambruticin synthases or can be inactivated in the ambruticin producer.

Alternatively, the unmodified polyketide compounds can be produced in the recombinant host cell, and the desired modification (e.g., oxidation) steps carried out in vitro (e.g., using purified enzymes, isolated from native sources or recombinantly produced) or in vivo in a converting cell different from the host cell (e.g., by supplying the converting cell with the unmodified polyketide).

It will be apparent to one of skill in the art that a variety of recombinant vectors can be utilized in the practice of aspects of the invention. As used herein, "vector" refers to polynucleotide elements that are used to introduce recombinant nucleic acid into cells for either expression or replication. Selection and use of such vehicles is routine in the art. An "expression vector" includes vectors capable of expressing DNAs that are operatively linked with regulatory sequences, such as promoter regions. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or those that integrate into the host cell genome.

The vectors used to perform the various operations to replace the enzymatic activity in the host PKS genes or to support mutations in these regions of the host PKS genes may be chosen to contain control sequences operably linked to the resulting coding sequences in a manner that expression of the coding sequences may be effected in an appropriate host. Suitable control sequences include those that function in eucaryotic and procaryotic host cells. If the cloning vectors employed to obtain PKS genes encoding derived PKS lack control sequences for expression operably linked to the encoding nucleotide sequences, the nucleotide sequences are inserted into appropriate expression vectors. This can be done individually, or using a pool of isolated encoding nucleotide sequences, which can be inserted into host vectors, the resulting vectors transformed or transfected into host cells, and the resulting cells plated out into individual colonies. Suitable control sequences for single cell cultures of various types of organisms are well known in the art. Control systems for expression in yeast are widely available and are routinely used. Control elements include promoters, optionally containing operator sequences, and other elements depending on the nature of the host, such as ribosome binding sites. Particularly useful promoters for procaryotic hosts include those from PKS gene clusters that result in the production of polyketides as secondary metabolites, including those from Type I or aromatic (Type II) PKS gene clusters. Examples are act promoters, tcm promoters, spiramycin promoters, and the like. However, other bacterial promoters, such as those derived from sugar metabolizing enzymes, such as galactose, lactose (lac) and maltose, are also useful. Additional examples include promoters derived from biosynthetic enzymes such as for tryptophan (trp), the β-lactamase (bla), bacteriophage lambda PL, and T5. In addition, synthetic promoters, such as the tac promoter (U.S. Pat. No. 4,551,433), can be used.

As noted, particularly useful control sequences are those which themselves, or with suitable regulatory systems, activate expression during transition from growth to stationary phase in the vegetative mycelium. The system contained in the plasmid identified as pCK7, i.e., the actI/actIII promoter pair and the actII-ORF4 (an activator gene), is particularly preferred. Particularly preferred hosts are those that lack their own means for producing polyketides so that a cleaner result is obtained. Illustrative control sequences, vectors, and host cells of these types include the modified *S. coelicolor* CH999 and vectors described in PCT publication WO 96/40968 and similar strains of *S. lividans*. See U.S. Pat. Nos. 5,672,491; 5,830,750; 5,843,718; and 6,177,262, each of which is incorporated herein by reference.

Other regulatory sequences may also be desirable which allow for regulation of expression of the PKS sequences relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

Selectable markers can also be included in the recombinant expression vectors. A variety of markers are known which are useful in selecting for transformed cell lines and generally comprise a gene whose expression confers a selectable phenotype on transformed cells when the cells are grown in an appropriate selective medium. Such markers include, for example, genes that confer antibiotic resistance or sensitivity to the plasmid. Alternatively, several polyketides are naturally colored, and this characteristic provides a built-in marker for screening cells successfully transformed by the present constructs.

The various PKS nucleotide sequences, or a mixture of such sequences, can be cloned into one or more recombinant vectors as individual cassettes, with separate control elements or under the control of a single promoter. The PKS subunits or components can include flanking restriction sites to allow for the easy deletion and insertion of other PKS subunits so that hybrid or chimeric PKSs can be generated. The design of such restriction sites is known to those of skill in the art and can be accomplished using the techniques described above, such as site-directed mutagenesis and PCR. Methods for introducing the recombinant vectors of the present invention into suitable hosts are known to those of skill in the art and typically include the use of $CaCl_2$ or other agents, such as divalent cations, lipofection, DMSO, protoplast transformation, conjugation, and electroporation.

Thus, the present invention provides recombinant DNA molecules and vectors comprising those recombinant DNA molecules that encode at least a portion of the ambruticin PKS and that, when transformed into a host cell and the host cell is cultured under conditions that lead to the expression of said ambruticin PKS enzymes, results in the production of polyketides including but not limited to ambruticin and/or analogs or derivatives thereof in useful quantities. The present invention also provides recombinant host cells comprising those recombinant vectors.

Suitable culture conditions for production of polyketides using the cells of the invention will vary according to the host cell and the nature of the polyketide being produced, but will be know to those of skill in the art. See, for example, the examples below and WO 98/27203 and WO 01/83803. The polyketide product produced by host cells of the invention can be recovered (i.e., separated from the producing cells and at least partially purified) using routine techniques (e.g., extraction from broth followed by chromatography). The compositions, cells and methods of the invention may be directed to the preparation of an individual polyketide or a number of polyketides. The polyketide may or may not be novel, but the method of preparation permits a more convenient or alternative method of preparing it.

EXAMPLES

The following Examples are intended to illustrate, but not limit, the scope of the invention.

Example 1

Isolation of Transposon Insertions in So ce10

Transposons insertions in So ce10 were isolated by methods developed by Julien and Fehd (2003) *Appl. Environ. Microbiol.* 69:6299-6301; incorporated herein by reference). So ce10 was grown in 307 seed medium to an $OD_{600}$ of 1.0, and 10 ml of cells were centrifuged. 307 seed medium consists of (per liter): 9 gm casitone (Difco), 3 gm fructose, 0.5 gm $MgSO_4 \cdot 7H_2O$, 0.5 gm $CaCl_2 \cdot 2H_2O$, and 25 mL of 1 M HEPES, pH 7.6.

The So ce10 pellet was resuspended in ~200 µl of 307 seed medium and mixed with 10 ml of *E. coli* strain harboring plasmids pGZ119EH, pKOS111-47, and pKOS249-52B or pKOS375-57B1 that also had been pelleted. The mixed cells were spotted on an S42 plate and incubated at 30° C. overnight. The next day, the cells were resuspended in 10 ml 307 seed medium and aliquots were plated on S42 plates (Jaoua et al., 1992, *Plasmid* 28:157-165), incorporated herein in its entirety by reference) containing phleomycin (50 µg/ml) and kanamycin (50 µg/ml). The plates were incubated 7 days at 32° C.

To screen the transposon insertion strains for production of ambruticin, individual colonies were picked into 96 well microtiter plates containing S4s2 medium. After 7 days of incubation, the plates were overlaid with *Candida parapsilopsis* in YPD top agar. After two days of incubation at 30° C., the plates were examined for growth of the *Candida*. Those that showed growth indicate the lack of ambruticin production, and thus are candidates for transposon insertion in genes for biosynthesis or export of ambruticin.

Example 2

Isolation of Ambruticin PKS Cosmids

Genomic DNA was isolated from *Sorangium cellulosum* So ce10 using an established protocol (Jaoua, S., Neff, S., and Schupp, T. "Transfer of mobilizable plasmids to *Sorangium cellulosum* and evidence for their integration into the chromosome," 1992 *Plasmid* 28:157-165). The DNA was partially digested with Sau3AI using a serial dilution method and libraries were constructed in SuperKOS (a smaller derivative of SuperCos-1) using the protocol for SuperCos-1 from Stratagene. Colonies were picked, cosmid DNA was isolated on the Qiagen robot, and the DNA was submitted for end sequencing. The data was analyzed by BLAST™ and all PKS positive cosmids were prepared in larger amounts for further analysis.

From about 1000 end sequences of the So ce10cosmid library, six cosmids were found which encoded multimodular PKS at one end. The other end of each of these six did not encode a gene that was obviously from a PKS cluster. The six sequences fell roughly into three types: two that matched cis-AT type PKS typical of myxobacteria (10K2C2, 10K7F6), two that look like possible trans-AT type PKS (10K10B3, 10K7F10), and two that matched polyether/polyene type PKS (10K1B5, 10K10D10). By restriction digestion and gel analysis, the banding patterns indicated that no pair of these cosmids shared a significant overlap; however, subsequent DNA sequence analysis revealed overlaps that were not apparent from restriction analysis.

The sequence of the insertion site of one of the transposon mutants described in Example 1 above was identical to the PKS sequence at the end of cosmid 10K10B3 so this cosmid was shotgun sequenced. This cosmid was found to contain a PKS loading module and seven PKS extender modules having a domain organization consistent with the structure of ambruticin (except for an apparent malonyl-specific AT in module 4 where incorporation of a methylmalonyl unit was expected, but this is not unprecedented). Additional transposon insertions that knocked out ambruticin production also matched sequence in this cosmid, verifying that it encodes the ambruticin PKS.

Cosmids or plasmids representing regions upstream and downstream of cosmid 10K10B3 were isolated from libraries prepared from genomic DNA of So ce10strains having transposon insertions at the ends of cosmid 10K10B3 (strains with insertions 1A11, 2B8 and 5F7 were used). The libraries were plated on LB medium containing both carbenicillin and phleomycin to select only those cosmids (or plasmids) having the transposon. After end sequencing the clones obtained, those that covered the greatest amount of sequence upstream or downstream of 10K10B3 were chosen for complete shotgun sequencing.

Example 3

Heterologous Expression of the Ambruticin Biosynthetic Genes and Production of Ambruticin in *Myxococcus xanthus*

Chromosomal DNA is embedded in agarose using the Chef bacterial genomic DNA kit from Biorad. So ce10is grown in 307 seed medium (see Example 1) to an $OD_{600}$ ~4.0 (~4×10$^8$ cells/ml). A 20 ml aliquot of cell is centrifuged, resuspended in 2 ml of milli Q water, and added to 2 ml of melted 2% agarose from the kit. The agarose cell suspension is transferred to plug molds. After hardening, the agar plugs are placed into lysozyme buffer and lysozyme is added to 1 mg/ml. The plugs are incubated at 37° C. overnight. The next day the plugs are washed 2 times with 50 ml of milli Q water and placed in proteinase K buffer containing proteinase K. The plugs are incubated at 50° C. overnight. The next day the plugs are washed several times with TE (10 mM Tris pH7.6, 1 mM EDTA). The BAC library is constructed by Amplicon Express (Pullman, Wash.) by partially digesting the DNA with BamHI and ligating into pEC1BAC cleaved with BamHI. The average insert size of the library is ~100 kb.

To modify the BAC, plasmid pKOS375-151.1 is constructed. This plasmid harbors several important functions necessary for transfer and integration of a plasmid into the *M. xanthus*. First, it contains oriT, the region required for conjugative transfer of DNA. Second it contains the Mx9 integrase gene and the Mx9 attP required for site-specific integration (Julien (2003) *J. Bacteriol.* 185921):6324-6330). Third it contains the bleomycin resistance marker for selection in *M. xanthus*. Fourth, it contains a loxP site that can be used for Cre mediated site-specific integration with the loxP site on the BAC. Finally, it contains the R6Kγ replication origin. This origin requires the pir protein supplied only in certain *E. coli* strains and thus pKOS375-151.1 is a conditionally replicating plasmid.

The first step in constructing pKOS375-151.1 is to remove the p15A origin of replication from pACYC177 (New England Biolabs, Beverly, Mass.) and replace it with the R6Kγ conditionally replicating origin. This is done by cleaving pACYC177 with NheI and BstBI, making the DNA ends blunt with the Klenow fragment of DNA polymerase I, and ligating it with the blunt HindIII fragment from pKOS249-96.5 harboring the R6Kγ origin. This plasmid, pKOS375-109 replicates only in *E. coli* cells expressing the pir+ or the pir116 gene, such as *E. coli* strain EC100D (Epicentre).

Next the Mx9 int gene and attP site are added. Plasmid pKOS249-28 is cleaved with AseI and HindIII, the DNA ends are made blunt with the Klenow fragment of DNA polymerase I, and ligated to pKOS375-109 cleaved with XhoI and BstEII and the DNA ends blunt with the Klenow fragment of DNA polymerase I to create pKOS375-118.

To this plasmid is added the loxP site, oriT, and the bleomycin resistance gene. pKOS375-118 is cleaved with XbaI and EcoRI, the DNA ends made blunt with the Klenow fragment of DNA polymerase I and ligated to the NotI-EcoRI fragment from pKOS375-131.1 harboring the loxP, oriT, and bleomycin resistance genes. This plasmid is designated pKOS375-132.

In the final step to construct pKOS375-151.1, the ampicillin resistance gene is removed by cleaving pKOS375-132.1 with SspI and AhdI, making the DNA ends blunt with the Klenow fragment of DNA polymerase I, and relegating.

The complete nucleotide sequence of pKOS375-151.1 is depicted in FIG. 5 (SEQ ID NO:61) and features described in Table 3.

TABLE 3

Features on plasmid pKOS375-151.1.

| DNA fragment | Plasmid nucleotides | GenBank accession number | GenBank nucleotides |
|---|---|---|---|
| R6Kγori | 367-634 | M65025 | 434-168 |
| oriT | 1040-1405 | X54459 | 4606-4971 |
| Tn5 kanamycin resistance promoter | 1435-1759 | V00615, V00618 | 1196-1700, 1-125 |
| bleomycin resistance gene | 1785-2165 | X01702 | 65-446 |
| loxP | 2191-2224 | M10494 | 14-47 |
| Mx9 int | 2438-4099 | AY247757 | 607-2269 |

BAC clone, pKOS375-123.5K3, harbors the entire ambruticin biosynthetic gene cluster and is 200 kb, as determined by partial sequencing. To modify this BAC for conjugation and integration into *M. xanthus*, Cre mediated site-specific recombination with pKOS375-151.1 is performed. The conditions of the in vitro reaction is as follows: 3 µl of Cre buffer, 3 µl pKOS375-123.5K3 (500 ng DNA), 2 µl pKOS375-151.1 (50 ng), 22 µl Milli Q water, 1 µl Cre (New England Biolabs, Beverly, Mass.). The reaction is incubated at 37° C. for 60 minutes and then at 65° C. for 10 minutes to inactivate the Cre protein. A 5 µl aliquot is dialyzed and electroporated into DH10B cells harboring pKOS111-47 (constructed by digesting with NsiI and self-ligating the RP4 helper plasmid to remove the kanamycin resistance gene (Pansegrau et al. (1994) *J. Mol. Biol.* 239: 623-663)) and pRG1 (Griffen and Kolodner (1990) *J. Bacteriol.* 172:6291-6299), a plasmid expressing the lacI repressor gene, used to repress transcription from the T7A1 promoter that transcribes the Mx9 int gene. This modified BAC is designated pKOS375-162.3.3.

To transfer and integrate the ambruticin genes, *M. xanthus* strain DZ1 is grown in CYE medium at 30° C. to an $OD_{600}$ between 0.5 and 1.0. Approximately 1×10$^9$ cells are concentrated into 100 µl and mixed with approximately 1×10$^8$ DH10B (pKOS375-162.3.3, pRG1, pKOS111-47) cells. The cells are spotted onto the center of a CYE plate and incubated at 30° C. overnight. The next day the cells are resuspended in 5 ml CYE, 5 µl of approximately 1×10$^{12}$ T3 phage/ml are added, and the cells are incubated at 30° C. for 2 hours to lyse the *E. coli* cells. Aliquots are plated in CYE top agar containing gentamycin (60 µg/ml) and phleomycin (50 µg/ml). The plates are incubated until colonies appeared, at least 5 days.

To detect the production of ambruticins, individual colonies are fermented in MOM medium with XAD1180 resin. The fermentations are started by growing seed cultures in 3 ml of CYE overnight at 30° C. The next day, 6 µl of methyl oleate is added and the cultures are grown for an additional day. The cultures are subcultured in 50 ml of CYE containing 50 µl of methyl oleate and grown for two days at 30° C. at 150 rpm. The cultures are then diluted into 50 ml fermentation medium (25 ml 2×CTS, 2.5 ml HEPES (1 M pH 7.6), 350 µl methyl oleate, 200 µl trace metals, and 22 ml Milli Q water) containing XAD1180 resin. The cultures are incubated at 30° C. shaking at 125 rpm. After 24 hours, the shaking is increased to 150 rpm and the cultures are incubated an additional 5 days.

The XAD1180 resin is harvested by decanting the medium and cells and washing the XAD twice with Milli Q water. The ambruticins are eluted with 25 ml of 100% methanol. Aliquots are analyzed using LC/MS. Ambruticin VS3 is the major product, and ambruticin VS4 and ambruticin VS5 are produced in detectable amounts.

All publications and patent documents cited herein are incorporated herein by reference as if each such publication or document were specifically and individually indicated to be incorporated herein by reference.

Although the present invention has been described in detail with reference to specific embodiments, those of skill in the art will recognize that modifications and improvements are within the scope and spirit of the invention. Citation of publications and patent documents is not intended as an admission that any such document is pertinent prior art, nor does it constitute any admission as to the contents or date of the same. The invention having now been described by way of written description, those of skill in the art will recognize that the invention can be practiced in a variety of embodiments and that the foregoing description are for purposes of illustration and not limitation of the following claims.

What is claimed is:

1. A purified or recombinant polypeptide comprising the β-ketoacylsynthase, the acyltransferase, or the acyl carrier protein domain of SEQ ID NO:3.

2. The purified or recombinant polypeptide of claim 1 comprising the amino acid sequence of SEQ ID NO:3.

* * * * *

SEQUENCE LISTING

<160> NUMBER OF SEQ ID NOS: 61

<210> SEQ ID NO 1
<211> LENGTH: 78869
<212> TYPE: DNA
<213> ORGANISM: Sorangium cellulosum

<400> SEQUENCE: 1

```
gatctggtcc acgacgccca gccccgtgc gagctcgcgg gcgccgcccg ctcgaggtgc      60
ccgaagatca ccggcagccc gccgtccgag cggccgaggg cacgggtggg gcctggacct     120
gcaagaccag cgcgccaagc gggggtccga gctcgtgcgg ggcggccgac acgagcctcg     180
cggatctggc ttgcccccg ctccgtacct gctcgacagg ggaccaccca gcgcacgctg     240
tcattcggtc gagcacccgc cttctgttcg cagggagcgc cttgaagagc cggacaggga     300
gccttccgga aagccagttg cctggtatcc accatgtttc cggtgtgctt cggctcaggc     360
aacgggccac atccgcccgg gcgactcgat cggatgcaac gtgatcgagt ccgcatggtc     420
ggcagcggtc cccgccccct cctgcctctg acaacagcgg atcgcagccc cgcctgtgat     480
gccggcagcg gcacatctac acagatgaat gttcacccgg cggcaatgt tccgggctga      540 aaagaataat ccagtctcag ttcaatgagg tgccatggcg gcgccaaact caccacatcg     600
cactcggcgc aatcagtcga ccatagaatt gaaatgtaag acaaattaca tgcgaaaatg     660
cttgaaatat cataaaaaag aatggattga ttggttgcgt agatcaccgt tgatgctagc     720
ctcgactcgg acactctttg tgccttgcgg ccgcccttgt tttcatgggc ttcccgtgca     780
tccgcagggt ttcggggtcc gcagcgtctc cggccacctg tgtcaaggtg cgccggacct     840
tcagatccag gccgttccgc gccgcccggt ctacgaaaag tgcccaagtc gaggctcgct     900
tgtcacgcat cttctctatg cccgacacgt cgtcgtctag ccccgtacta gcgatggggc     960
tacgggattc agatgcccgg ttcgtggagg atacgccgcc tgcctcggac cgccctcgtc    1020
cattcgcggg cattgcggtg gtgggaatgg gatgtcgctt gccggcggc gtcgattcgc     1080 ccgaatcctt gtgggcggcc ctatccgaag ggcgcgacct tatcagcgag gtcccgccgg    1140
acaggtggga tgtcaatgcc cactacgacg ccgacgcgag tgtccccggg aagatcgcga    1200
cccgtcatgg cggcttcctc gccggggtcg cggcgttcga cgcgcccttc ttcgacctct    1260
cgccgcgcga ggcgaagcat atggatccgc agcagcgcct cggcctcgag acggcgtggg    1320
aggcgctgga ggacgcaggc ctggacgcga ggagcttgcg gggcagccgg gcaggggtgt    1380
tcgtcggctc gatgtgggcg gagtacgacg tgctcgcgtc gcgacacccc gaatccatct    1440
cgccgcacgg ggccacgggg agcgaccgg ggatgatcgc ggcgcgcatc gcctacacct    1500
tcggccttcg tgggccggcc ttgtcggtga atacggcgtc gtcgtcctcc ctcgtggcgg    1560
```

-continued

```
tgcacctcgc attgcaaagc ttgcagagcg gagagtgcga gctcgcgctg gccggtggcg    1620
cgaacctcat cctgaccccg tacaacacga tcaagatgac gaagctcggg acgatgtcgc    1680
ccgacggccg gtgcaaggcg ttcgaccacc gcgccaacgg ctacgtgcgc gccgagggcg    1740
tcgggttcgt ggtcctgaag cggctgtcgc gcgcgaccgc ggacggggat cgcatctatg    1800
cggtcgtgcg tggctcggcc gtgaacaacg acgggctcac cgaggggctg accgcgccga    1860
gcgtggaggc gcaggaggcc gtgctgcgag aggcgtacgc gcgcgccggg gtgtctcccg    1920
ccgaggtgga ctacgtcgag gcgcatggga cggggacgcc gctcggcgat cgcgtggagg    1980
cgacggcgct gggacgggtg ctcggcgcag acgcgcggc ggatcgcgcg ctgcgggtcg    2040
gttcggtcaa gaccaacctc ggtcacgcgg aagcagccgc cggggtcgcc ggtctgatga    2100
agacggcgct gtcgctgcgc cacggatcgc ttccggcgag cctgcacgtc gagcgcccga    2160
accccgagat accctcgaa gcgctgggcc tccggctcca gacggagctc ggcgcatggc    2220
cggaggtcga tcggccccgg cgagcaggcg tgagctcctt cggcttcggc ggcacgaact    2280
gccatgtggt gctcgaggag tggcgcgag cgtcgagca gagcgccgcc gagacgggca    2340
gcgaacccgg cgccgccgta tcgccgcctg cccttcccct ggtgctgtcg gcgagggacc    2400
acggggcgct gcgggcgcag gcgggccggt gggcggcgtg gctcacggag caccgcgagg    2460
cgcgctgggc ggacgtcatc cacacggcgg cagcgcggcg gacgcacctg ggcgctcggg    2520
ccacggtggt ggcggcgggc gtggccgaag ccgtcgatgc gctgagggcc ctggccgacg    2580
ggcgcgccca cggggccgtg acggtcggcg aggcgcgcga gcggggcaag gtggtcttcg    2640
tgtttccggg ccagggcagc cagtggccgg cgatggggcg agcgctcctg tccgcgtcga    2700
gggtgttcgc cgaggccgtc gaggcgtgcg atgcggcgct gaggccgctg acgggctggt    2760
cggtgctctc gttgctgcgc ggcgacgccg gggaggcagc gccgtcgctc gaccgcgtcg    2820
acgcggtgca gccggccctg ttcgcgatgg ccgtcggcct gtccgcgtc tttcgcgcgt    2880 ggggcctcga tccttcggcc gtggtgggcc acagccaagg cgaggtcccg gcggcgtacg    2940 tcgcggggc gctctcgctc gacgacgcgg cgcgggtcgt ggcggtccga agcgcgctcg    3000
tgcggcggct ctcgggcgca ggggcgatgg cggcggtgga gctgccggcc ggcgaggtgg    3060
agcgccgcct ggcgccgttc gggggggctc tgtccgttgc ggtggtcaac acgtcgagct    3120
cgacggccgt ttcgggagac gccgaggcgg tggacaggct ggtcgcgcag ctcgaggccg    3180
aaggcatctt ctgccgaaaag gtgaacgtcg attacgcatc ccacagcgcg cacgtggacg    3240
tcgtgctgcc agagctcctg gagcgcctgg cgccgatccg accaggggcc acgaggatcc    3300
ccttctattc gaccgtgacc ggcggtgtgc tggaggggac ggcgctcgac ggggcgtact    3360
ggtgccgcaa cctgcgccag ccggtacggc tggaccgcgc gctcgcccgg ctgctggacg    3420
acggccatgg cgtcttcgtg gaggtcagtg cgcacccgt gctggcgtcg ccgctgaccg    3480
cggcgtgcgc cgagcgcgag ggcgtcgtgg tcggcagcct gcaccgcgac gacggcgggc    3540
ttgcgcggct gctgggcgcg ctgggcgcgc tgcatgtgca gggccagccg gtcgattggc    3600
gcgcggtgct ggcgccgttc ggcggcggcc tggtgaacct gccgacgtac gcattccagc    3660
gccagcgcta ctggttcgat accgacgaga gcgttgcgct cgcagcggcg tccagcattg    3720
cggaagagtc gtggtcagag aagctggccg ggctgtctcc cgcgcgacgg gaagaacggc    3780
tgctcgaatg ggtgcgcgca gaaatcgcgc cggtgctcgg gctggaggcg ccggcggtgc    3840
cgccggacgt cccgctgcgg gatctcgggt tgaaatcgcc gatcgccgtg gagctgggga    3900
```

-continued

```
gccgcctggg acgcaggaca cgccggaagc tgcccgtgtc cttcgtttac aaccacccga    3960
cgccacgagc gatcgctcgc gccctcctgg agggaatgtt ttcttcgagc aaggactctc    4020
ctccgagcac cgctgacgac cgccggccgc cggggtgcc cgccggcgtt gcgccccac      4080
aggcgctgga gacgtccgag atgtccgacg acagctgtt ccagtccatc gatgcgctcg     4140
tctaggaaga ccgagctctc gtcgaaaaag accgttcaac gctgcgaggc gaggattgct    4200
cgtggatcga agcgataaac tgcgtgcgta tctggagaag accacggcat cgctggtcga    4260
ggcgaaaagc cggatccggg agctggaggc gcgttcgcgc gagccgatcg cgatcgtggc    4320
gatggcgtgc cggtttccgg gcggcgtcga cagccccgag aagctctggg ccctgctcga    4380
cgaggagagg gacgtcatca ccgaggtgcc gccctcgcga tgggacctcg agcgcttcta    4440
tgaccccgat ccggacgccg caggcaagac ctacagccgc tggggcggct cgtgggcga     4500
tctggatcgt ttcgacgcgg cgttcttcgg gatcagccct cgcgaggccc ggagcatcga    4560
cccgcaagag cgctggctgc tggagaccac gtgggaggcc ctcgagcggg ccggcgtgcg    4620
cgcggacacg ctggaaggga ccctgggggg cgtttacatc ggcctgtccg gctcggagta    4680
ccaggcggag gcatttcacg atgcggagcg catcgatgcc tattcgctga ccggcgcttc    4740
gccgagcaca accgtggggc gcctcgccta ctggctcggg ctacgaggtc ccgcggtcgc    4800
cgtggacacg gcgtgcagct cctcgctcgt cgcggtgcac ctggcctgcc aggcgctgcg    4860
gaacggggag tgcgatttttg cgctggcagg cggcgtcaac gcgctcctgg cccccgagag    4920
ctatgttgcc ttctgccgcc tcagggcgct gtcccccacc gggcgctgcc ggacctttc    4980
cgcgaacgcc gatggctacg tgcgcgcgga agggtgcggg gtgctgctgc tcaagcgcct    5040
gtcgacgcg cagcgggatg gagaccgtgt gctcgcggtc atccggggca atgccatcaa    5100
ccaggacggt cgcagccagg ggttgacggc gcccaatggg ctcgcccagg aggacgtcat    5160
ccgcagggcg ctgtcgcaag ccgcggtgga gccgacgacg gtcgatgtgg tcgaatgcca    5220
cgggaccggc acggcgcttg gcgatccgat cgaggtccag gcgctcgggg cggtttacgg    5280
ccatgggcgc cccggagaca ggccgctcgt gatcggctcc gtcaagacga acctcggtca    5340
caccgaggcg gccgcaggca tggccggcct catcaaggcc gtcctttcgc tgcagcacgc    5400
ccaggtgcct cgatcgctgc acttcgctgc gccgagcgat tacattccct gggatacccct    5460
ccccgtccgg gtggccgcgc agcgcgtcgc atgggagcga cgcgagcacc cgcggcgcgc    5520
cggggtctcg tcgttcggga tcagcggcac caacgcgcac gtgatcctcg aggaggcgcc    5580
ggcgtcggaa gcgccggcaa cggcgccggt ggcggcgccg gtggcggcgc cgttgccggc    5640
gacgctgccg ctgctcgtgt cggggcggga cgaggcggcg ctcagggcgc aagccgggca    5700
gtgggcggcg tggctcgcgg cgcacccgga ggctccctgg gcggacgtgg tgcacacggc    5760
cgccgcgcgg cgcacgcacc tggaggcgcg cgcggcggtg gcggcgggga cgccgccga    5820
cgcggccgcg gcgctagagg cgctggccgc cggacacccg cacagggcgg tgtcgctggg    5880
cgaggcgcgc gcgcgcggcg aggtcgtgtt cgtgtatccg gggcagggca gccagtggcc    5940
ggcgatgggg cgcgcgctgc tggccgagtc cgaggtgttc gccgccgcgg tcgcggcctg    6000
cgacgcggcg ctgcggccgc tgacgggctg gtcggtgctc tcggtgctgc gcggcgagca    6060
gggagaggcg gtgccgcccg cggaccgcgt ggacgtggtg cagccggcgc tgttcgcgat    6120
ggccgtgggg ctctcggcgg tctggcgggc gtggggcatc gagccttcgg cggtcgtcgg    6180
ccacagccag ggcgaggtcg cggcggcgta cgtcgcgggg gcgctgacgc tcgaggacgc    6240
ggcgcgggtc gtggcgctgc gcagccagct cgtgcggcgc atccgcggcg gcggcgcgat    6300
```

```
ggccgtgatc gagcgcccgg tcggcgaggt ggagcagcgg ctctctcgct tcggagggca    6360
gctgtccgtg gcggcggtga acacgccggg ctcgacggtg gtgtccgggg acgccgcagc    6420
ggtcgatcgc ttgctggccg agctggaggc cgagcgggtc ttcgcgcggc ggatcaaggt    6480
cgattacgcg tcgcacagcg cgcacgtgga cgcgatcctg ccggagctcg aggccacgct    6540
ggcctcggtc gagcccgtg cctgcaccat cccgctgtac tcgacggtga cgggagaagt     6600
gctcgccggc ccggagctcg cggcggcta ctggtgccgc aacctgcgcg agccggtgcg     6660
gctcgaccgg gcgctctcgc ggctgctggc ggacgggcac ggggtgttcg tcgaggtcag    6720
cgcgcatccg gtgctggcca tgccgctgtc ggccgcgagc gccgagcgcg cggcgttgt     6780
ggtcggcagc ctgcagcgcg acgacggcgg tctgggcgg ctggcgtcga tgctgggcgc     6840
gctgcacgtc cagggccacg ccgtgaactg gcagcgggtg ctggcgccgt acggcggggc    6900
gctcgtggat ctgccgacgt acgcgttcca gcgccagcgc cactggctcg aggcgccgcg    6960
gtacgcggcg gaggacacgg acggcgcggc gcggcgcgac ccgctgtacc gggtcacgtg    7020
gatcgaggcg cgcgctggagg aggcgccctg ggcggccgag cgccacgtcg tgctcggcgc    7080
ggacggcgcg ctggcgtcgg ggctgggggc gctcgcgctg gcggggctgc cggagctgct    7140
cgaggcgctg gagaacgggg cggcggcgcc cgagcggctg gtgctggacc tgacggaggg    7200
ccgcccaggc gcggtggcgg agtccgtgca cgccacgacg cgcagcgcgc tcgcgctggt    7260
gcaggcatgg ctcgcggcgc cgcggctttc gggcaccgag ctggtcgtgg tgacgcggga    7320
ggcggtggcg gccggtccgg acgagggcgt ggcggcgctg gccccgcgg cggtctgggg     7380
gctgctgcgc acggtccgcg tcgagcaccc cgagcgcgcg gtgcgctcgg tggatctggg    7440
gcgcgagccg ccggatgtcg cggtcttgcg gcgggcgctg gggacggcgg ccgagccgga    7500
gctcgcgctg cgcgcgggcg gggcgcgggc gccgcgcctg cgcgcggtca acgccggcgc    7560
ggacgccagg gcgccagcgg cggcgctgga cccgcagggc acggtgtgga tcacgggcgg    7620
caccggggag ctcgggcggc aggtcgcgcg gcacctggtc gcggcgcacg gcgtgcggca    7680
cctcctgctg acgtcgcggc gaggcgcggc cgcgccggac gccgaggcgc tggtcgaaca    7740
gctgcgggcc gacggcgccg agacggtcga ggtcgtggcg tgcgacgtga cggacggcgc    7800
ggcgcttttcg gcagcagtcc aggtcgccgc ggcgaagcgc ccgctgacgg ccgtggtgca    7860
caccgccggg gtgctggcgg acggggtgct cacggcgctg acgcggagc agctcacgcg     7920
ggccctggcc ccgaaggtcg acggggcgtg ccacgtgtac gccgccgcgc aggaccagcc    7980
gctcgcggcc ttcgtgctgt tctcctcgat cgtcggtacg ctgggcaacg cgggccaggc    8040
gaactacggg gctgccaatg cgttcctgga cgcgttcgcg gcgcagctcc gcgcgcgcg     8100
cgtgccggcg acgagcctcg cctggggctt ctgggagcag gccgggctcg gcatgacggc    8160
gcacctcggc gccgccgacc tggcacgcct cggacggcag ggccttgtgc cgctgtcggt    8220
cgcgcagggc ctgcgcctcc tcgaccgggc gctcgcgcac ccggaggcga cgctggtgcc    8280
ggcggcgctc gacctgtcgg cgctccagcg tgcggcgagc gacgccggac gggtgccgcc    8340
gctgctgcgc gggctggtgc gcgcgagccc cggccgcccc acggcgaccg cgaccccga     8400
agccggacca gcggccgcgt cggcgctgcg cgcacggctc tcggcgttgc ccgaggccga    8460
gcgggcgggc gcgctgctcg agctggtgcg cgcggaggtg gcggtcgtgc tgcggctggc    8520
aggtccggcg caggtgcccg cggacaagcc gctgaaggag ctggggctcg attcgctcac    8580
ggccgtcgag ctgaagaacc gcctcggcgc gcgcgccgag acggtgctgc cgacgaccct    8640
```

-continued

| | |
|---|---|
| cgcgttcgac catccgacgc cgcgcgcgat cgcggatctg ctgcttcagc gtgcgttctc | 8700 |
| ggagctcgcg ggggcgacgc gcgcacaggc cccgcgcgcg cggggagcgc acgacgagcc | 8760 |
| gatcgcgatc gtgtcgatgg cgtgccggct cccgggcggc gtcgataccc ccgcggcgct | 8820 |
| gtgggacctg ctctcggagg gccggacgcg gatcgggccg ttccccgagg ggcgcggctg | 8880 |
| ggatgtggcg gggctgtacg accccgaccc ggacgcccg ggcaagtcga tcaccacgca | 8940 |
| gggcggcttc ctctacgacg ccgatcgctt cgatccgacc ttcttcggca tcagcccgcg | 9000 |
| cgaagcggag cgcatggacc cgcagcagcg gctgctgctc gagtgcgcct gggaggcgct | 9060 |
| cgagcgcgcg ggcctcgcgc cccacgcgct cgaggcgagc gccaccggcg tcttcttcgg | 9120 |
| gctcgctcac ggggactacg gcgggcggct cttgcagcag ctcgagtcct tcgacggcca | 9180 |
| cgtcctcacc ggcaacttcc tcagcgtcgg ctcggggcgc atcgcctaca cgctgggcgt | 9240 |
| ccgcggcccc gcggtcaccg tcgacacggc gtgctcgtcg tgctcgtgg cggtccacct | 9300 |
| cgcgtgcatg tcgctccgcg ccggcgagtg cgacctggcc ctcgccggcg gcgccaccgt | 9360 |
| gatggccacg ccgatgatct tcgtcgagtt cagccgccag cgcggcacgg cgctggacgg | 9420 |
| tcgttgcaag gccttcggcg ccggggccga tggcgccggc tggtcggagg gctgcgggat | 9480 |
| cctggcgctg aagcggctgt cggacgcgcg gcgcgacggc gaccgcgtgc tggcggtcat | 9540 |
| ccgcagctcc gccgtcaacc aggacgcgcg cagccagggg ctcaccgccc ccaacggccc | 9600 |
| ggcccagcag gacgtcatcc gccaggccct ggccgcggcg gggctgaccc cggcggacat | 9660 |
| cgacgccgtc gaggcgcacg gcaccggaac gcgcctcggt gacccatcg aggcgcaggc | 9720 |
| gctgctggcg acctacggca ccgcgcacac cgccgagcgg ccgctctggc tcggctcgct | 9780 |
| caagtccaac ctcgggcaca cgcaggtcgc gcgggcgtg tcggggctga tgaagctggt | 9840 |
| gctggcgatg cagcacgcag agctgccgag gacgctgcac gccgaccgc cctcgccgca | 9900 |
| cgtcgactgg tcgcagggc acgtcaagct cctgaacgag cccgcgccgt ggccgcgcac | 9960 |
| ggaccggccg cggcgcgcgg cggtctcgtc cttcggcatc agcggcacca acgcgcacgt | 10020 |
| catcgtcgag gaggcgccgg agccggcgcc cgcggcggac gcgaaggcgg tggaggcgct | 10080 |
| tccgatcctg ccgctgctgg tctcgggggc ggacgaggcg gcgctgcgcg cgcaggtgcg | 10140 |
| gcggttggtg gagcacttgc ggtcgcaccc ggaccagcgg ctgctggacg tggcagcgag | 10200 |
| ccttgcgacc acgcgcacgc atctcgccac gcggctcgcg ctgcccgtct cggcggggc | 10260 |
| gccccgggat gcgtggatgg atgagctgga ggcgtttgcc aggggaggag cggctccgac | 10320 |
| gcaggcatcg cagaccccg tcgagagcag cacgggcaag gtcgcggtgc tgttcaccgg | 10380 |
| ccagggcagc cagcgcgccg gcatggggcg cgccctgtat gccacccacc ccgtcttccg | 10440 |
| cgccgcgctc gacgccgcct gcgccgagct cgaccgccac ctcgaccggc ccctcatgag | 10500 |
| cgtcctcttc gccgacgccg gctccgaggc cgcggcgctg ctcgaccaga cagcctgggc | 10560 |
| tcagcccgcc ctgttcgctc tcgaggtggc cctctaccgc cagtgggatg cctggggcct | 10620 |
| gcgccccgag ctgctgctcg gccacagcat cggcgagctc gccgccgccc acatcgccgg | 10680 |
| cgtgctcgac ctcgccgacg cctccgccct ggtcgccgcc cgcgggcggc tcatgcaggc | 10740 |
| cctcccctc ggcggcgcca tggcctccgt cgaggccacc gaggacgagc tacgccctt | 10800 |
| gctcgaccag cacacaggac gcctctcgct cgccgccctc aacacccac gccagtcggt | 10860 |
| cgtcagcggc gacgagcccg ccgtcgacca agtctgcgcc cacttcaccg ccctcggccg | 10920 |
| acgcgccaag cggctcgtcg tcagccacgc cttccactcg gcgcacatgg agcccatgct | 10980 |
| cgacgccttc gcccgcgtcg ctcgcggcct gaccttccac ccgccccggc tgcccatcgt | 11040 |

```
cagcagcgtc accggcgcac gcgcctccgc cgacgagctc acctcgcccg actactgggt    11100
ccgccaggtg cgcgagcccg tccgcttcgt cgacggcatg cgcgcactgc acgccgccgg    11160
cgcggccacc ttcgtcgagt gcgggccgca cggcgtgctc agcgccgccg cgcagagtg     11220 cctcgctccc gacggcgctc gcgacgccgg cttcgtcccc agcctccgca acgaacgcga    11280
cgaggccctc gccctggtcc acgccgcctg cgccgtccat gtacgcggac acgccctcga    11340
ctggctccgc ttcttcgacg ccaccggcgc gcgccgcgtc gagctgccca cctacgcctt    11400
ccagcgacag cgctactggc tccaggcgcc gaggcctcgc cccagcctcg agggcgttgg    11460
cctcaccgcc gcaaaccacc catggctcgg cgcagccgtc cgcctcgccg accgcgatgg    11520
ctacgtcctc agcggccgcc tctccaccag cgaccacccg tgggtcctgg accacgtggt    11580
gctgggcacg gcgctgctcc cgggcacggg cttcgtcgag ctggcgtggg cggcggccga    11640
ggcggtcggg ctgtccgggg tatcggagct ggcgatcgag gcgccgctgg cgctcccggc    11700
gcgcggggcg gtggcgctgc aggtcgcgat cgaggccccg gacccggcgg ggcggcgcgg    11760
catcgcgatc tacagccgcc ccgacggcgc agccgacgcg ccctggacag cgcacgcgcg    11820
cggcgtgctg ggcgccgcgg cgtccgacag ggacgcggcc tgggcgcagg gcgcgtggcc    11880
gccgccgggg gccgtaccgg tcgacgtgac gcagtggctc gagatcgtgg acgcgtgggt    11940
cggcccggcg ttccggggcg tcgtggcgct gtggcgcgtc gggcggacga tctacgcgga    12000
cgtggcgctg ccggacggtg tggcgggcac ggcgcaggat ttcgggctgc atccggcctt    12060
gctcgatgtg gcgctacgcg cgttcctgag agcggagctc agcgccgatc cgtcgccacg    12120
agagggcacg gtggtgccgt tcgcgtggtc ggacgtggcg ctcgaggcgc gtgggacggc    12180
ggcgctgcgg gtgcgcgccg aggtggaggc cggtggggat ggcgacgcga tcaccgcgtc    12240
gatccagctg gccgacgggc agggccgccc ggtcgcgcgg gtgggcgcgc tccagatgcg    12300
gtggacgacg gccgagcggg tgcgcgcggc cgccgccgcg ggcgcggcgg agcgcgatct    12360
gtaccgcgtc gcgtggacgg acgtggcgct ggacgacacg gcgtttgtgc cggaggagca    12420
cgtcgtggtc ggcggcgacg gcgcgctggc ggcggcgctc ggtgcacgcg cggtggcggg    12480
gctgcccgag ctgctcgcgt cgctgccgga cggcgcggcg gcgccacgcc gcctggtggt    12540
ggacctcacg gcggacgccg cgggcgcggt cgtcgacgcc gtgcacgccg cggcgcgcga    12600
cgcgctgtcc ctggtgcagg ggtggctggc ggcgccgcag ctggcggcga cggagctcgt    12660
cgtcgtgacg cgcggcgcgg tggcggtcgc gccggacgag ggcgtggcgg cgctgggtcc    12720
cgctgcggtc tgggggctgc tccgcgcgac gcgcgtcgag cacgcggatc gcacggttcg    12780
catgctcgat ctggggcccg gggcgccgga catggcgctc ttgcgccggg cgctcacggc    12840
ggccgaggag ccagagctcg cgctgcgcgc gggcggggcg cgggcgccgc gcctcgacgc    12900
ggccggcgag accgacggag agctggcgcc gcccgacggg gcgcgctctc ttcgcctgtc    12960
catccggacg aaaggctcgt tcgacgcgct ccacctcgcg gacgctcccg atgcgctgcg    13020
cccgctcggg ccggggcagg tccggctcgc ggtccgcgct acggggctca acttccgcga    13080
tgtcttgaac gtcctgggga cgtaccgcgg cgaagcgggg cctctcggtc tggagggggc    13140
cggggtggtg ctggacgtgg gcgagggagt cactgcccct cgaccggcg accgggtgat     13200 gggcatcctg cacgcgggca tggcgaccca tgcggtcgtc gacgcccggc tgctgacgca    13260
catcccgcgg gggctttcct tcgtggaagc ggcgacgatc ccagcggcct tcctcaccgc    13320
tctgtacggg ctgcgcgacc tgggcgcgct gaaggcgggg cagcgcgtgc tggtgcacgc    13380
```

```
cgcggccggc ggggtcggca tggcggcggt ccagctggcg cgcctctggg gagccgaggt   13440
gttcgcgacg gcgagcgagg gcaagtggcc ggcgctgcgc gggatgggga tcgaccaggc   13500
ccatatcgcc tcgtcgcgaa ccctccactt caggaaagcc ttcctcgacg cgacgcgggg   13560
acagggcgtc gacgtggtgc tcgacgcgct cgcgggcgag ttcgtcgacg cttcgctcga   13620
cctgctcccg cgcgggggcc ggttcgtgga gatgggcaag agcgatgtgc gcgaccccga   13680
gcgcgtcgcc aaggaccacc ccggcgttcg ctacacggcc ttcgatctgc tcgacgcggg   13740
gcccgaccac atccaggcga tgctgcggga gctcgtcccg ctgttcgagg agggcgtcct   13800
cgctcccctc cccttcgcgg tccacgacct gcgtcgcgcc ccgcacgcct tccgatccat   13860
ggccaacgcg cgccacgtgg gcaagctcgt gctggtgccg cctgcggcgc tcgaccctga   13920
cggcacggcc ttgatcacgg gcgggacggg ggagctcggg cggcagatcg cgcggcacct   13980
ggtggcggcg cacggcgtgc gccacctggt gctcacgtcc cggcgcggga tggacgcgcc   14040
cgacgccgcg cgcgctggtgg gatcgctgcg cgcggcgggc gccgcgacgg tggaggtcgc   14100
ggcgtgcgat gtgacagacc gtgacgcgct cgcggccgtc gtgcaggcga tccccgcggc   14160
gcgcccgctg accgccatcg tgcacacggc cgccgtgctg gacgacggca tcgtggcggg   14220
gctctcggcc gagcagctcg cgcgcgtgct gcggccgaag gtcgacggcg cctggcggct   14280
ctacgaggcg acgcgggacg cgccgctcgc ggcgttcatg ctcttctcgt cggtcgccgg   14340
cacgctgggc agctcggggc aggcgaacta cgccgccgcg aacgcgttcc tcgacgggct   14400
ggcggcagag ctccgcacgc gcggcgtgcc ggcgatgagc ctcgcgtggg gcttctggga   14460
gcagggcggg atcgggatga cggcgcacct cggcgccgcc gacctggcgc ggctgaagcg   14520
gcagggcatc gcgccgatga cggtcgcgca cggcctgcgg ctgctcgacc gcgccctcga   14580
gcgcccggac gcggcgctgg tgccggcctc cctggacgtg gcggtgatcc agcgggcggc   14640
gagcgaccac cgtcaggtgc cgcccatgct gcgcgggctc gtccgcgtcg cgccgcggca   14700
ggcggcaggg gcagccaacg gcaggagcca tgaagcctcg accctgcggc agcagctcgc   14760
cgccctgccc gaaccggagc ggcagcgagc gttgctcgat ctggtccgga ccgaggcggc   14820
cgccgtcctg gtgctgcgcg ggccggacgc cgtccccgcc gacaagccgc tcagggagct   14880
cgggctcgac tcgctcacgg cagtggagct caggaatcgg ctcaggaccc gtgcgcagac   14940
cgatctccca tcgaccctcg ccttcgacta cccgacgccg aaggcggtcg ccgtgtatct   15000
agcccaggag ctcgacgttc acgacgtcat gacggagatg cgcggaccga gcttgcgctc   15060
tgacgacgag atcaagtcgg ccatcgcgag catccggatc tcgacgctac gccaggcggg   15120
gctgctcgac agcctgcttc ggctcgccgc cagcgaagcc gtctccacat ccagcgacac   15180
gacacctgaa accgacgagc tgacgctgca gcatgttgga gacgatgagc tggcacggct   15240
tgtcttcgac ctcgccggag gagcgcaatg aaagaagata tctccgcccg tcaagctctc   15300
gagaagagct tcattgaact tcgccgtatc aagcgggagc tcgatcagct caaggcgaag   15360
tcgagcgagc cgatcgcgat cgtgtcgatg gcgtgccggc tcccgggcgg cgtcgatacc   15420
cccgcggcgc tgtggcagct gctctcggag ggccgggacg cgatcgggcc gttccccgag   15480
gggcgcggct gggatgtggc ggggctgtac gaccccgacc cggacgcgcc gggcaagtcg   15540
atcaccgcgc agggcggctt cctctacgac gccgaccgct tcgatccggc gttcttcgcc   15600
atcagcccgc gcgaagcgga gcgcatggac ccgcagcagc ggctgctgct cgagtgcgcc   15660
tgggaggcgc tcgagcgcgc gggcctggcg cctcactcgc tcgaggcgag cgccaccggc   15720
gtcttcgtcg ggctgtcggt cacggactac ggcgggcggc tgctgcacga gcccgaggcc   15780
```

```
ctcgacggct acatcgccac cggcaccctg cccagcgtcg gctcggggcg catcgcctac    15840
acgctggggc tccgcggccc cgcggtcacc gtggacacgg cgtgctcgtc gtcgctcgtg    15900
tccctccacc tcgcgtgcat gtcgctccgc gccggcgagt gcgacctggc cctcgccggc    15960
ggcgccaccg tgatggccac gcccatggcc ttcatcgagt tcagccgaca gcgcggcacg    16020
gcgctggacg gtcgttgcaa ggcgttcggc gccggggccg atggcgccgg ctggtcggag    16080
ggctgcggga tcctgacgct gaagcggctg tcggacgcgc ggcgcgacgg cgaccgcgtg    16140
ctggctgtca tccgcggctc cgccgtcaac caggacggcc gcagccaggg gctcaccgcc    16200
cccaacggcc cggcccagca ggacgtcatc cgccaggccc tggccgcggc ggggctcacg    16260
cccgccgacg tcgacgccgt cgaggcgcac ggcaccggca cgcgcctcgg cgaccccatc    16320
gaggcgcagg cgctgctggc gacctacggc accgcgcaca ccgcggagcg gccgctctgg    16380
ctcggctcgc tcaagtccaa cctcgggcac acgcaggccg ccgcgggcgt gtcggggctg    16440
atgaagctgg tgctggcgat gcagcacgca gagctgccga ggacgctgca cgccgacccg    16500
ccctcgccgc acgtcgactg gtcgcgtggg cacgtcaagc tcctgaacga gcccgtgccg    16560
tggccgcgca cggaccggcc gcggcgcgcg gcggtctcgt ccttcggctt cagcggcacc    16620
aacgcgcacg tcatcgtcga ggaggcgccg gcggcctcca ccgaggcgac gacccgcggg    16680
gagaagacgc ccgcggccgc gccgccgtcg accctgccgc tgctggtctc gggggcggac    16740
gaggcggcgc tacgagcgca tgcggggcgg tgggcggcgt ggctcgcggc gcacccggag    16800
gcgggctggg cggacgtggt gtacaccgcg gcagcgcgtc ggacgcacct gggggcgcgc    16860
gcggcgctga cggcggcgga cgcggccggc gcggtcgcag cgctgacggc gctctcgcag    16920
gggcagccgc acgccgcgct cgccgtgggc gaggcgcgcg ctcggggggaa ggtcgtcttc    16980 gtgtttccgg gccagggcag ccagtggccg gcgatggggc gggcgctgct ctcgcagtcg    17040
gaggtgttcg ccgcgcggt cgcggcgtgc gacgcggcgc tgcggccgtt caccggctgg    17100
tcggtgctct cggtgctgcg cggcgacacg ggcgcggagg tgccgccgct ggagcgcgtc    17160
gacgtcgtgc agccggcgct gttcgcgatg cggtgggc tcgccgcggt gtggcgcgcg    17220
tggggcctcg agccgtcggc ggtggtgggc cacagccagg gggaggtccc ggcggcgtac    17280
gtcgcggggg cgctgtcgct cgaggacgcg gcgcggatcg tggcgctgcg cagccggctc    17340
gtgcggcgcc tgtccggaac tggcgcgatg gccgtgatcg agctcccggt gggcgaggtc    17400
gagcaacggc tctcgcggtt cggcggcgcg ctgtcggtgg cggcggtcaa cacgccgcgc    17460
tcgacggtgg tgtcgggcga tgccgaggcg gtcgatcgac tgctgacgga gttcgagggc    17520
gagcaagtct tcgcgcggaa ggtcaacgtc gactacgcgt cgcacagccg acacatcgac    17580
gggctgctgc cagagctgga ggacggcctg ggcgcggtgc ggccgcgcgc gagcacgatc    17640
ccgttctact cgacggtgac cgggacggtg ctgacgggcg cggagctgga cgcggcgtac    17700
tggtgtcgca acctgcgcga gccggtgcgg ctcgaccggg cgctctcgcg gctcctggac    17760
gacgggcacg gcctgttcgt cgaggtcagc gcgcacccgg tgctgacgct gccgctcaca    17820
ggagcgagcg cgacgagcgg cggtgtggtg gtcggcagcc tgcagcgcga cgacggcggg    17880 ctggacggc tcctgggggt gctggccgcg ctgcacgtgc acggccacga cgtcgactgg    17940
cgcgcggtgc tggcgccgtg gggcggaggc gtggcggact gccgaccta cgcgttccag    18000 cggcagcgct actggctcga ggccgcgcgc ggccgggcag ggctggagag cggagggctc    18060
ctggcggtga agcacccgtg gctcagcgcg gcggtgcggc tggccgaccg cgacggctac    18120
```

-continued

```
gtgctgagcg gacggctgtc gacggtcgag cacgcgtggg tcctggacca cgtggtgctg    18180
ggcacggtga tcctcccggg cacggcgttc gtcgagctgg cgctcgcggc ggccgatgcc    18240
gtcggactgc cctcggtgtc agagctcacg atcgaggcgc cgctggcgct gccggcgcgc    18300
ggggcggtga cgctgcaggt gacggtggag gcgttggacg cgacggggcg gcggggcttc    18360
gcggtccaca gccggcccga cggcgcgcac gacgcgccgt ggacggcgca cgcgcgcggc    18420
gtgctgggcg cagcgcccgc ggcggccacg acggcgtggg cggcgggcgc gtggccgccg    18480 gcggggccg agccggtcga cgtcacgcgg tgggtcgagg cgctcgacgc gtgggtcggc     18540
ccggcgttcc ggggcgtgac ggcggcgtgg cgcgtggggc ggtcgatcta cgccgacctg    18600
gcgttgcccg aggggtctc ggagcgggcg caggacttcg gcttgcatcc ggccttgctc     18660
gatgcgcgcg tccaggccct cctgcgggcg gagctcggcg caggctcgtc gccgcggag     18720 ggcatcccga tgcccttcgc gtggtcggac gtggcgctcg aggcgcgggg ggcagcggcg    18780
ctgcgggcgc gcgtggaggt cgaggacgcc agcgatgggg accagctcgc ggcgtcgatc    18840
gagctggccg acgcgcaggg gcagccggtc gcgcgcgcag ggacgttccg ggcgcggtgg    18900
gcgacgcgcg agcacgtgcg caaagctgcg gcgggtgcga gcgagcgtga cctgtaccgg    18960
gtcacgtgga cggacgtggc gctggaagaa gcggcgtggg cgccggagga gcacatcgtg    19020
ctcggcggcg acggggcgct cgcgcgcgcg ctgggcgcgc gcacggcggc gctgccggag    19080
ctcatcgcgg cgctgccgga gggcgcggcc gcgccgcgcc ggctggtgat cgacgcggcc    19140
gcgggcgacc ccggcgacgg cctggtcgcg cggcgcacg cggcgacgca gcgggtcctg     19200
tcgctggtgc aggggtggct ctcggaggcg cggctcgcgg acagcgagct ggtggtggtg    19260 acgcgcggc ctgtggccgc cgggcccgac gacggcgtcg cggcgttgag ccacgcgccg     19320 ctgtggggc tcgtgcgcac ggcgcgccag gagaaccccg gccgggcggt cgcctcgtc     19380 gacctggggc ccgagccgct ggacggagcc ctcgtgcgcc gggcggtggc ggcggccgag    19440
gagccggagc tcgcgctgcg cggggcgcg gcgcgcgcgc cacgcctgcg cgaggtgcgc     19500
gcgggcgcgg ccgacgcggc gcgaccgacg cggctggatc ccggcgggac ggtgctgatc    19560
acgggcggca ccggggagct cgggcggcag gtcgcgcggc acctggtcgc ggcgcacggc    19620
gtgcggcacc tcgtgctcac gtcgcggcgc gggatggatg cgccggacgc cgcggcgctg    19680
gtggacgagc tgcgcgccgc gggcgccgcg acggtcgacg tcgcggcgtg cgacgtcgcc    19740
gacggcgcgg cgctggggc ggtcatcgcg gcgatcccgg ctgcacaccc cctcacggcg     19800
gtcgtgcaca tggcgggcgt gctggacgac gtcatcgtga cgaagctctc ggccgagcag    19860
ctcgcgcgcg tgctgcggcc gaagatcgac ggcggctggc acctggccgc ggcgacgcga    19920
ggccatcggc tcgcggcctt cgtgctgttc tcgtcggcgg ccggcacgct gggcagcgcg    19980
gggcaggcga actacgccgc ggccaacgcg ttcctggacg cgctcgcggc gcagctccgc    20040 gcgcgcggc tgcggcgat gagcctcgcc tggggcttct gggagcaggc cgggctcggc     20100
atgacggcgc acctcggcgc cgccgacctg gcacgcctca gacggcaggg catcgcgccg    20160
atcgcgctcg cgcagggcat gcagctgctg gaccgggcgc tcgcgcgccc ggaggcggcg    20220
ctggtgccgg cggcgctcga cctgtcggcg ctccagcgtg cggcgagcga cgccgggcag    20280
gtgccggcgc tgctgcgcgg gctcgtgcgc ccggcggccg gcggcgcgc ggcgtcgcct     20340 gcggccgccg cgaccggagc ggcggcgctg cgcgcgcgg tctcggcgct gcccgaggcc    20400 gagcgggcg gcgcgctgct cgagctggtg gcgcgcgagg cggcggccgt gctgcagctg    20460
gcaggtccgg cgcaggtccc cgcggacaag ccgctgaagg agctggggct cacctcgctc    20520
```

```
acggccgtcg agctgaggaa ccgcctcggc gcgcgcgccg agacggcgtt gccggcgacc    20580
ctcgcgttcg accatccgac gccgcgcgcg atcgcggatc tgctgcttca gcgtgcgttc    20640
tcggagctcg cggccgcggg ggcgacgcgc gcacaggccc cgcgcgcgcg gggagcgcac    20700
gacgagccga tcgcgatcgt gtcgatggcg tgccggctcc cgggcggcgt cgatacccccc   20760 gcggcgctgt ggcagctgct ctcggagggc cgggacgcca tcgggccgtt ccccgagggg    20820
cgcggctggg atgtggcggg gctgtacgac cccgacccgg acgccccggg caagtcggtc    20880
accaacctgg gcggcttcct ctacgacgct gaccgcttcg atccgacctt cttcggcatc    20940
agcccgcgcg aagcggagcg catggacccg cagcagcggc tgctgctcga gtgcgcctgg    21000
gaggcgctcg agcgcgcggg cctcgcgccc cattcgctcg aggcgagcgc caccggcgtc    21060
ttcgtcgggc tggtgtacag cgactacggc gggcggctgc tcgagcacct cgaggtcttc    21120
gacggctacg tcgccaccgg cagctttccc agcgtcggct cggggcgcat cgcctacacg    21180
ctggggctcc gcggccccgc ggtcaccgtc gacacggcgt gctcgtcgtc gctcgtgtcc    21240
ctccacctcg cgtgcatgtc gctccgcgcc ggcgagtgcg acctggccct cgccggcggc    21300
gccaccgtga tggccacgcc catggccttc atcgagttca gccgacagcg cggcatggcc    21360
ccggacgcac ggtgcaaggc cttcggggcg gcggcgaacg gcatcggccc cgcggagggc    21420
tgcgggctcc tggtgctcaa gcggctgtcg gacgcgcggc gcgacggcga ccgcgtgctg    21480
gccgtcctcc gcggctccgc cgtcaaccag gacggccgca gccaggggct caccgccccc    21540
aacgcccggg cccagcagga cgtcatccgc caggccctgg ccgcggcggg gctgaccccg    21600
gcggacatcg acgccgtcga ggcgcacggc actggcacgc gcctcggcga tcccatcgag    21660
gcgcaggcgc tgctggcgac ctacggcacc gcgcacaccg ccgagcggcc gctctggctc    21720
ggctcgatca agtccaacct cgggcacacg caggccgccg cgggcgtcgt ggggctgatg    21780
aagctggtgc tggcgatgca gcacgcagag ctgccaagga cgctgtatgc cgagcccga    21840 tcgccgcaca tcgactggtc gcaggggcac atcaacctcc tgaacgagcc cgtgccgtgg    21900
ccgcgcacga accggccgcg gcgcgcggcg gtctcgtcct tcggcatcag cggcaccaac    21960
gcgcacgtca tcgtcgagga ggcgccggcg gccgcgcaga cggcggcgga ggcggcggcg    22020
gcggtgccgt cgacgctgcc gctgctcctg tcgggtcgcg acgagccggc gctgcgcgcc    22080
caggccgggc ggctcgccga gcacctgcgc gcccacccgg accagcggct gctcgacgtc    22140
gccgcgagcc tggccacgac gcgcacgcac ctcgccacgc ggctcgcgct gccgctcgcg    22200
ccggacgcag ccacggagga gctgggcgcc cgccttgccg agttcgcctc aggcggcccg    22260
gcgcccagcg gcgccgccgt gaccgcgccg ggcagccgc ccggcaaggt cgcggtgctc     22320
ttcaccggcc agggcagcca gcgcgccggc atggggcgcg ccctgtacgc cacccacccc    22380
gtcttccgcg ccgcgctcga cgccgcctgc gccgagctcg accgccacct cgaccggccc    22440
ctcatgagcg tcctcttcgc cgacgccggc tccgaggccg cggcgctgct cgaccagaca    22500
gcctgggctc agcccgccct cttcgctctc gaggtggccc tctaccgcca gtgggatgcc    22560
tggggcctgc gccccgagct gctgctcggc cacagcatcg gcgagctcgc cgccgcccac    22620
atcgccggcg tgctcgacct cgccgacgcc tccgccctgg tcgccgcccg cgggcggctc    22680
atgcaggccc tcccctcgg cggcgccatg gcctccgtcg aggccaccga ggacgagcta    22740
cgccccttgc tcgaccagca cacaggacgc ctcgcgctcg ccgccctcaa caccccacgc    22800
cagtcggtcg tcagcggcga cgagcccgcc gtcgaccagg tctgcgccca cttcaccgcc    22860
```

```
ctcggccgac gcgccaagcg gctcgtggtc agccacgcct tccactcggc gcacatggag   22920
cccatgctcg acgccttcgc ccgcgtcgct cgcggcctga ccttccaccc gccccggctg   22980
cccatcgtca gcagcgtcac cggcgcacgc gcctccgccg acgagctcac ctcgcccgac   23040
tactgggtcc gccaggtgcg cgagcccgtc cgcttcgccg acggcatgcg cgcactgcac   23100
gccgcgggcg cggccacctt cgtcgagtgc gggccgcacg gcgtgctcag cgccgccggc   23160
gcagagtgcc tcgctcccga cggcgctcgc gacgccggct tcgtccccag cctccgcaag   23220
gaccgcgacg aggccctcgc cctggtccac gccgcctgcg ccgtccatgt ccgcgggcac   23280
gccctcgact ggctccgcct cttcgacccc tccggcgcgc gccgcgtcga gctgcccacc   23340
tacgccttcc agcgacagcg ctactggctc caggcgccga ggcctcgccc cagcctcgag   23400
ggcgttggcc tcaccgccgc aaaccaccca tggctcggcg cagccgtccg cctcgccgac   23460
cgcgatggct acgtcctcag cggccgcctc tccacactcg accaccgtg ggtcctggac   23520 cacgtggtgg caggcacggt gatcttgcca ggaacgcgct tcgtcgacct ggcgtgggcg   23580
gcggccgagg tggtgggcgc cgccgctgtg tccgaggtga ccttcacgac gccgctcgtg   23640
cttccgccgc gcagcgtggt ggagctgcag gtgaggatcg cgagccgga cgcgtccggg   23700 cggcggacgt tcgccgcgta cagccgcccg gacgcggcga gcgaggcgga gtggacgcaa   23760
cacgcgaccg gcgtgctgag cgcgcaggcg gcggccgggg ccgacgtggc ggaccttcg   23820 gtgtggccgc cgccgggcgc cgaggtggtg gcgctcgacg gcggctacgc gtggctggcg   23880
gcgcagggct acggctacgg cccggcgttc caggcgctgc gcgaggtgtg gcgcgcgggc   23940
acgacgctgt acgcgcgggt cgcgctgccg gacgcggtgg cggacacggc gcagagcttc   24000
gggatccatc cggcgctgct cgacgcggtg ctgcactcgt tgctggcgcg gtcgccgcag   24060
gaggaggcgt ccgacgacga caaggtgctg ctggcgttcg cgttctcgga cgtcgtgatc   24120
gaggcgcgcg gggcagcgga ggtgcgcgtc cgcctgaaca gcaggccgg agacgacggg   24180 gagggctca cggcgtcgat ccacctcgcc gacgcgcagg ggcggccggt cgcgcgcgtg   24240
ggggcgttcc aggcgcgggc gacgaccacg gagcgggtgc gcgcgctcgc gggcgcgagc   24300
gagcgcgatc tgcatcgggt cacgtggacg gacgtgacgc tggacgaggc gccgtgggcg   24360
cacgaggaca gcgtcgtggt cggcggcgac ggcgcgctgg cggcggcgct gggcgtgcgc   24420
gcggtggccg ggttgcccga gctgttcgcg ggcggcgcgg cggcgccgcg tcgtctggtg   24480
atcgacgcga ccgcgggcga ccccggcgac ggccttgtcg cggcgacgca cgcggcgacg   24540
cagcggggcc tcgcgctctt gcagggatgg ctcgcggagg cgcggctcgc gtcgacggag   24600
ctggtgctcg tgacgcgcgg cgcgacggcg gccgagccgg acgagggtgt ggcggcgctg   24660
agccacgcgc cgctctgggg gctcgtgcgc gcggcgcgcg aagagcaccc ggcgcgcgcg   24720
ctgcgcctgg tcgatctggg gcgcgaggcg ccggacgggg cggtcctgcg ccgggcgatc   24780
gcggcggacg acgagccgga gctcgtggtc cggcgcgggg cgctgcgggc ggcgcgcctg   24840
agcctcgccc acgccgcccc ggacgccgcg gggcgagcga cgcggctggc ccccggcggg   24900
acggtgctga tcacgggcgg cacggggag ctcgggcggc aggtcgcgcg gcacctggtg   24960
acggcgcacg gcgtgcgcca tctggtgctc acgtcccggc gcgggatgga cgcgcccgac   25020
gccgcggcgc ttgtggaagc gttgcgcgcg cgggcgccg cgacggtgga gatcgcggcg   25080
tgcgacgtgg cggaccgcga cgcgctggcg gcggtgctcc gggccatccc ggcggcgcac   25140
ccgctgaccg cggtcgtgca cacggcgggc gtgctcgaag acggcgtcgt gacggggctc   25200
tcggccgagc agctcgcgcg cgtgctgcgg ccgaaggtcg acggcgcctg gcagctctac   25260
```

```
gaggcgacga gggacgcgcc gctcgcggcg ttcatgctct tctcgtcggc ggcgggcacg   25320
ctgggcagcg cggggcaggc gaactacgcc gctgcgaacg cgttcctcga tgcgctggcg   25380
gcagagctcc gcacgcgcgg cgtgccggcg atgagcctgg cctggggctt ctgggagcaa   25440
ggtgggatcg ggatgacggc gcacctcggc gccgccgacc tggcgcggat gaagcggcag   25500
ggcatcgtac cgatggcggt cacgcacggc ctgcggctgc tggatcgcgc gctggagcgg   25560
cccgaggcga cgctggtgcc cctatcgctc gacgtggcgg cgctccagcg cgcggcgggc   25620
gacgccggac gggtgccggc gctgctgcgt ggcctggtgc gcccggcggc cgcccggcac   25680
acggcggtgc cggcggccgc ggcgacgggg gcgacagggc tccgcgcgcg gctcttgccg   25740
ttgtccgagg ccgagcgcca ggacgtgttg ctcgatctgg tgcgcacgga gatcgcggac   25800
atcctcgcgc tgtccgggcc agcggcggtg cctcccgatc aacccatcag ggagctgggg   25860
ctcgattcgc tcacggcggt ggacgttcgg agcggcttg tgcagaggag cgagatcgac   25920
ctccccgtga ccctcgcgta cgattatccg accgcgcgag cgatcgctgg acatctgagc   25980
gagcagatgg gcctcgaagg agcgccggaa gatcgggagt cggcgctcga cgaggcccag   26040
atccgcgccc tgctcatgca gattcctatt tccacgttgc gccagtcggg gctgctcgga   26100
gacctggttc gcctggcctc cccgcaagcg ccccccgcgcg aagaaggcga gagcgagacg   26160
ttgagcttcg atcaccttgg aaatgaagag ttcctcagcc tcgcgtcgaa gctcattgca   26220
gaagagggat catgaaccaa gagactgttc ttcggcagac actcgagaag agtctccaca   26280
agatccagca cctcaatcgg gagctcgagc gtctcaaggc gaagtcgagc gagccgatcg   26340
cgatcgtgtc gatggcgtgc cggtttccgg gcggcgtcga taccccccgcg gcgctgtggg   26400 acctgctctc ggagggccgg gacgcgatcg ggccgttccc cgaggggcgc ggctgggatg   26460
tggcggggct gtacgacccc gacccggacg ccccgggcaa gtcgatcacc acgcagggcg   26520
gcttcctcta cgacgctgac cgcttcgatc cgacgttctt cggcatcagc ccgcgcgaag   26580
cggagcgcat ggacccgcag cagcggctgc tgctcgagtg cgcctgggag gcgctcgagc   26640
gcgcgggcct cgcgccccat tcgctcgagg cgagcgccac cggcgtcttc gtcgggctgg   26700
tgtacagcga ctacggcggg cggctgctcg agcacctcga ggtcttcgac ggctacgtcg   26760
ccaccggcag cttcccagc gtcggctcgg ggcgcatcgc ctacacgctg gggctccgcg   26820
gcccccgcgt caccgtcgac acggcgtgct cgtcgtcgct cgtgtccctc cacctcgcgt   26880
gcatgtcgct ccgcgccggc gagtgcgacc tggcctcgc cggcggcgcc accgtgatgg   26940
ccacgcccat ggccttcatc gagttcagcc gacagcgcgg catggccccg gacgcacggt   27000
gcaaggcctt cggggcggcg gcgaacggca tcgcccccgc ggagggctgc gggctcctgg   27060
tgctcaagcg gctgtcggac gcgcggcgcg acggcgaccg cgtgctggcg gtcatccgca   27120
gctccgccgt caaccaggac ggccgcagcc aggggctcac cgcgcccaac ggtccggccc   27180
agcaggacgt catccgccag gccctggcgg cagcggggct cacgcccgcc gacgtcgacg   27240
ccgtcgaggc gcacggcacc ggcacgcccc tcggcgatcc catcgaggcg caggcgctgc   27300
tggcgaccta cggcaaggcg cacacagcgg agcggccgct ctggctcggc tcgatcaagt   27360
ccaacttcgg ccacacgcag gccgccgcag gggtcgcggg catcatcaag ctggtgctgg   27420
cgatgcagca cgcagagctg ccgaggacgc tgcacgccga ccccccgtcg ccgcgcgtcg   27480
actggtcgca ggggcacgtc aagctcctga acgagcccgt gccgtggccg cgcacggacc   27540
ggccgcggcg cgcggcggtc tcgtccttcg gcgtcagcgg caccaacgcg cacgtcatca   27600
```

```
tcgaggaggc gccggccgaa gcgccgacgg ccgcgcagac ggcggcagcg gcggcgacag   27660
agccggcggc ggcggtggtg ccgtcgacgc tgccgctgct cctgtcgggt cgcgacgagc   27720
cggcgctgcg cgcccaggcc gggcggctcg ccgagcacct gcgcgcccac ccggacctgc   27780
ggttgctcga cgtcgccgcg ggcctggcca cgacgcgcac gcacctcgcc acgcggctcg   27840
cgctgccgct cgcgccggac gcagccacgg aggagctggg cgcccgcctt gccgagttcg   27900
ccgccggcgg cccggcgccc agcggcgccg ccgtgaccgc gccggggcag ccgcccggca   27960
aggtcgcggt gctcttcacc ggccagggca gccagcgcgc cggcatgggg cgcgccctgt   28020
atgccaccca ccccgtcttc cgcgccgcgc tcgacgccgc ctgcgccgag ctcgaccgcc   28080
acctcgaccg gccccctcgtg agcgtcctct tcgccgacgc cggctccgag gccgcggcgc   28140
tgctcgacca gacagcctgg gctcagcccg ccctgttcgc tctcgaggtc gcgctctacc   28200
gacagtggga agcctgggc ctgcgcgccc acgcgctgct cggccacagc ctcggcgaga   28260
tcgtcgccgc ccacatcgcc ggcgtgctcg acctccacga cgcctccgcc ctggtcgccg   28320
cccgcgggcg gctcatgcag gccctccccc acggcggcgc catggcctcc atcgaggcca   28380
ccgagcacga gctccgaccc ctgctcgacc agcacacagg acgcgtctcg ctcgccgccc   28440
tcaacgctcc acgccagtcg gtcgtgagcg gcgaccagcc cgtcgtcgac caggtctgcg   28500
cccacttcaa ggccctcggc cgacgcgcca agcggctcga cgtcagccac gccttccact   28560
cggcccgcat ggaacccatg ctcgacgcct tcgcccacgt cgcccgcggc ctgacctacc   28620
gcgccccgcg cctgcccgtc gtgagcaatg tcaccgggcg catggccacc gccgacgagc   28680
tcacctcgcc cgactactgg gtgcgccacg tgcgcgagcc cgtgcgcttc gtcgccggcg   28740
tgcgcgcgct gcacgccacc ggcgtcacca cctacctcga gtgcgggccc gacccggtgc   28800
tcggcggcat ggccgcagac tgcctcaccc cggacgagac ccgcgacgtc ggcctgatcc   28860
cgagcctgcg caaggaccgc gacgaggccc tggccctcgc ccaggccgcc tgcgccctgt   28920
acgtccgcgg acacgccctc gactggctcc gcctcttcga cgccacccgc gcgcgccgcg   28980
tcgagctgcc cacctacgcc tttcaacgcc agcgctactg gatcgatgcg ccgcggcgcg   29040
cggcggggct cgacagcgtc gggctcacgg ccgcagatca cccctggctg ggcgcggcgg   29100
tgcggctcgc cgaccgggac gtccacgtgc tgagcgggcg gctgtcgacg gtcgaccacc   29160
cgtggatcct ggaccacgtg gtggcgggca cgccgctgat gccaggaacg ggcttcgtcg   29220
agctggcgtg ggcgacggcc caggcggtgg acgccgccgc gatcgcggag ctcaccctga   29280
cgacgccgct cgtgttgccg gcgcgcggcg cggtgcagct ccaggtgacg gtcgacgagg   29340
ccgacgcgaa tggccggcgg gcattcgcca tccacagccg gccgcatggc cccggcgacc   29400
tcgcgtggac gcaacacgcg accggcgtgc tgagcgcgga ggagccggcg ggagccgacg   29460
aggcggcggg gctctcggag tggccgccgc cgggcgcgga ggcggtggcg ctcgacggcg   29520
ggtacgagca gctgtccgag cacggctacg gccacgccc ggcgttccag ggctccgcg   29580 ggctctggcg cgcggaccgt acgctgtacg cgcacgtcgc gctgccggac gctgtcgcgg   29640
gcaccgagca gggcttcggg ctccatccgg cgctcttcga tgcggcgctg cagtcgctgg   29700
cgcggctgtc gcgcgaggaa gcggccgctg gcgacccggt gctggtgccg ttcgcgtgga   29760
cggacgtggc gctgtacgcg accggcgcga ccgagctgcg ggcgcgcatc gcgctggagc   29820
aggcggaggg cggcgcgccg gcggtggcgt cgctgctgct ggccgacgcg cacggacgaa   29880
ccgtggcgac gaccgggcgg gtgcgcgggg cgagcgcggc gcagacgcgg tccgccgcga   29940
gccgcgcgga gccgatgtac cgggtcgcgt ggacggacgt ggcgctggag gcggcgacgt   30000
```

```
gggcgcccga ggagcacgtc gtgctcggcg gtgacggtgc gctcgcgcg  gcgctgggcg    30060
tgcgcgcggc ggccgggctg ccggagctgc tcgaggcgct ggcggacggc gcggccgcgc    30120
cgcggcggct ggtcgtggac ctgacggcgg gcgatgcagg cgcggtcgtc gcggccgtgc    30180
acgccgcggt gcgcggcgcg ctggccctgg tgcagggtg  gctcgccgcg ccgcagctgg    30240
cggcgacgga gctcctggtg gtgacgcgct gcgcggtggc gaccgggccg gacgagggcg    30300
tggacgcgct ggggccggcg gccgtctggg gcctgctgcg ggccacgcgc gccgagtacc    30360
ccgaccgcgc ggtccgggtg ctggacgtgg ggcgcgagcc gctggacggg gcgctcttgc    30420
gtcgggcgct ggccgcgggg acggagccgg agctttcggt gcgcagcggc gaggcgcgcg    30480
cgccgcgcct gcgcgaggtg cgcgggagcg agccggccgc ggcgccggcg acgcggctgg    30540
atcccgacgg aacagcgctg atcacgggcg gcaccgggga gctcgggcgg catgtcgcga    30600
agcacctggt gacggcgcac ggcgtgcggc acctcgtgct gacgtcgcgg cgcgggatgg    30660
acgcgcccga cgccgcggcg ctggtggacg agctgcgcgc cgcgggcgcg gcgacggtcg    30720
acgtcgccgc gtgcgacgcg gcggacgcag cggcgctggc ggcggtggtg gaggcgatcc    30780
cggcggcgcg tccccctgacg gccgtcgtgc acaccgcagg tgtgctggac gacagcgtcg    30840
tgaccaagct ctcggccgag cagctggcgc gcgtgctgcg gccgaaggtc gacggcgcct    30900
ttcatctcca cgagctcacg aagcacgcgc cgctcgcggc cttcgtgctg ttctcgtccg    30960
cggcgggcac gctgggcagc ccggggcagg cgaactacgc cgcggccaac acgttcctgg    31020
acgcgctcgc gtcgcacctg cgcgcgcgcg gcgtgccccgc gatgagcctc gcatggggct    31080
tctgggcgca gactgggctc ggcatgacgg cgcacctcgg cgccgccgac atcgcccgga    31140
tgaagcggca cggcgtcgta tcgatgcccg tcgcgcaggg gttgcggctg ctcgatcgcg    31200
cgctcgcgca ggccgaggcg acgctggtgc cgctcgcgct cgacctctcg tcgctgcaac    31260
gcgcggggag caacgccggg ccggtgccgc cgctgctgcg cgggctcgtg cgcgcaccgg    31320
ccggccggcg cacggcggcg tccgctgctg gggcgaacgg gaacgggacg ggagcagcgg    31380
cgctgcgcgc gcggctctcg cccttgcccg gggccgagcc ccagaaggtg ctgctcgatc    31440
tggtgcgcac ggaaatcgcg gaggtgtttc agttgccggg ccctgcccac atccctgcgg    31500
acaggccgct gaaggagctg gggctcgact cgctcatgtc ggtggagctg cgcaatcgcc    31560
tgggcccgcg cgtcgaggcg gcgctgcccg cgacgctcgt gttcgactac cccacgcccg    31620
gggccattgc atcctatctg ggcacgttgc tcaacctctc cggcgaggac gcacacccgg    31680
gccaaacggg gcgcgacccg gacgaagaac acgagatccg ggccgcgata gcgcgcatcc    31740
cgataacaac cttgcgcgag gcagggctcc tccagagctt gctccgactc gcccccaacc    31800
agacggcgtc cgatgacgtc acgccgagga ctgatgagct gatggtcgaa cacctcggag    31860
atgaagagct gctgaagctt gctttcgcgt ccaccggagg agccaagtga aggacgaggt    31920
gctttcgttc cgccgcgctt tggagaagac ggtcgtcgag atccgccgcc tcaacacgga    31980
gatcgacggc ctgcgcgcga agtcggtcga gccgatcgcg atcgtgtcga tggcgtgccg    32040
ctacccgggc ggcgtggaca gcccgcggc  gctctggcag cttctctccg aggggcgaga    32100
cgcgatcggg ccgttccccg aggggcgcgg ctgggacgtg gcggggctgt acgacccga    32160
cccgacgcgc cgggcaagt cgatcaccac gcagggcggc ttcctctacg acgccgacca    32220
cttcgatccg atgttcttcg gcatcagccc gcgcgaggcc gagcgcatcg acccgcagca    32280
gcggctgctg ctcgagtgcg cctgggaggc gctcgagagc gcgggcatcg cgccccacac    32340
```

```
gctcggcgcg agcgccacgg gcgtcttcat cggactgatg tacacggagt atggcctgcg    32400
gctgatgaac cagcccgagg ccctcgacgg ctacatcggc atcggcagcg ccgggagcac    32460
ggcctccggg cgcatctcct acacgctggg gctccgcggc cccgcggtca ccgtcgacac    32520
ggcgtgctcg tcgtcgctcg tgtcgctcca cctggcgtgc acggcgctcc gccgtggaga    32580
gtgcgacctg gcgctggcgg gcggcgccgc cgtggtgtcg acgccggccc cgttcatcga    32640
gttcagccgg cagcgggccc tcgcggtcga cggtcgatgc aagtcgttcg cgccggggc    32700 cgacggcgtg agctggtcag agggttgcgg gctgctcgtc ctcaagcggc tgtcggacgc    32760
gcagcgcgac ggcgaccgcg tgctggccgt cctccgcgcg tccgccgtca accaggacgg    32820
ccgcagccag gggctcaccg cgcccaacgg cccggcccag caggacgtca tccgccaggc    32880
cctggctgcg gcggggctca ccccggcgga catcgacgcg gtggaggggc acggcaccgg    32940
cacgcccctc ggcgacccca tcgaggcgca ggcgctgctg gcgacctacg gcaaggcgca    33000
cacagcagag cggccgctct ggctcggctc gatcaagtcc aacttcggcc acacgcaggc    33060
cgccgcaggg gtcgcgggcg tgatgaagct cgtgctggcg atgcagcacg cagagctgcc    33120
gaggacgctg cgcgccaacc cgccctcgcc gcacgtcgac tggtcgcagg gcacatcgc    33180 gctcttgaat gagccagcgt cgtggccgcg cacggaccga ccgcggcgcg cggcggtctc    33240
gtccttcggc gtcagcggca ccaacgcgca cgtcatcatc gaggaggcgc cggcgcccgc    33300
cgcggaggtg acgagccctg gagcagagcc gcccgctgtc gcgctgccgc tgctggtgtc    33360
ggggcgggat gacgcggcgc tcagggcgca ggcggagcgc tgggcggcgt ggctcgcggc    33420
gcacccggag gcgcgctggg cggacgtggt gcacacggcc gccgtgcggc gcacgcacct    33480
ggaggcgcgc gcggcggtga cggcggcgag cgccgccgac gcggccgcgg ccctgacggc    33540
gctctcgcaa ggggagccgc accccgcggt gaccgcgggc gaggcgcgcg cgcgcggcaa    33600
ggtcgtgttc gtggctccgg gccaggggag ccagtggccg gcgatggggc gggcgctgct    33660
ggccgagtcc gaggtgtttg ccgccgcggt cgcggcctgc gacgcggcgc tgcggccgtt    33720
caccggctgg tcggtgctct cggtcctgcg cggcgagcag ggagaggcgg tgccgcccgc    33780
ggaccgcgtg gacgtggtgc agccggcgct gttcgcgatg gccgtggggc tctcggcggt    33840
ctggcgggcg tggggcatcg agccttcggc ggtcgtcggc cacagccagg gcgaggtcgc    33900
ggcggcgtac gtcgccgggg cgctgacgct cgaggacgcg gcgcgggtcg tggcgctgcg    33960
cagccagctc gtgcggcgca tcgcggcgg cggcgcgatg gccgtgatcg agcgcccggt    34020
cggcgaggtg gagcagcggc tctctcgctt cggagggcag ctgtccgtgg cggcggtgaa    34080
cacgccgggc tcgacggtgg tgtccgggga cgccgcagcg gtcgatcgct tgctggccga    34140
gctggagcac gaggaggtct tcgcgcggcg ggtcaacgtc gattacgcgt cgcacagcgc    34200
gcacgtggac gcgatcctgc cggagctcga ggcctgcctg gcctcggtcg agccccgtgc    34260
ctgcgccatc ccgctgtact cgacggtgac gggagaagtg ctcgccggcc cggagctcgg    34320
cgcggcatac tggtgccgca acctgcgcga gccggtgcgg ctcgaccggg cgctctcgcg    34380
gctgctggcg gacgggcacg gggtgttcgt cgaggtcagc gcgcatccgg tgctggccat    34440
cccgctgacg gccgcgagcg ccgagcgcgg cggcgttgtg gtgggcagct gcagcgcga    34500 cgacggcggc ctggggcgtc ttgtttcagc gctgggcgcg ctgcacgtcc aggggcattc    34560
ggtggagtgg gccagggtgc tcgcgccgta cggcggcaac ctggtggact gccgacgta    34620 cgcgttccag cggcagcgct actggctcga ggcgtcgagg agccggatcg acgcgagcga    34680
cctcgggctc gcggcgacgg gccgcccgct gctgggcgcc gcaacgcggg tcgccggcac    34740
```

-continued

```
ggacagctac atcctggcgg gtcggctgtc gacagcggag cacccgtggc tgtcgggaca   34800
ggtcgtcttc gagcggacgc tgttcccggc gacggggttt ctggagctgg cgctcgaagc   34860
cgctgacgcg atggggggtgg cggggggtgac cgagctggtc gtgcccgctc cgctgatctt   34920
gccggcgcgg ggtgcggtgc acgtccaggt tgcggtccag ggaccagacg aggcgggacg   34980
ccggccgttt tccgtgtaca gccgcgcgga aaccgcgggg ctggacgcgg aatgacgct   35040 gcatgccacg gggctgctcg ggggagcgcg cgccagtgcg gcggcggaca cgggcctcga   35100
ggcgtggccg ccggaggggag ccgcgccggt ggacgtcagc gacgcctatg cgcggctgga   35160
ggacgccggc gtgcgttatg cgccgagctt gcgagcgctc gtggaggcct ggcaggcgga   35220
gcggcgcatc tatgcgcgcg cggtgctgcc gggcggcgcg acgcagggcc acgggctcca   35280
cccggcgctg tgggacgcgg cgctgcacgc gctggcgctg gtggtcctcg ggcaggacgc   35340
ggagcacgcg ggcgtgctgt tgccccgggc ctggtcggac gtgacgctcg cggcgcaggg   35400
ggcgaccgag ctgcgggtgc gcgtcgagct cgcggacgcg gacgcggagc acgtgtcggc   35460
gtcgctgacg atggccgacg cggacggtca acccgtggcg acggtggggt cggtggaggt   35520
gcgtcgcgcg accgcggccc aggtgcgcgc catgagcacc gcgacccagc accttacgg   35580 ggtcgagtgg aaggcggtgg cgctggcgga ccgccgcgg tctgcggggg agcaggtcgt   35640
gctcggaccg gacggcgagc tcgcgacaag gctgggcgcg cgacgcgccg gcaacctcga   35700
tgagctgttt gccgacggcg aggcggcgcg ccccgcgccc aggcggctcg tggtcgacgc   35760
gcggacgcgc cgccgacggcg acgtgcctgc ggctgtgcac caggcgacgc gccaggccct   35820
cgagctcgtg cagcgatggc tggcggacgc gcgactgacg gacaccgagc tcgtggtgct   35880
gacgcgcgag gcggtgtcga ccggcccgga cgtgggggtc gaagacctgg gccacgcggc   35940
gctctgggga ttcttacgcg cagtgcggag tgagcacccg gaccgcgggg tgcgcctcat   36000
cgacctcgga cctgacgcct ctgcggcgga gctgctcgac agggccctcg agaccgtggc   36060
ggagcccgag ctggcgctcc ggcaggggat cgcgctggcg ccccggctcg gtgtgcctcg   36120
tgatcgcgcc ggcgccccgg cgccgatgcg gctggacccg gacgggacgg cgctgatcac   36180
cggcggcacc ggggagctcg ggcggcatgt cgcgaagcac ctggtgacgg cgcacggcgt   36240
gcggcacctc gtgctgacgt cgcggcgcgg gatggacgcg cccgacgccg cggcgctggt   36300
ggacgagctg cgcgccgcgg gcgcggcgac ggtcgacgtc gccgcgtgcg acgcggcgga   36360
cgcagcggcg ctggcggcgg tggtggaggc gatcccggcg gcgcgtcccc tgacggccgt   36420
cgtgcacacc gcaggtgtgc tggacgacag cgtcgtgacc aagctctcgg ccgagcagat   36480
ggcgcgcgtg ctgcggccga aggtcgacgg cgcctttcat ctccacgagc tcacgaagca   36540
cgcgccgctc gcggccttcg tgctgttctc gtccgcggcg ggcacgctgg gcagcccggg   36600
gcaggcgaac tacgccgcgg ccaacacgtt cctggacgcg ctcgcgtcgc acctgcgcgc   36660
gcgcggcgtg cccgcgatga gcctcgcatg gggcttctgg gcgcaggctg ggctcggcat   36720
gacggcgcac ctcggcgcgg ccgacatcgc ccggatgaag cgcctgggtg tcgtgacgat   36780
gtcgccgcaa gaagggctcg agctgctgga cgcgtcgctc cagcggccgg accgctgct   36840 ggtgccggcg ccgctcgatc tcgccgcgct cgagcgagcc gcgcgcgagg gcgcgcccgc   36900
ttcgccgatg ctgcgcgagc tggtgcgcgg cgcgcccgcg cggcgcgccg ccgcgggcga   36960
cggcgcgagc ggcaaggcct cggcgctgcg cgcgctcctg gcgcgacggc cccagagcga   37020
acgattcgcg gcggtcctcg agctcgtcag ggcggaggcg cgcgcgtgc tccggctgcc   37080
```

```
gggggccgcg gcagtgccgc cagatcggcc gctcaaggag ctggggctcg actccctcac   37140
cgcggtcgag ctgcggaacc ggctggcggc gcggacggaa gccaagcagc cggcgacgct   37200
cgtcttcgac catccgacgc ccagcgccat cagccgattc ctgctcaagc aagccggcgc   37260
tgatctcgct ccgagcgagg ccgcggcgag cctcgcaccg agcagccgac gtgctcccct   37320
ggatgagccg atcgcgatcg tcgccatggc gtgtcggtgc cccggcggag tcgatagccc   37380
cgaggcgctg tggaggctgc tctccgaggg acgcgacgcg atcggcccgc tcccggagga   37440
gcgaggctgg agcgtggagc agatcctcgg ccgtgatccg ggcgcctcga gcaaaccgtt   37500
cagcggccgg ggtggcttcc tctacggcgc cgaccagttc gacgccgagt tcttcgggat   37560
caccccgcgc gaggccaggt tcctcgaccc gcagcacgcc ttgctcctcg agtgcacctg   37620
ggaggcgctc gagcgcgcaa gcatcgtccc gcagtcgctg gaagggagct ccacgggtgt   37680
gttcgtgggc atggtgggcg gcatggccgc tggtcacggc tcggtatcga gcgagggcta   37740
tgcgctcacc gggaccgcgt tgagcaccgc ctcgggcgt atttcctacg cgctcggcct   37800
gcagggcgcg gcggtgacgg tcgacacggc gtgcagctcg tcggccgtgg cgattcacct   37860
cgcgtgcacg tcgttgcgga ccggagagtg cgatctggcg ctggcggggg cgtgaccgt   37920 catgggcagg cccgagatct tctcggagtt cggccggctc gacatcctcg cctcggacgg   37980
ccgatgcaag gcgttcgggg ccacggccga cggcgtcggc tggggcgaag gctgcggggt   38040
cttgctgctg aagcggctgt cggacgcgca gcgcgacggc gaccgggtgc tcgcggtgat   38100
ccgcggctcg gccgtcaacc aggacggccg cagccagggg ctcaccgcgc ccaacggccc   38160
gagccaggag gcggtcatcc agagagcgct ggcgtcggcc ggcctgacgg cggcggatgt   38220
cgacgccgtc gaggcgcacg gcaccggcac gcgcctcggc gacccgatcg aggcgcaggc   38280
gctgctctcg acctacggcc aggcccacgc gcgcggggcag ccgctgtggc tcggctcgat   38340
caagtccaac ctcgggcaca cgcaggccgc gcgcggggtc gcgggcgtga tcaagatggt   38400
gctggcgatg cagcacgggc agctcccgag gacgctgtac gccgacacgc cctcgccgga   38460
catcgattgg tcgcagggc acgtcaggct cctggtcgac gccgtgccgt ggccgcagag   38520
cgcgcggcgg aggcgcgcgg gcgtctcgtc gttcggcatc agcggcacca acgcgcacat   38580
cctcgtcgag gaggccccgg aaccgccgcg ggcggggggcc gcgccggaag cgccggtgac   38640
gctgcccttt ctgccgctgc tggtctccgg ccgcgacctc gcggcgttgc ggtcgcaggc   38700
agcgcgcctc gccgcgcacc tgcgtgagcg ccccgaccag cggctggtcg acgtgacggc   38760
gagccttgcc acgacgcgca cgcacctcgc cgcgcggctg gcgctgccgg tcgccgcgac   38820
cgctggacgc gacgagatat gcggcgcgct cgacgcgttc gcggcgcggg ggctggcctt   38880
gaacggcgcg tgggtcacac cggcgcaaca ccgcgccggc aaggtcgccg tgctgttcgc   38940
ggggcagggt gcccagcggc ccgcgatggg gcgtggcctc tacgaggcgc tgccggtgtt   39000
ccgcgaggcg ctggacgagg tgtgcgcgcg cctcgacgct cacctcggcg cgccctgaa   39060 ggacgtcctc ttctccgccg agggctcccc ggaagcgagc acgctgcacc agaccggatg   39120
ggcgcagccg gcgctgttcg cgctggaggt ggcgctgtac cggcagtggg aggcctgggg   39180
gctgcggccc gacgccttga tgggccacag cctcggcgag atcgtggcgg cgcacgtggc   39240 tgggggtgttc gacctcgcgg acgcgtgcgc gctgatcgcg gcgcgcgggc ggctgatgca   39300
ggcgctgccg acgggcggcg cgatggcctc catcgaggcc tccgaggacg acgtgcggcc   39360
gctgctcgat gcccagcagg gacgggcgtc gctggcggcg ctcaatggcc cgaggcagac   39420
cgtcgtcagc ggcgacgagg acgcggtcga ggcggtctgc gaccacttca aggcgcaggg   39480
```

```
gcgccgcgtc aaacggctga cggtcagcca cgcgttccac tcggcgcgca tggagccgat   39540
gctcgaagcg ttccgcgcgg tcgcggcgac gttgaccttc cgggcgccgc agatcccgat   39600
cgtgagcaac gtcacgggcg agcgggcgcc ggtcgaggcg ctgacgtcgc ccgactactg   39660
ggtccggcag gtgcgcgagg ccgttcgctg gacggacggc gtgcgcgcgc tcgaggcgga   39720
cggcatcacc acctacgtgg agtgcggccc ggatggggcg acgtgcgcga tggcatcgca   39780
gtgcgtgacg cgcgctgcga aggcccccgc gttcgtctcc agcctgaacc ggaagggcga   39840
cgaggttcag gcgctcgtca gcgccgcctg cgccgttcat gttcgcggcg actccctcga   39900
ctggagcgca ttcttcgcgg gctcgggcgc tcggcgggtg gagctgccga cctacgcgtt   39960
tcagcgacgg cgatacgggg tggacgagcc gagccctcgc cccgcggagg tccgggcccc   40020
ggataccacg cggacgcgcg tgcacgtgag cgcggacgat ccgacggtcc gcgggcacgt   40080
cgtcggctcg cagaccctct accctgccgc cagctacatc gacctcgcgc tccgtgtcgc   40140
cgcgagcgcc gggcaggcct gtgtgcgcgc cgcgaacatg gcctggttcg cccccgccat   40200
cgtgccgccc gagggcctgt cgctcgacgt ccagctacga cgcacgaagg ctggcctcga   40260
atgcgaggtc tccagtggag actccgacca gcggaccatc catttccagg gcaccctgct   40320
cggcggcgat cccggaccgt ggccggcggt cgacctccga cggatcatcg gagagtgctc   40380
tcttcgtctc gacagggccc acctctacgg catcttcgca aactacggat tcggctacga   40440
ccgggctttc cagtccgtcg cgtggctcgt cagcaacgcg aacgacgtgg tggggcgcgt   40500
ggagctgccg gcgtccgagt ccgcgaccgc cgagcaccac ctccagccga acctgctcga   40560
cggcgccttc cagaccatca tcgggctcga cgcggtgagc cgcgctgagcg ggcccacgcc   40620 cgacgcgggc ttcaacttcg tgccgtccgc catccaggat gtgcagatct tcgggcgcct   40680
tcgccgcgct gcgtacgttc acgcgacccg acgcggcaag gcgcacggct cgccctcgtg   40740
cgacttccag ctcctcggcg agaacggcga gccgatcgcg ctcgtcacgg gcctgacgtt   40800
ccgcaagctc cggtcccgag ctgagctcga cgcgccctcc gcgcccgcgc agagaccgag   40860
caacggagag gccgctcgcc ccaggaacgt gccagctcct gccaatgtgc cagctcctgc   40920
caacgtgcca gctcctggcg gtgaccacgc cgacgcgtct cctcgcgcgc cgtcggcgga   40980
ggtgctgttc ttctcgcccg catgggtccc ggagaagccc gtcatggccg cctccgtgac   41040
gggagacatc gtcgtgttcg gggacgacga cgcgcagatc acccatctcc ggggctcct   41100 gccgctggct cggctgattc acgtccgctc cggaccgggc tttcagcgca ccggtccgc   41160 cgcctacgcg gtccgacccg acagccagga ggatctctcc gcgctctta ccgagttcga   41220 cgacgctcgt tcgaagtcgc ttcgggccct ttatctctgg gagccgtccc gccgcgcggc   41280
cgagggctcg gcgcccccgg gcgacggcga cgtcgcggcg gcgatccgat cgttgttctg   41340
cctcttcaag gctcacatgg ccgagcggcg aaaagggatg cagctcctct atctcacgtc   41400
gtcggcgacg agcgcagtgc cggtgaacga agccgtgctg gcgttcttcc ggaccatccg   41460
cacggagaac ccgacgtatg tgggcaaggt gatcgccgtg gccgatccgg gtcacatcgg   41520
ccgcgcctgc gccacggagc tcggcctccc gaccggcagc gacgtggtcc agcatgtcga   41580
cggcgcgcgc cacgtccgga agctcttctc gcgagagccg gcccctcggg agcgcctgcg   41640
agacgcgctc ccgctggcgc cgggcggcac gttcgtcctg accggcggcg caggcaagat   41700
cggcctgctc ctgacggaca tgctggtgcg ggagtaccag gtgaacgtcg ccctcatcgg   41760
tcgctcgcag ctcgacgagc cccggcgaca ggccatcgac agcatccggt caggtcctgc   41820
```

```
ccgggcgctc tactactcgg cggacgtcgg ggtgctcagc gacaccgagc gggccatcgg    41880
agagatccgc gagacgctcg gccccatccg cggggcgatc catgcggcgg cgatcatccg    41940
cgacagcttc ttcatcaaga agaccctggc ggaggtcgac agcgtgctgc gaccgaaggt    42000
caacggcgcc atctacctgg acttcctcct gcgcgacgat ccgctcgagg tgttcgtctt    42060
gtgctcgggc ctggcctctc tcctgggcaa tcagggcaa tcggactacg cggccgcgaa    42120
cgggttcctc gatggattcg cgatccgcg cgaagcgctc cggcaagcag gccgacgtca    42180
ggggcgaaca atctccatca actggccgtt gtgggggggc gacggaggca tgggcgtgcc    42240
agattacatc gagaccgagc tcctgaagcg gggactcgtg ccgctcgaca tcagcgacgg    42300
cgtgacggcg tttcggcaag cgatcgccat gaaggagccg caggtggcgg tcgtcgccgg    42360
acagagggcc gcagcacggc ggctcctgcg cccgtggctt tcagaggggc gaacggagga    42420
tcatcaatga caagctggtt gctggcgaag acggaggaat ttctcgggga cctggtctcc    42480
gaggtcagtg agatccgccg ggacacgatc tctcccgacg ctgacttcca ggagtttggt    42540
ctcgactctc gcttcgtcat cgcgatgaac tcgaggctgg agcagtattt ttccggcctg    42600
cctcgcacgc tgttcttcga gtaccgtcc atccgcgccg tcgccagcta cctggtcgaa    42660
gagtttcaag accagctcca cgagctcttt cccgacggcg agccagccga ggcgtcgcga    42720
cctgcgcaga gcgtgccggt cgcccgaccc agcggcgcca ttcctagcgg cgcttcgccc    42780
agcggcgctt cgcccagcgg cgccatcccc agcggcgctt cgcccagcgg cgccatcccc    42840
agcggcgctt cgcccagcgg cgccatcccc agcggcgctt cgccacagac ctccacgagc    42900
tccgcggccg atctctccga tctcgcttcc ctgatccagc agatcccgct cccggaagcg    42960
gtcctgtcga gcgtcgagcg tccccgggtc gaccctcggc cggcggcacc cgctccctct    43020
gtggtcagag cgtcatccgg cgaccagagc ggcgatgaca tcgccgtgat cggggtggcg    43080
ggcagatacc cgaaggcaag aaacatcgag gagttctggc gcaatctgcg cgagggccgc    43140
gactgcatcg aaccgttgcc gaaggagaga tggagcccgg atccgtcgga cccgctccgc    43200
tggggcgggt atctcgacgg cgtcaccgat ttcgattcgc tcttcttcgg catctcgccg    43260
cgtgaaggag aagggatgga cccccaggag cggctcttcc tggaggtcgc ctgggagacc    43320
atcgagagcg ccggctacga cccccctcagg ctgggtcgca gcggagagcc agcgtccgtc    43380
ggcgtcttcg tgggtgtcat gtacggcgaa tatcaggtct ttggcgcaga gctgacgctc    43440
ctcggccagc cgaccctggt cagctcctcg tacgcgacga ttccgaaccg cgtctcgtac    43500
ttcctgaact tcagcggccc gagcctggcc ctggacacga tgtgctcgtc gtccctgacg    43560
gcgcttcacc tcgcgtgcgc gagcctgcgc tcaggagact gcaagatggc cctggtcgga    43620
gggaccaacg tcacgatcca tccaaacaag taccggctgc tggaagctgg gaagtacctg    43680
gcgagcgacg gccggtgccg gagctacggc gcggatggcg acgggtatgt ccccgccgag    43740
ggcgtcggcg cagtgctcat caagcccttg gccgacgctc gccgagacgg cgacacgatc    43800
tggggcgtca tcaagagcac gagcatcaac catggcgcgc gcgcgcgcgg ctacacgacc    43860
cccaatccca acgcgcaatc ggcctccctg tccctcgcgc tggagcgcgc gaagatcgag    43920
ccgcacacgc tcggatacat cgagggtcac gggactggca cgtcgctggg tgatccgatc    43980
gagatccgcg gcatccagaa ggccgtgggc cgtgtttcgg agaagatccc gatcggctcg    44040
gtcaagtcga acatcgggca cgcggagtct gccgcgggcg tcgcgggcct cacgaaggtg    44100
ctcttgcagc ttcgggcgcg ggagctcgtt ccctcgatcc actgcgagcc cccgaacccg    44160
aacatcgact tcgacagggc gcccatccag gtgcagcggc acgccgctcc ctggaaccgc    44220
```

```
aggaccatca cgtcgggtgg ggtcactcga gaggtccccc ggcgggccgt cgtctccgcc   44280
ttcggtgcgg gaggcagcaa cgcgcacgtc gtcgtcgagg aggccgacgc gccggcgctg   44340
caacgcaccg tgtccgcaca gcctcggttg ttcgtcctgt cggctcgttc cgtcgagcgg   44400
ctccgcgccc acgcgcagag ctttctcgac ttcttctcga ggatgccgac cctcagggag   44460
gccgaggcga gggagctctt ctacgatatg tgcgcgacgc tgtacttcgg ccgcgctccg   44520
ttcgaggcgc ggcttgccat cgtggccgag agtctgcgga cgttgcagca aaagctcgcc   44580
gcgttcgttt acgcgcctc gcgagacccg gacatcctcg tgagcgatgg gcgatcgctc   44640
gcggccacgg acggcgggca gcgtcagctc tctggcctcg ccgatctggg gcggcgctgg   44700
gtcgccggag aggcggtcga cgcgagcgag ctgtttccgc atccctggaa gaagctggca   44760
ctgcctacct atccgttcga acggcggcgg ctgtgggcgc cttccggaga gaagctgtac   44820
gatctcagat ccgccgcggc gccggctccg gcggctccac cagggaacgg ggcttcaccg   44880
agggaggtcc cagcgaacgt gccacgggcg gctcgtacgg acaccgcaga gacagccgtc   44940
gtgagcggtc cgcagcacgc acggatcgcg ccggccgagc ggaggctcgc cgtggccgag   45000
caggtgatcg aggtggccga gcgcccctca cccctgacc ggggcccgtc gacgagcgag   45060 acgcgggga gcgagagcga tccgcacgtc acgagcacgt tgaacggcca cacgagcgcg   45120
ttgaacggcc acacgagcgc attgaacggc cacgccgcgc gagcgacagg tcccgaacgc   45180
ccggcggcgg ccgttcaggc agcagatcag ggggcggccg tcgagatcgt ccaggagatg   45240
gtccgcgatc tcgtggcgca gatcctcttc gtcgaccgct ccaccatcct gcccgacgcg   45300
gcgctgttcg attatggcct cgagtccgtc agctctgtcg agctcgcgga gcgcctcaac   45360
gcgatgctcg gcacggacat cacgccgacg agcttctacg agttcaacac gctcgcacat   45420
ttcagccgtc acctggtcga gcgctacaac ctcgcggacc ggctctccgg tctgagcgcc   45480
ggtctcgccg gggggagctc cgctcccgcg ggccctccg tcgtggtgga ttcgccgcca   45540
cgagcggccg ccggagccga gggccccgtg gtcggcgcag cggccgccga gggcgctgcc   45600
gcgcctgcgg caggcggacc caccgtcgag gagctctggg ccagcgcgat gcacgccgaa   45660
gggctcgcgg cgctcccgag ccccgagccc cggcgctcgg cctccaaggc tccacgcccg   45720
gcgccgcccg ttcagccgtc ggatcaggcc acgcccgtcg agatcgtcca ggagatcgtc   45780
cgcgatctcg tggcgcagat tctcttcgtc gaccgctcca ccatcctgcc caccacggcg   45840
ctgttcgatt acgcctcga gtccgtcagc tctgtcgagc tcgcgagcg cctcaacgcg   45900 atgctcggca cggacatcac gccgacgagc ttctacgagt tcaacacgct cgcacatttc   45960
agccgtcacc tggtcgagcg ctacaacctt gcggaccggc tctccggcct gagcgccggt   46020
ctcgccgggg ggagctccgc tcccgcgcgg gccagcgcgc ctcgcgccca agggcccgcg   46080
gcgctctcga gctccgagcc ccgacgctcg gacgccggga tcgagctgca cgtgatccct   46140
ggcgtcgacg gacacgccgt ggagttcgcc acgctcggct cgggcgtacc gctcttcgtg   46200
ctcggtggcc tgctggcgac ccatgatgcg ctgaccttga acccggatat cctgtcgctc   46260
gggcagacct accgggtgat catggtgcat ccgcctggcg caggccggag cgagctgccg   46320
cgcggcgagc tcacgatgga tttcatcgtg cggcaggtcg aaggcgtgcg gcagtccctc   46380
ggcctctcgt ctgtcgtgct ggtcggctac tcgttcggtg gcctcgtcgc gcaggcctac   46440
gtcgcgcagt ttcccgagcg ggcgtcgaag ctcgtcctgg cgtgcacgac gtcggacccg   46500
gcgagcgtcg tgaacggcat gcacctcgtc gcggccgaag cgcagcgcca cccggacggc   46560
```

```
ctccgggcgc tgcagttcgc cgacgtgagc aagttcccgc tctactccca gctcagcacg   46620
cggctccggc cggagacgct cgcttacccc gccattccga ccctgatcgt ggcgggagcc   46680
gaggatcggt acgtgccgac catccacgcc gaacggctcg cgcgcgccaa tcccaacgcg   46740
acgctccaca tcgtcgaggg cgcggggcac ttcctcggcc tgtctcacgg tggcgtgctg   46800
gtccacctcg tgaatggctt cgtgctcggg gacaggaccg ctccggcgag gtctcctgcg   46860
gtcagcgcct cgcggcgcgg tgggttgcgc aagatgagcc aggagtcggt cggcgcgctg   46920
aagagctacc tggaagaggg agagatcgct tcggggggtgg aggcctcgcc cgtcgcgggt   46980
caggtcggct atttgctcaa ccggctcctg agcggacagg aagcgccgag cagcccctac   47040
cactgcttct tcatgccgtc cggcctcgag gcggtcgacg cagcgctgcg gttcggacgc   47100
cgtcgggcaa agctctccag gggcctcggc gacgcgaaga cgctcgtcct cgatcccgag   47160
ggagctctcc gccggcattt cgagttcctc ccgcaggagc ggctcttccc cgatctgatc   47220
ttcgtgggcg aatcgcgcga gctgctccgg ctgctgcaga gcgccgagga cgtcggcgcc   47280
gcgtacgtca ccacggcatg cgatgacgcc accctcgaga cggtcgcggc ggagtgcgcc   47340
cggcgcggga tcgtgtcggt gctcggagag ctgcacgcgg acaccggcga gctcgtctcg   47400
gcgaggctgc gctcgaagcc tgacgtcgtg gtgctcgacg aggccatcgc tggtttcgag   47460
ctgccgttcg gcgtgtgcgc gatacggcgc ttccatgaga gcggcgtgtg gacgcgccag   47520
cccgaggagt tcgcggtgcg agtcccgggg tcgatggcgg ggcccgcgct gaccgtcgtg   47580
agggagaaca tcctgcggcg attccgcgcc gtcgtgacga acgacaccac cgcgaacctg   47640
cgcgcgatcg ccgtggatca acggcgcacg aaggaggctc accggagcta tgtgaacccc   47700
gtgctcctgg agtcgctcga cgcgttcgga ctggcgggcc ggcaaaggca cgcggaccga   47760
cgcggctatg agatcgagcg agatgacgga agctcggccc gggtcatcaa cctgtacctc   47820
gtgacgagcg cgtcgtttcg agggcacacc ggctccgaga tcgcgcagtc ggtcctgggc   47880
acccacgaca tcacgaggga ctactgggcg gatctcgagc ggcgcatacc gcgcgagacg   47940
gacttcgggc gggtctttcc cgcggcgggc cccgcgacgg cggtcgagac ggcggtgaag   48000
ctcgggctgc tcgccgcgag gaagggctcg gcgctgctcg tcctcaaggg gagccccatc   48060
ttcacgcggc tcggggcgtt ggtctcgcac gcggagcccg gctcgccgct ggaggccctc   48120
gtggagagct gcccttggtc caaggtgatc gccgtcgatc cgttcggcga aggcgcggcc   48180
gccgagctcg aagcgaagct gacgtcggac gacgtcggat tcgtctggct cgagacgctg   48240
cagtcggact ggggtggtct acggagcgtt ccggatgccg tgctcgaggt gatcgacagg   48300
catcgggagc ggtcgggata cctggtgggc gtcgacgaga cctacacgag cctgggttgt   48360
ggccggatgt ttcactggca aggcaagctc gcccgccccg atgtcgtcgc ggtgtgcgtg   48420
ggctggacgg actgccagct cctggcgggc tacgtcctca ccaccgaaga ggtcgcggcg   48480
cgcgcgcggc agcgcaacga ggcggtggtc tccgcgctgc aggagcaact tcgctgccag   48540
ctcacggctc acgcgacgct gcgcctcctc gacgtcctga aggaggaccg gatcctggcg   48600
caaatcgccg agaccgagcg acgattctcc ggcgcattga acgacttcgc ggcggaatgc   48660
ggcatggtca agcgcgtctg gggggaaggg ctcttctggg cggtgcagtt cgacctcgat   48720
gggtggcccc gcttcgtccg tgactggttc tcgtcattcc tctggagtga gtgcttgcga   48780
gatccggtgg cgcccgtcgc ggtgtcgatg caaccgctga cgccagcgtg catccgcgtc   48840
gagccgcgct acgacatccc ggctgcggag ctcgacgccg cgatgggcac gctgaagcgc   48900
gtgctcggca agggtgtgga ggggatcgtc gcgagcgtcg ccgacgacgt cgagcgacgg   48960
```

```
ggagacgccc gccgcgcaga gctgtttcgg aggattcttc gagggttcaa gacgacatga    49020
gcgctcaacc tgagtactgc atcgttggcg gcgggcccat cggcatcggc atcgggaagt    49080
gcttcgccca ggaggggctg aaattcacga tcgtcgaggc cgatgaagac ttcggtggca    49140
catgggcgct gtcccagcgt tcgggcctcg tctacaaatc gacccacctg atctcatcga    49200
agaagaacac gcagttcctc gacttcccga tgccggagga ttacccgcat tatcccagcc    49260
atgcgcagat gctgtcctat ctgcgcagcc tggccacgca ttatggcctt tacgacagag    49320
cattgttcgg cacacgcgtc gagcacgtgg agccgaatgg cgcgggctgc cgcgttcgcc    49380
tctcgaacgg agaaacgcgg acgttctcgg ccgtcgtcgt ggccaacggg cgcatgcgca    49440
cgccccTgat cccgcgttat ccgggggtct cagcgggga gacgatgcac tcggccgcct    49500
acaagtcaca cgaggtcttc gcgggaagc gcgtgctcgt catcggcggc gggaactcgg    49560
gctgcgacat cgccgtggac gcagcgctgg cggccgagca gacgttccac agcacgcggc    49620
gtgggtacca ttacatgccc aagttcattc acggcaagcc cacccaggaa tggctcatgg    49680
acatggggtc gaagttccgc tcccaggacg attactggtc gttcgtccag cgggagttca    49740
aggcggccgg ctacgacccc gtcgattacg gtctgccgcg ccccgaccac gccattcatg    49800
aggcgcatcc gatcttgaac tccctcgtcc tctattacat cggtcacggg gacattcatc    49860
ccaagccgga tgtccggcgc ttcgagggac ggacggtaga gttcgtggat ggcacgcgcg    49920
cagaggtcga tctcatcctt tatgcgacag gctacgagat ggatttcccg ttcctggcgg    49980
aggatctgag gccgagcgac ggcgcgctgg agctgttcct gtcgatgttc caccggaagg    50040
ccgacagcct cgtgttcgtc ggatatttca cgcggcgtc ggggctcggc aacctgctca    50100
actgcgcgcg agctctggtc acagactatt tggtcgcccg cgagaagaac acagatgcat    50160
ttcgagtgct gcgcaggctc atccaagggc ccgagcccga tatcggcaga ggtcgcttcc    50220
tgaactcccc acggcaccgg gtcgagacg atctatggaa ggcgatgaag gtcatgaatt    50280
tcttccggtc agtgctcaat ccggcacggg cagccgggga cgtggtgcgc gcctgacgga    50340
ggccaagcgc gcttcgcagc cgcggtcgag tcgacccagg cggggcgacg tgagagcctc    50400
atgcccacgg cgctacctcc gcgggcggca cacgctcgac tcgccccgag actgcgctga    50460
atcgcttgac gtcagagccg cttcatcgta atcgtgactg aataaggctg caccttgcag    50520
tgcatgagca gggaaggaac aagctcgatg aacattggga gtccgttgcc gcccattgaa    50580
aatgctctgg acctgttcaa gcattacgcc acgagcgctc ccgaagcgag aatcgccgta    50640
ttcatcgagg aggaggggca ggagcagggc ctcacctaca gggagcttga gcgcgcggcc    50700
acgaacctca gcctcgagct cgcgtcggtc ccgcgccgg gtgacagggt cctcgtcgct    50760
tacgattccg gtcccatgta tctggtgggg gtatgggcgg ctctttatgc cggcatgatc    50820
gccgtccccg tagatccgct cggccctgat cgccccgcgg cgaacctcac gcgattgttg    50880
aacgtcaccg ccgactcggg cgccacggtt tgcatcgcgt cgcgcagcat gctcgatgcg    50940
gtgaagagcc acccaggcgc gcggcagctc acggagcagc tccgatgggt cgtcccctcg    51000
ctccccgatc tcctggggcg agcgcccggc tcccgccgg ctgccctgcg gaccgagaag    51060
gacgtcgcga tgctccagta cgcgtcgggc tcgaccggcg cgccgaaggg cacgatcgtg    51120
acgcacgcca gcctgctgat gctcgcgcgc gcgctgctca tctcgacctc ggccgaaagc    51180
ccgttcggcc gccccgacgt cgaggtcacg tggctccccc tgacccactc gacggctgga    51240
tacggcttga tcatgaagtg cctgacggga gcgacgatgt ccgcgtggta catcgcgccc    51300
```

```
agcgcgttcg cccggtcgcc cgcgatatgg ctgcggacga tctctcgcca caagggaaag    51360
caggtgtatt ccgtcgctcc gaacttcgcg cttgactggt gtgtctcgtc gacgacggag    51420
gccgagcgca agcagctcga tctgagctgc tggacgcacg tcatgagcat ggggagaag     51480 gtgcgccccg agacgtggaa ggcgttctcg gacgcgtttc gcgagagcgg cttccacccc    51540
aagctgttca tcgccgggta cggcatgtcg gagacgggat atgtctccgg ctcggtgaac    51600
ggcggcaaga cggttcgctt cgatcgtgcg gcgatggacg aaggcagctt ggtagaggcg    51660
ccggagggcg ggatccttct gctgtcgtcg tccgggttca cccttccgg cgtgcgcgtg     51720 gcgatcgtgg acccggagac cagagaggtc ctcccggagg gcaagatcgg cgagatctgg    51780
gtgtcgacgc ccacggccat gacgggctac tggaaccggc cagaggagac cgagcagcag    51840
tttcgcgcgc gggcggccga tggaagcggc cccttcttcc gcagcgggga catgggcgcc    51900
ttctatgggg gcaatctatt cgtgacgggc cggcgaaaga gcatcgtcgt catacgcggg    51960
cgcaagcact atgcggaaga catcgagtcg acgctcgagc gtgcgctcga ctggcttggc    52020
gcgaactcgt ccatcgcctt cgcggacgac gtgaacggcg tcgaggagct gttcatcgcg    52080
gtcgacccga ggggcgcgcg cgacggcgtc ggcttcgagg aacgcacgga cgccatacgc    52140
agcgtcgtcg cgcgtgagtt cggcgtccgc gttcacgagg tcctgttcct ggccgcgggg    52200
cagcttccgc ggaccagcat gggcaaggtc tcccgggtct cttgcaagga cctcttccgc    52260
agcggcgagc tcgagatcgc ggcgcggtcc ggcagcatcg cgcgtggcgg cgccgacctg    52320
ccggccgtgg accttcgcgc gatcctcgac gagccggacg cggagctgcg cgtcgcgcga    52380
atgaccgagt acatcaggag cctgctttcg gcatcgctct ctgttccggc cgacgcgctg    52440
agcctcacga gtcgttcga cgagcttgga gtcgactcga tgacggggt ccggtttcgc     52500 ggcgagctcg tccgcgcgct cggattggag ctccctgaat ccatcgtcta caattatccg    52560
accatcgcac aactcgcgtc cttcgtgtgc gagaagctga ccggcaccgc tggcagcaac    52620
gatgcggagc gggcggatcg aggtcccgcg gcgctcgcgg ctctcgacgt cgagagcatg    52680
tccgaggagg ccgccgcggc cgcgctgcgc gcccacctcg atggtcgaaa gtaggaaacg    52740
ggctggccga cgccagcacc ccggagtgaa gtgagatgag cgaatccggc gaactgtctc    52800
tcacgaagcg cgcgctcctc gccctgcaga aggcggagct cgagatcggc cggctccggg    52860
acgctcggcc ggagccgatc gcgatcatcg gcgtcggatg ccgcatcccc ggcggcgcca    52920
cgtcgccgag ccggttctgg aagctgctgg aggagggctt cgacgcgctc gccgagatac    52980
cggccgcgcg gcggaagctg ttcgagctcc agggagcccg cagcccgacg tcgggagggt    53040
tcctcgatga gatcgacaag ttcgatccat ccttcttctc gatctcccca cgggaggcca    53100
tctccatgga tccggcgcag cggctcctgc tcgaggtctc ggtcgaggcg ctcgaggacg    53160
gcggcgtccc gatggcacag atccggggca cccggacggg gacgttcatg gggttctccg    53220
ggtacagcgg ctatggctcg ctgaccggtg cgcaggtcga gcagctctac gccgtgaccg    53280
ggctctcgat caacgtggcc gccggccgga tctcgtacgt gctcgacctg caggggccat    53340
gcgtgtccgt ggacaccgcc tgttgctcgt cgctggtcgc ggtccacctc gcgtctcaga    53400
gcctccgcag ccgcgaatgc gacctcgccc tcgccggagg cgtcaacgtg atcgcggcga    53460
tggccggcaa cgaggcgatg gcggccacgg gagcgctctc ttcgtccggc ggacgttgca    53520
ggacgttcga cgcggcggcg gacggctaca tccggtcgga aggctgcggc gtggtcctcc    53580
tgaagcggct gacggacgcg atggaggcgg gagatcggat cctcggtgtc gtcgccggct    53640
ccgccgtgaa gcatgacgga catagcaacg ggctcaccgc gccgaacggc cgcgcgcagc    53700
```

```
agcagctcgt ccgcgaggcg ctggccgccg cgcgcgtccg acctgaagag atcgactaca    53760
tcgagacgca cgggactggc acgccgctcg gcgatcctat cgaggtcgat gcgctggcgg    53820
aggtctttgg cagctcgcac ggccccgacc ggcgcatcat gctgggctcg gtgaagacca    53880
acgtcgggca tccggagggg gcggccggca tcgtcggtct catcaaggtc ctcggaatgt    53940 tccgcgcgg catggtccca cgtcatcttc acttcaacac cccgaacccg cgagtcccct     54000
gggattcggt cccttcctg gtcccgcgcg acacgctccc ctggcctgcc accgacaagg     54060
tgcgggtggc cggcgtcagc gctttcgggt tcagcggcac catctcgcac gccatcgtca    54120
tggagccgcc gaaggcgccg gagcggagcg tggacgtcgg tccggcgacg gcggggcgcc    54180
cgctgctcct gcccatctcc gccaggaccc cggaggcgct gagggcctat gccgcgtcct    54240
atctcgatca cttgagcgcg gaggcgacgc cggaggagac cgatcgggat gtggcctata    54300
ccgccagtct gcggcgggat catcatgcgc accggctggc ggtggtgggc agcgatcgcg    54360
cagcgtggcg cgagaagctg cagagctacg tgtccggcga gggctgccgt ggtctggtcg    54420 aggggtggt gcccgaagcg cgtccgcgcc tcgccttcgt cttctgcggc cagggtccgc      54480
aatggtgggg gatgggcgg gagctgctgg acaaggagcc ggtgtttcgc ggcgcgctgg     54540
aagcgtgcca cgagcgcata cgggaggcgg gaggcccatc gctgctggac gagctgcggc    54600
gcgaggccga cacgtcgagg ttgaaccaga ccgaggtggc ccagccggcg ctgttcgcgc    54660
tgcaggtggc gctggcggcc ctctggcgtt cctggggagt acaggcggac gccgtggtgg    54720
gtcacagcat cggtgaggtg gccgccgccc acgtcgccgg cgcgctgagc ttggaggacg    54780
ccgcgcggct ggtggtccac cgcggtcgga tcatgcagcg agcgaccggc ctcggaaaga    54840
tgctgtctgt ggcgctaccg ctctcggcgg cgcagcggat cgtgagtgat tacgccagc     54900 gcatctccat cggcgcgagc aacagcccca catcgaccgt gctgtcggga gaggcagcgg    54960
ccctcgatga ggtcgtcgag cagcttcagg ggcggcaggt cgaggccaag tggctgccgg    55020
tcgagtatgc cttcacagc gcccagatgg agggctttgg ggaggagctg agcaaggagc     55080
tgcgcgggct cgccccgggg gcgaacggtc cgctgctgat gtcgacggtc accgcacag     55140 agcagcgcgg gacctcgttc gacgcggact actgggggca gcagatccgc aagccggtcc    55200
tcttcgcgca gtgcgtggag gagctggcgc gcaaagggtg cagcctcttc ctggagatcg    55260
ggccccaccc agtcctctcg gcgtccatga ccgagacgtt gctcgcccag gagaagagcg    55320
gccgcgtggt ggcctcgctg aggcgccgcg aagaggaggt acccacgctc ctcgaggcgc    55380 tgggcagct ccactgcgcc ggctacccgg tggactggtc gaagcagcac ccggtgcgcg     55440
gccgtaccgt ttcgctgccc acgtatccgt ggcagcggga gagctactgg ctcgaagccc    55500
cgaaatcgca gacgccgcgc cagcacggcg cggagcacca ctatgagacg gaatggcgcc    55560
tggccgagcg cgagcggccc gccgagcctc ggcggggcgg atggctgatc ctggacgacc    55620
aggcggagcg cgctgctgcg ctgcaggact acctcgaggc gcgcggccag acgtgtgttc    55680
gtgtggttgc tgccgacacc tacgcgcggc gcggcgcgcg cgactaccag atcgacccac    55740
gggagcccga gcactttgcc cggctcctgg gtgaacagga ggtggtggac gccctggccg    55800
acgcctctcc ttcagatcgg tgcggcgtgg tgcacctgtg gagcgcgcac agctcgcccg    55860
cgcccaccct cgaatcgatc cagcaggcgc aggcgctggg ttcgatcagc gcccttcacc    55920
tcgtccaggc cctggcgcgc gcgggatggc gacagccgcc gcgcctctgg ctcgtgacgc    55980
aggaggtcca ggccatcaag aacccgaccg tctcggtggc gcaggcgccc gtgtggggat    56040
```

-continued

```
ttggcgcgac cgtagcgctc gagatgccgg agctccagtg caccctgctc gacctggacg    56100
ccacgccgaa catcgatgct ctgggacagg aactcctctc cgccagcgac gaggatcgga    56160
tcgcgctgcg cggagccgag cgtcacgtcg cgaggctggt cccgcatgta ccggagcagc    56220
gcccggcccc ggagccgttg tcgttcaagg ccgacgcgac ctacctcctg accggaggcc    56280
tgggggggcat tggactggtg gtcctggagt ggatggcggc gcgaggcgcc aggcacttcg    56340
cgctgctggg gcggagcggc ccatccgcct cggcgcaacc cgtgctggac cggatgcgcg    56400
aggacggcgc gcaagtccgg actttctccg tcgatgtcgc cgaccgggag cggctccgca    56460
ccgtcctggc gcagatccag acgtcgatgc caccgctggc cgggatcatt cacgcggccg    56520
gggtgggaga tcagaaaatg atccccgacc tggacgggcc ctctctgcag gcgatcggcc    56580
ggccgaaggt cgacgggagc tggaatctgc acgagttgac gagcgagctg ccgctcgact    56640
tcttcgtcct gttctcctcc gtctcgtcgc tcttcggctc gcacgggcag tcgagctacg    56700
ccgccggcaa cgccttcctc gacgcgctgt cgcaccaccg gcgggcgctc ggcctcccgg    56760
cgctcagcct gaactggacg gcgtggaccg acgtcgggat ggcgacgccg atcatcgccc    56820
acacgtcgcg gtacctcgcc acgcaaggca tgggcgccct ctcctccagg gagggcgtcg    56880
ccgcgctgga gcagctcttt cgcgcctcct cggcccagat cggcgtcgtg ccgctgtcga    56940
tcccctcgct gccgaggaag ccgttctatt ccgtggtggc tccgcccacc gccccgacgc    57000
cgacggcgca gacggtccgg gcgtccgagc gcatcgctgc gcggccaccc ggggagcggc    57060
aggaggcgat cgagggcacg ctgcgggagc tgttcgccag agcgctgcgg atgccgcctg    57120
acaagctgaa gctgaccgag gcgctccaga acctgggtgt cgactccttg atcgccctcg    57180
agctccgccg ccgcatcgac gaagagctcg gcgtgaagct gcaggccgcc gagatcgcca    57240
gggtcgccaa cgtgcgtgag ctggcccagc tcgtgaccgc caagttcgac gcgctccacg    57300
gcagcgcggg cgtggcccag caagcgcggc tcgaggtccg cggcccattg accgtcctca    57360
agcccagccg gcagaggccg cgcttgcggc tggtctgctt ccccgcttcg ggcggcagcg    57420
ccggcgactt cgccgagtgg gcgaaggtga tgccggacga ctgcgagctc gtcgccgtgg    57480
aatacccggg gagcggcgcg cggcagctag agtcgtgcga gcatccgctg gccgcgctca    57540
cgctgcaagc ggccggcgcc ctcatggcga tgcccagggt gccgctcgtg ctcttcgggc    57600
acagcctggg gggcctcatc gcgcacgcga cggccgtgga gctggaacgg cacgccatgg    57660
gaccgtcgtg cgtggtcctg tccaatccag ccaatgtgat caccgtccag cgggacctcc    57720
cccgagacgg attccgtgac cagaagttcc tgacatggct ggccaggtcg accgggattt    57780
ccatcgagcc cgaagcgacc gacagcgatg ccacgcgtca gttcttgaag acgttcggcg    57840
agcagctcgc gtggacgttc gacttcgacc tggggtggcg ggtctcctgc ccggtcatta    57900
tttcgtgcgg tcgagacgac acgacgctcc acgccgagag cctcgagttc tggaggcgca    57960
gcggaggcga tctggaggag tggaccttcg ccggagccca cgactacatc cgccaggagt    58020
cgccgagat cgtgtccaaa atcatgaaca gggctgcggg taaagacaga acatgagccg    58080
tgcaatcgtt atcgggggca gcatcgcagg gatgtgcagc gctcgtgtgc tgtgcgattt    58140
cttcgatgag gtcgtgatcc tggaccggga ccagtttccc accgagatcg cgcctcggcc    58200
tggcgtgccg cagagccggc atacacatgt gctcctgccg cggggagagc aggagctcga    58260
ggagctcttt cccggctttt ccgcctcgat gatggccgcg ggtgcgctga aattcgacgt    58320
cgggacgggg atggcggtgc gacgcgtctt cggctggcag acggtcggac ccacgggccg    58380
cgagctactc tgggccagcc gtgacctgtt cgagggcacg atacgctcgc tgatgcgaca    58440
```

```
gcagaccaaa gtgcgcattc gggaaggctc tcaggtgctc gcgctgcgca gcacagcggg    58500
cgagaggcca aggatcaggg gcgtacttct gcgcgatgac gctgcggagc aggagcttga    58560
agccgacctg gtcgtcgatg ccagcggccg gcatacgcgc gccgagcagt ggctgaccga    58620
gctcgggcta cctgcgccca agacgcagtg cgtcgactcg cgcgctggct acgcctcgcg    58680
gttctacaag gtgcccccgc ccgagcgccg gccgtcggac tggtggtgga agggtctgtg    58740
ggtcgaggcg gagcccgacc ggccgcgggg cgctgtcgtc tttccgatcg agggcgatcg    58800
ctggctggtg accgcctcgg gcttcagcgg ctcgtatccg cccacggacg agcaaggttt    58860
tctcgagcac ctcgcgagcc tgagctcacc gatcgtggct cgggccgtgg cgctggccga    58920
gcccatctcg ccgatctacg gcaaccgctc catggccaac gtatcccgtg cttacgaccg    58980
ctgggagatc cagctccctg gcttcgtcgc tgttggcgac gcggcttgcg ccttcaaccc    59040
cgtctacggc cagggcatgt cgacctcgac cgtctctgcc gtcatcctgc gcgacgtgct    59100
gcgccgccgc ggcccaggcg cgggcttcga gccgggcttc ttccagcagc aagccaagtt    59160
cctgcgctcg gtctgggatt cgccacgcg ctccgatttc cgatggccgg ggacggtagg    59220
cgagcgcccg cacacgccgg cgatcatcgg cgcgtacgcg aagctcgcca tcgagtctgc    59280
tcatcatgac agcgccatac ggcgccatct gttcgacctca ccggctcggc    59340 gaccttgctc ttcgagcccc tcttcgtggg caaggtgctg ctctccgctg gccagcgtcg    59400
gctccgccag cgcctgctcg gcacacctcc gatccccgaa tcgccgcccg tgccgcggg    59460 tgtacctcga tgggcggccg cgcgccgccat gtgatggacg ccgcgagcgg gcgccagccg    59520
agagcaggcc tgctccggcg gaggcgtggt tgagtcacat ccgcttccca tggtaggaaa    59580
tgggcgaacg gaccccttcca gaacaaggag aatcaacaat gcgttacatg atcttcgtag    59640
cgagcgacga gtcgttgtgg gcgaacgcga ccccaagca gcgggaagag gtctacggca    59700
agtacatcca gtacaccgag gagatgcgga aggcgggcgt cctgcttgga ggcgaatccc    59760
tccagccgac gagcaagggc gcgcgcgtat cgatccggaa cggcgagcgg gtcgtcgtcg    59820
acggtccgtt cggcgagccg acggccatcg ggggccatgt cctcatcaag gtcaactcga    59880
aagaggaggc catcgaatgg gcggcgaaga gcccgggcgc cgtctacggg accatggagg    59940
tgcgcgaggt gaccgagttc ggctgacgcc gctcggtga aacgctcgcg cagcggcgtg    60000
ctgggacggt gatcacgagg cggcgagcgg cagcctgcgg gccgcgcgcg tggcctcgtg    60060
cccgtctccc gcctcaggcg tcgcctcggc cgcctgccca cggtagatcc gatcgatccg    60120
gtcgcgcgac gcgaccaggg ccttgtcgaa ccgaccaagg acattgccct tcaggatccc    60180
gcgcttgtcc gccagacggg acagcaacct catgtcaagg cgcagctcga gatccatggc    60240
cacccggagg ggaggccaga tcaatgagcc gagcccgaac tcgctccagc gccccaagct    60300
cgcgaagagg aacgtgtaga tctccgaaga ctccgggccc accggattga agaacacggc    60360
cgaccgaagc gggtatgtca cgacctcccg ggtcctcggg ttgatgaagg agtggtcgta    60420
gatcgcgtgc accggcgaga accgcgccgt ccattgacg acgaatttcg cgtcgtgcgg    60480
gatgcggaac atttctcca cgatccgggg gatgggccgc ttcggacccg tattgacgac    60540
ctggacggcg tcgtcggaca gggttacctg cgcctccacc tgcggcatct ggtcgagcga    60600
gtagccgagc atgaagtgga cgaacggcgt gtgctcgacc tcgatgaaat tgtcgagcgc    60660
cagctcgaac ggcacggcag cgcggtgccg gaggacaccg gccggcacgt acccctcggc    60720
atcgaagcgc gggaacgtgg cctgcgcccc tgcgcgcttc acccagattg cgccgtaccg    60780
```

```
ctccaccgcg tcgaacacat catcgcgccg cgcgcacggc cgtgccgccg gggtggcagg    60840
gatgtcgccc cggccgtccg cggcccagcg ccagccgtgg taggcacaca ccagccggtc    60900
gccctctacc catccctcgc tcaggcgcat gctgcggtgc gggcagcgat ccgtgaacgc    60960
cccgagtccg ccgctcgatg tccggaacac cacgatctcg cgacccgcga gccgcacgct    61020
gcggggcttg cggcggagct cgtggctgag gagtaccggg tgccaatggt cgagttcagc    61080
catgatcaat tcaccccctcg gagatgccgc gcgacgcgcg gcgcctcggc tgcgatgtcg    61140
cgaagctgcc ctgtgatggg attgcggaaa ccgatgaaga acagcccgg cgtcggcgtc    61200 ggtgcgccat gccagcgcgg gtagccgcgc tcgtccgtga agcgcgccgc gtcctcgagg    61260
aagtcgccga gcccggcccg gtagccggtg gcgagcacga cggcatcgaa gggcagctcg    61320
cgaccgtccg tgaagatcac gccggtctcg gtgaacgcgc gcgggccggg gaccaccgcg    61380
atctttccct gctggatcag cgcgagcgta cccatatcga tgagcggaat acgaccttcc    61440
ttcacggccc tggtacccgg gccgatctcg ggccgatgga tccccagcg cgacaggtcc    61500 cccaccgtgc gggacaggaa tgcggtcgcg agccggtccc ctacggccgg cgggagggct    61560
ccgtagaggg caagggcact gaactgggcg gggagcctga gcggatctcg cgggatcacg    61620
tgaataccgc tgcgcgcgga gacggtcgtc tccgccgcat gctcccagag gtccatcgcg    61680
atctcgccgc cagaattgcc ggagcccacc acgagcacgc gctgaccgcg gaatgccgcg    61740
cccgacccgt aggtggagct atggaggatg ggcccgcgaa agcgctcctg gccgggccag    61800
gtgggtacgt tgggaagacg gctgtagccc gtggccacga cgagggcgcg gctcgtgaac    61860
tctcccgcgc gcgtctgggt cacccaccgc gacccgtcgc ggtaagcgcg caccacctcg    61920
gcgccgaagc gcggctccag gcggaagcgc tcggcgtagc gctggaggta atcgaccatc    61980
tgcgcccggg agggatacgg cggggcatat ctgggccaag cgagcccggg cagcgaggag    62040
aattgcttga ccgtgtggag gtgcagccgt tgatagtggc gccgccagct ggcgccgacc    62100
gcatccgatt gctcgagcag gacgaatggg atgccccgct cgcgcagaca ggcgcccacc    62160
gctagcccag acggaccggc gccgatgatg atgacatggc tctcctcgat cacgaccgga    62220
gtttaaccga atttcgtcca gataccaacc acatcgactc gcggagcgag cgacgcgggc    62280
ggaccgccta caggaggtcc gcgagccggc cgagcagggg agtgcgcttg aacgtagcgc    62340
ggatcgccgc gcgcatcccg cggtacttgg ccgtcgtgta cgggaacagg agagggctgt    62400
tcagcggcat cgcaaagcgc tcgtggttga cgtgacgcgc gtagcacatc gcgcgcaacg    62460
agtcgtccga gtgcacgcgg ccgtagcccg agttcttgat cccgccgaac ggcgcctcgg    62520
gcgcgcagta cgagacgagc acgtcgttga tcatcacggt gcccgcctcg atccgctcgg    62580
cgaccgcccg cgcacgcgtc ttgtcccgcg agaagacgta cgccgtgcagc ccgagcggcg    62640 agtcgttcgc gatccggacg gcctcgtcct cgtcgcgcac tttcatgatg gggacgaccg    62700
ggccgaagat ctcttcgcgc atcacggtca tctcgggggt gcagcgggtc agcaccgtgg    62760
gctcgaagaa cattcccggc cccggcctgc gccgcccgcc cgtggccacg agcgcgccgc    62820
gcgcgacggc atccttgatg tgcgcctcgg cgatatccat ctgctttgcg aagatgatcg    62880
cgcccacgtc cacgtcgtcc gcgcgcgggt cgccctggcg aagctcacgc gtgagcgcca    62940
ccacgcggtc caccagccgg tcgtgcaccg cctcggtggc cagcacccgc tcgaccgaga    63000
tgcatagctg acccgaattg atgaagccgc cggcgacgat cgaccgtgcg gtgcgctcga    63060
tctcgcagtc gtcgcaggcg atgagcggcg ccttccgcc gagctcgagc acgcacggga    63120
tcaaccgctc agcgcacgcg gccccgacgc gccgcccgga gctcaccccg ccggtgaaga    63180
```

```
ccaccttctg cacgccggcg tcgatcagcg cagccccggt gcgggcatcg ccggtcacca   63240
cctggaatag atcggttgga atcccgatcg cgtccacgac ttccttggcc ttgagcagcg   63300
tgagcggcgt gacctccgag ggcttgacca ccacggcgtt accagcgatc agcgcctcga   63360
taacgctgcc catcgggatc gccagcggca gattccacgg cgagatcacg cgacgacgc    63420 ccattggcac gtacgtgacg tagctcccac gccacttcat atggtgtagc gtgatggacg   63480
tatcggcgag gatccggccg gcgtggcgcg tgaagtagtg gcacgcgtcc accaccgtga   63540
tccactcggc gagcgcgtcg ttgcgcggct tgccggtctc gagcaccacc gcgtccacca   63600
ggtcgtccag ccgctcgacg aatgcgtcga tcacgcgcgc cacgcgcccg gcgcgggtct   63660
cgatcgggag ctgcgcccag gcgcgctggg cgaggcgcgc gcgctccacc gcggcgtgca   63720
cctcggcatc gcccatcagc ggcacctcgc ccaggcgcga gccgtcgatt ggcgattgga   63780
ccacgagcgt gcgggtggag ggcgtcgtcg tcggggatgc gggaaaggct tgggccatga   63840
gcggctcctc gtttgctcga aagcggggcg gcagcttacc actcgcgccg gcggctcgc    63900 aatgggcgtc ccgcacgccg cgcgcgtcct ctgcggcgct cacgcgtggt gtggcagcat   63960
gggcgccagt ccttgcacga gtgccatgac ggcggacgcg agccatgctc cgaaacgtcc   64020
gaaatacgcg gcgcaccacc tgggcttgac aggatgacgg tcccgggtct ttctacgcga   64080
catgtctttc atttgtgcta caagccacag ctcggcgggc tcgcgcggct ccggaggagc   64140
gcaaccagct cctgggacgc gaggcggcca cggcagcgac agttggagcc gcgcgcggac   64200
aacgccaccc tgaacgcccg gcttcccag gcaccgctgg cggacacgat ggagcccaag    64260
gcgcacggaa cgatccccga ggaaatgatg caatcgacgg ccaccatcgc cccctggca    64320 gtcctgttcg tactgatggc catcgaggcg gtcgtggccc ggcatcggcg cggtgacacg   64380
acgtaccgcc tgcctgacac ggtggccagc gtgggcgtcg gtgtcgggta cttcgcgctg   64440
gtcgcgttct tcagcttcat ctcgatcgtg gtctacgaca tcgtctatga gcgctgggcg   64500
atcacgcacc atgctcgctc ggcggtgacg atcgtcttca ccatcttcgc ggcggacttt   64560
ctctactacc tgttccaccg cgccagccat cgcatcaacg tcctctgggc gatccacgtc   64620
gtacaccacc agagccgcga gcaaaacctg gcggtcaacc tccgcatgcc gtggctccag   64680
ccggcatacc agtggttctt ctatctgccg ctcgccttcc tggggatacc tccgccgtc    64740 ttcttgctcg cgcgcggggt aagcatctct tacaacgtct tcactcacac gcgcgcggtc   64800
gggaagctcg gcccgctcga gtatgtgctc aacacgccct cccaccaccg cgtgcatcat   64860
gggatggacg agcagtacct cgactgcaac tacggcggga tcttcatcgt gtgggatcgc   64920
ctcctcggga cgttcgtccc ggagggcaaa gagccgacct acggaacgcg cagaagggtg   64980
gtctcgtgga atccgatctg gctcaacgtg gagccgttca tccacctcgc gaagctatcg   65040
cgcgcagcca gatctccgtg ggatcgcgtc aaggtatggt tcatgccgcc cgagtggcag   65100
cccgccggcg tcctggaggc cagcgctccg cccgagccgc gcgacgtgga gagccgtggt   65160
tctacggctt cgtcgatcgc ccagatggcg ctcagcgtcg gcgtcacggt ggtcatcggc   65220
gcgatggtca tcatgtacac gggcacgtcg tcgacgatgc cgaggcttgc cctcctcgtg   65280
ctgctgctcg cgtcgctcgg cgcgcatgct cggtctctcg agagtcctgg cttcgcctgg   65340
aggtttgagc tcgcgcgcgc agccctgctc ctcgccgtcg cgggctggct cgacgccagc   65400
ggagcgaggc cgctgccagc cgtgccctg atgccggcg gcctctcggc cgcgagcggt     65460
gtcctgttcc gcctcgggcg ccgcccgcgc ggctcgcggg cggagggggc cgaggacgcc   65520
```

```
gccccgtcga tgtcgctccc aggatcgtag caggtcggcc gaggcgggcg cctcggccct    65580
gaccgcccgt cgcacgcagc tagccagggg attctctcct gatccggagg tgagacatgg    65640
cttcttccga agatggaacg cgcagctggt cgaacacgaa gagcctggcg ctacatgagc    65700
gcgcggcgaa ggtgatgccg ggaggccagg cgaacttcag gggaggtttg ttgagcactc    65760
ccctcttctt ctcccacgcg cgaggcgcgc gactgtggga cgtcgacggc aacgagtacg    65820
tcgacctgat caacgccggc ggtccgggca tcctcggcca caacgatccg gagtacatcg    65880
acgcgctgaa cgccagctc gacacggtgt actcgctcgg gtcggggatc tgccagaccg    65940
agcaggatat cgagctggcc gagaagatcg cgagccacgt cccgtgcgcc gagcgcgtcc    66000
gcttctgcgt caccggatcg gaggcggtac acctggccct acggctcgcg cgggcgtaca    66060
cgaagcgccc ctatttcatt cgcttccaga ctcactacca cggctggttt gacagcgtgc    66120 tgggggggtgt cgttgacgag caccccgaag ggcgacctct cccgctggag agcgagcaga    66180
gcttctttca caccgagggc agggtccccg acgcattcaa gtactcgttc ctcttgccct    66240
ggaacgacat cgatgtcctc gaggagacgc tgaagaagta cgggcacgag gtggccatga    66300
tccacatgga gccgatcctg gtgaacggcg gaggctgccc ccccaggccc ggctatctcg    66360
agcgtgtgcg cgagctctgc gaccagcatg gaatcgtgct cggcttcgac gaggtcatca    66420
ccggcttccg cgtgggcctc ggcggcgcgc aggcggcgct cggcgtcacg cccgatctgg    66480
cgacgttcgg taaggcgcta gggggtggga tgccgatggc ggccgtcgcc gggaaggcgg    66540
agatcatgga tcagctccgg accggcaagg tgacaggggc tggcacgttc aacggttatc    66600
ctctcggcgt ggccgcgtcc ctcgcgacgc tcaagatcct ggagagggac gatggcgcgg    66660
tctacaggag gatcgacatg atgcaggctc ggctcaagga gggcctgctc gatatctgca    66720
agcgacgtgg gatccccgcc ctggtgcagg ggccgcgcgg cgtcttcttc ttactcttca    66780
cggacaaacc cgtgatctat agcttccaag agctcatgga ggccgctctg cccaggcagt    66840
tcaagttcta ctcgacgatg cccgaggagg ggactctcct catgtacggc ggccgctggt    66900
acatctccgc ggcgttgacc gaggctgacg tggactgcgc gctggagagc gccgacagga    66960
ccttggctag aatctgacgt agtctcgctt ccgcaaacga cgttgacttg aacggtcggg    67020
tgcgctgaac gccggcccag aagaggagcc ccagcctggg gctggcgtct gttcgatgcc    67080
ccctacagaa gatttgaagc agatcttgga gcagctcggt tcggccaggt tgagccatga    67140
ggtcgagctg agccagctca tggcgccgct ctcgccagaa gaagtttttgt tttgctttct    67200 gttcatcaag tccggctcgg ccgagggctt cggcgaagag cccgttcggt tcaaggactt    67260
gccgagcgcg cctgacagat tctggaaggc gatggcgctg cacgtcggcg cgctctccgg    67320
gcagttcaag ccgctgccgc cgtcgtatct caaggatgcg tggctccgtt tcgtgaagga    67380
gcggcccggg gacgagccgc tgtcgctcct cgagtactac agcctcgccg cgcagctcct    67440
cagcgacacg gacagggtct tcatcaacca cgggtacgcg ttcctgaacc cagcagaggc    67500
gccctctctc gctgcctggg aggagccgtc gcgcctcagc atccacctct accacaagct    67560
cctgggcggc caggatttca cggggctcga tgtggtcgat atggcctgcg acgggggggg    67620
cggcagcctc tacctgaagc agcggaagga ggcccggctc gtcgccggca tcgacgcggt    67680
gcgcacccac gtgctgctcg cgcgagaagc ccatccctcg gtcgacgcg tctacttcct    67740 ccacggccga gcggaagaga taccgctgcc caccggtgcc ttcgacgcgc tgatcgcggt    67800
ggacgcggtc ttccacttcc cgctcaggga gttcctccac gaagcccatc gcgtggtgaa    67860
gccggggggg cgctgtttcc tcaatagctg gggcccgccg acctggtaca tggatctcga    67920
```

```
gggtgcggtc gagtcgtgtg gttggaagct cgagcacgcc gaggacatca cgacgggcgt    67980
cctcctggcc agagagcaat ggaggactca cgacatgttc acgtgggtcc gctcgcggcc    68040
gcgcaaatgc cggccggaga tctacatcga gttcgacagg atggtgatgt tgcccgtcga    68100
gggccgccgc tattacaatt tccacctcac ccggctcgac cagaaggcaa gctgaaccga    68160
ggcggcccac gctctcctcg acgcggctgg ctaccggtag gcgacgatgc caccgaacgg    68220
ccacttcgcg tggtcctcgg gcgccggata gacctcccat tcggagaacc cggccgcgcg    68280
gagcgacagc tcccactctt gcagcgtcag ataaccaaca tgctggcggc gaggcggatc    68340
gagcttggcc ttgctgtagg tgtgcagcat cgactgaaaa aattcattgg gaaagaacag    68400
cccgggccga tcgcggaacg acatggtgaa cgcgagctgg ccgcccggct tcagcatcgt    68460
gtggaacgcc tggagcgtgg cgtgaagatc gcgcacgtcg tagagcacgt gctcaaggac    68520
gatcagatcg accgaggcgg cccgggcgaa cgtgttgcca gcggagggca gcgcgtccag    68580
gtccaggcgc tggaaatgaa tgcgctgaaa caggtcagcc ggcgcgtggg tccgcagcca    68640
ctgcttcccc gtctccatca acagggcgct gatgtcggtg taatcgtaac ggacgaggtt    68700
cctgctcagc gggaggaacc tcggatcgga taacgcctgc cgcagcacca cgccgagccc    68760 cgcgccccc tcgaatacag agatccccgg cccctctgcg agcttggcca tcagcgcccg    68820
cgccagcatc acgttgcacg gcttcttggc gggaaggctg atcatcgagt attcccaaaa    68880
tttcagcgag gcctgcatcc cgtactggag atccatggtg ccagcgcgt ccttgcccgc    68940 cagcaccggc ccgccaggc cccgatagcg ctgcaggaac tcgaccattt cgccgagaat    69000
cgcgcggtct gcgagctcca tggcctccct ctcggcgacg cgctttcgca ccgcctcgct    69060
gggcaccagc cgcccgctgg ggtcctgat gaggtcgccc ttgtcgctga agtagtcgag    69120
cagcttcctg cgaaactggt aggcggtgac cgacggagcc gactccgggc gatcgtcgag    69180
cacctggacc gcgccgctct ggtcgacgag gtgctcgagc agaatctcac tggcaacaag    69240
ctcggtctga cgacggaatg cttctatgta agccgtgtaa gcgtcgttgt agagatcggt    69300
cacgtccagt cgttgtcgca tgcagatcct cgcgggtgtg gcgcccatcc tgcgcagcgc    69360
agggacgaag cagatcatgg aatggtccag ctcgccgtgg aacgcaagga tggaccggcc    69420
gccgcgggcg ggcgccgcgc ctccgagcgt cgcgcgccgg gccagctctg gccacctcga    69480
gggccacgcg tcacctggag ctcggcacct gcccgccgtt cccgcggttc ttgtgcacga    69540
tggcgtacag gatgagcacg taggcgagga gccggaacag gtacaggtaa tggatggcgt    69600
cttcctcgac gcggttcagg gcgacggcga tgcggcccag catcatcagc cagaacgccg    69660
ccgagaactt cgcgaacagc cggtcgcccg tcttcttcca gaagcggagg aagaagagcg    69720
cgatggtcgc atacccgagc gtcatcgcac cgatcaagaa gtcgttcaaa ggtactacct    69780
cgcctctacg tgcgtttact cgcgcaggtc ccagatgagg ccatacagga gcagggtcag    69840
cccgatgagc gcggtgaggt ggcgcaggga cgatagatcg atgctccgga tcacgacgag    69900
gtccacgaag agcaggatgt tgttcgcggc gagcccggcg aagcagagcc cgctccacaa    69960
gaggaggcgg accttgcgct gcgcgtatcc gcgcaggagc agcacggcgc acgcgatgct    70020
ggtcagggag cagagcatgt agaccgccgc tgccatggct agccctcctt tcccttcttc    70080
gtgatccgga atgcgtccga gaagctctgg atgtcgctcg gcggggggcgt ggcgtagatg    70140 tgattgatca cgctcagccg gcgctccttg taagcctgcg ccaggtcgtc gatcgtccgg    70200
cgggtgtcat cgtccgccgg ggcgtaccgg tagacgatgt cctccccgtc ctcccgggcc    70260
```

```
acgagcaggc ccctgctggc gaggcccccg aaccggtcct ggatcgacat cttgctggat   70320
cctatctcgc gcgccatcgc cgccgcactc cactcgcgct ccgccgtgcg acgcatcagc   70380
aggagcactt cgagctcttc gatcgaggag atgtgcgcgc caaggaagcg ctggacccgg   70440
tcggggagcc cgctagacac gagctcctcg ccggccgcgc gccctccgg tcaccggtgc    70500
aaccatagcc ggagcatagc gagcaggtgc tccggatcca ccggcttcga gatgtaatcg   70560
ttcgcgcccg cctcgaagca cttctcccgg tcgcccttca tcgccttggc cgtgaccgcg   70620
atgatgggca gcgcatggtg ctcgggcctc gcgcggatgg cacgatcgt gtcatagccg    70680
tccatctctg gcatcatgat gtccatgagc accatctcga tgtccggcgt ccgctgcagc   70740
atctcgatcg ccgctctgcc cgtctccacg tagaccgtct tcatatgctg ggcgtcgagg   70800
atggtcgtca tcgcgaagat gttccgaacg tcgtcgtcga cgaccagcac cttcttgccc   70860
acgagcacct tgttcgactg gtgcagctcc tcgacgatct gcagctgtcg ctcggagagc   70920
gccgccaccg ggcggtgcag gaacagggag acgtcatcga agagccgctc cttggagcgg   70980
acgtgcttga gcaccatcag ctggctgaag cggctcagct gcgcctcgtc tgcgggcgag   71040
atctcctccg gcgcgtagac caagacgggc aggtccgtgg accgctgcc ctgcgcgagc    71100
tgcccgatca gatcgaagca gcgcacgtcg ggcaggtcga ggcgcaggat gaggacgtcc   71160
ggccgctcgg tgacgagcgc gtcgagcgcc tcctcccgg aggccacact ccggatcgtg    71220
acgtcgtcgc cgccgaggag ctcgacgagc tcctggcgct cggcgtcgtc cggcccggcg   71280
agcacgatct tccgccggct cgacaccatg aactgcgaga ggcgcctgaa cgtctcgtcg   71340
agcgcgtccc gggtcttgag cggcttgcag agcacaccct tcgcgcccat ccgtagcgcg   71400
cgctcgcgct cctcgtccgt cgtgatcacc tggacgggga tgtgccgcgt ctcgagatcg   71460
cgcttcaccc ggtcgagcac gcgccagccg tccatgtccg gcaggttgat gtcgagcgtg   71520
atcgcgttca cccgccgctc acggacgatg gagagcgccg ccccgccgcg gtaggcgagg   71580
atcgccttga cccgtggtc gtgcgcgaca tccatgacga agtgcgcgaa gctcgcgtcg    71640
ttctcgacga tgagcaccac ggagtcgctg ggcttgaggc ccgcgctgtc gtcgacgctc   71700
tggttgagca ggtgcggcgg cggctcggcc gccgaccgcg gcgggacgtc gccggagacg   71760
acggccggcg gcgctgaggg cacctccacg gtctgctcct tcctgcgcgg gcgcgccggc   71820
gtgtacgtga gcggcaggta aagcgtgaag ctgctcccgc tccccggctt gctcgagagc   71880
ttgatctcgc cgcccagcat ccacgcgatc tcgcggctga tcgcgaggcc gaggccggtg   71940
ccgccgtact tccggctcgt cgagccgtca gcctgctgga aggcctcgaa gatgatctgc   72000
tgcttgtcat gcgggatgcc gatgcccgtg tcccgcaccg acatggcgat cgccgcgccg   72060
gcgcgcgaga ggccctcgtt ctcgggcgcc caccccgagg tgaccagatc gacgtcgagc   72120
gcgacgctgc cgcgctccgt gaacttgaag gagttcgaca gcaggttctt gagtacctgc   72180
tgtacgcgct tcgcgtccgt gtagatgacc tgcggcaggt tctgcgcgaa gttgagctcg   72240
aactcgagct tcttcgactc ggcgacgtga cggaaggtgc gctcgacgta gtcctgcaga   72300
tcgctgaacg acagctcgcc gacgtcgacg atcacggtcc cggactcgat cttgacagg    72360
tccaggatgt cgttgatgag cgcgagcagg tcgttgcccg acgagtggat cgtcttggcg   72420
aactcgacct gccgccccgt gaggttgcgg tcgttgttct tcgagagctg atcggacagg   72480
atgagcaggc tgttcagggg cgtccggagc tcgtgcgaca tgttcgcgag gaactcggac   72540
ttgtacttgg aggtgatggc gagctgccgc gccttctctt cgagcgcctg ccgcgcctgc   72600
tcgacctcgc ggttcttccg ctcgacctcg acgttctgct gggcgagcag gcgcgccttc   72660
```

```
tccccgagct ccgcgttcgt ctgctgcagc tcctcctgct ggctctggag ctcgcgcgcg   72720
agggactggg actgcttgag caggtcctct gtgcgcatgt tcgcctcgat cgtgttgagc   72780
acgatcccga tcgactccgt gagctggtcg aggaaggcct ggtgggtcgg gctgaagcgc   72840
tcgaacgacg cgagctcgat gaccgccttg acctgcccct cgaagagcac ggggatgacg   72900
atgatgttga ccggcggcgc ctcgccgagc ccgctcgtga tgcggatgta gtcgggggc    72960 gcgttgacga ggaggatctt ctccttctcg agcgcgcatt gcccgaccag cccttcgccg   73020
agcttgaaat ggttgtcgac gtgcttccgc accttgtacg cgtagctcgc gaggagcttg   73080
aggatcggct cctccttcgc cacgtccatc gtgaagaaca cgccctgctg cgcaccgacg   73140
accggggcca gctcggacag gatgagccga ccgaccgtga gcagatcctt ctgcccctgg   73200
agcaggcgcg agaacttggc gaggttggtc ttgagccaat cctgctcgct gttcttcagc   73260
gtcgtgtcct tgaggttccg gatcatctca ttgatggtgt ccttgagcga cgcgacctcc   73320
ccctgcgcct cgacccggat ggtccgggtg aggtcgccct tcgtcaccgc ggtcgcgacc   73380
tcggcgatgg cgcgcacctg cgtcgtcagg ttggcggcga gctggttcac gttgtcggtc   73440
aggtccttcc acgtgccggc cgcgccgggg acgctggcct gccgccgag cttgccctcg    73500 acgccgacct cgcgcgccac cgtggtcacc tggtcggcga aggtcgcgag cgtctcgatc   73560
acgccgttga tcgtatccgc cagcgccgcg atctcgccct tcgcgtcgaa ggccagcttg   73620
cgcttcaggt cgccgttcgc gaccgcggtc acgaccttgg cgatgccgcg cacctggttc   73680
gtcaggttgc cggccatgaa attcacgttg tcggtcaggt ccttccacgt gccggcgacg   73740
ccggggacgc tggcctgccc gccgagcttg ccctcggtgc ctacctcgcg cgccacgcgc   73800
gtcacctccg acgcgaaggc gttgagctgg tccaccatcg tgttgttgat ggtgttcttg   73860
agctccagga tctcgccgcg gacatcgacg gtgatcttct tcgacagatc gccgttggcg   73920
acggccgtgg tgacggcggc gatgttgcgc acctgcgcgg tcaggttcga cgccatcgag   73980
ttgacggagt cggtcaggtc cttccacgtg ccggcgacgc cggtcacctc cgcctgcccg   74040
ccgagcttgc cctcggtgcc tacctcgcgc gccacgcgcg tcacctcggc cgcgaaggag   74100
ctgagctgat ccaccatcgt gttgaaggtg ttcttcagct ccaggatctc gcccttgacg   74160
tcgacggtga tcttcttcga caggtcgccg cgggcgacgg ccgtggtgac gtcggcgatg   74220
ttgcgcacct gcgcggtcag gttcgacgcc atcgagttga cggagtcggt caggtccttc   74280
cacgtgccgg cgacgccggg gacgctggcc tgcccgccga gcttgccctc ggtgcctacc   74340
tcgcgcgcca cgcgcgtcac ctccgacgcg aacgagcgga gctgatccac catcgtgttg   74400
aaggtgtcct tcagctccag gatctcgccg cggacatcga cggtgatctt cttcgacagg   74460
tcgccgttgg cgaccgcggt ggtcacgtcg gcgatgttgc gcacctgcgc ggtcaggttc   74520
gacgccatcg agttgacgga gtcggtcagg tccttccacg tgccggcgac gccggtcacc   74580
tccgcctgcc cgccgagctt gccctcggtg cctacctcgc gcgccacgcg cgtcacctgg   74640
gccgcgaagg agcggagctg atccaccatc gtgttgaagg tgttcttcag ctccaggatc   74700
tcgccgcgga catcgacggt gatcttctgc gtcaggtcgc cgcgggcgac ggccgtggtg   74760
acggcggcga tgttgcggac ctgcgcggtc aggttcgacg ccatcgagtt gacggagtcg   74820
gtcaggtcct tccacgtgcc ggcgacgccc ttcacctccg cctgcccgcc gagcttgccc   74880
tcggtgccca cgtcgcgggc gacgcgcgtc acctcggccg cgaaggagct gagctgatcg   74940
accgtcgtgt tgatgacgtc cttgatctgg aggatctcgc cgcggacatc gacggtgatc   75000
```

```
ttctgcgtca gatcgccgtt cgcgatggcg gtcgcgacct tcgacacgtc gcggagctgg    75060
accgtgaggt tcgacgccat cgagttgacg gagtcggtca ggtccttcca cgtgccggcg    75120
acgcccttca cctccgcctg cccgccgagc ttgccctcgg tgcctacctc gcgcgccacg    75180
cgcgtcacct ccgacgcgaa cgagcggagc tgatccacca tcgtgttgaa ggtgtccttc    75240
agctccagga tctcgccgcg gacatcgacg gtgatcttct gggtcaggtc gccgcgggcg    75300
acggccgtgg tgacggcggc gatgttgcgc acctgcgcgg tcaggttcga cgccatcgag    75360
ttgacggagt cggtcaggtc cttccacgtg ccggcgacgc ccttcacctc cgcctgcccg    75420
ccgagcttgc cctcggtgcc tacctcgcgc gccacgcgcg tcacctccga cgcgaacgag    75480
cggagctgat ccaccatcgt gttgaaggtg tccttcagct ccaggatctc gcccttgacg    75540
tcgacggtga tcttctgggt caggtcgccg ttggcgacgg ccgtggtgac ggcggcgatg    75600
ttgcgcacct gcgcggtcag gttcgacgcc atcgagttga cggagtcggt caggtccttc    75660
cacgtgccgg cgacgccggg gacgctggcc tgcccgccga gcttgccctc ggtgcctacc    75720
tcgcgcgcca cgcgcgtcac ctccgacgcg aacgagcgga gctgatccac catcgtgttg    75780
aaggtgtcct tcagctccag gatctcgccg cggacatcga cggtgatctt ctgcgtcaga    75840
tcgccgttgg cgacggccgt ggtgacggcg gcgatgttgc gcacctgggc ggtgaggttg    75900
ccggccatcg agttgacgga atcggtcagg tccttccagg tgccggcgac gcccttcacc    75960
tccgcctgcc cgccgagctt gccctcggtg cctacctcgc gccacgcg cgtcacttcg    76020 gacgcgaagg agccgagctg atagaccacg gtgttcacgg tctgggcggt ctggaggaac    76080
tcgccctcca gcggccgccc gcccacctcg agcgccatcg tctgggagag atcgcccttg    76140
gcgaccgcgc cgatgacgcg cgccatctct ctcgtgggct gcacgagatc gccgatcagc    76200
gcgttgacgg aggcgacctc gtcggcccag gcgccgctca cctcgcccat cgagacgcgc    76260
tggccgatct tgccttcctt gccgaccgcg cggctcagcc gctcgagctc gaacgcgaac    76320
ttctcgttca tctcgacgac atcgttgaag gtgtcggcga tcttcccgtc cagcccctcg    76380
aggtcgatcg gcaggcgtac cgagaagtcc cccttcttga cgccaccag gaccgcgagc    76440 atctggccca tctcgagggc ctgccgcgcc ggccggcgca tgacgtcatc ctgcgcagcg    76500
cgccgccgcg ggcgtggcag gtcttcgaga tggacgggct gcgaccgctg ctgaagcgcg    76560
gtggcttgcg acgtccgggc cgcgccctct gcgcgcttgg ccgccgcgtt cttcccgttc    76620
ctggggtgct tgccgtcctt gccgttcgtg cccttcgcgg cgccgtcctt cgaggacgcc    76680
gtccggctcc gaggagacgc tatcttgccg ctcgtccgct gctccatgtt ggaccctctc    76740
cagggcggcg ccatgctaac gcgcgcggcg ggaggtgagc cacactaaag aacttcctgt    76800
atctaccctg tgagaggcgc ccaacacggg tcaggatgac cccgataccg ctggcggagc    76860
ttctcgcgcc cgtggcggac acagccctgg gaacatcgag gaagtacacg gttggtcagc    76920
gaacgaaagc caccttcgac aagcgggctc gaccgtcggt gagcggatac cgctctcgca    76980
gctccgtctg attacgccgt cccctcgcct ctcacccttg ctgcatttcg tgaccgcgtt    77040
cgcggcgccg cgcgccctgc cttcgccttt accgcccgc gcgcgccgct gctgctcgag    77100
gcgcccgtgc ccgcgcgcgg cgcgctctcg gccagcatct ccccccagcg cgagatcgcc    77160
tgcgcgaccg cctggaaccc ccgtccggag tcggtcagct cgtactccac ccggaccgga    77220
ggccccggca gcacgcgccg caccacgagg ccgagcgcct cgagctcctt cagccggctg    77280
gagagcatcc ggtcgctgat cgcgtcgagc cgctcgccga tctcgccgaa gcgcagcggg    77340
ccctcgtcga gcgtcgcgat gatgaggccg ttccacggct tcgcgagcac gtccatggcc    77400
```

```
gcctggaacc cgtcgcagag gtgctggcat gaatgcttca ttccgcgtcc tggacaggat     77460
gaccccttca ctaccaaaaa ggaagtccct tgacacgagg tagcgcgtgt ccatgatgct     77520
tccttgacgg atgctgcttc tctttcggaa gtaacatctt ctttacaagg agcatcgatc     77580
gtgaccactg ccgccgacct gctgttcagc cccttcaagc tcggcccct gtcgctgccg      77640 aaccgcctcg tgatggcgcc gatgacgcgc tgccgcgcgg gcgagggcaa cgtgcccacc     77700
gagctcaacg cggtgtatta cgagcagcgc gcgtccgccg gcctcatcat caccgaggcc     77760
acccaggtca gccagcaggg cgtggggtac ctccgcacgc cgggcatcca caccgacgcg     77820
caggtcgagg ggtggcggcg cgtcacggac gcggtgcacc gggcaggggg gcacatcttc     77880
gcccagctct ggcacgtcgg gcgggcgtcg cacgtctcgt tccagccggg ccggcaggcc     77940
cctgtctcgt cctcggccct ccccatccgc accggccacg cgcacacgcc cgagggcgcg     78000
cagccgtaca gcaccccgcg cgccctcgag acgcgcgaga tccccggcgt cgtcgcgcag     78060
ttcgaggacg gcgcgcgccg ggcgagggcg gccggcttcg atggaatcga gctccacgcg     78120
gcgaacggct acatcatcga ccagttcctc cgcgacggcg tgaaccagcg gacggaccag     78180 tatgcggct cggtcgagaa ccgggcgcgg ttcctgctcg agatcgtcga cgcggtgacc       78240
ggcgtcttcg acccggaccg ggtcggcgcg cgggtctcgc cgctgggcgg ctacaacgac     78300
atgagcgact cgaacccgaa ggcgatcttc ggccacgtcg ccgccgagct ctcggcgcgc     78360
aagctcgcct acctgcacgt cgtggagccc gtggacgggc aggcggagga cgccgcgggt     78420
cgcgtgatgc ccctgctccg cgagcggttc cgcggcgtcc tcatggcgaa cggcggctac     78480
acgctcgaga cagcggaggc ggcgctgcgg acgggcgcgg cggacctcgt ctcgttcggc     78540
gcgccgttcc tggccaaccc cgatctgccc gagcgcctgt cgcgccgggc gccgctcaac     78600
ccgcccgacg tgtcgacgtt ctactccgag gggccgcgcg gctacaccga ttatccgcgc     78660
ctcgccgagg cgcaggccgc cgcgcagccg tcggcctgag cgcggcatcc ggcgcaggcc     78720
cggcgagggc tcccgcgccg cggaccatgg taggctccag ggccgatgtc ggcggccctg     78780
gatctgttcc cgagagcggt cgttgttctg cgcgcgcgcg tcgatgagcg cccggcgccc     78840
ggcgcggcgc gctcgcccgc ggaggcgcc                                        78869
```

<210> SEQ ID NO 2
<211> LENGTH: 14172
<212> TYPE: DNA
<213> ORGANISM: Sorangium cellulosum

<400> SEQUENCE: 2

```
gatctcgtcg aggaacagcg tgccgccgtc ggcctcctcg aacctgccga tccggaggcg       60
cgcggcgccg gtgaaggcgc ccgcctcggc gccgaacagc tccgcctcga cgagctcgtc      120
ggggagcgcg ccggcgttca ccttcacgaa cggccggtcc cgccggcgcg agttggcctg     180
gacgatgccg gcgaggagct ccttgccggt cccgttcggc ccggtgatga gcaccggcac     240
gtccgcgggc gcgaccttca ccgcgaggct caccacctcg tgcatcgcgt cgctcgcgta     300
cacgagcccg ccgaggtcgt ggcgctcggc gagcctgtgc cgcgcgcgcc cgcgctgggc     360
gacgaggcgc gcgttctcct gctcgagcga ccgcagccgg gcgaggttgc tcaccacggc     420
gacgagcttc tggtcgtccc acggcttcgg cacgtagtcg ctcgcccgg ccttgatgag      480 ctcgaccgcg cccgcgatcg acgtgaacgc cgtcatggcg acgacgggca gctcggggtc     540
gatcgacttg atgcggcgga gcagctccat gccctcctcg cccgatgtcg cgctctgtcg     600
```

```
gaagttcatg tcctggacca cggccccgag ctcgtcgtcg agcaccgccg cgatcgccgc    660
gtccggcgtc gccgcgacgc ggacctccag cccgtgcagc tcgaagagcg tcgtcagcgc    720
gacgcagacc gcgggctgat cgtcgatgac caggatcttc ggcacccggg agcgtagcc     780 gctcccggcc gccggcaggc tcactcgtcc tggccagccc gcgaccagcc gccgagcttg    840
acgcccggcg tctgcgccag gaacgcctgc acggcgggcg gcggcgacgc ccacgccgcg    900
aggcgccccg ggctccgcgg gatcggcgcc gtcgccgagc gcgagtagga gctccacgcg    960
ccgtcgccgc aggcatagca ggccgagcgc gcgagctgcg cggtgagccg gagcgaccc     1020 cgcgcgtcgt aggccggcgc gatcttcacg agctgcgggg ggtccttctc tcgccgcgcg   1080
gcctccgggt cctcctcgag gtcgtcgagc gtcgcctcgg ccgcgcgctg cagcgacggg   1140
acgccggaca cctcggcgag caggtcgacc gccgcgccgc gctcggcgtc ccacacagtg   1200
aacgcggcgc cctcggagcc gtgcgcgccg cagagatcgc tgtacgtgcg ctcctcgatg   1260
aacaggtacg gccccacgct gccgatcagc gccgcgctgt gctggaactc gttgctctcg   1320
tcctggtcgg gcgccgtgat caccgcctgg cgctcgccgt ccccgcgcag cacgagctcc   1380
gcgtcggtcg ccgtgccctc gcccggctcg cgcgtgtccc cgtcccagag ctcgcagggc   1440
gtggtctcga cctccttcgc gcgcgcctcc cagcgccact ccccgcgccg gtcgccacg    1500 acgatcccgg gctcctcgcg gatcaccgcg ccgcctcgg cgacgtgcca cgtcctcggc    1560
gtcccctcgc ccgtgctgcc ccagatcagg accaccccgg ccgtcgcggc gtccccggcc   1620
gcctggggct cggacgggcg cggggcggc gcgagctgga tgtcggtgga agcggcgggc   1680
gcaggccggg gtcgggcggc acagccggag atcagcgcca gcgagacgat caacgcggca   1740
ggtcgggagc gcagcatgcg gagccgagag agcatggtgt gtgccgcgga ccgcggccag   1800
gaaagccgcg cggcgcgcgc tggaggtgta gccgcgcgcc cacgccgcgt ggcacgagcg   1860
ccccgtcacc gcctcgagat ccggcgatgg agcgccggcg cgggcagcgg caggaacggc   1920
gcgtcccccg tgtcggcgat cgcgccgtcc tcaggtgccg ggacccgagc gcgcctggcg   1980
caggagctcc cgctgcgcgg cgttcagccg gatcccgggc ctgcgctgcc ggatcccggg   2040
ctccatcgcg tcgacgtcgg cggcgagctc gcgctccagc agcagcgcgg tcgcgagggt   2100
cgccgatcgg ccgcggccgg aggcgcagtg caggtacacg ccgtccacgc cgcgcagccg   2160
cgcgaggagc tcccggagcc gctccacctc gggccccgtg ccgtcgagcg tcggcacgca   2220
gacgtagccg gggtggcgcc gcaccgcggc ggccgccgga aactcggccg tcatgtccac   2280
gaccagccgc acgcccgccg gcagctcgtg ggcgagcggc gccggccga cccagagccc    2340 gggcgccacc tcgttggcgc agtccgcccg cccgagcgcc cgctccgcgc gccataccgc   2400
ccaggtcagg aggaaatacg gaccgagcag gacgagcgcc cacgcggcct gcgtgccgtc   2460
aggctgcttg cccagcagcg cgggccggcg cgcgaggtac gcggcgccga caaggccgaa   2520
gctcagcgcc ggccagagca gcgcgagcgc agccccgccg gcgaggaagg cgagcgcggc   2580
gagggaggcg ctcaggacga ggaaggtcag gccgtatcgc atcgagcagg tcccgccccc   2640
ggcgcgggtg atcccggatc tagcgcgacg gcccgctgga tggcgtcgcg gagccaccgg   2700
tggccctcgt cgtgctcgga gcgctccggc cagacgagcg tcagcgtgta gccctcgagc   2760
tggaacgggc acgccgcac cacgagatcg agcctccgcg ccaggccgc ggcgacgcgc     2820 gcggacacgg tgagcagcag gtcggagccg gagacgatga acgggcgac caggaaatgg    2880 gacacggtca gcgtcacccg ccggcgcaat ccctgctccg ccagcgcccg atcgatgacg   2940
ccgtggtcct ctccgtgcgg cgagaccatc aggtgctcgc aggcagcgta gcgcgccgcg   3000
```

```
gtgagcggcc cccgtgacgc cgggtgtccg cggcgcatca cacagacgat ctcctcggcc    3060
gccagcagcg tcgaccggca gccgtcgggc acggggcccc cgcgcccgag cttgccgtcg    3120
agctcgccgc ggcgcaggag ctcggcgaag tcggccggga tgttccggca gcgcaggttg    3180
acgcgcggcg cctcgacggc gaggagcgcg gtcagcgccg ggagcacgag cagctccagg    3240
ttgtcggtcg cgaccagccg gaacgtgcgc tgcgaccgcc gcgggtcgaa ccgctcgacc    3300
gggcggaaga cgtgctcgag ccgctcgacc gcctcggccg cccgcggggc caggtcccgc    3360
gcgcgctcgc tcagcgtcat ctgccggccg acctggatga gcagcgggtc ctcgaaatgg    3420
gcgcgcagcc gcgcgagcgc gtggctcatc gagggctgcg tcacgcccac gcggcgcgcg    3480
gcgcgggtga cgctcttctc ctggagcagg gcgtgcaacg ccacgacgag gtgggtgtcg    3540
accgactgca ggcgcatggt cgatggatag cacggcgacc catcgacgct gtctatggat    3600
cgccgcgccg actgtcgatt cgacgcccgg agcgtgggtg cctatctctc ctctccggac    3660
ggcacatgcc gccgcgcggc gcgcccctgc cccccagccg aggagagcaa ccccatgatc    3720
atcgagtaca ttcgctacac gatccccgcg gagcaagaga aggagttcct ggccgcctac    3780
cgcgacgccg ccgcggagct gcgcggctcg gagcattgcc tcgatcacga gatctcccgc    3840
tgcgtcgaag atccgacgag cttcgtcgtc cgcatctgct gggactcgct acaaggccac    3900
ctccagggct tccgcaaggc ggcggcgttc ccgtcgttct tcgccaaggt gaagccgttc    3960
tacgagcgta tccaggagat gaggcactac gccttgaccg acgtcgccac gcggcaggcg    4020
gggaaggccg cgacgggctg aagggtagac ggcccgccga ccgctccccc tttgcaggtc    4080
gcgccggatc gatatcgagg ctaccctcgc gcgtcgaccc ctcatcggcc gcctctcgcg    4140
atcgcctgga gcaccctcat gccgcgcgcg ctggctctcg gactctcccct cccgctcctt    4200 ctctcgctct cgcactgcgc gggcgcgcgg agcccgagca cgcccccgc tgacccggat    4260 cgctcgcccg cgccggcgcc tggatcgagc gccgggccgg cgagcgagct cgacccggca    4320
ccggcgcccc tacccgacgg cgcgccgcag ccagctcccg gatccagcac gggcgacgcg    4380
tcgacgtccg atcccggcca ggcgcccgcg atcgctccgg gccggacacc tgagcccggt    4440
gaggcgcccg caccggacag cggggccgccc gcggggccct cgcgatgcgc ggcgccagcc    4500
cgtcccgcgc cgggcttcac cgactgcgcc cgccaggagg tctttgccgg cggatgctgc    4560
tatccgagct tcgaggccgc ctgcgccggc ctcggctgct cccgcccgc ctgcctgcgc    4620 ctcaaatcga gccccttgca ggccggtgtgc gcccggtgag gggcggtgtg acgccgcgat    4680
ccgggaaagc tgctgggcag accgcgcggc gccctccggg acgcgcgccc gacgcgccgc    4740
ttccgccgcg gcgcgggcag gtgcaggatg aggccatgag aatgcctccg gcgctcgacc    4800
gagaccaccg ccgcgccgcg cgcgcgcccg ccgtcgccct catcgcgctc ctcgcagccg    4860
gcgccgcgct cgcggcctgc tccaggagca ccggcgggcc gaagcaccgc gaggcggcgc    4920
cggagcgcga cagcgcctgc acggatccag cgaagcccag ggcgtacttc tatcctgcgg    4980
agaaccggac ggactacgcg cctgacgatc cctggaagga cggctgcgcc atgcggtgc    5040 cagatcacct gttctgctgt ccggagaagg cctccatcgg ctcgccctga tccgctccgc    5100
cccgcggcgc gccgcgggcg ccacaaggaa agaaggactc atggccgttc cctctggatt    5160
cgacctcacg agcgagcgct tcttcgccga tcccttcccg accctcgagc ggctccggac    5220
cgaggcgccc gtctacttct tcgagccgct acagtgcttc ctcatcaccg ctcctgccga    5280
tatcgagggg ctcgtgaaag actcgagctt caccgcgcgg cgggcgacgg cgctcctcgg    5340
```

```
cggcctcggc atgctcggcg aggacgagct ctcgaggaag acgttcgact ccctgtcgcg   5400
gctcgccttc ttccaggacc cgccgcgcca cacgcagctt cgacagctca tcatgaaagg   5460
gttctcgccc tcggccgtgg agtggatgcg cccgcgggtc gtggggctcg tacagcgggc   5520
catcgagggg gcgcgccgcg acggcgagat ggatgtcgtc tcggcgttct ccgaggcggt   5580
cgcgctcaac acgctggccg agatgttcgt gatacccgag gtcgatcgcc cgcagttcct   5640
gagatggtcg accgatctct tgaagctcgc cggcggcggg gtgagctcgg aggagcagaa   5700
gcgggcggtg aagcagagct gctgcgacat gctcgactac atgatgaggc tcgtcgagga   5760
gcgccggaag gcgccggggg aggacgtcgc gagcaggttc atcgcggcgg aggacggtga   5820
caccgagctc gcgggcgagg cggccatgca gtgcttccag atggtcgccg ccggattcgt   5880
cacctccgtg aaccagatcg cgaacaccgt gctcgcgctc ctcaaccacc ccgcagagct   5940
cgcgaagctg cgggaggcgc cgggcctcgt ccgcggcgcg gtcgaggaga gcctgcgctt   6000
cgagccgtcc gtgctctccc tcagccgcat gtgcaagaag gacaccgaga tccggggcgc   6060
cagggtgtcc gaggggcagt tcgtcttcgc gatgatcgcc gcagcgaacc gcgatcccgg   6120
gctgttctcc gagccggatc gattcgatat caccccggcag cagagccggc acctgacctt   6180
cgggagcggc gctcattact gcccgggggc cccgctcatc cggatggaag tagaggagtc   6240
gctgcgcgcc ctgctctcgc tgccgcgctg ggagctcgcc gaagagacgt tgagctacgc   6300
cgggtcgaac ctgcaggacc gcgggccgag ctcgctgcgc gttcgcttcc ccgcagcctg   6360
aagccgggcg agcgcggcgc cgcggcagga cggccgacgc gggtgccgca caacgcggca   6420
tgtcgcattt tgcgacggcg tcgggcgggc ggctggacgc gcgcacccgc ccgcgcgcc   6480 acctgcgcta cgacgccggg caatgaagct cgcgcgcaag ctgacgctcg ccctcgtgtt   6540
cggggtcttc ctcgtgctcg cgctgagcgc ctacgcccag atccgcagag acgccatggt   6600
gttcgagaac gacgtccagc gcgatcacca cacgatgggc cgcgcgctcg cggccgccgt   6660
catggaggtg tggcgctccg agggcgcggc gcgggcgctg cgcctggtgg aagacgccaa   6720
cgagcgggag cagcaggtga acatccgctg ggtctggctc gacggccagg ccgacgagcc   6780
ccatcgcccc cggctggctc cggagctgct cgtccccgtc atccgcggca cgttcacgat   6840
gctgaagccg ctggcggaca agcagggtgt cacgatcgtc gaggagggag acacgccgga   6900
tcggctggtc cacgccgacg ccgaccagct ccagcaggcg ctcacgaacg tggtggtcaa   6960
cgcgatccag gccatgccgt ccggcggcac gatcgcggtg cgtgtccagg ccgtccgcgc   7020
catcccaccg gccgatcagg gaggggccga gggcgactac atcgcgctgt cggtgcgcga   7080
cgagggacag ggcatgatgg ccggcgtcct cgagcacgtc ttcgagccgt tcttcacgac   7140
caagcccgtc ggcgagggca ccgggctcgg cctgtcggtc gcctacggca tcatcaagga   7200
gcacggcggc tggatcgacg tcgacagccg cgccggctcg gggagccagt tcacgatgta   7260
cctgccgcag gagaagccat gagcggtcgc gtcctgatcg tcgacgatga gcggggcgtc   7320
tgcgagctcc tcgacgccgg gctcaagaag cggggtttcc aggcggcgtg gcgcacgtcg   7380
gccgccgagg cgctcgagct cctcggcgcg gaggacttcg acgtcgtcgt caccgacatg   7440
accatgcgcg gcatgagcgg cctcgagctc tgcgagcgca tcgcccagaa ccggcccgat   7500
ctgccggtca tcgtcatcac cgcgttcggg agcctcgaca ccgccacgtc ggcgatccgc   7560
gccggcgcct acgacttcgt gaccaagccg ttcgagctcg acgcgctccg gctcaccgtc   7620
gagcgcgccc tgcgccaccg cgccctccgc gaggaggtgc gccggctgcg gcgcgccgtg   7680
gacgactccc accgttacga gcagatcctc ggcggcagcc cggcgatgaa gggcgtcttc   7740
```

```
gatctgctcg accgggtcgc cgactcggac acgtcgatcc tcatcacggg cgagagcggc    7800
accggcaagg agctcgtcgc gcgcgccgtg caccagcgca gccggcgcgg ccagggcgcg    7860
ttcgtcgcgg tgaactgcgc ggcggtcccg gacgccctgc tcgagagcga gctgttcggc    7920
cacgcgcggg gcgccttcac cgacgccaag gggccgagga gcggcctgtt cgcgcgggcc    7980
cacggcggca ccctgttcct cgacgagatc ggcgagctgc cggtcgggct ccagccgaag    8040
ctcctgcgcg ccctccagga gcgcgtcgtc cgccccgtcg gcgcggacga ggaggtcccc    8100
gtggacgtgc ggctcatcgc ggcgacgaac cgcgacctgg agaccgcgat cgaggagcgc    8160
cgcttccgcg aggacctcta ttaccggatc aacgtggtcc acgtcgatct gccgccgctc    8220
cgctcccgcg gcgccgacgt gctcctgctc gcgcagcgct tcctcgagca cttcgcgacc    8280
gtcaaggagc ggccgatcaa gggcctctcg gcgcccgcgg ccgagaagct cgtcgcctac    8340
gcgtggccag gcaacgtccg cgagctccag aactgcgtcg agcgggcggt cgcgctcgcg    8400
cggtacgatc agatcaccgt cgacgatctc cccgagaaga tacggagtta ccggagctcc    8460
cacgtcctgg tctccagcga cgacccgacc gagctcgtcc ccatggagga ggtcgagcgg    8520
cgctacatcc tgcgcgtcct ggaggtggtc ggcggaaaca agagccaggc agcccagatc    8580
ctgggcttcg atcgagcgac cctgtaccgg aagctcgagc ggtacggcct gcgcgcgggg    8640
cgcgcgagcg acccgaagcc gtgacccgcc cggcgtcgcg ccggaggtga tgcccggaga    8700
gcctcgcggc ggcgactccg ctcgtccctc gctgttgcag aacgcgacac ccgcgccgcc    8760
gcgcgatcgg cagcgccgct cgcgggcgcg cgcgggcgcc cgcgactctg cctcgtggca    8820
tgagagctgc ctgaaagccg ggcgcgaaca tgagccacac cacggcggag cctgtcgctc    8880
cgggtcggag agtgccagtc gactggatcg cgctcgcgaa cgcgttcgac aacatcgctc    8940
gaggcgtgcg ccatttcctt cacctcgaca cgggcgccgt gctccggctg aacgagcggc    9000
tcgtcgatcc cgccacgcgc gcgcgcatcg aggaggatcc ggggtgcgtg ctcatcgagg    9060
ccatcgccgc ccgggaccag tatcgatggc tgcaggcgtt cattccgacg gtcgacgatc    9120
tggagttccg gctggcgctc ctgcacagca tgcagggccc agggtcgttc cggcggttca    9180
aggccgcgct ctcgtccaga ccggagcagc tccgccgctg gcgcgccttc cggcaggagc    9240
agatccgggt cgccatcgtc cggtggtttc acgcccgcgg cctcacgccg gtcgccctcg    9300
agcacgcgcg gccggacgcg cgctccgagc cgccgaggtc gcgctccgcc gacgcggccc    9360
gccagcagct ttacgccgcg gcggacagcc tctctcccca ggacctccac gcgctgacgt    9420
cgctcgccga gttcctgcgc gcggcgcgct ccgcgctgcg gatccccgcg gattcatcca    9480
tgggagacgc cgcgcgggcc gtccgcctgc tcccttgaag gcgagcgcgg cagatcgatc    9540
cggaagaccg agccggcgcc gggacggctc tcgacgagga gccggccgcc gtgcgcctcg    9600
acgatgcgct tcgccaccgt gaggccgagg cccgtgcccg ggatggatcc agacgaggac    9660
ttgagtcgcc ggaacggctc gaagaggtgc gccagctccg cgggctcgat cccgagccct    9720
cgatcgcgaa tggcgatctc ggccccgtcg ccgccggcgc ggaccgccac gtcgatctgc    9780
cccccggcgg gagaatactt gagcgcgttc gacagcaggt tgttcagcac ctgcgcgatc    9840
cgggtcgcgt cgcaggggac gagcaccggt gtctcgggga gcgacagctc gatgggtgc    9900 tccgcgagga cagggcgata gaggtccacc gcctcctgcg cgaggtcgcg cagatcgcgc    9960
tcctccaccc ggagctcgag cttgcaggcc tcgatctggg acgcgtcgag gaggtccccg    10020
accatgcgct cgagccggtc gacctgccgc cccacgagcg ccatggtgcg gcgcacgctc    10080
```

```
gacgccgggg gcaggctgtc gaggtcgagg acgtgcacgg acatccggag cgccgacagc    10140
gggttcctga ggtcgtgggc cacgccgccg aggaacgcga actgcgcctc gcgctggcgc    10200
tccagcgact ccgccatgtc gttgaaggcg cgcgcgatct ccccgagctc gcgcggcccg    10260
atcagcggcg cgcgcgcggc gcggtcgccc gcgccgtagc gcccgatcgc ctgctggatc    10320
gcgacgatgg ggcggtagat gagccgccgc gcgctgagga ggaccgtgga agcgcccgcg    10380
aggaagaaca cgaccgccgc cacgccgcg ccggtcgtgc gccgggtcag gtacgcgacg    10440
agcgcctccg acgcgcgggc ctgctcgagg ttgatctcga ccaggcgatc gagcgccctg    10500
aacgcctcgt cgagggcggg atcgtgcacg ccgagcaggg cgggatcgcg cgcgccaggc    10560
gccgacggga gctcgcgggc gtcggcggcg cggcgccggg cgaggtagtc ctccacgcgc    10620
cgctccgcgt gctcgaggat ctcgccctcc tccgggctgc tcacgtggcc gcgcgccgcc    10680
gcgaggccgc tcctcaggcc gcgctcccac gccgccaggg agggggccag ctccccgcgg    10740
tcggagccga ccgcgcggcc gctctgctgc gcgtcgagca ggaggtcgat ctccagccgc    10800
tccacgagcc ggacgctctc gaccgtggcg ccgaggatcc tggtggcctg ttgcatggtc    10860
gtcgacgcga ccatcagcgc gctggcgacc acgatggcca cgctcgtgag aagaagcgtg    10920
gcggccccga ggagcgcgct caggcgcacg ggccgcggaa aacggagcca gctcaggccc    10980
cgcggagttg gccgtcccat cctcctgcgt tggttcggat ccgcgccgga tgcaacgtcg    11040
cctcgatgga gagatcgaac tgcagaggga cagagcacat cgagacagcg agcgatacgc    11100
gcggcgcccc cgcggcgctc cccgcgcccc cgcgccggcc tcaccggcgc ctcgcgcccc    11160
ggtcagctcg gtcctctgga cggtgatccc cgtttcatcg acactacgcg cgatgcccgc    11220 gcgcacccc cgcaagcccc cgccgcccgc ctcgcccgct ggtcccgccg gcgcgccgga    11280
cgacctcagc gacagcgatc gcgacgcgct cttgcgctgg cggctcgcgc tcgggcccga    11340
ggccgagcgg gtcgacccgc gcctctccct gggcgggctc ggcggcgcgg cgcccgcgct    11400
cgacgtcgac ccgcggcggc tgggcgacct cgacaaggcg ctgtcgttca tctacgacga    11460
gcgcgccggc aacctcggcg gctcgcggcc gtacgtgccc gagtggctct ccgccgtgcg    11520
cgagttcttc agccacgagg tcgtcgccct cgtccagaag gacgccatcg agcgaaaggg    11580
gctgacgcag ctgctcttcg agcccgagac gctgccgttc ctcgagaaga acgtcgagct    11640
cgtcgccacg ctcatgagcg ccaagggcct catccccgac gccgcgcggg agaccgcccg    11700
gcagatcgtg cgcgaggtcg tcgaggaggt gcggcgcgcg ctcgagtccg aggtccgcac    11760
cgccgtcctc ggcgcgctgc gccggaacac gacgagcccg ctgcgcgtcc tcaggaacct    11820
cgactggaag cgcaccatcc gcaagaacct gaagggtgg gacgcgggagc ggcgccgcct    11880 cgtcccggac aagctctatt tctgggcgaa ccagacgcga aggcacgagt gggacgtggc    11940
catcctcgtc gaccagtcgg gctcgatggg cgagagcgtc gtctacagct ccatcatggc    12000
ggcgatcttc gcgtcgctcg acgtcctccg cacccggctc ctcttcttcg acaccgaggt    12060
cgtcgacgtg actccgatgc tcgtcgatcc ggtcgacgtg ctgttcacgg cgcagctcgg    12120
cggcggcacc gacatcaacc gcgccgtggc ctacgcccag gcgaacttca tcgagcgacc    12180
cgagaagacg ctgctcatcc tgatcaccga cctgttcgag ggcggcaacg ccgaggagct    12240
cgtcgcgcgc atgcgccagc tcgccgacag caaggtgaag tcgatctgcc tgctcgcgct    12300
gtcggacggc ggaaagccct cgtacgacca cgagatggcg cagaagctcg ccgccctcgg    12360
gaccccgtgt tcggctgca cgccaaagct gctcgtcaag gtggtggagc ggctcatgcg    12420
aggtcaggac ctcggcccgc tgctcggcgc cgaggcgcgg taaagccacg gaggcacaga    12480
```

-continued

```
ggacacagag gttcttgcct ctcctctgcg tcgtctgtgc ctccgtggcc gcccgtcagg    12540
ggccccgaga ccgaccggcg cggcttgcga acgtcgtcga cgtcagcgaa ggcgcgcccg    12600
ggacatccgc ggccgcgcag gccgcgtcac ggcgcgcgac ggatcgcctt ggcggcgcgc    12660
tcgtccgccc gccgggcggc ggcgcgcttt cgcgacgtgg cgccgtgggc agcgctcgcg    12720
gagacgcgac ggcgggtgcc ggccgcgcga accaccgctt cgagcgaggg tgactggccc    12780
atgagaggac cagtgctgat cgaggggccg actaggctga tagaaagttt cacttgacta    12840
ccgatgtggt ggcggaccga tcacgtcgct cagcggaggg ctcgtcgacc tataaactgt    12900
tttgatcttt tacgcagcgt cacggtgcgg agatcacgaa ccctgagcgc ccgtccggac    12960
gtgaacttgt ccaccgggga ggtccactcg ccttccgcct ctcacgacgg acgcatgcac    13020
gcacacacca cggaggcacg aaggcacggg tctgggttcg ctccgtgcct tcgtgtctcc    13080
gcggtgctcg gcgagggact gccccggagg ttgcaccggg cgctctgtta tgattccaag    13140
aagcacgatg caggccaacg atggcccgat gccggcctcg cccgttttcc ggggatggcc    13200
gtgggccgcc tttcatggtt gaaaccatcg gttgcaacca tggcgcaacg gagcggcgtc    13260
cctgtccgcg gggcgccagg cgaccctggg agcatgcctc tcggccggca ggaccggtca    13320
gcgaggatcc agggcgctgg cccagcggcc ccgacgatcc agccgcgcgg ggcagaagcg    13380
tcagcgccgc ctgggacctc gccccaggcc cggcgcgcgc tcgacctgga tgctcccgcc    13440 gtgggcccg aggatctggt ccacgacgcc cagcccccgt gcgagctcgc gggcgccgcc    13500
cgctcgaggt gcccgaagat caccggcagc ccgccgtccg agcggccgag gcacgggtg    13560 gggcctggac ctgcaagacc agcgcgccaa gcggggtcc gagctcgtgc ggggcggccg    13620
acacgagcct cgcggatctg gcttgccccc cgctccgtac ctgctcgaca ggggaccacc    13680
cagcgcacgc tgtcattcgg tcgagcaccc gccttctgtt cgcagggagc gccttgaaga    13740
gccggacagg gagccttccg gaaagccagt tgcctggtat ccaccatgtt tccggtgtgc    13800
ttcggctcag gcaacgggcc acatccgccc gggcgactcg atcggatgca acgtgatcga    13860
gtccgcatgg tcggcagcgg tccccgcccc ctcctgcctc tgacaacagc ggatcgcagc    13920
cccgcctgtg atgccggcag cggcacatct acacagatga atgttcaccc ggcgggcaat    13980
gttccgggct gaaaagaata atccagtctc agttcaatga ggtgccatgg cggcgccaaa    14040
ctcaccacat cgcactcggc gcaatcagtc gaccatagaa ttgaaatgta agacaaatta    14100
catgcgaaaa tgcttgaaat atcataaaaa agaatggatt gattggttgc gtagatcacc    14160
gttgatgcta gc                                                       14172
```

<210> SEQ ID NO 3
<211> LENGTH: 1126
<212> TYPE: PRT
<213> ORGANISM: Sorangium cellulosum

<400> SEQUENCE: 3

```
Met Gly Phe Pro Cys Ile Arg Arg Val Ser Gly Ser Ala Ala Ser Pro
1               5                   10                  15

Ala Thr Cys Val Lys Val Arg Arg Thr Phe Arg Ser Arg Pro Phe Arg
                20                  25                  30

Ala Ala Arg Ser Thr Lys Ser Ala Gln Val Glu Ala Arg Leu Ser Arg
            35                  40                  45

Ile Phe Ser Met Pro Asp Thr Ser Ser Ser Ser Pro Val Leu Ala Met
        50                  55                  60
```

-continued

```
Gly Leu Arg Asp Ser Asp Ala Arg Phe Val Glu Asp Thr Pro Pro Ala
 65                  70                  75                  80

Ser Asp Arg Pro Arg Pro Phe Ala Gly Ile Ala Val Val Gly Met Gly
                 85                  90                  95

Cys Arg Leu Pro Gly Gly Val Asp Ser Pro Glu Ser Leu Trp Ala Ala
            100                 105                 110

Leu Ser Glu Gly Arg Asp Leu Ile Ser Glu Val Pro Pro Asp Arg Trp
        115                 120                 125

Asp Val Asn Ala His Tyr Asp Ala Asp Ala Ser Val Pro Gly Lys Ile
130                 135                 140

Ala Thr Arg His Gly Gly Phe Leu Ala Gly Val Ala Ala Phe Asp Ala
145                 150                 155                 160

Pro Phe Phe Asp Leu Ser Pro Arg Glu Ala Lys His Met Asp Pro Gln
                165                 170                 175

Gln Arg Leu Gly Leu Glu Thr Ala Trp Glu Ala Leu Glu Asp Ala Gly
            180                 185                 190

Leu Asp Ala Arg Ser Leu Arg Gly Ser Arg Ala Gly Val Phe Val Gly
        195                 200                 205

Ser Met Trp Ala Glu Tyr Asp Val Leu Ala Ser Arg His Pro Glu Ser
    210                 215                 220

Ile Ser Pro His Gly Ala Thr Gly Ser Asp Pro Gly Met Ile Ala Ala
225                 230                 235                 240

Arg Ile Ala Tyr Thr Phe Gly Leu Arg Gly Pro Ala Leu Ser Val Asn
                245                 250                 255

Thr Ala Ser Ser Ser Leu Val Ala Val His Leu Ala Leu Gln Ser
            260                 265                 270

Leu Gln Ser Gly Glu Cys Glu Leu Ala Leu Ala Gly Gly Ala Asn Leu
        275                 280                 285

Ile Leu Thr Pro Tyr Asn Thr Ile Lys Met Thr Lys Leu Gly Thr Met
    290                 295                 300

Ser Pro Asp Gly Arg Cys Lys Ala Phe Asp His Arg Ala Asn Gly Tyr
305                 310                 315                 320

Val Arg Ala Glu Gly Val Gly Phe Val Val Leu Lys Arg Leu Ser Arg
                325                 330                 335

Ala Thr Ala Asp Gly Asp Arg Ile Tyr Ala Val Val Arg Gly Ser Ala
            340                 345                 350

Val Asn Asn Asp Gly Leu Thr Glu Gly Leu Thr Ala Pro Ser Val Glu
        355                 360                 365

Ala Gln Glu Ala Val Leu Arg Glu Ala Tyr Ala Arg Ala Gly Val Ser
    370                 375                 380

Pro Ala Glu Val Asp Tyr Val Glu Ala His Gly Thr Gly Thr Pro Leu
385                 390                 395                 400

Gly Asp Arg Val Glu Ala Thr Ala Leu Gly Arg Val Leu Gly Ala Gly
                405                 410                 415

Arg Ala Ala Asp Arg Ala Leu Arg Val Gly Ser Val Lys Thr Asn Leu
            420                 425                 430

Gly His Ala Glu Ala Ala Gly Val Ala Gly Leu Met Lys Thr Ala
        435                 440                 445

Leu Ser Leu Arg His Gly Ser Leu Pro Ala Ser Leu His Val Glu Arg
    450                 455                 460

Pro Asn Pro Glu Ile Pro Leu Glu Ala Leu Gly Leu Arg Leu Gln Thr
465                 470                 475                 480

Glu Leu Gly Ala Trp Pro Glu Val Asp Arg Pro Arg Arg Ala Gly Val
```

-continued

```
                485                 490                 495
Ser Ser Phe Gly Phe Gly Gly Thr Asn Cys His Val Val Leu Glu Glu
            500                 505                 510

Trp Arg Gly Gly Val Glu Gln Ser Ala Ala Glu Thr Gly Ser Glu Pro
            515                 520                 525

Gly Ala Ala Val Ser Pro Pro Ala Leu Pro Leu Val Leu Ser Ala Arg
            530                 535                 540

Asp His Gly Ala Leu Arg Ala Gln Ala Gly Arg Trp Ala Ala Trp Leu
545                 550                 555                 560

Thr Glu His Arg Glu Ala Arg Trp Ala Asp Val Ile His Thr Ala Ala
                565                 570                 575

Ala Arg Arg Thr His Leu Gly Ala Arg Ala Thr Val Val Ala Ala Gly
                580                 585                 590

Val Ala Glu Ala Val Asp Ala Leu Arg Ala Leu Ala Asp Gly Arg Ala
                595                 600                 605

His Gly Ala Val Thr Val Gly Glu Ala Arg Glu Arg Gly Lys Val Val
            610                 615                 620

Phe Val Phe Pro Gly Gln Gly Ser Gln Trp Pro Ala Met Gly Arg Ala
625                 630                 635                 640

Leu Leu Ser Ala Ser Arg Val Phe Ala Glu Ala Val Glu Ala Cys Asp
                645                 650                 655

Ala Ala Leu Arg Pro Leu Thr Gly Trp Ser Val Leu Ser Leu Leu Arg
                660                 665                 670

Gly Asp Ala Gly Glu Ala Ala Pro Ser Leu Asp Arg Val Asp Ala Val
            675                 680                 685

Gln Pro Ala Leu Phe Ala Met Ala Val Gly Leu Ser Ala Val Phe Arg
            690                 695                 700

Ala Trp Gly Leu Asp Pro Ser Ala Val Val Gly His Ser Gln Gly Glu
705                 710                 715                 720

Val Pro Ala Ala Tyr Val Ala Gly Ala Leu Ser Leu Asp Asp Ala Ala
                725                 730                 735

Arg Val Val Ala Val Arg Ser Ala Leu Val Arg Arg Leu Ser Gly Ala
                740                 745                 750

Gly Ala Met Ala Ala Val Glu Leu Pro Ala Gly Glu Val Glu Arg Arg
            755                 760                 765

Leu Ala Pro Phe Gly Gly Ala Leu Ser Val Ala Val Val Asn Thr Ser
            770                 775                 780

Ser Ser Thr Ala Val Ser Gly Asp Ala Glu Ala Val Asp Arg Leu Val
785                 790                 795                 800

Ala Gln Leu Glu Ala Glu Gly Ile Phe Cys Arg Lys Val Asn Val Asp
                805                 810                 815

Tyr Ala Ser His Ser Ala His Val Asp Val Val Leu Pro Glu Leu Leu
                820                 825                 830

Glu Arg Leu Ala Pro Ile Arg Pro Gly Ala Thr Arg Ile Pro Phe Tyr
                835                 840                 845

Ser Thr Val Thr Gly Gly Val Leu Glu Gly Thr Ala Leu Asp Gly Ala
            850                 855                 860

Tyr Trp Cys Arg Asn Leu Arg Gln Pro Val Arg Leu Asp Arg Ala Leu
865                 870                 875                 880

Ala Arg Leu Leu Asp Asp Gly His Gly Val Phe Val Glu Val Ser Ala
                885                 890                 895

His Pro Val Leu Ala Ser Pro Leu Thr Ala Ala Cys Ala Glu Arg Glu
            900                 905                 910
```

```
Gly Val Val Gly Ser Leu His Arg Asp Asp Gly Gly Leu Ala Arg
            915                 920                 925

Leu Leu Gly Ala Leu Gly Ala Leu His Val Gln Gly Gln Pro Val Asp
        930                 935                 940

Trp Arg Ala Val Leu Ala Pro Phe Gly Gly Gly Leu Val Asn Leu Pro
945                 950                 955                 960

Thr Tyr Ala Phe Gln Arg Gln Arg Tyr Trp Phe Asp Thr Asp Glu Ser
                965                 970                 975

Val Ala Leu Ala Ala Ala Ser Ser Ile Ala Glu Glu Ser Trp Ser Glu
            980                 985                 990

Lys Leu Ala Gly Leu Ser Pro Ala Arg Arg Glu Glu Arg Leu Leu Glu
        995                 1000                1005

Trp Val Arg Ala Glu Ile Ala Ala Val Leu Gly Leu Glu Ala Pro
    1010                1015                1020

Ala Val Pro Pro Asp Val Pro Leu Arg Asp Leu Gly Leu Lys Ser
    1025                1030                1035

Pro Ile Ala Val Glu Leu Gly Ser Arg Leu Gly Arg Arg Thr Arg
    1040                1045                1050

Arg Lys Leu Pro Val Ser Phe Val Tyr Asn His Pro Thr Pro Arg
    1055                1060                1065

Ala Ile Ala Arg Ala Leu Leu Glu Gly Met Phe Ser Ser Ser Lys
    1070                1075                1080

Asp Ser Pro Pro Ser Thr Ala Asp Asp Arg Arg Pro Pro Gly Val
    1085                1090                1095

Pro Ala Gly Val Ala Pro Pro Gln Ala Leu Glu Thr Ser Glu Met
    1100                1105                1110

Ser Asp Asp Glu Leu Phe Gln Ser Ile Asp Ala Leu Val
    1115                1120                1125

<210> SEQ ID NO 4
<211> LENGTH: 3689
<212> TYPE: PRT
<213> ORGANISM: Sorangium cellulosum

<400> SEQUENCE: 4

Met Asp Arg Ser Asp Lys Leu Arg Ala Tyr Leu Glu Lys Thr Thr Ala
1               5                   10                  15

Ser Leu Val Glu Ala Lys Ser Arg Ile Arg Glu Leu Glu Ala Arg Ser
            20                  25                  30

Arg Glu Pro Ile Ala Ile Val Ala Met Ala Cys Arg Phe Pro Gly Gly
        35                  40                  45

Val Asp Ser Pro Glu Lys Leu Trp Ala Leu Leu Asp Glu Glu Arg Asp
    50                  55                  60

Val Ile Thr Glu Val Pro Pro Ser Arg Trp Asp Leu Glu Arg Phe Tyr
65                  70                  75                  80

Asp Pro Asp Pro Asp Ala Ala Gly Lys Thr Tyr Ser Arg Trp Gly Gly
                85                  90                  95

Phe Val Gly Asp Leu Asp Arg Phe Asp Ala Ala Phe Phe Gly Ile Ser
            100                 105                 110

Pro Arg Glu Ala Arg Ser Ile Asp Pro Gln Glu Arg Trp Leu Leu Glu
        115                 120                 125

Thr Thr Trp Glu Ala Leu Glu Arg Ala Gly Val Arg Ala Asp Thr Leu
    130                 135                 140

Glu Gly Thr Leu Gly Gly Val Tyr Ile Gly Leu Ser Gly Ser Glu Tyr
```

```
            145                 150                 155                 160
Gln Ala Glu Ala Phe His Asp Ala Glu Arg Ile Asp Ala Tyr Ser Leu
                165                 170                 175
Thr Gly Ala Ser Pro Ser Thr Thr Val Gly Arg Leu Ala Tyr Trp Leu
                180                 185                 190
Gly Leu Arg Gly Pro Ala Val Ala Val Asp Thr Ala Cys Ser Ser Ser
                195                 200                 205
Leu Val Ala Val His Leu Ala Cys Gln Ala Leu Arg Asn Gly Glu Cys
                210                 215                 220
Asp Phe Ala Leu Ala Gly Gly Val Asn Ala Leu Leu Ala Pro Glu Ser
225                 230                 235                 240
Tyr Val Ala Phe Cys Arg Leu Arg Ala Leu Ser Pro Thr Gly Arg Cys
                245                 250                 255
Arg Thr Phe Ser Ala Asn Ala Asp Gly Tyr Val Arg Ala Glu Gly Cys
                260                 265                 270
Gly Val Leu Leu Leu Lys Arg Leu Ser Asp Ala Gln Arg Asp Gly Asp
                275                 280                 285
Arg Val Leu Ala Val Ile Arg Gly Asn Ala Ile Asn Gln Asp Gly Arg
                290                 295                 300
Ser Gln Gly Leu Thr Ala Pro Asn Gly Leu Ala Gln Glu Asp Val Ile
305                 310                 315                 320
Arg Arg Ala Leu Ser Gln Ala Ala Val Glu Pro Thr Thr Val Asp Val
                325                 330                 335
Val Glu Cys His Gly Thr Gly Thr Ala Leu Gly Asp Pro Ile Glu Val
                340                 345                 350
Gln Ala Leu Gly Ala Val Tyr Gly His Gly Arg Pro Gly Asp Arg Pro
                355                 360                 365
Leu Val Ile Gly Ser Val Lys Thr Asn Leu Gly His Thr Glu Ala Ala
                370                 375                 380
Ala Gly Met Ala Gly Leu Ile Lys Ala Val Leu Ser Leu Gln His Ala
385                 390                 395                 400
Gln Val Pro Arg Ser Leu His Phe Ala Ala Pro Ser Asp Tyr Ile Pro
                405                 410                 415
Trp Asp Thr Leu Pro Val Arg Val Ala Ala Gln Arg Val Ala Trp Glu
                420                 425                 430
Arg Arg Glu His Pro Arg Arg Ala Gly Val Ser Ser Phe Gly Ile Ser
                435                 440                 445
Gly Thr Asn Ala His Val Ile Leu Glu Glu Ala Pro Ala Ser Glu Ala
                450                 455                 460
Pro Ala Thr Ala Pro Val Ala Pro Val Ala Pro Leu Pro Ala
465                 470                 475                 480
Thr Leu Pro Leu Leu Val Ser Gly Arg Asp Glu Ala Ala Leu Arg Ala
                485                 490                 495
Gln Ala Gly Gln Trp Ala Ala Trp Leu Ala Ala His Pro Glu Ala Pro
                500                 505                 510
Trp Ala Asp Val Val His Thr Ala Ala Ala Arg Arg Thr His Leu Glu
                515                 520                 525
Ala Arg Ala Ala Val Ala Ala Gly Ser Ala Ala Asp Ala Ala Ala Ala
                530                 535                 540
Leu Glu Ala Leu Ala Ala Gly His Pro His Arg Ala Val Ser Leu Gly
545                 550                 555                 560
Glu Ala Arg Ala Arg Gly Glu Val Val Phe Val Tyr Pro Gly Gln Gly
                565                 570                 575
```

```
Ser Gln Trp Pro Ala Met Gly Arg Ala Leu Leu Ala Glu Ser Glu Val
            580                 585                 590

Phe Ala Ala Ala Val Ala Ala Cys Asp Ala Ala Leu Arg Pro Leu Thr
            595                 600                 605

Gly Trp Ser Val Leu Ser Val Leu Arg Gly Glu Gln Gly Glu Ala Val
            610                 615                 620

Pro Pro Ala Asp Arg Val Asp Val Gln Pro Ala Leu Phe Ala Met
625                 630                 635                 640

Ala Val Gly Leu Ser Ala Val Trp Arg Ala Trp Gly Ile Glu Pro Ser
            645                 650                 655

Ala Val Val Gly His Ser Gln Gly Glu Val Ala Ala Tyr Val Ala
            660                 665                 670

Gly Ala Leu Thr Leu Glu Asp Ala Ala Arg Val Val Ala Leu Arg Ser
            675                 680                 685

Gln Leu Val Arg Arg Ile Ala Gly Gly Ala Met Ala Val Ile Glu
            690                 695                 700

Arg Pro Val Gly Glu Val Glu Gln Arg Leu Ser Arg Phe Gly Gly Gln
705                 710                 715                 720

Leu Ser Val Ala Ala Val Asn Thr Pro Gly Ser Thr Val Val Ser Gly
            725                 730                 735

Asp Ala Ala Ala Val Asp Arg Leu Leu Ala Glu Leu Glu Ala Glu Arg
            740                 745                 750

Val Phe Ala Arg Arg Ile Lys Val Asp Tyr Ala Ser His Ser Ala His
            755                 760                 765

Val Asp Ala Ile Leu Pro Glu Leu Glu Ala Thr Leu Ala Ser Val Glu
            770                 775                 780

Pro Arg Ala Cys Thr Ile Pro Leu Tyr Ser Thr Val Thr Gly Glu Val
785                 790                 795                 800

Leu Ala Gly Pro Glu Leu Gly Gly Tyr Trp Cys Arg Asn Leu Arg
            805                 810                 815

Glu Pro Val Arg Leu Asp Arg Ala Leu Ser Arg Leu Leu Ala Asp Gly
            820                 825                 830

His Gly Val Phe Val Glu Val Ser Ala His Pro Val Leu Ala Met Pro
            835                 840                 845

Leu Ser Ala Ala Ser Ala Glu Arg Gly Gly Val Val Gly Ser Leu
850                 855                 860

Gln Arg Asp Asp Gly Gly Leu Gly Arg Leu Ala Ser Met Leu Gly Ala
865                 870                 875                 880

Leu His Val Gln Gly His Ala Val Asn Trp Gln Arg Val Leu Ala Pro
            885                 890                 895

Tyr Gly Gly Ala Leu Val Asp Leu Pro Thr Tyr Ala Phe Gln Arg Gln
            900                 905                 910

Arg His Trp Leu Glu Ala Pro Arg Tyr Ala Ala Glu Asp Thr Asp Gly
            915                 920                 925

Ala Ala Arg Arg Asp Pro Leu Tyr Arg Val Thr Trp Ile Glu Ala Ala
            930                 935                 940

Leu Glu Glu Ala Pro Trp Ala Ala Glu Arg His Val Val Leu Gly Ala
945                 950                 955                 960

Asp Gly Ala Leu Ala Ser Gly Leu Gly Ala Leu Ala Leu Ala Gly Leu
            965                 970                 975

Pro Glu Leu Leu Glu Ala Leu Glu Asn Gly Ala Ala Ala Pro Glu Arg
            980                 985                 990
```

-continued

```
Leu Val Leu Asp Leu Thr Glu Gly Arg Pro Gly Ala Val  Ala Glu Ser
        995                 1000                1005

Val His Ala Thr Thr Arg Ser Ala Leu Ala Leu Val  Gln Ala Trp
    1010                1015                1020

Leu Ala Ala Pro Arg Leu Ser Gly Thr Glu Leu Val  Val Val Thr
    1025                1030                1035

Arg Glu Ala Val Ala Ala Gly Pro Asp Glu Gly Val  Ala Ala Leu
    1040                1045                1050

Gly Pro Ala Ala Val Trp Gly Leu Leu Arg Thr Val  Arg Val Glu
    1055                1060                1065

His Pro Glu Arg Ala Val Arg Ser Val Asp Leu Gly  Arg Glu Pro
    1070                1075                1080

Pro Asp Val Ala Val Leu Arg Arg Ala Leu Gly Thr  Ala Ala Glu
    1085                1090                1095

Pro Glu Leu Ala Leu Arg Ala Gly Gly Ala Arg Ala  Pro Arg Leu
    1100                1105                1110

Arg Ala Val Asn Ala Gly Ala Asp Ala Arg Ala Pro  Ala Ala Ala
    1115                1120                1125

Leu Asp Pro Gln Gly Thr Val Trp Ile Thr Gly Gly  Thr Gly Glu
    1130                1135                1140

Leu Gly Arg Gln Val Ala Arg His Leu Val Ala Ala  His Gly Val
    1145                1150                1155

Arg His Leu Leu Leu Thr Ser Arg Arg Gly Ala Ala  Ala Pro Asp
    1160                1165                1170

Ala Glu Ala Leu Val Glu Gln Leu Arg Ala Asp Gly  Ala Glu Thr
    1175                1180                1185

Val Glu Val Val Ala Cys Asp Val Thr Asp Gly Ala  Ala Leu Ser
    1190                1195                1200

Ala Ala Val Gln Val Ala Ala Lys Arg Pro Leu  Thr Ala Val
    1205                1210                1215

Val His Thr Ala Gly Val Leu Ala Asp Gly Val Leu  Thr Ala Leu
    1220                1225                1230

Thr Ala Glu Gln Leu Thr Arg Ala Leu Ala Pro Lys  Val Asp Gly
    1235                1240                1245

Ala Cys His Val Tyr Ala Ala Ala Gln Asp Gln Pro  Leu Ala Ala
    1250                1255                1260

Phe Val Leu Phe Ser Ser Ile Val Gly Thr Leu Gly  Asn Ala Gly
    1265                1270                1275

Gln Ala Asn Tyr Gly Ala Ala Asn Ala Phe Leu Asp  Ala Phe Ala
    1280                1285                1290

Ala Gln Leu Arg Ala Arg Gly Val Pro Ala Thr Ser  Leu Ala Trp
    1295                1300                1305

Gly Phe Trp Glu Gln Ala Gly Leu Gly Met Thr Ala  His Leu Gly
    1310                1315                1320

Ala Ala Asp Leu Ala Arg Leu Gly Arg Gln Gly Leu  Val Pro Leu
    1325                1330                1335

Ser Val Ala Gln Gly Leu Arg Leu Leu Asp Arg Ala  Leu Ala His
    1340                1345                1350

Pro Glu Ala Thr Leu Val Pro Ala Ala Leu Asp Leu  Ser Ala Leu
    1355                1360                1365

Gln Arg Ala Ala Ser Asp Ala Gly Arg Val Pro Pro  Leu Leu Arg
    1370                1375                1380

Gly Leu Val Arg Ala Ser Pro Gly Arg Pro Thr Ala  Thr Ala Thr
```

-continued

```
            1385                1390                1395

Pro Glu Ala Gly Pro Ala Ala Ala Ser Ala Leu Arg Ala Arg Leu
    1400                1405                1410

Ser Ala Leu Pro Glu Ala Glu Arg Ala Gly Ala Leu Leu Glu Leu
    1415                1420                1425

Val Arg Ala Glu Val Ala Val Val Leu Arg Leu Ala Gly Pro Ala
    1430                1435                1440

Gln Val Pro Ala Asp Lys Pro Leu Lys Glu Leu Gly Leu Asp Ser
    1445                1450                1455

Leu Thr Ala Val Glu Leu Lys Asn Arg Leu Gly Ala Arg Ala Glu
    1460                1465                1470

Thr Val Leu Pro Thr Thr Leu Ala Phe Asp His Pro Thr Pro Arg
    1475                1480                1485

Ala Ile Ala Asp Leu Leu Leu Gln Arg Ala Phe Ser Glu Leu Ala
    1490                1495                1500

Gly Ala Thr Arg Ala Gln Ala Pro Arg Ala Arg Gly Ala His Asp
    1505                1510                1515

Glu Pro Ile Ala Ile Val Ser Met Ala Cys Arg Leu Pro Gly Gly
    1520                1525                1530

Val Asp Thr Pro Ala Ala Leu Trp Asp Leu Leu Ser Glu Gly Arg
    1535                1540                1545

Asp Ala Ile Gly Pro Phe Pro Glu Gly Arg Gly Trp Asp Val Ala
    1550                1555                1560

Gly Leu Tyr Asp Pro Asp Pro Asp Ala Pro Gly Lys Ser Ile Thr
    1565                1570                1575

Thr Gln Gly Gly Phe Leu Tyr Asp Ala Asp Arg Phe Asp Pro Thr
    1580                1585                1590

Phe Phe Gly Ile Ser Pro Arg Glu Ala Glu Arg Met Asp Pro Gln
    1595                1600                1605

Gln Arg Leu Leu Leu Glu Cys Ala Trp Glu Ala Leu Glu Arg Ala
    1610                1615                1620

Gly Leu Ala Pro His Ala Leu Glu Ala Ser Ala Thr Gly Val Phe
    1625                1630                1635

Phe Gly Leu Ala His Gly Asp Tyr Gly Gly Arg Leu Leu Gln Gln
    1640                1645                1650

Leu Glu Ser Phe Asp Gly His Val Leu Thr Gly Asn Phe Leu Ser
    1655                1660                1665

Val Gly Ser Gly Arg Ile Ala Tyr Thr Leu Gly Leu Arg Gly Pro
    1670                1675                1680

Ala Val Thr Val Asp Thr Ala Cys Ser Ser Ser Leu Val Ala Val
    1685                1690                1695

His Leu Ala Cys Met Ser Leu Arg Ala Gly Glu Cys Asp Leu Ala
    1700                1705                1710

Leu Ala Gly Gly Ala Thr Val Met Ala Thr Pro Met Ile Phe Val
    1715                1720                1725

Glu Phe Ser Arg Gln Arg Gly Thr Ala Leu Asp Gly Arg Cys Lys
    1730                1735                1740

Ala Phe Gly Ala Gly Ala Asp Gly Ala Gly Trp Ser Glu Gly Cys
    1745                1750                1755

Gly Ile Leu Ala Leu Lys Arg Leu Ser Asp Ala Arg Arg Asp Gly
    1760                1765                1770

Asp Arg Val Leu Ala Val Ile Arg Ser Ser Ala Val Asn Gln Asp
    1775                1780                1785
```

-continued

Gly Arg Ser Gln Gly Leu Thr Ala Pro Asn Gly Pro Ala Gln Gln
         1790                1795                1800

Asp Val Ile Arg Gln Ala Leu Ala Ala Ala Gly Leu Thr Pro Ala
         1805                1810                1815

Asp Ile Asp Ala Val Glu Ala His Gly Thr Gly Thr Arg Leu Gly
         1820                1825                1830

Asp Pro Ile Glu Ala Gln Ala Leu Leu Ala Thr Tyr Gly Thr Ala
         1835                1840                1845

His Thr Ala Glu Arg Pro Leu Trp Leu Gly Ser Leu Lys Ser Asn
         1850                1855                1860

Leu Gly His Thr Gln Val Ala Ala Gly Val Ser Gly Leu Met Lys
         1865                1870                1875

Leu Val Leu Ala Met Gln His Ala Glu Leu Pro Arg Thr Leu His
         1880                1885                1890

Ala Asp Pro Pro Ser Pro His Val Asp Trp Ser Gln Gly His Val
         1895                1900                1905

Lys Leu Leu Asn Glu Pro Ala Pro Trp Pro Arg Thr Asp Arg Pro
         1910                1915                1920

Arg Arg Ala Ala Val Ser Ser Phe Gly Ile Ser Gly Thr Asn Ala
         1925                1930                1935

His Val Ile Val Glu Glu Ala Pro Glu Pro Ala Pro Ala Ala Asp
         1940                1945                1950

Ala Lys Ala Val Glu Ala Leu Pro Ile Leu Pro Leu Leu Val Ser
         1955                1960                1965

Gly Ala Asp Glu Ala Ala Leu Arg Ala Gln Val Arg Arg Leu Val
         1970                1975                1980

Glu His Leu Arg Ser His Pro Asp Gln Arg Leu Leu Asp Val Ala
         1985                1990                1995

Ala Ser Leu Ala Thr Thr Arg Thr His Leu Ala Thr Arg Leu Ala
         2000                2005                2010

Leu Pro Val Ser Ala Gly Ala Pro Arg Asp Ala Trp Met Asp Glu
         2015                2020                2025

Leu Glu Ala Phe Ala Arg Gly Gly Ala Ala Pro Thr Gln Ala Ser
         2030                2035                2040

Gln Thr Pro Val Glu Ser Ser Thr Gly Lys Val Ala Val Leu Phe
         2045                2050                2055

Thr Gly Gln Gly Ser Gln Arg Ala Gly Met Gly Arg Ala Leu Tyr
         2060                2065                2070

Ala Thr His Pro Val Phe Arg Ala Ala Leu Asp Ala Ala Cys Ala
         2075                2080                2085

Glu Leu Asp Arg His Leu Asp Arg Pro Leu Met Ser Val Leu Phe
         2090                2095                2100

Ala Asp Ala Gly Ser Glu Ala Ala Ala Leu Leu Asp Gln Thr Ala
         2105                2110                2115

Trp Ala Gln Pro Ala Leu Phe Ala Leu Glu Val Ala Leu Tyr Arg
         2120                2125                2130

Gln Trp Asp Ala Trp Gly Leu Arg Pro Glu Leu Leu Leu Gly His
         2135                2140                2145

Ser Ile Gly Glu Leu Ala Ala Ala His Ile Ala Gly Val Leu Asp
         2150                2155                2160

Leu Ala Asp Ala Ser Ala Leu Val Ala Ala Arg Gly Arg Leu Met
         2165                2170                2175

-continued

```
Gln Ala Leu Pro Leu Gly Gly Ala Met Ala Ser Val Glu Ala Thr
    2180            2185                2190
Glu Asp Glu Leu Arg Pro Leu Leu Asp Gln His Thr Gly Arg Leu
    2195            2200                2205
Ser Leu Ala Ala Leu Asn Thr Pro Arg Gln Ser Val Val Ser Gly
    2210            2215                2220
Asp Glu Pro Ala Val Asp Gln Val Cys Ala His Phe Thr Ala Leu
    2225            2230                2235
Gly Arg Arg Ala Lys Arg Leu Val Val Ser His Ala Phe His Ser
    2240            2245                2250
Ala His Met Glu Pro Met Leu Asp Ala Phe Ala Arg Val Ala Arg
    2255            2260                2265
Gly Leu Thr Phe His Pro Pro Arg Leu Pro Ile Val Ser Ser Val
    2270            2275                2280
Thr Gly Ala Arg Ala Ser Ala Asp Glu Leu Thr Ser Pro Asp Tyr
    2285            2290                2295
Trp Val Arg Gln Val Arg Glu Pro Val Arg Phe Val Asp Gly Met
    2300            2305                2310
Arg Ala Leu His Ala Ala Gly Ala Ala Thr Phe Val Glu Cys Gly
    2315            2320                2325
Pro His Gly Val Leu Ser Ala Ala Gly Ala Glu Cys Leu Ala Pro
    2330            2335                2340
Asp Gly Ala Arg Asp Ala Gly Phe Val Pro Ser Leu Arg Asn Glu
    2345            2350                2355
Arg Asp Glu Ala Leu Ala Leu Val His Ala Ala Cys Ala Val His
    2360            2365                2370
Val Arg Gly His Ala Leu Asp Trp Leu Arg Phe Phe Asp Ala Thr
    2375            2380                2385
Gly Ala Arg Arg Val Glu Leu Pro Thr Tyr Ala Phe Gln Arg Gln
    2390            2395                2400
Arg Tyr Trp Leu Gln Ala Pro Arg Pro Arg Pro Ser Leu Glu Gly
    2405            2410                2415
Val Gly Leu Thr Ala Ala Asn His Pro Trp Leu Gly Ala Ala Val
    2420            2425                2430
Arg Leu Ala Asp Arg Asp Gly Tyr Val Leu Ser Gly Arg Leu Ser
    2435            2440                2445
Thr Ser Asp His Pro Trp Val Leu Asp His Val Val Leu Gly Thr
    2450            2455                2460
Ala Leu Leu Pro Gly Thr Gly Phe Val Glu Leu Ala Trp Ala Ala
    2465            2470                2475
Ala Glu Ala Val Gly Leu Ser Gly Val Ser Glu Leu Ala Ile Glu
    2480            2485                2490
Ala Pro Leu Ala Leu Pro Ala Arg Gly Ala Val Ala Leu Gln Val
    2495            2500                2505
Ala Ile Glu Ala Pro Asp Pro Ala Gly Arg Arg Gly Ile Ala Ile
    2510            2515                2520
Tyr Ser Arg Pro Asp Gly Ala Ala Asp Ala Pro Trp Thr Ala His
    2525            2530                2535
Ala Arg Gly Val Leu Gly Ala Ala Ala Ser Asp Arg Asp Ala Ala
    2540            2545                2550
Trp Ala Gln Gly Ala Trp Pro Pro Gly Ala Val Pro Val Asp
    2555            2560                2565
Val Thr Gln Trp Leu Glu Ile Val Asp Ala Trp Val Gly Pro Ala
```

-continued

```
             2570                2575                2580
Phe Arg Gly Val Val Ala Leu Trp Arg Val Gly Arg Thr Ile Tyr
    2585                2590                2595
Ala Asp Val Ala Leu Pro Asp Gly Val Ala Gly Thr Ala Gln Asp
    2600                2605                2610
Phe Gly Leu His Pro Ala Leu Leu Asp Val Ala Leu Arg Ala Phe
    2615                2620                2625
Leu Arg Ala Glu Leu Ser Ala Asp Pro Ser Pro Arg Glu Gly Thr
    2630                2635                2640
Val Val Pro Phe Ala Trp Ser Asp Val Ala Leu Glu Ala Arg Gly
    2645                2650                2655
Thr Ala Ala Leu Arg Val Arg Ala Glu Val Glu Ala Gly Gly Asp
    2660                2665                2670
Gly Asp Ala Ile Thr Ala Ser Ile Gln Leu Ala Asp Gly Gln Gly
    2675                2680                2685
Arg Pro Val Ala Arg Val Gly Ala Leu Gln Met Arg Trp Thr Thr
    2690                2695                2700
Ala Glu Arg Val Arg Ala Ala Ala Ala Gly Ala Ala Glu Arg
    2705                2710                2715
Asp Leu Tyr Arg Val Ala Trp Thr Asp Val Ala Leu Asp Asp Thr
    2720                2725                2730
Ala Phe Val Pro Glu Glu His Val Val Val Gly Asp Gly Ala
    2735                2740                2745
Leu Ala Ala Ala Leu Gly Ala Arg Ala Val Ala Gly Leu Pro Glu
    2750                2755                2760
Leu Leu Ala Ser Leu Pro Asp Gly Ala Ala Ala Pro Arg Arg Leu
    2765                2770                2775
Val Val Asp Leu Thr Ala Asp Ala Ala Gly Ala Val Val Asp Ala
    2780                2785                2790
Val His Ala Ala Ala Arg Asp Ala Leu Ser Leu Val Gln Gly Trp
    2795                2800                2805
Leu Ala Ala Pro Gln Leu Ala Ala Thr Glu Leu Val Val Val Thr
    2810                2815                2820
Arg Gly Ala Val Ala Val Ala Pro Asp Glu Gly Val Ala Ala Leu
    2825                2830                2835
Gly Pro Ala Ala Val Trp Gly Leu Leu Arg Ala Thr Arg Val Glu
    2840                2845                2850
His Ala Asp Arg Thr Val Arg Met Leu Asp Leu Gly Pro Gly Ala
    2855                2860                2865
Pro Asp Met Ala Leu Leu Arg Arg Ala Leu Thr Ala Ala Glu Glu
    2870                2875                2880
Pro Glu Leu Ala Leu Arg Ala Gly Gly Ala Arg Ala Pro Arg Leu
    2885                2890                2895
Asp Ala Ala Gly Glu Thr Asp Gly Glu Leu Ala Pro Pro Asp Gly
    2900                2905                2910
Ala Arg Ser Leu Arg Leu Ser Ile Arg Thr Lys Gly Ser Phe Asp
    2915                2920                2925
Ala Leu His Leu Ala Asp Ala Pro Asp Ala Leu Arg Pro Leu Gly
    2930                2935                2940
Pro Gly Gln Val Arg Leu Ala Val Arg Ala Thr Gly Leu Asn Phe
    2945                2950                2955
Arg Asp Val Leu Asn Val Leu Gly Thr Tyr Arg Gly Glu Ala Gly
    2960                2965                2970
```

-continued

```
Pro Leu Gly Leu Glu Gly Ala Gly Val Val Leu Asp Val Gly Glu
    2975                2980                2985
Gly Val Thr Ala Leu Arg Pro Gly Asp Arg Val Met Gly Ile Leu
    2990                2995                3000
His Ala Gly Met Ala Thr His Ala Val Val Asp Ala Arg Leu Leu
    3005                3010                3015
Thr His Ile Pro Arg Gly Leu Ser Phe Val Glu Ala Ala Thr Ile
    3020                3025                3030
Pro Ala Ala Phe Leu Thr Ala Leu Tyr Gly Leu Arg Asp Leu Gly
    3035                3040                3045
Ala Leu Lys Ala Gly Gln Arg Val Leu Val His Ala Ala Ala Gly
    3050                3055                3060
Gly Val Gly Met Ala Ala Val Gln Leu Ala Arg Leu Trp Gly Ala
    3065                3070                3075
Glu Val Phe Ala Thr Ala Ser Glu Gly Lys Trp Pro Ala Leu Arg
    3080                3085                3090
Gly Met Gly Ile Asp Gln Ala His Ile Ala Ser Ser Arg Thr Leu
    3095                3100                3105
His Phe Arg Lys Ala Phe Leu Asp Ala Thr Arg Gly Gln Gly Val
    3110                3115                3120
Asp Val Val Leu Asp Ala Leu Ala Gly Glu Phe Val Asp Ala Ser
    3125                3130                3135
Leu Asp Leu Leu Pro Arg Gly Gly Arg Phe Val Glu Met Gly Lys
    3140                3145                3150
Ser Asp Val Arg Asp Pro Glu Arg Val Ala Lys Asp His Pro Gly
    3155                3160                3165
Val Arg Tyr Thr Ala Phe Asp Leu Leu Asp Ala Gly Pro Asp His
    3170                3175                3180
Ile Gln Ala Met Leu Arg Glu Leu Val Pro Leu Phe Glu Glu Gly
    3185                3190                3195
Val Leu Ala Pro Leu Pro Phe Ala Val His Asp Leu Arg Arg Ala
    3200                3205                3210
Pro His Ala Phe Arg Ser Met Ala Asn Ala Arg His Val Gly Lys
    3215                3220                3225
Leu Val Leu Val Pro Pro Ala Ala Leu Asp Pro Asp Gly Thr Ala
    3230                3235                3240
Leu Ile Thr Gly Gly Thr Gly Glu Leu Gly Arg Gln Ile Ala Arg
    3245                3250                3255
His Leu Val Ala Ala His Gly Val Arg His Leu Val Leu Thr Ser
    3260                3265                3270
Arg Arg Gly Met Asp Ala Pro Asp Ala Ala Ala Leu Val Gly Ser
    3275                3280                3285
Leu Arg Ala Ala Gly Ala Ala Thr Val Glu Val Ala Ala Cys Asp
    3290                3295                3300
Val Thr Asp Arg Asp Ala Leu Ala Ala Val Val Gln Ala Ile Pro
    3305                3310                3315
Ala Ala Arg Pro Leu Thr Ala Ile Val His Thr Ala Ala Val Leu
    3320                3325                3330
Asp Asp Gly Ile Val Ala Gly Leu Ser Ala Glu Gln Leu Ala Arg
    3335                3340                3345
Val Leu Arg Pro Lys Val Asp Gly Ala Trp Arg Leu Tyr Glu Ala
    3350                3355                3360
```

```
Thr Arg Asp Ala Pro Leu Ala Ala Phe Met Leu Phe Ser Ser Val
    3365                3370                3375

Ala Gly Thr Leu Gly Ser Ser Gly Gln Ala Asn Tyr Ala Ala Ala
    3380                3385                3390

Asn Ala Phe Leu Asp Gly Leu Ala Ala Glu Leu Arg Thr Arg Gly
    3395                3400                3405

Val Pro Ala Met Ser Leu Ala Trp Gly Phe Trp Glu Gln Gly Gly
    3410                3415                3420

Ile Gly Met Thr Ala His Leu Gly Ala Ala Asp Leu Ala Arg Leu
    3425                3430                3435

Lys Arg Gln Gly Ile Ala Pro Met Thr Val Ala His Gly Leu Arg
    3440                3445                3450

Leu Leu Asp Arg Ala Leu Glu Arg Pro Asp Ala Ala Leu Val Pro
    3455                3460                3465

Ala Ser Leu Asp Val Ala Val Ile Gln Arg Ala Ala Ser Asp His
    3470                3475                3480

Arg Gln Val Pro Pro Met Leu Arg Gly Leu Val Arg Val Ala Pro
    3485                3490                3495

Arg Gln Ala Ala Gly Ala Ala Asn Gly Arg Ser His Glu Ala Ser
    3500                3505                3510

Thr Leu Arg Gln Gln Leu Ala Ala Leu Pro Glu Pro Glu Arg Gln
    3515                3520                3525

Arg Ala Leu Leu Asp Leu Val Arg Thr Glu Ala Ala Ala Val Leu
    3530                3535                3540

Val Leu Arg Gly Pro Asp Ala Val Pro Ala Asp Lys Pro Leu Arg
    3545                3550                3555

Glu Leu Gly Leu Asp Ser Leu Thr Ala Val Glu Leu Arg Asn Arg
    3560                3565                3570

Leu Arg Thr Arg Ala Gln Thr Asp Leu Pro Ser Thr Leu Ala Phe
    3575                3580                3585

Asp Tyr Pro Thr Pro Lys Ala Val Ala Val Tyr Leu Ala Gln Glu
    3590                3595                3600

Leu Asp Val His Asp Val Met Thr Glu Met Arg Gly Pro Ser Leu
    3605                3610                3615

Arg Ser Asp Asp Glu Ile Lys Ser Ala Ile Ala Ser Ile Arg Ile
    3620                3625                3630

Ser Thr Leu Arg Gln Ala Gly Leu Leu Asp Ser Leu Leu Arg Leu
    3635                3640                3645

Ala Ala Ser Glu Ala Val Ser Thr Ser Ser Asp Thr Thr Pro Glu
    3650                3655                3660

Thr Asp Glu Leu Thr Leu Gln His Val Gly Asp Asp Glu Leu Ala
    3665                3670                3675

Arg Leu Val Phe Asp Leu Ala Gly Gly Ala Gln
    3680                3685

<210> SEQ ID NO 5
<211> LENGTH: 3655
<212> TYPE: PRT
<213> ORGANISM: Sorangium cellulosum

<400> SEQUENCE: 5

Met Lys Glu Asp Ile Ser Ala Arg Gln Ala Leu Glu Lys Ser Phe Ile
1               5                   10                  15

Glu Leu Arg Arg Ile Lys Arg Glu Leu Asp Gln Leu Lys Ala Lys Ser
                20                  25                  30
```

-continued

```
Ser Glu Pro Ile Ala Ile Val Ser Met Ala Cys Arg Leu Pro Gly Gly
            35                  40                  45

Val Asp Thr Pro Ala Ala Leu Trp Gln Leu Leu Ser Glu Gly Arg Asp
        50                  55                  60

Ala Ile Gly Pro Phe Pro Glu Gly Arg Gly Trp Asp Val Ala Gly Leu
65                  70                  75                  80

Tyr Asp Pro Asp Pro Asp Ala Pro Gly Lys Ser Ile Thr Ala Gln Gly
                85                  90                  95

Gly Phe Leu Tyr Asp Ala Asp Arg Phe Asp Pro Ala Phe Phe Ala Ile
            100                 105                 110

Ser Pro Arg Glu Ala Glu Arg Met Asp Pro Gln Gln Arg Leu Leu Leu
        115                 120                 125

Glu Cys Ala Trp Glu Ala Leu Glu Arg Ala Gly Leu Ala Pro His Ser
    130                 135                 140

Leu Glu Ala Ser Ala Thr Gly Val Phe Val Gly Leu Ser Val Thr Asp
145                 150                 155                 160

Tyr Gly Gly Arg Leu Leu His Glu Pro Glu Ala Leu Asp Gly Tyr Ile
                165                 170                 175

Ala Thr Gly Thr Leu Pro Ser Val Gly Ser Gly Arg Ile Ala Tyr Thr
            180                 185                 190

Leu Gly Leu Arg Gly Pro Ala Val Thr Val Asp Thr Ala Cys Ser Ser
        195                 200                 205

Ser Leu Val Ser Leu His Leu Ala Cys Met Ser Leu Arg Ala Gly Glu
    210                 215                 220

Cys Asp Leu Ala Leu Ala Gly Gly Ala Thr Val Met Ala Thr Pro Met
225                 230                 235                 240

Ala Phe Ile Glu Phe Ser Arg Gln Arg Gly Thr Ala Leu Asp Gly Arg
                245                 250                 255

Cys Lys Ala Phe Gly Ala Gly Ala Asp Gly Ala Gly Trp Ser Glu Gly
            260                 265                 270

Cys Gly Ile Leu Thr Leu Lys Arg Leu Ser Asp Ala Arg Arg Asp Gly
        275                 280                 285

Asp Arg Val Leu Ala Val Ile Arg Gly Ser Ala Val Asn Gln Asp Gly
    290                 295                 300

Arg Ser Gln Gly Leu Thr Ala Pro Asn Gly Pro Ala Gln Gln Asp Val
305                 310                 315                 320

Ile Arg Gln Ala Leu Ala Ala Ala Gly Leu Thr Pro Ala Asp Val Asp
                325                 330                 335

Ala Val Glu Ala His Gly Thr Gly Thr Arg Leu Gly Asp Pro Ile Glu
            340                 345                 350

Ala Gln Ala Leu Leu Ala Thr Tyr Gly Thr Ala His Thr Ala Glu Arg
        355                 360                 365

Pro Leu Trp Leu Gly Ser Leu Lys Ser Asn Leu Gly His Thr Gln Ala
    370                 375                 380

Ala Ala Gly Val Ser Gly Leu Met Lys Leu Val Leu Ala Met Gln His
385                 390                 395                 400

Ala Glu Leu Pro Arg Thr Leu His Ala Asp Pro Ser Pro His Val
                405                 410                 415

Asp Trp Ser Arg Gly His Val Lys Leu Leu Asn Glu Pro Val Pro Trp
            420                 425                 430

Pro Arg Thr Asp Arg Pro Arg Arg Ala Ala Val Ser Ser Phe Gly Phe
        435                 440                 445
```

```
Ser Gly Thr Asn Ala His Val Ile Val Glu Glu Ala Pro Ala Ala Ser
    450                 455                 460

Thr Glu Ala Thr Thr Arg Gly Glu Lys Thr Pro Ala Ala Pro Pro
465                 470                 475                 480

Ser Thr Leu Pro Leu Leu Val Ser Gly Ala Asp Glu Ala Ala Leu Arg
                485                 490                 495

Ala His Ala Gly Arg Trp Ala Ala Trp Leu Ala Ala His Pro Glu Ala
                500                 505                 510

Gly Trp Ala Asp Val Val Tyr Thr Ala Ala Arg Arg Thr His Leu
                515                 520                 525

Gly Ala Arg Ala Ala Leu Thr Ala Ala Asp Ala Ala Gly Ala Val Ala
    530                 535                 540

Ala Leu Thr Ala Leu Ser Gln Gly Gln Pro His Ala Ala Leu Ala Val
545                 550                 555                 560

Gly Glu Ala Arg Ala Arg Gly Lys Val Val Phe Val Phe Pro Gly Gln
                565                 570                 575

Gly Ser Gln Trp Pro Ala Met Gly Arg Ala Leu Leu Ser Gln Ser Glu
                580                 585                 590

Val Phe Ala Ala Val Ala Ala Cys Asp Ala Ala Leu Arg Pro Phe
595                 600                 605

Thr Gly Trp Ser Val Leu Ser Val Leu Arg Gly Asp Thr Gly Ala Glu
    610                 615                 620

Val Pro Pro Leu Glu Arg Val Asp Val Val Gln Pro Ala Leu Phe Ala
625                 630                 635                 640

Met Ala Val Gly Leu Ala Ala Val Trp Arg Ala Trp Gly Leu Glu Pro
                645                 650                 655

Ser Ala Val Val Gly His Ser Gln Gly Glu Val Pro Ala Ala Tyr Val
                660                 665                 670

Ala Gly Ala Leu Ser Leu Glu Asp Ala Ala Arg Ile Val Ala Leu Arg
    675                 680                 685

Ser Arg Leu Val Arg Arg Leu Ser Gly Thr Gly Ala Met Ala Val Ile
690                 695                 700

Glu Leu Pro Val Gly Glu Val Glu Gln Arg Leu Ser Arg Phe Gly Gly
705                 710                 715                 720

Ala Leu Ser Val Ala Ala Val Asn Thr Pro Arg Ser Thr Val Val Ser
                725                 730                 735

Gly Asp Ala Glu Ala Val Asp Arg Leu Leu Thr Glu Phe Glu Gly Glu
                740                 745                 750

Gln Val Phe Ala Arg Lys Val Asn Val Asp Tyr Ala Ser His Ser Arg
    755                 760                 765

His Ile Asp Gly Leu Leu Pro Glu Leu Glu Asp Gly Leu Gly Ala Val
    770                 775                 780

Arg Pro Arg Ala Ser Thr Ile Pro Phe Tyr Ser Thr Val Thr Gly Thr
785                 790                 795                 800

Val Leu Thr Gly Ala Glu Leu Asp Ala Ala Tyr Trp Cys Arg Asn Leu
                805                 810                 815

Arg Glu Pro Val Arg Leu Asp Arg Ala Leu Ser Arg Leu Leu Asp Asp
                820                 825                 830

Gly His Gly Leu Phe Val Glu Val Ser Ala His Pro Val Leu Thr Leu
    835                 840                 845

Pro Leu Thr Gly Ala Ser Ala Thr Ser Gly Val Val Val Gly Ser
850                 855                 860

Leu Gln Arg Asp Asp Gly Gly Leu Gly Arg Leu Leu Gly Val Leu Ala
```

-continued

```
865                 870                 875                 880
Ala Leu His Val His Gly His Asp Val Asp Trp Arg Ala Val Leu Ala
                885                 890                 895
Pro Trp Gly Gly Gly Val Ala Asp Leu Pro Thr Tyr Ala Phe Gln Arg
            900                 905                 910
Gln Arg Tyr Trp Leu Glu Ala Pro Arg Gly Arg Ala Gly Leu Glu Ser
        915                 920                 925
Gly Gly Leu Leu Ala Val Lys His Pro Trp Leu Ser Ala Ala Val Arg
    930                 935                 940
Leu Ala Asp Arg Asp Gly Tyr Val Leu Ser Gly Arg Leu Ser Thr Val
945                 950                 955                 960
Glu His Ala Trp Val Leu Asp His Val Val Leu Gly Thr Val Ile Leu
                965                 970                 975
Pro Gly Thr Ala Phe Val Glu Leu Ala Leu Ala Ala Ala Asp Ala Val
            980                 985                 990
Gly Leu Pro Ser Val Ser Glu Leu  Thr Ile Glu Ala Pro  Leu Ala Leu
        995                 1000                1005
Pro Ala Arg Gly Ala Val Thr  Leu Gln Val Thr Val  Glu Ala Leu
    1010                1015                1020
Asp Ala Thr Gly Arg Arg Gly  Phe Ala Val His Ser  Arg Pro Asp
    1025                1030                1035
Gly Ala His Asp Ala Pro Trp  Thr Ala His Ala Arg  Gly Val Leu
    1040                1045                1050
Gly Ala Ala Pro Ala Ala Ala  Thr Thr Ala Trp Ala  Ala Gly Ala
    1055                1060                1065
Trp Pro Pro Ala Gly Ala Glu  Pro Val Asp Val Thr  Arg Trp Val
    1070                1075                1080
Glu Ala Leu Asp Ala Trp Val  Gly Pro Ala Phe Arg  Gly Val Thr
    1085                1090                1095
Ala Ala Trp Arg Val Gly Arg  Ser Ile Tyr Ala Asp  Leu Ala Leu
    1100                1105                1110
Pro Glu Gly Val Ser Glu Arg  Ala Gln Asp Phe Gly  Leu His Pro
    1115                1120                1125
Ala Leu Leu Asp Ala Ala Leu  Gln Ala Leu Leu Arg  Ala Glu Leu
    1130                1135                1140
Gly Ala Gly Ser Ser Pro Arg  Glu Gly Ile Pro Met  Pro Phe Ala
    1145                1150                1155
Trp Ser Asp Val Ala Leu Glu  Ala Arg Gly Ala Ala  Ala Leu Arg
    1160                1165                1170
Ala Arg Val Glu Val Glu Asp  Ala Ser Asp Gly Asp  Gln Leu Ala
    1175                1180                1185
Ala Ser Ile Glu Leu Ala Asp  Ala Gln Gly Gln Pro  Val Ala Arg
    1190                1195                1200
Ala Gly Thr Phe Arg Ala Arg  Trp Ala Thr Ala Glu  His Val Arg
    1205                1210                1215
Lys Ala Ala Ala Gly Ala Ser  Glu Arg Asp Leu Tyr  Arg Val Thr
    1220                1225                1230
Trp Thr Asp Val Ala Leu Glu  Glu Ala Ala Trp Ala  Pro Glu Glu
    1235                1240                1245
His Ile Val Leu Gly Gly Asp  Gly Ala Leu Ala Ala  Ala Leu Gly
    1250                1255                1260
Ala Arg Thr Ala Ala Leu Pro  Glu Leu Ile Ala Ala  Leu Pro Glu
    1265                1270                1275
```

-continued

```
Gly Ala Ala Ala Pro Arg Arg Leu Val Ile Asp Ala Ala Ala Gly
    1280                1285                1290

Asp Pro Gly Asp Gly Leu Val Ala Ala Ala His Ala Ala Thr Gln
    1295                1300                1305

Arg Val Leu Ser Leu Val Gln Gly Trp Leu Ser Glu Ala Arg Leu
    1310                1315                1320

Ala Asp Ser Glu Leu Val Val Thr Arg Gly Ala Val Ala Ala
    1325                1330                1335

Gly Pro Asp Asp Gly Val Ala Ala Leu Ser His Ala Pro Leu Trp
    1340                1345                1350

Gly Leu Val Arg Thr Ala Arg Gln Glu Asn Pro Gly Arg Ala Val
    1355                1360                1365

Arg Leu Val Asp Leu Gly Pro Glu Pro Leu Asp Gly Ala Leu Val
    1370                1375                1380

Arg Arg Ala Val Ala Ala Glu Glu Pro Glu Leu Ala Leu Arg
    1385                1390                1395

Gly Gly Ala Ala Arg Ala Pro Arg Leu Arg Glu Val Arg Ala Gly
    1400                1405                1410

Ala Ala Asp Ala Ala Arg Pro Thr Arg Leu Asp Pro Gly Gly Thr
    1415                1420                1425

Val Leu Ile Thr Gly Gly Thr Gly Glu Leu Gly Arg Gln Val Ala
    1430                1435                1440

Arg His Leu Val Ala Ala His Gly Val Arg His Leu Val Leu Thr
    1445                1450                1455

Ser Arg Arg Gly Met Asp Ala Pro Asp Ala Ala Ala Leu Val Asp
    1460                1465                1470

Glu Leu Arg Ala Ala Gly Ala Ala Thr Val Asp Val Ala Ala Cys
    1475                1480                1485

Asp Val Ala Asp Gly Ala Ala Leu Gly Ala Val Ile Ala Ala Ile
    1490                1495                1500

Pro Ala Ala His Pro Leu Thr Ala Val Val His Met Ala Gly Val
    1505                1510                1515

Leu Asp Asp Val Ile Val Thr Lys Leu Ser Ala Glu Gln Leu Ala
    1520                1525                1530

Arg Val Leu Arg Pro Lys Ile Asp Gly Gly Trp His Leu Ala Ala
    1535                1540                1545

Ala Thr Arg Gly His Arg Leu Ala Ala Phe Val Leu Phe Ser Ser
    1550                1555                1560

Ala Ala Gly Thr Leu Gly Ser Ala Gly Gln Ala Asn Tyr Ala Ala
    1565                1570                1575

Ala Asn Ala Phe Leu Asp Ala Leu Ala Ala Gln Leu Arg Ala Arg
    1580                1585                1590

Gly Val Pro Ala Met Ser Leu Ala Trp Gly Phe Trp Glu Gln Ala
    1595                1600                1605

Gly Leu Gly Met Thr Ala His Leu Gly Ala Ala Asp Leu Ala Arg
    1610                1615                1620

Leu Arg Arg Gln Gly Ile Ala Pro Ile Ala Leu Ala Gln Gly Met
    1625                1630                1635

Gln Leu Leu Asp Arg Ala Leu Ala Arg Pro Glu Ala Ala Leu Val
    1640                1645                1650

Pro Ala Ala Leu Asp Leu Ser Ala Leu Gln Arg Ala Ala Ser Asp
    1655                1660                1665
```

-continued

Ala Gly Gln Val Pro Ala Leu Leu Arg Gly Leu Val Arg Pro Ala
1670                1675                1680

Ala Gly Arg Arg Ala Ala Ser Pro Ala Ala Ala Thr Gly Ala
1685                1690                1695

Ala Ala Leu Arg Ala Arg Leu Ser Ala Leu Pro Glu Ala Glu Arg
1700                1705                1710

Ala Gly Ala Leu Leu Glu Leu Val Arg Ala Glu Ala Ala Val
1715                1720                1725

Leu Gln Leu Ala Gly Pro Ala Gln Val Pro Ala Asp Lys Pro Leu
1730                1735                1740

Lys Glu Leu Gly Leu Thr Ser Leu Thr Ala Val Glu Leu Arg Asn
1745                1750                1755

Arg Leu Gly Ala Arg Ala Glu Thr Ala Leu Pro Ala Thr Leu Ala
1760                1765                1770

Phe Asp His Pro Thr Pro Arg Ala Ile Ala Asp Leu Leu Leu Gln
1775                1780                1785

Arg Ala Phe Ser Glu Leu Ala Ala Ala Gly Ala Thr Arg Ala Gln
1790                1795                1800

Ala Pro Arg Ala Arg Gly Ala His Asp Glu Pro Ile Ala Ile Val
1805                1810                1815

Ser Met Ala Cys Arg Leu Pro Gly Gly Val Asp Thr Pro Ala Ala
1820                1825                1830

Leu Trp Gln Leu Leu Ser Glu Gly Arg Asp Ala Ile Gly Pro Phe
1835                1840                1845

Pro Glu Gly Arg Gly Trp Asp Val Ala Gly Leu Tyr Asp Pro Asp
1850                1855                1860

Pro Asp Ala Pro Gly Lys Ser Val Thr Asn Leu Gly Gly Phe Leu
1865                1870                1875

Tyr Asp Ala Asp Arg Phe Asp Pro Thr Phe Phe Gly Ile Ser Pro
1880                1885                1890

Arg Glu Ala Glu Arg Met Asp Pro Gln Gln Arg Leu Leu Leu Glu
1895                1900                1905

Cys Ala Trp Glu Ala Leu Glu Arg Ala Gly Leu Ala Pro His Ser
1910                1915                1920

Leu Glu Ala Ser Ala Thr Gly Val Phe Val Gly Leu Val Tyr Ser
1925                1930                1935

Asp Tyr Gly Gly Arg Leu Leu Glu His Leu Glu Val Phe Asp Gly
1940                1945                1950

Tyr Val Ala Thr Gly Ser Phe Pro Ser Val Gly Ser Gly Arg Ile
1955                1960                1965

Ala Tyr Thr Leu Gly Leu Arg Gly Pro Ala Val Thr Val Asp Thr
1970                1975                1980

Ala Cys Ser Ser Ser Leu Val Ser Leu His Leu Ala Cys Met Ser
1985                1990                1995

Leu Arg Ala Gly Glu Cys Asp Leu Ala Leu Ala Gly Gly Ala Thr
2000                2005                2010

Val Met Ala Thr Pro Met Ala Phe Ile Glu Phe Ser Arg Gln Arg
2015                2020                2025

Gly Met Ala Pro Asp Ala Arg Cys Lys Ala Phe Gly Ala Ala Ala
2030                2035                2040

Asn Gly Ile Gly Pro Ala Glu Gly Cys Gly Leu Leu Val Leu Lys
2045                2050                2055

Arg Leu Ser Asp Ala Arg Arg Asp Gly Asp Arg Val Leu Ala Val

-continued

```
               2060                2065                2070
Leu Arg  Gly Ser Ala Val  Asn Gln Asp Gly  Arg Ser Gln Gly  Leu
        2075                2080                2085

Thr Ala  Pro Asn Gly Pro  Ala Gln Gln Asp  Val Ile Arg Gln  Ala
        2090                2095                2100

Leu Ala  Ala Ala Gly Leu  Thr Pro Ala Asp  Ile Asp Ala Val  Glu
        2105                2110                2115

Ala His  Gly Thr Gly Thr  Arg Leu Gly Asp  Pro Ile Glu Ala  Gln
        2120                2125                2130

Ala Leu  Leu Ala Thr Tyr  Gly Thr Ala His  Thr Ala Glu Arg  Pro
        2135                2140                2145

Leu Trp  Leu Gly Ser Ile  Lys Ser Asn Leu  Gly His Thr Gln  Ala
        2150                2155                2160

Ala Ala  Gly Val Val Gly  Leu Met Lys Leu  Val Leu Ala Met  Gln
        2165                2170                2175

His Ala  Glu Leu Pro Arg  Thr Leu Tyr Ala  Glu Pro Arg Ser  Pro
        2180                2185                2190

His Ile  Asp Trp Ser Gln  Gly His Ile Asn  Leu Leu Asn Glu  Pro
        2195                2200                2205

Val Pro  Trp Pro Arg Thr  Asp Arg Pro Arg  Ala Ala Val Ser
        2210                2215                2220

Ser Phe  Gly Ile Ser Gly  Thr Asn Ala His  Val Ile Val Glu  Glu
        2225                2230                2235

Ala Pro  Ala Ala Ala Gln  Thr Ala Ala Glu  Ala Ala Ala Val
        2240                2245                2250

Pro Ser  Thr Leu Pro Leu  Leu Leu Ser Gly  Arg Asp Glu Pro  Ala
        2255                2260                2265

Leu Arg  Ala Gln Ala Gly  Arg Leu Ala Glu  His Leu Arg Ala  His
        2270                2275                2280

Pro Asp  Gln Arg Leu Leu  Asp Val Ala Ala  Ser Leu Ala Thr  Thr
        2285                2290                2295

Arg Thr  His Leu Ala Thr  Arg Leu Ala Leu  Pro Leu Ala Pro  Asp
        2300                2305                2310

Ala Ala  Thr Glu Glu Leu  Gly Ala Arg Leu  Ala Glu Phe Ala  Ser
        2315                2320                2325

Gly Gly  Pro Ala Pro Ser  Gly Ala Ala Val  Thr Ala Pro Gly  Gln
        2330                2335                2340

Pro Pro  Gly Lys Val Ala  Val Leu Phe Thr  Gly Gln Gly Ser  Gln
        2345                2350                2355

Arg Ala  Gly Met Gly Arg  Ala Leu Tyr Ala  Thr His Pro Val  Phe
        2360                2365                2370

Arg Ala  Ala Leu Asp Ala  Ala Cys Ala Glu  Leu Asp Arg His  Leu
        2375                2380                2385

Asp Arg  Pro Leu Met Ser  Val Leu Phe Ala  Asp Ala Gly Ser  Glu
        2390                2395                2400

Ala Ala  Ala Leu Leu Asp  Gln Thr Ala Trp  Ala Gln Pro Ala  Leu
        2405                2410                2415

Phe Ala  Leu Glu Val Ala  Leu Tyr Arg Gln  Trp Asp Ala Trp  Gly
        2420                2425                2430

Leu Arg  Pro Glu Leu Leu  Leu Gly His Ser  Ile Gly Glu Leu  Ala
        2435                2440                2445

Ala Ala  His Ile Ala Gly  Val Leu Asp Leu  Ala Asp Ala Ser  Ala
        2450                2455                2460
```

-continued

```
Leu Val Ala Ala Arg Gly Arg Leu Met Gln Ala Leu Pro Leu Gly
2465                2470                2475

Gly Ala Met Ala Ser Val Glu Ala Thr Glu Asp Glu Leu Arg Pro
2480                2485                2490

Leu Leu Asp Gln His Thr Gly Arg Leu Ser Leu Ala Ala Leu Asn
2495                2500                2505

Thr Pro Arg Gln Ser Val Val Ser Gly Asp Glu Pro Ala Val Asp
2510                2515                2520

Gln Val Cys Ala His Phe Thr Ala Leu Gly Arg Arg Ala Lys Arg
2525                2530                2535

Leu Val Val Ser His Ala Phe His Ser Ala His Met Glu Pro Met
2540                2545                2550

Leu Asp Ala Phe Ala Arg Val Ala Arg Gly Leu Thr Phe His Pro
2555                2560                2565

Pro Arg Leu Pro Ile Val Ser Ser Val Thr Gly Ala Arg Ala Ser
2570                2575                2580

Ala Asp Glu Leu Thr Ser Pro Asp Tyr Trp Val Arg Gln Val Arg
2585                2590                2595

Glu Pro Val Arg Phe Ala Asp Gly Met Arg Ala Leu His Ala Ala
2600                2605                2610

Gly Ala Ala Thr Phe Val Glu Cys Gly Pro His Gly Val Leu Ser
2615                2620                2625

Ala Ala Gly Ala Glu Cys Leu Ala Pro Asp Gly Ala Arg Asp Ala
2630                2635                2640

Gly Phe Val Pro Ser Leu Arg Lys Asp Arg Asp Glu Ala Leu Ala
2645                2650                2655

Leu Val His Ala Ala Cys Ala Val His Val Arg Gly His Ala Leu
2660                2665                2670

Asp Trp Leu Arg Leu Phe Asp Pro Ser Gly Ala Arg Arg Val Glu
2675                2680                2685

Leu Pro Thr Tyr Ala Phe Gln Arg Gln Arg Tyr Trp Leu Gln Ala
2690                2695                2700

Pro Arg Pro Arg Pro Ser Leu Glu Gly Val Gly Leu Thr Ala Ala
2705                2710                2715

Asn His Pro Trp Leu Gly Ala Ala Val Arg Leu Ala Asp Arg Asp
2720                2725                2730

Gly Tyr Val Leu Ser Gly Arg Leu Ser Thr Leu Asp His Pro Trp
2735                2740                2745

Val Leu Asp His Val Val Ala Gly Thr Val Ile Leu Pro Gly Thr
2750                2755                2760

Ala Phe Val Asp Leu Ala Trp Ala Ala Ala Glu Val Val Gly Ala
2765                2770                2775

Ala Ala Val Ser Glu Val Thr Phe Thr Thr Pro Leu Val Leu Pro
2780                2785                2790

Pro Arg Ser Val Val Glu Leu Gln Val Arg Ile Gly Glu Pro Asp
2795                2800                2805

Ala Ser Gly Arg Arg Thr Phe Ala Ala Tyr Ser Arg Pro Asp Ala
2810                2815                2820

Ala Ser Glu Ala Glu Trp Thr Gln His Ala Thr Gly Val Leu Ser
2825                2830                2835

Ala Gln Ala Ala Ala Gly Ala Asp Val Ala Asp Leu Ser Val Trp
2840                2845                2850
```

-continued

```
Pro Pro Pro Gly Ala Glu Val Ala Leu Asp Gly Gly Tyr Ala
    2855             2860             2865

Trp Leu Ala Ala Gln Gly Tyr Gly Tyr Gly Pro Ala Phe Gln Ala
    2870             2875             2880

Leu Arg Glu Val Trp Arg Ala Gly Thr Thr Leu Tyr Ala Arg Val
    2885             2890             2895

Ala Leu Pro Asp Ala Val Ala Asp Thr Ala Gln Ser Phe Gly Ile
    2900             2905             2910

His Pro Ala Leu Leu Asp Ala Val Leu His Ser Leu Leu Ala Arg
    2915             2920             2925

Ser Pro Gln Glu Glu Ala Ser Asp Asp Asp Lys Val Leu Leu Ala
    2930             2935             2940

Phe Ala Phe Ser Asp Val Val Ile Glu Ala Arg Gly Ala Ala Glu
    2945             2950             2955

Val Arg Val Arg Leu Asn Lys Gln Ala Gly Asp Asp Gly Glu Gly
    2960             2965             2970

Leu Thr Ala Ser Ile His Leu Ala Asp Ala Gln Gly Arg Pro Val
    2975             2980             2985

Ala Arg Val Gly Ala Phe Gln Ala Arg Ala Thr Thr Thr Glu Arg
    2990             2995             3000

Val Arg Ala Leu Ala Gly Ala Ser Glu Arg Asp Leu His Arg Val
    3005             3010             3015

Thr Trp Thr Asp Val Thr Leu Asp Glu Ala Pro Trp Ala His Glu
    3020             3025             3030

Asp Ser Val Val Val Gly Gly Asp Gly Ala Leu Ala Ala Ala Leu
    3035             3040             3045

Gly Val Arg Ala Val Ala Gly Leu Pro Glu Leu Phe Ala Gly Gly
    3050             3055             3060

Ala Ala Ala Pro Arg Arg Leu Val Ile Asp Ala Thr Ala Gly Asp
    3065             3070             3075

Pro Gly Asp Gly Leu Val Ala Ala Thr His Ala Ala Thr Gln Arg
    3080             3085             3090

Gly Leu Ala Leu Leu Gln Gly Trp Leu Ala Glu Ala Arg Leu Ala
    3095             3100             3105

Ser Thr Glu Leu Val Leu Val Thr Arg Gly Ala Thr Ala Ala Glu
    3110             3115             3120

Pro Asp Glu Gly Val Ala Ala Leu Ser His Ala Pro Leu Trp Gly
    3125             3130             3135

Leu Val Arg Ala Ala Arg Glu Glu His Pro Ala Arg Ala Leu Arg
    3140             3145             3150

Leu Val Asp Leu Gly Arg Glu Ala Pro Asp Gly Ala Val Leu Arg
    3155             3160             3165

Arg Ala Ile Ala Ala Asp Asp Glu Pro Glu Leu Val Val Arg Arg
    3170             3175             3180

Gly Ala Leu Arg Ala Ala Arg Leu Ser Leu Ala His Ala Ala Pro
    3185             3190             3195

Asp Ala Ala Gly Arg Ala Thr Arg Leu Ala Pro Gly Gly Thr Val
    3200             3205             3210

Leu Ile Thr Gly Gly Thr Gly Glu Leu Gly Arg Gln Val Ala Arg
    3215             3220             3225

His Leu Val Thr Ala His Gly Val Arg His Leu Val Leu Thr Ser
    3230             3235             3240

Arg Arg Gly Met Asp Ala Pro Asp Ala Ala Ala Leu Val Glu Ala
```

-continued

```
            3245                3250                3255
Leu Arg Ala Ala Gly Ala Ala Thr Val Glu Ile Ala Ala Cys Asp
        3260                3265                3270
Val Ala Asp Arg Asp Ala Leu Ala Ala Val Leu Arg Ala Ile Pro
        3275                3280                3285
Ala Ala His Pro Leu Thr Ala Val Val His Thr Ala Gly Val Leu
        3290                3295                3300
Glu Asp Gly Val Val Thr Gly Leu Ser Ala Glu Gln Leu Ala Arg
        3305                3310                3315
Val Leu Arg Pro Lys Val Asp Gly Ala Trp Gln Leu Tyr Glu Ala
        3320                3325                3330
Thr Arg Asp Ala Pro Leu Ala Ala Phe Met Leu Phe Ser Ser Ala
        3335                3340                3345
Ala Gly Thr Leu Gly Ser Ala Gly Gln Ala Asn Tyr Ala Ala Ala
        3350                3355                3360
Asn Ala Phe Leu Asp Ala Leu Ala Ala Glu Leu Arg Thr Arg Gly
        3365                3370                3375
Val Pro Ala Met Ser Leu Ala Trp Gly Phe Trp Glu Gln Gly Gly
        3380                3385                3390
Ile Gly Met Thr Ala His Leu Gly Ala Ala Asp Leu Ala Arg Met
        3395                3400                3405
Lys Arg Gln Gly Ile Val Pro Met Ala Val Thr His Gly Leu Arg
        3410                3415                3420
Leu Leu Asp Arg Ala Leu Glu Arg Pro Glu Ala Thr Leu Val Pro
        3425                3430                3435
Leu Ser Leu Asp Val Ala Ala Leu Gln Arg Ala Ala Gly Asp Ala
        3440                3445                3450
Gly Arg Val Pro Ala Leu Leu Arg Gly Leu Val Arg Pro Ala Ala
        3455                3460                3465
Ala Arg His Thr Ala Val Pro Ala Ala Ala Ala Thr Gly Ala Thr
        3470                3475                3480
Gly Leu Arg Ala Arg Leu Leu Pro Leu Ser Glu Ala Glu Arg Gln
        3485                3490                3495
Asp Val Leu Leu Asp Leu Val Arg Thr Glu Ile Ala Asp Ile Leu
        3500                3505                3510
Ala Leu Ser Gly Pro Ala Ala Val Pro Pro Asp Gln Pro Ile Arg
        3515                3520                3525
Glu Leu Gly Leu Asp Ser Leu Thr Ala Val Asp Val Arg Ser Arg
        3530                3535                3540
Leu Val Gln Arg Ser Glu Ile Asp Leu Pro Val Thr Leu Ala Tyr
        3545                3550                3555
Asp Tyr Pro Thr Ala Arg Ala Ile Ala Gly His Leu Ser Glu Gln
        3560                3565                3570
Met Gly Leu Glu Gly Ala Pro Glu Asp Arg Glu Ser Ala Leu Asp
        3575                3580                3585
Glu Ala Gln Ile Arg Ala Leu Leu Met Gln Ile Pro Ile Ser Thr
        3590                3595                3600
Leu Arg Gln Ser Gly Leu Leu Gly Asp Leu Val Arg Leu Ala Ser
        3605                3610                3615
Pro Gln Ala Pro Pro Arg Glu Glu Gly Glu Ser Glu Thr Leu Ser
        3620                3625                3630
Phe Asp His Leu Gly Asn Glu Glu Phe Leu Ser Leu Ala Ser Lys
        3635                3640                3645
```

```
Leu Ile Ala Glu Glu Gly Ser
    3650            3655

<210> SEQ ID NO 6
<211> LENGTH: 1892
<212> TYPE: PRT
<213> ORGANISM: Sorangium cellulosum

<400> SEQUENCE: 6

Met Asn Gln Glu Thr Val Leu Arg Gln Thr Leu Glu Lys Ser Leu His
1               5                   10                  15

Lys Ile Gln His Leu Asn Arg Glu Leu Glu Arg Leu Lys Ala Lys Ser
            20                  25                  30

Ser Glu Pro Ile Ala Ile Val Ser Met Ala Cys Arg Phe Pro Gly Gly
        35                  40                  45

Val Asp Thr Pro Ala Ala Leu Trp Asp Leu Ser Glu Gly Arg Asp
    50                  55                  60

Ala Ile Gly Pro Phe Pro Glu Gly Arg Gly Trp Asp Val Ala Gly Leu
65                  70                  75                  80

Tyr Asp Pro Asp Pro Asp Ala Pro Gly Lys Ser Ile Thr Thr Gln Gly
                85                  90                  95

Gly Phe Leu Tyr Asp Ala Asp Arg Phe Asp Pro Thr Phe Phe Gly Ile
            100                 105                 110

Ser Pro Arg Glu Ala Glu Arg Met Asp Pro Gln Gln Arg Leu Leu Leu
        115                 120                 125

Glu Cys Ala Trp Glu Ala Leu Glu Arg Ala Gly Leu Ala Pro His Ser
130                 135                 140

Leu Glu Ala Ser Ala Thr Gly Val Phe Val Gly Leu Val Tyr Ser Asp
145                 150                 155                 160

Tyr Gly Gly Arg Leu Leu Glu His Leu Glu Val Phe Asp Gly Tyr Val
                165                 170                 175

Ala Thr Gly Ser Phe Pro Ser Val Gly Ser Gly Arg Ile Ala Tyr Thr
            180                 185                 190

Leu Gly Leu Arg Gly Pro Ala Val Thr Val Asp Thr Ala Cys Ser Ser
        195                 200                 205

Ser Leu Val Ser Leu His Leu Ala Cys Met Ser Leu Arg Ala Gly Glu
    210                 215                 220

Cys Asp Leu Ala Leu Ala Gly Gly Ala Thr Val Met Ala Thr Pro Met
225                 230                 235                 240

Ala Phe Ile Glu Phe Ser Arg Gln Arg Gly Met Ala Pro Asp Ala Arg
                245                 250                 255

Cys Lys Ala Phe Gly Ala Ala Ala Asn Gly Ile Gly Pro Ala Glu Gly
            260                 265                 270

Cys Gly Leu Leu Val Leu Lys Arg Leu Ser Asp Ala Arg Arg Asp Gly
        275                 280                 285

Asp Arg Val Leu Ala Val Ile Arg Ser Ser Ala Val Asn Gln Asp Gly
    290                 295                 300

Arg Ser Gln Gly Leu Thr Ala Pro Asn Gly Pro Ala Gln Gln Asp Val
305                 310                 315                 320

Ile Arg Gln Ala Leu Ala Ala Gly Leu Thr Pro Ala Asp Val Asp
                325                 330                 335

Ala Val Glu Ala His Gly Thr Gly Thr Pro Leu Gly Asp Pro Ile Glu
            340                 345                 350

Ala Gln Ala Leu Leu Ala Thr Tyr Gly Lys Ala His Thr Ala Glu Arg
```

-continued

```
            355                 360                 365
Pro Leu Trp Leu Gly Ser Ile Lys Ser Asn Phe Gly His Thr Gln Ala
    370                 375                 380
Ala Ala Gly Val Ala Gly Ile Ile Lys Leu Val Leu Ala Met Gln His
385                 390                 395                 400
Ala Glu Leu Pro Arg Thr Leu His Ala Asp Pro Pro Ser Pro Arg Val
                405                 410                 415
Asp Trp Ser Gln Gly His Val Lys Leu Leu Asn Glu Pro Val Pro Trp
                420                 425                 430
Pro Arg Thr Asp Arg Pro Arg Arg Ala Val Ser Ser Phe Gly Val
                435                 440                 445
Ser Gly Thr Asn Ala His Val Ile Ile Glu Glu Ala Pro Ala Glu Ala
    450                 455                 460
Pro Thr Ala Ala Gln Thr Ala Ala Ala Ala Thr Glu Pro Ala Ala
465                 470                 475                 480
Ala Val Val Pro Ser Thr Leu Pro Leu Leu Ser Gly Arg Asp Glu
                485                 490                 495
Pro Ala Leu Arg Ala Gln Ala Gly Arg Leu Ala Glu His Leu Arg Ala
                500                 505                 510
His Pro Asp Leu Arg Leu Leu Asp Val Ala Ala Gly Leu Ala Thr Thr
                515                 520                 525
Arg Thr His Leu Ala Thr Arg Leu Ala Leu Pro Leu Ala Pro Asp Ala
    530                 535                 540
Ala Thr Glu Glu Leu Gly Ala Arg Leu Ala Glu Phe Ala Ala Gly Gly
545                 550                 555                 560
Pro Ala Pro Ser Gly Ala Ala Val Thr Ala Pro Gly Gln Pro Pro Gly
                565                 570                 575
Lys Val Ala Val Leu Phe Thr Gly Gln Gly Ser Gln Arg Ala Gly Met
                580                 585                 590
Gly Arg Ala Leu Tyr Ala Thr His Pro Val Phe Arg Ala Ala Leu Asp
                595                 600                 605
Ala Ala Cys Ala Glu Leu Asp Arg His Leu Asp Arg Pro Leu Val Ser
    610                 615                 620
Val Leu Phe Ala Asp Ala Gly Ser Glu Ala Ala Ala Leu Leu Asp Gln
625                 630                 635                 640
Thr Ala Trp Ala Gln Pro Ala Leu Phe Ala Leu Glu Val Ala Leu Tyr
                645                 650                 655
Arg Gln Trp Glu Ala Trp Gly Leu Arg Ala His Ala Leu Leu Gly His
                660                 665                 670
Ser Leu Gly Glu Ile Val Ala Ala His Ile Ala Gly Val Leu Asp Leu
                675                 680                 685
His Asp Ala Ser Ala Leu Val Ala Ala Arg Gly Arg Leu Met Gln Ala
    690                 695                 700
Leu Pro His Gly Gly Ala Met Ala Ser Ile Glu Ala Thr Glu His Glu
705                 710                 715                 720
Leu Arg Pro Leu Leu Asp Gln His Thr Gly Arg Val Ser Leu Ala Ala
                725                 730                 735
Leu Asn Ala Pro Arg Gln Ser Val Val Ser Gly Asp Gln Pro Val Val
                740                 745                 750
Asp Gln Val Cys Ala His Phe Lys Ala Leu Gly Arg Arg Ala Lys Arg
                755                 760                 765
Leu Asp Val Ser His Ala Phe His Ser Ala Arg Met Glu Pro Met Leu
                770                 775                 780
```

-continued

```
Asp Ala Phe Ala His Val Ala Arg Gly Leu Thr Tyr Arg Ala Pro Arg
785                 790                 795                 800

Leu Pro Val Val Ser Asn Val Thr Gly Arg Met Ala Thr Ala Asp Glu
            805                 810                 815

Leu Thr Ser Pro Asp Tyr Trp Val Arg His Val Arg Glu Pro Val Arg
            820                 825                 830

Phe Val Ala Gly Val Arg Ala Leu His Ala Thr Gly Val Thr Thr Tyr
            835                 840                 845

Leu Glu Cys Gly Pro Asp Pro Val Leu Gly Gly Met Ala Ala Asp Cys
850                 855                 860

Leu Thr Pro Asp Glu Thr Arg Asp Val Gly Leu Ile Pro Ser Leu Arg
865                 870                 875                 880

Lys Asp Arg Asp Glu Ala Leu Ala Leu Ala Gln Ala Ala Cys Ala Leu
                885                 890                 895

Tyr Val Arg Gly His Ala Leu Asp Trp Leu Arg Leu Phe Asp Ala Thr
            900                 905                 910

Arg Ala Arg Arg Val Glu Leu Pro Thr Tyr Ala Phe Gln Arg Gln Arg
            915                 920                 925

Tyr Trp Ile Asp Ala Pro Arg Arg Ala Ala Gly Leu Asp Ser Val Gly
            930                 935                 940

Leu Thr Ala Ala Asp His Pro Trp Leu Gly Ala Ala Val Arg Leu Ala
945                 950                 955                 960

Asp Arg Asp Val His Val Leu Ser Gly Arg Leu Ser Thr Val Asp His
            965                 970                 975

Pro Trp Ile Leu Asp His Val Val Ala Gly Thr Pro Leu Met Pro Gly
            980                 985                 990

Thr Gly Phe Val Glu Leu Ala Trp Ala Thr Ala Gln Ala Val Asp Ala
            995                 1000                1005

Ala Ala Ile Ala Glu Leu Thr Leu Thr Thr Pro Leu Val Leu Pro
    1010                1015                1020

Ala Arg Gly Ala Val Gln Leu Gln Val Thr Val Asp Glu Ala Asp
    1025                1030                1035

Ala Asn Gly Arg Arg Ala Phe Ala Ile His Ser Arg Pro His Gly
    1040                1045                1050

Pro Gly Asp Leu Ala Trp Thr Gln His Ala Thr Gly Val Leu Ser
    1055                1060                1065

Ala Glu Glu Pro Ala Gly Ala Asp Glu Ala Ala Gly Leu Ser Glu
    1070                1075                1080

Trp Pro Pro Pro Gly Ala Glu Ala Val Ala Leu Asp Gly Gly Tyr
    1085                1090                1095

Glu Gln Leu Ser Glu His Gly Tyr Gly His Gly Pro Ala Phe Gln
    1100                1105                1110

Gly Leu Arg Gly Leu Trp Arg Ala Asp Arg Thr Leu Tyr Ala His
    1115                1120                1125

Val Ala Leu Pro Asp Ala Val Ala Gly Thr Glu Gln Gly Phe Gly
    1130                1135                1140

Leu His Pro Ala Leu Phe Asp Ala Ala Leu Gln Ser Leu Ala Arg
    1145                1150                1155

Leu Ser Arg Glu Glu Ala Ala Ala Gly Asp Pro Val Leu Val Pro
    1160                1165                1170

Phe Ala Trp Thr Asp Val Ala Leu Tyr Ala Thr Gly Ala Thr Glu
    1175                1180                1185
```

-continued

```
Leu Arg Ala Arg Ile Ala Leu Glu Gln Ala Glu Gly Gly Ala Pro
    1190            1195                1200
Ala Val Ala Ser Leu Leu Leu Ala Asp Ala His Gly Arg Thr Val
    1205            1210                1215
Ala Thr Thr Gly Arg Val Arg Gly Ala Ser Ala Ala Gln Thr Arg
    1220            1225                1230
Ser Ala Ala Ser Arg Ala Glu Pro Met Tyr Arg Val Ala Trp Thr
    1235            1240                1245
Asp Val Ala Leu Glu Ala Ala Thr Trp Ala Pro Glu Glu His Val
    1250            1255                1260
Val Leu Gly Gly Asp Gly Ala Leu Ala Ala Ala Leu Gly Val Arg
    1265            1270                1275
Ala Ala Ala Gly Leu Pro Glu Leu Leu Glu Ala Leu Ala Asp Gly
    1280            1285                1290
Ala Ala Ala Pro Arg Arg Leu Val Val Asp Leu Thr Ala Gly Asp
    1295            1300                1305
Ala Gly Ala Val Val Ala Ala Val His Ala Ala Val Arg Gly Ala
    1310            1315                1320
Leu Ala Leu Val Gln Gly Trp Leu Ala Ala Pro Gln Leu Ala Ala
    1325            1330                1335
Thr Glu Leu Leu Val Val Thr Arg Cys Ala Val Ala Thr Gly Pro
    1340            1345                1350
Asp Glu Gly Val Asp Ala Leu Gly Pro Ala Ala Val Trp Gly Leu
    1355            1360                1365
Leu Arg Ala Thr Arg Ala Glu Tyr Pro Asp Arg Ala Val Arg Val
    1370            1375                1380
Leu Asp Val Gly Arg Glu Pro Leu Asp Gly Ala Leu Leu Arg Arg
    1385            1390                1395
Ala Leu Ala Ala Gly Thr Glu Pro Glu Leu Ser Val Arg Ser Gly
    1400            1405                1410
Glu Ala Arg Ala Pro Arg Leu Arg Glu Val Arg Gly Ser Glu Pro
    1415            1420                1425
Ala Ala Ala Pro Ala Thr Arg Leu Asp Pro Asp Gly Thr Ala Leu
    1430            1435                1440
Ile Thr Gly Gly Thr Gly Glu Leu Gly Arg His Val Ala Lys His
    1445            1450                1455
Leu Val Thr Ala His Gly Val Arg His Leu Val Leu Thr Ser Arg
    1460            1465                1470
Arg Gly Met Asp Ala Pro Asp Ala Ala Ala Leu Val Asp Glu Leu
    1475            1480                1485
Arg Ala Ala Gly Ala Ala Thr Val Asp Val Ala Ala Cys Asp Ala
    1490            1495                1500
Ala Asp Ala Ala Ala Leu Ala Ala Val Val Glu Ala Ile Pro Ala
    1505            1510                1515
Ala Arg Pro Leu Thr Ala Val Val His Thr Ala Gly Val Leu Asp
    1520            1525                1530
Asp Ser Val Val Thr Lys Leu Ser Ala Glu Gln Leu Ala Arg Val
    1535            1540                1545
Leu Arg Pro Lys Val Asp Gly Ala Phe His Leu His Glu Leu Thr
    1550            1555                1560
Lys His Ala Pro Leu Ala Ala Phe Val Leu Phe Ser Ser Ala Ala
    1565            1570                1575
Gly Thr Leu Gly Ser Pro Gly Gln Ala Asn Tyr Ala Ala Ala Asn
```

```
                      1580                1585                1590

Thr Phe Leu Asp Ala Leu Ala Ser His Leu Arg Ala Arg Gly Val
    1595                1600                1605

Pro Ala Met Ser Leu Ala Trp Gly Phe Trp Ala Gln Thr Gly Leu
    1610                1615                1620

Gly Met Thr Ala His Leu Gly Ala Ala Asp Ile Ala Arg Met Lys
    1625                1630                1635

Arg His Gly Val Val Ser Met Pro Val Ala Gln Gly Leu Arg Leu
    1640                1645                1650

Leu Asp Arg Ala Leu Ala Gln Ala Glu Ala Thr Leu Val Pro Leu
    1655                1660                1665

Ala Leu Asp Leu Ser Ser Leu Gln Arg Ala Gly Ser Asn Ala Gly
    1670                1675                1680

Pro Val Pro Pro Leu Leu Arg Gly Leu Val Arg Ala Pro Ala Gly
    1685                1690                1695

Arg Arg Thr Ala Ala Ser Ala Ala Gly Ala Asn Gly Asn Gly Thr
    1700                1705                1710

Gly Ala Ala Ala Leu Arg Ala Arg Leu Ser Pro Leu Pro Gly Ala
    1715                1720                1725

Glu Arg Gln Lys Val Leu Leu Asp Leu Val Arg Thr Glu Ile Ala
    1730                1735                1740

Glu Val Phe Gln Leu Pro Gly Pro Ala His Ile Pro Ala Asp Arg
    1745                1750                1755

Pro Leu Lys Glu Leu Gly Leu Asp Ser Leu Met Ser Val Glu Leu
    1760                1765                1770

Arg Asn Arg Leu Gly Pro Arg Val Glu Ala Ala Leu Pro Ala Thr
    1775                1780                1785

Leu Val Phe Asp Tyr Pro Thr Pro Gly Ala Ile Ala Ser Tyr Leu
    1790                1795                1800

Gly Thr Leu Leu Asn Leu Ser Gly Glu Asp Ala His Pro Gly Gln
    1805                1810                1815

Thr Gly Arg Asp Pro Asp Glu Glu His Glu Ile Arg Ala Ala Ile
    1820                1825                1830

Ala Arg Ile Pro Ile Thr Thr Leu Arg Glu Ala Gly Leu Leu Gln
    1835                1840                1845

Ser Leu Leu Arg Leu Ala Pro Asn Gln Thr Ala Ser Asp Asp Val
    1850                1855                1860

Thr Pro Arg Thr Asp Glu Leu Met Val Glu His Leu Gly Asp Glu
    1865                1870                1875

Glu Leu Leu Lys Leu Ala Phe Ala Ser Thr Gly Gly Ala Lys
    1880                1885                1890

<210> SEQ ID NO 7
<211> LENGTH: 3507
<212> TYPE: PRT
<213> ORGANISM: Sorangium cellulosum

<400> SEQUENCE: 7

Met Lys Asp Glu Val Leu Ser Phe Arg Arg Ala Leu Glu Lys Thr Val
1               5                   10                  15

Val Glu Ile Arg Arg Leu Asn Thr Glu Ile Asp Gly Leu Arg Ala Lys
            20                  25                  30

Ser Val Glu Pro Ile Ala Ile Val Ser Met Ala Cys Arg Tyr Pro Gly
        35                  40                  45
```

```
Gly Val Asp Ser Pro Ala Ala Leu Trp Gln Leu Leu Ser Glu Gly Arg
 50                  55                  60

Asp Ala Ile Gly Pro Phe Pro Glu Gly Arg Gly Trp Asp Val Ala Gly
 65                  70                  75                  80

Leu Tyr Asp Pro Asp Pro Asp Ala Pro Gly Lys Ser Ile Thr Thr Gln
                 85                  90                  95

Gly Gly Phe Leu Tyr Asp Ala Asp His Phe Asp Pro Met Phe Phe Gly
                100                 105                 110

Ile Ser Pro Arg Glu Ala Glu Arg Ile Asp Pro Gln Gln Arg Leu Leu
                115                 120                 125

Leu Glu Cys Ala Trp Glu Ala Leu Glu Ser Ala Gly Ile Ala Pro His
    130                 135                 140

Thr Leu Gly Ala Ser Ala Thr Gly Val Phe Ile Gly Leu Met Tyr Thr
145                 150                 155                 160

Glu Tyr Gly Leu Arg Leu Met Asn Gln Pro Glu Ala Leu Asp Gly Tyr
                165                 170                 175

Ile Gly Ile Gly Ser Ala Gly Ser Thr Ala Ser Gly Arg Ile Ser Tyr
                180                 185                 190

Thr Leu Gly Leu Arg Gly Pro Ala Val Thr Val Asp Thr Ala Cys Ser
    195                 200                 205

Ser Ser Leu Val Ser Leu His Leu Ala Cys Thr Ala Leu Arg Arg Gly
210                 215                 220

Glu Cys Asp Leu Ala Leu Ala Gly Gly Ala Ala Val Val Ser Thr Pro
225                 230                 235                 240

Ala Pro Phe Ile Glu Phe Ser Arg Gln Arg Ala Leu Ala Val Asp Gly
                245                 250                 255

Arg Cys Lys Ser Phe Gly Ala Gly Ala Asp Gly Val Ser Trp Ser Glu
                260                 265                 270

Gly Cys Gly Leu Leu Val Leu Lys Arg Leu Ser Asp Ala Gln Arg Asp
    275                 280                 285

Gly Asp Arg Val Leu Ala Val Leu Arg Gly Ser Ala Val Asn Gln Asp
    290                 295                 300

Gly Arg Ser Gln Gly Leu Thr Ala Pro Asn Gly Pro Ala Gln Gln Asp
305                 310                 315                 320

Val Ile Arg Gln Ala Leu Ala Ala Ala Gly Leu Thr Pro Ala Asp Ile
                325                 330                 335

Asp Ala Val Glu Gly His Gly Thr Gly Thr Pro Leu Gly Asp Pro Ile
                340                 345                 350

Glu Ala Gln Ala Leu Leu Ala Thr Tyr Gly Lys Ala His Thr Ala Glu
    355                 360                 365

Arg Pro Leu Trp Leu Gly Ser Ile Lys Ser Asn Phe Gly His Thr Gln
    370                 375                 380

Ala Ala Ala Gly Val Ala Gly Val Met Lys Leu Val Leu Ala Met Gln
385                 390                 395                 400

His Ala Glu Leu Pro Arg Thr Leu Arg Ala Asn Pro Ser Pro His
                405                 410                 415

Val Asp Trp Ser Gln Gly His Ile Ala Leu Leu Asn Glu Pro Ala Ser
                420                 425                 430

Trp Pro Arg Thr Asp Arg Pro Arg Arg Ala Ala Val Ser Ser Phe Gly
    435                 440                 445

Val Ser Gly Thr Asn Ala His Val Ile Ile Glu Glu Ala Pro Ala Pro
450                 455                 460

Ala Ala Glu Val Thr Ser Pro Gly Ala Glu Pro Pro Ala Val Ala Leu
```

```
              465                 470                 475                 480
Pro Leu Leu Val Ser Gly Arg Asp Asp Ala Ala Leu Arg Ala Gln Ala
                    485                 490                 495
Glu Arg Trp Ala Ala Trp Leu Ala Ala His Pro Glu Ala Arg Trp Ala
                500                 505                 510
Asp Val Val His Thr Ala Ala Val Arg Arg Thr His Leu Glu Ala Arg
                515                 520                 525
Ala Ala Val Thr Ala Ala Ser Ala Ala Asp Ala Ala Ala Ala Leu Thr
                530                 535                 540
Ala Leu Ser Gln Gly Glu Pro His Pro Ala Val Thr Ala Gly Glu Ala
545                 550                 555                 560
Arg Ala Arg Gly Lys Val Val Phe Val Ala Pro Gly Gln Gly Ser Gln
                565                 570                 575
Trp Pro Ala Met Gly Arg Ala Leu Leu Ala Glu Ser Glu Val Phe Ala
                580                 585                 590
Ala Ala Val Ala Ala Cys Asp Ala Ala Leu Arg Pro Phe Thr Gly Trp
                595                 600                 605
Ser Val Leu Ser Val Leu Arg Gly Glu Gln Gly Glu Ala Val Pro Pro
                610                 615                 620
Ala Asp Arg Val Asp Val Val Gln Pro Ala Leu Phe Ala Met Ala Val
625                 630                 635                 640
Gly Leu Ser Ala Val Trp Arg Ala Trp Gly Ile Glu Pro Ser Ala Val
                    645                 650                 655
Val Gly His Ser Gln Gly Glu Val Ala Ala Ala Tyr Val Ala Gly Ala
                    660                 665                 670
Leu Thr Leu Glu Asp Ala Ala Arg Val Val Ala Leu Arg Ser Gln Leu
                675                 680                 685
Val Arg Arg Ile Ala Gly Gly Gly Ala Met Ala Val Ile Glu Arg Pro
                690                 695                 700
Val Gly Glu Val Glu Gln Arg Leu Ser Arg Phe Gly Gly Gln Leu Ser
705                 710                 715                 720
Val Ala Ala Val Asn Thr Pro Gly Ser Thr Val Val Ser Gly Asp Ala
                    725                 730                 735
Ala Ala Val Asp Arg Leu Leu Ala Glu Leu Glu His Glu Glu Val Phe
                740                 745                 750
Ala Arg Arg Val Asn Val Asp Tyr Ala Ser His Ser Ala His Val Asp
                755                 760                 765
Ala Ile Leu Pro Glu Leu Glu Ala Cys Leu Ala Ser Val Glu Pro Arg
                770                 775                 780
Ala Cys Ala Ile Pro Leu Tyr Ser Thr Val Thr Gly Glu Val Leu Ala
785                 790                 795                 800
Gly Pro Glu Leu Gly Ala Ala Tyr Trp Cys Arg Asn Leu Arg Glu Pro
                    805                 810                 815
Val Arg Leu Asp Arg Ala Leu Ser Arg Leu Leu Ala Asp Gly His Gly
                820                 825                 830
Val Phe Val Glu Val Ser Ala His Pro Val Leu Ala Ile Pro Leu Thr
                835                 840                 845
Ala Ala Ser Ala Glu Arg Gly Gly Val Val Gly Ser Leu Gln Arg
                850                 855                 860
Asp Asp Gly Gly Leu Gly Arg Leu Val Ser Ala Leu Gly Ala Leu His
865                 870                 875                 880
Val Gln Gly His Ser Val Glu Trp Ala Arg Val Leu Ala Pro Tyr Gly
                    885                 890                 895
```

```
Gly Asn Leu Val Asp Leu Pro Thr Tyr Ala Phe Gln Arg Gln Arg Tyr
            900                 905                 910

Trp Leu Glu Ala Ser Arg Ser Arg Ile Asp Ala Ser Asp Leu Gly Leu
        915                 920                 925

Ala Ala Thr Gly Arg Pro Leu Leu Gly Ala Ala Thr Arg Val Ala Gly
        930                 935                 940

Thr Asp Ser Tyr Ile Leu Ala Gly Arg Leu Ser Thr Ala Glu His Pro
945                 950                 955                 960

Trp Leu Ser Gly Gln Val Val Phe Glu Arg Thr Leu Phe Pro Ala Thr
            965                 970                 975

Gly Phe Leu Glu Leu Ala Leu Glu Ala Ala Asp Ala Met Gly Val Ala
        980                 985                 990

Gly Val Thr Glu Leu Val Val Pro Ala Pro Leu Ile Leu Pro Ala Arg
        995                 1000                1005

Gly Ala Val His Val Gln Val Ala Val Gln Gly Pro Asp Glu Ala
        1010                1015                1020

Gly Arg Arg Pro Phe Ser Val Tyr Ser Arg Ala Glu Thr Ala Gly
        1025                1030                1035

Leu Asp Ala Glu Trp Thr Leu His Ala Thr Gly Leu Leu Gly Gly
        1040                1045                1050

Ala Arg Ala Ser Ala Ala Ala Asp Thr Gly Leu Glu Ala Trp Pro
        1055                1060                1065

Pro Glu Gly Ala Ala Pro Val Asp Val Ser Asp Ala Tyr Ala Arg
        1070                1075                1080

Leu Glu Asp Ala Gly Val Arg Tyr Ala Pro Ser Leu Arg Ala Leu
        1085                1090                1095

Val Glu Ala Trp Gln Ala Glu Arg Arg Ile Tyr Ala Arg Ala Val
        1100                1105                1110

Leu Pro Gly Gly Ala Thr Gln Gly His Gly Leu His Pro Ala Leu
        1115                1120                1125

Trp Asp Ala Ala Leu His Ala Leu Ala Leu Val Val Leu Gly Gln
        1130                1135                1140

Asp Ala Glu His Ala Gly Val Leu Leu Pro Arg Ala Trp Ser Asp
        1145                1150                1155

Val Thr Leu Ala Ala Gln Gly Ala Thr Glu Leu Arg Val Arg Val
        1160                1165                1170

Glu Leu Ala Asp Ala Asp Ala Glu His Val Ser Ala Ser Leu Thr
        1175                1180                1185

Met Ala Asp Ala Asp Gly Gln Pro Val Ala Thr Val Gly Ser Val
        1190                1195                1200

Glu Val Arg Arg Ala Thr Ala Ala Gln Val Arg Ala Met Ser Thr
        1205                1210                1215

Ala Thr Gln His Leu Tyr Gly Val Glu Trp Lys Ala Val Ala Leu
        1220                1225                1230

Ala Glu Pro Pro Arg Ser Ala Gly Glu Gln Val Val Leu Gly Pro
        1235                1240                1245

Asp Gly Glu Leu Ala Thr Arg Leu Gly Ala Arg Arg Ala Gly Asn
        1250                1255                1260

Leu Asp Glu Leu Phe Ala Asp Gly Glu Ala Ala Arg Pro Ala Pro
        1265                1270                1275

Arg Arg Leu Val Val Asp Ala Arg Thr Arg Arg Asp Gly Asp Val
        1280                1285                1290
```

```
Pro Ala Ala Val His Gln Ala Thr Arg Gln Ala Leu Glu Leu Val
    1295                1300                1305
Gln Arg Trp Leu Ala Asp Ala Arg Leu Thr Asp Thr Glu Leu Val
    1310                1315                1320
Val Leu Thr Arg Glu Ala Val Ser Thr Gly Pro Asp Val Gly Val
    1325                1330                1335
Glu Asp Leu Gly His Ala Ala Leu Trp Gly Phe Leu Arg Ala Val
    1340                1345                1350
Arg Ser Glu His Pro Asp Arg Gly Val Arg Leu Ile Asp Leu Gly
    1355                1360                1365
Pro Asp Ala Ser Ala Ala Glu Leu Leu Asp Arg Ala Leu Glu Thr
    1370                1375                1380
Val Ala Glu Pro Glu Leu Ala Leu Arg Gln Gly Ile Ala Leu Ala
    1385                1390                1395
Pro Arg Leu Gly Val Pro Arg Asp Arg Ala Gly Ala Pro Ala Pro
    1400                1405                1410
Met Arg Leu Asp Pro Asp Gly Thr Ala Leu Ile Thr Gly Gly Thr
    1415                1420                1425
Gly Glu Leu Gly Arg His Val Ala Lys His Leu Val Thr Ala His
    1430                1435                1440
Gly Val Arg His Leu Val Leu Thr Ser Arg Arg Gly Met Asp Ala
    1445                1450                1455
Pro Asp Ala Ala Ala Leu Val Asp Glu Leu Arg Ala Ala Gly Ala
    1460                1465                1470
Ala Thr Val Asp Val Ala Ala Cys Asp Ala Ala Asp Ala Ala Ala
    1475                1480                1485
Leu Ala Ala Val Val Glu Ala Ile Pro Ala Ala Arg Pro Leu Thr
    1490                1495                1500
Ala Val Val His Thr Ala Gly Val Leu Asp Asp Ser Val Val Thr
    1505                1510                1515
Lys Leu Ser Ala Glu Gln Met Ala Arg Val Leu Arg Pro Lys Val
    1520                1525                1530
Asp Gly Ala Phe His Leu His Glu Leu Thr Lys His Ala Pro Leu
    1535                1540                1545
Ala Ala Phe Val Leu Phe Ser Ser Ala Ala Gly Thr Leu Gly Ser
    1550                1555                1560
Pro Gly Gln Ala Asn Tyr Ala Ala Ala Asn Thr Phe Leu Asp Ala
    1565                1570                1575
Leu Ala Ser His Leu Arg Ala Arg Gly Val Pro Ala Met Ser Leu
    1580                1585                1590
Ala Trp Gly Phe Trp Ala Gln Ala Gly Leu Gly Met Thr Ala His
    1595                1600                1605
Leu Gly Ala Ala Asp Ile Ala Arg Met Lys Arg Leu Gly Val Val
    1610                1615                1620
Thr Met Ser Pro Gln Glu Gly Leu Glu Leu Leu Asp Ala Ser Leu
    1625                1630                1635
Gln Arg Pro Asp Pro Leu Leu Val Pro Ala Pro Leu Asp Leu Ala
    1640                1645                1650
Ala Leu Glu Arg Ala Ala Arg Glu Gly Ala Pro Ala Ser Pro Met
    1655                1660                1665
Leu Arg Glu Leu Val Arg Gly Ala Pro Ala Arg Arg Ala Ala Ala
    1670                1675                1680
Gly Asp Gly Ala Ser Gly Lys Ala Ser Ala Leu Arg Ala Leu Leu
```

-continued

```
            1685                1690                1695

Ala Arg Arg Pro Gln Ser Glu Arg Phe Ala Ala Val Leu Glu Leu
        1700                1705                1710

Val Arg Ala Glu Ala Ala Arg Val Leu Arg Leu Pro Gly Ala Ala
        1715                1720                1725

Ala Val Pro Pro Asp Arg Pro Leu Lys Glu Leu Gly Leu Asp Ser
        1730                1735                1740

Leu Thr Ala Val Glu Leu Arg Asn Arg Leu Ala Ala Arg Thr Glu
        1745                1750                1755

Ala Lys Gln Pro Ala Thr Leu Val Phe Asp His Pro Thr Pro Ser
        1760                1765                1770

Ala Ile Ser Arg Phe Leu Leu Lys Gln Ala Gly Ala Asp Leu Ala
        1775                1780                1785

Pro Ser Glu Ala Ala Ala Ser Leu Ala Pro Ser Ser Arg Arg Ala
        1790                1795                1800

Pro Leu Asp Glu Pro Ile Ala Ile Val Ala Met Ala Cys Arg Cys
        1805                1810                1815

Pro Gly Gly Val Asp Ser Pro Glu Ala Leu Trp Arg Leu Leu Ser
        1820                1825                1830

Glu Gly Arg Asp Ala Ile Gly Pro Leu Pro Glu Glu Arg Gly Trp
        1835                1840                1845

Ser Val Glu Gln Ile Leu Gly Arg Asp Pro Gly Ala Ser Ser Lys
        1850                1855                1860

Pro Phe Ser Gly Arg Gly Phe Leu Tyr Gly Ala Asp Gln Phe
        1865                1870                1875

Asp Ala Glu Phe Phe Gly Ile Thr Pro Arg Glu Ala Arg Phe Leu
        1880                1885                1890

Asp Pro Gln His Ala Leu Leu Leu Glu Cys Thr Trp Glu Ala Leu
        1895                1900                1905

Glu Arg Ala Ser Ile Val Pro Gln Ser Leu Glu Gly Ser Ser Thr
        1910                1915                1920

Gly Val Phe Val Gly Met Val Gly Gly Met Ala Ala Gly His Gly
        1925                1930                1935

Ser Val Ser Ser Glu Gly Tyr Ala Leu Thr Gly Thr Ala Leu Ser
        1940                1945                1950

Thr Ala Ser Gly Arg Ile Ser Tyr Ala Leu Gly Leu Gln Gly Ala
        1955                1960                1965

Ala Val Thr Val Asp Thr Ala Cys Ser Ser Ser Ala Val Ala Ile
        1970                1975                1980

His Leu Ala Cys Thr Ser Leu Arg Thr Gly Glu Cys Asp Leu Ala
        1985                1990                1995

Leu Ala Gly Gly Val Thr Val Met Gly Arg Pro Glu Ile Phe Ser
        2000                2005                2010

Glu Phe Gly Arg Leu Asp Ile Leu Ala Ser Asp Gly Arg Cys Lys
        2015                2020                2025

Ala Phe Gly Ala Thr Ala Asp Gly Val Gly Trp Gly Glu Gly Cys
        2030                2035                2040

Gly Val Leu Leu Leu Lys Arg Leu Ser Asp Ala Gln Arg Asp Gly
        2045                2050                2055

Asp Arg Val Leu Ala Val Ile Arg Gly Ser Ala Val Asn Gln Asp
        2060                2065                2070

Gly Arg Ser Gln Gly Leu Thr Ala Pro Asn Gly Pro Ser Gln Glu
        2075                2080                2085
```

-continued

```
Ala Val Ile Gln Arg Ala Leu Ala Ser Ala Gly Leu  Thr Ala Ala
    2090                2095                2100

Asp Val Asp Ala Val Glu Ala His Gly Thr Gly Thr  Arg Leu Gly
    2105                2110                2115

Asp Pro Ile Glu Ala Gln Ala Leu Leu Ser Thr Tyr  Gly Gln Ala
    2120                2125                2130

His Ala Ala Gly Gln Pro Leu Trp Leu Gly Ser Ile  Lys Ser Asn
    2135                2140                2145

Leu Gly His Thr Gln Ala Ala Ala Gly Val Ala Gly  Val Ile Lys
    2150                2155                2160

Met Val Leu Ala Met Gln His Gly Gln Leu Pro Arg  Thr Leu Tyr
    2165                2170                2175

Ala Asp Thr Pro Ser Pro Asp Ile Asp Trp Ser Gln  Gly His Val
    2180                2185                2190

Arg Leu Leu Val Asp Ala Val Pro Trp Pro Gln Ser  Ala Arg Arg
    2195                2200                2205

Arg Arg Ala Gly Val Ser Ser Phe Gly Ile Ser Gly  Thr Asn Ala
    2210                2215                2220

His Ile Leu Val Glu Glu Ala Pro Glu Pro Pro Arg  Ala Gly Ala
    2225                2230                2235

Ala Pro Glu Ala Pro Val Thr Leu Pro Phe Leu Pro  Leu Leu Val
    2240                2245                2250

Ser Gly Arg Asp Leu Ala Ala Leu Arg Ser Gln Ala  Ala Arg Leu
    2255                2260                2265

Ala Ala His Leu Arg Glu Arg Pro Asp Gln Arg Leu  Val Asp Val
    2270                2275                2280

Thr Ala Ser Leu Ala Thr Thr Arg Thr His Leu Ala  Ala Arg Leu
    2285                2290                2295

Ala Leu Pro Val Ala Ala Thr Ala Gly Arg Asp Glu  Ile Cys Gly
    2300                2305                2310

Ala Leu Asp Ala Phe Ala Ala Arg Gly Leu Ala Leu  Asn Gly Ala
    2315                2320                2325

Trp Val Thr Pro Ala Gln His Arg Ala Gly Lys Val  Ala Val Leu
    2330                2335                2340

Phe Ala Gly Gln Gly Ala Gln Arg Pro Ala Met Gly  Arg Gly Leu
    2345                2350                2355

Tyr Glu Ala Leu Pro Val Phe Arg Glu Ala Leu Asp  Glu Val Cys
    2360                2365                2370

Ala Arg Leu Asp Ala His Leu Gly Ala Pro Leu Lys  Asp Val Leu
    2375                2380                2385

Phe Ser Ala Glu Gly Ser Pro Glu Ala Ser Thr Leu  His Gln Thr
    2390                2395                2400

Gly Trp Ala Gln Pro Ala Leu Phe Ala Leu Glu Val  Ala Leu Tyr
    2405                2410                2415

Arg Gln Trp Glu Ala Trp Gly Leu Arg Pro Asp Ala  Leu Met Gly
    2420                2425                2430

His Ser Leu Gly Glu Ile Val Ala Ala His Val Ala  Gly Val Phe
    2435                2440                2445

Asp Leu Ala Asp Ala Cys Ala Leu Ile Ala Ala Arg  Gly Arg Leu
    2450                2455                2460

Met Gln Ala Leu Pro Thr Gly Gly Ala Met Ala Ser  Ile Glu Ala
    2465                2470                2475
```

-continued

```
Ser Glu Asp Asp Val Arg Pro Leu Leu Asp Ala Gln Gln Gly Arg
    2480                2485                2490

Ala Ser Leu Ala Ala Leu Asn Gly Pro Arg Gln Thr Val Val Ser
    2495                2500                2505

Gly Asp Glu Asp Ala Val Glu Ala Val Cys Asp His Phe Lys Ala
    2510                2515                2520

Gln Gly Arg Arg Val Lys Arg Leu Thr Val Ser His Ala Phe His
    2525                2530                2535

Ser Ala Arg Met Glu Pro Met Leu Glu Ala Phe Arg Ala Val Ala
    2540                2545                2550

Ala Thr Leu Thr Phe Arg Ala Pro Gln Ile Pro Ile Val Ser Asn
    2555                2560                2565

Val Thr Gly Glu Arg Ala Pro Val Glu Ala Leu Thr Ser Pro Asp
    2570                2575                2580

Tyr Trp Val Arg Gln Val Arg Glu Ala Val Arg Trp Thr Asp Gly
    2585                2590                2595

Val Arg Ala Leu Glu Ala Asp Gly Ile Thr Thr Tyr Val Glu Cys
    2600                2605                2610

Gly Pro Asp Gly Ala Thr Cys Ala Met Ala Ser Gln Cys Val Thr
    2615                2620                2625

Arg Ala Ala Lys Ala Pro Ala Phe Val Ser Ser Leu Asn Arg Lys
    2630                2635                2640

Gly Asp Glu Val Gln Ala Leu Val Ser Ala Ala Cys Ala Val His
    2645                2650                2655

Val Arg Gly Asp Ser Leu Asp Trp Ser Ala Phe Phe Ala Gly Ser
    2660                2665                2670

Gly Ala Arg Arg Val Glu Leu Pro Thr Tyr Ala Phe Gln Arg Arg
    2675                2680                2685

Arg Tyr Gly Val Asp Glu Pro Ser Pro Arg Pro Ala Glu Val Arg
    2690                2695                2700

Ala Pro Asp Thr Thr Arg Thr Arg Val His Val Ser Ala Asp Asp
    2705                2710                2715

Pro Thr Val Arg Gly His Val Val Gly Ser Gln Thr Leu Tyr Pro
    2720                2725                2730

Ala Ala Ser Tyr Ile Asp Leu Ala Leu Arg Val Ala Ala Ser Ala
    2735                2740                2745

Gly Gln Ala Cys Val Arg Ala Ala Asn Met Ala Trp Phe Ala Pro
    2750                2755                2760

Ala Ile Val Pro Pro Glu Gly Leu Ser Leu Asp Val Gln Leu Arg
    2765                2770                2775

Arg Thr Lys Ala Gly Leu Glu Cys Glu Val Ser Ser Gly Asp Ser
    2780                2785                2790

Asp Gln Arg Thr Ile His Phe Gln Gly Thr Leu Leu Gly Gly Asp
    2795                2800                2805

Pro Gly Pro Trp Pro Ala Val Asp Leu Arg Arg Ile Ile Gly Glu
    2810                2815                2820

Cys Ser Leu Arg Leu Asp Arg Ala His Leu Tyr Gly Ile Phe Ala
    2825                2830                2835

Asn Tyr Gly Phe Gly Tyr Asp Arg Ala Phe Gln Ser Val Ala Trp
    2840                2845                2850

Leu Val Ser Asn Ala Asn Asp Val Val Gly Arg Val Glu Leu Pro
    2855                2860                2865

Ala Ser Glu Ser Ala Thr Ala Glu His His Leu Gln Pro Asn Leu
```

```
                    2870            2875            2880

Leu Asp Gly Ala Phe Gln Thr Ile Ile Gly Leu Asp Ala Val Ser
2885                2890                2895

Ala Leu Ser Gly Pro Thr Pro Asp Ala Gly Phe Asn Phe Val Pro
2900                2905                2910

Ser Ala Ile Gln Asp Val Gln Ile Phe Gly Arg Leu Arg Arg Ala
2915                2920                2925

Ala Tyr Val His Ala Thr Arg Arg Gly Lys Ala His Gly Ser Pro
2930                2935                2940

Ser Cys Asp Phe Gln Leu Leu Gly Glu Asn Gly Glu Pro Ile Ala
2945                2950                2955

Leu Val Thr Gly Leu Thr Phe Arg Lys Leu Arg Ser Arg Ala Glu
2960                2965                2970

Leu Asp Ala Pro Ser Ala Pro Ala Gln Arg Pro Ser Asn Gly Glu
2975                2980                2985

Ala Ala Arg Pro Arg Asn Val Pro Ala Pro Ala Asn Val Pro Ala
2990                2995                3000

Pro Ala Asn Val Pro Ala Pro Gly Gly Asp His Ala Asp Ala Ser
3005                3010                3015

Pro Arg Ala Pro Ser Ala Glu Val Leu Phe Phe Ser Pro Ala Trp
3020                3025                3030

Val Pro Glu Lys Pro Val Met Ala Ala Ser Val Thr Gly Asp Ile
3035                3040                3045

Val Val Phe Gly Asp Asp Ala Gln Ile Thr His Leu Arg Gly
3050                3055                3060

Leu Leu Pro Leu Ala Arg Leu Ile His Val Arg Ser Gly Pro Gly
3065                3070                3075

Phe Gln Arg Thr Gly Pro Ala Ala Tyr Ala Val Arg Pro Asp Ser
3080                3085                3090

Gln Glu Asp Leu Ser Ala Leu Phe Thr Glu Phe Asp Asp Ala Arg
3095                3100                3105

Ser Lys Ser Leu Arg Ala Leu Tyr Leu Trp Glu Pro Ser Arg Arg
3110                3115                3120

Ala Ala Glu Gly Ser Ala Pro Pro Gly Asp Gly Asp Val Ala Ala
3125                3130                3135

Ala Ile Arg Ser Leu Phe Cys Leu Phe Lys Ala His Met Ala Glu
3140                3145                3150

Arg Arg Lys Gly Met Gln Leu Leu Tyr Leu Thr Ser Ser Ala Thr
3155                3160                3165

Ser Ala Val Pro Val Asn Glu Ala Val Leu Ala Phe Phe Arg Thr
3170                3175                3180

Ile Arg Thr Glu Asn Pro Thr Tyr Val Gly Lys Val Ile Ala Val
3185                3190                3195

Ala Asp Pro Gly His Ile Gly Arg Ala Cys Ala Thr Glu Leu Gly
3200                3205                3210

Leu Pro Thr Gly Ser Asp Val Val Gln His Val Asp Gly Ala Arg
3215                3220                3225

His Val Arg Lys Leu Phe Ser Arg Glu Pro Ala Pro Arg Glu Arg
3230                3235                3240

Leu Arg Asp Ala Leu Pro Leu Ala Pro Gly Gly Thr Phe Val Leu
3245                3250                3255

Thr Gly Gly Ala Gly Lys Ile Gly Leu Leu Leu Thr Asp Met Leu
3260                3265                3270
```

-continued

Val Arg Glu Tyr Gln Val Asn Val Ala Leu Ile Gly Arg Ser Gln
    3275                3280                3285

Leu Asp Glu Pro Arg Arg Gln Ala Ile Asp Ser Ile Arg Ser Gly
    3290                3295                3300

Pro Ala Arg Ala Leu Tyr Tyr Ser Ala Asp Val Gly Val Leu Ser
    3305                3310                3315

Asp Thr Glu Arg Ala Ile Gly Glu Ile Arg Glu Thr Leu Gly Pro
    3320                3325                3330

Ile Arg Gly Ala Ile His Ala Ala Ala Ile Ile Arg Asp Ser Phe
    3335                3340                3345

Phe Ile Lys Lys Thr Leu Ala Glu Val Asp Ser Val Leu Arg Pro
    3350                3355                3360

Lys Val Asn Gly Ala Ile Tyr Leu Asp Phe Leu Leu Arg Asp Asp
    3365                3370                3375

Pro Leu Glu Val Phe Val Leu Cys Ser Gly Leu Ala Ser Leu Leu
    3380                3385                3390

Gly Asn Gln Gly Gln Ser Asp Tyr Ala Ala Ala Asn Gly Phe Leu
    3395                3400                3405

Asp Gly Phe Ala Ile Gln Arg Glu Ala Leu Arg Gln Ala Gly Arg
    3410                3415                3420

Arg Gln Gly Arg Thr Ile Ser Ile Asn Trp Pro Leu Trp Gly Gly
    3425                3430                3435

Asp Gly Gly Met Gly Val Pro Asp Tyr Ile Glu Thr Glu Leu Leu
    3440                3445                3450

Lys Arg Gly Leu Val Pro Leu Asp Ile Ser Asp Gly Val Thr Ala
    3455                3460                3465

Phe Arg Gln Ala Ile Ala Met Lys Glu Pro Gln Val Ala Val Val
    3470                3475                3480

Ala Gly Gln Arg Ala Ala Ala Arg Arg Leu Leu Arg Pro Trp Leu
    3485                3490                3495

Ser Glu Gly Arg Thr Glu Asp His Gln
    3500                3505

<210> SEQ ID NO 8
<211> LENGTH: 2197
<212> TYPE: PRT
<213> ORGANISM: Sorangium cellulosum

<400> SEQUENCE: 8

Met Thr Ser Trp Leu Leu Ala Lys Thr Glu Glu Phe Leu Gly Asp Leu
1               5                   10                  15

Val Ser Glu Val Ser Glu Ile Arg Arg Asp Thr Ile Ser Pro Asp Ala
                20                  25                  30

Asp Phe Gln Glu Phe Gly Leu Asp Ser Arg Phe Val Ile Ala Met Asn
            35                  40                  45

Ser Arg Leu Glu Gln Tyr Phe Ser Gly Leu Pro Arg Thr Leu Phe Phe
        50                  55                  60

Glu Tyr Pro Ser Ile Arg Ala Val Ala Ser Tyr Leu Val Glu Glu Phe
65                  70                  75                  80

Gln Asp Gln Leu His Glu Leu Phe Pro Asp Gly Glu Pro Ala Glu Ala
                85                  90                  95

Ser Arg Pro Ala Gln Ser Val Pro Val Ala Arg Pro Ser Gly Ala Ile
            100                 105                 110

Pro Ser Gly Ala Ser Pro Ser Gly Ala Ser Pro Ser Gly Ala Ile Pro

-continued

```
                115                 120                 125
Ser Gly Ala Ser Pro Ser Gly Ala Ile Pro Ser Gly Ala Ser Pro Ser
            130                 135                 140
Gly Ala Ile Pro Ser Gly Ala Ser Pro Gln Thr Ser Thr Ser Ser Ala
145                 150                 155                 160
Ala Asp Leu Ser Asp Leu Ala Ser Leu Ile Gln Gln Ile Pro Leu Pro
                165                 170                 175
Glu Ala Val Leu Ser Ser Val Glu Arg Pro Arg Val Asp Pro Arg Pro
                180                 185                 190
Ala Ala Pro Ala Pro Ser Val Val Arg Ala Ser Ser Gly Asp Gln Ser
                195                 200                 205
Gly Asp Asp Ile Ala Val Ile Gly Val Ala Gly Arg Tyr Pro Lys Ala
            210                 215                 220
Arg Asn Ile Glu Glu Phe Trp Arg Asn Leu Arg Glu Gly Arg Asp Cys
225                 230                 235                 240
Ile Glu Pro Leu Pro Lys Glu Arg Trp Ser Pro Asp Pro Ser Asp Pro
                245                 250                 255
Leu Arg Trp Gly Gly Tyr Leu Asp Gly Val Thr Asp Phe Asp Ser Leu
            260                 265                 270
Phe Phe Gly Ile Ser Pro Arg Glu Gly Glu Gly Met Asp Pro Gln Glu
            275                 280                 285
Arg Leu Phe Leu Glu Val Ala Trp Glu Thr Ile Glu Ser Ala Gly Tyr
            290                 295                 300
Asp Pro Leu Arg Leu Gly Arg Ser Gly Glu Pro Ala Ser Val Gly Val
305                 310                 315                 320
Phe Val Gly Val Met Tyr Gly Glu Tyr Gln Val Phe Gly Ala Glu Leu
                325                 330                 335
Thr Leu Leu Gly Gln Pro Thr Leu Val Ser Ser Tyr Ala Thr Ile
            340                 345                 350
Pro Asn Arg Val Ser Tyr Phe Leu Asn Phe Ser Gly Pro Ser Leu Ala
            355                 360                 365
Leu Asp Thr Met Cys Ser Ser Ser Leu Thr Ala Leu His Leu Ala Cys
            370                 375                 380
Ala Ser Leu Arg Ser Gly Asp Cys Lys Met Ala Leu Val Gly Gly Thr
385                 390                 395                 400
Asn Val Thr Ile His Pro Asn Lys Tyr Arg Leu Leu Glu Ala Gly Lys
                405                 410                 415
Tyr Leu Ala Ser Asp Gly Arg Cys Arg Ser Tyr Gly Ala Asp Gly Asp
            420                 425                 430
Gly Tyr Val Pro Ala Glu Gly Val Gly Ala Val Leu Ile Lys Pro Leu
            435                 440                 445
Ala Asp Ala Arg Arg Asp Gly Asp Thr Ile Trp Gly Val Ile Lys Ser
            450                 455                 460
Thr Ser Ile Asn His Gly Ala Arg Ala Arg Gly Tyr Thr Thr Pro Asn
465                 470                 475                 480
Pro Asn Ala Gln Ser Ala Ser Leu Ser Leu Ala Leu Glu Arg Ala Lys
                485                 490                 495
Ile Glu Pro His Thr Leu Gly Tyr Ile Glu Gly His Gly Thr Gly Thr
                500                 505                 510
Ser Leu Gly Asp Pro Ile Glu Ile Arg Gly Ile Gln Lys Ala Val Gly
            515                 520                 525
Arg Val Ser Glu Lys Ile Pro Ile Gly Ser Val Lys Ser Asn Ile Gly
530                 535                 540
```

```
His Ala Glu Ser Ala Ala Gly Val Ala Gly Leu Thr Lys Val Leu Leu
545                 550                 555                 560

Gln Leu Arg Ala Arg Glu Leu Val Pro Ser Ile His Cys Glu Pro Pro
                565                 570                 575

Asn Pro Asn Ile Asp Phe Asp Arg Ala Pro Ile Gln Val Gln Arg His
            580                 585                 590

Ala Ala Pro Trp Asn Arg Arg Thr Ile Thr Ser Gly Gly Val Thr Arg
        595                 600                 605

Glu Val Pro Arg Arg Ala Val Val Ser Ala Phe Gly Ala Gly Gly Ser
    610                 615                 620

Asn Ala His Val Val Glu Glu Ala Asp Ala Pro Ala Leu Gln Arg
625                 630                 635                 640

Thr Val Ser Ala Gln Pro Arg Leu Phe Val Leu Ser Ala Arg Ser Val
                645                 650                 655

Glu Arg Leu Arg Ala His Ala Gln Ser Phe Leu Asp Phe Phe Ser Arg
                660                 665                 670

Met Pro Thr Leu Arg Glu Ala Glu Ala Arg Glu Leu Phe Tyr Asp Met
            675                 680                 685

Cys Ala Thr Leu Tyr Phe Gly Arg Ala Pro Phe Glu Ala Arg Leu Ala
        690                 695                 700

Ile Val Ala Glu Ser Leu Arg Thr Leu Gln Gln Lys Leu Ala Ala Phe
705                 710                 715                 720

Val Tyr Gly Ala Ser Arg Asp Pro Asp Ile Leu Val Ser Asp Gly Arg
                725                 730                 735

Ser Leu Ala Ala Thr Asp Gly Gly Gln Arg Gln Leu Ser Gly Leu Ala
                740                 745                 750

Asp Leu Gly Arg Arg Trp Val Ala Gly Glu Ala Val Asp Ala Ser Glu
            755                 760                 765

Leu Phe Pro His Pro Trp Lys Lys Leu Ala Leu Pro Thr Tyr Pro Phe
        770                 775                 780

Glu Arg Arg Arg Leu Trp Ala Pro Ser Gly Glu Lys Leu Tyr Asp Leu
785                 790                 795                 800

Arg Ser Ala Ala Ala Pro Ala Pro Ala Pro Pro Gly Asn Gly Ala
                805                 810                 815

Ser Pro Arg Glu Val Pro Ala Asn Val Pro Arg Ala Ala Arg Thr Asp
                820                 825                 830

Thr Ala Glu Thr Ala Val Val Ser Gly Pro Gln His Ala Arg Ile Ala
            835                 840                 845

Pro Ala Glu Arg Arg Leu Ala Val Ala Glu Gln Val Ile Glu Val Ala
        850                 855                 860

Glu Arg Pro Ser Pro Pro Asp Arg Gly Pro Ser Thr Ser Glu Thr Arg
865                 870                 875                 880

Gly Ser Glu Ser Asp Pro His Val Thr Ser Thr Leu Asn Gly His Thr
                885                 890                 895

Ser Ala Leu Asn Gly His Thr Ser Ala Leu Asn Gly His Ala Ala Arg
                900                 905                 910

Ala Thr Gly Pro Glu Arg Pro Ala Ala Val Gln Ala Ala Asp Gln
            915                 920                 925

Gly Ala Ala Val Glu Ile Val Gln Glu Met Val Arg Asp Leu Val Ala
        930                 935                 940

Gln Ile Leu Phe Val Asp Arg Ser Thr Ile Leu Pro Asp Ala Ala Leu
945                 950                 955                 960
```

```
Phe Asp Tyr Gly Leu Glu Ser Val Ser Val Glu Leu Ala Glu Arg
            965                 970                 975

Leu Asn Ala Met Leu Gly Thr Asp Ile Thr Pro Thr Ser Phe Tyr Glu
            980                 985                 990

Phe Asn Thr Leu Ala His Phe Ser Arg His Leu Val Glu Arg Tyr Asn
        995                 1000                1005

Leu Ala Asp Arg Leu Ser Gly Leu Ser Ala Gly Leu Ala Gly Gly
    1010                1015                1020

Ser Ser Ala Pro Ala Gly Pro Ser Gly Arg Gly Asp Ser Pro Pro
    1025                1030                1035

Arg Ala Ala Gly Ala Glu Gly Pro Val Val Gly Ala Ala Ala
    1040                1045                1050

Ala Glu Gly Ala Ala Ala Pro Ala Ala Gly Gly Pro Thr Val Glu
    1055                1060                1065

Glu Leu Trp Ala Ser Ala Met His Ala Glu Gly Leu Ala Ala Leu
    1070                1075                1080

Pro Ser Pro Glu Pro Arg Arg Ser Ala Ser Lys Ala Pro Arg Pro
    1085                1090                1095

Ala Pro Pro Val Gln Pro Ser Asp Gln Ala Thr Pro Val Glu Ile
    1100                1105                1110

Val Gln Glu Ile Val Arg Asp Leu Val Ala Gln Ile Leu Phe Val
    1115                1120                1125

Asp Arg Ser Thr Ile Leu Pro Thr Thr Ala Leu Phe Asp Tyr Gly
    1130                1135                1140

Leu Glu Ser Val Ser Ser Val Glu Leu Ala Glu Arg Leu Asn Ala
    1145                1150                1155

Met Leu Gly Thr Asp Ile Thr Pro Thr Ser Phe Tyr Glu Phe Asn
    1160                1165                1170

Thr Leu Ala His Phe Ser Arg His Leu Val Glu Arg Tyr Asn Leu
    1175                1180                1185

Ala Asp Arg Leu Ser Gly Leu Ser Ala Gly Leu Ala Gly Gly Ser
    1190                1195                1200

Ser Ala Pro Ala Arg Ala Ser Ala Pro Arg Ala Gln Gly Pro Ala
    1205                1210                1215

Ala Leu Ser Ser Ser Glu Pro Arg Arg Ser Asp Ala Gly Ile Glu
    1220                1225                1230

Leu His Val Ile Pro Gly Val Asp Gly His Ala Val Glu Phe Ala
    1235                1240                1245

Thr Leu Gly Ser Gly Val Pro Leu Phe Val Leu Gly Gly Leu Leu
    1250                1255                1260

Ala Thr His Asp Ala Leu Thr Leu Asn Pro Asp Ile Leu Ser Leu
    1265                1270                1275

Gly Gln Thr Tyr Arg Val Ile Met Val His Pro Gly Ala Gly
    1280                1285                1290

Arg Ser Glu Leu Pro Arg Gly Glu Leu Thr Met Asp Phe Ile Val
    1295                1300                1305

Arg Gln Val Glu Gly Val Arg Gln Ser Leu Gly Leu Ser Ser Val
    1310                1315                1320

Val Leu Val Gly Tyr Ser Phe Gly Gly Leu Val Ala Gln Ala Tyr
    1325                1330                1335

Val Ala Gln Phe Pro Glu Arg Ala Ser Lys Leu Val Leu Ala Cys
    1340                1345                1350

Thr Thr Ser Asp Pro Ala Ser Val Val Asn Gly Met His Leu Val
```

-continued

```
            1355                1360                1365

Ala  Ala  Glu  Ala  Gln  Arg  His  Pro  Asp  Gly  Leu  Arg  Ala  Leu  Gln
     1370                1375                1380

Phe  Ala  Asp  Val  Ser  Lys  Phe  Pro  Leu  Tyr  Ser  Gln  Leu  Ser  Thr
     1385                1390                1395

Arg  Leu  Arg  Pro  Glu  Thr  Leu  Ala  Tyr  Pro  Ala  Ile  Pro  Thr  Leu
     1400                1405                1410

Ile  Val  Ala  Gly  Ala  Glu  Asp  Arg  Tyr  Val  Pro  Thr  Ile  His  Ala
     1415                1420                1425

Glu  Arg  Leu  Ala  Arg  Ala  Asn  Pro  Asn  Ala  Thr  Leu  His  Ile  Val
     1430                1435                1440

Glu  Gly  Ala  Gly  His  Phe  Leu  Gly  Leu  Ser  His  Gly  Gly  Val  Leu
     1445                1450                1455

Val  His  Leu  Val  Asn  Gly  Phe  Val  Leu  Gly  Asp  Arg  Thr  Ala  Pro
     1460                1465                1470

Ala  Arg  Ser  Pro  Ala  Val  Ser  Ala  Ser  Arg  Arg  Gly  Gly  Leu  Arg
     1475                1480                1485

Lys  Met  Ser  Gln  Glu  Ser  Val  Gly  Ala  Leu  Lys  Ser  Tyr  Leu  Glu
     1490                1495                1500

Glu  Gly  Glu  Ile  Ala  Ser  Gly  Val  Glu  Ala  Ser  Pro  Val  Ala  Gly
     1505                1510                1515

Gln  Val  Gly  Tyr  Leu  Leu  Asn  Arg  Leu  Leu  Ser  Gly  Gln  Glu  Ala
     1520                1525                1530

Pro  Ser  Ser  Pro  Tyr  His  Cys  Phe  Phe  Met  Pro  Ser  Gly  Leu  Glu
     1535                1540                1545

Ala  Val  Asp  Ala  Ala  Leu  Arg  Phe  Gly  Arg  Arg  Arg  Ala  Lys  Leu
     1550                1555                1560

Ser  Arg  Gly  Leu  Gly  Asp  Ala  Lys  Thr  Leu  Val  Leu  Asp  Pro  Glu
     1565                1570                1575

Gly  Ala  Leu  Arg  Arg  His  Phe  Glu  Phe  Leu  Pro  Gln  Glu  Arg  Leu
     1580                1585                1590

Phe  Pro  Asp  Leu  Ile  Phe  Val  Gly  Glu  Ser  Arg  Glu  Leu  Leu  Arg
     1595                1600                1605

Leu  Leu  Gln  Ser  Ala  Glu  Asp  Val  Gly  Ala  Ala  Tyr  Val  Thr  Thr
     1610                1615                1620

Ala  Cys  Asp  Asp  Ala  Thr  Leu  Glu  Thr  Val  Ala  Ala  Glu  Cys  Ala
     1625                1630                1635

Arg  Arg  Gly  Ile  Val  Ser  Val  Leu  Gly  Glu  Leu  His  Ala  Asp  Thr
     1640                1645                1650

Gly  Glu  Leu  Val  Ser  Ala  Arg  Leu  Arg  Ser  Lys  Pro  Asp  Val  Val
     1655                1660                1665

Val  Leu  Asp  Glu  Ala  Ile  Ala  Gly  Phe  Glu  Leu  Pro  Phe  Gly  Val
     1670                1675                1680

Cys  Ala  Ile  Arg  Arg  Phe  His  Glu  Ser  Gly  Val  Trp  Thr  Arg  Gln
     1685                1690                1695

Pro  Glu  Glu  Phe  Ala  Val  Arg  Val  Pro  Gly  Ser  Met  Ala  Gly  Pro
     1700                1705                1710

Ala  Leu  Thr  Val  Val  Arg  Glu  Asn  Ile  Leu  Arg  Arg  Phe  Arg  Ala
     1715                1720                1725

Val  Val  Thr  Asn  Asp  Thr  Thr  Ala  Asn  Leu  Arg  Ala  Ile  Ala  Val
     1730                1735                1740

Asp  Gln  Arg  Arg  Thr  Lys  Glu  Ala  His  Arg  Ser  Tyr  Val  Asn  Pro
     1745                1750                1755
```

```
Val Leu Leu Glu Ser Leu Asp Ala Phe Gly Leu Ala Gly Arg Gln
    1760            1765            1770

Arg His Ala Asp Arg Arg Gly Tyr Glu Ile Glu Arg Asp Asp Gly
    1775            1780            1785

Ser Ser Ala Arg Val Ile Asn Leu Tyr Leu Val Thr Ser Ala Ser
    1790            1795            1800

Phe Arg Gly His Thr Gly Ser Glu Ile Ala Gln Ser Val Leu Gly
    1805            1810            1815

Thr His Asp Ile Thr Arg Asp Tyr Trp Ala Asp Leu Glu Arg Arg
    1820            1825            1830

Ile Pro Arg Glu Thr Asp Phe Gly Arg Val Phe Pro Ala Ala Gly
    1835            1840            1845

Pro Ala Thr Ala Val Glu Thr Ala Val Lys Leu Gly Leu Leu Ala
    1850            1855            1860

Ala Arg Lys Gly Ser Ala Leu Leu Val Leu Lys Gly Ser Pro Ile
    1865            1870            1875

Phe Thr Arg Leu Gly Ala Leu Val Ser His Ala Glu Pro Gly Ser
    1880            1885            1890

Pro Leu Glu Ala Leu Val Glu Ser Cys Pro Trp Ser Lys Val Ile
    1895            1900            1905

Ala Val Asp Pro Phe Gly Glu Gly Ala Ala Ala Glu Leu Glu Ala
    1910            1915            1920

Lys Leu Thr Ser Asp Asp Val Gly Phe Val Trp Leu Glu Thr Leu
    1925            1930            1935

Gln Ser Asp Trp Gly Gly Leu Arg Ser Val Pro Asp Ala Val Leu
    1940            1945            1950

Glu Val Ile Asp Arg His Arg Glu Arg Ser Gly Tyr Leu Val Gly
    1955            1960            1965

Val Asp Glu Thr Tyr Thr Ser Leu Gly Cys Gly Arg Met Phe His
    1970            1975            1980

Trp Gln Gly Lys Leu Ala Arg Pro Asp Val Val Ala Val Cys Val
    1985            1990            1995

Gly Trp Thr Asp Cys Gln Leu Leu Ala Gly Tyr Val Leu Thr Thr
    2000            2005            2010

Glu Glu Val Ala Ala Arg Ala Arg Gln Arg Asn Glu Ala Val Val
    2015            2020            2025

Ser Ala Leu Gln Glu Gln Leu Arg Cys Gln Leu Thr Ala His Ala
    2030            2035            2040

Thr Leu Arg Leu Leu Asp Val Leu Lys Glu Asp Arg Ile Leu Ala
    2045            2050            2055

Gln Ile Ala Glu Thr Glu Arg Arg Phe Ser Gly Ala Leu Asn Asp
    2060            2065            2070

Phe Ala Ala Glu Cys Gly Met Val Lys Arg Val Trp Gly Glu Gly
    2075            2080            2085

Leu Phe Trp Ala Val Gln Phe Asp Leu Asp Gly Trp Pro Arg Phe
    2090            2095            2100

Val Arg Asp Trp Phe Ser Ser Phe Leu Trp Ser Glu Cys Leu Arg
    2105            2110            2115

Asp Pro Val Ala Pro Val Ala Val Ser Met Gln Pro Leu Thr Pro
    2120            2125            2130

Ala Cys Ile Arg Val Glu Pro Arg Tyr Asp Ile Pro Ala Ala Glu
    2135            2140            2145
```

-continued

```
Leu Asp Ala Ala Met Gly Thr Leu Lys Arg Val Leu Gly Lys Gly
    2150                2155                2160

Val Glu Gly Ile Val Ala Ser Val Ala Asp Asp Val Glu Arg Arg
    2165                2170                2175

Gly Asp Ala Arg Arg Ala Glu Leu Phe Arg Ile Leu Arg Gly
    2180                2185                2190

Phe Lys Thr Thr
    2195

<210> SEQ ID NO 9
<211> LENGTH: 736
<212> TYPE: PRT
<213> ORGANISM: Sorangium cellulosum

<400> SEQUENCE: 9

Met Ser Arg Glu Gly Thr Ser Ser Met Asn Ile Gly Ser Pro Leu Pro
1               5                   10                  15

Pro Ile Glu Asn Ala Leu Asp Leu Phe Lys His Tyr Ala Thr Ser Ala
                20                  25                  30

Pro Glu Ala Arg Ile Ala Val Phe Ile Glu Glu Gly Gln Glu Gln
            35                  40                  45

Gly Leu Thr Tyr Arg Glu Leu Glu Arg Ala Ala Thr Asn Leu Ser Leu
    50                  55                  60

Glu Leu Ala Ser Val Ala Ala Pro Gly Asp Arg Val Leu Val Ala Tyr
65                  70                  75                  80

Asp Ser Gly Pro Met Tyr Leu Val Gly Val Trp Ala Ala Leu Tyr Ala
                85                  90                  95

Gly Met Ile Ala Val Pro Val Asp Pro Leu Gly Pro Asp Arg Pro Ala
            100                 105                 110

Ala Asn Leu Thr Arg Leu Leu Asn Val Thr Ala Asp Ser Gly Ala Thr
        115                 120                 125

Val Cys Ile Ala Ser Arg Ser Met Leu Asp Ala Val Lys Ser His Pro
    130                 135                 140

Gly Ala Arg Gln Leu Thr Glu Gln Leu Arg Trp Val Val Pro Ser Leu
145                 150                 155                 160

Pro Asp Leu Leu Gly Arg Ala Pro Gly Ser Pro Pro Ala Ala Leu Arg
                165                 170                 175

Thr Glu Lys Asp Val Ala Met Leu Gln Tyr Ala Ser Gly Ser Thr Gly
            180                 185                 190

Ala Pro Lys Gly Thr Ile Val Thr His Ala Ser Leu Leu Met Leu Ala
        195                 200                 205

Arg Ala Leu Leu Ile Ser Thr Ser Ala Glu Ser Pro Phe Gly Arg Pro
    210                 215                 220

Asp Val Glu Val Thr Trp Leu Pro Leu Thr His Ser Thr Ala Gly Tyr
225                 230                 235                 240

Gly Leu Ile Met Lys Cys Leu Thr Gly Ala Thr Met Ser Ala Trp Tyr
                245                 250                 255

Ile Ala Pro Ser Ala Phe Ala Arg Ser Pro Ala Ile Trp Leu Arg Thr
            260                 265                 270

Ile Ser Arg His Lys Gly Lys Gln Val Tyr Ser Val Ala Pro Asn Phe
        275                 280                 285

Ala Leu Asp Trp Cys Val Ser Ser Thr Thr Glu Ala Glu Arg Lys Gln
    290                 295                 300

Leu Asp Leu Ser Cys Trp Thr His Val Met Ser Met Gly Glu Lys Val
305                 310                 315                 320
```

-continued

```
Arg Pro Glu Thr Trp Lys Ala Phe Ser Asp Ala Phe Arg Glu Ser Gly
                325                 330                 335
Phe His Pro Lys Leu Phe Ile Ala Gly Tyr Gly Met Ser Glu Thr Gly
                340                 345                 350
Tyr Val Ser Gly Ser Val Asn Gly Gly Lys Thr Val Arg Phe Asp Arg
                355                 360                 365
Ala Ala Met Asp Glu Gly Ser Leu Val Glu Ala Pro Glu Gly Gly Ile
                370                 375                 380
Leu Leu Leu Ser Ser Ser Gly Phe Thr Leu Pro Gly Val Arg Val Ala
385                 390                 395                 400
Ile Val Asp Pro Glu Thr Arg Glu Val Leu Pro Glu Gly Lys Ile Gly
                405                 410                 415
Glu Ile Trp Val Ser Thr Pro Thr Ala Met Thr Gly Tyr Trp Asn Arg
                420                 425                 430
Pro Glu Glu Thr Glu Gln Gln Phe Arg Ala Arg Ala Ala Asp Gly Ser
                435                 440                 445
Gly Pro Phe Phe Arg Ser Gly Asp Met Gly Ala Phe Tyr Gly Gly Asn
                450                 455                 460
Leu Phe Val Thr Gly Arg Arg Lys Ser Ile Val Val Ile Arg Gly Arg
465                 470                 475                 480
Lys His Tyr Ala Glu Asp Ile Glu Ser Thr Leu Glu Arg Ala Leu Asp
                485                 490                 495
Trp Leu Gly Ala Asn Ser Ser Ile Ala Phe Asp Asp Val Asn Gly
                500                 505                 510
Val Glu Glu Leu Phe Ile Ala Val Asp Pro Arg Gly Ala Arg Asp Gly
                515                 520                 525
Val Gly Phe Glu Glu Arg Thr Asp Ala Ile Arg Ser Val Val Ala Arg
                530                 535                 540
Glu Phe Gly Val Arg Val His Glu Val Leu Phe Leu Ala Ala Gly Gln
545                 550                 555                 560
Leu Pro Arg Thr Ser Met Gly Lys Val Ser Arg Val Ser Cys Lys Asp
                565                 570                 575
Leu Phe Arg Ser Gly Glu Leu Glu Ile Ala Ala Arg Ser Gly Ser Ile
                580                 585                 590
Ala Arg Gly Gly Ala Asp Leu Pro Ala Val Asp Leu Arg Ala Ile Leu
                595                 600                 605
Asp Glu Pro Asp Ala Glu Leu Arg Val Ala Arg Met Thr Glu Tyr Ile
                610                 615                 620
Arg Ser Leu Leu Ser Ala Ser Leu Ser Val Pro Ala Asp Ala Leu Ser
625                 630                 635                 640
Leu Thr Lys Ser Phe Asp Glu Leu Gly Val Asp Ser Met Thr Gly Val
                645                 650                 655
Arg Phe Arg Gly Glu Leu Val Arg Ala Leu Gly Leu Glu Leu Pro Glu
                660                 665                 670
Ser Ile Val Tyr Asn Tyr Pro Thr Ile Ala Gln Leu Ala Ser Phe Val
                675                 680                 685
Cys Glu Lys Leu Thr Gly Thr Ala Gly Ser Asn Asp Ala Glu Arg Ala
                690                 695                 700
Asp Arg Gly Pro Ala Ala Leu Ala Leu Asp Val Glu Ser Met Ser
705                 710                 715                 720
Glu Glu Ala Ala Ala Ala Leu Arg Ala His Leu Asp Gly Arg Lys
                725                 730                 735
```

<210> SEQ ID NO 10
<211> LENGTH: 1766
<212> TYPE: PRT
<213> ORGANISM: Sorangium cellulosum

<400> SEQUENCE: 10

```
Met Ser Glu Ser Gly Glu Leu Ser Leu Thr Lys Arg Ala Leu Leu Ala
1               5                   10                  15

Leu Gln Lys Ala Glu Leu Glu Ile Gly Arg Leu Arg Asp Ala Arg Pro
            20                  25                  30

Glu Pro Ile Ala Ile Ile Gly Val Gly Cys Arg Ile Pro Gly Gly Ala
        35                  40                  45

Thr Ser Pro Ser Arg Phe Trp Lys Leu Leu Glu Glu Gly Phe Asp Ala
    50                  55                  60

Leu Ala Glu Ile Pro Ala Ala Arg Arg Lys Leu Phe Glu Leu Gln Gly
65                  70                  75                  80

Ala Arg Ser Pro Thr Ser Gly Gly Phe Leu Asp Glu Ile Asp Lys Phe
                85                  90                  95

Asp Pro Ser Phe Phe Ser Ile Ser Pro Arg Glu Ala Ile Ser Met Asp
            100                 105                 110

Pro Ala Gln Arg Leu Leu Leu Glu Val Ser Val Glu Ala Leu Glu Asp
        115                 120                 125

Gly Gly Val Pro Met Ala Gln Ile Arg Gly Thr Arg Thr Gly Thr Phe
    130                 135                 140

Met Gly Phe Ser Gly Tyr Ser Gly Tyr Gly Ser Leu Thr Gly Ala Gln
145                 150                 155                 160

Val Glu Gln Leu Tyr Ala Val Thr Gly Leu Ser Ile Asn Val Ala Ala
                165                 170                 175

Gly Arg Ile Ser Tyr Val Leu Asp Leu Gln Gly Pro Cys Val Ser Val
            180                 185                 190

Asp Thr Ala Cys Cys Ser Ser Leu Val Ala Val His Leu Ala Ser Gln
        195                 200                 205

Ser Leu Arg Ser Arg Glu Cys Asp Leu Ala Leu Ala Gly Gly Val Asn
    210                 215                 220

Val Ile Ala Ala Met Ala Gly Asn Glu Ala Met Ala Ala Thr Gly Ala
225                 230                 235                 240

Leu Ser Ser Ser Gly Gly Arg Cys Arg Thr Phe Asp Ala Ala Ala Asp
                245                 250                 255

Gly Tyr Ile Arg Ser Glu Gly Cys Gly Val Val Leu Leu Lys Arg Leu
            260                 265                 270

Thr Asp Ala Met Glu Ala Gly Asp Arg Ile Leu Gly Val Val Ala Gly
        275                 280                 285

Ser Ala Val Lys His Asp Gly His Ser Asn Gly Leu Thr Ala Pro Asn
    290                 295                 300

Gly Arg Ala Gln Gln Leu Val Arg Glu Ala Leu Ala Ala Ala Ala Arg
305                 310                 315                 320

Val Arg Pro Glu Glu Ile Asp Tyr Ile Glu Thr His Gly Thr Gly Thr
                325                 330                 335

Pro Leu Gly Asp Pro Ile Glu Val Asp Ala Leu Ala Glu Val Phe Gly
            340                 345                 350

Ser Ser His Gly Pro Asp Arg Arg Ile Met Leu Gly Ser Val Lys Thr
        355                 360                 365

Asn Val Gly His Pro Glu Gly Ala Ala Gly Ile Val Gly Leu Ile Lys
    370                 375                 380
```

-continued

```
Val Leu Gly Met Phe Arg Arg Gly Met Val Pro Arg His Leu His Phe
385                 390                 395                 400

Asn Thr Pro Asn Pro Arg Val Pro Trp Asp Ser Val Pro Phe Leu Val
            405                 410                 415

Pro Arg Asp Thr Leu Pro Trp Pro Ala Thr Asp Lys Val Arg Val Ala
            420                 425                 430

Gly Val Ser Ala Phe Gly Phe Ser Gly Thr Ile Ser His Ala Ile Val
            435                 440                 445

Met Glu Pro Pro Lys Ala Pro Glu Arg Ser Val Asp Val Gly Pro Ala
450                 455                 460

Thr Ala Gly Arg Pro Leu Leu Leu Pro Ile Ser Ala Arg Thr Pro Glu
465                 470                 475                 480

Ala Leu Arg Ala Tyr Ala Ala Ser Tyr Leu Asp His Leu Ser Ala Glu
            485                 490                 495

Ala Thr Pro Glu Glu Thr Asp Arg Asp Val Ala Tyr Thr Ala Ser Leu
            500                 505                 510

Arg Arg Asp His His Ala His Arg Leu Ala Val Val Gly Ser Asp Arg
            515                 520                 525

Ala Ala Trp Arg Glu Lys Leu Gln Ser Tyr Val Ser Gly Glu Gly Cys
530                 535                 540

Arg Gly Leu Val Glu Gly Val Pro Glu Ala Arg Pro Arg Leu Ala
545                 550                 555                 560

Phe Val Phe Cys Gly Gln Gly Pro Gln Trp Trp Gly Met Gly Arg Glu
                565                 570                 575

Leu Leu Asp Lys Glu Pro Val Phe Arg Gly Ala Leu Glu Ala Cys His
            580                 585                 590

Glu Arg Ile Arg Glu Ala Gly Gly Pro Ser Leu Leu Asp Glu Leu Arg
            595                 600                 605

Arg Glu Ala Asp Thr Ser Arg Leu Asn Gln Thr Glu Val Ala Gln Pro
610                 615                 620

Ala Leu Phe Ala Leu Gln Val Ala Leu Ala Ala Leu Trp Arg Ser Trp
625                 630                 635                 640

Gly Val Gln Ala Asp Ala Val Val Gly His Ser Ile Gly Glu Val Ala
            645                 650                 655

Ala Ala His Val Ala Gly Ala Leu Ser Leu Glu Asp Ala Ala Arg Leu
            660                 665                 670

Val Val His Arg Gly Arg Ile Met Gln Arg Ala Thr Gly Leu Gly Lys
            675                 680                 685

Met Leu Ser Val Ala Leu Pro Leu Ser Ala Ala Gln Arg Ile Val Ser
690                 695                 700

Asp Tyr Gly Gln Arg Ile Ser Ile Gly Ala Ser Asn Ser Pro Thr Ser
705                 710                 715                 720

Thr Val Leu Ser Gly Glu Ala Ala Leu Asp Glu Val Val Glu Gln
            725                 730                 735

Leu Gln Gly Arg Gln Val Glu Ala Lys Trp Leu Pro Val Glu Tyr Ala
            740                 745                 750

Phe His Ser Ala Gln Met Glu Gly Phe Gly Glu Glu Leu Ser Lys Glu
            755                 760                 765

Leu Arg Gly Leu Ala Pro Gly Ala Asn Gly Pro Leu Leu Met Ser Thr
            770                 775                 780

Val Thr Gly Thr Glu Gln Arg Gly Thr Ser Phe Asp Ala Asp Tyr Trp
785                 790                 795                 800
```

-continued

```
Gly Gln Gln Ile Arg Lys Pro Val Leu Phe Ala Gln Cys Val Glu Glu
                805                 810                 815
Leu Ala Arg Lys Gly Cys Ser Leu Phe Leu Glu Ile Gly Pro His Pro
                820                 825                 830
Val Leu Ser Ala Ser Met Thr Glu Thr Leu Leu Ala Gln Glu Lys Ser
                835                 840                 845
Gly Arg Val Val Ala Ser Leu Arg Arg Arg Glu Glu Glu Val Pro Thr
        850                 855                 860
Leu Leu Glu Ala Leu Gly Gln Leu His Cys Ala Gly Tyr Pro Val Asp
865                 870                 875                 880
Trp Ser Lys Gln His Pro Val Arg Gly Arg Thr Val Ser Leu Pro Thr
                885                 890                 895
Tyr Pro Trp Gln Arg Glu Ser Tyr Trp Leu Glu Ala Pro Lys Ser Gln
                900                 905                 910
Thr Pro Arg Gln His Gly Ala Glu His His Tyr Glu Thr Glu Trp Arg
                915                 920                 925
Leu Ala Glu Arg Glu Arg Pro Ala Glu Pro Arg Arg Gly Gly Trp Leu
        930                 935                 940
Ile Leu Asp Asp Gln Ala Glu Arg Ala Ala Ala Leu Gln Asp Tyr Leu
945                 950                 955                 960
Glu Ala Arg Gly Gln Thr Cys Val Arg Val Ala Ala Asp Thr Tyr
                965                 970                 975
Ala Arg Arg Gly Ala Arg Asp Tyr Gln Ile Asp Pro Arg Glu Pro Glu
                980                 985                 990
His Phe Ala Arg Leu Leu Gly Glu Gln Glu Val Val Asp Ala Leu Ala
                995                 1000                1005
Asp Ala Ser Pro Ser Asp Arg Cys Gly Val Val His Leu Trp Ser
        1010                1015                1020
Ala His Ser Ser Pro Ala Pro Thr Leu Glu Ser Ile Gln Gln Ala
        1025                1030                1035
Gln Ala Leu Gly Ser Ile Ser Ala Leu His Leu Val Gln Ala Leu
        1040                1045                1050
Ala Arg Ala Gly Trp Arg Gln Pro Pro Arg Leu Trp Leu Val Thr
        1055                1060                1065
Gln Glu Val Gln Ala Ile Lys Asn Pro Thr Val Ser Val Ala Gln
        1070                1075                1080
Ala Pro Val Trp Gly Phe Gly Ala Thr Val Ala Leu Glu Met Pro
        1085                1090                1095
Glu Leu Gln Cys Thr Leu Leu Asp Leu Asp Ala Thr Pro Asn Ile
        1100                1105                1110
Asp Ala Leu Gly Gln Glu Leu Leu Ser Ala Ser Asp Glu Asp Arg
        1115                1120                1125
Ile Ala Leu Arg Gly Ala Glu Arg His Val Ala Arg Leu Val Pro
        1130                1135                1140
His Val Pro Glu Gln Arg Pro Ala Pro Glu Pro Leu Ser Phe Lys
        1145                1150                1155
Ala Asp Ala Thr Tyr Leu Leu Thr Gly Gly Leu Gly Gly Ile Gly
        1160                1165                1170
Leu Val Val Leu Glu Trp Met Ala Ala Arg Gly Ala Arg His Phe
        1175                1180                1185
Ala Leu Leu Gly Arg Ser Gly Pro Ser Ala Ser Ala Gln Pro Val
        1190                1195                1200
Leu Asp Arg Met Arg Glu Asp Gly Ala Gln Val Arg Thr Phe Ser
```

-continued

```
            1205                1210                1215

Val  Asp  Val  Ala  Asp  Arg  Glu  Arg  Leu  Arg  Thr  Val  Leu  Ala  Gln
         1220                1225                1230

Ile  Gln  Thr  Ser  Met  Pro  Pro  Leu  Ala  Gly  Ile  Ile  His  Ala  Ala
         1235                1240                1245

Gly  Val  Gly  Asp  Gln  Lys  Met  Ile  Pro  Asp  Leu  Asp  Gly  Pro  Ser
         1250                1255                1260

Leu  Gln  Ala  Ile  Gly  Arg  Pro  Lys  Val  Asp  Gly  Ser  Trp  Asn  Leu
         1265                1270                1275

His  Glu  Leu  Thr  Ser  Glu  Leu  Pro  Leu  Asp  Phe  Phe  Val  Leu  Phe
         1280                1285                1290

Ser  Ser  Val  Ser  Ser  Leu  Phe  Gly  Ser  His  Gly  Gln  Ser  Ser  Tyr
         1295                1300                1305

Ala  Ala  Gly  Asn  Ala  Phe  Leu  Asp  Ala  Leu  Ser  His  His  Arg  Arg
         1310                1315                1320

Ala  Leu  Gly  Leu  Pro  Ala  Leu  Ser  Leu  Asn  Trp  Thr  Ala  Trp  Thr
         1325                1330                1335

Asp  Val  Gly  Met  Ala  Thr  Pro  Ile  Ile  Ala  His  Thr  Ser  Arg  Tyr
         1340                1345                1350

Leu  Ala  Thr  Gln  Gly  Met  Gly  Ala  Leu  Ser  Ser  Arg  Glu  Gly  Val
         1355                1360                1365

Ala  Ala  Leu  Glu  Gln  Leu  Phe  Arg  Ala  Ser  Ser  Ala  Gln  Ile  Gly
         1370                1375                1380

Val  Val  Pro  Leu  Ser  Ile  Pro  Ser  Leu  Pro  Arg  Lys  Pro  Phe  Tyr
         1385                1390                1395

Ser  Val  Val  Ala  Pro  Pro  Thr  Ala  Pro  Thr  Pro  Thr  Ala  Gln  Thr
         1400                1405                1410

Val  Arg  Ala  Ser  Glu  Arg  Ile  Ala  Ala  Arg  Pro  Gly  Glu  Arg
         1415                1420                1425

Gln  Glu  Ala  Ile  Glu  Gly  Thr  Leu  Arg  Glu  Leu  Phe  Ala  Arg  Ala
         1430                1435                1440

Leu  Arg  Met  Pro  Pro  Asp  Lys  Leu  Lys  Leu  Thr  Glu  Ala  Leu  Gln
         1445                1450                1455

Asn  Leu  Gly  Val  Asp  Ser  Leu  Ile  Ala  Leu  Glu  Leu  Arg  Arg  Arg
         1460                1465                1470

Ile  Asp  Glu  Glu  Leu  Gly  Val  Lys  Leu  Gln  Ala  Ala  Glu  Ile  Ala
         1475                1480                1485

Arg  Val  Ala  Asn  Val  Arg  Glu  Leu  Ala  Gln  Leu  Val  Thr  Ala  Lys
         1490                1495                1500

Phe  Asp  Ala  Leu  His  Gly  Ser  Ala  Gly  Val  Ala  Gln  Gln  Ala  Arg
         1505                1510                1515

Leu  Glu  Val  Arg  Gly  Pro  Leu  Thr  Val  Leu  Lys  Pro  Ser  Arg  Gln
         1520                1525                1530

Arg  Pro  Arg  Leu  Arg  Leu  Val  Cys  Phe  Pro  Ala  Ser  Gly  Gly  Ser
         1535                1540                1545

Ala  Gly  Asp  Phe  Ala  Glu  Trp  Ala  Lys  Val  Met  Pro  Asp  Asp  Cys
         1550                1555                1560

Glu  Leu  Val  Ala  Val  Glu  Tyr  Pro  Gly  Ser  Gly  Ala  Arg  Gln  Leu
         1565                1570                1575

Glu  Ser  Cys  Glu  His  Pro  Leu  Ala  Ala  Leu  Thr  Leu  Gln  Ala  Ala
         1580                1585                1590

Gly  Ala  Leu  Met  Ala  Met  Pro  Arg  Val  Pro  Leu  Val  Leu  Phe  Gly
         1595                1600                1605
```

```
His  Ser  Leu  Gly  Gly  Leu  Ile  Ala  His  Ala  Thr  Ala  Val  Glu  Leu
     1610                1615                     1620

Glu  Arg  His  Ala  Met  Gly  Pro  Ser  Cys  Val  Val  Leu  Ser  Asn  Pro
     1625                1630                     1635

Ala  Asn  Val  Ile  Thr  Val  Gln  Arg  Asp  Leu  Pro  Arg  Asp  Gly  Phe
     1640                1645                     1650

Arg  Asp  Gln  Lys  Phe  Leu  Thr  Trp  Leu  Ala  Arg  Ser  Thr  Gly  Ile
     1655                1660                     1665

Ser  Ile  Glu  Pro  Glu  Ala  Thr  Asp  Ser  Asp  Ala  Thr  Arg  Gln  Phe
     1670                1675                     1680

Leu  Lys  Thr  Phe  Gly  Glu  Gln  Leu  Ala  Trp  Thr  Phe  Asp  Phe  Asp
     1685                1690                     1695

Leu  Gly  Trp  Arg  Val  Ser  Cys  Pro  Val  Ile  Ile  Ser  Cys  Gly  Arg
     1700                1705                     1710

Asp  Asp  Thr  Thr  Leu  His  Ala  Glu  Ser  Leu  Glu  Phe  Trp  Arg  Arg
     1715                1720                     1725

Ser  Gly  Gly  Asp  Leu  Glu  Glu  Trp  Thr  Phe  Ala  Gly  Ala  His  Asp
     1730                1735                     1740

Tyr  Ile  Arg  Gln  Glu  Phe  Ala  Glu  Ile  Val  Ser  Lys  Ile  Met  Asn
     1745                1750                     1755

Arg  Ala  Ala  Gly  Lys  Asp  Arg  Thr
     1760                1765

<210> SEQ ID NO 11
<211> LENGTH: 439
<212> TYPE: PRT
<213> ORGANISM: Sorangium cellulosum

<400> SEQUENCE: 11

Met  Ser  Ala  Gln  Pro  Glu  Tyr  Cys  Ile  Val  Gly  Gly  Pro  Ile  Gly
 1              5                    10                       15

Ile  Gly  Ile  Gly  Lys  Cys  Phe  Ala  Gln  Glu  Gly  Leu  Lys  Phe  Thr  Ile
                20                    25                       30

Val  Glu  Ala  Asp  Glu  Asp  Phe  Gly  Gly  Thr  Trp  Ala  Leu  Ser  Gln  Arg
                35                    40                       45

Ser  Gly  Leu  Val  Tyr  Lys  Ser  Thr  His  Leu  Ile  Ser  Ser  Lys  Lys  Asn
        50                    55                       60

Thr  Gln  Phe  Leu  Asp  Phe  Pro  Met  Pro  Glu  Asp  Tyr  Pro  His  Tyr  Pro
65                    70                    75                       80

Ser  His  Ala  Gln  Met  Leu  Ser  Tyr  Leu  Arg  Ser  Leu  Ala  Thr  His  Tyr
                85                    90                       95

Gly  Leu  Tyr  Asp  Arg  Ala  Leu  Phe  Gly  Thr  Arg  Val  Glu  His  Val  Glu
                    100                   105                      110

Pro  Asn  Gly  Ala  Gly  Cys  Arg  Val  Arg  Leu  Ser  Asn  Gly  Glu  Thr  Arg
                    115                   120                      125

Thr  Phe  Ser  Ala  Val  Val  Val  Ala  Asn  Gly  Arg  Met  Arg  Thr  Pro  Leu
        130                   135                      140

Ile  Pro  Arg  Tyr  Pro  Gly  Val  Phe  Ser  Gly  Glu  Thr  Met  His  Ser  Ala
145                   150                   155                      160

Ala  Tyr  Lys  Ser  His  Glu  Val  Phe  Arg  Gly  Lys  Arg  Val  Leu  Val  Ile
                    165                   170                      175

Gly  Gly  Gly  Asn  Ser  Gly  Cys  Asp  Ile  Ala  Val  Asp  Ala  Ala  Leu  Ala
                    180                   185                      190

Ala  Glu  Gln  Thr  Phe  His  Ser  Thr  Arg  Arg  Gly  Tyr  His  Tyr  Met  Pro
```

-continued

```
            195                 200                 205
Lys Phe Ile His Gly Lys Pro Thr Gln Glu Trp Leu Met Asp Met Gly
        210                 215                 220

Ser Lys Phe Arg Ser Gln Asp Asp Tyr Trp Ser Phe Val Gln Arg Glu
225                 230                 235                 240

Phe Lys Ala Ala Gly Tyr Asp Pro Val Asp Tyr Gly Leu Pro Arg Pro
                245                 250                 255

Asp His Ala Ile His Glu Ala His Pro Ile Leu Asn Ser Leu Val Leu
        260                 265                 270

Tyr Tyr Ile Gly His Gly Asp Ile His Pro Lys Pro Asp Val Arg Arg
            275                 280                 285

Phe Glu Gly Arg Thr Val Glu Phe Val Asp Gly Thr Arg Ala Glu Val
        290                 295                 300

Asp Leu Ile Leu Tyr Ala Thr Gly Tyr Glu Met Asp Phe Pro Phe Leu
305                 310                 315                 320

Ala Glu Asp Leu Arg Pro Ser Asp Gly Ala Leu Glu Leu Phe Leu Ser
                325                 330                 335

Met Phe His Arg Lys Ala Asp Ser Leu Val Phe Val Gly Tyr Phe Asn
            340                 345                 350

Ala Ala Ser Gly Leu Gly Asn Leu Leu Asn Cys Gly Gly Ala Leu Val
        355                 360                 365

Thr Asp Tyr Leu Val Ala Arg Glu Lys Asn Thr Asp Ala Phe Arg Val
    370                 375                 380

Leu Arg Arg Leu Ile Gln Gly Pro Glu Pro Asp Ile Gly Arg Gly Arg
385                 390                 395                 400

Phe Leu Asn Ser Pro Arg His Arg Val Glu Thr Asp Leu Trp Lys Ala
                405                 410                 415

Met Lys Val Met Asn Phe Phe Arg Ser Val Leu Asn Pro Ala Arg Ala
            420                 425                 430

Ala Gly Asp Val Val Arg Ala
        435

<210> SEQ ID NO 12
<211> LENGTH: 473
<212> TYPE: PRT
<213> ORGANISM: Sorangium cellulosum

<400> SEQUENCE: 12

Met Ser Arg Ala Ile Val Ile Gly Gly Ser Ile Ala Gly Met Cys Ser
1               5                   10                  15

Ala Arg Val Leu Cys Asp Phe Asp Glu Val Val Ile Leu Asp Arg
            20                  25                  30

Asp Gln Phe Pro Thr Glu Ile Ala Pro Arg Pro Gly Val Pro Gln Ser
        35                  40                  45

Arg His Thr His Val Leu Leu Pro Arg Gly Glu Gln Glu Leu Glu Glu
    50                  55                  60

Leu Phe Pro Gly Phe Ser Ala Ser Met Met Ala Ala Gly Ala Leu Lys
65                  70                  75                  80

Phe Asp Val Gly Thr Gly Met Ala Val Arg Arg Val Phe Gly Trp Gln
            85                  90                  95

Thr Val Gly Pro Thr Gly Arg Glu Leu Leu Trp Ala Ser Arg Asp Leu
        100                 105                 110

Phe Glu Gly Thr Ile Arg Ser Leu Met Arg Gln Gln Thr Lys Val Arg
    115                 120                 125
```

```
Ile Arg Glu Gly Ser Gln Val Leu Ala Leu Arg Ser Thr Ala Gly Glu
130                 135                 140

Arg Pro Arg Ile Arg Gly Val Leu Leu Arg Asp Asp Ala Ala Glu Gln
145                 150                 155                 160

Glu Leu Glu Ala Asp Leu Val Val Asp Ala Ser Gly Arg His Thr Arg
                165                 170                 175

Ala Glu Gln Trp Leu Thr Glu Leu Gly Leu Pro Ala Pro Lys Thr Gln
                180                 185                 190

Cys Val Asp Ser Arg Ala Gly Tyr Ala Ser Arg Phe Tyr Lys Val Pro
                195                 200                 205

Pro Pro Glu Arg Arg Pro Ser Asp Trp Trp Lys Gly Leu Trp Val
210                 215                 220

Glu Ala Glu Pro Asp Arg Pro Arg Gly Ala Val Val Phe Pro Ile Glu
225                 230                 235                 240

Gly Asp Arg Trp Leu Val Thr Ala Ser Gly Phe Ser Gly Ser Tyr Pro
                245                 250                 255

Pro Thr Asp Glu Gln Gly Phe Leu Glu His Leu Ala Ser Leu Ser Ser
                260                 265                 270

Pro Ile Val Ala Arg Ala Val Ala Leu Ala Glu Pro Ile Ser Pro Ile
                275                 280                 285

Tyr Gly Asn Arg Ser Met Ala Asn Val Ser Arg Ala Tyr Asp Arg Trp
290                 295                 300

Glu Ile Gln Leu Pro Gly Phe Val Ala Val Gly Asp Ala Ala Cys Ala
305                 310                 315                 320

Phe Asn Pro Val Tyr Gly Gln Gly Met Ser Thr Ser Thr Val Ser Ala
                325                 330                 335

Val Ile Leu Arg Asp Val Leu Arg Arg Gly Pro Gly Ala Gly Phe
                340                 345                 350

Glu Pro Gly Phe Phe Gln Gln Gln Ala Lys Phe Leu Arg Ser Val Trp
                355                 360                 365

Asp Phe Ala Thr Arg Ser Asp Phe Arg Trp Pro Gly Thr Val Gly Glu
                370                 375                 380

Arg Pro His Thr Pro Ala Ile Ile Gly Ala Tyr Ala Lys Leu Ala Ile
385                 390                 395                 400

Glu Ser Ala His His Asp Ser Ala Ile Arg Arg His Leu Phe Pro Ala
                405                 410                 415

Phe Asp Leu Thr Gly Ser Ala Thr Leu Leu Phe Glu Pro Leu Phe Val
                420                 425                 430

Gly Lys Val Leu Leu Ser Ala Gly Gln Arg Arg Leu Arg Gln Arg Leu
                435                 440                 445

Leu Gly Thr Pro Pro Ile Pro Glu Ser Pro Val Pro Ala Gly Val
    450                 455                 460

Pro Arg Trp Ala Ala Gly Ala Ala Met
465                 470

<210> SEQ ID NO 13
<211> LENGTH: 395
<212> TYPE: PRT
<213> ORGANISM: Sorangium cellulosum

<400> SEQUENCE: 13

Met Ile Cys Phe Val Pro Ala Leu Arg Arg Met Gly Ala Thr Pro Ala
1               5                   10                  15

Arg Ile Cys Met Arg Gln Arg Leu Asp Val Thr Asp Leu Tyr Asn Asp
                20                  25                  30
```

```
Ala Tyr Thr Ala Tyr Ile Glu Ala Phe Arg Arg Gln Thr Glu Leu Val
            35                  40                  45

Ala Ser Glu Ile Leu Leu Glu His Leu Val Asp Gln Ser Gly Ala Val
 50                  55                  60

Gln Val Leu Asp Asp Arg Pro Glu Ser Ala Pro Ser Val Thr Ala Tyr
 65                  70                  75                  80

Gln Phe Arg Arg Lys Leu Leu Asp Tyr Phe Ser Asp Lys Gly Asp Leu
                 85                  90                  95

Ile Gln Asp Pro Ser Gly Arg Leu Val Pro Ser Glu Ala Val Arg Lys
            100                 105                 110

Arg Val Ala Glu Arg Glu Ala Met Glu Leu Ala Asp Arg Ala Ile Leu
        115                 120                 125

Gly Glu Met Val Glu Phe Leu Gln Arg Tyr Arg Gly Leu Ala Gly Pro
        130                 135                 140

Val Leu Ala Gly Lys Asp Ala Leu Ala Thr Met Asp Leu Gln Tyr Gly
145                 150                 155                 160

Met Gln Ala Ser Leu Lys Phe Trp Glu Tyr Ser Met Ile Ser Leu Pro
                165                 170                 175

Ala Lys Lys Pro Cys Asn Val Met Leu Ala Arg Ala Leu Met Ala Lys
            180                 185                 190

Leu Ala Glu Gly Pro Gly Ile Ser Val Phe Glu Gly Gly Ala Gly Leu
        195                 200                 205

Gly Val Val Leu Arg Gln Ala Leu Ser Asp Pro Arg Phe Leu Pro Leu
        210                 215                 220

Ser Arg Asn Leu Val Arg Tyr Asp Tyr Thr Asp Ile Ser Ala Leu Leu
225                 230                 235                 240

Met Glu Thr Gly Lys Gln Trp Leu Arg Thr His Ala Pro Ala Asp Leu
                245                 250                 255

Phe Gln Arg Ile His Phe Gln Arg Leu Asp Leu Asp Ala Leu Pro Ser
            260                 265                 270

Ala Gly Asn Thr Phe Ala Arg Ala Ser Val Asp Leu Ile Val Leu
        275                 280                 285

Glu His Val Leu Tyr Asp Val Arg Asp Leu His Ala Thr Leu Gln Ala
        290                 295                 300

Phe His Thr Met Leu Lys Pro Gly Gly Gln Leu Ala Phe Thr Met Ser
305                 310                 315                 320

Phe Arg Asp Arg Pro Gly Leu Phe Phe Pro Asn Glu Phe Phe Gln Ser
                325                 330                 335

Met Leu His Thr Tyr Ser Lys Ala Lys Leu Asp Pro Pro Arg Arg Gln
            340                 345                 350

His Val Gly Tyr Leu Thr Leu Gln Glu Trp Glu Leu Ser Leu Arg Ala
        355                 360                 365

Ala Gly Phe Ser Glu Trp Glu Val Tyr Pro Ala Pro Glu Asp His Ala
        370                 375                 380

Lys Trp Pro Phe Gly Gly Ile Val Ala Tyr Arg
385                 390                 395

<210> SEQ ID NO 14
<211> LENGTH: 542
<212> TYPE: PRT
<213> ORGANISM: Sorangium cellulosum

<400> SEQUENCE: 14

Met Arg Asp Ala His Cys Glu Pro Arg Gly Ala Ser Gly Lys Leu Pro
```

-continued

```
1               5                   10                  15
Pro Arg Phe Arg Ala Asn Glu Glu Pro Leu Met Ala Gln Ala Phe Pro
                20                  25                  30
Ala Ser Pro Thr Thr Thr Pro Ser Thr Arg Thr Leu Val Val Gln Ser
            35                  40                  45
Pro Ile Asp Gly Ser Arg Leu Gly Glu Val Pro Leu Met Gly Asp Ala
        50                  55                  60
Glu Val His Ala Ala Val Glu Arg Ala Arg Leu Ala Gln Arg Ala Trp
65                  70                  75                  80
Ala Gln Leu Pro Ile Glu Thr Arg Ala Gly Arg Val Ala Arg Val Ile
                85                  90                  95
Asp Ala Phe Val Glu Arg Leu Asp Asp Leu Val Asp Ala Val Val Leu
            100                 105                 110
Glu Thr Gly Lys Pro Arg Asn Asp Ala Leu Ala Glu Trp Ile Thr Val
        115                 120                 125
Val Asp Ala Cys His Tyr Phe Thr Arg His Ala Gly Arg Ile Leu Ala
    130                 135                 140
Asp Thr Ser Ile Thr Leu His His Met Lys Trp Arg Gly Ser Tyr Val
145                 150                 155                 160
Thr Tyr Val Pro Met Gly Val Val Ala Val Ile Ser Pro Trp Asn Leu
                165                 170                 175
Pro Leu Ala Ile Pro Met Gly Ser Val Ile Glu Ala Leu Ile Ala Gly
            180                 185                 190
Asn Ala Val Val Val Lys Pro Ser Glu Val Thr Pro Leu Thr Leu Leu
        195                 200                 205
Lys Ala Lys Glu Val Val Asp Ala Ile Gly Ile Pro Thr Asp Leu Phe
    210                 215                 220
Gln Val Val Thr Gly Asp Ala Arg Thr Gly Ala Ala Leu Ile Asp Ala
225                 230                 235                 240
Gly Val Gln Lys Val Val Phe Thr Gly Gly Val Ser Ser Gly Arg Arg
                245                 250                 255
Val Gly Ala Ala Cys Ala Glu Arg Leu Ile Pro Cys Val Leu Glu Leu
            260                 265                 270
Gly Gly Lys Ala Pro Leu Ile Ala Cys Asp Asp Cys Glu Ile Glu Arg
        275                 280                 285
Thr Ala Arg Ser Ile Val Ala Gly Gly Phe Ile Asn Ser Gly Gln Leu
    290                 295                 300
Cys Ile Ser Val Glu Arg Val Leu Ala Thr Glu Ala Val His Asp Arg
305                 310                 315                 320
Leu Val Asp Arg Val Ala Leu Thr Arg Glu Leu Arg Gln Gly Asp
                325                 330                 335
Pro Arg Ala Asp Asp Val Asp Val Gly Ala Ile Ile Phe Ala Lys Gln
            340                 345                 350
Met Asp Ile Ala Glu Ala His Ile Lys Asp Ala Val Ala Arg Gly Ala
        355                 360                 365
Leu Val Ala Thr Gly Gly Arg Arg Pro Gly Pro Gly Met Phe Phe
    370                 375                 380
Glu Pro Thr Val Leu Thr Arg Cys Thr Pro Glu Met Thr Val Met Arg
385                 390                 395                 400
Glu Glu Ile Phe Gly Pro Val Pro Ile Met Lys Val Arg Asp Glu
                405                 410                 415
Asp Glu Ala Val Arg Ile Ala Asn Asp Ser Pro Leu Gly Leu His Ala
            420                 425                 430
```

Tyr Val Phe Ser Arg Asp Lys Thr Arg Ala Arg Ala Val Ala Glu Arg
        435                 440                 445

Ile Glu Ala Gly Thr Val Met Ile Asn Asp Val Leu Val Ser Tyr Cys
    450                 455                 460

Ala Pro Glu Ala Pro Phe Gly Gly Ile Lys Asn Ser Gly Tyr Gly Arg
465                 470                 475                 480

Val His Ser Asp Asp Ser Leu Arg Ala Met Cys Tyr Ala Arg His Val
                485                 490                 495

Asn His Glu Arg Phe Ala Met Pro Leu Asn Ser Pro Leu Leu Phe Pro
            500                 505                 510

Tyr Thr Thr Ala Lys Tyr Arg Gly Met Arg Ala Ala Ile Arg Ala Thr
            515                 520                 525

Phe Lys Arg Thr Pro Leu Leu Gly Arg Leu Ala Asp Leu Leu
            530                 535                 540

<210> SEQ ID NO 15
<211> LENGTH: 376
<212> TYPE: PRT
<213> ORGANISM: Sorangium cellulosum

<400> SEQUENCE: 15

Met Val Ile Glu Glu Ser His Val Ile Ile Gly Ala Gly Pro Ser
1               5                   10                  15

Gly Leu Ala Val Gly Ala Cys Leu Arg Glu Arg Gly Ile Pro Phe Val
                20                  25                  30

Leu Leu Glu Gln Ser Asp Ala Val Gly Ala Ser Trp Arg Arg His Tyr
            35                  40                  45

Gln Arg Leu His Leu His Thr Val Lys Gln Phe Ser Ser Leu Pro Gly
    50                  55                  60

Leu Ala Trp Pro Arg Tyr Ala Pro Pro Tyr Pro Ser Arg Ala Gln Met
65                  70                  75                  80

Val Asp Tyr Leu Gln Arg Tyr Ala Glu Arg Phe Arg Leu Glu Pro Arg
                85                  90                  95

Phe Gly Ala Glu Val Val Arg Ala Tyr Arg Asp Gly Ser Arg Trp Val
                100                 105                 110

Thr Gln Thr Arg Ala Gly Glu Phe Thr Ser Arg Ala Leu Val Val Ala
            115                 120                 125

Thr Gly Tyr Ser Arg Leu Pro Asn Val Pro Thr Trp Pro Gly Gln Glu
    130                 135                 140

Arg Phe Arg Gly Pro Ile Leu His Ser Ser Thr Tyr Gly Ser Gly Ala
145                 150                 155                 160

Ala Phe Arg Gly Gln Arg Val Leu Val Val Gly Ser Gly Asn Ser Gly
                165                 170                 175

Gly Glu Ile Ala Met Asp Leu Trp Glu His Ala Ala Glu Thr Thr Val
                180                 185                 190

Ser Ala Arg Ser Gly Ile His Val Ile Pro Arg Asp Pro Leu Arg Leu
            195                 200                 205

Pro Ala Gln Phe Ser Ala Leu Ala Leu Tyr Gly Ala Leu Pro Pro Ala
    210                 215                 220

Val Gly Asp Arg Leu Ala Thr Ala Phe Leu Ser Arg Thr Val Gly Asp
225                 230                 235                 240

Leu Ser Arg Trp Gly Ile His Arg Pro Glu Ile Gly Pro Gly Thr Arg
                245                 250                 255

Ala Val Lys Glu Gly Arg Ile Pro Leu Ile Asp Met Gly Thr Leu Ala

-continued

```
                    260                 265                 270
Leu Ile Gln Gln Gly Lys Ile Ala Val Val Pro Gly Pro Arg Ala Phe
                275                 280                 285
Thr Glu Thr Gly Val Ile Phe Thr Asp Gly Arg Glu Leu Pro Phe Asp
            290                 295                 300
Ala Val Val Leu Ala Thr Gly Tyr Arg Ala Gly Leu Gly Asp Phe Leu
305                 310                 315                 320
Glu Asp Ala Ala Arg Phe Thr Asp Glu Arg Gly Tyr Pro Arg Trp His
                325                 330                 335
Gly Ala Pro Thr Pro Thr Pro Gly Leu Phe Phe Ile Gly Phe Arg Asn
            340                 345                 350
Pro Ile Thr Gly Gln Leu Arg Asp Ile Ala Ala Glu Ala Pro Arg Val
                355                 360                 365
Ala Arg His Leu Arg Gly Val Asn
            370                 375
```

<210> SEQ ID NO 16
<211> LENGTH: 356
<212> TYPE: PRT
<213> ORGANISM: Sorangium cellulosum

<400> SEQUENCE: 16

```
Met Ala Glu Leu Asp His Trp His Pro Val Leu Leu Ser His Glu Leu
1               5                   10                  15
Arg Arg Lys Pro Arg Ser Val Arg Leu Ala Gly Arg Glu Ile Val Val
                20                  25                  30
Phe Arg Thr Ser Ser Gly Gly Leu Gly Ala Phe Thr Asp Arg Cys Pro
            35                  40                  45
His Arg Ser Met Arg Leu Ser Glu Gly Trp Val Glu Gly Asp Arg Leu
        50                  55                  60
Val Cys Ala Tyr His Gly Trp Arg Trp Ala Ala Asp Gly Arg Gly Asp
65                  70                  75                  80
Ile Pro Ala Thr Pro Ala Ala Arg Pro Cys Ala Arg Arg Asp Asp Val
                85                  90                  95
Phe Asp Ala Val Glu Arg Tyr Gly Ala Ile Trp Val Lys Arg Ala Gly
            100                 105                 110
Ala Gln Ala Thr Phe Pro Arg Phe Asp Ala Glu Gly Tyr Val Pro Ala
        115                 120                 125
Gly Val Leu Arg His Arg Ala Ala Val Pro Phe Glu Leu Ala Leu Asp
    130                 135                 140
Asn Phe Ile Glu Val Glu His Thr Pro Phe Val His Phe Met Leu Gly
145                 150                 155                 160
Tyr Ser Leu Asp Gln Met Pro Gln Val Glu Ala Gln Val Thr Leu Ser
                165                 170                 175
Asp Asp Ala Val Gln Val Val Asn Thr Gly Pro Lys Arg Pro Ile Pro
            180                 185                 190
Arg Ile Val Glu Lys Met Phe Arg Ile Pro His Asp Ala Lys Phe Val
        195                 200                 205
Val Glu Trp Thr Ala Arg Phe Ser Pro Val His Ala Ile Tyr Asp His
    210                 215                 220
Ser Phe Ile Asn Pro Arg Thr Arg Glu Val Thr Tyr Pro Leu Arg
225                 230                 235                 240
Ser Ala Val Phe Phe Asn Pro Val Gly Pro Glu Ser Ser Glu Ile Tyr
                245                 250                 255
```

```
Thr Phe Leu Phe Ala Ser Leu Gly Arg Trp Ser Glu Phe Gly Leu Gly
        260                 265                 270

Ser Leu Ile Trp Pro Pro Leu Arg Val Ala Met Asp Leu Glu Leu Arg
        275                 280                 285

Leu Asp Met Arg Leu Leu Ser Arg Leu Ala Asp Lys Arg Gly Ile Leu
        290                 295                 300

Lys Gly Asn Val Leu Gly Arg Phe Asp Lys Ala Leu Val Ala Ser Arg
305                 310                 315                 320

Asp Arg Ile Asp Arg Ile Tyr Arg Gly Gln Ala Ala Glu Ala Thr Pro
                325                 330                 335

Glu Ala Gly Asp Gly His Glu Ala Thr Arg Ala Ala Arg Arg Leu Pro
                340                 345                 350

Leu Ala Ala Ser
        355

<210> SEQ ID NO 17
<211> LENGTH: 534
<212> TYPE: PRT
<213> ORGANISM: Sorangium cellulosum

<400> SEQUENCE: 17

Met Val Trp Gln His Gly Arg Gln Ser Leu His Glu Cys His Asp Gly
1               5                   10                  15

Gly Arg Glu Pro Cys Ser Glu Thr Ser Glu Ile Arg Gly Ala Pro Pro
            20                  25                  30

Gly Leu Asp Arg Met Thr Val Pro Gly Leu Ser Thr Arg His Val Phe
        35                  40                  45

His Leu Cys Tyr Lys Pro Gln Leu Gly Gly Leu Ala Arg Leu Arg Arg
    50                  55                  60

Ser Ala Thr Ser Ser Trp Asp Ala Arg Arg Pro Arg Gln Arg Gln Leu
65                  70                  75                  80

Glu Pro Arg Ala Asp Asn Ala Thr Leu Asn Ala Arg Leu Pro Gln Ala
                85                  90                  95

Pro Leu Ala Asp Thr Met Glu Pro Lys Ala His Gly Thr Ile Pro Glu
            100                 105                 110

Glu Met Met Gln Ser Thr Ala Thr Ile Ala Pro Leu Ala Val Leu Phe
        115                 120                 125

Val Leu Met Ala Ile Glu Ala Val Ala Arg His Arg Arg Gly Asp
    130                 135                 140

Thr Thr Tyr Arg Leu Pro Asp Thr Val Ala Ser Val Gly Val Gly Val
145                 150                 155                 160

Gly Tyr Phe Ala Leu Val Ala Phe Phe Ser Phe Ile Ser Ile Val Val
                165                 170                 175

Tyr Asp Ile Val Tyr Glu Arg Trp Ala Ile Thr His His Ala Arg Ser
            180                 185                 190

Ala Val Thr Ile Val Phe Thr Ile Phe Ala Ala Asp Phe Leu Tyr Tyr
        195                 200                 205

Leu Phe His Arg Ala Ser His Arg Ile Asn Val Leu Trp Ala Ile His
    210                 215                 220

Val Val His His Gln Ser Arg Glu Gln Asn Leu Ala Val Asn Leu Arg
225                 230                 235                 240

Met Pro Trp Leu Gln Pro Ala Tyr Gln Trp Phe Phe Tyr Leu Pro Leu
                245                 250                 255

Ala Phe Leu Gly Ile Pro Pro Ala Val Phe Leu Leu Ala Arg Gly Val
            260                 265                 270
```

```
Ser Ile Ser Tyr Asn Val Phe Thr His Thr Arg Ala Val Gly Lys Leu
            275                 280                 285

Gly Pro Leu Glu Tyr Val Leu Asn Thr Pro Ser His His Arg Val His
        290                 295                 300

His Gly Met Asp Glu Gln Tyr Leu Asp Cys Asn Tyr Gly Gly Ile Phe
305                 310                 315                 320

Ile Val Trp Asp Arg Leu Leu Gly Thr Phe Val Pro Glu Gly Lys Glu
                325                 330                 335

Pro Thr Tyr Gly Thr Arg Arg Val Val Ser Trp Asn Pro Ile Trp
                340                 345                 350

Leu Asn Val Glu Pro Phe Ile His Leu Ala Lys Leu Ser Arg Ala Ala
            355                 360                 365

Arg Ser Pro Trp Asp Arg Val Lys Val Trp Phe Met Pro Pro Glu Trp
        370                 375                 380

Gln Pro Ala Gly Val Leu Glu Ala Ser Ala Pro Pro Glu Pro Arg Asp
385                 390                 395                 400

Val Glu Ser Arg Gly Ser Thr Ala Ser Ser Ile Ala Gln Met Ala Leu
                405                 410                 415

Ser Val Gly Val Thr Val Val Ile Gly Ala Met Val Ile Met Tyr Thr
            420                 425                 430

Gly Thr Ser Ser Thr Met Pro Arg Leu Ala Leu Leu Val Leu Leu Leu
        435                 440                 445

Ala Ser Leu Gly Ala His Ala Arg Ser Leu Glu Ser Pro Gly Phe Ala
450                 455                 460

Trp Arg Phe Glu Leu Ala Arg Ala Ala Leu Leu Leu Ala Val Ala Gly
465                 470                 475                 480

Trp Leu Asp Ala Ser Gly Ala Arg Pro Leu Ala Ser Val Ala Leu Met
                485                 490                 495

Ala Gly Gly Leu Ser Ala Ala Ser Gly Val Leu Phe Arg Leu Gly Arg
            500                 505                 510

Arg Pro Arg Gly Ser Arg Ala Gly Gly Ala Glu Asp Ala Ala Pro Ser
            515                 520                 525

Met Ser Leu Pro Gly Ser
        530

<210> SEQ ID NO 18
<211> LENGTH: 446
<212> TYPE: PRT
<213> ORGANISM: Sorangium cellulosum

<400> SEQUENCE: 18

Met Ala Ser Ser Glu Asp Gly Thr Arg Ser Trp Ser Asn Thr Lys Ser
1               5                   10                  15

Leu Ala Leu His Glu Arg Ala Ala Lys Val Met Pro Gly Gly Gln Ala
            20                  25                  30

Asn Phe Arg Gly Gly Leu Leu Ser Thr Pro Leu Phe Phe Ser His Ala
        35                  40                  45

Arg Gly Ala Arg Leu Trp Asp Val Asp Gly Asn Glu Tyr Val Asp Leu
    50                  55                  60

Ile Asn Ala Gly Gly Pro Gly Ile Leu Gly His Asn Asp Pro Glu Tyr
65                  70                  75                  80

Ile Asp Ala Leu Lys Arg Gln Leu Asp Thr Val Tyr Ser Leu Gly Ser
                85                  90                  95

Gly Ile Cys Gln Thr Glu Gln Asp Ile Glu Leu Ala Glu Lys Ile Ala
```

```
                100             105             110
Ser His Val Pro Cys Ala Glu Arg Val Arg Phe Cys Val Thr Gly Ser
            115                 120                 125
Glu Ala Val His Leu Ala Leu Arg Leu Ala Arg Ala Tyr Thr Lys Arg
        130                 135                 140
Pro Tyr Phe Ile Arg Phe Gln Thr His Tyr His Gly Trp Phe Asp Ser
145                 150                 155                 160
Val Leu Gly Gly Val Asp Glu His Pro Glu Gly Arg Pro Leu Pro
                165                 170                 175
Leu Glu Ser Glu Gln Ser Phe Phe His Thr Glu Gly Arg Val Pro Asp
            180                 185                 190
Ala Phe Lys Tyr Ser Phe Leu Leu Pro Trp Asn Asp Ile Asp Val Leu
        195                 200                 205
Glu Glu Thr Leu Lys Lys Tyr Gly His Glu Val Ala Met Ile His Met
225                 230                 235                 240
Glu Pro Ile Leu Val Asn Gly Gly Cys Pro Pro Arg Pro Gly Tyr
225                 230                 235                 240
Leu Glu Arg Val Arg Glu Leu Cys Asp Gln His Gly Ile Val Leu Gly
            245                 250                 255
Phe Asp Glu Val Ile Thr Gly Phe Arg Val Gly Leu Gly Gly Ala Gln
        260                 265                 270
Ala Ala Leu Gly Val Thr Pro Asp Leu Ala Thr Phe Gly Lys Ala Leu
    275                 280                 285
Gly Gly Gly Met Pro Met Ala Ala Val Ala Gly Lys Ala Glu Ile Met
290                 295                 300
Asp Gln Leu Arg Thr Gly Lys Val Thr Gly Ala Gly Thr Phe Asn Gly
305                 310                 315                 320
Tyr Pro Leu Gly Val Ala Ala Ser Leu Ala Thr Leu Lys Ile Leu Glu
            325                 330                 335
Arg Asp Asp Gly Ala Val Tyr Arg Arg Ile Asp Met Met Gln Ala Arg
        340                 345                 350
Leu Lys Glu Gly Leu Leu Asp Ile Cys Lys Arg Arg Gly Ile Pro Ala
    355                 360                 365
Leu Val Gln Gly Pro Arg Gly Val Phe Phe Leu Leu Phe Thr Asp Lys
370                 375                 380
Pro Val Ile Tyr Ser Phe Gln Glu Leu Met Glu Ala Ala Leu Pro Arg
385                 390                 395                 400
Gln Phe Lys Phe Tyr Ser Thr Met Pro Glu Gly Thr Leu Leu Met
            405                 410                 415
Tyr Gly Gly Arg Trp Tyr Ile Ser Ala Ala Leu Thr Glu Ala Asp Val
        420                 425                 430
Asp Cys Ala Leu Glu Ser Ala Asp Arg Thr Leu Ala Arg Ile
    435                 440                 445

<210> SEQ ID NO 19
<211> LENGTH: 359
<212> TYPE: PRT
<213> ORGANISM: Sorangium cellulosum

<400> SEQUENCE: 19

Met Pro Pro Thr Glu Asp Leu Lys Gln Ile Leu Glu Gln Leu Gly Ser
1               5                   10                  15
Ala Arg Leu Ser His Glu Val Glu Leu Ser Gln Leu Met Ala Pro Leu
            20                  25                  30
```

-continued

```
Ser Pro Glu Val Leu Phe Cys Phe Leu Phe Ile Lys Ser Gly Ser
        35                  40                  45

Ala Glu Gly Phe Gly Glu Pro Val Arg Phe Lys Asp Leu Pro Ser
 50                  55                  60

Ala Pro Asp Arg Phe Trp Lys Ala Met Ala Leu His Val Gly Ala Leu
 65                  70                  75                   80

Ser Gly Gln Phe Lys Pro Leu Pro Pro Ser Tyr Leu Lys Asp Ala Trp
                 85                  90                  95

Leu Arg Phe Val Lys Glu Arg Pro Gly Asp Glu Pro Leu Ser Leu Leu
                100                 105                 110

Glu Tyr Tyr Ser Leu Ala Ala Gln Leu Leu Ser Asp Thr Asp Arg Val
                115                 120                 125

Phe Ile Asn His Gly Tyr Ala Phe Leu Asn Pro Ala Glu Ala Pro Ser
            130                 135                 140

Leu Ala Ala Trp Glu Glu Pro Ser Arg Leu Ser Ile His Leu Tyr His
145                 150                 155                 160

Lys Leu Leu Gly Gly Gln Asp Phe Thr Gly Leu Asp Val Val Asp Met
                165                 170                 175

Ala Cys Gly Arg Gly Gly Ser Leu Tyr Leu Lys Gln Arg Lys Glu
            180                 185                 190

Ala Arg Leu Val Ala Gly Ile Asp Ala Val Arg Thr His Val Leu Leu
        195                 200                 205

Ala Arg Glu Ala His Pro Ser Val Asp Gly Val Tyr Phe Leu His Gly
        210                 215                 220

Arg Ala Glu Glu Ile Pro Leu Pro Thr Gly Ala Phe Asp Ala Leu Ile
225                 230                 235                 240

Ala Val Asp Ala Val Phe His Phe Pro Leu Arg Glu Phe Leu His Glu
                245                 250                 255

Ala His Arg Val Val Lys Pro Gly Gly Arg Cys Phe Leu Asn Ser Trp
            260                 265                 270

Gly Pro Pro Thr Trp Tyr Met Asp Leu Glu Gly Ala Val Glu Ser Cys
        275                 280                 285

Gly Trp Lys Leu Glu His Ala Glu Asp Ile Thr Thr Gly Val Leu Leu
    290                 295                 300

Ala Arg Glu Gln Trp Arg Thr His Asp Met Phe Thr Trp Val Arg Ser
305                 310                 315                 320

Arg Pro Arg Lys Cys Arg Pro Glu Ile Tyr Ile Glu Phe Asp Arg Met
                325                 330                 335

Val Met Leu Pro Val Glu Gly Arg Arg Tyr Tyr Asn Phe His Leu Thr
                340                 345                 350

Arg Leu Asp Gln Lys Ala Ser
        355
```

<210> SEQ ID NO 20
<211> LENGTH: 255
<212> TYPE: PRT
<213> ORGANISM: Sorangium cellulosum

<400> SEQUENCE: 20

```
Met Pro Lys Ile Leu Val Ile Asp Asp Gln Pro Ala Val Cys Val Ala
 1               5                  10                  15

Leu Thr Thr Leu Phe Glu Leu His Gly Leu Glu Val Arg Val Ala Ala
                20                  25                  30

Thr Pro Asp Ala Ala Ile Ala Ala Val Leu Asp Asp Glu Leu Gly Ala
            35                  40                  45
```

```
Val Val Gln Asp Met Asn Phe Arg Gln Ser Ala Thr Ser Gly Glu Glu
     50                  55                  60

Gly Met Glu Leu Leu Arg Arg Ile Lys Ser Ile Asp Pro Glu Leu Pro
 65                  70                  75                  80

Val Val Ala Met Thr Ala Phe Thr Ser Ile Ala Gly Ala Val Glu Leu
                 85                  90                  95

Ile Lys Ala Gly Ala Ser Asp Tyr Val Pro Lys Pro Trp Asp Asp Gln
                100                 105                 110

Lys Leu Val Ala Val Val Ser Asn Leu Ala Arg Leu Arg Ser Leu Glu
                115                 120                 125

Gln Glu Asn Ala Arg Leu Val Ala Gln Arg Gly Arg Ala Arg His Arg
                130                 135                 140

Leu Ala Glu Arg His Asp Leu Gly Gly Leu Val Tyr Ala Ser Asp Ala
145                 150                 155                 160

Met His Glu Val Val Ser Leu Ala Val Lys Val Ala Pro Ala Asp Val
                    165                 170                 175

Pro Val Leu Ile Thr Gly Pro Asn Gly Thr Gly Lys Glu Leu Leu Ala
                180                 185                 190

Gly Ile Val Gln Ala Asn Ser Arg Arg Arg Asp Arg Pro Phe Val Lys
                195                 200                 205

Val Asn Ala Gly Ala Leu Pro Asp Glu Leu Val Glu Ala Glu Leu Phe
210                 215                 220

Gly Ala Glu Ala Gly Ala Phe Thr Gly Ala Ala Arg Leu Arg Ile Gly
225                 230                 235                 240

Arg Phe Glu Glu Ala Asp Gly Gly Thr Leu Phe Leu Asp Glu Ile
                245                 250                 255

<210> SEQ ID NO 21
<211> LENGTH: 316
<212> TYPE: PRT
<213> ORGANISM: Sorangium cellulosum

<400> SEQUENCE: 21

Met Arg Leu Gln Ser Val Asp Thr His Leu Val Val Ala Leu His Ala
 1               5                  10                  15

Leu Leu Gln Glu Lys Ser Val Thr Arg Ala Ala Arg Arg Val Gly Val
                 20                  25                  30

Thr Gln Pro Ser Met Ser His Ala Leu Ala Arg Leu Arg Ala His Phe
                 35                  40                  45

Glu Asp Pro Leu Leu Ile Gln Val Gly Arg Gln Met Thr Leu Ser Glu
     50                  55                  60

Arg Ala Arg Asp Leu Ala Pro Arg Ala Glu Ala Val Glu Arg Leu
 65                  70                  75                  80

Glu His Val Phe Arg Pro Val Glu Arg Phe Asp Pro Arg Arg Ser Gln
                 85                  90                  95

Arg Thr Phe Arg Leu Val Ala Thr Asp Asn Leu Glu Leu Leu Val Leu
                100                 105                 110

Pro Ala Leu Thr Ala Leu Leu Ala Val Glu Ala Pro Arg Val Asn Leu
                115                 120                 125

Arg Cys Arg Asn Ile Pro Ala Asp Phe Ala Glu Leu Leu Arg Arg Gly
                130                 135                 140

Glu Leu Asp Gly Lys Leu Gly Arg Gly Gly Pro Val Pro Asp Gly Cys
145                 150                 155                 160

Arg Ser Thr Leu Leu Ala Ala Glu Glu Ile Val Cys Val Met Arg Arg
```

```
                    165                 170                 175
Gly His Pro Ala Ser Arg Gly Pro Leu Thr Ala Ala Arg Tyr Ala Ala
                180                 185                 190

Cys Glu His Leu Met Val Ser Pro His Gly Glu Asp His Gly Val Ile
            195                 200                 205

Asp Arg Ala Leu Ala Glu Gln Gly Leu Arg Arg Val Thr Leu Thr
        210                 215                 220

Val Ser His Phe Leu Val Ala Pro Phe Ile Val Ser Gly Ser Asp Leu
225                 230                 235                 240

Leu Leu Thr Val Ser Ala Arg Val Ala Ala Leu Ala Arg Arg Leu
                245                 250                 255

Asp Leu Val Val Arg Pro Cys Pro Phe Gln Leu Glu Gly Tyr Thr Leu
            260                 265                 270

Thr Leu Val Trp Pro Glu Arg Ser Glu His Asp Glu Gly His Arg Trp
        275                 280                 285

Leu Arg Asp Ala Ile Gln Arg Ala Val Ala Leu Asp Pro Gly Ser Pro
        290                 295                 300

Ala Pro Gly Ala Gly Pro Ala Arg Cys Asp Thr Ala
305                 310                 315

<210> SEQ ID NO 22
<211> LENGTH: 148
<212> TYPE: PRT
<213> ORGANISM: Sorangium cellulosum

<400> SEQUENCE: 22

Met Asp Arg Arg Ala Asp Cys Arg Phe Asp Ala Arg Ser Val Gly Ala
1               5                   10                  15

Tyr Leu Ser Ser Pro Asp Gly Thr Cys Arg Arg Ala Ala Arg Pro Cys
            20                  25                  30

Pro Pro Ala Glu Glu Ser Asn Pro Met Ile Ile Glu Tyr Ile Arg Tyr
        35                  40                  45

Thr Ile Pro Ala Glu Gln Glu Lys Glu Phe Leu Ala Ala Tyr Arg Asp
    50                  55                  60

Ala Ala Ala Glu Leu Arg Gly Ser Glu His Cys Leu Asp His Glu Ile
65                  70                  75                  80

Ser Arg Cys Val Glu Asp Pro Thr Ser Phe Val Val Arg Ile Cys Trp
                85                  90                  95

Asp Ser Leu Gln Gly His Leu Gln Gly Phe Arg Lys Ala Ala Ala Phe
            100                 105                 110

Pro Ser Phe Phe Ala Lys Val Lys Pro Phe Tyr Glu Arg Ile Gln Glu
        115                 120                 125

Met Arg His Tyr Ala Leu Thr Asp Val Ala Thr Arg Gln Ala Gly Lys
    130                 135                 140

Ala Ala Thr Gly
145

<210> SEQ ID NO 23
<211> LENGTH: 406
<212> TYPE: PRT
<213> ORGANISM: Sorangium cellulosum

<400> SEQUENCE: 23

Met Ala Val Pro Ser Gly Phe Asp Leu Thr Ser Glu Arg Phe Phe Ala
1               5                   10                  15

Asp Pro Phe Pro Thr Leu Glu Arg Leu Arg Thr Glu Ala Pro Val Tyr
```

-continued

```
                    20                  25                  30
Phe Phe Glu Pro Leu Gln Cys Phe Leu Ile Thr Ala Pro Ala Asp Ile
            35                  40                  45
Glu Gly Leu Val Lys Asp Ser Ser Phe Thr Ala Arg Arg Ala Thr Ala
 50                  55                  60
Leu Leu Gly Gly Leu Gly Met Leu Gly Glu Asp Glu Leu Ser Arg Lys
 65                  70                  75                  80
Thr Phe Asp Ser Leu Ser Arg Leu Ala Phe Phe Gln Asp Pro Pro Arg
                85                  90                  95
His Thr Gln Leu Arg Gln Leu Ile Met Lys Gly Phe Ser Pro Ser Ala
               100                 105                 110
Val Glu Trp Met Arg Pro Arg Val Gly Leu Val Gln Arg Ala Ile
           115                 120                 125
Glu Gly Ala Arg Arg Asp Gly Glu Met Asp Val Val Ser Ala Phe Ser
130                 135                 140
Glu Ala Val Ala Leu Asn Thr Leu Ala Glu Met Phe Val Ile Pro Glu
145                 150                 155                 160
Val Asp Arg Pro Gln Phe Leu Arg Trp Ser Thr Asp Leu Leu Lys Leu
               165                 170                 175
Ala Gly Gly Gly Val Ser Ser Glu Glu Gln Lys Arg Ala Val Lys Gln
           180                 185                 190
Ser Cys Cys Asp Met Leu Asp Tyr Met Met Arg Leu Val Glu Glu Arg
           195                 200                 205
Arg Lys Ala Pro Gly Glu Asp Val Ala Ser Arg Phe Ile Ala Ala Glu
210                 215                 220
Asp Gly Asp Thr Glu Leu Ala Gly Glu Ala Met Gln Cys Phe Gln
225                 230                 235                 240
Met Val Ala Ala Gly Phe Val Thr Ser Val Asn Gln Ile Ala Asn Thr
               245                 250                 255
Val Leu Ala Leu Leu Asn His Pro Ala Glu Leu Ala Lys Leu Arg Glu
           260                 265                 270
Ala Pro Gly Leu Val Arg Gly Ala Val Glu Glu Ser Leu Arg Phe Glu
       275                 280                 285
Pro Ser Val Leu Ser Leu Ser Arg Met Cys Lys Lys Asp Thr Glu Ile
290                 295                 300
Arg Gly Ala Arg Val Ser Glu Gly Gln Phe Val Phe Ala Met Ile Ala
305                 310                 315                 320
Ala Ala Asn Arg Asp Pro Gly Leu Phe Ser Pro Arg Phe Asp
               325                 330                 335
Ile Thr Arg Gln Gln Ser Arg His Leu Thr Phe Gly Ser Gly Ala His
               340                 345                 350
Tyr Cys Pro Gly Ala Pro Leu Ile Arg Met Glu Val Glu Glu Ser Leu
           355                 360                 365
Arg Ala Leu Leu Ser Leu Pro Arg Trp Glu Leu Ala Glu Glu Thr Leu
       370                 375                 380
Ser Tyr Ala Gly Ser Asn Leu Gln Asp Arg Gly Pro Ser Ser Leu Arg
385                 390                 395                 400
Val Arg Phe Pro Ala Ala
               405

<210> SEQ ID NO 24
<211> LENGTH: 259
<212> TYPE: PRT
<213> ORGANISM: Sorangium cellulosum
```

```
<400> SEQUENCE: 24

Met Lys Leu Ala Arg Lys Leu Thr Leu Ala Leu Val Phe Gly Val Phe
1               5                   10                  15

Leu Val Leu Ala Leu Ser Ala Tyr Ala Gln Ile Arg Arg Asp Ala Met
            20                  25                  30

Val Phe Glu Asn Asp Val Gln Arg Asp His His Thr Met Gly Arg Ala
        35                  40                  45

Leu Ala Ala Val Met Glu Val Trp Arg Ser Glu Gly Ala Ala Arg
50                  55                  60

Ala Leu Arg Leu Val Glu Asp Ala Asn Glu Arg Glu Gln Gln Val Asn
65                  70                  75                  80

Ile Arg Trp Val Trp Leu Asp Gly Gln Ala Asp Glu Pro His Arg Pro
                85                  90                  95

Arg Leu Ala Pro Glu Leu Leu Val Pro Val Ile Arg Gly Thr Phe Thr
            100                 105                 110

Met Leu Lys Pro Leu Ala Asp Lys Gln Gly Val Thr Ile Val Glu Glu
        115                 120                 125

Gly Asp Thr Pro Asp Arg Leu Val His Ala Asp Ala Gln Leu Gln
    130                 135                 140

Gln Ala Leu Thr Asn Val Val Val Asn Ala Ile Gln Ala Met Pro Ser
145                 150                 155                 160

Gly Gly Thr Ile Ala Val Arg Val Gln Ala Val Arg Ala Ile Pro Pro
                165                 170                 175

Ala Asp Gln Gly Gly Ala Glu Gly Asp Tyr Ile Ala Leu Ser Val Arg
            180                 185                 190

Asp Glu Gly Gln Gly Met Met Ala Gly Val Leu Glu His Val Phe Glu
        195                 200                 205

Pro Phe Phe Thr Thr Lys Pro Val Gly Glu Gly Thr Gly Leu Gly Leu
    210                 215                 220

Ser Val Ala Tyr Gly Ile Ile Lys Glu His Gly Gly Trp Ile Asp Val
225                 230                 235                 240

Asp Ser Arg Ala Gly Ser Gly Ser Gln Phe Thr Met Tyr Leu Pro Gln
                245                 250                 255

Glu Lys Pro

<210> SEQ ID NO 25
<211> LENGTH: 461
<212> TYPE: PRT
<213> ORGANISM: Sorangium cellulosum

<400> SEQUENCE: 25

Met Ser Gly Arg Val Leu Ile Val Asp Asp Glu Arg Gly Val Cys Glu
1               5                   10                  15

Leu Leu Asp Ala Gly Leu Lys Lys Arg Gly Phe Gln Ala Ala Trp Arg
            20                  25                  30

Thr Ser Ala Ala Glu Ala Leu Glu Leu Leu Gly Ala Glu Asp Phe Asp
        35                  40                  45

Val Val Val Thr Asp Met Thr Met Arg Gly Met Ser Gly Leu Glu Leu
    50                  55                  60

Cys Glu Arg Ile Ala Gln Asn Arg Pro Asp Leu Pro Val Ile Val Ile
65                  70                  75                  80

Thr Ala Phe Gly Ser Leu Asp Thr Ala Thr Ser Ala Ile Arg Ala Gly
                85                  90                  95
```

```
Ala Tyr Asp Phe Val Thr Lys Pro Phe Glu Leu Asp Ala Leu Arg Leu
            100                 105                 110

Thr Val Glu Arg Ala Leu Arg His Arg Ala Leu Arg Glu Glu Val Arg
        115                 120                 125

Arg Leu Arg Arg Ala Val Asp Asp Ser His Arg Tyr Glu Gln Ile Leu
    130                 135                 140

Gly Gly Ser Pro Ala Met Lys Gly Val Phe Asp Leu Leu Asp Arg Val
145                 150                 155                 160

Ala Asp Ser Asp Thr Ser Ile Leu Ile Thr Gly Glu Ser Gly Thr Gly
                165                 170                 175

Lys Glu Leu Val Ala Arg Ala Val His Gln Arg Ser Arg Arg Gly Gln
            180                 185                 190

Gly Ala Phe Val Ala Val Asn Cys Ala Ala Val Pro Asp Ala Leu Leu
        195                 200                 205

Glu Ser Glu Leu Phe Gly His Ala Arg Gly Ala Phe Thr Asp Ala Lys
    210                 215                 220

Gly Pro Arg Ser Gly Leu Phe Ala Arg Ala His Gly Gly Thr Leu Phe
225                 230                 235                 240

Leu Asp Glu Ile Gly Glu Leu Pro Val Gly Leu Gln Pro Lys Leu Leu
                245                 250                 255

Arg Ala Leu Gln Glu Arg Val Val Arg Pro Val Gly Ala Asp Glu Glu
            260                 265                 270

Val Pro Val Asp Val Arg Leu Ile Ala Ala Thr Asn Arg Asp Leu Glu
        275                 280                 285

Thr Ala Ile Glu Glu Arg Arg Phe Arg Glu Asp Leu Tyr Tyr Arg Ile
    290                 295                 300

Asn Val Val His Val Asp Leu Pro Pro Leu Arg Ser Arg Gly Ala Asp
305                 310                 315                 320

Val Leu Leu Leu Ala Gln Arg Phe Leu Glu His Phe Ala Thr Val Lys
                325                 330                 335

Glu Arg Pro Ile Lys Gly Leu Ser Ala Pro Ala Ala Glu Lys Leu Val
            340                 345                 350

Ala Tyr Ala Trp Pro Gly Asn Val Arg Glu Leu Gln Asn Cys Val Glu
        355                 360                 365

Arg Ala Val Ala Leu Ala Arg Tyr Asp Gln Ile Thr Val Asp Asp Leu
    370                 375                 380

Pro Glu Lys Ile Arg Ser Tyr Arg Ser Ser His Val Leu Val Ser Ser
385                 390                 395                 400

Asp Asp Pro Thr Glu Leu Val Pro Met Glu Glu Val Glu Arg Arg Tyr
                405                 410                 415

Ile Leu Arg Val Leu Glu Val Val Gly Gly Asn Lys Ser Gln Ala Ala
            420                 425                 430

Gln Ile Leu Gly Phe Asp Arg Ala Thr Leu Tyr Arg Lys Leu Glu Arg
        435                 440                 445

Tyr Gly Leu Arg Ala Gly Arg Ala Ser Asp Pro Lys Pro
    450                 455                 460

<210> SEQ ID NO 26
<211> LENGTH: 508
<212> TYPE: PRT
<213> ORGANISM: Sorangium cellulosum

<400> SEQUENCE: 26

Met Gly Arg Pro Thr Pro Arg Gly Leu Ser Trp Leu Arg Phe Pro Arg
1               5                   10                  15
```

-continued

```
Pro Val Arg Leu Ser Ala Leu Leu Gly Ala Ala Thr Leu Leu Thr
         20                  25                  30

Ser Val Ala Ile Val Val Ala Ser Ala Leu Met Val Ala Ser Thr Thr
             35                  40                  45

Met Gln Gln Ala Thr Arg Ile Leu Gly Ala Thr Val Glu Ser Val Arg
 50                  55                  60

Leu Val Glu Arg Leu Glu Ile Asp Leu Leu Asp Ala Gln Gln Ser
 65                  70                  75                  80

Gly Arg Ala Val Gly Ser Asp Arg Gly Glu Leu Ala Pro Ser Leu Ala
                 85                  90                  95

Ala Trp Glu Arg Gly Leu Arg Ser Gly Leu Ala Ala Arg Gly His
             100                 105                 110

Val Ser Ser Pro Glu Gly Glu Ile Leu Glu His Ala Glu Arg Arg
             115                 120                 125

Val Glu Asp Tyr Leu Ala Arg Arg Ala Ala Asp Ala Arg Glu Leu
 130                 135                 140

Pro Ser Ala Pro Gly Ala Arg Asp Pro Ala Leu Leu Gly Val His Asp
145                 150                 155                 160

Pro Ala Leu Asp Glu Ala Phe Arg Ala Leu Asp Arg Leu Val Glu Ile
                 165                 170                 175

Asn Leu Glu Gln Ala Arg Ala Ser Glu Ala Leu Val Ala Tyr Leu Thr
             180                 185                 190

Arg Arg Thr Thr Gly Ala Gly Val Ala Ala Val Phe Phe Leu Ala
             195                 200                 205

Gly Ala Ser Thr Val Leu Leu Ser Ala Arg Arg Leu Ile Tyr Arg Pro
210                 215                 220

Ile Val Ala Ile Gln Gln Ala Ile Gly Arg Tyr Gly Ala Gly Asp Arg
225                 230                 235                 240

Ala Ala Arg Ala Pro Leu Ile Gly Pro Arg Glu Leu Gly Glu Ile Ala
                 245                 250                 255

Arg Ala Phe Asn Asp Met Ala Glu Ser Leu Glu Arg Gln Arg Glu Ala
             260                 265                 270

Gln Phe Ala Phe Leu Gly Gly Val Ala His Asp Leu Arg Asn Pro Leu
         275                 280                 285

Ser Ala Leu Arg Met Ser Val His Val Leu Asp Leu Asp Ser Leu Pro
     290                 295                 300

Pro Ala Ser Ser Val Arg Arg Thr Met Ala Leu Val Gly Arg Gln Val
305                 310                 315                 320

Asp Arg Leu Glu Arg Met Val Gly Asp Leu Leu Asp Ala Ser Gln Ile
                 325                 330                 335

Glu Ala Cys Lys Leu Glu Leu Arg Val Glu Arg Asp Leu Arg Asp
             340                 345                 350

Leu Ala Gln Glu Ala Val Asp Leu Tyr Arg Pro Val Ser Pro Glu His
         355                 360                 365

Pro Ile Glu Leu Ser Leu Pro Glu Thr Pro Val Leu Val Pro Cys Asp
     370                 375                 380

Ala Thr Arg Ile Ala Gln Val Leu Asn Asn Leu Leu Ser Asn Ala Leu
385                 390                 395                 400

Lys Tyr Ser Pro Ala Gly Gly Gln Ile Asp Val Ala Val Arg Ala Gly
                 405                 410                 415

Gly Asp Gly Ala Glu Ile Ala Ile Arg Asp Arg Gly Leu Gly Ile Glu
             420                 425                 430
```

```
Pro Ala Glu Leu Ala His Leu Phe Glu Pro Phe Arg Arg Leu Lys Ser
        435                 440                 445

Ser Ser Gly Ser Ile Pro Gly Thr Gly Leu Gly Leu Thr Val Ala Lys
    450                 455                 460

Arg Ile Val Glu Ala His Gly Arg Leu Leu Val Glu Ser Arg Pro
465                 470                 475                 480

Gly Ala Gly Ser Val Phe Arg Ile Asp Leu Pro Arg Ser Pro Ser Arg
                485                 490                 495

Glu Gln Ala Asp Gly Pro Arg Gly Val Ser His Gly
            500                 505

<210> SEQ ID NO 27
<211> LENGTH: 477
<212> TYPE: PRT
<213> ORGANISM: Sorangium cellulosum

<400> SEQUENCE: 27

Met Gln Arg Arg Leu Asp Gly Glu Ile Glu Leu Gln Arg Asp Arg Ala
1               5                   10                  15

His Arg Asp Ser Glu Arg Tyr Ala Arg Arg Pro Arg Gly Ala Pro Arg
            20                  25                  30

Ala Pro Ala Pro Ala Ser Pro Ala Pro Arg Ala Pro Val Ser Ser Val
        35                  40                  45

Leu Trp Thr Val Ile Pro Val Ser Ser Thr Leu Arg Ala Met Pro Ala
    50                  55                  60

Arg Thr Pro Arg Lys Pro Pro Pro Ala Ser Pro Ala Gly Pro Ala
65                  70                  75                  80

Gly Ala Pro Asp Asp Leu Ser Asp Ser Asp Arg Asp Ala Leu Leu Arg
                85                  90                  95

Trp Arg Leu Ala Leu Gly Pro Glu Ala Glu Arg Val Asp Pro Arg Leu
            100                 105                 110

Ser Leu Gly Gly Leu Gly Gly Ala Pro Ala Leu Asp Val Asp Pro
        115                 120                 125

Arg Arg Leu Gly Asp Leu Asp Lys Ala Leu Ser Phe Ile Tyr Asp Glu
    130                 135                 140

Arg Ala Gly Asn Leu Gly Gly Ser Arg Pro Tyr Val Pro Glu Trp Leu
145                 150                 155                 160

Ser Ala Val Arg Glu Phe Phe Ser His Glu Val Val Ala Leu Val Gln
                165                 170                 175

Lys Asp Ala Ile Glu Arg Lys Gly Leu Thr Gln Leu Leu Phe Glu Pro
            180                 185                 190

Glu Thr Leu Pro Phe Leu Glu Lys Asn Val Glu Leu Val Ala Thr Leu
        195                 200                 205

Met Ser Ala Lys Gly Leu Ile Pro Asp Ala Ala Arg Glu Thr Ala Arg
    210                 215                 220

Gln Ile Val Arg Glu Val Val Glu Val Arg Arg Ala Leu Glu Ser
225                 230                 235                 240

Glu Val Arg Thr Ala Val Leu Gly Ala Leu Arg Arg Asn Thr Thr Ser
                245                 250                 255

Pro Leu Arg Val Leu Arg Asn Leu Asp Trp Lys Arg Thr Ile Arg Lys
            260                 265                 270

Asn Leu Lys Gly Trp Asp Ala Glu Arg Arg Leu Val Pro Asp Lys
        275                 280                 285

Leu Tyr Phe Trp Ala Asn Gln Thr Arg Arg His Glu Trp Asp Val Ala
    290                 295                 300
```

```
Ile Leu Val Asp Gln Ser Gly Ser Met Gly Glu Ser Val Val Tyr Ser
305                 310                 315                 320

Ser Ile Met Ala Ala Ile Phe Ala Ser Leu Asp Val Leu Arg Thr Arg
                325                 330                 335

Leu Leu Phe Phe Asp Thr Glu Val Val Asp Val Thr Pro Met Leu Val
            340                 345                 350

Asp Pro Val Asp Val Leu Phe Thr Ala Gln Leu Gly Gly Gly Thr Asp
                355                 360                 365

Ile Asn Arg Ala Val Ala Tyr Ala Gln Ala Asn Phe Ile Glu Arg Pro
        370                 375                 380

Glu Lys Thr Leu Leu Ile Leu Ile Thr Asp Leu Phe Glu Gly Gly Asn
385                 390                 395                 400

Ala Glu Glu Leu Val Ala Arg Met Arg Gln Leu Ala Asp Ser Lys Val
                405                 410                 415

Lys Ser Ile Cys Leu Leu Ala Leu Ser Asp Gly Gly Lys Pro Ser Tyr
            420                 425                 430

Asp His Glu Met Ala Gln Lys Leu Ala Ala Leu Gly Thr Pro Cys Phe
        435                 440                 445

Gly Cys Thr Pro Lys Leu Leu Val Lys Val Val Glu Arg Leu Met Arg
    450                 455                 460

Gly Gln Asp Leu Gly Pro Leu Gly Ala Glu Ala Arg
465                 470                 475

<210> SEQ ID NO 28
<211> LENGTH: 2087
<212> TYPE: PRT
<213> ORGANISM: Sorangium cellulosum

<400> SEQUENCE: 28

Met Ala Pro Pro Trp Arg Gly Ser Asn Met Glu Gln Arg Thr Ser Gly
1               5                   10                  15

Lys Ile Ala Ser Pro Arg Ser Arg Thr Ala Ser Ser Lys Asp Gly Ala
            20                  25                  30

Ala Lys Gly Thr Asn Gly Lys Asp Gly Lys His Pro Arg Asn Gly Lys
        35                  40                  45

Asn Ala Ala Ala Lys Arg Ala Glu Gly Ala Ala Arg Thr Ser Gln Ala
    50                  55                  60

Thr Ala Leu Gln Gln Arg Ser Gln Pro Val His Leu Glu Asp Leu Pro
65                  70                  75                  80

Arg Pro Arg Arg Arg Ala Ala Gln Asp Asp Val Met Arg Arg Pro Ala
                85                  90                  95

Arg Gln Ala Leu Glu Met Gly Gln Met Leu Ala Val Leu Val Ala Leu
            100                 105                 110

Lys Lys Gly Asp Phe Ser Val Arg Leu Pro Ile Asp Leu Glu Gly Leu
        115                 120                 125

Asp Gly Lys Ile Ala Asp Thr Phe Asn Asp Val Val Glu Met Asn Glu
    130                 135                 140

Lys Phe Ala Phe Glu Leu Gly Arg Leu Ser Arg Ala Val Gly Lys Glu
145                 150                 155                 160

Gly Lys Ile Gly Gln Arg Val Ser Met Gly Glu Val Ser Gly Ala Trp
                165                 170                 175

Ala Asp Glu Val Ala Ser Val Asn Ala Leu Ile Gly Asp Leu Val Gln
            180                 185                 190

Pro Thr Arg Glu Met Ala Arg Val Ile Gly Ala Val Ala Lys Gly Asp
```

-continued

```
                195                 200                 205
Leu Ser Gln Thr Met Ala Leu Glu Val Gly Gly Arg Pro Leu Glu Gly
    210                 215                 220
Glu Phe Leu Gln Thr Ala Gln Thr Val Asn Thr Val Tyr Gln Leu
225                 230                 235                 240
Gly Ser Phe Ala Ser Glu Val Thr Arg Val Ala Arg Glu Val Gly Thr
                245                 250                 255
Glu Gly Lys Leu Gly Gly Gln Ala Glu Val Lys Gly Val Ala Gly Thr
                260                 265                 270
Trp Lys Asp Leu Thr Asp Ser Val Asn Ser Met Ala Gly Asn Leu Thr
            275                 280                 285
Ala Gln Val Arg Asn Ile Ala Ala Val Thr Thr Ala Val Ala Asn Gly
        290                 295                 300
Asp Leu Thr Gln Lys Ile Thr Val Asp Val Arg Gly Glu Ile Leu Glu
305                 310                 315                 320
Leu Lys Asp Thr Phe Asn Thr Met Val Asp Gln Leu Arg Ser Phe Ala
                325                 330                 335
Ser Glu Val Thr Arg Val Ala Arg Glu Val Gly Thr Glu Gly Lys Leu
                340                 345                 350
Gly Gly Gln Ala Ser Val Pro Gly Val Ala Gly Thr Trp Lys Asp Leu
            355                 360                 365
Thr Asp Ser Val Asn Ser Met Ala Ser Asn Leu Thr Ala Gln Val Arg
        370                 375                 380
Asn Ile Ala Ala Val Thr Thr Ala Val Ala Asn Gly Asp Leu Thr Gln
385                 390                 395                 400
Lys Ile Thr Val Asp Val Lys Gly Glu Ile Leu Glu Leu Lys Asp Thr
                405                 410                 415
Phe Asn Thr Met Val Asp Gln Leu Arg Ser Phe Ala Ser Glu Val Thr
                420                 425                 430
Arg Val Ala Arg Glu Val Gly Thr Glu Gly Lys Leu Gly Gly Gln Ala
            435                 440                 445
Glu Val Lys Gly Val Ala Gly Thr Trp Lys Asp Leu Thr Asp Ser Val
        450                 455                 460
Asn Ser Met Ala Ser Asn Leu Thr Ala Gln Val Arg Asn Ile Ala Ala
465                 470                 475                 480
Val Thr Thr Ala Val Ala Arg Gly Asp Leu Thr Gln Lys Ile Thr Val
                485                 490                 495
Asp Val Arg Gly Glu Ile Leu Glu Leu Lys Asp Thr Phe Asn Thr Met
            500                 505                 510
Val Asp Gln Leu Arg Ser Phe Ala Ser Glu Val Thr Arg Val Ala Arg
        515                 520                 525
Glu Val Gly Thr Glu Gly Lys Leu Gly Gly Gln Ala Glu Val Lys Gly
    530                 535                 540
Val Ala Gly Thr Trp Lys Asp Leu Thr Asp Ser Val Asn Ser Met Ala
545                 550                 555                 560
Ser Asn Leu Thr Val Gln Leu Arg Asp Val Ser Lys Val Ala Thr Ala
                565                 570                 575
Ile Ala Asn Gly Asp Leu Thr Gln Lys Ile Thr Val Asp Val Arg Gly
            580                 585                 590
Glu Ile Leu Gln Ile Lys Asp Val Ile Asn Thr Thr Val Asp Gln Leu
        595                 600                 605
Ser Ser Phe Ala Ala Glu Val Thr Arg Val Ala Arg Asp Val Gly Thr
    610                 615                 620
```

-continued

```
Glu Gly Lys Leu Gly Gly Gln Ala Glu Val Lys Gly Val Ala Gly Thr
625                 630                 635                 640

Trp Lys Asp Leu Thr Asp Ser Val Asn Ser Met Ala Ser Asn Leu Thr
            645                 650                 655

Ala Gln Val Arg Asn Ile Ala Ala Val Thr Thr Ala Val Ala Arg Gly
                660                 665                 670

Asp Leu Thr Gln Lys Ile Thr Val Asp Val Arg Gly Glu Ile Leu Glu
            675                 680                 685

Leu Lys Asn Thr Phe Asn Thr Met Val Asp Gln Leu Arg Ser Phe Ala
690                 695                 700

Ala Gln Val Thr Arg Val Ala Arg Glu Val Gly Thr Glu Gly Lys Leu
705                 710                 715                 720

Gly Gly Gln Ala Glu Val Thr Gly Val Ala Gly Thr Trp Lys Asp Leu
                725                 730                 735

Thr Asp Ser Val Asn Ser Met Ala Ser Asn Leu Thr Ala Gln Val Arg
            740                 745                 750

Asn Ile Ala Asp Val Thr Thr Ala Val Ala Asn Gly Asp Leu Ser Lys
            755                 760                 765

Lys Ile Thr Val Asp Val Arg Gly Glu Ile Leu Glu Leu Lys Asp Thr
770                 775                 780

Phe Asn Thr Met Val Asp Gln Leu Arg Ser Phe Ala Ser Glu Val Thr
785                 790                 795                 800

Arg Val Ala Arg Glu Val Gly Thr Glu Gly Lys Leu Gly Gly Gln Ala
                805                 810                 815

Ser Val Pro Gly Val Ala Gly Thr Trp Lys Asp Leu Thr Asp Ser Val
            820                 825                 830

Asn Ser Met Ala Ser Asn Leu Thr Ala Gln Val Arg Asn Ile Ala Asp
            835                 840                 845

Val Thr Thr Ala Val Ala Arg Gly Asp Leu Ser Lys Lys Ile Thr Val
850                 855                 860

Asp Val Lys Gly Glu Ile Leu Glu Leu Lys Asn Thr Phe Asn Thr Met
865                 870                 875                 880

Val Asp Gln Leu Ser Ser Phe Ala Ala Glu Val Thr Arg Val Ala Arg
                885                 890                 895

Glu Val Gly Thr Glu Gly Lys Leu Gly Gly Gln Ala Glu Val Thr Gly
            900                 905                 910

Val Ala Gly Thr Trp Lys Asp Leu Thr Asp Ser Val Asn Ser Met Ala
            915                 920                 925

Ser Asn Leu Thr Ala Gln Val Arg Asn Ile Ala Ala Val Thr Thr Ala
930                 935                 940

Val Ala Asn Gly Asp Leu Ser Lys Lys Ile Thr Val Asp Val Arg Gly
945                 950                 955                 960

Glu Ile Leu Glu Leu Lys Asn Thr Ile Asn Thr Met Val Asp Gln
                965                 970                 975

Leu Asn Ala Phe Ala Ser Glu Val Thr Arg Val Ala Arg Glu Val Gly
            980                 985                 990

Thr Glu Gly Lys Leu Gly Gly Gln Ala Ser Val Pro Gly Val Ala Gly
            995                 1000                1005

Thr Trp Lys Asp Leu Thr Asp Asn Val Asn Phe Met Ala Gly Asn
        1010                1015                1020

Leu Thr Asn Gln Val Arg Gly Ile Ala Lys Val Val Thr Ala Val
        1025                1030                1035
```

```
Ala Asn Gly Asp Leu Lys Arg Lys Leu Ala Phe Asp Ala Lys Gly
1040                1045                1050

Glu Ile Ala Ala Leu Ala Asp Thr Ile Asn Gly Val Ile Glu Thr
1055                1060                1065

Leu Ala Thr Phe Ala Asp Gln Val Thr Thr Val Ala Arg Glu Val
1070                1075                1080

Gly Val Glu Gly Lys Leu Gly Gly Gln Ala Ser Val Pro Gly Ala
1085                1090                1095

Ala Gly Thr Trp Lys Asp Leu Thr Asp Asn Val Asn Gln Leu Ala
1100                1105                1110

Ala Asn Leu Thr Thr Gln Val Arg Ala Ile Ala Glu Val Ala Thr
1115                1120                1125

Ala Val Thr Lys Gly Asp Leu Thr Arg Thr Ile Arg Val Glu Ala
1130                1135                1140

Gln Gly Glu Val Ala Ser Leu Lys Asp Thr Ile Asn Glu Met Ile
1145                1150                1155

Arg Asn Leu Lys Asp Thr Thr Leu Lys Asn Ser Glu Gln Asp Trp
1160                1165                1170

Leu Lys Thr Asn Leu Ala Lys Phe Ser Arg Leu Leu Gln Gly Gln
1175                1180                1185

Lys Asp Leu Leu Thr Val Gly Arg Leu Ile Leu Ser Glu Leu Ala
1190                1195                1200

Pro Val Val Gly Ala Gln Gln Gly Val Phe Phe Thr Met Asp Val
1205                1210                1215

Ala Lys Glu Glu Pro Ile Leu Lys Leu Leu Ala Ser Tyr Ala Tyr
1220                1225                1230

Lys Val Arg Lys His Val Asp Asn His Phe Lys Leu Gly Glu Gly
1235                1240                1245

Leu Val Gly Gln Cys Ala Leu Glu Lys Glu Lys Ile Leu Leu Val
1250                1255                1260

Asn Ala Pro Pro Asp Tyr Ile Arg Ile Thr Ser Gly Leu Gly Glu
1265                1270                1275

Ala Pro Pro Val Asn Ile Ile Val Ile Pro Val Leu Phe Glu Gly
1280                1285                1290

Gln Val Lys Ala Val Ile Glu Leu Ala Ser Phe Glu Arg Phe Ser
1295                1300                1305

Pro Thr His Gln Ala Phe Leu Asp Gln Leu Thr Glu Ser Ile Gly
1310                1315                1320

Ile Val Leu Asn Thr Ile Glu Ala Asn Met Arg Thr Glu Asp Leu
1325                1330                1335

Leu Lys Gln Ser Gln Ser Leu Ala Arg Glu Leu Gln Ser Gln Gln
1340                1345                1350

Glu Glu Leu Gln Gln Thr Asn Ala Glu Leu Gly Glu Lys Ala Arg
1355                1360                1365

Leu Leu Ala Gln Gln Asn Val Glu Val Glu Arg Lys Asn Arg Glu
1370                1375                1380

Val Glu Gln Ala Arg Gln Ala Leu Glu Glu Lys Ala Arg Gln Leu
1385                1390                1395

Ala Ile Thr Ser Lys Tyr Lys Ser Glu Phe Leu Ala Asn Met Ser
1400                1405                1410

His Glu Leu Arg Thr Pro Leu Asn Ser Leu Leu Ile Leu Ser Asp
1415                1420                1425

Gln Leu Ser Lys Asn Asn Asp Arg Asn Leu Thr Gly Arg Gln Val
```

```
            1430              1435              1440
Glu Phe Ala Lys Thr Ile His Ser Ser Gly Asn Asp Leu Leu Ala
    1445              1450              1455

Leu Ile Asn Asp Ile Leu Asp Leu Ser Lys Ile Glu Ser Gly Thr
    1460              1465              1470

Val Ile Val Asp Val Gly Glu Leu Ser Phe Ser Asp Leu Gln Asp
    1475              1480              1485

Tyr Val Glu Arg Thr Phe Arg His Val Ala Glu Ser Lys Lys Leu
    1490              1495              1500

Glu Phe Glu Leu Asn Phe Ala Gln Asn Leu Pro Gln Val Ile Tyr
    1505              1510              1515

Thr Asp Ala Lys Arg Val Gln Gln Val Leu Lys Asn Leu Leu Ser
    1520              1525              1530

Asn Ser Phe Lys Phe Thr Glu Arg Gly Ser Val Ala Leu Asp Val
    1535              1540              1545

Asp Leu Val Thr Ser Gly Trp Ala Pro Glu Asn Glu Gly Leu Ser
    1550              1555              1560

Arg Ala Gly Ala Ala Ile Ala Met Ser Val Arg Asp Thr Gly Ile
    1565              1570              1575

Gly Ile Pro His Asp Lys Gln Gln Ile Ile Phe Glu Ala Phe Gln
    1580              1585              1590

Gln Ala Asp Gly Ser Thr Ser Arg Lys Tyr Gly Gly Thr Gly Leu
    1595              1600              1605

Gly Leu Ala Ile Ser Arg Glu Ile Ala Trp Met Leu Gly Gly Glu
    1610              1615              1620

Ile Lys Leu Ser Ser Lys Pro Gly Ser Gly Ser Ser Phe Thr Leu
    1625              1630              1635

Tyr Leu Pro Leu Thr Tyr Thr Pro Ala Arg Pro Arg Arg Lys Glu
    1640              1645              1650

Gln Thr Val Glu Val Pro Ser Ala Pro Pro Ala Val Val Ser Gly
    1655              1660              1665

Asp Val Pro Pro Arg Ser Ala Ala Glu Pro Pro His Leu Leu
    1670              1675              1680

Asn Gln Ser Val Asp Asp Ser Ala Gly Leu Lys Pro Ser Asp Ser
    1685              1690              1695

Val Val Leu Ile Val Glu Asn Asp Ala Ser Phe Ala His Phe Val
    1700              1705              1710

Met Asp Val Ala His Asp His Gly Phe Lys Ala Ile Leu Ala Tyr
    1715              1720              1725

Arg Gly Gly Ala Ala Leu Ser Ile Val Arg Glu Arg Arg Val Asn
    1730              1735              1740

Ala Ile Thr Leu Asp Ile Asn Leu Pro Asp Met Asp Gly Trp Arg
    1745              1750              1755

Val Leu Asp Arg Val Lys Arg Asp Leu Glu Thr Arg His Ile Pro
    1760              1765              1770

Val Gln Val Ile Thr Thr Asp Glu Glu Arg Glu Arg Ala Leu Arg
    1775              1780              1785

Met Gly Ala Lys Gly Val Leu Cys Lys Pro Leu Lys Thr Arg Asp
    1790              1795              1800

Ala Leu Asp Glu Thr Phe Arg Arg Leu Ser Gln Phe Met Val Ser
    1805              1810              1815

Ser Arg Arg Lys Ile Val Leu Ala Gly Pro Asp Asp Ala Glu Arg
    1820              1825              1830
```

```
Gln Glu Leu Val Glu Leu Leu Gly Gly Asp Asp Val Thr Ile Arg
    1835                1840                1845

Ser Val Ala Ser Gly Glu Glu Ala Leu Asp Ala Leu Val Thr Glu
    1850                1855                1860

Arg Pro Asp Val Leu Ile Leu Arg Leu Asp Leu Pro Asp Val Arg
    1865                1870                1875

Cys Phe Asp Leu Ile Gly Gln Leu Ala Gln Gly Ser Gly Ser Thr
    1880                1885                1890

Asp Leu Pro Val Leu Val Tyr Ala Pro Glu Glu Ile Ser Pro Ala
    1895                1900                1905

Asp Glu Ala Gln Leu Ser Arg Phe Ser Gln Leu Met Val Leu Lys
    1910                1915                1920

His Val Arg Ser Lys Glu Arg Leu Phe Asp Asp Val Ser Leu Phe
    1925                1930                1935

Leu His Arg Pro Val Ala Ala Leu Ser Glu Arg Gln Leu Gln Ile
    1940                1945                1950

Val Glu Glu Leu His Gln Ser Asn Lys Val Leu Val Gly Lys Lys
    1955                1960                1965

Val Leu Val Val Asp Asp Asp Val Arg Asn Ile Phe Ala Met Thr
    1970                1975                1980

Thr Ile Leu Asp Ala Gln His Met Lys Thr Val Tyr Val Glu Thr
    1985                1990                1995

Gly Arg Ala Ala Ile Glu Met Leu Gln Arg Thr Pro Asp Ile Glu
    2000                2005                2010

Met Val Leu Met Asp Ile Met Met Pro Glu Met Asp Gly Tyr Asp
    2015                2020                2025

Thr Ile Arg Ala Ile Arg Ala Arg Pro Glu His His Ala Leu Pro
    2030                2035                2040

Ile Ile Ala Val Thr Ala Lys Ala Met Lys Gly Asp Arg Glu Lys
    2045                2050                2055

Cys Phe Glu Ala Gly Ala Asn Asp Tyr Ile Ser Lys Pro Val Asp
    2060                2065                2070

Pro Glu His Leu Leu Ala Met Leu Arg Leu Trp Leu His Arg
    2075                2080                2085

<210> SEQ ID NO 29
<211> LENGTH: 235
<212> TYPE: PRT
<213> ORGANISM: Sorangium cellulosum

<400> SEQUENCE: 29

Met Gly Thr Leu Pro Ser Pro Ala Arg Gln Arg Val Ile Gly Ala Ile
1               5                   10                  15

Thr Arg Arg Phe Gly Ser Asp Arg Gly Pro Ser Leu Lys Gly Leu Asn
                20                  25                  30

Ser Arg Ser Ala Ala Val Val Thr Ile Asp Ala Pro Cys Lys Glu Asp
        35                  40                  45

Val Thr Ser Glu Arg Glu Ala Ala Ser Val Lys Glu Ala Ser Trp Thr
    50                  55                  60

Arg Ala Thr Ser Cys Gln Gly Thr Ser Phe Leu Val Val Lys Gly Ser
65                  70                  75                  80

Ser Cys Pro Gly Arg Gly Met Lys His Ser Cys Gln His Leu Cys Asp
                85                  90                  95

Gly Phe Gln Ala Ala Met Asp Val Leu Ala Lys Pro Trp Asn Gly Leu
```

-continued

```
                    100                 105                 110
Ile Ile Ala Thr Leu Asp Glu Gly Pro Leu Arg Phe Gly Glu Ile Gly
            115                 120                 125

Glu Arg Leu Asp Ala Ile Ser Asp Arg Met Leu Ser Ser Arg Leu Lys
    130                 135                 140

Glu Leu Glu Ala Leu Gly Leu Val Val Arg Val Leu Pro Gly Pro
145                 150                 155                 160

Pro Val Arg Val Glu Tyr Glu Leu Thr Asp Ser Gly Arg Gly Phe Gln
                165                 170                 175

Ala Val Ala Gln Ala Ile Ser Arg Trp Gly Glu Met Leu Ala Glu Ser
            180                 185                 190

Ala Pro Arg Ala Gly Thr Gly Ala Ser Ser Ser Gly Ala Arg Gly
        195                 200                 205

Arg Val Lys Ala Lys Ala Gly Arg Ala Ala Pro Arg Thr Arg Ser Arg
    210                 215                 220

Asn Ala Ala Arg Val Arg Gly Glu Gly Thr Ala
225                 230                 235

<210> SEQ ID NO 30
<211> LENGTH: 372
<212> TYPE: PRT
<213> ORGANISM: Sorangium cellulosum

<400> SEQUENCE: 30

Met Thr Thr Ala Ala Asp Leu Leu Phe Ser Pro Phe Lys Leu Gly Pro
1               5                   10                  15

Leu Ser Leu Pro Asn Arg Leu Val Met Ala Pro Met Thr Arg Cys Arg
            20                  25                  30

Ala Gly Glu Gly Asn Val Pro Thr Glu Leu Asn Ala Val Tyr Tyr Glu
        35                  40                  45

Gln Arg Ala Ser Ala Gly Leu Ile Ile Thr Glu Ala Thr Gln Val Ser
    50                  55                  60

Gln Gln Gly Val Gly Tyr Leu Arg Thr Pro Gly Ile His Thr Asp Ala
65                  70                  75                  80

Gln Val Glu Gly Trp Arg Arg Val Thr Asp Ala Val His Arg Ala Gly
                85                  90                  95

Gly His Ile Phe Ala Gln Leu Trp His Val Gly Arg Ala Ser His Val
            100                 105                 110

Ser Phe Gln Pro Gly Arg Gln Ala Pro Val Ser Ser Ser Ala Leu Pro
        115                 120                 125

Ile Arg Thr Gly His Ala His Thr Pro Glu Gly Ala Gln Pro Tyr Ser
    130                 135                 140

Thr Pro Arg Ala Leu Glu Thr Arg Glu Ile Pro Gly Val Val Ala Gln
145                 150                 155                 160

Phe Glu Asp Gly Ala Arg Arg Ala Arg Ala Ala Gly Phe Asp Gly Ile
                165                 170                 175

Glu Leu His Ala Ala Asn Gly Tyr Ile Ile Asp Gln Phe Leu Arg Asp
            180                 185                 190

Gly Val Asn Gln Arg Thr Asp Gln Tyr Gly Gly Ser Val Glu Asn Arg
        195                 200                 205

Ala Arg Phe Leu Leu Glu Ile Val Asp Ala Val Thr Gly Val Phe Asp
    210                 215                 220

Pro Asp Arg Val Gly Ala Arg Val Ser Pro Leu Gly Gly Tyr Asn Asp
225                 230                 235                 240
```

```
Met Ser Asp Ser Asn Pro Lys Ala Ile Phe Gly His Val Ala Ala Glu
                245                 250                 255

Leu Ser Ala Arg Lys Leu Ala Tyr Leu His Val Val Glu Pro Val Asp
            260                 265                 270

Gly Gln Ala Glu Asp Ala Ala Gly Arg Val Met Pro Leu Leu Arg Glu
        275                 280                 285

Arg Phe Arg Gly Val Leu Met Ala Asn Gly Gly Tyr Thr Leu Glu Thr
    290                 295                 300

Ala Glu Ala Ala Leu Arg Thr Gly Ala Ala Asp Leu Val Ser Phe Gly
305                 310                 315                 320

Ala Pro Phe Leu Ala Asn Pro Asp Leu Pro Glu Arg Leu Ser Arg Arg
                325                 330                 335

Ala Pro Leu Asn Pro Pro Asp Val Ser Thr Phe Tyr Ser Glu Gly Pro
            340                 345                 350

Arg Gly Tyr Thr Asp Tyr Pro Arg Leu Ala Glu Ala Gln Ala Ala Ala
        355                 360                 365

Gln Pro Ser Ala
    370

<210> SEQ ID NO 31
<211> LENGTH: 4
<212> TYPE: PRT
<213> ORGANISM: Sorangium cellulosum

<400> SEQUENCE: 31

Gly His Ser Gln
1

<210> SEQ ID NO 32
<211> LENGTH: 4
<212> TYPE: PRT
<213> ORGANISM: Sorangium cellulosum

<400> SEQUENCE: 32

Tyr Ala Ser His
1

<210> SEQ ID NO 33
<211> LENGTH: 3381
<212> TYPE: DNA
<213> ORGANISM: Sorangium cellulosum

<400> SEQUENCE: 33
atgggcttcc cgtgcatccg cagggtttcg gggtccgcag cgtctccggc cacctgtgtc      60
aaggtgcgcc ggaccttcag atccaggccg ttccgcgccg cccggtctac gaaaagtgcc     120
caagtcgagg ctcgcttgtc acgcatcttc tctatgcccg acacgtcgtc gtctagcccc     180
gtactagcga tggggctacg ggattcagat gcccggttcg tggaggatac gccgcctgcc     240
tcggaccgcc ctcgtccatt cgcgggcatt gcggtggtgg gaatgggatg tcgcttgccc     300
ggcggcgtcg attcgcccga atccttgtgg gcggccctat ccgaagggcg cgaccttatc     360
agcgaggtcc cgccggacag gtgggatgtc aatgcccact acgacgccga cgcgagtgtc     420
cccgggaaga tcgcgacccg tcatggcggc ttcctcgccg gggtcgcggc gttcgacgcg     480
cccttcttcg acctctcgcc gcgcgaggcg aagcatatgg atccgcagca gcgcctcggc     540
ctcgagacgg cgtggaggc gctggaggac gcaggcctgg acgcgaggag cttgcgggc     600 agccgggcag gggtgttcgt cggctcgatg tgggcggagt acgacgtgct cgcgtcgcga     660
```

```
caccccgaat ccatctcgcc gcacggggcc acggggagcg acccgggdat gatcgcggcg    720
cgcatcgcct acaccttcgg ccttcgtggg ccggccttgt cggtgaatac ggcgtcgtcg    780
tcctccctcg tggcggtgca cctcgcattg caaagcttgc agagcggaga gtgcgagctc    840
gcgctggccg gtggcgcgaa cctcatcctg accccgtaca acacgatcaa gatgacgaag    900
ctcggggacga tgtcgcccga cggccggtgc aaggcgttcg accaccgcgc caacggctac    960
gtgcgcgccg agggcgtcgg gttcgtggtc ctgaagcggc tgtcgcgcgc gaccgcggac   1020
ggggatcgca tctatgcggt cgtgcgtggc tcggccgtga acaacgacgg gctcaccgag   1080
gggctgaccg cgccgagcgt ggaggcgcag gaggccgtgt tgcgagaggc gtacgcgcgc   1140
gccggggtgt ctcccgccga ggtggactac gtcgaggcgc atgggacggg gacgccgctc   1200
ggcgatcgcg tggaggcgac ggcgctggga cgggtgctcg gcgcaggacg cgcggcggat   1260
cgcgcgctgc gggtcggttc ggtcaagacc aacctcggtc acgcggaagc agccgccggg   1320
gtcgccggtc tgatgaagac ggcgctgtcg ctgcgccacg gatcgcttcc ggcgagcctg   1380
cacgtcgagc gcccgaaccc cgagatacccc ctcgaagcgc tgggcctccg gctccagacg   1440
gagctcggcc catggccgga ggtcgatcgg ccccggcgag caggcgtgag ctccttcggc   1500
ttcggcggca cgaactgcca tgtggtgctc gaggagtggc gcggaggcgt cgagcagagc   1560
gccgccgaga cgggcagcga acccggcgcc gccgtatcgc cgcctgccct tcccctggtg   1620
ctgtcggcga gggaccacgg ggcgctgcgg gcgcaggcgg gccggtgggc ggcgtggctc   1680
acggagcacc gcgaggcgcg ctgggcggac gtcatccaca cggcggcagc gcggcggacg   1740
cacctgggcg ctcgggccac ggtggtggcg gcgggcgtgg ccgaagccgt cgatgcgctg   1800
agggccctgg ccgacgggcg cgcccacggg gccgtgacgg tcggcgaggc gcgcgagcgg   1860
ggcaaggtgg tcttcgtgtt tccgggccag ggcagccagt ggccggcgat ggggcgagcg   1920
ctcctgtccg cgtcgagggt gttcgccgag gccgtcgagg cgtgcgatgc ggcgctgagg   1980
ccgctgacgg gctggtcggt gctctcgttg ctgcgcggcg acgccgggga ggcagcgccg   2040
tcgctcgacc gcgtcgacgc ggtgcagccg gccctgttcg cgatggccgt cggcctgtcc   2100
gcggtctttc gcgcgtgggg cctcgatcct tcggccgtgg tgggccacag ccaaggcgag   2160
gtcccggcgg cgtacgtcgc gggggcgctc tcgctcgacg acgcggcgcg ggtcgtggcg   2220
gtccgaagcg cgctcgtgcg gcggctctcg ggcgcagggg cgatggcggc ggtggagctg   2280
ccggccggcg aggtggagcg ccgcctggcc ccgttcgggg gggctctgtc cgttgcggtg   2340
gtcaacacgt cgagctcgac ggccgtttcg ggagacgccg aggcggtgga caggctggtc   2400
gcgcagctcg aggccgaagg catcttctgc cgaaaggtga acgtcgatta cgcatcccac   2460
agcgcgcacg tggacgtcgt gctgccagag ctcctggagc cctggcgcc gatccgacca   2520
ggggccacga ggatcccctt ctattcgacc gtgaccggcg gtgtgctgga ggggacggcg   2580
ctcgacgggg cgtactggtg ccgcaacctg cgccagccgg tacggctgga ccgcgcgctc   2640
gcccggctgc tggacgacgg ccatggcgtc ttcgtggagg tcagtgcgca cccggtgctg   2700
gcgtcgccgc tgaccgcggc gtgcgccgag cgcgagggcc tcgtggtcgg cagcctgcac   2760
cgcgacgacg gcgggcttgc gcggctgctg ggcgcgctgg gcgcgctgca tgtgcagggc   2820
cagccggtcg attggcgcgc ggtgctggcg ccgttcggcg gcggcctggt gaacctgccg   2880
acgtacgcat tccagcgcca gcgctactgg ttcgataccg acgagagcgt tgcgctcgca   2940
gcggcgtcca gcattgcgga agagtcgtgg tcagagaagc tggccgggct gtctcccgcg   3000
cgacgggaag aacggctgct cgaatgggtg cgcgcagaaa tcgcggcggt gctcgggctg   3060
```

```
gaggcgccgg cggtgccgcc ggacgtcccg ctgcgggatc tcgggttgaa atcgccgatc   3120
gccgtggagc tggggagccg cctgggacgc aggacacgcc ggaagctgcc cgtgtccttc   3180
gtttacaacc acccgacgcc acgagcgatc gctcgcgccc tcctggaggg aatgttttct   3240
tcgagcaagg actctcctcc gagcaccgct gacgaccgcc ggccgccggg ggtgcccgcc   3300
ggcgttgcgc ccccacaggc gctggagacg tccgagatgt ccgacgacga gctgttccag   3360
tccatcgatg cgctcgtcta g                                             3381
```

<210> SEQ ID NO 34
<211> LENGTH: 11070
<212> TYPE: DNA
<213> ORGANISM: Sorangium cellulosum

<400> SEQUENCE: 34

```
gtggatcgaa gcgataaact gcgtgcgtat ctggagaaga ccacggcatc gctggtcgag     60
gcgaaaagcc ggatccggga gctggaggcg cgttcgcgcg agccgatcgc gatcgtggcg    120
atggcgtgcc ggtttccggg cggcgtcgac agccccgaga gctctgggcc cctgctcgac    180
gaggagaggg acgtcatcac cgaggtgccg ccctcgcgat gggacctcga gcgcttctat    240
gaccccgatc cggacgccgc aggcaagacc tacagccgct ggggcggctt cgtgggcgat    300
ctggatcgtt tcgacgcggc gttcttcggg atcagccctc gcgaggcccg gagcatcgac    360
ccgcaagagc gctggctgct ggagaccacg tgggaggccc tcgagcgggc cggcgtgcgc    420
gcggacacgg tggaagggac cctgggggggc gtttacatcg gcctgtccgg ctcggagtac    480
caggcggagg catttcacga tgcggagcgc atcgatgcct attcgctgac cggcgcttcg    540
ccgagcacaa ccgtggggcg cctcgcctac tggctcgggc tacgaggtcc cgcggtcgcc    600
gtggacacgg cgtgcagctc ctcgctcgtc gcggtgcacc tggcctgcca ggcgctgcgg    660
aacggggagt gcgattttgc gctggcaggc ggcgtcaacg cgctcctggc ccccagagagc    720 tatgttgcct tctgccgcct cagggcgctg tcccccaccg ggcgctgccg gaccttttcc    780
gcgaacgccc atggctacgt gcgcgcggaa gggtgcgggg tgctgctgct caagcgcctg    840
tcggacgcgc agcgggatgg agaccgtgtg ctcgcggtca tccggggcaa tgccatcaac    900
caggacggtc gcagccaggg gttgacggcg cccaatgggc tcgcccagga ggacgtcatc    960
cgcagggcgc tgtcgcaagc gcgcggtggag ccgacgacgg tcgatgtggt cgaatgccac   1020
gggaccggca cggcgcttgg cgatccgatc gaggtccagg cgctcgggc ggtttacggc   1080 catgggcgcc ccggagacag gccgctcgtg atcggctccg tcaagacgaa cctcggtcac   1140
accgaggcgg ccgcaggcat ggccggcctc atcaaggccg tcctttcgct gcagcacgcc   1200
caggtgcctc gatcgctgca cttcgctgcg ccgagcgatt acattccctg ggatacccctc   1260 cccgtccggg tggccgcgca gcgcgtcgca tgggagcgac gcgagcaccc gcggcgcgcc   1320
ggggtctcgt cgttcgggat cagcggcacc aacgcgcacg tgatcctcga ggaggcgccg   1380
gcgtcggaag cgccggcaac ggcgccggtg gcggcgccgg tggcggcgcc gttgccggcg   1440
acgctgccgc tgctcgtgtc ggggcgggac gaggcggcgc tcagggcgca agccgggcag   1500
tgggcggcgt ggctcgcggc gcacccggag gctccctggg cggacgtggt gcacacggcc   1560
gccgcgcggg gcacgcacct ggaggcgcgc gcggcggtgg cggcggggag cgccgccgac   1620
gcggccgcgg cgctagaggc gctgccgcc ggacacccgc acaggcggt gtcgctgggc   1680 gaggcgcgcg cgcgcggcga ggtcgtgttc gtgtatccgg ggcagggcag ccagtggccg   1740
```

```
gcgatggggc gcgcgctgct ggccgagtcc gaggtgttcg ccgccgcggt cgcggcctgc    1800
gacgcggcgc tgcggccgct gacgggctgg tcggtgctct cggtgctgcg cggcgagcag    1860
ggagaggcgg tgccgcccgc ggaccgcgtg gacgtggtgc agccggcgct gttcgcgatg    1920
gccgtggggc tctcggcggt ctggcgggcg tgggcatcg  agccttcggc ggtcgtcggc    1980
cacagccagg gcgaggtcgc ggcggcgtac gtcgccgggg cgctgacgct cgaggacgcg    2040
gcgcgggtcg tggcgctgcg cagccagctc gtgcggcgca tcgccggcgg cggcgcgatg    2100
gccgtgatcg agcgcccggt cggcgaggtg gagcagcggc tctctcgctt cggagggcag    2160
ctgtccgtgg cggcggtgaa cacgccgggc tcgacggtgg tgtccgggga cgccgcagcg    2220
gtcgatcgct tgctggccga gctggaggcc gagcgggtct tcgcgcggcg gatcaaggtc    2280
gattacgcgt cgcacagcgc gcacgtggac gcgatcctgc cggagctcga ggccacgctg    2340
gcctcggtcg agcccgtgc  ctgcaccatc ccgctgtact cgacggtgac gggagaagtg    2400
ctcgccggcc cggagctcgg cggcggctac tggtgccgca acctgcgcga gccggtgcgg    2460
ctcgaccggg cgctctcgcg gctgctggcg gacgggcacg gggtgttcgt cgaggtcagc    2520
gcgcatccgg tgctggccat gccgctgtcg gccgcgagcg ccgagcgcgg cggcgttgtg    2580
gtcggcagcc tgcagcgcga cgacggcggt ctggggcggc tggcgtcgat gctgggcgcg    2640
ctgcacgtcc agggccacgc cgtgaactgg cagcgggtgc tggcgccgta cggcggggcg    2700
ctcgtggatc tgccgacgta cgcgttccag cgccagcgcc actggctcga ggcgccgcgg    2760
tacgcggcgg aggacacgga cggcgcgcg  cggcgcgacc cgctgtaccg ggtcacgtgg    2820
atcgaggcgg cgctggagga ggcgccctgg gcggccgagc gccacgtcgt gctcggcgcg    2880
gacggcgcgc tggcgtcggg gctggggcg  ctcgcgctgg cggggctgcc ggagctgctc    2940
gaggcgctgg agaacggggc ggcggcgccc gagcggctgg tgctggacct gacggagggc    3000
cgcccaggcg cggtggcgga gtccgtgcac gccacgacgc gcagcgcgct cgcgctggtg    3060
caggcatggc tcgcggcgcc gcggcttcg  ggcaccgagc tggtcgtggt gacgcgggag    3120
gcggtggcgg ccggtccgga cgagggcgtg gcggcgctgg gccccgcggc ggtctggggg    3180
ctgctgcgca cggtccgcgt cgagcacccc gagcgcgcgg tgcgctcggt ggatctgggg    3240
cgcgagccgc cggatgtcgc ggtcttgcgg cgggcgctgg ggacggcggc cgagccggag    3300
ctcgcgctgc gcgcgggcgg ggcgcgggcg ccgcgcctgc gcgcggtcaa cgccggcgcg    3360
gacgccaggg cgccagcggc ggcgctggac ccgcagggca cggtgtggat cacgggcggc    3420
accggggagc tcgggcggca ggtcgcgcgg cacctggtcg cggcgcacgg cgtgcggcac    3480
ctcctgctga cgtcgcggcg aggcgcggcc gcgccggacg ccgaggcgct ggtcgaacag    3540
ctgcggggcc acgcgccga  gacggtcgag gtcgtggcgt gcgacgtgac ggacggcgcg    3600
gcgctttcgg cagcagtcca ggtcgccgcg gcgaagcgcc cgctgacggc cgtggtgcac    3660
accgccgggg tgctggcgga cggggtgctc acggcgctga cggcggagca gctcacgcgg    3720
gccctggcgc cgaaggtcga cggggcgtgc cacgtgtacg ccgccgcgca ggaccagccg    3780
ctcgcggcct tcgtgctgtt ctcctcgatc gtcggtacgc tggcaacgc  gggccaggcg    3840
aactacgggg ctgccaatgc gttcctggac gcgttcgcgg cgcagctccg cgcgcgcggc    3900
gtgccggcga cgagcctcgc ctggggcttc tgggagcagg ccgggctcgg catgacggcg    3960
cacctcggcg ccgccgacct ggcacgcctc ggacggcagg gccttgtgcc gctgtcggtc    4020
gcgcagggcc tgcgcctcct cgaccgggcg ctcgcgcacc cggaggcgac gctggtgccg    4080
gcggcgctcg acctgtcggc gctccagcgt gcggcgagcg acgccggacg ggtgccgccg    4140
```

```
ctgctgcgcg ggctggtgcg cgcgagcccc ggccgcccca cggcgaccgc gacccccgaa    4200
gccggaccag cggccgcgtc ggcgctgcgc gcacggctct cggcgttgcc cgaggccgag    4260
cgggcgggcg cgctgctcga gctggtgcgc gcggaggtgg cggtcgtgct gcggctggca    4320
ggtccggcgc aggtgcccgc ggacaagccg ctgaaggagc tggggctcga ttcgctcacg    4380
gccgtcgagc tgaagaaccg cctcggcgcg cgcgccgaga cggtgctgcc gacgaccctc    4440
gcgttcgacc atccgacgcc gcgcgcgatc gcggatctgc tgcttcagcg tgcgttctcg    4500
gagctcgcgg gggcgacgcg cgcacaggcc ccgcgcgcgc gggagcgca cgacgagccg     4560 atcgcgatcg tgtcgatggc gtgccggctc ccgggcggcg tcgatacccc cgcggcgctg    4620
tgggacctgc tctcggaggg ccgggacgcg atcgggccgt tccccgaggg gcgcggctgg    4680
gatgtggcgg ggctgtacga ccccgacccg gacgccccgg gcaagtcgat caccacgcag    4740
ggcggcttcc tctacgacgc cgatcgcttc gatccgacct tcttcggcat cagcccgcgc    4800
gaagcggagc gcatggaccc gcagcagcgg ctgctgctcg agtgcgcctg ggaggcgctc    4860
gagcgcgcgg gcctcgcgcc ccacgcgctc gaggcgagcg ccaccggcgt cttcttcggg    4920
ctcgctcacg gggactacgg cgggcggctc ttgcagcagc tcgagtcctt cgacggccac    4980
gtcctcaccg gcaacttcct cagcgtcggc tcgggcgca tcgcctacac gctgggcgctc     5040 cgcggccccg cggtcaccgt cgacacgcg tgctcgtcgt cgctcgtggc ggtccacctc      5100
gcgtgcatgt cgctccgcgc cggcgagtgc gacctggccc tcgccggcgg cgccaccgtg    5160
atggccacgc cgatgatctt cgtcgagttc agccgccagc gcggcacggc gctggacggt    5220
cgttgcaagg ccttcggcgc cggggccgat ggcgccggct ggtcggaggg ctgcgggatc    5280
ctggcgctga gcggctgtc ggacgcgcgg cgcgacggcg accgcgtgct ggcggtcatc     5340
cgcagctccg ccgtcaacca ggacggccgc agccaggggc tcaccgcccc caacggcccg    5400
gcccagcagg acgtcatccg ccaggccctg gccgcgcgg ggctgacccc ggcggacatc     5460
gacgccgtcg aggcgcacgg caccggaacg cgcctcggtg accccatcga ggcgcaggcg    5520
ctgctggcga cctacggcac cgcgcacacc gccgagcggc cgctctggct cggctcgctc    5580
aagtccaacc tcgggcacac gcaggtcgcc gcgggcgtgt cggggctgat gaagctggtg    5640
ctggcgatgc agcacgcaga gctgccgagg acgctgcacg ccgacccgcc ctcgccgcac    5700
gtcgactggt cgcaggggca cgtcaagctc ctgaacgagc ccgcgccgtg ccgcgcacg     5760 gaccggccgc ggcgcgcggc ggtctcgtcc ttcggcatca gcggcaccaa cgcgcacgtc    5820
atcgtcgagg aggcgccgga gccggcgccc gcggcggacg cgaaggcggt ggaggcgctt    5880
ccgatcctgc cgctgctggt ctcggggcg gacgaggcgg cgctgcgcgc gcaggtgcgg    5940
cggttggtgg agcacttgcg gtcgcacccg gaccagcggc tgctggacgt ggcagcgagc    6000
cttgcgacca cgcgcacgca tctcgccacg cggctcgcgc tgcccgtctc ggcggggcg   6060 ccccgggatg cgtggatgga tgagctggag gcgtttgcca ggggaggagc ggctccgacg    6120
caggcatcgc agaccccgt cgagagcagc acgggcaagg tcgcggtgct gttcaccggc    6180
cagggcagcc agcgcgccgg catggggcgc gccctgtatg ccacccaccc cgtcttccgc    6240
gccgcgctcg acgccgcctg cgccgagctc gaccgcacc tcgaccggcc cctcatgagc    6300
gtcctcttcg ccgacgccgg ctccgaggcc gcggcgctgc tcgaccagac agcctgggct    6360
cagcccgccc tgttcgctct cgaggtggcc ctctaccgcc agtgggatgc ctggggcctg    6420
cgccccgagc tgctgctcgg ccacagcatc ggcgagctcg ccgccgccca catcgccggc    6480
```

```
gtgctcgacc tcgccgacgc ctccgccctg gtccgcgccc gcgggcggct catgcaggcc    6540 ctcccctcg gcggcgccat ggcctccgtc gaggccaccg aggacgagct acgcccttg     6600 ctcgaccagc acacaggacg cctctcgctc gccgccctca acaccccacg ccagtcggtc    6660
gtcagcggcg acgagcccgc cgtcgaccaa gtctgcgccc acttcaccgc cctcggccga    6720
cgcgccaagc ggctcgtcgt cagccacgcc ttccactcgg cgcacatgga gcccatgctc    6780
gacgccttcg cccgcgtcgc tcgcggcctg accttccacc cgcccggct gcccatcgtc    6840 agcagcgtca ccggcgcacg cgcctccgcc gacgagctca cctcgcccga ctactgggtc    6900
cgccaggtgc gcgagcccgt ccgcttcgtc gacggcatgc gcgcactgca cgccgccggc    6960
gcggccacct tcgtcgagtg cgggccgcac ggcgtgctca cgccgccgg cgcagagtgc    7020 ctcgctcccg acgcgctcg cgacgccggc ttcgtcccca gcctccgcaa cgaacgcgac    7080
gaggccctcg ccctggtcca cgccgcctgc gccgtccatg tacgcggaca cgccctcgac    7140
tggctccgct tcttcgacgc caccggcgcg cgccgcgtcg agctgcccac ctacgccttc    7200
cagcgacagc gctactggct ccaggcgccg aggcctcgcc ccagcctcga gggcgttggc    7260
ctcaccgccg caaaccaccc atggctcggc gcagccgtcc gcctcgccga ccgcgatggc    7320
tacgtcctca gcggccgcct ctccaccagc gaccacccgt gggtcctgga ccacgtggtg    7380
ctgggcacgg cgctgctccc gggcacgggc ttcgtcgagc tggcgtgggc ggcggccgag    7440
gcggtcgggc tgtccggggt atcggagctg gcgatcgagg cgccgctggc gctcccggcg    7500 cgcggggcg tggcgctgca ggtcgcgatc gaggcccgg accggcggg gcggcgcggc    7560 atcgcgatct acagccgccc cgacggcgca gccgacgcgc cctggacagc gcacgcgcgc    7620
ggcgtgctgg gcgccgcggc gtccgacagg gacgcgcct gggcgcaggg cgcgtggccg    7680
ccgccggggg ccgtaccggt cgacgtgacg cagtggctcg agatcgtgga cgcgtgggtc    7740
ggcccggcgt tccggggcgt cgtggcgctg tggcgcgtcg gcggacgat ctacgcggac    7800 gtggcgctgc cggacggtgt ggcgggcacg gcgcaggatt tcgggctgca tccggccttg    7860
ctcgatgtgg cgctacgcgc gttcctgaga gcggagctca gcgccgatcc gtcgccacga    7920
gagggcacgg tggtgccgtt cgcgtggtcg gacgtggcgc tcgaggcgcg tgggacggcg    7980
gcgctgcggg tgcgcgccga ggtggaggcc ggtggggatg gcgacgcgat caccgcgtcg    8040
atccagctgg ccgacgggca gggccgcccg gtcgcgcggg tgggcgcgct ccagatgcgg    8100
tggacgacgg ccgagcgggt gcgcgcggcc gccgccgcgg gcgcggcgga gcgcgatctg    8160
taccgcgtcg cgtggacgga cgtggcgctg acgacacgg cgtttgtgcc ggaggagcac    8220
gtcgtggtcg gcggcgacgg cgcgctggcg gcggcgctcg gtgcacgcgc ggtggcgggg    8280
ctgcccgagc tgctcgcgtc gctgccggac ggcgcggcgg cgccacgccg cctggtggtg    8340
gacctcacgg cggacgccgc gggcgcggtc gtcgacgccg tgcacgccgc ggcgcgcgac    8400
gcgctgtccc tggtgcaggg gtggctggcg gcgccgcagc tggcggcgac ggagctcgtc    8460
gtcgtgacgc gcggcgcggt ggcggtcgcg ccggacgagg gcgtggcggc gctgggtccc    8520
gctgcggtct gggggctgct ccgcgcgacg cgcgtcgagc acgcggatcg cacgttcgc    8580 atgctcgatc tggggcccgg ggcgccggac atggcgctct gcgccgggc gctcacggcg    8640 gccgaggagc cagagctcgc gctgcgcgcg ggcggggcgc gggcgccgcg cctcgacgcg    8700
gccggcgaga ccgacggaga gctggcgccg cccgacgggg cgcgctctct tcgcctgtcc    8760
atccggacga aaggctcgtt cgacgcgctc cacctcgcgg acgctcccga tgcgctgcgc    8820
ccgctcgggc cggggcaggt ccggctcgcg gtccgcgcta cggggctcaa cttccgcgat    8880
```

```
gtcttgaacg tcctggggac gtaccgcggc gaagcggggc ctctcggtct ggagggggcc     8940
ggggtggtgc tggacgtggg cgagggagtc actgcccttc gacccggcga ccgggtgatg     9000
ggcatcctgc acgcgggcat ggcgacccat gcgtcgtcg acgcccggct gctgacgcac      9060
atcccgcggg ggctttcctt cgtggaagcg gcgacgatcc cagcggcctt cctcaccgct     9120
ctgtacgggc tgcgcgacct gggcgcgctg aaggcggggc agcgcgtgct ggtgcacgcc     9180
gcggccggcg gggtcggcat ggcggcggtc cagctggcgc gcctctgggg agccgaggtg     9240
ttcgcgacgg cgagcgaggg caagtggccg gcgctgcgcg ggatggggat cgaccaggcc     9300
catatcgcct cgtcgcgaac cctccacttc aggaaagcct tcctcgacgc gacgcgggga     9360
cagggcgtcg acgtggtgct cgacgcgctc gcgggcgagt tcgtcgacgc ttcgctcgac     9420
ctgctcccgc gcggggccg gttcgtggag atgggcaaga gcgatgtgcg cgaccccgag      9480
cgcgtcgcca aggaccaccc cggcgttcgc tacacggcct tcgatctgct cgacgcgggg     9540
cccgaccaca tccaggcgat gctgcgggag ctcgtcccgc tgttcgagga gggcgtcctc     9600
gctcccctcc ccttcgcggt ccacgacctg cgtcgcgccc cgcacgcctt ccgatccatg     9660
gccaacgcgc gccacgtggg caagctcgtg ctggtgccgc ctgcgcgct cgaccctgac      9720 ggcacggcct tgatcacggg cgggacgggg gagctcgggc ggcagatcgc gcggcacctg     9780
gtggcggcgc acggcgtgcg ccacctggtg ctcacgtccc ggcgcgggat ggacgcgccc     9840
gacgccgcgg cgctggtggg atcgctgcgc gcggcgggcg ccgcgacggt ggaggtcgcg     9900
gcgtgcgatg tgacagaccg tgacgcgctc gcggccgtcg tgcaggcgat ccccgcggcg     9960
cgcccgctga ccgccatcgt gcacacggcc gccgtgctgg acgacggcat cgtggcgggg     10020
ctctcggccg agcagctcgc gcgcgtgctg cggccgaagg tcgacggcgc ctggcggctc     10080
tacgaggcga cgcgggacgc gccgctcgcg gcgttcatgc tcttctcgtc ggtcgccggc     10140
acgctgggca gctcggggca ggcgaactac gccgccgcga acgcgttcct cgacgggctg     10200
gcggcagagc tccgcacgcg cggcgtgccg gcgatgagcc tcgcgtgggg cttctgggag     10260
cagggcggga tcgggatgac ggcgcacctc ggcgccgccg acctggcgcg gctgaagcgg     10320
cagggcatcg cgccgatgac ggtcgcgcac ggcctgcggc tgctcgaccg cgccctcgag     10380
cgcccggacg cggcgctggt gccggcctcc ctggacgtgg cggtgatcca gcggcggcg      10440 agcgaccacc gtcaggtgcc gcccatgctg cgcgggctcg tccgcgtcgc cgcgcggcag     10500
gcggcagggg cagccaacgg caggagccat gaagcctcga ccctgcggca gcagctcgcc     10560
gccctgcccg aaccggagcg gcagcgagcg ttgctcgatc tggtccggac cgaggcggcc     10620
gccgtcctgg tgctgcgcgg gccggacgcc gtccccgccg acaagccgct cagggagctc     10680
gggctcgact cgctcacggc agtggagctc aggaatcggc tcaggacccg tgcgcagacc     10740
gatctcccat cgaccctcgc cttcgactac ccgacgccga aggcggtcgc cgtgtatcta     10800
gcccaggagc tcgacgttca cgacgtcatg acggagatgc gcggaccgag cttgcgctct     10860
gacgacgaga tcaagtcggc catcgcgagc atccggatct cgacgctacg ccaggcgggg     10920
ctgctcgaca gcctgcttcg gctcgccgcc agcgaagccg tctccacatc cagcgacacg     10980
acacctgaaa ccgacgagct gacgctgcag catgttggag acgatgagct ggcacggctt     11040
gtcttcgacc tcgccggagg agcgcaatga                                     11070

<210> SEQ ID NO 35
<211> LENGTH: 10968
<212> TYPE: DNA
```

<213> ORGANISM: Sorangium cellulosum

<400> SEQUENCE: 35

```
atgaaagaag atatctccgc ccgtcaagct ctcgagaaga gcttcattga acttcgccgt    60
atcaagcggg agctcgatca gctcaaggcg aagtcgagcg agccgatcgc gatcgtgtcg   120
atggcgtgcc ggctcccggg cggcgtcgat accccgcgg cgctgtggca gctgctctcg   180
gagggccggg acgcgatcgg gccgttcccc gaggggcgcg gctgggatgt ggcggggctg   240
tacgaccccg acccggacgc gccgggcaag tcgatcaccg cgcagggcgg cttcctctac   300
gacgccgacc gcttcgatcc ggcgttcttc gccatcagcc cgcgcgaagc ggagcgcatg   360
gacccgcagc agcggctgct gctcgagtgc gcctgggagg cgctcgagcg cgcgggcctg   420
gcgcctcact cgctcgaggc gagcgccacc ggcgtcttcg tcgggctgtc ggtcacggac   480
tacggcgggc ggctgctgca cgagcccgag gccctcgacg ctacatcgc caccggcacc   540
ctgcccagcg tcggctcggg gcgcatcgcc tacacgctgg ggctccgcgg ccccgcggtc   600
accgtggaca cggcgtgctc gtcgtcgctc gtgtccctcc acctcgcgtg catgtcgctc   660
cgcgccggcg agtgcgacct ggccctcgcc ggcggcgcca ccgtgatggc cacgcccatg   720
gccttcatcg agttcagccg acagcgcggc acggcgctgg acggtcgttg caaggcgttc   780
ggcgccgggg ccgatggcgc cggctggtcg gagggctgcg ggatcctgac gctgaagcgg   840
ctgtcggacg cgcggcgcga cggcgaccgc gtgctggctg tcatccgcgg ctccgccgtc   900
aaccaggacg gccgcagcca ggggctcacc gcccccaacg gccgcgccca gcaggacgtc   960
atccgccagg ccctggccgc ggcggggctc acgcccgccg acgtcgacgc cgtcgaggcg  1020
cacggcaccg gcacgcgcct cggcgacccc atcgaggcgc aggcgctgct ggcgacctac  1080
ggcaccgcgc acaccgcgga cggccgctc tggctcggct cgctcaagtc caacctcggg  1140
cacacgcagg ccgccgcggg cgtgtcgggg ctgatgaagc tggtgctggc gatgcagcac  1200
gcagagctgc cgaggacgct gcacgccgac ccgccctcgc cgcacgtcga ctggtcgcgt  1260
gggcacgtca agctcctgaa cgagcccgtg ccgtggccgc gcacggaccg gccgcggcgc  1320
gcggcggtct cgtccttcgg cttcagcggc accaacgcgc acgtcatcgt cgaggaggcg  1380
ccggcggcct ccaccgaggc gacgacccgc ggggagaaga cgcccgcggc cgcgccgccg  1440
tcgaccctgc cgctgctggt ctcggggggcg acgaggcgg cgctacgagc gcatgcgggg  1500
cggtgggcgg cgtggctcgc ggcgcacccg gaggcgggct gggcggacgt ggtgtacacc  1560
gcggcagcgc gtcggacgca cctggggcg cgcgcggcg tgacggcggc ggacgcggcc  1620
ggcgcggtcg cagcgctgac ggcgctctcg caggggcagc cgcacgccgc gctcgccgtg  1680
ggcgaggcgc gcgctcgggg gaaggtcgtc ttcgtgtttc cgggccaggg cagccagtgg  1740
ccggcgatgg ggcgggcgct gctctcgcag tcggaggtgt cgccgcggc ggtcgcggcg  1800
tgcgacgcgc cgctgcggcc gttcaccggc tggtcggtgc tctcggtgct gcgcggcgac  1860
acgggcgcgg aggtgccgcc gctggagcgc gtcgacgtcg tgcagccggc gctgttcgcg  1920
atggcggtgg ggctcgccgc ggtgtggcgc gcgtggggcc tcgagccgtc ggcggtggtg  1980
ggccacagcc agggggaggt cccggcggcg tacgtcgcgg gggcgctgtc gctcgaggac  2040
gcggcgcgga tcgtgcgct cgcagccgg ctcgtgcggc gcctgtccgg aactggcgcg  2100
atggccgtga tcgagctccc ggtgggcgag gtcgagcaac ggctctcgcg gttcggcggc  2160
gcgctgtcgg tggcggcggt caacacgccg cgctcgacgg tggtgtcggg cgatgccgag  2220
gcggtcgatc gactgctgac ggagttcgag ggcgagcaag tcttcgcgcg gaaggtcaac  2280
```

```
gtcgactacg cgtcgcacag ccgacacatc gacgggctgc tgccagagct ggaggacggc   2340
ctgggcgcgg tgcggccgcg cgcgagcacg atcccgttct actcgacggt gaccgggacg   2400
gtgctgacgg gcgcggagct ggacgcggcg tactggtgtc gcaacctgcg cgagccggtg   2460
cggctcgacc gggcgctctc gcggctcctg gacgacgggc acggcctgtt cgtcgaggtc   2520
agcgcgcacc cggtgctgac gctgccgctc acaggagcga gcgcgacgag cggcggtgtg   2580
gtggtcggca gcctgcagcg cgacgacggc gggctgggac ggctcctggg ggtgctggcc   2640
gcgctgcacg tgcacggcca cgacgtcgac tggcgcgcgg tgctggcgcc gtggggcgga   2700
ggcgtggcgg acttgccgac ctacgcgttc cagcggcagc gctactggct cgaggcgccg   2760
cgcggccggg cagggctgga gagcggaggg ctcctggcgg tgaagcaccc gtggctcagc   2820
gcggcggtgc ggctggccga ccgcgacggc tacgtgctga gcggacggct gtcgacggtc   2880
gagcacgcgt gggtcctgga ccacgtggtg ctgggcacgg tgatcctccc gggcacggcg   2940
ttcgtcgagc tggcgctcgc ggcggccgat gccgtcggac tgccctcggt gtcagagctc   3000
acgatcgagg cgccgctggc gctgccggcg cgcggggcgg tgacgctgca ggtgacggtg   3060
gaggcgttgg acgcgacggg gcggcggggc ttcgcggtcc acagccggcc cgacggcgcg   3120
cacgacgcgc cgtggacggc gcacgcgcgc ggcgtgctgg gcgcagcgcc cgcggcggcc   3180
acgacggcgt gggcggcggg cgcgtggccg ccggcggggg ccgagccggt cgacgtcacg   3240
cggtgggtcg aggcgctcga cgcgtgggtc ggcccggcgt tccggggcgt gacggcggcg   3300
tggcgcgtgg ggcggtcgat ctacgccgac ctggcgttgc ccgaggggt ctcggagcgg   3360 gcgcaggact tcggcttgca tccggccttg ctcgatgcgg cgctccaggc cctcctgcgg   3420
gcggagctcg gcgcaggctc gtcgccgcgg gagggcatcc cgatgcccttt cgcgtggtcg   3480 gacgtggcgc tcgaggcgcg gggggcagcg gcgctgcggg cgcgcgtgga ggtcgaggac   3540
gccagcgatg gggaccagct cgcggcgtcg atcgagctgg ccgacgcgca ggggcagccg   3600
gtcgcgcgcg caggacgtt ccgggcgcgg tgggcgacgg cggagcacgt gcgcaaagct   3660
gcggcgggtg cgagcgagcg tgacctgtac cgggtcacgt ggacggacgt ggcgctggaa   3720
gaagcggcgt gggcgccgga ggagcacatc gtgctcggcg gcgacggggc gctcgcggcg   3780
gcgctgggcg cgcgcacggc ggcgctgccg gagctcatcg cggcgctgcc ggagggcgcg   3840
gccgcgccgc gccggctggt gatcgacgcg gccgcgggcg accccggcga cggcctggtc   3900
gcggcggcgc acgcggcgac gcagcgggtc ctgtcgctgg tgcaggggtg gctctcggag   3960
gcgcggctcg cggacagcga gctggtggtg gtgacgcgcg gcgctgtggc cgccgggccc   4020
gacgacggcg tcgcggcgtt gagccacgcg ccgctgtggg ggctcgtgcg cacggcgcgc   4080
caggagaacc ccggccgggc ggtgcgcctc gtcgacctgg ggcccgagcc gctggacgga   4140
gcgctcgtgc gccgggcggt ggcggcggcc gaggagccgg agctcgcgct gcgcggggc   4200 gcggcgcgcg cgccacgcct gcgcgaggtg cgcgcgggcg cggccgacgc ggcgcgaccg   4260
acgcggctgg atcccggcgg gacggtgctg atcacgggcg gcaccgggga gctcgggcgg   4320
caggtcgcgc ggcacctggt cgcggcgcac ggcgtgcgg acctcgtgct cacgtcgcgg   4380
cgcgggatgg atgcgccgga cgccgcgcg ctggtgacg agctgcgcgc cgcgggcgcc   4440
gcgacggtcg acgtcgcggc gtgcgacgtc ccgacggcc cggcgctggg ggcggtcatc   4500
gcggcgatcc cggctgcaca cccccctcacg gcggtcgtgc acatggcggg cgtgctggac   4560
gacgtcatcg tgacgaagct ctcggccgag cagctcgcgc gcgtgctgcg gccgaagatc   4620
```

```
gacggcggct ggcacctggc cgcggcgacg cgaggccatc ggctcgcggc cttcgtgctg   4680
ttctcgtcgg cggccggcac gctgggcagc gcggggcagg cgaactacgc cgcggccaac   4740
gcgttcctgg acgcgctcgc ggcgcagctc cgcgcgcgcg cgtgccggc gatgagcctc    4800 gcctggggct tctgggagca ggccgggctc ggcatgacgg cgcacctcgg cgccgccgac   4860
ctggcacgcc tcagacggca gggcatcgcg ccgatcgcgc tcgcgcaggg catgcagctg   4920
ctggaccggg cgctcgcgcg cccggaggcg cgctgctgc cggcggcgct cgacctgtcg    4980
gcgctccagc gtgcggcgag cgacgccggg caggtgccgg cgctgctgcg cgggctcgtg   5040
cgcccggcgg ccgggcggcg cgcggcgtcg cctgcgccg ccgcgaccgg agcggcggcg    5100
ctgcgcgcgc ggctctcggc gctgcccgag gccgagcggg cgggcgcgct gctcgagctg   5160
gtgcgcgcgg aggcggcggc cgtgctgcag ctggcaggtc cggcgcaggt ccccgcggac   5220
aagccgctga aggagctggg gctcacctcg ctcacggccg tcgagctgag gaaccgcctc   5280
ggcgcgcgcg ccgagacggc gttgccggcg accctcgcgt tcgaccatcc gacgccgcgc   5340
gcgatcgcgg atctgctgct tcagcgtgcg ttctcggagc tcgcggccgc gggggcgacg   5400
cgcgcacagg ccccgcgcgc gcggggagcg cacgacgagc cgatcgcgat cgtgtcgatg   5460
gcgtgccggc tcccgggcgg cgtcgatacc cccgcggcgc tgtggcagct gctctcggag   5520
ggccgggacg ccatcgggcc gttccccgag gggcgcggct gggatgtggc ggggctgtac   5580
gaccccgacc cggacgcccc gggcaagtcg gtcaccaacc tgggcggctt cctctacgac   5640
gctgaccgct tcgatccgac cttcttcggc atcagcccgc gcgaagcgga gcgcatggac   5700
ccgcagcagc ggctgctgct cgagtgcgcc tgggaggcgc tcgagcgcgc gggcctcgcg   5760
ccccattcgc tcgaggcgag cgccaccggc gtcttcgtcg ggctggtgta cagcgactac   5820
ggcgggcggc tgctcgagca cctcgaggtc ttcgacggct acgtcgccac cggcagcttt   5880
cccagcgtcg gctcggggcg catcgcctac acgctgggc tccgcggccc cgcggtcacc    5940
gtcgacacgg cgtgctcgtc gtcgctcgtg tccctccacc tcgcgtgcat gtcgctccgc   6000
gccggcgagt gcgacctggc cctcgccggc ggcgccaccg tgatggccac gcccatggcc   6060
ttcatcgagt tcagccgaca gcgcggcatg gccccggacg cacggtgcaa ggccttcggg   6120
gcggcggcga acggcatcgg ccccgcggag ggctgcgggc tcctggtgct caagcggctg   6180
tcggacgcgc ggcgcgacgg cgaccgcgtg ctggccgtcc tccgcggctc cgccgtcaac   6240
caggacggcc gcagccaggg gctcaccgcc cccaacggcc cggccagca ggacgtcatc    6300 cgccaggccc tggccgcggc ggggctgacc ccggcggaca tcgacgccgt cgaggcgcac   6360
ggcactggca cgcgcctcgg cgatcccatc gaggcgcagg cgctgctggc gacctacggc   6420
accgcgcaca ccgccgagcg gccgctctgg ctcggctcga tcaagtccaa cctcgggcac   6480
acgcaggccg ccgcgggcgt cgtgggggctg atgaagctgg tgctggcgat gcagcacgca   6540
gagctgccaa ggacgctgta tgccgagccc cgatcgccgc acatcgactg gtcgcagggg   6600
cacatcaacc tcctgaacga gcccgtgccg tggccgcgca cggaccggcc gcggcgcgcg   6660
gcggtctcgt ccttcggcat cagcggcacc aacgcgcacg tcatcgtcga ggaggcgccg   6720
gcggccgcgc agacggcggc ggaggcggcg cggcggtgc cgtcgacgct gccgctgctc    6780
ctgtcgggtc gcgacgagcc ggcgctgcgc gcccaggccg gcggctcgc cgagcacctg    6840 cgcgcccacc cggaccagcg gctgctcgac gtcgccgcga gcctggccac gacgcgcacg   6900
cacctcgcca cgcggctcgc gctgccgctc gcgccggacg cagccacgga ggagctgggc   6960
gcccgccttg ccgagttcgc ctcaggcggc ccggcgccca gcggcgccgc cgtgaccgcg   7020
```

```
ccggggcagc cgcccggcaa ggtcgcggtg ctcttcaccg gccagggcag ccagcgcgcc    7080
ggcatggggc gcgccctgta cgccacccac cccgtcttcc gcgccgcgct cgacgccgcc    7140
tgcgccgagc tcgaccgcca cctcgaccgg cccctcatga gcgtcctctt cgccgacgcc    7200
ggctccgagg ccgcggcgct gctcgaccag acagcctggg ctcagcccgc cctcttcgct    7260
ctcgaggtgg ccctctaccg ccagtgggat gcctggggcc tgcgcccga gctgctgctc     7320 ggccacagca tcggcgagct cgccgccgcc cacatcgccg gcgtgctcga cctcgccgac    7380
gcctccgccc tggtcgccgc ccgcgggcgg ctcatgcagg ccctccccct cggcggcgcc    7440
atggcctccg tcgaggccac cgaggacgag ctacgcccct gctcgacca gcacacagga    7500 cgcctctcgc tcgccgccct caacacccca cgccagtcgg tcgtcagcgg cgacgagccc    7560
gccgtcgacc aggtctgcgc ccacttcacc gccctcggcc gacgcgccaa gcggctcgtg    7620
gtcagccacg ccttccactc ggcgcacatg gagcccatgc tcgacgcctt cgcccgcgtc    7680
gctcgcggcc tgaccttcca cccgcccgg ctgcccatcg tcagcagcgt caccggcgca    7740
cgcgcctccg ccgacgagct cacctcgccc gactactggg tccgccaggt gcgcgagccc    7800
gtccgcttcg ccgacggcat gcgcgcactg cacgccgcgg gcgcggccac cttcgtcgag    7860
tgcgggccgc acggcgtgct cagcgccgcc ggcgcagagt gcctcgctcc cgacggcgct    7920
cgcgacgccg gcttcgtccc cagcctccgc aaggaccgcg acgaggccct cgccctggtc    7980
cacgccgcct gcgccgtcca tgtccgcggg cacgccctcg actggctccg cctcttcgac    8040
ccctccggcg cgcgccgcgt cgagctgccc acctacgcct tccagcgaca gcgctactgg    8100
ctccaggcgc cgaggcctcg ccccagcctc gagggcgttg gcctcaccgc cgcaaaccac    8160
ccatggctcg gcgcagccgt ccgcctcgcc gaccgcgatg gctacgtcct cagcggccgc    8220
ctctccacac tcgaccaccc gtgggtcctg gaccacgtgg tggcaggcac ggtgatcttg    8280
ccaggaacgg cgttcgtcga cctggcgtgg gcggcggccg aggtggtggg cgccgccgct    8340
gtgtccgagg tgaccttcac gacgccgctc gtgcttccgc cgcgcagcgt ggtggagctg    8400
caggtgagga tcggcgagcc ggacgcgtcc gggcggcgga cgttcgccgc gtacagccgc    8460
ccggacgcgg cgagcgaggc ggagtggacg caacacgcga ccggcgtgct gagcgcgcag    8520
gcggcggccg gggccgacgt ggcggacctt tcggtgtggc cgccgccggg cgccgaggtg    8580
gtggcgctcg acggcggcta cgcgtggctg gcggcgcagg gctacggcta cggcccggcg    8640
ttccaggcgc tgcgcgaggt gtggcgcgcg ggcacgacgc tgtacgcgcg ggtcgcgctg    8700
ccggacgcgg tggcggacac ggcgcagagc ttcgggatcc atccggcgct gctcgacgcg    8760
gtgctgcact cgttgctggc gcggtcgccg caggaggagg cgtccgacga cgacaaggtg    8820
ctgctggcgt tcgcgttctc ggacgtcgtg atcgaggcgc gcggggcagc ggaggtgcgc    8880
gtccgcctga acaagcaggc cggagacgac ggggaggggc tcacgcgtc gatccacctc    8940 gccgacgcgc aggggcggcc ggtcgcgcgc gtggggggcgt tccaggcgcg gcgacgacc    9000 acggagcggg tgcgcgcgct cgcgggcgcg agcgagcgcg atctgcatcg ggtcacgtgg    9060
acggacgtga cgctggacga ggcgccgtgg gcgcacgagg acagcgtcgt ggtcggcggc    9120
gacggcgcgc tggcggcggc gctgggcgtg cgcgcggtgg ccgggttgcc cgagctgttc    9180
gcgggcggcg cggcggcgcc gcgtcgtctg gtgatcgacg cgaccgcggg cgaccccggc    9240
gacggccttg tcgcgcgcga gcacgcggcg acgcagcggg gcctcgcgct cttgcaggga    9300
tggctcgcgg aggcgcggct cgcgtcgacg gagctggtgc tcgtgacgcg cggcgcgacg    9360
```

```
gcggccgagc cggacgaggg tgtggcggcg ctgagccacg cgccgctctg ggggctcgtg      9420
cgcgcggcgc gcgaagagca cccggcgcgc gcgctgcgcc tggtcgatct ggggcgcgag      9480
gcgccggacg gggcggtcct gcgccgggcg atcgcggcgg acgacgagcc ggagctcgtg      9540
gtccggcgcg gggcgctgcg ggcggcgcgc ctgagcctcg cccacgccgc cccggacgcc      9600
gcggggcgag cgacgcggct ggcccccggc ggacggtgc tgatcacggg cggcacgggg       9660
gagctcgggc ggcaggtcgc gcggcacctg gtgacgcgc acggcgtgcg ccatctggtg       9720
ctcacgtccc ggcgcgggat ggacgcgccc gacgccgcgg cgcttgtgga agcgttgcgc      9780
gcggcgggcg ccgcgacggt ggagatcgcg gcgtgcgacg tggcggaccg cgacgcgctg      9840
gcggcggtgc tccgggccat cccggcggcg cacccgctga ccgcggtcgt gcacacggcg      9900
ggcgtgctcg aagacggcgt cgtgacgggg ctctcggccg agcagctcgc gcgcgtgctg      9960
cggccgaagg tcgacggcgc ctggcagctc tacgaggcga cgagggacgc gccgctcgcg      10020
gcgttcatgc tcttctcgtc ggcggcgggc acgctgggca gcgcggggca ggcgaactac      10080
gccgctgcga acgcgttcct cgatgcgctg gcggcagagc tccgcacgcg cggcgtgccg      10140
gcgatgagcc tggcctgggg cttctgggag caaggtggga tcgggatgac ggcgcacctc      10200
ggcgccgccg acctggcgcg gatgaagcgg cagggcatcg taccgatggc ggtcacgcac      10260
ggcctgcggc tgctggatcg cgcgctggag cggcccgagg cgacgctggt gcccctatcg      10320
ctcgacgtgg cggcgctcca gcgcgcggcg ggcgacgccg gacgggtgcc ggcgctgctg      10380
cgtggcctgg tgcgcccggc ggccgcccgg cacacggcgg tgccggcggc cgcggcgacg      10440
ggggcgacag ggctccgcgc gcggctcttg ccgttgtccg aggccgagcg ccaggacgtg      10500
ttgctcgatc tggtgcgcac ggagatcgcg gacatcctcg cgctgtccgg gccagcggcg      10560
gtgcctcccg atcaacccat cagggagctg ggctcgatt cgctcacggc ggtggacgtt       10620
cggagccggc ttgtgcagag gagcgagatc gacctccccg tgaccctcgc gtacgattat      10680
ccgaccgcgc gagcgatcgc tggacatctg agcgagcaga tgggcctcga aggagcgccg      10740
gaagatcggg agtcggcgct cgacgaggcc cagatccgcg ccctgctcat gcagattcct      10800
atttccacgt tgcgccagtc ggggctgctc ggagacctgg ttcgcctggc ctccccgcaa      10860
gcgcccccgc gcgaagaagg cgagagcgag acgttgagct tcgatcacct tggaaatgaa      10920
gagttcctca gcctcgcgtc gaagctcatt gcagaagagg gatcatga                  10968
```

<210> SEQ ID NO 36
<211> LENGTH: 5679
<212> TYPE: DNA
<213> ORGANISM: Sorangium cellulosum

<400> SEQUENCE: 36

```
atgaaccaag agactgttct tcggcagaca ctcgagaaga gtctccacaa gatccagcac       60
ctcaatcggg agctcgagcg tctcaaggcg aagtcgagcg agccgatcgc gatcgtgtcg      120
atggcgtgcc ggtttccggg cggcgtcgat acccccgcgg cgctgtggga cctgctctcg      180
gagggccggg acgcgatcgg gccgttcccc gaggggcgcg gctgggatgt ggcggggctg      240
tacgaccccg acccggacgc cccgggcaag tcgatcacca cgcagggcgg cttcctctac      300
gacgctgacc gcttcgatcc gacgttcttc ggcatcagcc cgcgcgaagc ggagcgcatg      360
gacccgcagc agcggctgct gctcgagtgc gcctgggagg cgctcgagcg cgcgggcctc      420
gcgccccatt cgctcgaggc gagcgccacc ggcgtcttcg tcgggctggt gtacagcgac      480 tacgcgggc ggctgctcga gcacctcgag gtcttcgacg gctacgtcgc caccggcagc       540
```

```
tttcccagcg tcggctcggg gcgcatcgcc tacacgctgg ggctccgcgg ccccgcggtc    600
accgtcgaca cggcgtgctc gtcgtcgctc gtgtccctcc acctcgcgtg catgtcgctc    660
cgcgccggcg agtgcgacct ggccctcgcc ggcggcgcca ccgtgatggc cacgcccatg    720
gccttcatcg agttcagccg acagcgcggc atggccccgg acgcacggtg caaggccttc    780
ggggcggcg cgaacggcat cggccccgcg gagggctgcg ggctcctggt gctcaagcgg     840
ctgtcggacg cgcggcgcga cggcgaccgc gtgctggcgg tcatccgcag ctccgccgtc    900
aaccaggacg gccgcagcca ggggctcacc gcgcccaacg gtccggccca gcaggacgtc    960
atccgccagg ccctggcggc agcggggctc acgcccgccg acgtcgacgc cgtcgaggcg   1020
cacggcaccg gcacgcccct cggcgatccc atcgaggcgc aggcgctgct ggcgacctac   1080
ggcaaggcgc acacagcgga gcggccgctc tggctcggct cgatcaagtc caacttcggc   1140
cacacgcagg ccgccgcagg ggtcgcgggc atcatcaagc tggtgctggc gatgcagcac   1200
gcagagctgc cgaggacgct gcacgccgac cccccgtcgc cgcgcgtcga ctggtcgcag   1260
gggcacgtca agctcctgaa cgagcccgtg ccgtggccgc gcacggaccg gccgcggcgc   1320
gcggcggtct cgtccttcgg cgtcagcggc accaacgcgc acgtcatcat cgaggaggcg   1380
ccggccgaag cgccgacggc cgcgcagacg gcggcagcgg cggcgacaga ccggcggcg    1440
gcggtggtgc cgtcgacgct gccgctgctc ctgtcgggtc gcgacgagcc ggcgctgcgc   1500
gcccaggccg ggcggctcgc cgagcacctg cgcgcccacc cggacctgcg gttgctcgac   1560
gtcgccgcgg gcctggccac gacgcgcacg cacctcgcca cgcggctcgc gctgccgctc   1620
gcgccggacg cagccacgga ggagctgggc gcccgccttg ccgagttcgc cgccggcggc   1680
ccggcgccca gcggcgccgc cgtgaccgcg ccggggcagc cgcccggcaa ggtcgcggtg   1740
ctcttcaccg gccagggcag ccagcgcgcc ggcatggggc gcgccctgta tgccacccac   1800
cccgtcttcc gcgccgcgct cgacgccgcc tgcgccgagc tcgaccgcca cctcgaccgg   1860
cccctcgtga gcgtcctctt cgccgacgcc ggctccgagg ccgcggcgct gctcgaccag   1920
acagcctggg ctcagcccgc cctgttcgct ctcgaggtcg cgctctaccg acagtgggaa   1980
gcctggggcc tgcgcgccca cgcgctgctc ggccacagcc tcggcgagat cgtcgccgcc   2040
cacatcgccg gcgtgctcga cctccacgac gcctccgccc tggtcgccgc ccgcgggcgg   2100
ctcatgcagg ccctccccca cggcggcgcc atggcctcca tcgaggccac cgagcacgag   2160
ctccgacccc tgctcgacca gcacacagga cgcgtctcgc tcgccgccct caacgctcca   2220
cgccagtcgg tcgtgagcgg cgaccagccc gtcgtcgacc aggtctgcgc ccacttcaag   2280
gccctcggcc gacgcgccaa gcggctcgac gtcagccacg ccttccactc ggcccgcatg   2340
gaacccatgc tcgacgcctt cgcccacgtc gcccgcggcc tgacctaccg cgccccgcgc   2400
ctgcccgtcg tgagcaatgt caccgggcgc atggccaccg ccgacgagct cacctcgccc   2460
gactactggg tgcgccacgt gcgcgagccc gtgcgcttcg tcgccggcgt gcgcgcgctg   2520
cacgccaccg cgcgtcaccac ctacctcgag tgcgggcccg acccggtgct cggcggcatg   2580
gccgcagact gcctcacccc ggacgagacc cgcgacgtcg gcctgatccc gagcctgcgc   2640
aaggaccgcg acgaggccct ggccctcgcc caggccgcct gcgccctgta cgtccgcgga   2700
cacgccctcg actggctccg cctcttcgac gccaccgcg cgcgccgcgt cgagctgccc    2760
acctacgcct tcaacgcca gcgctactgg atcgatgcgc cgcggcgcgc ggcggggctc   2820
gacagcgtcg ggctcacggc cgcagatcac ccctggctgg gcgcggcggt gcggctcgcc   2880
```

```
gaccgggacg tccacgtgct gagcgggcgg ctgtcgacgg tcgaccaccc gtggatcctg   2940
gaccacgtgg tggcgggcac gccgctgatg ccaggaacgg gcttcgtcga gctggcgtgg   3000
gcgacggccc aggcggtgga cgccgccgcg atcgcggagc tcaccctgac gacgccgctc   3060
gtgttgccgg cgcgcggcgc ggtgcagctc caggtgacgg tcgacgaggc cgacgcgaat   3120
ggccggcggg cattcgccat ccacagccgg ccgcatggcc ccggcgacct cgcgtggacg   3180
caacacgcga ccggcgtgct gagcgcggag gagccggcgg gagccgacga ggcggcgggg   3240
ctctcggagt ggccgccgcc gggcgcggag gcggtggcgc tcgacggcgg gtacgagcag   3300
ctgtccgagc acggctacgg ccacggcccg gcgttccagg ggctccgcgg gctctggcgc   3360
gcggaccgta cgctgtacgc gcacgtcgcg ctgccggacg ctgtcgcggg caccgagcag   3420
ggcttcgggc tccatccggc gctcttcgat gcggcgctgc agtcgctggc gcggctgtcg   3480
cgcgaggaag cggccgctgg cgacccggtg ctggtgccgt tcgcgtggac ggacgtggcg   3540
ctgtacgcga ccgggcgcgac cgagctgcgg gcgcgcatcg cgctggagca ggcggagggc   3600
ggcgcgccgg cggtggcgtc gctgctgctg gccgacgcgc acggacgaac cgtggcgacg   3660
accgggcggg tgcgcggggc gagcgcgcg cagacgcggt ccgccgcgag ccgcgcggag   3720
ccgatgtacc gggtcgcgtg gacggacgtg gcgctggagg cggcgacgtg ggcgcccgag   3780
gagcacgtcg tgctcggcgg tgacggtgcg ctcgcggcgg cgctgggcgt gcgcgcggcg   3840
gccgggctgc cggagctgct cgaggcgctg gcggacggcg cggccgcgcc gcggcggctg   3900
gtcgtggacc tgacggcggg cgatgcaggc gcggtcgtcg cggccgtgca cgccgcggtg   3960
cgcggcgcgc tggccctggt gcaggggtgg ctcgccgcgc cgcagctggc ggcgacggag   4020
ctcctggtgg tgacgcgctg cgcggtggcg accgggccgg acgagggcgt ggacgcgctg   4080
gggccggcgg ccgtctgggg cctgctgcgg gccacgcgcg ccgagtaccc cgaccgcgcg   4140
gtccgggtgc tggacgtggg gcgcgagccg ctggacgggg cgctcttgcg tcgggcgctg   4200
gccgcgggga cggagccgga gctttcggtg cgcagcggcg aggcgcgcgc gccgcgcctg   4260
cgcgaggtgc gcgggagcga gccggccgcg gcgccggcga cgcggctgga tcccgacgga   4320
acagcgctga tcacgggcgg caccggggag ctcgggcggc atgtcgcgaa gcacctggtg   4380
acggcgcacg gcgtgcggca cctcgtgctg acgtcgcggc gcgggatgga cgcgcccgac   4440
gccgcggcgc tggtggacga gctgcgcgcc gcggggcgcg cgacggtcga cgtcgccgcg   4500
tgcgacgcgg cggacgcagc ggcgctggcg gcggtggtgg aggcgatccc ggcggcgcgt   4560 ccctgacgg ccgtcgtgca caccgcaggt gtgctggacg acagcgtcgt gaccaagctc   4620
tcggccgagc agctggcgcg cgtgctgcgg ccgaaggtcg acggcgcctt tcatctccac   4680
gagctcacga agcacgcgcc gctcgcggcc ttcgtgctgt tctcgtccgc ggcgggcacg   4740
ctgggcagcc cggggcaggc gaactacgcc gcggccaaca cgttcctgga cgcgctcgcg   4800
tcgcacctgc gcgcgcgcgg cgtgcccgcg atgagcctcg catggggctt ctgggcgcag   4860
actgggctcg gcatgacggc gcacctcggc gccgccgaca tcgcccggat gaagcggcac   4920
ggcgtcgtat cgatgcccgt cgcgcagggg ttgcggctgc tcgatcgcgc gctcgcgcag   4980
gccgaggcga cgctggtgcc gctcgcgctc gacctctcgt cgctgcaacg cgcggggagc   5040
aacgccgggc cggtgccgcc gctgctgcgc gggctcgtgc gcgcaccggc cggccggcgc   5100
acggcggcgt ccgctgctgg ggcgaacggg aacgggacgg gagcagcggc gctgcgcgcg   5160
cggctctcgc ccttgcccgg ggccgagcgc cagaaggtgc tgctcgatct ggtgcgcacg   5220
gaaatcgcgg aggtgtttca gttgccgggc cctgcccaca tccctgcgga caggccgctg   5280
```

-continued

```
aaggagctgg ggctcgactc gctcatgtcg gtggagctgc gcaatcgcct gggcccgcgc    5340
gtcgaggcgg cgctgcccgc gacgctcgtg ttcgactacc ccacgcccgg ggccattgca    5400
tcctatctgg gcacgttgct caacctctcc ggcgaggacg cacacccggg ccaaacgggg    5460
cgcgacccgg acgaagaaca cgagatccgg gccgcgatag cgcgcatccc gataacaacc    5520
ttgcgcgagg cagggctcct ccagagcttg ctccgactcg cccccaacca gacgcgtcc     5580 gatgacgtca cgccgaggac tgatgagctg atggtcgaac acctcggaga tgaagagctg    5640
ctgaagcttg ctttcgcgtc caccggagga gccaagtga                          5679
```

<210> SEQ ID NO 37
<211> LENGTH: 10524
<212> TYPE: DNA
<213> ORGANISM: Sorangium cellulosum

<400> SEQUENCE: 37

```
gtgaaggacg aggtgctttc gttccgccgc gctttggaga agacggtcgt cgagatccgc      60
cgcctcaaca cggagatcga cggcctgcgc gcgaagtcgg tcgagccgat cgcgatcgtg     120
tcgatggcgt gccgctaccc gggcggcgtg gacagccccg cggcgctctg gcagcttctc     180
tccgaggggc gagacgcgat cgggccgttc cccgaggggc gcggctggga cgtggcgggg     240
ctgtacgacc ccgacccgga cgcgccgggc aagtcgatca ccacgcaggg cggcttcctc     300
tacgacgccg accacttcga tccgatgttc ttcggcatca gcccgcgcga ggccgagcgc     360
atcgacccgc agcagcggct gctgctcgag tgcgcctggg aggcgctcga gagcgcgggc     420
atcgcgcccc acacgctcgg cgcgagcgcc acgggcgtct tcatcggact gatgtacacg     480
gagtatggcc tgcggctgat gaaccagccc gaggccctcg acggctacat cggcatcggc     540
agcgccggga gcacggcctc cgggcgcatc tcctacacgc tggggctccg cggccccgcg     600
gtcaccgtcg acacgcgtg ctcgtcgtcg ctcgtgtcgc tccacctggc gtgcacggcg     660
ctccgccgtg gagagtgcga cctggcgctg gcgggcggcg ccgccgtggt gtcgacgccg     720
gccccgttca tcgagttcag ccggcagcgg gccctcgcgg tcgacggtcg atgcaagtcg     780
ttcggcgccg ggccgacgg cgtgagctgg tcagagggtt gcgggctgct cgtcctcaag     840
cggctgtcgg acgcgcagcg cgacggcgac gcgtgctgg ccgtcctccg cggctccgcc     900
gtcaaccagg acggccgcag ccaggggctc accgcgccca acggcccggc ccagcaggac     960
gtcatccgcc aggccctggc tgcggcgggg ctcaccccgg cggacatcga cgcggtggag    1020
gggcacggca ccggcacgcc cctcggcgac cccatcgagg cgcaggcgct gctggcgacc    1080
tacggcaagg cgcacacagc agagcggccg ctctggctcg gctcgatcaa gtccaacttc    1140
ggccacacgc aggccgccgc aggggtcgcg ggcgtgatga agctcgtgct ggcgatgcag    1200
cacgcagagc tgccgaggac gctgcgcgcc aacccgccct cgccgcacgt cgactggtcg    1260
caggggcaca tcgcgctctt gaatgagcca gcgtcgtggc cgcgcacgga ccgaccgcgg    1320 cgcgcggcg tctcgtcctt cggcgtcagc ggcaccaacg cgcacgtcat catcgaggag    1380
gcgccggcgc ccgccgcgga ggtgacgagc cctggagcag agccgcccgc tgtcgcgctg    1440
ccgctgctgg tgtcggggcg ggatgacgcg cgctcaggg cgcaggcgga gcgctgggcg    1500
gcgtggctcg cggcgcaccc ggaggcgcgc tgggcggacg tggtgcacac ggccgccgtg    1560
cggcgcacgc acctggaggc gcgcgcggcg gtgacggcgg cgagcgccgc cgacgcggcc    1620
gcggccctga cggcgctctc gcaagggggag ccgcacccccg cggtgaccgc gggcgaggcg    1680
```

-continued

```
cgcgcgcgcg gcaaggtcgt gttcgtggct ccgggccagg ggagccagtg gccggcgatg      1740
gggcgggcgc tgctggccga gtccgaggtg tttgccgccg cggtcgcggc ctgcgacgcg      1800
gcgctgcggc cgttcaccgg ctggtcggtg ctctcggtcc tgcgcggcga gcagggagag      1860
gcggtgccgc ccgcggaccg cgtggacgtg gtgcagccgg cgctgttcgc gatggccgtg      1920
gggctctcgg cggtctggcg ggcgtggggc atcgagcctt cggcggtcgt cggccacagc      1980
cagggcgagg tcgcggcggc gtacgtcgcc ggggcgctga cgctcgagga cgcggcgcgg      2040
gtcgtggcgc tgcgcagcca gctcgtgcgg cgcatcgccg gcggcggcgc gatggccgtg      2100
atcgagcgcc cggtcggcga ggtggagcag cggctctctc gcttcggagg gcagctgtcc      2160
gtggcggcgg tgaacacgcc gggctcgacg gtggtgtccg gggacgccgc agcggtcgat      2220
cgcttgctgg ccgagctgga gcacgaggag gtcttcgcgc ggcgggtcaa cgtcgattac      2280
gcgtcgcaca gcgcgcacgt ggacgcgatc ctgccggagc tcgaggcctg cctggcctcg      2340
gtcgagcccc gtgcctgcgc catcccgctg tactcgacgg tgacgggaga agtgctcgcc      2400
ggcccggagc tcggcgcggc atactggtgc cgcaacctgc gcgagccggt gcggctcgac      2460
cgggcgctct cgcggctgct ggcggacggg cacggggtgt tcgtcgaggt cagcgcgcat      2520
ccggtgctgg ccatcccgct gacggccgcg agcgccgagc gcggcggcgt tgtggtgggc      2580
agcttgcagc gcgacgacgg cggcctgggg cgtcttgttt cagcgctggg cgcgctgcac      2640
gtccaggggc attcggtgga gtgggccagg gtgctcgcgc gtacggcgg caacctggtg      2700
gacttgccga cgtacgcgtt ccagcggcag cgctactggc tcgaggcgtc gaggagccgg      2760
atcgacgcga gcgacctcgg gctcgcggcg acgggccgcc cgctgctggg cgccgcaacg      2820
cgggtcgccg gcacggacag ctacatcctg gcgggtcggc tgtcgacagc ggagcacccg      2880
tggctgtcgg gacaggtcgt cttcgagcgg acgctgttcc cggcgacggg gtttctggag      2940
ctggcgctcg aagccgctga cgcgatgggg gtggcggggg tgaccgagct ggtcgtgccc      3000
gctccgctga tcttgccggc gcggggtgcg gtgcacgtcc aggttgcggt ccagggacca      3060
gacgaggcgg gacgccggcc gttttccgtg tacagccgcg cggaaaccgc ggggctggac      3120
gcggaatgga cgctgcatgc cacggggctg ctcggggag cgcgcgccag tgcggcggcg      3180
gacacgggcc tcgaggcgtg gccgccggag ggagccgcgc cggtggacgt cagcgacgcc      3240
tatgcgcggc tggaggacgc cggcgtgcgt tatgcgccga gcttgcgagc gctcgtggag      3300
gcctggcagg cggagcggcg catctatgcg cgcgcggtgc tgccgggcgg cgcgacgcag      3360
ggccacgggc tccacccggc gctgtgggac gcggcgctgc acgcgctggc gctggtggtc      3420
ctcgggcagg acgcggagca cgcgggcgtg ctgttgcccc gggcctggtc ggacgtgacg      3480
ctcgcggcgc aggggcgac cgagctgcgg gtgcgcgtcg agctcgcgga cgcggacgcg      3540
gagcacgtgt cggcgtcgct gacgatggcc gacgcggacg gtcaacccgt ggcgacggtg      3600
gggtcggtgg aggtgcgtcg cgcgaccgcg gcccaggtgc gcgccatgag caccgcgacc      3660
cagcacctt acggggtcga gtggaaggcg gtggcgctgg cggagccgcc gcggtctgcg      3720
ggggagcagg tcgtgctcgg accggacggc gagctcgcga caaggctggg cgcgcgacgc      3780
gccggcaacc tcgatgagct gtttgccgac ggcgaggcgg cgcgcccgc gcccaggcgg      3840
ctcgtggtcg acgcgcggac gcgccgcgac ggcgacgtgc ctgcggctgt gcaccaggcg      3900
acgcgccagg ccctcgagct cgtgcagcga tggctggcgg acgcgcgact gacggacacc      3960
gagctcgtgt tgctgacgcg cgaggcgtg tcgaccggcc cggacgtggg ggtcgaagac      4020
ctgggccacg cggcgctctg gggattctta cgcgcagtgc ggagtgagca cccggaccgc      4080
```

```
ggggtgcgcc tcatcgacct cggacctgac gcctctgcgg cggagctgct cgacagggcc    4140
ctcgagaccg tggcggagcc cgagctggcg ctccggcagg ggatcgcgct ggcgccccgg    4200
ctcggtgtgc tcgtgatcg cgccggcgcc ccggcgccga tgcggctgga cccggacggg    4260
acggcgctga tcaccggcgg caccggggag ctcggcggc atgtcgcgaa gcacctggtg    4320
acggcgcacg gcgtgcggca cctcgtgctg acgtcgcggc gcgggatgga cgcgcccgac    4380
gccgcggcgc tggtggacga gctgcgcgcc gcgggcgcgg cgacggtcga cgtcgccgcg    4440
tgcgacgcgg cggacgcagc ggcgctggcg cggtggtgg aggcgatccc ggcggcgcgt    4500
cccctgacgg ccgtcgtgca caccgcaggt gtgctggacg acagcgtcgt gaccaagctc    4560
tcggccgagc agatggcgcg cgtgctgcgg ccgaaggtcg acggcgcctt tcatctccac    4620
gagctcacga agcacgcgcc gctcgcggcc ttcgtgctgt tctcgtccgc ggcgggcacg    4680
ctgggcagcc cggggcaggc gaactacgcc gcggccaaca cgttcctgga cgcgctcgcg    4740
tcgcacctgc gcgcgcgcgg cgtgcccgcg atgagcctcg catggggctt ctgggcgcag    4800
gctgggctcg gcatgacggc gcacctcggc gcggccgaca tcgcccggat gaagcgcctg    4860
ggtgtcgtga cgatgtcgcc gcaagaaggg ctcgagctgc tggacgcgtc gctccagcgg    4920
ccggaccccgc tgctggtgcc ggcgccgctc gatctcgccg cgctcgagcg agccgcgcgc    4980
gagggcgcgc ccgcttcgcc gatgctgcgc gagctggtgc gcggcgcgcc cgcgcggcgc    5040
gccgccgcgg gcgacggcgc gagcggcaag gcctcggcgc tgcgcgcgct cctggcgcga    5100
cggcccagea gcgaacgatt cgcggcggtc ctcgagctcg tcagggcgga ggcggcgcgc    5160
gtgctccggc tgccggggc cgcggcagtg ccgccagatc ggccgctcaa ggagctgggg    5220
ctcgactccc tcaccgcggt cgagctgcgg aaccggctgg cggcgcggac ggaagccaag    5280
cagccggcga cgctcgtctt cgaccatccg acgcccagcg ccatcagccg attcctgctc    5340
aagcaagccg cgctgatct cgctccgagc gaggccgcgg cgagcctcgc accgagcagc    5400
cgacgtgctc ccctggatga gccgatcgcg atcgtcgcca tggcgtgtcg gtgccccggc    5460
ggagtcgata gccccgaggc gctgtggagg ctgctctccg agggacgcga cgcgatcggc    5520
ccgctcccgg aggagcgagg ctggagcgtg gagcagatcc tcggccgtga tccgggcgcc    5580
tcgagcaaac cgttcagcgg ccggggtggc ttcctctacg gcgccgacca gttcgacgcc    5640
gagttcttcg ggatcacccc gcgcgaggcc aggttcctcg acccgcagca cgccttgctc    5700
ctcgagtgca cctgggaggc gctcgagcgc gcaagcatcg tcccgcagtc gctggaaggg    5760
agctccacgg gtgtgttcgt gggcatggtg ggcggcatgg ccgctggtca cggctcggta    5820
tcgagcgagg gctatgcgct caccgggacc gcgttgagca ccgcctcggg gcgtatttcc    5880
tacgcgctcg gcctgcaggg cgcggcggtg acggtcgaca cggcgtgcag ctcgtcggcc    5940
gtggcgattc acctcgcgtg cacgtcgttg cggaccggag agtgcgatct ggcgctggcg    6000
gggggcgtga ccgtcatggg caggcccgag atcttctcgg agttcggccg gctcgacatc    6060
ctcgcctcgg acgccgatg caaggcgttc ggggccacgg ccgacggcgt cggctggggc    6120
gaaggctgcg gggtcttgct gctgaagcgg ctgtcggacg cgcagcgcga cggcgaccgg    6180
gtgctcgcgc tgatccgcgg ctcggccgtc aaccaggacg gccgcagcca ggggctcacc    6240
gcgcccaacg gcccgagcca ggaggcggtc atccagagag cgctggcgtc ggccggcctg    6300
acggcggcgg atgtcgacgc cgtcgaggcg cacggcaccg gcacgcgcct cggcgacccg    6360
atcgaggcgc aggcgctgct ctcgacctac ggccaggccc acgccgcggg gcagccgctg    6420
```

```
tggctcggct cgatcaagtc caacctcggg cacacgcagg ccgccgcggg ggtcgcgggc   6480
gtgatcaaga tggtgctggc gatgcagcac gggcagctcc cgaggacgct gtacgccgac   6540
acgccctcgc cggacatcga ttggtcgcag gggcacgtca ggctcctggt cgacgccgtg   6600
ccgtggccgc agagcgcgcg gcggaggcgc gcgggcgtct cgtcgttcgg catcagcggc   6660
accaacgcgc acatcctcgt cgaggaggcc ccggaaccgc cgcgggcggg ggccgcgccg   6720
gaagcgccgg tgacgctgcc ctttctgccg ctgctggtct ccggccgcga cctcgcggcg   6780
ttgcggtcgc aggcagcgcg cctcgccgcg cacctgcgtg agcgccccga ccagcggctg   6840
gtcgacgtga cggcgagcct tgccacgacg cgcacgcacc tcgccgcgcg gctggcgctg   6900
ccggtcgccg cgaccgctgg acgcgacgag atatgcggcg cgctcgacgc gttcgcggcg   6960
cgggggctgg ccttgaacgg cgcgtgggtc acaccggcgc aacaccgcgc cggcaaggtc   7020
gccgtgctgt tcgcggggca gggtgcccag cggcccgcga tggggcgtgg cctctacgag   7080
gcgctgccgg tgttccgcga ggcgctggac gaggtgtgcg cgcgcctcga cgctcacctc   7140
ggcgcgcccc tgaaggacgt cctcttctcc gccgagggct ccccggaagc gagcacgctg   7200
caccagaccg gatgggcgca gccggcgctg ttcgcgctgg aggtggcgct gtaccggcag   7260
tgggaggcct gggggctgcg gcccgacgcc ttgatgggcc acagcctcgg cgagatcgtg   7320
gcggcgcacg tggctggggt gttcgacctc gcggacgcgt gcgcgctgat cgcggcgcgc   7380
gggcggctga tgcaggcgct gccgacgggc ggcgcgatgg cctccatcga ggcctccgag   7440
gacgacgtgc ggccgctgct cgatgcccag cagggacggg cgtcgctggc ggcgctcaat   7500
ggcccgaggc agaccgtcgt cagcggcgac gaggacgcgg tcgaggcggt ctgcgaccac   7560
ttcaaggcgc aggggcgccg cgtcaaacgg ctgacggtca gccacgcgtt ccactcggcg   7620
cgcatggagc cgatgctcga agcgttccgc gcggtcgcgg cgacgttgac cttccgggcg   7680
ccgcagatcc cgatcgtgag caacgtcacg ggcgagcggg cgccggtcga ggcgctgacg   7740
tcgcccgact actgggtccg gcaggtgcgc gaggccgttc gctggacgga cggcgtgcgc   7800
gcgctcgagg cggacggcat caccacctac gtggagtgcg gcccgatgg ggcgacgtgc   7860
gcgatggcat cgcagtgcgt gacgcgcgct gcgaaggccc ccgcgttcgt ctccagcctg   7920
aaccggaagg gcgacgaggt tcaggcgctc gtcagcgccg cctgcgccgt tcatgttcgc   7980
ggcgactccc tcgactggag cgcattcttc gcgggctcgg gcgctcggcg ggtggagctg   8040
ccgacctacg cgtttcagcg acggcgatac gggggtggacg agccgagccc tcgcccccgcg   8100
gaggtccggg ccccggatac cacgcggacg cgcgtgcacg tgagcgcgga cgatccgacg   8160
gtccgcgggc acgtcgtcgg ctcgcagacc ctctaccctg ccgccagcta catcgacctc   8220
gcgctccgtg tcgccgcgag cgccgggcag gcctgtgtgc gcgccgcgaa catggcctgg   8280
ttcgcccccg ccatcgtgcc gcccgagggc ctgtcgctcg acgtccagct acgacgcacg   8340
aaggctggcc tcgaatgcga ggtctccagt ggagactccg accagcggac catccatttc   8400
cagggcaccc tgctcggcgg cgatcccgga ccgtggccgg cggtcgacct ccgacggatc   8460
atcggagagt gctctcttcg tctcgacagg gcccacctct acggcatctt cgcaaactac   8520
ggattcggct acgaccgggc tttccagtcc gtcgcgtggc tcgtcagcaa cgcgaacgac   8580
gtggtggggc gcgtggagct gccggcgtcc gagtccgcga ccgccgagca ccacctccag   8640
ccgaacctgc tcgacggcgc cttccagacc atcatcgggc tcgacgcggt gagcgcgctg   8700
agcgggccca cgcccgacgc gggcttcaac ttcgtgccgt ccgccatcca ggatgtgcag   8760
atcttcgggc gccttcgccg cgctgcgtac gttcacgcga cccgacgcgg caaggcgcac   8820
```

-continued

```
ggctcgccct cgtgcgactt ccagctcctc ggcgagaacg gcgagccgat cgcgctcgtc    8880
acgggcctga cgttccgcaa gctccggtcc cgagctgagc tcgacgcgcc ctccgcgccc    8940
gcgcagagac cgagcaacgg agaggccgct cgcccagga acgtgccagc tcctgccaat     9000
gtgccagctc ctgccaacgt gccagctcct ggcggtgacc acgccgacgc gtctcctcgc    9060
gcgccgtcgg cggaggtgct gttcttctcg cccgcatggg tcccgagaa gcccgtcatg     9120
gccgcctccg tgacgggaga catcgtcgtg ttcggggacg acgacgcgca gatcacccat    9180
ctccggggc cctgccgct ggctcggctg attcacgtcc gctccggacc gggctttcag      9240
cgcaccggtc ccgccgccta cgcggtccga cccgacagcc aggaggatct ctccgcgctc    9300
tttaccgagt cgacgacgc tcggtcgaag tcgcttcggg cccttttatct ctgggagccg    9360
tcccgccgcg cggccgaggg ctcggcgccc ccgggcgacg gcgacgtcgc ggcggcgatc    9420
cgatcgttgt tctgcctctt caaggctcac atggccgagc ggcgaaaagg gatgcagctc    9480
ctctatctca cgtcgtcggc gacgagcgca gtgccggtga acgaagccgt gctggcgttc    9540
ttccggacca tccgcacgga gaacccgacg tatgtgggca aggtgatcgc cgtggccgat    9600
ccgggtcaca tcggccgcgc ctgcgccacg gagctcggcc tcccgaccgg cagcgacgtg    9660
gtccagcatg tcgacggcgc gcgccacgtc cggaagctct tctcgcgaga gccggccct     9720
cgggagcgcc tgcgagacgc gctcccgctg gcgccgggcg gcacgttcgt cctgaccggc    9780
ggcgcaggca agatcggcct gctcctgacg gacatgctgg tgcgggagta ccaggtgaac    9840
gtcgccctca tcggtcgctc gcagctcgac gagcccggc gacaggccat cgacagcatc     9900
cggtcaggtc ctgcccgggc gctctactac tcggcggacg tcggggtgct cagcgacacc    9960
gagcgggcca tcggagagat ccgcgagacg ctcggcccca tccgcggggc gatccatgcg   10020
gcggcgatca tccgcgacag cttcttcatc aagaagaccc tggcggaggt cgacagcgtg   10080
ctgcgaccga aggtcaacgg cgccatctac ctggacttcc tcctgcgcga cgatccgctc   10140
gaggtgttcg tcttgtgctc gggcctggcc tctctcctgg caatcaggg gcaatcggac    10200
tacgcggccg cgaacgggtt cctcgatgga ttcgcgatcc agcgcgaagc gctccggcaa   10260
gcaggccgac gtcaggggcg aacaatctcc atcaactggc cgttgtgggg gggcgacgga   10320
ggcatgggcg tgccagatta catcgagacc gagctcctga gcggggact cgtgccgctc     10380
gacatcagcg acggcgtgac ggcgtttcgg caagcgatcg ccatgaagga gccgcaggtg   10440
gcggtcgtcg ccggacagag ggccgcagca cggcggctcc tgcgcccgtg gctttcagag   10500
gggcgaacgg aggatcatca atga                                         10524
```

<210> SEQ ID NO 38  
<211> LENGTH: 6594  
<212> TYPE: DNA  
<213> ORGANISM: Sorangium cellulosum

<400> SEQUENCE: 38

```
atgacaagct ggttgctggc gaagacggag gaatttctcg ggacctggt ctccgaggtc        60
agtgagatcc gccgggacac gatctctccc gacgctgact tccaggagtt tggtctcgac      120
tctcgcttcg tcatcgcgat gaactcgagg ctggagcagt attttccgg cctgcctcgc       180
acgctgttct tcgagtaccc gtccatccgc gccgtcgcca gctacctggt cgaagagttt      240
caagaccagc tccacgagct ctttcccgac ggcgagccag ccgagcgtc gcgacctgcg      300
cagagcgtgc cggtcgcccg acccagcggc gccattccta gcggcgcttc gcccagcggc      360
```

```
gcttcgccca gcggcgccat ccccagcggc gcttcgccca gcggcgccat ccccagcggc    420
gcttcgccca gcggcgccat ccccagcggc gcttcgccac agacctccac gagctccgcg    480
gccgatctct ccgatctcgc ttccctgatc cagcagatcc cgctcccgga agcggtcctg    540
tcgagcgtcg agcgtccccg ggtcgaccct cggccggcgg cacccgctcc ctctgtggtc    600
agagcgtcat ccggcgacca gagcggcgat gacatcgccg tgatcggggt ggcgggcaga    660
tacccgaagg caagaaacat cgaggagttc tggcgcaatc tgcgcgaggg ccgcgactgc    720
atcgaaccgt tgccgaagga gagatggagc ccggatccgt cggacccgct ccgctggggc    780
gggtatctcg acggcgtcac cgatttcgat tcgctcttct tcggcatctc gccgcgtgaa    840
ggagaaggga tggaccccca ggagcggctc ttcctggagg tcgcctggga gaccatcgag    900
agcgccggct acgaccccct caggctgggt cgcagcggag agccagcgtc cgtcggcgtc    960
ttcgtgggtg tcatgtacgg cgaatatcag gtctttggcg cagagctgac gctcctcggc   1020
cagccgaccc tggtcagctc ctcgtacgcg acgattccga accgcgtctc gtacttcctg   1080
aacttcagcg gcccgagcct ggccctggac acgatgtgct cgtcgtccct gacggcgctt   1140
cacctcgcgt gcgcgagcct gcgctcagga gactgcaaga tggccctggt cggagggacc   1200
aacgtcacga tccatccaaa caagtaccgg ctgctggaag ctgggaagta cctggcgagc   1260 gacgccggt ccggagcta cggcgcgat ggcgacgggt atgtccccgc cgagggcgtc   1320
ggcgcagtgc tcatcaagcc cttggccgac gctcgccgag acggcgacac gatctggggc   1380
gtcatcaaga gcacgagcat caaccatggc gcgcgcgcgc gcggctacac gaccccccaat   1440 cccaacgcgc aatcggcctc cctgtccctc gcgctggagc gcgcgaagat cgagccgcac   1500 acgtcggat acatcgaggg tcacgggact ggcacgtcgc tgggtgatcc gatcgagatc   1560
cgcggcatcc agaaggccgt gggccgtgtt tcggagaaga tcccgatcgg ctcggtcaag   1620
tcgaacatcg ggcacgcgga gtctgccgcg ggcgtcgcgg gcctcacgaa ggtgctcttg   1680
cagcttcggg cgcgggagct cgttccctcg atccactgcg agcccccgaa cccgaacatc   1740
gacttcgaca gggcgcccat ccaggtgcag cggcacgccg ctccctggaa ccgcaggacc   1800
atcacgtcgg gtggggtcac tcgagaggtc ccccggcggg ccgtcgtctc cgccttcggt   1860
gcgggaggca gcaacgcgca cgtcgtcgtc gaggaggccg acgcgccggc gctgcaacgc   1920
accgtgtccg cacagcctcg gttgttcgtc ctgtcggctc gttccgtcga gcggctccgc   1980
gcccacgcgc agagctttct cgacttcttc tcgaggatgc cgaccctcag ggaggccgag   2040
gcgagggagc tcttctacga tatgtgcgcg acgctgtact tcggccgcgc tccgttcgag   2100
gcgcggcttg ccatcgtggc cgagagtctg cggacgttgc agcaaaagct cgccgcgttc   2160
gtttacggcg cctcgcgaga cccggacatc ctcgtgagcg atgggcgatc gctcgcggcc   2220
acggacggcg ggcagcgtca gctctctggc ctcgccgatc tggggcggcg ctgggtcgcc   2280
ggagaggcgg tcgacgcgag cgagctgttt ccgcatccct ggaagaagct ggcactgcct   2340
acctatccgt tcgaacggcg gcggctgtgg gcgccttccg agagaagct gtacgatctc   2400 agatccgccg cggcgccggc tccggcggct ccaccaggga acggggcttc accgagggag   2460
gtcccagcga acgtgccacg ggcggctcgt acggacaccg cagagacagc cgtcgtgagc   2520
ggtccgcagc acgcacggat cgcgccggcc gagcggaggc tcgccgtggc cgagcaggtg   2580
atcgaggtgg ccgagcgccc ctcaccccct gaccggggcc cgtcgacgag cgagacgcgg   2640
gggagcgaga gcgatccgca cgtcacgagc acgttgaacg gccacacgag cgcgttgaac   2700
ggccacacga gcgcattgaa cggccacgcc gcgcgagcga caggtcccga acgcccggcg   2760
```

```
gcggccgttc aggcagcaga tcaggggcg gccgtcgaga tcgtccagga gatggtccgc   2820
gatctcgtgg cgcagatcct cttcgtcgac cgctccacca tcctgcccga cgcggcgctg   2880
ttcgattatg gcctcgagtc cgtcagctct gtcgagctcg cggagcgcct caacgcgatg   2940
ctcggcacgg acatcacgcc gacgagcttc tacgagttca acacgctcgc acatttcagc   3000
cgtcacctgg tcgagcgcta caacctcgcg gaccggctct ccggtctgag cgccggtctc   3060
gccgggggga gctccgctcc cgcgggcccc tccggtcgtg gtgattcgcc gccacgagcg   3120
gccgccggag ccgagggccc cgtggtcggc gcagcggccg ccgagggcgc tgccgcgcct   3180
gcggcaggcg gacccaccgt cgaggagctc tgggccagcg cgatgcacgc cgaagggctc   3240
gcggcgctcc cgagcccga gccccggcgc tcggcctcca aggctccacg cccggcgccg   3300
cccgttcagc cgtcggatca ggccacgccc gtcgagatcg tccaggagat cgtccgcgat   3360
ctcgtggcgc agattctctt cgtcgaccgc tccaccatcc tgcccaccac ggcgctgttc   3420
gattacggcc tcgagtccgt cagctctgtc gagctcgcgg agcgcctcaa cgcgatgctc   3480
ggcacggaca tcacgccgac gagcttctac gagttcaaca cgctcgcaca tttcagccgt   3540
cacctggtcg agcgctacaa ccttgcggac cggctctccg gctgagcgc cggtctcgcc   3600 gggggagct ccgctcccgc gcgggccagc gcgcctcgcg cccaagggcc cgcggcgctc   3660
tcgagctccg agccccgacg ctcggacgcc gggatcgagc tgcacgtgat ccctggcgtc   3720
gacggacacg ccgtggagtt cgccacgctc ggctcgggcg taccgctctt cgtgctcggt   3780
ggcctgctgg cgacccatga tgcgctgacc ttgaacccgg atatcctgtc gctcgggcag   3840
acctaccggg tgatcatggt gcatccgcct ggcgcaggcc ggagcgagct gccgcgcggc   3900
gagctcacga tggatttcat cgtgcggcag gtcgaaggcg tgcggcagtc cctcggcctc   3960
tcgtctgtcg tgctggtcgg ctactcgttc ggtggcctcg tcgcgcaggc ctacgtcgcg   4020
cagtttcccg agcgggcgtc gaagctcgtc ctggcgtgca cgacgtcgga cccggcgagc   4080
gtcgtgaacg gcatgcacct cgtcgcggcc gaagcgcagc gccacccgga cggcctccgg   4140
gcgctgcagt tcgccgacgt gagcaagttc ccgctctact cccagctcag cacgcggctc   4200
cggccggaga cgctcgctta ccccgccatt ccgaccctga tcgtggcggg agccgaggat   4260
cggtacgtgc cgaccatcca cgccgaacgg ctcgcgcgcg ccaatcccaa cgcgacgctc   4320
cacatcgtcg agggcgcggg gcacttcctc ggcctgtctc acggtggcgt gctggtccac   4380
ctcgtgaatg gcttcgtgct cggggacagg accgctccgg cgaggtctcc tgcggtcagc   4440
gcctcgcggc gcggtgggtt gcgcaagatg agccaggagt cggtcggcgc gctgaagagc   4500
tacctggaag agggagagat cgcttcgggg gtggaggcct cgcccgtcgc gggtcaggtc   4560
ggctatttgc tcaaccggct cctgagcgga caggaagcgc cgagcagccc ctaccactgc   4620
ttcttcatgc cgtccggcct cgaggcggtc gacgcagcgc tgcggttcgg acgccgtcgg   4680
gcaaagctct ccaggggcct cggcgacgcg aagacgctcg tcctcgatcc cgagggagct   4740
ctccgccgga atttcgagtt cctcccgcag gagcggctct tccccgatct gatcttcgtg   4800
ggcgaatcgc gcgagctgct ccggctgctg cagagcgccg aggacgtcgg cgccgcgtac   4860
gtcaccacgg catgcgatga cgccacccctc gagacggtcg cggcggagtg cgcccggcgc   4920
gggatcgtgt cggtgctcgg agagctgcac gcggacaccg cgcagctcgt ctcggcgagg   4980
ctgcgctcga agcctgacgt cgtggtgctc gacgaggcca tcgctggttt cgagctgccg   5040
ttcggcgtgt gcgcgatacg gcgcttccat gagagcggcg tgtggacgcg ccagcccgag   5100
```

```
gagttcgcgg tgcgagtccc ggggtcgatg gcggggcccg cgctgaccgt cgtgagggag    5160
aacatcctgc ggcgattccg cgccgtcgtg acgaacgaca ccaccgcgaa cctgcgcgcg    5220
atcgccgtgg atcaacggcg cacgaaggag gctcaccgga gctatgtgaa ccccgtgctc    5280
ctggagtcgc tcgacgcgtt cggactggcg ggccggcaaa ggcacgcgga ccgacgcggc    5340
tatgagatcg agcgagatga cggaagctcg gcccgggtca tcaacctgta cctcgtgacg    5400
agcgcgtcgt ttcgagggca caccggctcc gagatcgcgc agtcggtcct gggcacccac    5460
gacatcacga gggactactg ggcggatctc gagcggcgca taccgcgcga acggacttc     5520 gggcgggtct ttcccgcggc gggccccgcg acggcggtcg agacggcggt gaagctcggg    5580
ctgctcgccg cgaggaaggg ctcggcgctg ctcgtcctca aggggagccc catcttcacg    5640
cggctcgggg cgttggtctc gcacgcggag cccggctcgc cgctggaggc cctcgtggag    5700
agctgcccct tggtccaagt gatcgccgtc gatccgttcg gcgaaggcgc ggccgccgag    5760
ctcgaagcga agctgacgtc ggacgacgtc ggattcgtct ggctcgagac gctgcagtcg    5820
gactggggtg gtctacggag cgttccggat gccgtgctcg aggtgatcga caggcatcgg    5880
gagcggtcgg gataccctggt gggcgtcgac gagacctaca cgagcctggg ttgtggccgg    5940
atgtttcact ggcaaggcaa gctcgcccgc cccgatgtcg tcgcggtgtg cgtgggctgg    6000
acggactgcc agtcctggc gggctacgtc ctcaccaccg aagaggtcgc ggcgcgcgcg    6060
cggcagcgca acgaggcggt ggtctccgcg ctgcaggagc aacttcgctg ccagctcacg    6120
gctcacgcga cgctgcgcct cctcgacgtc ctgaaggagg accggatcct ggcgcaaatc    6180
gccgagaccg agcgacgatt ctccggcgca ttgaacgact tcgcggcgga atgcggcatg    6240
gtcaagcgcg tctgggggga agggctcttc tgggcggtgc agttcgacct cgatgggtgg    6300
ccccgcttcg tccgtgactg gttctcgtca ttcctctgga gtgagtgctt gcgagatccg    6360
gtggcgcccg tcgcggtgtc gatgcaaccg ctgacgccag cgtgcatccg cgtcgagccg    6420
cgctacgaca tcccggctgc ggagctcgac gccgcgatgg gcacgctgaa gcgcgtgctc    6480
ggcaagggtg tggaggggat cgtcgcgagc gtcgccgacg acgtcgagcg acggggagac    6540
gcccgccgcg cagagctgtt tcggaggatt cttcgagggt tcaagacgac atga          6594
```

<210> SEQ ID NO 39
<211> LENGTH: 2211
<212> TYPE: DNA
<213> ORGANISM: Sorangium cellulosum

<400> SEQUENCE: 39

```
atgagcaggg aaggaacaag ctcgatgaac attgggagtc cgttgccgcc cattgaaaat      60
gctctggacc tgttcaagca ttacgccacg agcgctcccg aagcgagaat cgccgtattc     120
atcgaggagg aggggcagga gcagggcctc acctacaggg agcttgagcg cgcggccacg     180
aacctcagcc tcgagctcgc gtcggtcgcc gcgccgggtg acagggtcct cgtcgcttac     240
gattccggtc ccatgtatct ggtgggggta tgggcggctc tttatgccgg catgatcgcc     300
gtccccgtag atccgctcgg ccctgatcgc ccgcggcga acctcacgcg attgttgaac     360
gtcaccgccg actcgggcgc cacggttttgc atcgcgtcgc gcagcatgct cgatgcggtg    420
aagagccacc caggcgcgcg gcagctcacg gagcagctcc gatgggtcgt cccctcgctc    480
cccgatctcc tggggcgagc gcccggctcc ccgccggctg ccctgcggac cgagaaggac    540
gtcgcgatgc tccagtacgc gtcgggctcg accggcgcgc cgaagggcac gatcgtgacg    600
cacgccagcc tgctgatgct cgcgcgcgcg ctgctcatct cgacctcggc cgaaagcccg    660
```

```
ttcggccgcc ccgacgtcga ggtcacgtgg ctcccccgtga cccactcgac ggctggatac      720
ggcttgatca tgaagtgcct gacgggagcg acgatgtccg cgtggtacat cgcgcccagc      780
gcgttcgccc ggtcgcccgc gatatggctg cggacgatct ctcgccacaa gggaaagcag      840
gtgtattccg tcgctccgaa cttcgcgctt gactggtgtg tctcgtcgac gacggaggcc      900
gagcgcaagc agctcgatct gagctgctgg acgcacgtca tgagcatggg ggagaaggtg      960
cgccccgaga cgtggaaggc gttctcggac gcgtttcgcg agagcggctt ccaccccaag     1020
ctgttcatcg ccggggtacgg catgtcgag acgggatatg tctccggctc ggtgaacggc     1080
ggcaagacgg ttcgcttcga tcgtgcggcg atggacgaag gcagcttggt agaggcgccg     1140
gagggcggga tccttctgct gtcgtcgtcc gggttcaccc ttcccggcgt gcgcgtggcg     1200
atcgtggacc cggagaccag agaggtcctc ccggagggca agatcggcga gatctgggtg     1260
tcgacgccca cggccatgac gggctactgg aaccggccag aggagaccga gcagcagttt     1320
cgcgcgcggg cggccgatgg aagcggcccc ttcttccgca gcggggacat gggcgccttc     1380
tatgggggca atctattcgt gacgggccgg cgaaagagca tcgtcgtcat acgcgggcgc     1440
aagcactatg cggaagacat cgagtcgacg ctcgagcgtg cgctcgactg gcttggcgcg     1500
aactcgtcca tcgccttcgc ggacgacgtg aacggcgtcg aggagctgtt catcgcggtc     1560
gacccgaggg gcgcgcgcga cggcgtcggc ttcgaggaac gcacggacgc catacgcagc     1620
gtcgtcgcgc gtgagttcgg cgtccgcgtt cacgaggtcc tgttcctggc cgcggggcag     1680
cttccgcgga ccagcatggg caaggtctcc cgggtctctt gcaaggacct cttccgcagc     1740
ggcgagctcg agatcgcggc gcggtccggc agcatcgcgc gtggcggcgc cgacctgccg     1800
gccgtggacc ttcgcgcgat cctcgacgag ccggacgcgg agctgcgcgt cgcgcgaatg     1860
accgagtaca tcaggagcct gctttcggca tcgctctctg ttccggccga cgcgctgagc     1920
ctcacgaagt cgttcgacga gcttggagtc gactcgatga cggggggtccg gttctcgcggc     1980 gagctcgtcc gcgcgctcgg attggagctc cctgaatcca tcgtctacaa ttatccgacc     2040
atcgcacaac tcgcgtcctt cgtgtgcgag aagctgaccg gcaccgctgg cagcaacgat     2100
gcggagcggg cggatcgagg tcccgcggcg ctcgcggctc tcgacgtcga gagcatgtcc     2160
gaggaggccg ccgcggccgc gctgcgcgcc cacctcgatg gtcgaaagta g              2211
```

<210> SEQ ID NO 40
<211> LENGTH: 5301
<212> TYPE: DNA
<213> ORGANISM: Sorangium cellulosum

<400> SEQUENCE: 40

```
atgagcgaat ccggcgaact gtctctcacg aagcgcgcgc tcctcgccct gcagaaggcg       60
gagctcgaga tcgccggct ccgggacgct cggccggagc cgatcgcgat catcggcgtc      120
ggatgccgca tccccggcgg cgccacgtcg ccgagccggt tctggaagct gctggaggag      180
ggcttcgacg cgctcgccga gataccggcc gcgcggcgga agctgttcga gctccaggga      240 gccccgcagcc cgacgtcggg agggttcctc gatgagatcg acaagttcga tccatccttc      300
ttctcgatct ccccacggga ggccatctcc atggatccgg cgcagcggct cctgctcgag      360
gtctcggtcg aggcgctcga ggacggcggc gtcccgatgg cacagatccg gggcacccgg      420
acggggacgt tcatgggggtt ctccgggtac agcggctatg gctcgctgac cggtgcgcag      480
gtcgagcagc tctacgccgt gaccgggctc tcgatcaacg tggccgccgg ccggatctcg      540
```

```
tacgtgctcg acctgcaggg gccatgcgtg tccgtggaca ccgcctgttg ctcgtcgctg    600
gtcgcggtcc acctcgcgtc tcagagcctc cgcagccgcg aatgcgacct cgccctcgcc    660
ggaggcgtca acgtgatcgc ggcgatggcc ggcaacgagg cgatggcggc cacgggagcg    720
ctctcttcgt ccggcggacg ttgcaggacg ttcgacgcgg cggcggacgg ctacatccgg    780
tcggaaggct gcggcgtggt cctcctgaag cggctgacgg acgcgatgga ggcgggagat    840
cggatcctcg gtgtcgtcgc cggctccgcc gtgaagcatg acggacatag caacgggctc    900
accgcgccga acggccgcgc gcagcagcag ctcgtccgcg aggcgctggc cgccgcgcgc    960
gtccgacctg aagagatcga ctacatcgag acgcacggga ctggcacgcc gctcggcgat   1020
cctatcgagg tcgatgcgct ggcggaggtc tttggcagct cgcacggccc cgaccggcgc   1080
atcatgctgg gctcggtgaa gaccaacgtc gggcatccgg aggggcggc cggcatcgtc   1140
ggtctcatca aggtcctcgg aatgttccgg cgcggcatgg tcccacgtca tcttcacttc   1200
aacaccccga acccgcgagt cccctgggat tcggtcccct tcctggtccc cgcgacacg   1260
ctcccctggc ctgccaccga caaggtgcgg gtggccggcg tcagcgcttt cgggttcagc   1320
ggcaccatct cgcacgccat cgtcatggag ccgccgaagg cgccggagcg gagcgtggac   1380
gtcggtccgg cgacggcggg gcgcccgctg ctcctgccca tctccgccag gaccccggag   1440
gcgctgaggg cctatgccgc gtcctatctc gatcacttga gcgcggaggc gacgccggag   1500
gagaccgatc gggatgtggc ctataccgcc agtctgcggc gggatcatca tgcgcaccgg   1560
ctggcggtgg tgggcagcga tcgcgcagcg tggcgcgaga agctgcagag ctacgtgtcc   1620
ggcgagggct gccgtggtct ggtcgagggg gtggtgcccg aagcgcgtcc gcgcctcgcc   1680
ttcgtcttct gcggccaggg tccgcaatgg tgggggatgg ggcgggagct gctggacaag   1740
gagccggtgt ttcgcggcgc gctggaagcg tgccacgagc gcatacggga ggcgggaggc   1800
ccatcgctgc tggacgagct gcggcgcgag gccgacacgt cgaggttgaa ccagaccgag   1860
gtggcccagc cggcgctgtt cgcgctgcag gtggcgctgg cggccctctg gcgttcctgg   1920
ggagtacagg cggacgccgt ggtgggtcac agcatcggtg aggtggccgc cgcccacgtc   1980
gccggcgcgc tgagcttgga ggacgccgcg cggctggtgg tccaccgcgg tcggatcatg   2040
cagcgagcga ccggcctcgg aaagatgctg tctgtggcgc taccgctctc ggcggcgcag   2100
cggatcgtga gtgattacgg ccagcgcatc tccatcggcg cgagcaacag ccccacatcg   2160
accgtgctgt cggagagggc agcggccctc gatgaggtcg tcgagcagct tcaggggcgg   2220
caggtcgagg ccaagtggct gccggtcgag tatgcctttc acagcgccca gatggagggc   2280
tttggggagg agctgagcaa ggagctgcgc gggctcgccc cggggggcgaa cggtccgctg   2340
ctgatgtcga cggtcaccgg cacagagcag cgcgggacct cgttcgacgc ggactactgg   2400
gggcagcaga tccgcaagcc ggtcctcttc gcgcagtgcg tggaggagct ggcgcgcaaa   2460
gggtgcagcc tcttcctgga gatcgggccc cacccagtcc tctcggcgtc catgaccgag   2520
acgttgctcg cccaggagaa gagcggccgc gtggtggcct cgctgaggcg ccgcgaagag   2580
gaggtaccca cgctcctcga ggcgctgggg cagctccact gcgccggcta cccggtggac   2640
tggtcgaagc agcacccggt gcgcggccgt accgtttcgc tgcccacgta tccgtggcag   2700
cgggagagct actggctcga agcccgaaa tcgcagacgc cgcgccagca cggcgcgag   2760
caccactatg agacggaatg gcgcctggcc gagcgcgagc ggcccgccga gcctcggcgg   2820
ggcggatggc tgatcctgga cgaccaggcg gagcgcgctg ctgcgctgca ggactacctc   2880
gaggcgcgcg gccagacgtg tgttcgtgtg gttgctgccg acacctacgc gcggcgcggc   2940
```

```
gcgcgcgact accagatcga cccacgggag cccgagcact ttgcccggct cctgggtgaa  3000
caggaggtgg tggacgccct ggccgacgcc tctccttcag atcggtgcgg cgtggtgcac  3060
ctgtggagcg cgcacagctc gcccgcgccc accctcgaat cgatccagca ggcgcaggcg  3120
ctgggttcga tcagcgccct tcacctcgtc caggccctgg cgcgcgcggg atggcgacag  3180
ccgccgcgcc tctggctcgt gacgcaggag gtccaggcca tcaagaaccc gaccgtctcg  3240
gtggcgcagg cgcccgtgtg gggatttggc gcgaccgtag cgctcgagat gccggagctc  3300
cagtgcaccc tgctcgacct ggacgccacg ccgaacatcg atgctctggg acaggaactc  3360
ctctccgcca gcgacgagga tcggatcgcg ctgcgcggag ccgagcgtca cgtcgcgagg  3420
ctggtcccgc atgtaccgga gcagcgcccg gccccggagc cgttgtcgtt caaggccgac  3480
gcgacctacc tcctgaccgg aggcctgggg ggcattggac tggtggtcct ggagtggatg  3540
gcggcgcgag cgccaggca cttcgcgctg ctggggcgga gcggcccatc cgcctcggcg  3600
caacccgtgc tggaccggat gcgcgaggac ggcgcgcaag tccggacttt ctccgtcgat  3660
gtcgccgacc gggagcggct ccgcaccgtc ctggcgcaga tccagacgtc gatgccaccg  3720
ctggccggga tcattcacgc ggccggggtg ggagatcaga aaatgatccc cgacctggac  3780
gggccctctc tgcaggcgat cggccggccg aaggtcgacg ggagctggaa tctgcacgag  3840
ttgacgagcg agctgccgct cgacttcttc gtcctgttct cctccgtctc gtcgctcttc  3900
ggctcgcacg gcagtcgag ctacgccgcc ggcaacgcct tcctcgacgc gctgtcgcac  3960
caccggcggg cgctcggcct cccggcgctc agcctgaact ggacggcgtg gaccgacgtc  4020
gggatggcga cgccgatcat cgcccacacg tcgcggtacc tcgccacgca aggcatgggc  4080
gccctctcct ccagggaggg cgtcgccgcg ctggagcagc tctttcgcgc ctcctcggcc  4140
cagatcggcg tcgtgccgct gtcgatcccc tcgctgccga ggaagccgtt ctattccgtg  4200
gtggctccgc ccaccgcccc gacgccgacg gcgcagacgg tccgggcgtc cgagcgcatc  4260
gctgcgcggc cacccgggga cggcaggag gcgatcgagg gcacgctgcg ggagctgttc  4320
gccagagcgc tgcggatgcc gcctgacaag ctgaagctga ccgagcgcgct ccagaacctg  4380 ggtgtcgact ccttgatcgc cctcgagctc cgccgccgca tcgacgaaga gctcggcgtg  4440
aagctgcagg ccgccgagat cgccaggtc gccaacgtgc gtgagctggc ccagctcgtg  4500
accgccaagt tcgacgcgct ccacggcagc gcgggcgtgg cccagcaagc gcggctcgag  4560
gtccgcggcc cattgaccgt cctcaagccc agccggcaga ggccgcgctt gcggctggtc  4620
tgcttccccg cttcgggcgg cagcgccggc gacttcgccg agtgggcgaa ggtgatgccg  4680
gacgactgcg agctcgtcgc cgtggaatac ccggggagcg cgcgcggca gctagagtcg  4740 tgcgagcatc cgctggccgc gctcacgctg caagcggccg gcgccctcat ggcgatgccc  4800
agggtgccgc tcgtgctctt cgggcacagc ctggggggcc tcatcgcgca cgcgacggcc  4860
gtggagctgg aacggcacgc catgggaccg tcgtgcgtgg tcctgtccaa tcagccaat  4920 gtgatcaccg tccagcggga cctccccga gacggattcc gtgaccagaa gttcctgaca  4980
tggctggcca ggtcgaccgg gatttccatc gagcccgaag cgaccgacag cgatgccacg  5040
cgtcagttct tgaagacgtt cggcgagcag ctcgcgtgga cgttcgactt cgacctgggg  5100
tggcgggtct cctgcccggt cattatttcg tgcggtcgac acgacacgac gctccacgcc  5160
gagagcctcg agttctggag gcgcagcgga ggcgatctgg aggagtggac cttcgccgga  5220
gcccacgact acatccgcca ggagttcgcc gagatcgtgt ccaaaatcat gaacagggct  5280
```

```
gcgggtaaag acagaacatg a                                              5301
```

<210> SEQ ID NO 41
<211> LENGTH: 1320
<212> TYPE: DNA
<213> ORGANISM: Sorangium cellulosum

<400> SEQUENCE: 41

```
atgagcgctc aacctgagta ctgcatcgtt ggcggcgggc ccatcggcat cggcatcggg      60
aagtgcttcg cccaggaggg gctgaaattc acgatcgtcg aggccgatga agacttcggt     120
ggcacatggg cgctgtccca gcgttcgggc ctcgtctaca atcgacccca cctgatctca     180
tcgaagaaga acacgcagtt cctcgacttc ccgatgccgg aggattaccc gcattatccc     240
agccatgcgc agatgctgtc ctatctgcgc agcctggcca cgcattatgg cctttacgac     300
agagcattgt tcggcacacg cgtcgagcac gtggagccga atggcgcggg ctgccgcgtt     360
cgcctctcga acgagaaac gcggacgttc tcggccgtcg tcgtggccaa cgggcgcatg     420
cgcacgcccc tgatcccgcg ttatccgggg gtcttcagcg gggagacgat gcactcggcc     480
gcctacaagt cacacgaggt cttccgcggg aagcgcgtgc tcgtcatcgg cggcgggaac     540
tcgggctgcg acatcgccgt ggacgcagcg ctggcggccg agcagacgtt ccacagcacg     600
cggcgtgggt accattacat gcccaagttc attcacggca gcccaccca ggaatggctc      660
atggacatgg ggtcgaagtt ccgctcccag gacgattact ggtcgttcgt ccagcgggag     720
ttcaaggcgg ccggctacga ccccgtcgat tacggtctgc cgcgcccccga ccacgccatt     780
catgaggcgc atccgatctt gaactccctc gtcctctatt acatcggtca cggggacatt     840
catcccaagc cggatgtccg cgcgcttgag gacggacgg tagagttcgt ggatggcacg     900
cgcgcagagg tcgatctcat cctttatgcg acaggctacg agatggattt cccgttcctg     960
gcggaggatc tgaggccgag cgacggcgcg ctggagctgt tcctgtcgat gttccaccgg    1020
aaggccgaca gcctcgtgtt cgtcggatat ttcaacgcgg cgtcggggct cggcaacctg    1080
ctcaactgcg gcggagctct ggtcacagac tatttggtcg cccgcgagaa gaacacagat    1140
gcatttcgag tgctgcgcag gctcatccaa gggcccgagc ccgatatcgg cagaggtcgc    1200
ttcctgaact ccccacggca ccgggtcgag acgatctat ggaaggcgat gaaggtcatg    1260
aatttcttcc ggtcagtgct caatccggca cgggcagccg gggacgtggt gcgcgcctga    1320
```

<210> SEQ ID NO 42
<211> LENGTH: 1422
<212> TYPE: DNA
<213> ORGANISM: Sorangium cellulosum

<400> SEQUENCE: 42

```
atgagccgtg caatcgttat cgggggcagc atcgcaggga tgtgcagcgc tcgtgtgctg      60
tgcgatttct tcgatgaggt cgtgatcctg gaccgggacc agtttcccac cgagatcgcg     120
cctcggcctg gcgtgccgca gagccggcat acacatgtgc tcctgccgcg gggagagcag     180
gagctcgagg agctctttcc cggcttttcc gcctcgatga tggccgcggg tgcgctgaaa     240
ttcgacgtcg ggacgggcat ggcggtgcga cgcgtcttcg gctggcagac ggtcggaccc     300
acgggccgcg agctactctg gccagccgt gacctgttcg agggcacgat acgctcgctg     360
atgcgacagc agaccaaagt gcgcattcgg gaaggctctc aggtgctcgc gctgcgcagc     420
acagcgggcg agaggccaag gatcaggggc gtacttctgc gcgatgacgc tgcggagcag     480
gagcttgaag ccgacctggt cgtcgatgcc agcggccggc atacgcgcgc cgagcagtgg     540
```

```
ctgaccgagc tcgggctacc tgcgcccaag acgcagtgcg tcgactcgcg cgctggctac    600
gcctcgcggt tctacaaggt gccccgccc gagcgccggc cgtcggactg gtggtggaag    660
ggtctgtggg tcgaggcgga gcccgaccgg ccgcggggcg ctgtcgtctt tccgatcgag    720
ggcgatcgct ggctggtgac cgcctcgggc ttcagcggct cgtatccgcc cacggacgag    780
caaggttttc tcgagcacct cgcgagcctg agctcaccga tcgtggctcg ggccgtggcg    840
ctggccgagc ccatctcgcc gatctacggc aaccgctcca tggccaacgt atcccgtgct    900
tacgaccgct gggagatcca gctccctggc ttcgtcgctg ttggcgacgc ggcttgcgcc    960
ttcaaccccg tctacggcca gggcatgtcg acctcgaccg tctctgccgt catcctgcgc   1020
gacgtgctgc gccgccgcgg cccaggcgcg ggcttcgagc cgggcttctt ccagcagcaa   1080
gccaagttcc tgcgctcggt ctgggatttc gccacgcgct ccgatttccg atggccgggg   1140
acggtaggcg agcgcccgca cacgccggcg atcatcggcg cgtacgcgaa gctcgccatc   1200
gagtctgctc atcatgacag cgccatacgg cgccatctgt tcccggcgtt cgacctcacc   1260
ggctcggcga ccttgctctt cgagcccctc ttcgtgggca aggtgctgct ctccgctggc   1320
cagcgtcggc tccgccagcg cctgctcggc acacctccga tccccgaatc gccgcccgtg   1380
cccgcgggtg tacctcgatg gcggccggc gccgccatgt ga                      1422

<210> SEQ ID NO 43
<211> LENGTH: 1188
<212> TYPE: DNA
<213> ORGANISM: Sorangium cellulosum

<400> SEQUENCE: 43
ctaccggtag cgacgatgc caccgaacgg ccacttcgcg tggtcctcgg gcgccggata     60
gacctcccat tcggagaacc cggccgcgcg gagcgacagc tcccactctt gcagcgtcag    120
ataaccaaca tgctggcggc gaggcggatc gagcttggcc ttgctgtagg tgtgcagcat    180
cgactgaaaa aattcattgg gaaagaacag cccgggccga tcgcggaacg acatggtgaa    240
cgcgagctgg ccgcccggct tcagcatcgt gtggaacgcc tggagcgtgg cgtgaagatc    300
gcgcacgtcg tagagcacgt gctcaaggac gatcagatcg accgaggcgg cccgggcgaa    360
cgtgttgcca gcggagggca gcgcgtccag gtccaggcgc tggaaatgaa tgcgctgaaa    420
caggtcagcc ggcgcgtggg tccgcagcca ctgcttcccc gtctccatca acagggcgct    480
gatgtcggtg taatcgtaac ggacgaggtt cctgctcagc gggaggaacc tcggatcgga    540
taacgcctgc cgcagcacca cgccgagccc cgcgcccccc tcgaatacag agatccccgg    600 ccctctgcg agcttggcca tcagcgcccg cgccagcatc acgttgcacg gcttcttggc    660
gggaaggctg atcatcgagt attcccaaaa tttcagcgag gcctgcatcc cgtactggag    720
atccatggtg ccagcgcgt ccttgcccgc cagcaccggc ccggccaggc cccgatagcg    780
ctgcaggaac tcgaccattt cgccgagaat cgcgcggtct gcgagctcca tggcctccct    840
ctcggcgacg cgctttcgca ccgctcgct gggaccagc cgcccgctgg ggtcctggat    900
gaggtcgccc ttgtcgctga agtagtcgag cagcttcctg cgaaactggt aggcggtgac    960
cgacggagcc gactccgggc gatcgtcgag cacctggacc gcgccgctct ggtcgacgag   1020
gtgctcgagc agaatctcac tggcaacaag ctcggtctga cgacggaatg cttctatgta   1080
agccgtgtaa gctcgttgt agagatcggt cacgtccagt cgttgtcgca tgcagatcct   1140
cgcgggtgtg gcgcccatcc tgcgcagcgc agggacgaag cagatcat               1188
```

<210> SEQ ID NO 44
<211> LENGTH: 1629
<212> TYPE: DNA
<213> ORGANISM: Sorangium cellulosum

<400> SEQUENCE: 44

| | | | | | |
|---|---|---|---|---|---|
| ctacaggagg | tccgcgagcc | ggccgagcag | gggagtgcgc | ttgaacgtag | cgcggatcgc | 60 |
| cgcgcgcatc | ccgcggtact | tggccgtcgt | gtacgggaac | aggagagggc | tgttcagcgg | 120 |
| catcgcaaag | cgctcgtggt | tgacgtgacg | cgcgtagcac | atcgcgcgca | acgagtcgtc | 180 |
| cgagtgcacg | cggccgtagc | ccgagttctt | gatcccgccg | aacggcgcct | cgggcgcgca | 240 |
| gtacgagacg | agcacgtcgt | tgatcatcac | ggtgcccgcc | tcgatccgct | cggcgaccgc | 300 |
| ccgcgcacgc | gtcttgtccc | gcgagaagac | gtacgcgtgc | agcccgagcg | gcgagtcgtt | 360 |
| cgcgatccgg | acggcctcgt | cctcgtcgcg | cactttcatg | atggggacga | ccgggccgaa | 420 |
| gatctcttcg | cgcatcacgg | tcatctcggg | ggtgcagcgg | gtcagcaccg | tgggctcgaa | 480 |
| gaacattccc | ggccccggcc | tgcgccgccc | gccgtggcc | acgagcgcgc | cgcgcgcgac | 540 |
| ggcatccttg | atgtgcgcct | cggcgatatc | catctgcttt | gcgaagatga | tcgcgcccac | 600 |
| gtccacgtcg | tccgcgcgcg | ggtcgccctg | gcgaagctca | cgcgtgagcg | ccaccacgcg | 660 |
| gtccaccagc | cggtcgtgca | ccgcctcggt | ggccagcacc | cgctcgaccg | agatgcatag | 720 |
| ctgacccgaa | ttgatgaagc | cgccggcgac | gatcgaccgt | gcggtgcgct | cgatctcgca | 780 |
| gtcgtcgcag | gcgatgagcg | gcgccttccc | gccgagctcg | agcacgcacg | ggatcaaccg | 840 |
| ctcagcgcac | gcggccccga | cgcgccgccc | ggagctcacc | ccgccggtga | agaccacctt | 900 |
| ctgcacgccg | gcgtcgatca | gcgcagcccc | ggtgcgggca | tcgccggtca | ccacctggaa | 960 |
| tagatcggtt | ggaatcccga | tcgcgtccac | gacttccttg | gccttgagca | gcgtgagcgg | 1020 |
| cgtgacctcc | gagggcttga | ccaccacggc | gttaccagcg | atcagcgcct | cgataacgct | 1080 |
| gcccatcggg | atcgccagcg | gcagattcca | cggcgagatc | acggcgacga | cgcccattgg | 1140 |
| cacgtacgtg | acgtagctcc | cacgccactt | catatggtgt | agcgtgatgg | acgtatcggc | 1200 |
| gaggatccgg | ccggcgtggc | gcgtgaagta | gtggcacgcg | tccaccaccg | tgatccactc | 1260 |
| ggcgagcgcg | tcgttgcgcg | gcttgccggt | ctcgagcacc | accgcgtcca | ccaggtcgtc | 1320 |
| cagccgctcg | acgaatgcgt | cgatcacgcg | cgccacgcgc | ccggcgcggg | tctcgatcgg | 1380 |
| gagctgcgcc | caggcgcgct | gggcgaggcg | cgcgcgctcc | accgcggcgt | gcacctcggc | 1440 |
| atcgcccatc | agcggcacct | cgcccaggcg | cgagccgtcg | attggcgatt | ggaccacgag | 1500 |
| cgtgcgggtg | gagggcgtcg | tcgtcgggga | tgcgggaaag | gcttgggcca | tgagcggctc | 1560 |
| ctcgtttgct | cgaaagcggg | gcggcagctt | accactcgcg | ccgcgcggct | cgcaatgggc | 1620 |
| gtcccgcac | | | | | | 1629 |

<210> SEQ ID NO 45
<211> LENGTH: 1131
<212> TYPE: DNA
<213> ORGANISM: Sorangium cellulosum

<400> SEQUENCE: 45

| | | | | | |
|---|---|---|---|---|---|
| tcaattcacc | cctcggagat | gccgcgcgac | gcgcggcgcc | tcggctgcga | tgtcgcgaag | 60 |
| ctgccctgtg | atgggattgc | ggaaaccgat | gaagaacagc | cccggcgtcg | gcgtcggtgc | 120 |
| gccatgccag | cgcgggtagc | cgcgctcgtc | cgtgaagcgc | gccgcgtcct | cgaggaagtc | 180 |
| gccgagcccg | gcccggtagc | cggtggcgag | cacgacggca | tcgaagggca | gctcgcgacc | 240 |

-continued

```
gtccgtgaag atcacgccgg tctcggtgaa cgcgcgcggg ccggggacca ccgcgatctt    300
tccctgctgg atcagcgcga gcgtacccat atcgatgagc ggaatacgac cttccttcac    360
ggccctggta cccgggccga tctcgggccg atggatcccc cagcgcgaca ggtcccccac    420
cgtgcgggac aggaatgcgg tcgcgagccg gtccctacg gccggcggga gggctccgta     480
gagggcaagg gcactgaact gggcggggag cctgagcgga tctcgcggga tcacgtgaat    540
accgctgcgc gcggagacgg tcgtctccgc cgcatgctcc cagaggtcca tcgcgatctc    600
gccgccagaa ttgccggagc ccaccacgag cacgcgctga ccgcggaatg ccgcgcccga    660
cccgtaggtg gagctatgga ggatgggccc gcgaaagcgc tcctggccgg gccaggtggg    720
tacgttggga agacggctgt agcccgtggc cacgacgagg gcgcggctcg tgaactctcc    780
cgcgcgcgtc tgggtcaccc accgcgaccc gtcgcggtaa gcgcgcacca cctcggcgcc    840
gaagcgcggc tccaggcgga agcgctcggc gtagcgctgg aggtaatcga ccatctgcgc    900
ccgggaggga tacggcgggg catatctggg ccaagcgagc ccgggcagcg aggagaattg    960
cttgaccgtg tggaggtgca gccgttgata gtggcgccgc cagctggcgc cgaccgcatc    1020
cgattgctcg agcaggacga atgggatgcc ccgctcgcgc agacaggcgc ccaccgctag    1080
cccagacgga ccggcgccga tgatgatgac atggctctcc tcgatcacga c            1131
```

<210> SEQ ID NO 46
<211> LENGTH: 1071
<212> TYPE: DNA
<213> ORGANISM: Sorangium cellulosum

<400> SEQUENCE: 46

```
tcacgaggcg gcgagcggca gcctgcgggc cgcgcgcgtg gcctcgtgcc cgtctcccgc     60
ctcaggcgtc gcctcggccg cctgcccacg gtagatccga tcgatccggt cgcgcgacgc    120
gaccagggcc ttgtcgaacc gaccaaggac attgcccttc aggatcccgc gcttgtccgc    180
cagacgggac agcaacctca tgtcaaggcg cagctcgaga tccatggcca cccggagggg    240
aggccagatc aatgagccga gcccgaactc gctccagcgc ccaagctcg gaagaggaa     300 cgtgtagatc tccgaagact ccgggcccac cggattgaag aacacggccg accgaagcgg    360
gtatgtcacg acctcccggg tcctcgggtt gatgaaggag tggtcgtaga tcgcgtgcac    420
cggcgagaac cgcgccgtcc attcgacgac gaatttcgcg tcgtgcggga tgcggaacat    480
tttctccacg atccggggga tgggccgctt cggacccgta ttgacgacct ggacggcgtc    540
gtcggacagg gttacctgcg cctccacctg cggcatctgg tcgagcgagt agccgagcat    600
gaagtggacg aacggcgtgt gctcgacctc gatgaaattg tcgagcgcca gctcgaacgg    660
cacggcagcg cggtgccgga ggacaccggc cggcacgtac ccctcggcat cgaagcgcgg    720
gaacgtggcc tgcgccctg cgcgcttcac ccagattgcg ccgtaccgct ccaccgcgtc    780
gaacacatca tcgcgccgcg cgcacggccg tgccgccggg gtggcaggga tgtcgccccg    840
gccgtccgcg gcccagcgcc agccgtggta ggcacacacc agccggtcgc cctctaccca    900
tccctcgctc aggcgcatgc tgcggtgcgg gcagcgatcc gtgaacgccc cgagtccgcc    960
gctcgatgtc cggaacacca cgatctcgcg accgcgagc cgcacgctgc ggggcttgcg    1020
gcggagctcg tggctgagga gtaccgggtg ccaatggtcg agttcagcca t             1071
```

<210> SEQ ID NO 47
<211> LENGTH: 1605
<212> TYPE: DNA

<213> ORGANISM: Sorangium cellulosum

<400> SEQUENCE: 47

```
gtggtgtggc agcatgggcg ccagtccttg cacgagtgcc atgacggcgg acgcgagcca      60
tgctccgaaa cgtccgaaat acgcggcgca ccacctgggc ttgacaggat gacggtcccg     120
ggtctttcta cgcgacatgt ctttcatttg tgctacaagc cacagctcgg cgggctcgcg     180
cggctccgga ggagcgcaac cagctcctgg gacgcgaggc ggccacggca gcgacagttg     240
gagccgcgcg cggacaacgc caccctgaac gcccggcttc cccaggcacc gctggcggac     300
acgatggagc ccaaggcgca cggaacgatc cccgaggaaa tgatgcaatc gacggccacc     360
atcgccccc tggcagtcct gttcgtactg atggccatcg aggcggtcgt ggcccggcat      420
cggcgcggtg acacgacgta ccgcctgcct gacacggtgg ccagcgtggg cgtcggtgtc     480
gggtacttcg cgctggtcgc gttcttcagc ttcatctcga tcgtggtcta cgacatcgtc     540
tatgagcgct gggcgatcac gcaccatgct cgctcggcgg tgacgatcgt cttcaccatc     600
ttcgcggcgg actttctcta ctacctgttc caccgcgcca gccatcgcat caacgtcctc     660
tgggcgatcc acgtcgtaca ccaccagagc cgcgagcaaa acctggcggt caacctccgc     720
atgccgtggc tccagccggc ataccagtgg ttcttctatc tgccgctcgc cttcctgggg     780
atacctccgg ccgtcttctt gctcgcgcgc ggggtaagca tctcttacaa cgtcttcact     840
cacacgcgcg cggtcgggaa gctcggcccg ctcgagtatg tgctcaacac gccctcccac     900
caccgcgtgc atcatgggat ggacgagcag tacctcgact gcaactacgg cgggatcttc     960
atcgtgtggg atcgcctcct cgggacgttc gtcccggagg gcaaagagcc gacctacgga    1020
acgcgcagaa gggtggtctc gtggaatccg atctggctca acgtggagcc gttcatccac    1080
ctcgcgaagc tatcgcgcgc agccagatct ccgtgggatc gcgtcaaggt atggttcatg    1140
ccgcccgagt ggcagcccgc cggcgtcctg gaggccagcg ctccgcccga ccgcgcgac     1200
gtggagagcc gtggttctac ggcttcgtcg atcgcccaga tggcgctcag cgtcggcgtc    1260
acggtggtca tcggcgcgat ggtcatcatg tacacgggca cgtcgtcgac gatgccgagg    1320
cttgccctcc tcgtgctgct gctcgcgctcg ctcggcgcgc atgctcggtc tctcgagagt    1380
cctggcttcg cctggaggtt tgagctcgcg cgcgcagccc tgctcctcgc cgtcgcgggc    1440
tggctcgacg ccagcggagc gaggccgctg ccagcgtgg ccctgatggc cggcggcctc     1500
tcggccgcga gcggtgtcct gttccgcctc gggcgccgcc cgcgcggctc gcgggcggga    1560
ggggccgagg acgccgcccc gtcgatgtcg ctcccaggat cgtag                   1605
```

<210> SEQ ID NO 48
<211> LENGTH: 1341
<212> TYPE: DNA
<213> ORGANISM: Sorangium cellulosum

<400> SEQUENCE: 48

```
atggcttctt ccgaagatgg aacgcgcagc tggtcgaaca cgaagagcct ggcgctacat      60
gagcgcgcgg cgaaggtgat gccggggagc caggcgaact tcaggggagg tttgttgagc     120
actcccctct tcttctccca cgcgcgaggc gcgcgactgt gggacgtcga cggcaacgag     180
tacgtcgacc tgatcaacgc cggcggtccg ggcatcctcg ccacaacga tccggagtac      240
atcgacgcgc tgaagcgcca gctcgacacg gtgtactcgc tcgggtcggg gatctgccag     300
accgagcagg atatcgagct ggccgagaag atcgcgagcc acgtcccgtg cgccgagcgc    360
gtccgcttct gcgtcaccgg atcggaggcg gtacacctgg ccctacgggct cgcgcgggcg    420
```

```
tacacgaagc gccectattt cattcgcttc cagactcact accacggctg gtttgacagc      480
gtgctggggg gtgtcgttga cgagcacccc gaagggcgac ctctcccgct ggagagcgag      540
cagagcttct ttcacaccga gggcagggtc cccgacgcat tcaagtactc gttcctcttg      600
ccctggaacg acatcgatgt cctcgaggag acgctgaaga agtacgggca cgaggtggcc      660
atgatccaca tggagccgat cctggtgaac ggcggaggct gccccccag gcccggctat       720 ctcgagcgtg tgcgcgagct ctgcgaccag catggaatcg tgctcggctt cgacgaggtc      780
atcaccggct tccgcgtggg cctcggcggc gcgcaggcgg cgctcggcgt cacgcccgat      840
ctggcgacgt tcggtaaggc gctaggtggt gggatgccga tggcggccgt cgccgggaag      900
gcggagatca tggatcagct ccggaccggc aaggtgacag gggctggcac gttcaacggt      960
tatcctctcg gcgtggccgc gtccctcgcg acgctcaaga tcctggagag ggacgatggc     1020
gcggtctaca ggaggatcga catgatgcag gctcggctca aggagggcct gctcgatatc     1080
tgcaagcgac gtgggatccc cgccctggtg caggggccgc gcggcgtctt cttcttactc     1140
ttcacggaca aacccgtgat ctatagcttc caagagctca tggaggccgc tctgcccagg     1200
cagttcaagt tctactcgac gatgcccgag gaggggactc tcctcatgta cggcggccgc     1260
tggtacatct ccgcggcgtt gaccgaggct gacgtggact gcgcgctgga gagcgccgac     1320
aggaccttgg ctagaatctg a                                               1341

<210> SEQ ID NO 49
<211> LENGTH: 1080
<212> TYPE: DNA
<213> ORGANISM: Sorangium cellulosum

<400> SEQUENCE: 49 atgccccta cagaagattt gaagcagatc ttggagcagc tcggttcggc caggttgagc        60
catgaggtcg agctgagcca gctcatggcg ccgctctcgc cagaagaagt tttgttttgc      120
tttctgttca tcaagtccgg ctcggccgag ggcttcggcg aagagcccgt tcggttcaag      180
gacttgccga gcgcgcctga cagattctgg aaggcgatgg cgctgcacgt cggcgcgctc      240
tccgggcagt tcaagccgct gccgccgtcg tatctcaagg atgcgtggct ccgtttcgtg      300
aaggagcggc ccggggacga gccgctgtcg ctcctcgagt actacagcct cgccgcgcag      360
ctcctcagcg acacggacag ggtcttcatc aaccacgggt acgcgttcct gaacccagca      420
gaggcgccct ctctcgctgc ctgggaggag ccgtcgcgcc tcagcatcca cctctaccac      480
aagctcctgg gcggccagga tttcacgggg ctcgatgtgg tcgatatggc ctgcggacgg      540
gggggcggca gcctctacct gaagcagcgg aaggaggccc ggctcgtcgc cggcatcgac      600
gcggtgcgca cccacgtgct gctcgcgcga gaagcccatc cctcggtcga cggcgtctac      660
ttcctccacg gccgagcgga agagataccg ctgcccaccg tgccttcga cgcgctgatc       720 gcggtggacg cggtcttcca cttcccgctc agggagttcc tccacgaagc ccatcgcgtg      780
gtgaagccgg gggggcgctg tttcctcaat agctgggggcc gccgacctg gtacatggat     840 ctcgagggtg cggtcgagtc gtgtggttgg aagctcgagc acgccgagga catcacgacg      900
ggcgtcctcc tggccagaga gcaatggagg actcacgaca tgttcacgtg gtccgctcg       960 cggccgcgca aatgccggcc ggagatctac atcgagttcg acaggatggt gatgttgccc     1020
gtcgagggcc gccgctatta caatttccac ctcacccggc tcgaccagaa ggcaagctga     1080

<210> SEQ ID NO 50
```

<211> LENGTH: 765
<212> TYPE: DNA
<213> ORGANISM: Sorangium cellulosum

<400> SEQUENCE: 50

```
gatctcgtcg aggaacagcg tgccgccgtc ggcctcctcg aacctgccga tccggaggcg      60
cgcggcgccg gtgaaggcgc ccgcctcggc gccgaacagc tccgcctcga cgagctcgtc     120
ggggagcgcg ccggcgttca ccttcacgaa cggccggtcc cgccggcgcg agttggcctg     180
gacgatgccg cgaggagct ccttgccggt cccgttcggc ccggtgatga gcaccggcac      240
gtccgcgggc gcgaccttca ccgcgaggct caccacctcg tgcatcgcgt cgctcgcgta     300
cacgagcccg ccgaggtcgt ggcgctcggc gagcctgtgc cgcgcgcgcc cgcgctgggc     360
gacgaggcgc gcgttctcct gctcgagcga ccgcagccgg gcgaggttgc tcaccacggc     420
gacgagcttc tggtcgtccc acggcttcgg cacgtagtcg ctcgccccgg ccttgatgag     480
ctcgaccgcg cccgcgatcg acgtgaacgc cgtcatggcg acgacgggca gctcggggtc     540
gatcgacttg atgcggcgga gcagctccat gccctcctcg cccgatgtcg cgctctgtcg     600
gaagttcatg tcctggacca cggccccgag ctcgtcgtcg agcaccgccg cgatcgccgc     660
gtccggcgtc gccgcgacgc ggacctccag cccgtgcagc tcgaagagcg tcgtcagcgc     720
gacgcagacc gcgggctgat cgtcgatgac caggatcttc ggcac                     765
```

<210> SEQ ID NO 51
<211> LENGTH: 951
<212> TYPE: DNA
<213> ORGANISM: Sorangium cellulosum

<400> SEQUENCE: 51

```
tcaggccgta tcgcatcgag caggtcccgc ccccggcgcg ggtgatcccg gatctagcgc      60
gacggcccgc tggatggcgt cgcggagcca ccggtggccc tcgtcgtgct cggagcgctc     120
cggccagacg agcgtcagcg tgtagccctc gagctggaac gggcacggcc gcaccacgag     180
atcgagcctc cgcgccaggg ccgcggcgac gcgcgcggac acggtgagca gcaggtcgga     240
gccggagacg atgaacgggg cgaccaggaa atgggacacg gtcagcgtca cccgccggcg     300
caatccctgc tccgccagcg cccgatcgat gacgccgtgg tcctctccgt gcggcgagac     360
catcaggtgc tcgcaggcag cgtagcgcgc gcggtgagc ggccccgtg acgccgggtg       420
tccgcggcgc atcacacaga cgatctcctc ggccgccagc agcgtcgacc ggcagccgtc     480
gggcacgggg cccccgcgcc cgagcttgcc gtcgagctcg ccgcggcgca ggagctcggc     540
gaagtcggcc gggatgttcc ggcagcgcag gttgacgcgc ggcgcctcga cggcgaggag     600
cgcggtcagc gccgggagca cgagcagctc caggttgtcg gtcgcgacca gccggaacgt     660
gcgctgcgac cgccgcgggt cgaaccgctc gaccgggcgg aagacgtgct cgagccgctc     720
gaccgcctcg gccgccgcg gggccaggtc ccgcgcgcgc tcgctcagcg tcatctgccg     780
gccgacctgg atgagcagcg ggtcctcgaa atgggcgcgc agccgcgcga gcgcgtggct     840
catcgagggc tgcgtcacgc ccacgcggcg cgcggcgcg gtgacgctct tctcctggag      900
cagggcgtgc aacgccacga cgaggtgggt gtcgaccgac tgcaggcgca t              951
```

<210> SEQ ID NO 52
<211> LENGTH: 447
<212> TYPE: DNA
<213> ORGANISM: Sorangium cellulosum

<400> SEQUENCE: 52

-continued

```
atggatcgcc gcgccgactg tcgattcgac gcccggagcg tgggtgccta tctctcctct     60
ccggacggca catgccgccg cgcggcgcgc ccctgccccc cagccgagga gagcaacccc    120
atgatcatcg agtacattcg ctacacgatc cccgcggagc aagagaagga gttcctggcc    180
gcctaccgcg acgccgccgc ggagctgcgc ggctcggagc attgcctcga tcacgagatc    240
tcccgctgcg tcgaagatcc gacgagcttc gtcgtccgca tctgctggga ctcgctacaa    300
ggccacctcc agggcttccg caaggcggcg cgttcccgt cgttcttcgc caaggtgaag     360
ccgttctacg agcgtatcca ggagatgagg cactacgcct tgaccgacgt cgccacgcgg    420
caggcgggga aggccgcgac gggctga                                         447
```

<210> SEQ ID NO 53
<211> LENGTH: 1221
<212> TYPE: DNA
<213> ORGANISM: Sorangium cellulosum

<400> SEQUENCE: 53

```
atggccgttc cctctggatt cgacctcacg agcgagcgct tcttcgccga tcccttcccg     60
accctcgagc ggctccggac cgaggcgccc gtctacttct tcgagccgct acagtgcttc    120
ctcatcaccg ctcctgccga tatcgagggg ctcgtgaaag actcgagctt caccgcgcgg    180
cgggcgacgg cgctcctcgg cggcctcggc atgctcggcg aggacgagct ctcgaggaag    240
acgttcgact ccctgtcgcg gctcgccttc ttccaggacc cgccgcgcca cacgcagctt    300
cgacagctca tcatgaaagg gttctcgccc tcggccgtgg agtggatgcg cccgcgggtc    360
gtggggctcg tacagcgggc catcgagggg cgcgccgcg acggcgagat ggatgtcgtc     420
tcggcgttct ccgaggcggt cgcgctcaac acgctggccg agatgttcgt gatacccgag    480
gtcgatcgcc gcagttcct gagatggtcg accgatctct gaagctcgc cggcggcggg      540 gtgagctcgg aggagcagaa gcgggcggtg aagcagagct gctgcgacat gctcgactac    600
atgatgaggc tcgtcgagga gcgccggaag gcgccggggg aggacgtcgc gagcaggttc    660 atcgcggcg aggacggtga caccgagctc gcgggcgagg cggccatgca gtgcttccag      720
atggtcgccg ccggattcgt cacctccgtg aaccagatcg cgaacaccgt gctcgcgctc    780
ctcaaccacc ccgcagagct cgcgaagctg cgggaggcgc cgggcctcgt ccgcggcgcg    840
gtcgaggaga gcctgcgctt cgagccgtcc gtgctctccc tcagccgcat gtgcaagaag    900
gacaccgaga tccggggcgc cagggtgtcc gaggggcagt tcgtcttcgc gatgatcgcc    960
gcagcgaacc gcgatcccgg gctgttctcc gagccggatc gattcgatat cacccggcag   1020
cagagccggc acctgacctt cgggagcggc gctcattact gcccgggggc cccgctcatc   1080
cggatggaag tagaggagtc gctgcgcgcc ctgctctcgc tgccgcgctg ggagctcgcc   1140
gaagagacgt tgagctacgc cgggtcgaac ctgcaggacc gcgggccgag ctcgctgcgc   1200
gttcgcttcc ccgcagcctg a                                              1221
```

<210> SEQ ID NO 54
<211> LENGTH: 780
<212> TYPE: DNA
<213> ORGANISM: Sorangium cellulosum

<400> SEQUENCE: 54

```
atgaagctcg cgcgcaagct gacgctcgcc ctcgtgttcg ggtcttcct cgtgctcgcg      60 ctgagcgcct acgcccagat ccgcagagac gccatggtgt tcgagaacga cgtccagcgc    120
```

```
gatcaccaca cgatgggccg cgcgctcgcg gccgccgtca tggaggtgtg gcgctccgag      180
ggcgcggcgc gggcgctgcg cctggtggaa gacgccaacg agcgggagca gcaggtgaac      240
atccgctggg tctggctcga cggccaggcc gacgagcccc atcgccccg gctggctccg       300 gagctgctcg tccccgtcat ccgcggcacg ttcacgatgc tgaagccgct ggcggacaag      360
cagggtgtca cgatcgtcga ggagggagac acgccggatc ggctggtcca cgccgacgcc      420
gaccagctcc agcaggcgct cacgaacgtg gtggtcaacg cgatccaggc catgccgtcc      480
ggcggcacga tcgcggtgcg tgtccaggcc gtccgcgcca tcccaccggc cgatcaggga      540
ggggccgagg gcgactacat cgcgctgtcg gtgcgcgacg agggacaggg catgatggcc      600
ggcgtcctcg agcacgtctt cgagccgttc ttcacgacca gcccgtcgg cgagggcacc       660 gggctcggcc tgtcggtcgc ctacggcatc atcaaggagc acggcggctg gatcgacgtc      720
gacagccgcg ccggctcggg gagccagttc acgatgtacc tgccgcagga gaagccatga      780
```

<210> SEQ ID NO 55
<211> LENGTH: 1386
<212> TYPE: DNA
<213> ORGANISM: Sorangium cellulosum

<400> SEQUENCE: 55

```
atgagcggtc gcgtcctgat cgtcgacgat gagcggggcg tctgcgagct cctcgacgcc       60
gggctcaaga gcggggtttt ccaggcggcg tggcgcacgt cggccgccga ggcgctcgag      120
ctcctcggcg cggaggactt cgacgtcgtc gtcaccgaca tgaccatgcg cggcatgagc      180
ggcctcgagc tctgcgagcg catcgcccag aaccggcccg atctgccggt catcgtcatc      240
accgcgttcg ggagcctcga caccgccacg tcggcgatcc gcgccggcgc ctacgacttc      300
gtgaccaagc cgttcgagct cgacgcgctc cggctcaccg tcgagcgcgc cctgcgccac      360
cgcgccctcc gcgaggaggt gcgccggctg cggcgcgccg tggacgactc ccaccgttac      420
gagcagatcc tcggcggcag cccggcgatg aagggcgtct tcgatctgct cgaccgggtc      480
gccgactcgg acacgtcgat cctcatcacg ggcgagagcg gcaccggcaa ggagctcgtc      540
gcgcgcgccg tgcaccagcg cagccggcgc ggccagggcg cgttcgtcgc ggtgaactgc      600
gcggcggtcc cggacgccct gctcgagagc gagctgttcg ccacgcgcg gggcgccttc       660 accgacgcca aggggccgag gagcggcctg ttcgcgcggg cccacggcgg caccctgttc      720
ctcgacgaga tcgcgagct gccggtcggg ctccagccga agctcctgcg cgccctccag       780
gagcgcgtcg tccgccccgt cggcgcggac gaggaggtcc ccgtgacgt gcggctcatc       840 gcggcgacga accgcgacct ggagaccgcg atcgaggagc ccgcttccg cgaggacctc       900 tattaccgga tcaacgtggt ccacgtcgat ctgccgccgc tccgctcccg cggcgccgac      960
gtgctcctgc tcgcgcagcg cttcctcgag cacttcgcga ccgtcaagga gcggccgatc     1020
aagggcctct cggcgcccgc ggccgagaag ctcgtcgcct acgcgtggcc aggcaacgtc     1080
cgcgagctcc agaactgcgt cgagcgggcg gtcgcgctcg cgcggtacga tcagatcacc     1140
gtcgacgatc tccccgagaa gatacggagt taccggagct cccacgtcct ggtctccagc     1200
gacgacccga ccgagctcgt ccccatggag gaggtcgagc ggcgctacat cctgcgcgtc     1260
ctggaggtgg tcggcggaaa caagagccag gcagcccaga tcctgggctt cgatcgagcg     1320
accctgtacc ggaagctcga gcggtacggc ctgcgcgcgg ggcgcgcgag cgacccgaag     1380
ccgtga                                                                1386
```

<210> SEQ ID NO 56
<211> LENGTH: 1527
<212> TYPE: DNA
<213> ORGANISM: Sorangium cellulosum

<400> SEQUENCE: 56

| | | | | | | |
|---|---|---|---|---|---|---|
| tcatccatgg | gagacgccgc | gcgggccgtc | cgcctgctcc | cttgaaggcg | agcgcggcag | 60 |
| atcgatccgg | aagaccgagc | cggcgccggg | acggctctcg | acgaggagcc | ggccgccgtg | 120 |
| cgcctcgacg | atgcgcttcg | ccaccgtgag | gccgaggccc | gtgcccggga | tggatccaga | 180 |
| cgaggacttg | agtcgccgga | acggctcgaa | gaggtgcgcc | agctccgcgg | gctcgatccc | 240 |
| gagccctcga | tcgcgaatgg | cgatctcggc | cccgtcgccg | ccggcgcgga | ccgccacgtc | 300 |
| gatctgcccc | ccggcgggag | aatacttgag | cgcgttcgac | agcaggttgt | tcagcacctg | 360 |
| cgcgatccgg | gtcgcgtcgc | aggggacgag | caccggtgtc | tcggggagcg | acagctcgat | 420 |
| ggggtgctcc | ggcgagacag | ggcgatagag | gtccaccgcc | tcctgcgcga | ggtcgcgcag | 480 |
| atcgcgctcc | tccacccgga | gctcgagctt | gcaggcctcg | atctgggacg | cgtcgaggag | 540 |
| gtccccgacc | atgcgctcga | gccggtcgac | ctgccgcccc | acgagcgcca | tggtgcggcg | 600 |
| cacgctcgac | gccggggggca | ggctgtcgag | gtcgaggacg | tgcacggaca | tccggagcgc | 660 |
| cgacagcggg | ttcctgaggt | cgtgggccac | gccgccgagg | aacgcgaact | gcgcctcgcg | 720 |
| ctggcgctcc | agcgactccg | ccatgtcgtt | gaaggcgcgc | gcgatctccc | cgagctcgcg | 780 |
| cggcccgatc | agcggcgcgc | gcggcggcgcg | gtcgcccgcg | ccgtagcgcc | cgatcgcctg | 840 |
| ctggatcgcg | acgatggggc | ggtagatgag | ccgccgcgcg | ctgaggagga | ccgtggaagc | 900 |
| gcccgcgagg | aagaacacga | ccgccgccac | gccggcgccg | gtcgtgcgcc | gggtcaggta | 960 |
| cgcgacgagc | gcctccgacg | cgcgggcctg | ctcgaggttg | atctcgacca | ggcgatcgag | 1020 |
| cgccctgaac | gcctcgtcga | gggcgggatc | gtgcacgccg | agcagggcgg | gatcgcgcgc | 1080 |
| gccaggcgcc | gacgggagct | cgcgggcgtc | ggcggcgcgg | cgccgggcga | ggtagtcctc | 1140 |
| cacgcgccgc | tccgcgtgct | cgaggatctc | gccctcctcc | gggctgctca | cgtggccgcg | 1200 |
| cgccgccgcg | aggccgctcc | tcaggccgcg | ctcccacgcc | gccagggagg | gggccagctc | 1260 |
| cccgcggtcg | gagccgaccg | cgcggccgct | ctgctgcgcg | tcgagcagga | ggtcgatctc | 1320 |
| cagccgctcc | acgagccgga | cgctctcgac | cgtggcgccg | aggatcctgg | tggcctgttg | 1380 |
| catggtcgtc | gacgcgacca | tcagcgcgct | ggcgaccacg | atggccacgc | tcgtgagaag | 1440 |
| aagcgtggcg | gccccgagga | gcgcgctcag | gcgcacgggc | cgcggaaaac | ggagccagct | 1500 |
| caggccccgc | ggagttggcc | gtcccat | | | | 1527 |

<210> SEQ ID NO 57
<211> LENGTH: 1434
<212> TYPE: DNA
<213> ORGANISM: Sorangium cellulosum

<400> SEQUENCE: 57

| | | | | | | |
|---|---|---|---|---|---|---|
| atgcaacgtc | gcctcgatgg | agagatcgaa | ctgcagaggg | acagagcaca | tcgagacagc | 60 |
| gagcgatacg | cgcggcgccc | ccgcggcgct | ccccgcgccc | ccgcgccggc | ctcaccggcg | 120 |
| cctcgcgccc | cggtcagctc | ggtcctctgg | acggtgatcc | ccgtttcatc | gacactacgc | 180 |
| gcgatgcccg | cgcgcacccc | ccgcaagccc | ccgccgcccc | cctcgcccgc | tggtcccgcc | 240 |
| ggcgcgccgg | acgacctcag | cgacagcgat | cgcgacgcgc | tcttgcgctg | gcggctcgcg | 300 |
| ctcgggcccg | aggccgagcg | ggtcgacccg | cgcctctccc | tggcgggct | cggcggcgcg | 360 |

-continued

```
gcgcccgcgc tcgacgtcga cccgcggcgg ctgggcgacc tcgacaaggc gctgtcgttc       420
atctacgacg agcgcgccgg caacctcggc ggctcgcggc cgtacgtgcc cgagtggctc       480
tccgccgtgc gcgagttctt cagccacgag gtcgtcgccc tcgtccagaa ggacgccatc       540
gagcgaaagg ggctgacgca gctgctcttc gagcccgaga cgctgccgtt cctcgagaag       600
aacgtcgagc tcgtcgccac gctcatgagc gccaagggcc tcatcccga cgccgcgcgg        660 gagaccgccc ggcagatcgt gcgcgaggtc gtcgaggagg tgcggcgcgc gctcgagtcc       720
gaggtccgca ccgccgtcct cggcgcgctg cgccggaaca cgacgagccc gctgcgcgtc       780
ctcaggaacc tcgactggaa gcgcaccatc cgcaagaacc tgaaggggtg ggacgcggag       840
cggcgccgcc tcgtcccgga caagctctat ttctgggcga accagacgcg aaggcacgag       900
tgggacgtgg ccatcctcgt cgaccagtcg ggctcgatgg gcgagagcgt cgtctacagc       960
tccatcatgg cggcgatctt cgcgtcgctc gacgtcctcc gcacccggct cctcttcttc      1020
gacaccgagg tcgtcgacgt gactccgatg ctcgtcgatc cggtcgacgt gctgttcacg      1080
gcgcagctcg gcggcggcac cgacatcaac cgcgccgtgg cctacgccca ggcgaacttc      1140
atcgagcgac ccgagaagac gctgctcatc ctgatcaccg acctgttcga gggcggcaac      1200
gccgaggagc tcgtcgcgcg catgcgccag ctcgccgaca gcaaggtgaa gtcgatctgc      1260
ctgctcgcgc tgtcggacgg cggaaagccc tcgtacgacc acgagatggc gcagaagctc      1320
gccgccctcg ggaccccgtg cttcggctgc acgccaaagc tgctcgtcaa ggtggtggag      1380
cggctcatgc gaggtcagga cctcggcccg ctgctcggcg ccgaggcgcg gtaa           1434
```

<210> SEQ ID NO 58
<211> LENGTH: 6264
<212> TYPE: DNA
<213> ORGANISM: Sorangium cellulosum

<400> SEQUENCE: 58

```
tcaccggtgc aaccatagcc ggagcatagc gagcaggtgc tccggatcca ccggcttcga        60
gatgtaatcg ttcgcgcccg cctcgaagca cttctcccgg tcgcccttca tcgccttggc       120
cgtgaccgcg atgatgggca gcgcatggtg ctcgggcctc gcgcggatgg cacgcgatcgt      180 gtcatagccg tccatctctg gcatcatgat gtccatgagc accatctcga tgtccggcgt      240
ccgctgcagc atctcgatcg ccgctctgcc cgtctccacg tagaccgtct tcatatgctg      300
ggcgtcgagg atggtcgtca tcgcgaagat gttccgaacg tcgtcgtcga cgaccagcac      360
cttcttgccc acgagcacct tgttcgactg gtgcagctcc tcgacgatct gcagctgtcg      420
ctcggagagc gccgccaccg ggcggtgcag gaacagggag acgtcatcga agagccgctc      480 cttgagcgg acgtgcttga gcaccatcag ctggctgaag cggctcagct cgcctcgtc        540 tgcgggcgag atctcctccg gcgcgtagac caagacgggc aggtccgtgg acccgctgcc      600
ctgcgcgagc tgcccgatca gatcgaagca gcgcacgtcg ggcaggtcga ggcgcaggat      660
gaggacgtcc ggccgctcgg tgacgagcgc gtcgagcgcc tcctcccgg aggccacact       720 ccggatcgtg acgtcgtcgc cgccgaggag ctcgacgagc cctggcgct cggcgtcgtc       780 cggcccggcg agcacgatct tccgccggct cgacaccatg aactgcgaga ggcgcctgaa      840
cgtctcgtcg agcgcgtccc gggtcttgag cggcttgcag agcacaccct tcgcgcccat      900
ccgtagcgcg cgctcgcgct cctcgtccgt cgtgatcacc tggacgggga tgtgccgcgt      960
ctcgagatcg cgcttcaccc ggtcgagcac gcgccagccg tccatgtccg gcaggttgat     1020
gtcgagcgtg atcgcgttca cccgccgctc acggacgatg gagagcgccg ccccgccgcg    1080
```

```
gtaggcgagg atcgccttga acccgtggtc gtgcgcgaca tccatgacga agtgcgcgaa   1140
gctcgcgtcg ttctcgacga tgagcaccac ggagtcgctg ggcttgaggc ccgcgctgtc   1200
gtcgacgctc tggttgagca ggtgcggcgg cggctcggcc gccgaccgcg gcgggacgtc   1260
gccggagacg acggccggcg gcgctgaggg cacctccacg gtctgctcct tcctgcgcgg   1320
gcgcgccggc gtgtacgtga gcggcaggta aagcgtgaag ctgctcccgc tccccggctt   1380
gctcgagagc ttgatctcgc cgcccagcat ccacgcgatc tcgcggctga tcgcgaggcc   1440
gaggccggtg ccgccgtact tccggctcgt cgagccgtca gcctgctgga aggcctcgaa   1500
gatgatctgc tgcttgtcat gcgggatgcc gatgcccgtg tcccgcaccg acatggcgat   1560
cgccgcgccg gcgcgcgaga ggccctcgtt ctcgggcgcc caccccgagg tgaccagatc   1620
gacgtcgagc gcgacgctgc cgcgctccgt gaacttgaag gagttcgaca gcaggttctt   1680
gagtacctgc tgtacgcgct tcgcgtccgt gtagatgacc tgcggcaggt tctgcgcgaa   1740
gttgagctcg aactcgagct tcttcgactc ggcgacgtga cggaaggtgc gctcgacgta   1800
gtcctgcaga tcgctgaacg acagctcgcc gacgtcgacg atcacggtcc cggactcgat   1860
cttggacagg tccaggatgt cgttgatgag cgcgagcagg tcgttgcccg acgagtggat   1920
cgtcttggcg aactcgacct gccgcccgt gaggttgcgg tcgttgttct tcgagagctg   1980
atcggacagg atgagcaggc tgttcagggg cgtccggagc tcgtgcgaca tgttcgcgag   2040
gaactcggac ttgtacttgg aggtgatggc gagctgccgc gccttctctt cgagcgcctg   2100
ccgcgcctgc tcgacctcgc ggttcttccg ctcgacctcg acgttctgct gggcgagcag   2160
gcgcgccttc tccccgagct ccgcgttcgt ctgctgcagc tcctcctgct ggctctggag   2220
ctcgcgcgcg agggactggg actgcttgag caggtcctct gtgcgcatgt tcgcctcgat   2280
cgtgttgagc acgatcccga tcgactccgt gagctggtcg aggaaggcct ggtgggtcgg   2340
gctgaagcgc tcgaacgacg cgagctcgat gaccgccttg acctgcccct cgaagagcac   2400
ggggatgacg atgatgttga ccggcggcgc ctcgccgagc ccgctcgtga tgcggatgta   2460
gtcgggggc gcgttgacga ggaggatctt ctccttctcg agcgcgcatt gcccgaccag   2520
cccttcgccg agcttgaaat ggttgtcgac gtgcttccgc accttgtacg cgtagctcgc   2580
gaggagcttg aggatcggct cctccttcgc cacgtccatc gtgaagaaca cgccctgctg   2640
cgcaccgacg accggggcca gctcggacag gatgagccga ccgaccgtga gcagatcctt   2700
ctgcccctgg agcaggcgcg agaacttggc gaggttggtc ttgagccaat cctgctcgct   2760
gttcttcagc gtcgtgtcct tgaggttccg gatcatctca ttgatggtgt ccttgagcga   2820
cgcgacctcc cctgcgcct cgacccggat ggtccgggtg aggtcgccct tcgtcaccgc   2880
ggtcgcgacc tcggcgatgg cgcgcacctg cgtcgtcagg ttggcggcga gctggttcac   2940
gttgtcggtc aggtccttcc acgtgccggc cgcgccgggg acgctggcct gcccgccgag   3000
cttgccctcg acgccgacct cgcgcgccac cgtggtcacc tggtcggcga aggtcgcgag   3060
cgtctcgatc acgccgttga tcgtatccgc cagcgccgcg atctcgccct tcgcgtcgaa   3120
ggccagcttg cgcttcaggt cgccgttcgc gaccgcggtc acgaccttgg cgatgccgcg   3180
cacctggttc gtcaggttgc cggccatgaa attcacgttg tcggtcaggt ccttccacgt   3240
gccggcgacg ccggggacgc tggcctgccc gccgagcttg ccctcggtgc ctacctcgcg   3300
cgccacgcgc gtcacctccg acgcgaaggc gttgagctgg tccaccatcg tgttgttgat   3360
ggtgttcttg agctccagga tctcgccgcg gacatcgacg tgatcttct tcgacagatc   3420
```

```
gccgttggcg acggccgtgg tgacggcggc gatgttgcgc acctgcgcgg tcaggttcga    3480
cgccatcgag ttgacggagt cggtcaggtc cttccacgtg ccggcgacgc cggtcacctc    3540
cgcctgcccg ccgagcttgc cctcggtgcc tacctcgcgc gccacgcgcg tcacctcggc    3600
cgcgaaggag ctgagctgat ccaccatcgt gttgaaggtg ttcttcagct ccaggatctc    3660
gcccttgacg tcgacggtga tcttcttcga caggtcgccg cgggcgacgg ccgtggtgac    3720
gtcggcgatg ttgcgcacct gcgcggtcag gttcgacgcc atcgagttga cggagtcggt    3780
caggtccttc cacgtgccgg cgacgccggg gacgctggcc tgcccgccga gcttgccctc    3840
ggtgcctacc tcgcgcgcca cgcgcgtcac ctccgacgcg aacgagcgga gctgatccac    3900
catcgtgttg aaggtgtcct tcagctccag gatctcgccg cggacatcga cggtgatctt    3960
cttcgacagg tcgccgttgg cgaccgcggt ggtcacgtcg gcgatgttgc gcacctgcgc    4020
ggtcaggttc gacgccatcg agttgacgga gtcggtcagg tccttccacg tgccggcgac    4080
gccggtcacc tccgcctgcc cgccgagctt gccctcggtg cctacctcgc gccacgcg    4140
cgtcacctgg gccgcgaagg agcggagctg atccaccatc gtgttgaagg tgttcttcag    4200
ctccaggatc tcgccgcgga catcgacggt gatcttctgc gtcaggtcgc gcgggcgac    4260
ggccgtggtg acggcggcga tgttgcggac ctgcgcggtc aggttcgacg ccatcgagtt    4320
gacgagtcg gtcaggtcct tccacgtgcc ggcgacgccc ttcacctccg cctgcccgcc    4380
gagcttgccc tcggtgccca gtcgcgggc gacgcgcgtc acctcggccg cgaaggagct    4440
gagctgatcg accgtcgtgt tgatgacgtc cttgatctgg aggatctcgc gcggacatc    4500
gacggtgatc ttctgcgtca gatcgccgtt cgcgatggcg gtcgcgacct tcgacacgtc    4560
gcggagctgg accgtgaggt tcgacgccat cgagttgacg gagtcggtca ggtccttcca    4620
cgtgccggcg acgcccttca cctccgcctg ccgccgagc ttgccctcgg tgcctacctc    4680
gcgcgccacg cgcgtcacct ccgacgcgaa cgagcggagc tgatccacca tcgtgttgaa    4740
ggtgtccttc agctccagga tctcgccgcg gacatcgacg gtgatcttct gggtcaggtc    4800
gccgcgggcg acggccgtgg tgacggcggc gatgttgcgc acctgcgcgg tcaggttcga    4860
cgccatcgag ttgacggagt cggtcaggtc cttccacgtg ccggcgacgc ccttcacctc    4920
cgcctgcccg ccgagcttgc cctcggtgcc tacctcgcgc gccacgcgcg tcacctccga    4980
cgcgaacgag cggagctgat ccaccatcgt gttgaaggtg tccttcagct ccaggatctc    5040
gcccttgacg tcgacggtga tcttctgggt caggtcgccg ttggcgacgg ccgtggtgac    5100
ggcggcgatg ttgcgcacct gcgcggtcag gttcgacgcc atcgagttga cggagtcggt    5160
caggtccttc cacgtgccgg cgacgccggg gacgctggcc tgcccgccga gcttgccctc    5220
ggtgcctacc tcgcgcgcca cgcgcgtcac ctccgacgcg aacgagcgga gctgatccac    5280
catcgtgttg aaggtgtcct tcagctccag gatctcgccg cggacatcga cggtgatctt    5340
ctgcgtcaga tcgccgttgg cgacggccgt ggtgacggcg gcgatgttgc gcacctgggc    5400
ggtgaggttg ccggccatcg agttgacgga atcggtcagg tccttccagg tgccggcgac    5460
gcccttcacc tccgcctgcc cgccgagctt gccctcggtg cctacctcgc gccacgcg    5520
cgtcacttcg gacgcgaagg agccgagctg atagaccacg gttcacgg tctgggcgt    5580
ctggaggaac tcgccctcca gcggccgccc gccacctcg agcgccatcg tctgggagag    5640
atcgccttg gcgaccgcgc cgatgacgcg cgccatctct ctcgtgggct gcacgagatc    5700
gccgatcagc gcgttgacgg aggcgacctc gtcggcccag gcgccgctca cctcgcccat    5760
cgagacgcgc tggccgatct tgccttcctt gccgaccgcg cggctcagcc gctcgagctc    5820
```

| | |
|---|---:|
| gaacgcgaac ttctcgttca tctcgacgac atcgttgaag gtgtcggcga tcttcccgtc | 5880 |
| cagcccctcg aggtcgatcg gcaggcgtac cgagaagtcc cccttcttga gcgccaccag | 5940 |
| gaccgcgagc atctggccca tctcgagggc ctgccgcgcc ggccggcgca tgacgtcatc | 6000 |
| ctgcgcagcg cgccgccgcg ggcgtggcag gtcttcgaga tggacgggct gcgaccgctg | 6060 |
| ctgaagcgcg gtggcttgcg acgtccgggc gcgccctct gcgcgcttgg ccgccgcgtt | 6120 |
| cttcccgttc ctggggtgct tgccgtcctt gccgttcgtg cccttcgcgg cgccgtcctt | 6180 |
| cgaggacgcc gtccggctcc gaggagacgc tatcttgccg ctcgtccgct gctccatgtt | 6240 |
| ggaccctctc cagggcggcg ccat | 6264 |

<210> SEQ ID NO 59
<211> LENGTH: 708
<212> TYPE: DNA
<213> ORGANISM: Sorangium cellulosum

<400> SEQUENCE: 59

| | |
|---|---:|
| ttacgccgtc ccctcgcctc tcacccttgc tgcatttcgt gaccgcgttc gcggcgccgc | 60 |
| gcgccctgcc ttcgccttta cccgcccgcg cgcgccgctg ctgctcgagg cgcccgtgcc | 120 |
| cgcgcgcggc gcgctctcgg ccagcatctc ccccagcgc gagatcgcct gcgcgaccgc | 180 |
| ctggaacccc cgtccggagt cggtcagctc gtactccacc cggaccggag gccccggcag | 240 |
| cacgcgccgc accacgaggc cgagcgcctc gagctccttc agccggctgg agagcatccg | 300 |
| gtcgctgatc gcgtcgagcc gctcgccgat ctcgccgaag cgcagcgggc cctcgtcgag | 360 |
| cgtcgcgatg atgaggccgt tccacggctt cgcgagcacg tccatggccg cctggaaccc | 420 |
| gtcgcagagg tgctggcatg aatgcttcat tccgcgtcct ggacaggatg accccttcac | 480 |
| taccaaaaag gaagtccctt gacacgaggt agcgcgtgtc catgatgctt ccttgacgga | 540 |
| tgctgcttct ctttcggaag taacatcttc tttacaagga gcatcgatcg tgaccactgc | 600 |
| cgccgacctg ctgttcagcc ccttcaagct cggccccctg tcgctgccga accgcctcgt | 660 |
| gatggcgccg atgacgcgct gccgcgcggg cgagggcaac gtgcccac | 708 |

<210> SEQ ID NO 60
<211> LENGTH: 1119
<212> TYPE: DNA
<213> ORGANISM: Sorangium cellulosum

<400> SEQUENCE: 60

| | |
|---|---:|
| gtgaccactg ccgccgacct gctgttcagc cccttcaagc tcggccccct gtcgctgccg | 60 |
| aaccgcctcg tgatggcgcc gatgacgcgc tgccgcgcgg gcgagggcaa cgtgcccacc | 120 |
| gagctcaacg cggtgtatta cgagcagcgc gcgtccgccg gcctcatcat caccgaggcc | 180 |
| acccaggtca gccagcaggg cgtggggtac ctccgcacgc cgggcatcca caccgacgcg | 240 |
| caggtcgagg ggtggcggcg cgtcacggac gcggtgcacc gggcagggggcacatcttc | 300 |
| gcccagctct ggcacgtcgg gcgggcgtcg cacgtctcgt tccagccggg ccggcaggcg | 360 |
| cctgtctcgt cctcggccct ccccatccgc accgccacg cgcacacgcc cgagggcgcg | 420 |
| cagccgtaca gcaccccgcg cgccctcgag acgcgcgaga tccccggcgt cgtcgcgcag | 480 |
| ttcgaggacg gcgcgcgccg ggcgaggggcg gccggcttcg atggaatcga gctccacgcg | 540 |
| gcgaacggct acatcatcga ccagttcctc cgcgacggcg tgaaccagcg gacgaccag | 600 |
| tatggcggct cggtcgagaa ccgggcgcgg ttcctgctcg agatcgtcga cgcggtgacc | 660 |

```
ggcgtcttcg acccggaccg ggtcggcgcg cgggtctcgc cgctgggcgg ctacaacgac      720
atgagcgact cgaacccgaa ggcgatcttc ggccacgtcg ccgccgagct ctcggcgcgc      780
aagctcgcct acctgcacgt cgtggagccc gtggacgggc aggcggagga cgccgcgggt      840
cgcgtgatgc ccctgctccg cgagcggttc cgcgcgtcc tcatggcgaa cggcggctac       900
acgctcgaga cagcggaggc ggcgctgcgg acgggcgcgg cggacctcgt ctcgttcggc      960
gcgccgttcc tggccaaccc cgatctgccc gagcgcctgt cgcgcgggc gccgctcaac      1020 ccgcccgacg tgtcgacgtt ctactccgag gggccgcgcg gctacaccga ttatccgcgc    1080
ctcgccgagg cgcaggccgc cgcgcagccg tcggcctga                           1119

<210> SEQ ID NO 61
<211> LENGTH: 4524
<212> TYPE: DNA
<213> ORGANISM: Sorangium cellulosum

<400> SEQUENCE: 61
aataatgagt caggcaacta tggatgaacg aaatagacag atcgctgaga taggtgcctc       60
actgattaag cattggtaac tgtcagacca agtttactca tatatacttt agattgattt      120
aaaacttcat ttttaattta aaaggatcta ggtgaagatc cttttgata atctcatgac       180 caaaatccct taacgtgagt tttcgttcca ctgagcgtca gacccttaa taagatgatc       240 ttcttgagat cgttttggtc tgcgcgtaat ctcttgctct gaaaacgaaa aaaccgcctt      300
gcagggcggt ttttcgagct tcgtggatcc agatctgaag ctcttgttgg ctagtgcgta      360
gtcgttggca gttcaacctg ttgatagtac gtactaagct ctcatgtttc acgtactaag      420
ctctcatgtt taacgtacta agctctcatg tttaacgaac taaaccctca tggctaacgt      480
actaagctct catggctaac gtactaagct ctcatgtttc acgtactaag ctctcatgtt      540
tgaacaataa aattaatata atcagcaac ttaaatagcc tctaaggttt taagttttat       600
aagaaaaaaa agaatatata aggcttttaa agctctagcg ctgaggtctg cctcgtgaag      660
aaggtgttgc tgactcatac caggcctgaa tcgccccatc atccagccag aaagtgaggg      720
agccacggtt gatgagagct tgttgtagg tggaccagtt ggtgattttg aacttttgct       780
ttgccacgga acgtctgcg ttgtcggaa gatgcgtgat ctgatccttc aactcagcaa        840
aagttcgatt tattcaacaa agccacgttg tgtctcaaaa tctctgatgt acattgcac      900 aagataaaaa tatatcatca tgaacaataa aactgtctgc ttacataaac agtaatacaa      960
ggggtgttat gagccatatt caacgggaaa cgtcttgctc gattaatcag ataaaatcta     1020
gaattcccgg gcatagatcc gcttgccctc atctgttacg ccggcggtag ccggccagcc     1080
tcgcagagca ggattcccgt tgagcaccgc caggtgcgaa taaggacag tgaagaagga      1140 acacccgctc gcgggtgggc ctacttcacc tatcctgccc ggctgacgcc gttggataca     1200
ccaaggaaag tctacacgaa ccctttggca aaatcctgta tatcgtgcga aaaggatgg      1260 atataccgaa aaaatcgcta taatgacccc gaagcagggt tatgcagcgg aaaagcgctg     1320
cttccctgct gttttgtgga atatctaccg actggaaaca ggcaaatgca ggaaattact     1380
gaactgaggg gacaggcgag agacgggcc tagagcggcc aattcctgca gcccagcttc     1440
acgctgccgc aagcactcag ggcgcaaggg ctgctaaagg aagcggaaca cgtagaaagc     1500
cagtccgcag aaacggtgct gaccccggat gaatgtcagc tactgggcta tctggacaag     1560
ggaaaacgca agcgcaaaga gaaagcaggt agcttgcagt gggcttacat ggcgatagct     1620
agactgggcg gttttatgga cagcaagcga accggaattg ccagctgggg cgccctctgg    1680
```

```
taaggttggg aagccctgca aagtaaactg gatggctttc ttgccgccaa ggatctgatg    1740
gcgcagggga tcaagatcaa ttcattaaag aggagaaatt aaccatggcc gaccaagcga    1800
cgcccaacct gccatcacga gatttcgatt ccaccgccgc cttctatgaa aggttgggct    1860
tcggaatcgt tttccgggac gccggctgga tgatcctcca gcgcgggat ctcatgctgg     1920 agttcttcgc ccaccccggg ctcgatcccc tcgcgagttg gttcagctgc tgcctgaggc    1980
tggacgacct cgcggagttc taccggcagt gcaaatccgt cggcatccag gaaaccagca    2040
gcggctatcc gcgcatccat gccccgaac tgcaggagtg gggaggcacg atggccgctt     2100
tggtcgaccc ggacgggacg ctcctgcgcc tgatacagaa cgaattgctt gcaggcatct    2160
catgaagctt atgtccggta ccgtcgactg ataacttcgt ataatgtatg ctatacgaag    2220
ttatgcggcc atcgatcgcg cgcagatctg tcatgatgat attgcaattg gatccatata    2280
tagggcccgg gttataatta cctcaggtcg acgtcccatg tcgagaaaat ttatcaaaaa    2340
gagtgttgac ttgtgagcgg ataacaatga tacttagatt caattgtgag cggataacaa    2400
tttcacacag aattcattaa agaggagaaa ttaaccatgg cgctcagggg tgcgtcggac    2460
gccactacca acccctctcg acttgtgcag tccgtcgccg ccggcccgcg tgcgactccg    2520
tggggtgtca gtgcgtcgtg gtacctgcta gggcgtacag caacgggga gtacatcgtg     2580 agtagcgacg cggcgaagaa gggccatcca atggcaactg cggcggagcg gttgccgacg    2640
tcaccaatcg acgtcaacgc tctggcgctg gaggtggccc ggcttgtggc cctccagcag    2700
caaagtgcga cgccgccatc gtccggccgc actttcggcg cggtggcgga tgactggctc    2760
atcactgagg ccaagcgcct cgtgtgcccc gacaatgagc gccgccatct tcgccatatg    2820
gaggcgctct ggggcatgac ggatgtggag ctcacgccgc gcgtcgtgaa ggcgcacctg    2880
gcgggacttc tcaagccaga ggggccgctg agcgcagcca ccgtcaataa ggtgcgctca    2940
gccggcaagc gcatcatcaa ggcggcgcaa atcaacggcg agtggggccc ggtgaatcct    3000
ttcggcgtgc tcgaccgcga aaaagaggcg aaggccgagc gcctcacgct gacggcagcg    3060
gagtgccggg cggtgctccc gcacttccgc gcggaccggc gccgcgagtt tctcttccag    3120
gtctttctgg ggccacgccc cggcgaagag aaggcgctcc tcaaggaaga tgtggacgtc    3180
gaggcgcgca ccgtcatttt ccggcgcagc aatggacgag acacgacaaa gacgggacgc    3240
gagcgtcgcg tgccggtgcc ggatgagttg tggcccgtgc tcctcgatgc gatgcaggcc    3300
agtccgtctg acctcgtttt cccgaacgcg aagggtgaga ggcagcgcgc agacacgaag    3360
atgacgcgcg tgctgcgcac tgcgctatcc gcggctggtg tcgtggtggg ctgggattac    3420
atctgccgca cgcagggctg cggctaccga gatgtgcagt ctggtggcgc gcgccaggag    3480
cgtcggtgcc ccgcctgcga caagcgcatg tgggccagtg gtcgccccaa acccgccgtc    3540
tggtacgggc tccgtcacac cgcggcgaca ctgcacagga aggcgggctg cgacccgctc    3600
gtcatcaagc tcgtgctggg gcatgcggct gtcgacacca cggacgacgt gtacacgcac    3660
ctcgacgagg actactgccg cgccgaactt aacaagttgt cgctgaaggc cccgccgcca    3720
ccacctactc accagggagg aagtgacggc ggccctgact caggacgcaa cacctacggt    3780
gaaggaggca ccatgcacgg attgggagat ttgcagcatc accgggcgag agcttgggaa    3840
gctcgtgctc taccaactga gctaccaccg cggaacttgg ccggggtat accggcgccg     3900 ctgctgagcg tcaaggacgt tgcggcttca ctctcagtga gcacggcgaa ggtgtaccag    3960
ctcctcgccg ccggcgtcct gcctaccgtg tgggtgggcc agtcgcgccg cgtcaagcgt    4020
```

```
gaggacctgg acgcctacat cgcccgcgcg acggccaccg gcgggaagcg gggtggcaaa    4080
tgagccgctg ccctgagcca attgggatcc tgcaggaatt gccaagctgt caccatcctg    4140
tcggctgtgg cacaggctga acgccggagg atcctagagc gcacgaatga gggccgacag    4200
gaagcaaagc tgaaaggaat caaatttggc cgcaggcgta ccgtggacag gaacgtcgtg    4260
ctgacgcttc atcagaaggg cactggtgca acggaaattg ctcatcagct cagtattgcc    4320
cgctccacgg tttataaaat tcttgaagac gaaagggcct cgtgatacgc ctatttttat    4380
aggttaatgt catgataata atggtttctt agacgtcagg tggcactttt cggggaaatg    4440
tgcgcggaac ccctatttgt ttatttttct aaatacattc aaatatgtat ccgctcatga    4500
gacaataacc ctgataaatg cttc                                          4524
```